US011505538B1

(12) United States Patent
Cianchetta et al.

(10) Patent No.: US 11,505,538 B1
(45) Date of Patent: Nov. 22, 2022

(54) THERAPEUTICALLY ACTIVE COMPOUNDS AND THEIR METHODS OF USE

(71) Applicant: Agios Pharmaceuticals, Inc., Cambridge, MA (US)

(72) Inventors: Giovanni Cianchetta, Waltham, MA (US); Byron DeLaBarre, Arlington, MA (US); Janeta Popovici-Muller, Waltham, MA (US); Francesco G. Salituro, Marlborough, MA (US); Jeffrey O. Saunders, Lincoln, MA (US); Jeremy Travins, Southborough, MA (US); Shunqi Yan, Irvine, CA (US); Tao Guo, Dayton, NJ (US); Li Zhang, Shanghai (CN)

(73) Assignee: Servier Pharmaceuticals LLC, Boston, MA (US)

( * ) Notice: Subject to any disclaimer, the term of this patent is extended or adjusted under 35 U.S.C. 154(b) by 20 days.

(21) Appl. No.: 16/905,736

(22) Filed: Jun. 18, 2020

Related U.S. Application Data

(60) Continuation of application No. 16/388,801, filed on Apr. 18, 2019, now abandoned, which is a continuation of application No. 15/638,279, filed on Jun. 29, 2017, now Pat. No. 10,294,215, which is a division of application No. 13/735,467, filed on Jan. 7, 2013, now Pat. No. 9,732,062.

(60) Provisional application No. 61/584,214, filed on Jan. 6, 2012.

(51) Int. Cl.
*C07D 251/18* (2006.01)
*A61K 31/53* (2006.01)
*C07D 401/14* (2006.01)
*A61K 31/5377* (2006.01)
*C07D 401/12* (2006.01)
*C07D 413/14* (2006.01)
*C07D 405/14* (2006.01)
*C07D 403/04* (2006.01)
*C07D 405/12* (2006.01)
*C07D 413/04* (2006.01)
*C07D 413/12* (2006.01)
*C07D 417/04* (2006.01)
*C07D 493/08* (2006.01)

(52) U.S. Cl.
CPC ............ *C07D 401/14* (2013.01); *A61K 31/53* (2013.01); *A61K 31/5377* (2013.01); *C07D 251/18* (2013.01); *C07D 401/12* (2013.01); *C07D 403/04* (2013.01); *C07D 405/12* (2013.01); *C07D 405/14* (2013.01); *C07D 413/04* (2013.01); *C07D 413/12* (2013.01); *C07D 413/14* (2013.01); *C07D 417/04* (2013.01); *C07D 493/08* (2013.01)

(58) Field of Classification Search
None
See application file for complete search history.

(56) References Cited

U.S. PATENT DOCUMENTS

| | | | |
|---|---|---|---|
| 2,390,529 | A | 12/1945 | Friedheim |
| 3,755,322 | A | 8/1973 | Winter et al. |
| 3,867,383 | A | 2/1975 | Winter |
| 4,084,053 | A | 4/1978 | Desai et al. |
| 4,693,726 | A | 9/1987 | Meininger et al. |
| 5,160,346 | A | 11/1992 | Fuso et al. |
| 5,489,591 | A | 2/1996 | Kobayashi et al. |
| 5,834,485 | A | 11/1998 | Dyke et al. |
| 5,965,559 | A | 10/1999 | Faull et al. |
| 5,984,882 | A | 11/1999 | Rosenschein et al. |
| 6,274,620 | B1 | 8/2001 | Labrecque et al. |
| 6,399,358 | B1 | 6/2002 | Williams et al. |
| 6,723,730 | B2 | 4/2004 | Bakthavatchalam et al. |
| 6,979,675 | B2 | 12/2005 | Tidmarsh |
| 7,173,025 | B1 | 2/2007 | Stocker et al. |
| 7,858,782 | B2 | 12/2010 | Tao et al. |
| 8,133,900 | B2 | 3/2012 | Hood et al. |
| 8,465,673 | B2 | 6/2013 | Yasuda et al. |
| 9,487,495 | B2 | 11/2016 | Cisar et al. |
| 9,512,107 | B2 | 12/2016 | Cianchetta et al. |
| 9,656,999 | B2 | 5/2017 | Cianchetta et al. |
| 9,732,062 | B2 | 8/2017 | Cianchetta et al. |
| 10,294,215 | B2 | 5/2019 | Cianchetta et al. |
| 2003/0109527 | A1 | 6/2003 | Jin et al. |
| 2003/0213405 | A1 | 11/2003 | Harada et al. |
| 2004/0067234 | A1 | 4/2004 | Einat et al. |
| 2004/0248221 | A1 | 12/2004 | Stockwell |
| 2006/0084645 | A1 | 4/2006 | Pal et al. |
| 2006/0281122 | A1 | 12/2006 | Bryant et al. |
| 2007/0244088 | A1 | 10/2007 | Brickmann et al. |
| 2008/0300208 | A1 | 12/2008 | Einat et al. |
| 2009/0093526 | A1 | 4/2009 | Miller et al. |
| 2009/0163508 | A1 | 6/2009 | Kori et al. |

(Continued)

FOREIGN PATENT DOCUMENTS

| | | |
|---|---|---|
| CN | 101575408 A | 11/2009 |
| CN | 102659765 A | 9/2012 |

(Continued)

OTHER PUBLICATIONS

Advisory action for U.S. Appl. No. 13/735,467 dated Mar. 22, 2016 (3 pages).
Advisory action for U.S. Appl. No. 13/735,467 dated Jun. 10, 2016 (3 pages).
Ansell et al. "The interactions of artificial coenzymes with alcohol dehydrogenase and other NAD(P)(H) dependent enzymes" Journal of Molecular Catalysis B: Enzymatic (1999) vol. 6, No. 1-2, pp. 111-123.
Balss, "Analysis of the IDH1 codon 132 mutation in brain tumors", Acta Neuropathol (2008) vol. 116, pp. 597-602.

(Continued)

*Primary Examiner* — Savitha M Rao
*Assistant Examiner* — Gregg Polansky
(74) *Attorney, Agent, or Firm* — Jones Day

(57) ABSTRACT

Provided are compounds useful for treating cancer and methods of treating cancer comprising administering to a subject in need thereof a compound described herein.

8 Claims, No Drawings

(56) References Cited

U.S. PATENT DOCUMENTS

| | | |
|---|---|---|
| 2009/0163545 A1 | 6/2009 | Goldfarb |
| 2010/0129350 A1 | 5/2010 | Zacharie et al. |
| 2010/0144722 A1 | 6/2010 | Alexander et al. |
| 2011/0073007 A1 | 3/2011 | Yasuda et al. |
| 2011/0288065 A1 | 11/2011 | Fujihara et al. |
| 2012/0121515 A1 | 5/2012 | Dang et al. |
| 2012/0164143 A1 | 6/2012 | Teeling et al. |
| 2012/0202818 A1 | 8/2012 | Tao et al. |
| 2012/0238576 A1 | 9/2012 | Tao et al. |
| 2012/0277233 A1 | 11/2012 | Tao et al. |
| 2013/0035329 A1 | 2/2013 | Saunders et al. |
| 2013/0183281 A1 | 7/2013 | Su et al. |
| 2013/0190287 A1 | 7/2013 | Cianchetta et al. |

FOREIGN PATENT DOCUMENTS

| | | |
|---|---|---|
| CN | 103097340 A | 5/2013 |
| DE | 3314663 A1 | 10/1983 |
| DE | 3512630 A1 | 10/1986 |
| EP | 0384228 A1 | 8/1990 |
| EP | 0385237 A2 | 9/1990 |
| EP | 0945446 A1 | 9/1999 |
| FR | 2735127 | 12/1996 |
| JP | H4099768 | 3/1992 |
| JP | H9291034 | 11/1997 |
| JP | 11158073 | 6/1999 |
| JP | 2004107220 A | 4/2004 |
| JP | 2009237115 A | 10/2009 |
| JP | 2010079130 A | 4/2010 |
| JP | 2010181540 A | 8/2010 |
| JP | 4753336 B2 | 8/2011 |
| WO | WO 2001/016097 A1 | 3/2001 |
| WO | WO 2002/102313 A2 | 12/2002 |
| WO | WO 2003/016289 | 2/2003 |
| WO | WO 2003/037346 | 5/2003 |
| WO | WO 2004/009562 A1 | 1/2004 |
| WO | WO 2004/046120 A2 | 6/2004 |
| WO | WO 2004/050033 A2 | 6/2004 |
| WO | WO 2004/073619 A2 | 9/2004 |
| WO | WO 2004/074438 A2 | 9/2004 |
| WO | WO 2005/035507 A2 | 4/2005 |
| WO | WO 2005/060956 A1 | 7/2005 |
| WO | WO 2005/065691 A1 | 7/2005 |
| WO | WO 2006/070198 A1 | 7/2006 |
| WO | WO 2006/079791 A1 | 8/2006 |
| WO | WO 2007/023186 A1 | 3/2007 |
| WO | WO 2008/070661 A1 | 6/2008 |
| WO | WO 2008/076883 A2 | 6/2008 |
| WO | WO 2008/131547 A1 | 11/2008 |
| WO | WO 2008/154026 A1 | 12/2008 |
| WO | WO 2009/013126 A1 | 1/2009 |
| WO | WO 2009/118567 A2 | 10/2009 |
| WO | WO 2009/150248 A1 | 12/2009 |
| WO | WO 2010/028099 A1 | 3/2010 |
| WO | WO 2010/007756 A1 | 10/2010 |
| WO | WO 2010/144338 A1 | 12/2010 |
| WO | WO 2011/005210 A1 | 1/2011 |
| WO | WO 2011/072174 A1 | 6/2011 |
| WO | WO 2012/009678 A1 | 1/2012 |
| WO | WO 2012/074999 A1 | 6/2012 |
| WO | WO 2012/160034 A1 | 11/2012 |
| WO | WO 2012171506 A1 | 12/2012 |
| WO | WO 2013/102431 A1 | 7/2013 |
| WO | WO 2013/107291 A1 | 7/2013 |
| WO | WO 2013/107405 A1 | 7/2013 |
| WO | WO 2013/133367 A1 | 9/2013 |

OTHER PUBLICATIONS

Benner et al., "Evolution, language and analogy in functional genomics", Trends in Genetics (2001) vol. 17, pp. 414-418.

Berge et al., Pharmaceutical Salts, Journal of Pharmaceutical Sceiences, Jan. 1977, vol. 66(1), pp. 1-19.

Bhushan et al. "Reversed-phase liquid chromatographic resolution of diastereomers of protein and non-protein amino acids prepared with newly synthesized chiral derivatizing reagents based on cyanuric chloride" Amino Acids (2011) vol. 40, pp. 403-409.

Bleeker et al., "IDH1 mutations at residue p.R132 (IDH1 (R132)) occur frequently in highgrade 18-22 gliomas but not in other solid tumors." Hum Mutal., (2009) vol. 30, No. 1, pp. 7-11.

Braun et al. "Triazine-based polymers: 4. MALDI-MS of triazine-based polyamines" Polymer (1996) vol. 37, No. 5, pp. 777-783.

Cairns et al. "Oncogenic Isocitrate Dehydrogenase Mutations: Mechanisms, Models, and Clinical Opportunities" Cancer Discovery (2013) vol. 3, Iss 7, pp. 730-741.

Cecil Textbook of Medicine, edited by Bennet and Plum, (1997) 20th edition, vol. 1, pp. 1004-1010.

Chan et al. "Multi-domain hydrogen-bond forming metal chelates: X-ray crystal structures of dicyclopalladated 2,3-bis[6-(2-amino-4-phenylamino-1,3,5-triazinyl)]pyrazine (H2L) [Pd2Br2L] and 2,6-bis[6-(2-amino-4-phenylamino-1,3,5-triazinylium)]—pyridine dichloride" Chemical Communications (1996) No. 1, pp. 81-83.

Chapman et al. "Substituted aminopyrimidine protein kinase B (PknB) inhibitors show activity against *Mycobacterium tuberculosis*" Bioorganic & Medicinal Chemistry Letters (2012) vol. 22, pp. 3349-3353.

Chen et al. "Cytotoxicity, Hemolysis, and Acute in Vivo Toxicity of Dendrimers Based on Melamine, Candidate Vehicles for Delivery" J. Am. Chem. Soc. (2004) vol. 126, No. 32, pp. 10044-1004.

Cocco et al. "Synthesis of Triflouromethylated Pyridinecarbonitriles" Journal of Heterocyclic Chemistry (1995) vol. 32, pp. 543-545.

Dang et al., "Cancer-associated IDH1 mutations produce 2-hydroxyglutarate" Nature (2009) vol. 462, No. 7274, pp. 739-744.

Dang et al. "IDH Mutations in Glioma and Acute Myeloid Leukemia" Trends in Molecular Medicine (2010) vol. 16, No. 9, pp. 387-397.

Dermer "another Anniversary for the War on Cancer" Bio/Technology (1994) vol. 12, p. 320.

Dohner et al. "Impact of Genetic Features on Treatment Decisions in AML" American Society of Hematology (2011) pp. 36-42.

Dorwald, "Side reactions in organic synthesis," Wiley: VCH, Weinheim, p. IX (2005).

Duanmu et al. "Dendron-Functionalized Superparamagnetic Nanoparticles with Switchable Solubility in Organic and Aqueous Media: Matriced for Homogeneous Catalysis and Potential MRI Contrast Agents" Chem. Mater. (2006) vol. 18, No. 25, pp. 5973-5981.

EP Search Report & Written Opinion for EP 10825706 dated Mar. 20, 2013.

European Search Report for Application No. 10751525.6 dated Dec. 14, 2012.

European Search Report for European Application No. 12799802.9 dated Sep. 24, 2014.

European Search Report for European Application No. EP 12800001.5 dated Oct. 10, 2014.

Eurpoean Search Report for EP Application No. 11763425.3 dated Sep. 23, 2013.

Final office action for U.S. Appl. No. 13/735,467 dated Dec. 3, 2015 (21 pages).

Gewald et al. "Discovery of triazines as potent, selective and orally active PDE4 inhibitors" Bioorganic & medicinal Chemistry Letters (2013) vol. 23, pp. 4308-4314.

Golub et al. "Molecular Classification of Cancer: Class Discovery and Class Prediction by Gene Expression Monitoring" Science (1999) vol. 286, pp. 531-537.

Hai et al., "IDH1 and IDH2 Mutations in Gilomas", New England Journal of Medicine, Massachusetts Medical Society, Boston, MA, US, (2009) vol. 360, No. 8, pp. 765-773.

Hartmann et al. "Type and Frequency of IDH1 and IDH2 mutations are related to astrocytic and oligodendroglial differentiation and age: a study of 1010 diffuse gliomas" Acta Neuropathologica (2009) vol. 118, pp. 469-474.

Holmes et al. "750 MHz 1H NMR spectroscopy characterisation of the complex metabolic pattern of urine from patients with inborn errors of metabolism: 2-hydroxyglutaric aciduria and maple syrup mine disease" Journal of Pharmaceutical and Biomedical Analysis (1997) vol. 15, pp. 1647-1659.

(56) References Cited

OTHER PUBLICATIONS

Hu et al., "Solid-phase synthesis and antitumor evaluation of 2,4-diamino-6-aryl-1,3,5-triazines," J. Comb. Chem., 11(2):267-273 (2009).
Internation Search Report for PCT/US2011/067752 dated Feb. 22, 2012.
International Preliminary Report for related application No. PCT/US2010/059778 dated Jun. 12, 2012.
International Preliminary Report on Patentability for PCT/CN2012/000841 dated Dec. 17, 2013.
International Preliminary Report on Patentability for PCT/CN2012/077096 dated Dec. 17, 2013.
International Preliminary Report on Patentability for PCT/US2010/027253 dated Sep. 13, 2011.
International Preliminary Report on Patentability for PCT/US2010/040486 dated Jan. 12, 2012.
International Preliminary Report on Patentability for PCT/US2010/053623 dated Apr. 24, 2012.
International Preliminary Report on Patentability for PCT/US2010/053624 dated Apr. 24, 2012.
International Preliminary Report on Patentability for PCT/US2011/030692 dated Oct. 2, 2012.
International Preliminary Report on Patentability for PCT/US2011/067752 dated Apr. 11, 2013.
International Search Report & Written Opinion for PCT/CN2013/070755 dated Apr. 25, 2013.
International Search Report and Written Opinion for International Application No. PCT/CN2013/080105 dated Jul. 11, 2014.
International Search Report and Written Opinion for International Application No. PCT/CN2013/081170 dated Apr. 30, 2014.
International Search Report and Written Opinion for International Application No. PCT/CN2014/081957 dated Sep. 30, 2014.
International Search Report and Written Opinion for International Application No. PCT/CN2014/081958 dated Sep. 29, 2014.
International Search Report and Written Opinion for International Application No. PCT/US2014/046202 dated Sep. 30, 2014.
International Search Report and Written Opinion for International Application No. PCT/US2014/049469 dated Jan. 22, 2015.
International Search Report and Written Opinion for International Application No. PCT/CN2014/082869 dated Sep. 30, 2014.
International Search Report for International Application No. PCT/CN2013/079184 dated Jan. 12, 2015.
International Search Report for International Application No. PCT/CN2013/079200 dated Jan. 12, 2015.
International Search Report for International Application No. PCT/US2014/046204 dated Oct. 1, 2014.
International Search Report for PCT/CN2012/000841 dated Sep. 27, 2012.
International Search Report for PCT/CN2012/077096 dated Oct. 4, 2012.
International Search Report for PCT/CN2013/000009 dated Apr. 18, 2013.
International Search Report for PCT/CN2013/000068 dated Apr. 25, 2013.
International Search Report for PCT/US2010/027253 dated Aug. 19, 2010.
International Search Report for PCT/US2010/053624 dated Apr. 7, 2011.
International Search Report for PCT/US2010/059778 dated Mar. 17, 2011.
International Search Report for PCT/US2010/53623 dated Jan. 18, 2011.
International Search Report for PCT/US2011/044254 dated May 10, 2011.
International Search Report for PCT/US2013/064601 dated Feb. 24, 2014.
International Serach Report for PCT/US2011/030692 dated Jun. 27, 2011.

Irikura et al. "New s-Triazine Derivatives as Depressants for Reticuloendothelial Hyperfunction Induced by Bacterial Endotoxin" Journal of Medicinal Chemistry (1970) vol. 13, pp. 1081-1089.
Jennings et al. "Expression and mutagenesis of mammalian cytosolic NADP+-specific isocitrate dehydrogenase" Biochemistry (1997) vol. 36, pp. 13743-13747.
Kaila et al. "A convenient one-pot synthesis of trisubstituted 1,3,5-triazines through intenuediary amidinothioureas" Tetrahedron Letters (2010) vol. 51, pp. 1486-1489.
Kelarev et al. "Synthesis and properties of sym-triazines. 10 Synthesis of 2,4-diamino-sym-triazines containing a sterically hindered phenol substituent" Chemistry of Heterocyclic Compounds (1992) vol. 28, No. 10, pp. 1189-1193.
Kim et al. "Identification and Functional Characterization of a Novel, Tissue-specific NAD+-dependent Isocitrate Dehydrogenase b Subunit Isoform" JBC (1999) vol. 274, No. 52, pp. 36866-36875.
Kim et al. "Ser95, Asn97, and Thr78 are important for the catalytic function of porcine NADP-dependent isocitrate dehydrogenase" Protein Science (2005) vol. 14, pp. 140-147.
Koshelev et al. "Synthesis of 1-3,7 N-substituted 2,4-diamino-1,3,5-triazines containing pyridyl groups" Russian Journal of Organic Chemistry (1995) vol. 31, No. 2, pp. 260-263.
Kranendijk et al. "IDH2 Mutations in Patients with D-2-Hydroxyglutaric Aciduria" Science (2010) vol. 330, p. 336.
Krell et al., "IDH mutations in tumorigenesis and their potential role as novel therapeutic targets" Future Oncology (2013) vol. 9, Iss 12, pp. 1923-1935.
Kusakabe et al. Chemical Abstracts vol. 152, No. 191956, Abstract for WO2010007756 (2010).
Lee et al. "Combinatorial Solid-Phase Synthesis of 6-Aryl-1,3,4-triazines via Suzuki Coupling" Aust. J. Chem. (2011) vol. 64, pp. 540-544.
Madsen-Duggan et al. "Lead optimization of 5.6-diarylpyridines as CB1 receptor inverse agonists" Bioorganic & Medicinal Chemistry Letters (2007) vol. 17, pp. 2031-2035.
May et al. "How many species are there on earth" Science (1988) vol. 241, p. 1441-1449.
Moreno et al. "Identification of diamine linkers with differing reactivity and their applicationin the synthesis of melamine dendrimers" Tetrahedron Letters (2008) vol. 49, pp. 1152-1154.
Moreno et al. "Molecular recognition in dendrimers based on melamine" Polymer Preprints (2005) vol. 46, No. 2, pp. 1127.
Non final office action for U.S. Appl. No. 13/735,467 dated May 22, 2015 (17 pages).
Notice of Allowance for U.S. Appl. No. 13/735,467 dated Jan. 27, 2017 (29 pages).
Notice of Allowance for U.S. Appl. No. 13/735,467 dated Mar. 31, 2017 (11 pages).
Notice of Allowance for U.S. Appl. No. 15/173,519 dated Jun. 27, 2016 (10 pages).
Notice of Allowance for U.S. Appl. No. 15/173,519 dated Aug. 10, 2016 (21 pages).
Notice of Allowance for U.S. Appl. No. 15/173,519 dated Sep. 29, 2016 (10 pages).
Notice of Allowance for U.S. Appl. No. 15/337,683 dated Jan. 17, 2017 (9 pages).
Non final office action for U.S. 15/638,279 dated Jun. 29, 2018 (22 pages).
Notice of Allowance for U.S. Appl. No. 15/638,279 dated Jan. 15, 2019 (8 pages).
Non final office action for U.S. Appl. No. 16/388,801 dated Dec. 19, 2019 (12 pages).
PUBCHEM CID 4078245 [online]; Sep. 13, 2005 [retrieved on Feb. 4, 2012]; retrieved from http://pubchem.ncbi.nim.nih.gov/; 2d-structure.
PUBCHEM CID 4854170 [online]; Sep. 17, 2005 [retrieved on Feb. 4, 2012]; retrieved from http://pubchem.ncbi.nim.nih.gov/; 2d-structure.
Raynaud et al. "Absence of R140Q Mutation of Isocitrate Dehydrogenase 2 in Gliomas and Breast Cancers" Oncology Letters (2010) vol. 1, No. 5, pp. 883-884.

(56) References Cited

OTHER PUBLICATIONS

Reitman et al. "Isocitrate Dehydrogenase 1 and 2 Mutations in Cancer: Alterations at a Crossroads of Cellular Metabolism" Journal of the National Cancer Institute (2010) vol. 102, No. 13, pp. 932-941.
Rohle et al. "An Inhibitor of Mutant IDH1 Delays Growth and Promotes Differentiation of Glioma Cells" Science (2013) vol. 340, No. 6132, pp. 626-630.
Scharn et al. "Spatially Addressed Synthesis of Amino- and Amino-Oxy-Substituted 1,3,5-Triazine Arrays on Polymeric Membranes" Journal of Combinatorial Chemistry (2000) vol. 2, No. 4, pp. 361-369.
Shih et al. "The Role of Mutations in Epigenetic Regulators in Myeloid Malignancies" Nature Reviews Cancer (2012) vol. 12, No. 9, pp. 599-612.
Sirkanyan et al. "Synthesis of new derivatives of piperazine-substituted pyrano[3,4-c]pyridines" Hayastani Kimiakan Handes—Chemical Journal of Aimenia (2009) vol. 62, No. 3-4 pp. 378-385. English Abstract Only.
Sonoda et al. "Analysis of IDH1 and IDH2 mutations in Japanese glioma patients" Cancer Science, vol. 100, No. 10, pp. 1996-1998 (2009).
STN File CA, Registry No. 1023444-33-8, entered STN on May 29, 2008, Chemical Abstracts IndexName "Benzenesulfonamide, 3-[[4-(l,3-benzodioxol-5-ylmethyl)-l-piperazinyl]carbonyl]-N-(4-butylphenyl)-4-methyl-".
STN File CA, Registry No. 1090629-29-0, entered STN on Dec. 28, 2008, Chemical Abstracts IndexName "Benzenesulfonamide, 3-[[4-[(2,5-dimethoxyphenyl)methyl]-1-piperazinyl]carbonyl]-N-(4-methoxyphenyl)-4-methyl-".
STN File CA, Registry No. 134538-28-6, entered STN on Jun. 28, 1991, Chemical Abstracts IndexName "IH-Pyrano[3,4-c]pyridine-5-carbonitrile, 3,4-dihydro-3,3-dimethyl-6-[4-(1-oxobutyl)-1-piperazinyl]-8-phenyl-", disclosed in Paronikyan et al. Aimyanskii Khimicheskii Zhurnal, 1990, vol. 43, No. 8.
STN File CA, Registry No. 134538-29-7, entered STN on Jun. 28, 1991, Chemical Abstracts IndexName "1H-Pyrano[3,4-c]pyridine-5-carbonitrile, 3,4-dihydro-3,3-dimethyl-6-[4-(2-methyl-1-oxopropyl)-1-piperazinyl]-8-phenyl-", disclosed in Paronikyan et al. Armyanskii Khimicheskii Zhurnal, 1990, vol. 43, No. 8.
STN File CA, Registry No. 134538-30-0, entered STN on Jun. 28, 1991, Chemical Abstracts IndexName "1H-Pyrano[3,4-c]pyridine-5-carbonitrile, 6-(4-benzoyl-1-piperazinyl)-3,4-dihydro-3,3-dimethyl-8-phenyl-", disclosed in Paronikyan et al. Aimyanskii Khimicheskii Zhumal, 1990, vol. 43, No. 8.
STN File CA, Registry No. 134538-31-1, entered STN on Jun. 28, 1991, Chemical Abstracts IndexName "1H-Pyrano[3,4-c]pyridine-5-carbonitrile, 6-[4-(2-furanylcarbonyl)-1-piperazinyl]-3,4-dihydro-3,3-dimethyl-8-phenyl-", disclosed in Paronikyan et al. Aimyanskii Khimicheskii Zhumal, 1990, vol. 43, No. 8.
STN File CA, Registry No. 380466-24-0 entered STN on Jan. 4, 2002, Chemical Abstracts IndexName "Benzenesulfonamide, N-methyl-N-phenyl-3-[[4-(2-pyridinyl)-1-piperazinyl]carbonyl]".
STN File CA, Registry No. 713505-78-3, entered STN on Jul. 21, 2004, Chemical Abstracts IndexName "1-Piperazinecarboxylic acid, 4-[4-methyl-3-[(phenylamino)sulfonyl]benzoyl]-, ethyl ester".
STN File CA, Registry No. 736168-79-9 entered STN on Aug. 31, 2004, Chemical Abstracts IndexName "Benzenesulfonamide, 3,4-difluoro-N-[3-334-(phenylmethyl0-1-piperazinyl]carbonyl]phenyl".
STN File CA, Registry No. 847757-57-7, entered STN on Apr. 1, 2005, Chemical Abstracts IndexName "Benzenesulfonamide, 3-[[4-(1,3-benzodioxol-5-ylmethyl)-1-piperazinyl]carbonyl]-N-(4-ethoxyphenyl)-N,4-dimethyl-" or "Piperazine, 1-(1,3-benzodioxol-5-ylmethyl)-4-[5-[[(4-ethoxyphenyl)methylamino]sulfonyl]-2-methylbenzoyl]-".
STN Registry, L23 Answer 2 oF 3 (Cas No. 1032450-21-7), Database: ASINEX Ltd.,Entered STN: Jul. 3, 2008 (Jul. 3, 2008).
STN Registry. L23 Answer 1 of 3 (Cas No. 1038821-72-5),Database: ChemDB (University of California Irvine), Entered STN: Aug. 5, 2008 (Aug. 5, 2008).
Struys et al. "Investigations by mass isotopomer analysis of the foimation of D-2-hydroxyglutarate by cultured lymphoblasts from two patients with D-2-hydroxyglutaric aciduria" FEBS Letters (2004) vol. 557, pp. 115-120.
Struys et al. "Mutations in the D-2-hydroxyglutarate dehydrogenase gene cause D-2-hydroxyglutaric aciduria" American Journal of Human Genetics (2005) vol. 76, pp. 358-360.
Supplementary European Search Report for EP Application No. 10825707.2 dated Jun. 28, 2013.
Takagi et al. "Synthesis of poly(triazinylstyrene) containing nitrogen-bawed ligand and function as metal ion adsorbent and oxidation catalyst" Reactive & Functional Polymers (2006) vol. 31, pp. 1718-1724.
Thompson, "Metabolic Enzymes as Oncogenes or Tumor Suppressors." The New England Journal of Medicine (2009) vol. 360, No. 8, pp. 813-815.
Van Schaftingen et al. "L-2-Hydroglutaric aciduria, a disorder of metabolite repair" J Inherit. Metab. Dis. (2009) vol. 32, pp. 135-142.
Wang et al. "Facile Synthesis of 2,4-Dianiino-6-alkyi- or 6-Aryl-Pyrimidine Derivatives" Journal of Heterocyclic Chemistry (2010) vol. 47 pp. 1056-1061.
Wang et al. "A novel ligand N,N'-di(2-pyridyl)-2,4-diamino-6-phenyl-1,3,5-triazine (dpdapt) and its complexes: [Cu(dpdapt)Cl2] and [Cu(dpdapt)(NO3)(H2O)] $NO_3$ $H_2O$" Polyhedron (2006) vol. 25, No. 1, pp. 195-202.
Ward et al. "The Common Feature of Leukemia-Associated IDH1 and IDH2 Mutations Is a Neomorphic Enzyme Activity Converting [alpha]-Ketoglutarate to 2-Hydroxyglutarate" Cancer Cell (2010) vol. 17, No. 3 pp. 225-234.
Watanabe et al., "IDH1 Mutations Are Early Events in the Development of Astrocytomas and Oligodendrogliomas" American Journal of Pathology (2009) vol. 174, No. 4, pp. 1149-1153; Abstract, p. 1150, col. 1.
Written Opinion for PCT/US2010/027253 dated Aug. 19, 2010.
Written Opinion of International Search Authority for PCT/CN2013/000009 dated Apr. 18, 2013.
Written Opinion of Search Authority for PCT/US2010/53623 dated Jan. 18, 2011.
Written Opinion of the International Searching Authority for PCT/US2011/067752 dated Mar. 5, 2012.
Yan et al., "IDH1 and IDH2 Mutations in Gliomas." The New England Journal of Medicine, (2009) vol. 360, No. 8, pp. 765-773.
Zhao et al. "Glioma-derived mutations in IDH1 dominantly inhibit IDH1 catalytic activity and induce HIF-1alpha", Science (2009) vol. 324, No. 5924, pp. 261-265.

THERAPEUTICALLY ACTIVE COMPOUNDS AND THEIR METHODS OF USE

CLAIM OF PRIORITY

This application is a continuation of U.S. application Ser. No. 16/388,801, filed Apr. 18, 2019, which is U.S. application Ser. No. 15/638,279, filed Jun. 29, 2017, which is a divisional of U.S. application Ser. No. 13/735,467, filed Jan. 7, 2013, which claims priority from U.S. Ser. No. 61/584,214, filed Jan. 6, 2012, each of which is incorporated herein by reference in its entirety.

BACKGROUND OF INVENTION

Isocitrate dehydrogenases (IDHs) catalyze the oxidative decarboxylation of isocitrate to 2-oxoglutarate (i.e., α-ketoglutarate). These enzymes belong to two distinct subclasses, one of which utilizes NAD(+) as the electron acceptor and the other NADP(+). Five isocitrate dehydrogenases have been reported: three NAD(+)-dependent isocitrate dehydrogenases, which localize to the mitochondrial matrix, and two NADP(+)-dependent isocitrate dehydrogenases, one of which is mitochondrial and the other predominantly cytosolic. Each NADP(+)-dependent isozyme is a homodimer.

IDH2 (isocitrate dehydrogenase 2 (NADP+), mitochondrial) is also known as IDH; IDP; IDHM; IDPM; ICD-M; or mNADP-IDH. The protein encoded by this gene is the NADP(+)-dependent isocitrate dehydrogenase found in the mitochondria. It plays a role in intermediary metabolism and energy production. This protein may tightly associate or interact with the pyruvate dehydrogenase complex. Human IDH2 gene encodes a protein of 452 amino acids. The nucleotide and amino acid sequences for IDH2 can be found as GenBank entries NM_002168.2 and NP_002159.2 respectively. The nucleotide and amino acid sequence for human IDH2 are also described in, e.g., Huh et al., Submitted (November-1992) to the EMBL/GenBank/DDBJ databases; and The MGC Project Team, Genome Res. 14:2121-2127(2004).

Non-mutant, e.g., wild type, IDH2 catalyzes the oxidative decarboxylation of isocitrate to α-ketoglutarate (α-KG) thereby reducing NAD$^+$ (NADP$^+$) to NADH (NADPH), e.g., in the forward reaction:

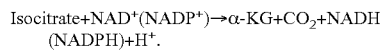

Isocitrate+NAD$^+$(NADP$^+$)→α-KG+CO$_2$+NADH (NADPH)+H$^+$.

It has been discovered that mutations of IDH2 present in certain cancer cells result in a new ability of the enzyme to catalyze the NADPH-dependent reduction of α-ketoglutarate to R(−)-2-hydroxyglutarate (2HG). 2HG is not formed by wild-type IDH2. The production of 2HG is believed to contribute to the formation and progression of cancer (Dang, L et al, Nature 2009, 462:739-44).

The inhibition of mutant IDH2 and its neoactivity is therefore a potential therapeutic treatment for cancer. Accordingly, there is an ongoing need for inhibitors of IDH2 mutants having alpha hydroxyl neoactivity.

SUMMARY OF INVENTION

Described herein are compounds of Structural Formula I, or a pharmaceutically acceptable salt or hydrate thereof:

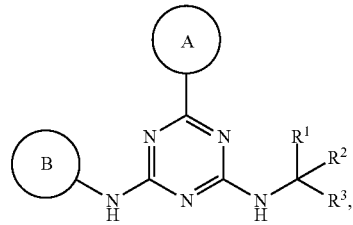

(I)

wherein:
ring A is an optionally substituted 5-6 member monocyclic aryl or monocyclic heteroaryl;
ring B is an optionally substituted 5-6 member monocyclic aryl or monocyclic heteroaryl;
$R^1$ and $R^3$ are each independently selected from hydrogen, $C_1$-$C_4$ alkyl, $C_1$-$C_4$ haloalkyl, —O—$C_1$-$C_4$ alkyl, and CN, wherein any alkyl portion of $R^1$ is optionally substituted with —OH, NH$_2$, NH($C_1$-$C_4$ alkyl), or N($C_1$-$C_4$ alkyl)$_2$;
$R^2$ is selected from: —($C_1$-$C_6$ alkyl), —($C_2$-$C_6$ alkenyl or alkynyl), —($C_1$-$C_6$ alkylene)-N($R^6$)—($C_1$-$C_6$ alkylene)-O—($C_1$-$C_6$ alkyl), —($C_1$-$C_6$ alkylene)-N($R^6$)—($C_0$-$C_6$ alkylene)-Q, —($C_1$-$C_6$ alkylene)-N($R^6$)($R^6$), —($C_1$-$C_6$ alkylene)-N($R^6$)—S(O)$_{1-2}$—($C_1$-$C_6$ alkyl), —($C_1$-$C_6$ alkylene)-N($R^6$)—S(O)$_{1-2}$—($C_0$-$C_6$ alkyl)-Q, —($C_1$-$C_6$ alkylene)-S(O)$_{1-2}$—N($R^6$)($R^6$), —($C_1$-$C_4$ alkylene)-S(O)$_{1-2}$—N($R^6$)—($C_1$-$C_6$ alkylene)-Q, —C(O)N($R^6$)—($C_1$-$C_6$ alkylene)-C(O)—($C_0$-$C_6$ alkylene)-O—($C_1$-$C_6$ alkyl), —C(O)N($R^6$)—($C_1$-$C_6$ alkylene)-C(O)—($C_0$-$C_6$ alkylene)-O—($C_0$-$C_6$ alkylene)-Q, —($C_1$-$C_6$ alkylene)-O—C(O)—($C_1$-$C_6$ alkyl), —($C_1$-$C_6$ alkylene)-O—C(O)—($C_0$-$C_6$ alkyl)-Q, —($C_1$-$C_6$ alkylene)-O—($C_1$-$C_6$ alkyl), —($C_1$-$C_6$ alkylene)-O—($C_1$-$C_6$ alkylene)-Q, —($C_0$-$C_6$ alkylene)-C(O)—($C_0$-$C_6$ alkylene)-O—($C_1$-$C_6$ alkyl), —($C_0$-$C_6$ alkylene)-C(O)—($C_0$-$C_6$ alkylene)-O—($C_1$-$C_6$ alkylene)-Q, —($C_1$-$C_6$ alkylene)-O—C(O)—($C_1$-$C_6$ alkyl), —($C_1$-$C_6$ alkylene)-O—C(O)—($C_0$-$C_6$ alkylene)-Q, —($C_0$-$C_6$ alkylene)-C(O)N($R^6$)—($C_1$-$C_6$ alkyl), —($C_0$-$C_6$ alkylene)-C(O)N($R^6$)—($C_0$-$C_6$ alkylene)-Q, —($C_1$-$C_6$ alkylene)-N($R^6$)C(O)—($C_1$-$C_6$ alkyl), —($C_1$-$C_6$ alkylene)-N($R^6$)C(O)—($C_0$-$C_6$ alkylene)-Q, —($C_0$-$C_6$ alkylene)-S(O)$_{0-2}$—($C_1$-$C_6$ alkyl), —($C_0$-$C_6$ alkylene)-S(O)$_{0-2}$—($C_0$-$C_6$ alkylene)-Q, —($C_1$-$C_6$ alkylene)-N($R^6$)—C(O)—N($R^6$)—($C_1$-$C_6$ alkyl), —($C_0$-$C_6$ alkylene)-Q, —($C_0$-$C_6$ alkylene)-C(O)—($C_1$-$C_6$ alkyl), —($C_0$-$C_6$ alkylene)-C(O)—($C_0$-$C_6$ alkylene)-Q, wherein:
any alkyl or alkylene moiety present in $R^2$ is optionally substituted with one or more —OH, —O($C_1$-$C_4$ alkyl) or halo;
any terminal methyl moiety present in $R^2$ is optionally replaced with —CH$_2$OH, CF$_3$, —CH$_2$F, —CH$_2$Cl, C(O)CH$_3$, C(O)CF$_3$, CN, or CO$_2$H;
each $R^6$ is independently selected from hydrogen and $C_1$-$C_6$ alkyl; and
Q is selected from aryl, heteroaryl, carbocyclyl and heterocyclyl, any of which is optionally substituted; or
$R^1$ and $R^3$ are optionally taken together with the carbon to which they are attached to form C(═O); or
$R^1$ and $R^2$ are optionally taken together to form substituted carbocyclyl, optionally substituted heterocyclyl or optionally substituted heteroaryl, wherein:

a. when ring A is unsubstituted phenyl, and ring B is phenyl substituted by methoxy or ethoxy; then said phenyl of ring B is not further substituted by oxazolyl;
b. when ring A is optionally substituted phenyl or optionally substituted pyridyl, and ring B is optionally substituted phenyl; then the portion of the compound represented by —NH—C($R^1$)($R^2$)($R^3$) is not —NH(CH$_2$)-aryl;
c. when ring A is optionally substituted phenyl, and ring B is optionally substituted phenyl or pyrrolyl; then the portion of the compound represented by —NH—C($R^1$)($R^2$)($R^3$) is not —NH(CH$_2$)C(O)NH$_2$;
d. when ring A is phenyl substituted with 2 or more hydroxyl or methoxy, and ring B is optionally substituted phenyl; then the portion of the compound represented by —NH—C($R^1$)($R^2$)($R^3$) is not —NH-cycloheptyl;
e. when ring A is optionally substituted phenyl and ring B is optionally substituted phenyl; then $R^1$ and $R^3$ do not form 2,2,6,6,-tetramethylpiperidin-4-yl;
f. when ring A and ring B are optionally substituted phenyl; then the portion of the compound represented by —NH—C($R^1$)($R^2$)($R^3$) is not cysteine, optionally substituted phenylalanine or leucine or methyl ester thereof;
g. when ring A is phenyl or pyridin-3-yl optionally substituted with one or more substituents selected from halo, methyl or CF$_3$, and ring B is phenyl optionally substituted with one or more substituents selected from halo, methyl, CF$_3$, methoxy, CH=C(phenyl)CN; then the portion of the compound represented by —NHC($R^1$)($R^2$)($R^3$) is other than —NH(C$_1$-C$_8$ alkylene)-N($R^a$)($R^a$), —NH-1-(aminomethyl)cyclopentylmethyl, —NH-4-(aminomethyl)cyclohexylmethyl, wherein each $R^a$ is hydrogen, C$_1$-C$_4$ alkyl or two $R^a$s are taken together with the nitrogen to which they are commonly bound to form morpholin-4-yl or pipieridin-1-yl;
h. when ring A is phenyl, 4-chlorophenyl or 4-methyl phenyl and ring B is 4-chlorophenyl or 3,4-dichlorophenyl; then the portion of the compound represented by —NHC($R^1$)($R^2$)($R^3$) is not —NH-isopropyl;
i. when ring A is unsubstituted phenyl and the portion of the compound represented by —NHC($R^1$)($R^2$)($R^3$) is —NH—CH$_2$CH$_2$N(CH$_3$)$_2$, —NH—CH$_2$CH$_2$-morpholin-4-yl or —NH—CH$_2$CH$_2$OH; then ring B is other than oxadiazole, imidazole, thiazole or oxazole each of which is substituted with —C(O)NHR$^b$, wherein R$^b$ is isopropyl, cyclopropyl or 2-chloro-6-methylphenyl;
j. when ring A is phenyl substituted with SO$_2$OH or SO$_2$Na and ring B is phenyl, or when ring B is phenyl substituted with SO$_2$OH and ring A is substituted phenyl; then the portion of the compound represented by —NHC($R^1$)($R^2$)($R^3$) is not —NH(CH$_2$)$_2$OH or —NH(CH$_2$)CH(OH)CH$_3$; and
k. the compound is other than:
(E)-3-(4-((4-((3-(diethylamino)propyl)amino)-6-phenyl-1,3,5-triazin-2-yl)amino)-2-methoxyphenyl)-2-phenylacrylonitrile,
4-((4-((furan-2-ylmethyl)amino)-6-(pyridin-4-yl)-1,3,5-triazin-2-yl)amino)phenol, 3-(4-((5-aminopentyl)amino)-6-((3-fluorophenyl)amino)-1,3,5-triazin-2-yl)phenol,
N$^2$,6-bis(3-fluorophenyl)-N$^4$-(piperidin-3-yl)-1,3,5-triazine-2,4-diamine,
N$^2$-butyl-6-phenyl-N$^4$-(p-tolyl)-1,3,5-triazine-2,4-diamine, N$^2$-cyclohexyl-N$^4$,6-diphenyl-1,3,5-triazine-2,4-diamine,
(R)-3-((4-(3-chlorophenyl)-6-(pyrrolidin-3-ylamino)-1,3,5-triazin-2-yl)amino)-4-methylbenzamide,
2-chloro-4-(methylsulfonyl)-N-[4-(phenylamino)-6-(2-pyridinyl)-1,3,5-triazin-2-yl]-benzamide,
N$^2$-(2-methoxyethyl)-N$^4$-phenyl-6-[5-[6-(2,2,2-trifluoroethoxy)-3-pyridinyl]-1,2,4-oxadiazol-3-yl]-1,3,5-triazine-2,4-diamine,
N$^2$-(2-furanylmethyl)-6-phenyl-N$^4$-[3-(trifluoromethyl)phenyl]-1,3,5-triazine-2,4-diamine,
6-(3-methoxyphenyl)-N$^2$-methyl-N$^4$-(3-nitrophenyl)-1,3,5-triazine-2,4-diamine,
N$^2$-butyl-N$^4$-(4-methylphenyl)-6-phenyl-1,3,5-triazine-2,4-diamine, and
4-[[4-(5-chloro-2-methylphenyl)-6-(methylamino)]-1,3,5-triazin-2-yl]amino-benzenemethanol.

The compound of Formula I or II or as described in any one of the embodiments herein inhibits mutant IDH2, particularly mutant IDH2 having alpha hydroxyl neoactivity. Also described herein are pharmaceutical compositions comprising a compound of Formula I and methods of using such compositions to treat cancers characterized by the presence of a mutant IDH2.

DETAILED DESCRIPTION

The details of construction and the arrangement of components set forth in the following description or illustrated in the drawings are not meant to be limiting. Other embodiments and different ways to practice the invention are expressly included. Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

Definitions

The term "halo" or "halogen" refers to any radical of fluorine, chlorine, bromine or iodine.

The term "alkyl" refers to a fully saturated or unsaturated hydrocarbon chain that may be a straight chain or branched chain, containing the indicated number of carbon atoms. For example, C$_1$-C$_{12}$ alkyl indicates that the group may have from 1 to 12 (inclusive) carbon atoms in it. The term "haloalkyl" refers to an alkyl in which one or more hydrogen atoms are replaced by halo, and includes alkyl moieties in which all hydrogens have been replaced by halo (e.g., perfluoroalkyl). The terms "arylalkyl" or "aralkyl" refer to an alkyl moiety in which an alkyl hydrogen atom is replaced by an aryl group. Aralkyl includes groups in which more than one hydrogen atom has been replaced by an aryl group. Examples of "arylalkyl" or "aralkyl" include benzyl, 2-phenylethyl, 3-phenylpropyl, 9-fluorenyl, benzhydryl, and trityl groups. The term "alkyl" includes "alkenyl" and "alkynyl".

The term "alkylene" refers to a divalent alkyl, e.g., —CH$_2$—, —CH$_2$CH$_2$—, —CH$_2$CH$_2$CH$_2$— and —CH$_2$CH(CH$_3$)CH$_2$—.

The term "alkenyl" refers to a straight or branched hydrocarbon chain containing 2-12 carbon atoms and having one or more double bonds. Examples of alkenyl groups include, but are not limited to, allyl, propenyl, 2-butenyl, 3-hexenyl and 3-octenyl groups. One of the double bond carbons may optionally be the point of attachment of the alkenyl substituent.

The term "alkynyl" refers to a straight or branched hydrocarbon chain containing 2-12 carbon atoms and characterized in having one or more triple bonds. Examples of alkynyl groups include, but are not limited to, ethynyl, propargyl, and 3-hexynyl. One of the triple bond carbons may optionally be the point of attachment of the alkynyl substituent.

The term "alkoxy" refers to an —O-alkyl radical. The term "haloalkoxy" refers to an alkoxy in which one or more hydrogen atoms are replaced by halo, and includes alkoxy moieties in which all hydrogens have been replaced by halo (e.g., perfluoroalkoxy).

Unless otherwise specified, the term "aryl" refers to a fully aromatic monocyclic, bicyclic, or tricyclic hydrocarbon ring system. Examples of aryl moieties are phenyl, naphthyl, and anthracenyl. Unless otherwise specified, any ring atom in an aryl can be substituted by one or more substituents. The term "monocyclic aryl" means a monocyclic fully romatic hydrocarbon ring system, optionally substituted by one or more substituents which can not form a fused bicyclic or tricyclic ring.

The term "carbocyclyl" refers to a non-aromatic, monocyclic, bicyclic, or tricyclic hydrocarbon ring system. Carbocyclyl groups include fully saturated ring systems (e.g., cycloalkyls), and partially saturated ring systems.

The term "cycloalkyl" as employed herein includes saturated cyclic, bicyclic, tricyclic, or polycyclic hydrocarbon groups having 3 to 12 carbons. Any ring atom can be substituted (e.g., by one or more substituents). Examples of cycloalkyl moieties include, but are not limited to, cyclopropyl, cyclohexyl, methylcyclohexyl, adamantyl, and norbornyl.

Unless otherwise specified, the term "heteroaryl" refers to a fully aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (or the oxidized forms such as $N^+$—$O^-$, $S(O)$ and $S(O)_2$). The term "monocyclic heteroaryl" means a monocyclic fully romatic ring system having 1-3 heteroatoms, optionally substituted by one or more substituents which can not form a fused bicyclic or tricyclic ring.

The term "heterocyclyl" refers to a nonaromatic, 3-10 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (or the oxidized forms such as $N^+$—$O^-$, $S(O)$ and $S(O)_2$). The heteroatom may optionally be the point of attachment of the heterocyclyl substituent. Examples of heterocyclyl include, but are not limited to, tetrahydrofuranyl, tetrahydropyranyl, piperidinyl, morpholino, pyrrolinyl, pyrimidinyl, and pyrrolidinyl. Heterocyclyl groups include fully saturated ring systems, and partially saturated ring systems.

Bicyclic and tricyclic ring systems containing one or more heteroatoms and both aromatic and non-aromatic rings are considered to be heterocyclyl or heteroaryl groups. Bicyclic or tricyclic ring systems where an aryl or a heteroaryl is fused to a carbocyclyl or heterocyclyl and the point of attachment from the ring system to the rest of the molecule is through an aromatic ring are considered to be aryl or heteroaryl groups, respectively. Bicyclic or tricyclic ring systems where an aryl or a heteroaryl is fused to a carbocyclyl or heterocyclyl and the point of attachment from the ring system to the rest of the molecule is through the non-aromatic ring are considered to be carbocyclyl (e.g., cycloalkyl) or heterocyclyl groups, respectively.

Aryl, heteroaryl, carbocyclyl (including cycloalkyl), and heterocyclyl groups, either alone or a part of a group (e.g., the aryl portion of an aralkyl group), are optionally substituted at one or more substitutable atoms with, unless specified otherwise, substituents independently selected from: halo, —C≡N, $C_1$-$C_4$ alkyl, =O, —$OR^b$, —$OR^{b'}$, —$SR^b$, —$SR^{b'}$, —($C_1$-$C_4$ alkyl)-N($R^b$)($R^b$), —($C_1$-$C_4$ alkyl)-N($R^b$)($R^{b'}$), —N($R^b$)($R^{b'}$), —N($R^b$)($R^{b'}$), —O—($C_1$-$C_4$ alkyl)-N($R^b$)($R^b$), —O—($C_1$-$C_4$ alkyl)-N($R^b$)($R^{b'}$), —($C_1$-$C_4$ alkyl)-O—($C_1$-$C_4$ alkyl)-N($R^b$)($R^{b'}$), —($C_1$-$C_4$ alkyl)-O—($C_1$-$C_4$ alkyl)-N($R^b$)($R^{b'}$), —C(O)—N($R^b$)($R^b$), —($C_1$-$C_4$ alkyl)-C(O)—N($R^b$)($R^b$), —($C_1$-$C_4$ alkyl)-C(O)—N($R^b$)($R^{b'}$), —$OR^{b'}$, $R^{b'}$, —C(O)($C_1$-$C_4$ alkyl), —C(O)$R^{b'}$, —C(O)N($R^{b'}$)($R^b$), —N($R^b$)C(O)($R^b$), —N($R^b$)C(O)($R^{b'}$), —N($R^b$)$SO_2$($R^b$), —$SO_2$N($R^b$)($R^b$), —N($R^b$)$SO_2$($R^{b'}$), and —$SO_2$N($R^b$)($R^{b'}$), wherein any alkyl substituent is optionally further substituted with one or more of —OH, —O—($C_1$-$C_4$ alkyl), halo, —$NH_2$, —NH($C_1$-$C_4$ alkyl), or —N($C_1$-$C_4$ alkyl)$_2$;

each $R^b$ is independently selected from hydrogen, and —$C_1$-$C_4$ alkyl; or two $R^b$s are taken together with the nitrogen atom to which they are bound to form a 4- to 8-membered heterocyclyl optionally comprising one additional heteroatom selected from N, S, and O; and each $R^{b'}$ is independently selected from $C_3$-$C_7$ carbocyclyl, phenyl, heteroaryl, and heterocyclyl, wherein one or more substitutable positions on said phenyl, cycloalkyl, heteroaryl or heterocycle substituent is optionally further substituted with one or more of —($C_1$-$C_4$ alkyl), —($C_1$-$C_4$ fluoroalkyl), —OH, —O—($C_1$-$C_4$ alkyl), —O—($C_1$-$C_4$ fluoroalkyl), halo, —$NH_2$, —NH($C_1$-$C_4$ alkyl), or —N($C_1$-$C_4$ alkyl)$_2$.

Heterocyclyl groups, either alone or as part of a group, are optionally substituted on one or more any substitutable nitrogen atom with oxo, —$C_1$-$C_4$ alkyl, or fluoro-substituted $C_1$-$C_4$ alkyl.

The term "substituted" refers to the replacement of a hydrogen atom by another group.

As used herein, the term "elevated levels of 2HG" means 10%, 20% 30%, 50%, 75%, 100%, 200%, 500% or more 2HG then is present in a subject that does not carry a mutant IDH2 allele. The term "elevated levels of 2HG" may refer to the amount of 2HG within a cell, within a tumor, within an organ comprising a tumor, or within a bodily fluid.

The term "bodily fluid" includes one or more of amniotic fluid surrounding a fetus, aqueous humour, blood (e.g., blood plasma), serum, Cerebrospinal fluid, cerumen, chyme, Cowper's fluid, female ejaculate, interstitial fluid, lymph, breast milk, mucus (e.g., nasal drainage or phlegm), pleural fluid, pus, saliva, sebum, semen, serum, sweat, tears, urine, vaginal secretion, or vomit.

As used herein, the terms "inhibit" or "prevent" include both complete and partial inhibition and prevention. An inhibitor may completely or partially inhibit the intended target.

The term "treat" means decrease, suppress, attenuate, diminish, arrest, or stabilize the development or progression of a disease/disorder (e.g., a cancer), lessen the severity of the disease/disorder (e.g., a cancer) or improve the symptoms associated with the disease/disorder (e.g., a cancer).

As used herein, an amount of a compound effective to treat a disorder, or a "therapeutically effective amount" refers to an amount of the compound which is effective, upon single or multiple dose administration to a subject, in treating a cell, or in curing, alleviating, relieving or improving a subject with a disorder beyond that expected in the absence of such treatment.

As used herein, the term "subject" is intended to include human and non-human animals. Exemplary human subjects include a human patient (referred to as a patient) having a disorder, e.g., a disorder described herein or a normal subject. The term "non-human animals" of one aspect of the invention includes all vertebrates, e.g., non-mammals (such as chickens, amphibians, reptiles) and mammals, such as non-human primates, domesticated and/or agriculturally useful animals, e.g., sheep, dog, cat, cow, pig, etc.

Compounds

Provided is a compound of Structural Formula I, or a pharmaceutically acceptable salt or hydrate thereof:

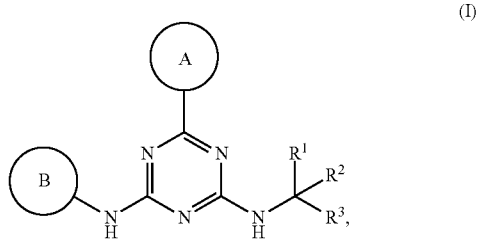

(I)

wherein:

ring A is an optionally substituted 5-6 member monocyclic aryl or monocyclic heteroaryl;

ring B is an optionally substituted 5-6 member monocyclic aryl or monocyclic heteroaryl;

$R^1$ and $R^3$ are each independently selected from hydrogen, $C_1$-$C_4$ alkyl, $C_1$-$C_4$ haloalkyl, —O—$C_1$-$C_4$ alkyl, and CN, wherein any alkyl portion of $R^1$ is optionally substituted with —OH, $NH_2$, $NH(C_1$-$C_4$ alkyl), or $N(C_1$-$C_4$ alkyl)$_2$;

$R^2$ is selected from: —($C_1$-$C_6$ alkyl), —($C_2$-$C_6$ alkenyl or alkynyl), —($C_1$-$C_6$ alkylene)-N($R^6$)—($C_1$-$C_6$ alkylene)-O—($C_1$-$C_6$ alkyl), —($C_1$-$C_6$ alkylene)-N($R^6$)—($C_0$-$C_6$ alkylene)-Q, —($C_1$-$C_6$ alkylene)-N($R^6$)($R^6$), —($C_1$-$C_6$ alkylene)-N($R^6$)—S(O)$_{1-2}$—($C_1$-$C_6$ alkyl), —($C_1$-$C_6$ alkylene)-N($R^6$)—S(O)$_{1-2}$—($C_0$-$C_6$ alkyl)-Q, —($C_1$-$C_6$ alkylene)-S(O)$_{1-2}$—N($R^6$)($R^6$), —($C_1$-$C_4$ alkylene)-S(O)$_{1-2}$—N($R^6$)—($C_1$-$C_6$ alkylene)-Q, —C(O)N($R^6$)—($C_1$-$C_6$ alkylene)-C(O)—($C_0$-$C_6$ alkylene)-O—($C_1$-$C_6$ alkyl), —C(O)N($R^6$)—($C_1$-$C_6$ alkylene)-C(O)—($C_0$-$C_6$ alkylene)-O—($C_0$-$C_6$ alkylene)-Q, —($C_1$-$C_6$ alkylene)-O—C(O)—($C_1$-$C_6$ alkyl), —($C_1$-$C_6$ alkylene)-O—C(O)—($C_0$-$C_6$ alkyl)-Q, —($C_1$-$C_6$ alkylene)-O—($C_1$-$C_6$ alkyl), —($C_1$-$C_6$ alkylene)-O—($C_1$-$C_6$ alkylene)-Q, —($C_0$-$C_6$ alkylene)-C(O)—($C_0$-$C_6$ alkylene)-O—($C_1$-$C_6$ alkyl), —($C_0$-$C_6$ alkylene)-C(O)—($C_0$-$C_6$ alkylene)-O—($C_1$-$C_6$ alkylene)-Q, —($C_1$-$C_6$ alkylene)-O—C(O)—($C_1$-$C_6$ alkyl), —($C_1$-$C_6$ alkylene)-O—C(O)—($C_0$-$C_6$ alkylene)-Q, —($C_0$-$C_6$ alkylene)-C(O)N($R^6$)—($C_1$-$C_6$ alkyl), —($C_0$-$C_6$ alkylene)-C(O)N($R^6$)—($C_0$-$C_6$ alkylene)-Q, —($C_1$-$C_6$ alkylene)-N($R^6$)C(O)—($C_1$-$C_6$ alkyl), —($C_1$-$C_6$ alkylene)-N($R^6$)C(O)—($C_0$-$C_6$ alkylene)-Q, —($C_0$-$C_6$ alkylene)-S(O)$_{0-2}$—($C_1$-$C_6$ alkyl), —($C_0$-$C_6$ alkylene)-S(O)$_{0-2}$—($C_0$-$C_6$ alkylene)-Q, —($C_1$-$C_6$ alkylene)-N($R^6$)—C(O)—N($R^6$)—($C_1$-$C_6$ alkyl), —($C_0$-$C_6$ alkylene)-Q, —($C_0$-$C_6$ alkylene)-C(O)—($C_1$-$C_6$ alkyl), —($C_0$-$C_6$ alkylene)-C(O)—($C_0$-$C_6$ alkylene)-Q, wherein:

any alkyl or alkylene moiety present in $R^2$ is optionally substituted with one or more —OH, —O($C_1$-$C_4$ alkyl) or halo;

any terminal methyl moiety present in $R^1$ is optionally replaced with —$CH_2$OH, $CF_3$, —$CH_2$F, —$CH_2$Cl, C(O)$CH_3$, C(O)$CF_3$, CN, or $CO_2$H;

each $R^6$ is independently selected from hydrogen and $C_1$-$C_6$ alkyl; and

Q is selected from aryl, heteroaryl, carbocyclyl and heterocyclyl; and Q is optionally substituted; or $R^1$ and $R^3$ are optionally taken together with the carbon to which they are attached to form C(=O); or $R^1$ and $R^2$ are optionally taken together to form an optionally substituted carbocyclyl, optionally substituted heterocyclyl or optionally substituted heteroaryl;

wherein:

a. when ring A is unsubstituted phenyl, and ring B is phenyl substituted by methoxy or ethoxy; then said phenyl of ring B is not further substituted by oxazolyl;

b. when ring A is optionally substituted phenyl or optionally substituted pyridyl, and ring B is optionally substituted phenyl; then the portion of the compound represented by —NH—C($R^1$)($R^2$)($R^3$) is not —NH($CH_2$)-aryl;

c. when ring A is optionally substituted phenyl, and ring B is optionally substituted phenyl or pyrrolyl; then the portion of the compound represented by —NH—C($R^1$)($R^2$)($R^3$) is not —NH($CH_2$)C(O)$NH_2$;

d. when ring A is phenyl substituted with 2 or more hydroxyl or methoxy, and ring B is optionally substituted phenyl; then the portion of the compound represented by —NH—C($R^1$)($R^2$)($R^3$) is not —NH-cycloheptyl;

e. when ring A is optionally substituted phenyl and ring B is optionally substituted phenyl; then $R^1$ and $R^3$ do not form 2,2,6,6,-tetramethylpiperidin-4-yl;

f. when ring A and ring B are optionally substituted phenyl; then the portion of the compound represented by —NH—C($R^1$)($R^2$)($R^3$) is not cysteine, optionally substituted phenylalanine or leucine or methyl ester thereof;

g. when ring A is phenyl or pyridin-3-yl optionally substituted with one or more substituents selected from halo, methyl or $CF_3$, and ring B is phenyl optionally substituted with one or more substituents selected from halo, methyl, $CF_3$, methoxy, CH=C(phenyl)CN; then the portion of the compound represented by —NHC($R^1$)($R^2$)($R^3$) is other than —NH($C_1$-$C_8$ alkylene)-N($R^a$)($R^a$), —NH-1-(aminomethyl)cyclopentylmethyl, —NH-4-(aminomethyl)cyclohexylmethyl, wherein each $R^a$ is hydrogen, $C_1$-$C_4$ alkyl or two $R^a$s are taken together with the nitrogen to which they are commonly bound to form morpholin-4-yl or pipieridin-1-yl;

h. when ring A is phenyl, 4-chlorophenyl or 4-methyl phenyl and ring B is 4-chlorophenyl or 3,4-dichlorophenyl; then the portion of the compound represented by —NHC($R^1$)($R^2$)($R^3$) is not —NH-isopropyl;

i. when ring A is unsubstituted phenyl and the portion of the compound represented by —NHC($R^1$)($R^2$)($R^3$) is —NH—$CH_2CH_2$N($CH_3$)$_2$, —NH—$CH_2CH_2$-morpholin-4-yl or —NH—$CH_2CH_2$OH; then ring B is other than oxadiazole, imidazole, thiazole or oxazole each of which is substituted with —C(O)NH$R^b$, wherein $R^b$ is isopropyl, cyclopropyl or 2-chloro-6-methylphenyl;

j. when ring A is phenyl substituted with $SO_2$OH or $SO_2$Na and ring B is phenyl, or when ring B is phenyl substituted with $SO_2$OH and ring A is substituted phenyl; then the portion of the compound represented by —NHC($R^1$)($R^2$)($R^3$) is not —NH($CH_2$)$_2$OH or —NH($CH_2$)CH(OH)$CH_3$; and k. the compound is other than:

(E)-3-(4-((4-((3-(diethylamino)propyl)amino)-6-phenyl-1,3,5-triazin-2-yl)amino)-2-methoxyphenyl)-2-phenylacrylonitrile, 4-((4-((furan-2-ylmethyl)amino)-6-(pyridin-4-yl)-1,3,5-triazin-2-yl)amino)phenol, 3-(4-((5-aminopentyl)amino)-6-((3-fluorophenyl)amino)-1,3,5-triazin-2-yl)phenol, $N^2$,6-bis(3-fluorophenyl)-$N^4$-(piperidin-3-yl)-1,3,5-triazine-2,4-diamine, $N^2$-butyl-6-phenyl-$N^4$-(p-tolyl)-1,3,5-triazine-2,4-diamine, $N^2$-cyclohexyl-$N^4$,6-diphenyl-1,3,5-triazine-2,4-diamine, (R)-3-((4-(3-chlorophenyl)-6-(pyrrolidin-3-ylamino)-1,3,5-triazin-2-yl)amino)-4-methylbenzamide, 2-chloro-4-(methylsulfonyl)-N-[4-(phenylamino)-6-(2-pyridinyl)-1,3,5-triazin-2-yl]-benzamide, $N^2$-(2-methoxyethyl)-$N^4$-phenyl-6-[5-[6-(2,2,2-trifluoroethoxy)-3-pyridinyl]-1,2,4-oxadiazol-3-yl]-1,3,5-triazine-2,4-diamine, $N^2$-(2-furanylmethyl)-6-phenyl-$N^4$-[3-(trifluoromethyl)phenyl]-1,3,5-triazine-2,4-diamine, 6-(3-methoxyphenyl)-$N^2$-methyl-$N^4$-(3-nitrophenyl)-1,3,5-triazine-2,4-diamine, $N^2$-butyl-$N^4$-(4-methylphenyl)-6-phenyl-1,3,5-triazine-2,4-diamine, and 4-[[4-(5-chloro-2-methylphenyl)-6-(methylamino)]-1,3,5-triazin-2-yl]amino-benzenemethanol.

Also provided is a compound of Structural Formula I, or a pharmaceutically acceptable salt or hydrate thereof:

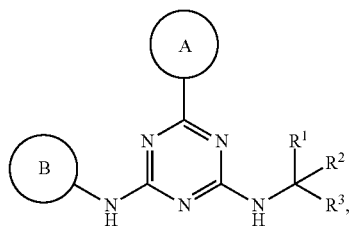

(I)

wherein:
- ring A is an optionally substituted 5-6 member monocyclic aryl or monocyclic heteroaryl;
- ring B is an optionally substituted 5-6 member monocyclic aryl or monocyclic heteroaryl;
- $R^1$ and $R^3$ are each independently selected from hydrogen, $C_1$-$C_4$ alkyl, $C_1$-$C_4$ haloalkyl, —O—$C_1$-$C_4$ alkyl, and CN, wherein any alkyl portion of $R^1$ is optionally substituted with —OH, $NH_2$, NH($C_1$-$C_4$ alkyl), or N($C_1$-$C_4$ alkyl)$_2$;
- $R^2$ is selected from: —($C_1$-$C_6$ alkyl), —($C_2$-$C_6$ alkenyl or alkynyl), —($C_1$-$C_6$ alkylene)-N($R^6$)—($C_1$-$C_6$ alkylene)-O—($C_1$-$C_6$ alkyl), —($C_1$-$C_6$ alkylene)-N($R^6$)—($C_0$-$C_6$ alkylene)-Q, —($C_1$-$C_6$ alkylene)-N($R^6$)($R^6$), —($C_1$-$C_6$ alkylene)-N($R^6$)—S(O)$_{1-2}$—($C_1$-$C_6$ alkyl), —($C_1$-$C_6$ alkylene)-N($R^6$)—S(O)$_{1-2}$—($C_0$-$C_6$ alkyl)-Q, —($C_1$-$C_6$ alkylene)-S(O)$_{1-2}$—N($R^6$)($R^6$), —($C_1$-$C_4$ alkylene)-S(O)$_{1-2}$—N($R^6$)—($C_1$-$C_6$ alkylene)-Q, —C(O)N($R^6$)—($C_1$-$C_6$ alkylene)-C(O)—($C_0$-$C_6$ alkylene)-O—($C_1$-$C_6$ alkyl), —C(O)N($R^6$)—($C_1$-$C_6$ alkylene)-C(O)—($C_0$-$C_6$ alkylene)-O—($C_0$-$C_6$ alkylene)-Q, —($C_1$-$C_6$ alkylene)-O—C(O)—($C_1$-$C_6$ alkyl), —($C_1$-$C_6$ alkylene)-O—C(O)—($C_0$-$C_6$ alkyl)-Q, —($C_1$-$C_6$ alkylene)-O—($C_1$-$C_6$ alkyl), —($C_1$-$C_6$ alkylene)-O—($C_1$-$C_6$ alkylene)-Q, —($C_0$-$C_6$ alkylene)-C(O)—($C_0$-$C_6$ alkylene)-O—($C_1$-$C_6$ alkyl), —($C_0$-$C_6$ alkylene)-C(O)—($C_0$-$C_6$ alkylene)-O—($C_1$-$C_6$ alkyl), —($C_0$-$C_6$ alkylene)-Q, —($C_0$-$C_6$ alkylene)-O—C(O)—($C_0$-$C_6$ alkyl), —($C_1$-$C_6$ alkylene)-O—C(O)—($C_0$-$C_6$ alkyl)-Q, —($C_0$-$C_6$ alkylene)-C(O)N($R^6$)—($C_1$-$C_6$ alkyl), —($C_0$-$C_6$ alkylene)-C(O)N($R^6$)—($C_0$-$C_6$ alkylene)-Q, —($C_1$-$C_6$ alkylene)-N($R^6$)C(O)—($C_1$-$C_6$ alkyl), —($C_1$-$C_6$ alkylene)-N($R^6$)C(O)—($C_0$-$C_6$ alkylene)-Q, —($C_0$-$C_6$ alkylene)-S(O)$_{0-2}$—($C_1$-$C_6$ alkyl), —($C_0$-$C_6$ alkylene)-S(O)$_{0-2}$—($C_0$-$C_6$ alkylene)-Q, —($C_1$-$C_6$ alkylene)-N($R^6$)—C(O)—N($R^6$)—($C_1$-$C_6$ alkyl), —($C_0$-$C_6$ alkylene)-Q, —($C_0$-$C_6$ alkylene)-C(O)—($C_1$-$C_6$ alkyl), —($C_0$-$C_6$ alkylene)-C(O)—($C_0$-$C_6$ alkylene)-Q, wherein:
- any alkyl or alkylene moiety present in $R^2$ is optionally substituted with one or more —OH, —O($C_1$-$C_4$ alkyl) or halo;
- any terminal methyl moiety present in $R^2$ is optionally replaced with —$CH_2OH$, $CF_3$, —$CH_2F$, —$CH_2Cl$, C(O)$CH_3$, C(O)$CF_3$, CN, or $CO_2H$;
- each $R^6$ is independently selected from hydrogen and $C_1$-$C_6$ alkyl; and
- Q is selected from aryl, heteroaryl, carbocyclyl and heterocyclyl, any of which is optionally substituted; or
- $R^1$ and $R^3$ are optionally taken together with the carbon to which they are attached to form C(=O), or
- $R^1$ and $R^2$ are optionally taken together to form substituted carbocyclyl or optionally substituted heterocyclyl, wherein:
  a. when ring A is unsubstituted phenyl, and ring B is phenyl substituted by methoxy or ethoxy; then said phenyl of ring B is not further substituted oxazolyl;
  b. when ring A is optionally substituted phenyl or optionally substituted pyridyl; then the portion of the compound represented by —NH—C($R^1$)($R^2$)($R^3$) is not —NH($CH_2$)-aryl;
  c. when ring A is optionally substituted phenyl, and ring B is optionally substituted phenyl or pyrrolyl; then the portion of the compound represented by —NH—C($R^1$)($R^2$)($R^3$) is not —NH($CH_2$)C(O)$NH_2$;
  d. when ring A is phenyl substituted with 2 or more hydroxyl or methoxy, and ring B is optionally substituted phenyl; then the portion of the compound represented by —NH—C($R^1$)($R^2$)($R^3$) is not —NH-cycloheptyl;
  e. when ring A is optionally substituted phenyl and ring B is optionally substituted phenyl; then $R^1$ and $R^3$ do not form 2,2,6,6,-tetramethylpiperidin-4-yl;
  f. when ring A and ring B are optionally substituted phenyl; then the portion of the compound represented by —NH—C($R^1$)($R^2$)($R^3$) is not cysteine, optionally substituted phenylalanine or leucine;
  g. when ring A is phenyl or pyridin-3-yl optionally substituted with one or more substituents selected from halo, methyl or $CF_3$, and ring B is phenyl optionally substituted with one or more substituents selected from halo, methyl or $CF_3$; then the portion of the compound represented by —NHC($R^1$)($R^2$)($R^3$) is other than —NH ($C_1$-$C_8$ alkylene)-N($R^a$)($R^a$), —NH-1-(aminomethyl)cyclopentylmethyl, —NH-4-(aminomethyl)cyclohexylmethyl, wherein each $R^a$ is hydrogen, $C_1$-$C_3$ alkyl or two $R^a$s are taken together with the nitrogen to which they are commonly bound to form morpholin-4-yl or pipieridin-1-yl;
  h. when ring A is phenyl, 4-chlorophenyl or 4-methyl phenyl and ring B is 4-chlorophenyl or 3,4-dichlorophenyl; then the portion of the compound represented by —NHC($R^1$)($R^2$)($R^3$) is not —NH-isopropyl;
  i. when ring A is unsubstituted phenyl and the portion of the compound represented by —NHC($R^1$)($R^2$)($R^3$) is —NH—$CH_2CH_2N(CH_3)_2$, —NH—$CH_2CH_2$-morpholin-4-yl or —NH—$CH_2CH_2OH$; then ring B is other than oxadiazole, thiazole or oxazole each of which is substituted with —C(O)NHR$^b$, wherein R$^b$ is isopropyl, cyclopropyl or 2-chloro-6-methylphenyl;

j. when ring A is phenyl substituted with SO$_2$OH or SO$_2$Na, and ring B is phenyl; then the portion of the compound represented by —NHC(R$^1$)(R$^2$)(R$^3$) is not —NH(CH$_2$)$_2$OH or —NH(CH$_2$)CH(OH)CH$_3$; and k. the compound is other than:

(E)-3-(4-((4-((3-(diethylamino)propyl)amino)-6-phenyl-1,3,5-triazin-2-yl)amino)-2-methoxyphenyl)-2-phenylacrylonitrile, 4-((4-((furan-2-ylmethyl)amino)-6-(pyridin-4-yl)-1,3,5-triazin-2-yl)amino)phenol, 3-(4-((5-aminopentyl)amino)-6-((3-fluorophenyl)amino)-1,3,5-triazin-2-yl)phenol, N$^2$,6-bis(3-fluorophenyl)-N$^4$-(piperidin-3-yl)-1,3,5-triazine-2,4-diamine, N$^2$-butyl-6-phenyl-N$^4$-(p-tolyl)-1,3,5-triazine-2,4-diamine, N$^2$-cyclohexyl-N$^4$,6-diphenyl-1,3,5-triazine-2,4-diamine, and (R)-3-((4-(3-chlorophenyl)-6-(pyrrolidin-3-ylamino)-1,3,5-triazin-2-yl)amino)-4-methylbenzamide.

In some embodiments, R$^1$ is independently selected from hydrogen, —CH$_3$, —CH$_2$CH$_3$, —CH$_2$OH, CN, or R$^1$ and R$^3$ are taken together to form =O.

In some embodiments, R$^1$ and R$^2$ are taken together to form carbocyclyl or heterocyclyl, either of which is optionally substituted with up to 3 substituents independently selected from halo. C$_1$-C$_4$ alkyl, C$_1$-C$_4$ haloalkyl, C$_1$-C$_4$ alkoxy, —CN, =O, —OH, and —C(O)C$_1$-C$_4$ alkyl.

In some embodiments, R$^2$ is —(C$_1$-C$_4$ alkyl) optionally substituted with fluoro or —OH; —(C$_0$-C$_4$ alkylene)-O—(C$_1$-C$_4$ alkyl), —(C$_0$-C$_2$ alkylene)-N(R$^6$)—(C$_1$-C$_6$ alkyl), —(C$_0$-C$_2$ alkylene)-Q, and —O—(C$_0$-C$_2$ alkylene)-Q, wherein Q is optionally substituted with up to 3 substituents independently selected from C$_1$-C$_4$ alkyl, C$_1$-C$_4$ haloalkyl, C$_1$-C$_4$ alkoxy, =O, —C(O)—C$_1$-C$_4$ alkyl, —CN, and halo. In one aspect of these embodiments, Q is selected from pyridinyl, tetrahydrofuranyl, cyclobutyl, cyclopropyl, phenyl, pyrazolyl, morpholinyl and oxetanyl, wherein Q is optionally substituted with up to 2 substituents independently selected from C$_1$-C$_4$ alkyl, C$_1$-C$_4$ haloalkyl, =O, fluoro, chloro, and bromo. In another aspect of these embodiments, Q is selected from pyridinyl, tetrahydrofuranyl, cyclobutyl, cyclopropyl, phenyl, pyrazolyl, morpholinyl and oxetanyl, wherein Q is optionally substituted with up to 2 substituents independently selected from —CH$_3$ and =O.

In some embodiments, R$^1$ and R$^2$ are taken together to form cyclopropyl, cyclobutyl, cyclopentyl, cyclohexyl, tetrahydrofuranyl, tetrahydropyranyl, oxetanyl, bicyclo[2.2.1]heptanyl, oxobicyclo[3.1.0]hexanyl, azetidinyl, phenyl and pyridinyl, any of which is optionally substituted with up to 2 substituents independently selected from C$_1$-C$_4$ alkyl, C$_1$-C$_4$ alkoxy, C$_3$-C$_6$ cycloalkyl, —OH, —C(O)CH$_3$, fluoro, and chloro.

In some embodiments, ring A is an optionally substituted 6-membered monocyclic aryl. In some embodiments, ring A is an optionally substituted 5-6 membered heteroaryl. In some embodiments, ring A is an optionally substituted 6 membered heteroaryl.

In some embodiments, ring A is selected from phenyl, pyrazolyl, oxazolyl, isoxazolyl, pyridinyl, pyrimidinyl, pyrazinyl, and thiazolyl, wherein ring A is optionally substituted with up to two substituents independently selected from halo, —C$_1$-C$_4$ alkyl, —C$_1$-C$_4$ haloalkyl, —C$_1$-C$_4$ hydroxyalkyl, —NH—S(O)$_2$—(C$_1$-C$_4$ alkyl), —S(O)$_2$NH(C$_1$-C$_4$ alkyl), —CN, —S(O)$_2$—(C$_1$-C$_4$ alkyl), C$_1$-C$_4$ alkoxy, —NH(C$_1$-C$_4$ alkyl), —OH, —OCF$_3$, —CN, —NH$_2$, —C(O)NH$_2$, —C(O)NH(C$_1$-C$_4$ alkyl), —C(O)—N(C$_1$-C$_4$ alkyl)$_2$, and cyclopropyl optionally substituted with OH.

In some embodiments, ring A is selected from phenyl, pyrazolyl, oxazolyl, isoxazolyl, pyridinyl, pyrimidinyl, pyrazinyl, and thiazolyl, wherein ring A is optionally substituted with up to two substituents independently selected from halo, —C$_1$-C$_4$ alkyl, —C$_1$-C$_4$ haloalkyl, —C$_1$-C$_4$ hydroxyalkyl, —NH—S(O)$_2$—(C$_1$-C$_4$ alkyl), —S(O)$_2$NH(C$_1$-C$_4$ alkyl), —CN, —S(O)$_2$—(C$_1$-C$_4$ alkyl), C$_1$-C$_4$ alkoxy, —NH(C$_1$-C$_4$ alkyl), —OH, —CN, and —NH$_2$.

In some embodiments, ring B is selected from phenyl, pyrazolyl, oxazolyl, isoxazolyl, thiazolyl, pyridinyl, pyrimidinyl, pyridazinyl, and pyrazinyl, wherein ring B is optionally substituted with up to two substituents independently selected from halo, —C$_1$-C$_4$ alkyl, —C$_2$-C$_4$ alkynyl, —C$_1$-C$_4$ haloalkyl, —C$_1$-C$_4$ hydroxyalkyl, C$_3$-C$_6$ cycloalkyl, —(C$_0$-C$_2$ alkylene)-O—C$_1$-C$_4$ alkyl, —O—(C$_1$-C$_4$ alkylene)-C$_3$-C$_6$ cycloalkyl, —NH—S(O)$_2$—(C$_1$-C$_4$ alkyl), —S(O)$_2$NH(C$_1$-C$_4$ alkyl), —S(O)$_2$—NH—(C$_3$-C$_6$ cycloalkyl), —S(O)$_2$-(saturated heterocyclyl), —CN, —S(O)$_2$—(C$_1$-C$_4$ alkyl), —NH(C$_1$-C$_4$ alkyl), —N(C$_1$-C$_4$ alkyl)$_2$, —OH, C(O)—O—(C$_1$-C$_4$ alkyl), saturated heterocyclyl, and —NH$_2$.

In another embodiment, the compound is a compound having Structural Formula II:

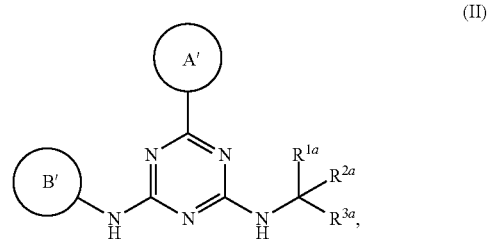

(II)

or a pharmaceutically acceptable salt thereof, wherein:

Ring A' is selected from phenyl and pyridin-2-yl, wherein ring A' is optionally substituted with one or two substituents independently selected from chloro, fluoro, —CF$_3$, —CHF$_2$, —CH$_3$, —CH$_2$CH$_3$, —CF$_2$CH$_3$, —OH, —OCH$_3$, —OCH$_2$CH$_3$, —NH$_2$, —NH(CH$_3$), and —N(CH$_3$)$_2$;

Ring B' is selected from pyridin-3-yl, pyridin-4-yl, isoxazoly-4-yl, isoxazol-3-yl, thiazol-5-yl, pyrimidin-5-yl and pyrazol-4-yl, wherein ring B' is optionally substituted with one to two substituents independently selected from halo; —CN; —OH; C$_1$-C$_4$ alkyl optionally substituted with halo, CN or —OH; —S(O)$_2$—C$_1$-C$_4$ alkyl; —S(O)—C$_1$-C$_4$ alkyl; —S(O)$_2$—NH—C$_1$-C$_4$ alkyl; —S(O)$_2$—N(C$_1$-C$_4$ alkyl)$_2$; —S(O)$_2$-azetidin-1-yl; —O—C$_1$-C$_4$ alkyl; —CH$_2$—O—CH$_3$, morpholin-4-yl, cyclopropyl, —S(O)$_2$—NH-cyclopropyl; —C(O)—O—CH$_3$; and —C(R$^{1a}$)(R$^{2a}$)(R$^{3a}$) is selected from C$_1$-C$_6$ alkyl optionally substituted with halo or —OH; —(C$_0$-C$_1$ alkylene)-cycloalkyl, wherein the alkylene is optionally substituted with methyl and the cycloalkyl is optionally substituted with halo, —OCH$_3$ or methyl; saturated heterocyclyl optionally substituted with halo or methyl; —C(O)—O—C$_1$-C$_6$ alkyl; —C(O)—(C$_0$-C$_1$ alkylene)-cyclopropyl; and C(O)-benzyl.

In certain embodiments of Formula II, ring A' is selected from 2-chlorophenyl, 2-fluorophenyl, 2-methoxyphenyl, 3-hydroxyphenyl, 6-aminopyridin-2-yl, 6-chloropyridin-2-yl, 6-trifluoromethylpyridin-2-yl, and phenyl.

In certain embodiments of Formula II, ring B' is selected from 2-(morpholin-4-yl)pyridin-4-yl, 2-dimethylaminopyridin-4-yl, 3-(2-methoxyethyl)phenyl, 3,5-difluorophenyl, 3-chlorophenyl, 3-cyanomethylphenyl, 3-cyanophenyl, 3-cyclopropylaminosulfonylphenyl, 3-dimethylaminosulfonylphenyl, 3-ethylsulfonylphenyl, 3-fluorophenyl, 3-methylsulfonylphenyl, 4-fluorophenyl, 5-chloropyridin-3-yl, 5-cyanopyridin-3-yl, 5-cyanopyridin-3-yl, 5-cyanopyridin-4-yl, 5-fluoropyridin-3-yl, 5-trifluoromethypyridin-3-yl, 6-chloropyridin-4-yl, 6-cyanopyridin-4-yl, 6-cyclopropylpyridin-4-yl, 6-ethoxypyridin-4-yl, 6-fluoropyridin-3-yl, 6-fluoropyridin-4-yl, 6-methylpyridin-4-yl, 6-trifluoromethylpyridin-4-yl, isoxazol-4-yl, phenyl, pyridin-4-yl, and thiazol-5-yl.

In certain embodiments of Formula II, the moiety represented by $C(R^{1a})(R^{2a})(R^{3a})$ is selected from 2-hydroxycyclopentyl, 3-hydroxycyclopentyl, 1-methylcyclopropyl, 2-methylcyclopropyl, 3,3-difluorocyclobutyl, bicycloheptanyl, —$(CH_2)_3CH_3$, —$CH(CH_3)$—$C(CH_3)_3$, —$CH(CH_3)$—$CH_2OCH_3$, —$C(O)$—$C(CH_3)_3$, —$C(O)$—$OC(CH_3)_3$, —$C(O)CH_2OH$, —$C(O)$—$CH(CH_3)_2$, —C(O)-1-hydroxycyclopropyl, —C(O)-2-pyrrolidinon-5-yl, —C(O)-2-pyrrolyl, —$C(O)CH_2OCH(CH_3)_2$, —C(O)-cyclopropyl, —$C(O)$—$CH_2$-cyclopropyl, —$C(O)$—$OC(CH_3)_3$, —$C(O)$$CH(CH_3)OH$, —C(O)-1H-pyrazol-5-yl, —$C(O)$$NHCH_2CH_3$, —$CH_2CH(CH_3)OCH_3$, —$CH_2CH_2CH_2OCH_3$, —$C(O)$—$OCH_2CH(CH_3)_2$, —$CH_2CH_2$—$OCH_3$, —$C(O)$—$OCH_3$, —$C(O)$—$CH_2CH_3$, —$CH(CH_3)$—$CH(CH_3)_2$, —$CH_2CH(CH_3)OH$, —$CH(CH_3)CH_2CH_3$, —$CH(CH_3)$—$CH_2CH_3$, —$CH(CH_3)$$CH_2OH$, —$CH_2C(CH_3)_3$, —$CH(CH_2OH)CH(CH_3)CH_3$, —$CH(CH_3)C(CH_3)_3$, —$CH_2C(CH_3)_2CH_2OH$, —$CH_2CH_2OH$, —$CH_2CH(CH_3)OH$, —$CH(CH_3)$$CH_2OCH_3$, —$CH_2$—$CH(CH_3)CH_2OH$, —$CH_2C(CH_3)_2$$OCH_3$, —$CH(C(CH_3)_3)CH_2OH$, —$CH_2C(CH_3)_2$—$OH$, —$CH_2C(CH_3)_3$, —$CH_2CF_3$, —$CH_2CH(CH_3)_2$, —$CH_2CH$$(CH_3)_2$, —$CH_2CH_2CF_3$, —$CH_2CH_2OCH_2CH_3$, —$CH_2CH$$(CH_3)$—$CH_2CH_3$, —$CH_2CH_2CH(CH_3)_2$, —$CHC(CH_3)_3$$CH_2OH$, —$CH(CH_2CH_3)CH_2OH$, —$CH_2C(CH_3)_2OH$, —$CH_2$-oxetan-2-yl, —$CH_2$-oxetan-3-yl, —$CH_2$-cyclopropyl, —$CH_2$-cyclobutyl, —$CH(CH_3)$-cyclopropyl, —C(O)-1-methylcyclopropyl, —C(O)-tetrahydrofuran-2-yl, —$CH_2$-tetrahydrofuran-2-yl, —C(O)-tetrahydrofuran-3-yl, —$CH_2$-morpholin-2-yl, —$CH_2$-1-methyltetrahydrofuran-2-yl, cyclobutyl, 3-methoxycyclobutyl, 3-cyclobutanone, cyclohexyl, 4-hydroxycyclohexyl, cyclopentyl, 3-hydroxycyclopentyl, 2-hydroxycyclopentyl, cyclopropyl, ethyl, isopropyl, isobutyl, n-propyl, n-butyl, oxetan-3-yl, oxobicyclohexanyl, tertrahydropyran-4-yl, 3-oxetanyl, 2-oxetanyl, tetrahydropyran-3-yl, 4,4-difluorocyclohexyl, 4-hydroxycyclohexyl, 3-hydroxycyclohexyl, 2-hydroxycyclohexyl, 3-tetrahydrofuranyl, 1-cyanocyclobutyl, 1-cyanocyclopropyl, 4-methoxycyclobutyl, 3-methyl-oxetan-3-yl, bicyclo[2.2.1]heptanyl, 3-oxabicyclo[3.1.0]hexanyl and 3-cyclohex-2-enonyl.

In certain embodiments of Formula II, the moiety represented by $C(R^{1a})(R^{2a})(R^{3a})$ is selected from 2-hydroxycyclopentyl, 2-methylcyclopropyl, 3,3-difluorocyclobutyl, bicycloheptanyl, —$(CH_2)_3CH_3$, —$CH(CH_3)$—$C(CH_3)_3$, —$CH(CH_3)$—$CH_2OCH_3$, —$C(O)$—$C(CH_3)_3$, —$C(O)$—$CH(CH_3)_2$, —C(O)-cyclopropyl, —$C(O)$—$OC(CH_3)_3$, —$C(O)$—$OCH_2CH(CH_3)_2$, —$C(O)$—$OCH_2CH_3$, —$CH$$(CH_3)$—$CH(CH_3)_2$, —$CH(CH_3)$—$CH_2CH_3$, —$CH_2C$$(CH_3)_2$ $CH_2OH$, $CH_2C(CH_3)_3$, —$CH_2CF_3$, —$CH_2CH$$(CH_3)_2$, —$CH_2CH(CH_3)$—$CH_2CH_3$, —$CH_2CH_2CH(CH_3)_2$, —$CH_2$-cyclopropyl, cyclobutyl, cyclohexyl, cyclopentyl, cyclopropyl, isopropyl, oxetan-3-yl, oxobicyclohexanyl, tertrahydropyran-4-yl, and tetrahydropyran-3-yl.

In another embodiment, the compound is a compound having Structural Formula II:

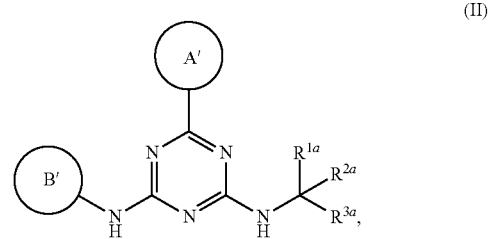

(II)

or a pharmaceutically acceptable salt thereof, wherein:

Ring A' is selected from phenyl, pyrimidin-2-yl, pyrimidin-4-yl, pyrimidin-5-yl, oxazol-4-yl, isoxazol-3-yl, thiazol-2-yl, pyridin-3-yl and pyridin-2-yl, wherein ring A' is optionally substituted with one or two substituents independently selected from 1-propenyl, -cyclopropyl-OH, chloro, fluoro, —$CF_3$, —$CHF_2$, —$CH_3$, —$CH_2CH_3$, —$CF_2CH_3$, —$S(O)CH_3$, —$S(O)_2CH_3$, —$CH_2OH$, —$CH(OH)CH_3$, —$CH(OH)CF_3$, —OH, —$OCH_3$, —$OCF_3$, —$OCH_2CH_3$, —$C(O)$—$NH_2$, —$CH_2NH_2$, —$NH_2$, —$NH(CH_3)$, —CN and —$N(CH_3)_2$;

Ring B' is selected from phenyl, pyridin-3-yl, pyridin-4-yl, pyridazin-4-yl, isoxazol-4-yl, isoxazol-3-yl, thiazol-5-yl, pyrimidin-5-yl and pyrazol-4-yl, wherein ring B' is optionally substituted with one to two substituents independently selected from halo; —CN; —OH; $C_1$-$C_4$ alkyl optionally substituted with halo, CN or —OH; —$S(O)_2$—$C_1$-$C_4$ alkyl; —S(O)—$C_1$-$C_4$ alkyl; —$S(O)_2$—NH—$C_1$-$C_4$ alkyl; —$S(O)_2$ —NH—$CH_2$—$CF_3$; —$S(O)_2$—N($C_1$-$C_4$ alkyl)$_2$; —$S(O)_2$-azetidin-1-yl; —O—$C_1$-$C_4$ alkyl; —$CH_2$—O—$CH_3$, morpholin-4-yl, cyclopropyl, cyclopropyl-$C_1$-$C_4$ alkyl, cyclopropyl-$C_1$-$C_4$ alkoxy, cyclopropyl-CN, —$S(O)_2$—NH-cyclopropyl; —$S(O)_2$—NH—$CH_2$-cyclopropyl; —C(O)—$C_1$-$C_4$ alkyl, —C(O)—O—$CH_3$; and —$C(R^{1a})(R^{2a})(R^{3a})$ is selected from $C_1$-$C_6$ alkyl optionally substituted with halo, —$OCH_3$, —$P(O)_3^{2-}$ or —OH; —($C_0$-$C_1$ alkylene)-cycloalkyl, wherein the alkylene is optionally substituted with methyl and the cycloalkyl is optionally substituted with —OH, —$CH_2OH$, halo, —$OCH_3$ or methyl; saturated or partially saturated —($C_0$-$C_1$ alkylene)-heterocyclyl wherein the heterocyclyl is optionally substituted with halo, —$S(O)_2$—$CH_2$—C(O)—$C_1$-$C_6$ alkyl, —$S(O)_2$—$C_1$-$C_6$ alkyl, —C(O)—O—$C_1$-$C_6$ alkyl, —C(O)—N($CH_3$)$_2$ or methyl; —C(O)—O—$C_1$-$C_6$ alkyl; —C(O)—($C_0$-$C_1$ alkylene)-cyclopropyl; and C(O)-benzyl.

In certain embodiments of Formula II, ring A' is selected from 2-chlorophenyl, 2-fluorophenyl, 2-methoxyphenyl, 3-hydroxyphenyl, 3-amidophenyl, 3-methylsulfinylphenyl, 3-methylsulfonylphenyl, 3-(1-methanol)phenyl, 3-methanaminephenyl, 3-methoxy-2-fluorophenyl, 5-methoxy-2-fluorophenyl, 3-hydroxy-2-fluorophenyl, 5-hydroxy-2-fluorophenyl, 5-hydroxy-3-fluorophenyl, 3-methanolphenyl, 3,5-dihydroxyphenyl, 3-trifluoromethyl-5-chlorophenyl, 3-(1-hydoxy-2,2,2-trifluoroethyl)phenyl, 3-(1-hydoxyethyl)phenyl, 3-(1-hydoxycyclopropyl)phenyl, 3-hydroxymethyl-5-phenol, pyridin-2-yl, 3-fluoropyridin-2-yl, 3-cyanopyridin-2-yl, 3,6-difluoropyridin-2-yl, 3-fluoro-6-methoxypyridin-2-yl, 3-fluoro-6-hydroxypyridin-2-yl, 3-fluoro-6-aminopyridin-2-yl, 4-fluoro-6-aminopyridin-2-yl, 6-propen-1-ylpyridin-2-yl, 6-prop-1-ylpyridin-2-yl, 6-methylaminopyridin-2-yl, 3-fluoro-6-trifluoromethylpyridin-2-yl, 4-chloro-6-aminopyridin-2-yl, 4-fluoro-6-aminopyridin-2-yl, 4-chloro-6-methoxypyridin-2-yl, 6-aminopyridin-3-yl, 2-methoxypyridin-3-yl, 6-aminopyridin-2-yl, 6-chloropyridin-2-yl, 6-trifluoromethylpyridin-2-yl, 6-difluoromethylpyridin-2-yl, 4-(CH₂OH)-6-trifluoromethylpyridin-2-yl, 4-(CH₂OH)-6-chloro-pyridin-2-yl, 6-(1,1-difluoroethyl)-4-fluoropyridin-2-yl, 4-trifluoromethylpyrimidin-2-yl, 4-aminopyrimidin-2-yl, 6-trifluoromethyl-4-aminopyrimidin-2-yl, 4-trifluoromethyl-6-aminopyrimidin-2-yl, 4-aminopyrimidin-2-yl, 2-aminopyrimidin-4-yl, 2-aminopyrimidin-5-yl, 4,6-dichloropyridin-2-yl, 3,5-dichlorophenyl, 2,6-difluorophenyl, 2-methyloxazol-4-yl, 3-methylisoxazol-5-yl, 4-trifluoromethyl-thiazol-2-yl, 4-methylthiazol-2-yl and phenyl.

In certain embodiments of Formula II, ring B' is selected from 2-(morpholin-4-yl)pyridin-4-yl, 2-dimethylaminopyridin-4-yl, 3-(2-methyoxyethyl)phenyl, 3,5-difluorophenyl, 3-chlorophenyl, 3-cyanomethylphenyl, 3-cyanophenyl, 3-(cyclopropylmethyl)phenyl, 3-cyclopropylaminosulfonylphenyl, 3-dimethylaminosulfonylphenyl, 3-ethylsulfonylphenyl, 3-fluorophenyl, 3-methylsulfonylphenyl, 4-fluorophenyl, 3-(1-hydroxyisopropyl)phenyl, 3-methylsulfonyl-5-chlorophenyl, 3-methylsulfonyl-5-fluorophenyl, 3-(N-2,2,2,-trifluoroethylaminosulfonyl)phenyl, 3-(N-cyclopropyl) benzamide, 5-chloropyridin-3-yl, 5-cyanopyridin-3-yl, 5-cyanopyridin-3-yl, 5-cyanopyridin-4-yl, 5-fluoropyridin-3-yl, 2-(1-hydroxyisopropyl)pyridin-4-yl, 5-trifluoromethylpyridin-3-yl, 2-trifluoromethylpyridin-4-yl, 2-difluoromethylpyridin-4-yl, 2-chloropyridin-4-yl, 6-chloropyridin-4-yl, 6-cyanopyridin-4-yl, 2-cyanopyridin-4-yl, 6-cyclopropylpyridin-4-yl, 6-ethoxypyridin-4-yl, 6-fluoropyridin-3-yl, 2-fluoropyridin-4-yl, 5,6-difluoropyridin-3-yl, 6-fluoropyridin-4-yl, 6-methylpyridin-4-yl, 2-difluoromethylpyridin-4-yl, 6-trifluoromethylpyridin-4-yl, 2-(1-methoxycyclopropyl)pyridin-4-yl, 2-cyclopropylpyridin-4-yl, 2-(propan-1-one)pyridin-4-yl, 2-(1-methylcyclopropyl)pyridin-4-yl, 2-(1-cyanocyclopropyl)pyridin-4-yl, 2-(1-cyanoisopropyl)pyridin-4-yl, isoxazol-4-yl, phenyl, pyridin-4-yl, picolinat-2-yl, pyrimidin-5-yl, 1-propylpyrazol-4-yl, 6-methylpyridazin-4-yl, and thiazol-5-yl.

In certain embodiments of Formula II, the moiety represented by C(R¹ᵃ)(R²ᵃ)(R³ᵃ) is selected from 2-hydroxycyclopentyl, 3-hydroxycyclopentyl, 1-methylcyclopropyl, 2-methylcyclopropyl, 3,3-difluorocyclobutyl, bicycloheptanyl, —(CH₂)₃CH₃, —CH(CH₃)—C(CH₃)₃, —CH(CH₃)—CH₂OCH₃, —C(O)—C(CH₃)₃, —C(O)—OC(CH₃)₃, —C(O)CH₂OH, —C(O)—CH(CH₃)₂, —C(O)-1-hydroxycyclopropyl, —C(O)-2-pyrrolidinon-5-yl, —C(O)-2-pyrrolyl, —C(O)CH₂OCH(CH₃)₂, —C(O)-cyclopropyl, —C(O)—CH₂-cyclopropyl, —C(O)—OC(CH₃)₃, —C(O)CH(CH₃)OH, —C(O)-1H-pyrazol-5-yl, —C(O)NHCH₂CH₃, —CH₂CH(CH₃)OCH₃, —CH₂CH₂CH₂OCH₃, —C(O)—OCH₂CH(CH₃)₂, —CH₂CH₂—OCH₃, —C(O)—OCH₂CH₃, —C(O)—CH₂CH₃, —CH(CH₃)—CH(CH₃)₂, —CH₂CH(CH₃)OH, —CH(CH₃)CH₂CH₃, —CH₂C(CH₃)₂OH, —CH(CH₃)—CH₂CH₃, —CH(CH₃)CH₂OH, —CH₂C(CH₃)₃, —CH(CH₂OH)CH(CH₃)CH₃, —CH(CH₃)C(CH₃)₃, —CH₂C(CH₃)₂—CH₂OH, —CH₂CH₂OH, —CH₂CH(CH₃)OH, —CH(CH₃)CH₂OCH₃, —CH₂—CH(CH₃)CH₂OH, —CH₂C(CH₃)₂OCH₃, —C(CH₃)₂CH₂OH, —CH₂CH(CH₃)OCH₃, —CH(CH₃)CH(CH₃)OH, —CH₂CH(CH₃)CH₂OH, —CH(C(CH₃)₃)CH₂OH, CH(CH₃)C(CH₃)₂OH, —CH₂C(CH₃)₂—OH, CH₂C(CH₃)₃, —CH₂CF₃, —CH₂CH(CH₃)₂, —CH₂CH(CH₃)₂, —CH₂CH₂CF₃, —CH₂CH₂OCH₂CH₃, —CH₂CH(CH₃)—CH₂CH₃, —CH₂CH₂CH(CH₃)₂, —CH(C(CH₃)₃)CH₂OH, —CH(CH₂CH₃)CH₂OH, —CH₂C(CH₃)₂OH, —CH₂-oxetan-2-yl, —CH₂-oxetan-3-yl, —CH₂-1-methyl-oxetan-3-yl, —CH₂-cyclopropyl, —CH₂-1-hydroxycyclopropyl, —CH₂-cyclobutyl, —CH(CH₃)-cyclopropyl, —C(O)-1-methylcyclopropyl, —C(O)-tetrahydrofuran-2-yl, —CH₂-tetrahydrofuran-2-yl, —CH₂-tetrahydrofuran-3-yl, —C(O)-tetrahydrofuran-3-yl, —CH₂-morpholin-2-yl, —CH₂-1-methyltetrahydrofuran-2-yl, cyclobutyl, 3-methoxycyclobutyl, 3-cyclobutanone, cyclohexyl, 4-hydroxycyclohexyl, cyclopentyl, 3-hydroxycyclopentyl, 2-hydroxycyclopentyl, cyclopropyl, ethyl, isopropyl, isobutyl, n-propyl, n-butyl, t-butyl, oxetan-3-yl, oxobicyclohexanyl, tetrahydropyran-4-yl, 3-oxetanyl, 2-oxetanyl, tetrahydropyran-3-yl, 4,4-difluorocyclohexyl, 4-hydroxycyclohexyl, 3-hydroxycyclohexyl, 2-hydroxycyclohexyl, 3-tetrahydrofuranyl, 1-cyanocyclobutyl, 1-cyanocyclopropyl, 1-methylcyclopropyl, 1-(hydroxymethyl)cyclopropyl, 2-methylcyclopropyl, 2-hydroxycyclopropyl, 4-methoxycyclobutyl, 3-methyl-oxetan-3-yl, bicyclo[2.2.1]heptanyl, 3-oxabicyclo[3.1.0]hex-6-yl, 1-(t-butylcarboxylate)piperidin-4-yl, piperidin-4-yl, 1-(methylcarboxylate)piperidin-4-yl, 1-(1-ethanone)piperidin-4-yl, 1-(methylsulfonyl)piperidin-4-yl, 1-methylpyrazol-4-yl, 1-methylpyrazol-5-yl, thiazol-5-yl, 7-oxa-bicyclo[2.2.1]hept-2-yl, tetrahydropyran-4-yl, and 3-cyclohex-2-enonyl.

In certain embodiments of Formula II, the moiety represented by C(R¹ᵃ)(R²ᵃ)(R³ᵃ) is selected from 2-hydroxycyclopentyl, 2-methylcyclopropyl, 3,3-difluorocyclobutyl, bicycloheptanyl, —(CH₂)₃CH₃, —CH(CH₃)—C(CH₃)₃, —CH(CH₃)—CH₂OCH₃, —C(O)—C(CH₃)₃, —C(O)—CH(CH₃)₂, —C(O)-cyclopropyl, —C(O)—OC(CH₃)₃, —C(O)—OCH₂CH(CH₃)₂, —C(O)—OCH₂CH₃, —CH(CH₃)—CH(CH₃)₂, —CH(CH₃)—CH₂CH₃, —CH₂C(CH₃)₂ —CH₂OH, —CH₂C(OH)(CH₃)₃, CH₂C(CH₃)₃, —CH₂CF₃, —CH₂CH(CH₃)₂, —CH₂CH(CH₃)—CH₂CH₃, —CH₂CH₂CH(CH₃)₂, —CH₂-cyclopropyl, cyclobutyl, cyclohexyl, cyclopentyl, cyclopropyl, isopropyl, t-butyl, oxetan-3-yl, oxobicyclohexanyl, tetrahydropyran-4-yl, and tetrahydropyran-3-yl.

In certain embodiments of Formula II, the moiety represented by C(R¹ᵃ)(R²ᵃ)(R³ᵃ) is selected from 2-methylcyclopropyl, —(CH₂)₃CH₃, —CH(CH₃)—C(CH₃)₃, —CH(CH₃)—CH₂OCH₃, —CH(CH₃)—CH(CH₃)₂, —CH(CH₃)—CH₂CH₃, —CH₂C(CH₃)₂—CH₂OH, —CH₂C(OH)(CH₃)₃, CH₂C(CH₃)₃, —CH₂CF₃, —CH₂CH(CH₃)₂, —CH(CH₃)₂, —CH₂CH(CH₃)—CH₂CH₃, —CH₂CH₂CH(CH₃)₂, —CH₂-cyclopropyl, isopropyl, and t-butyl.

Further embodiments provided herein include combinations of one or more of the particular embodiments set forth above.

In another embodiment, the compound is selected from any one of the compounds set forth in Table 1, below.

TABLE 1

Representative Compounds

| Cmpd No | Structure |
|---|---|
| 100 | 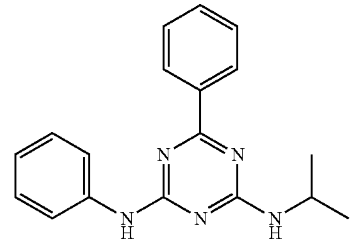 [SMILES: CC(C)Nc1nc(Nc2ccccc2)nc(-c2ccccc2)n1] |

TABLE 1-continued

Representative Compounds

| Cmpd No | Structure |
|---|---|
| 103 | 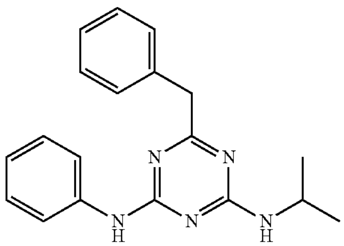 [SMILES: CC(C)Nc1nc(Cc2ccccc2)nc(Nc2ccccc2)n1] |
| 108 | 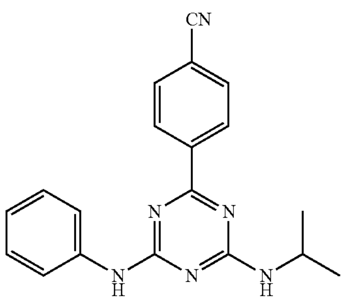 |
| 109 | 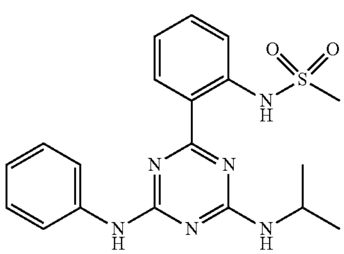 [SMILES: CC(C)Nc1nc(Nc2ccccc2)nc(-c2ccccc2NS(C)(=O)=O)n1] |
| 110 | 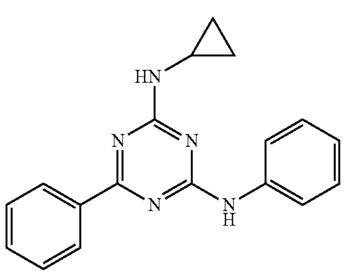 [SMILES: c1ccc(Nc2nc(NC3CC3)nc(-c3ccccc3)n2)cc1] |
| 111 | 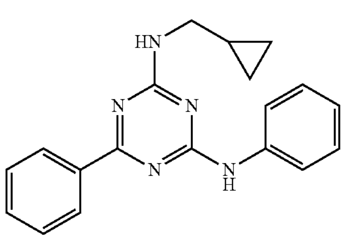 [SMILES: c1ccc(Nc2nc(NCC3CC3)nc(-c3ccccc3)n2)cc1] |
| 112 | |
| 113 | |
| 114 | |
| 115 | |
| 116 | |

TABLE 1-continued

Representative Compounds

| Cmpd No | Structure |
|---|---|
| 117 | 2,6-dimethylphenyl-triazine with NH-phenyl and NH-isopropyl substituents |
| 118 | 2,4-difluorophenyl-triazine with NH-phenyl and NH-isopropyl substituents |
| 119 | 1-methylpyrazol-5-yl-triazine with NH-phenyl and NH-isopropyl substituents |
| 120 | 2-methoxyphenyl-triazine with NH-phenyl and NH-isopropyl substituents |
| 121 | 2-chlorophenyl-triazine with NH-phenyl and NH-isopropyl substituents |
| 122 | 4-chlorophenyl-triazine with NH-phenyl and NH-isopropyl substituents |
| 123 | 2-methylphenyl-triazine with NH-phenyl and NH-isopropyl substituents |
| 126 | phenyl-triazine with NH-phenyl and NH-CH₂CF₃ substituents |
| 128 | 3-cyanophenyl-triazine with NH-phenyl and NH-isopropyl substituents |
| 129 | phenyl-triazine with NH-phenyl and NH-isopropyl substituents |

TABLE 1-continued

Representative Compounds

| Cmpd No | Structure |
|---|---|
| 130 | triazine with HN-isopropyl, phenyl, and NH-(3-cyanophenyl) substituents |
| 132 | triazine with HN-isopropyl, phenyl, and NH-(4-fluorophenyl) substituents |
| 133 | triazine with HN-isopropyl, phenyl, and NH-(4-hydroxyphenyl) substituents |
| 135 | triazine with HN-CH2-(2-pyridyl), phenyl, and NH-phenyl substituents |
| 137 | triazine with HN-isopropyl, phenyl, and NH-(tetrahydropyran-4-yl) substituents |
| 139 | triazine with 2-cyanophenyl, NH-phenyl, and NH-isopropyl substituents |
| 140 | triazine with phenyl, NH-(2,4-difluorophenyl), and NH-isopropyl substituents |
| 141 | triazine with HN-isopropyl, phenyl, and NH-(4-cyanophenyl) substituents |
| 143 | triazine with phenyl, NH-(4-chlorophenyl), and NH-isopropyl substituents |
| 145 | triazine with HN-isopropyl, phenyl, and NH-(4-methylsulfonylphenyl) substituents |

TABLE 1-continued

Representative Compounds

| Cmpd No | Structure |
|---|---|
| 146 | 3-(methylsulfonyl)phenyl-NH, phenyl, isopropyl-NH triazine |
| 147 | 2-methylphenyl-NH, phenyl, isopropyl-NH triazine |
| 148 | 1H-pyrazol-5-yl, phenyl-NH, isopropyl-NH triazine |
| 149 | phenyl-NH, isopropyl-NH, 3-chlorophenyl-NH triazine |
| 150 | isopropyl-NH, phenyl, 3-(hydroxymethyl)phenyl-NH triazine |
| 151 | 3-(methylsulfonyl)phenyl, phenyl-NH, isopropyl-NH triazine |
| 154 | phenyl, pyridin-3-yl-NH, isopropyl-NH triazine |
| 155 | phenyl, pyridin-2-yl-NH, isopropyl-NH triazine |
| 156 | pyridin-4-yl, phenyl-NH, isopropyl-NH triazine |
| 158 | 3-chlorophenyl, phenyl-NH, isopropyl-NH triazine |

TABLE 1-continued

Representative Compounds

| Cmpd No | Structure |
|---|---|
| 159 | N-isopropyl-6-phenyl-N'-(4-methoxyphenyl)-1,3,5-triazine-2,4-diamine |
| 160 | isopropyl (4-phenyl-6-(phenylamino)-1,3,5-triazin-2-yl)carbamate |
| 162 | N-(2-chlorophenyl)-N'-isopropyl-6-phenyl-1,3,5-triazine-2,4-diamine |
| 165 | 2-((4-(isopropylamino)-6-phenyl-1,3,5-triazin-2-yl)amino)benzonitrile |
| 167 | N-(4-phenyl-6-(phenylamino)-1,3,5-triazin-2-yl)isobutyramide |
| 168 | 6-phenyl-N-phenyl-N'-(tetrahydro-2H-pyran-4-yl)-1,3,5-triazine-2,4-diamine |
| 169 | N-isopropyl-N'-(isoxazol-3-yl)-6-phenyl-1,3,5-triazine-2,4-diamine |
| 170 | N-(4-(isopropylamino)-6-phenyl-1,3,5-triazin-2-yl)-2-phenylacetamide |
| 172 | 2-phenyl-N-(4-phenyl-6-(phenylamino)-1,3,5-triazin-2-yl)acetamide |
| 173 | N-(3-chlorophenyl)-6-phenyl-N'-(tetrahydro-2H-pyran-4-yl)-1,3,5-triazine-2,4-diamine |

TABLE 1-continued
Representative Compounds
| Cmpd No | Structure |
|---|---|
| 174 | 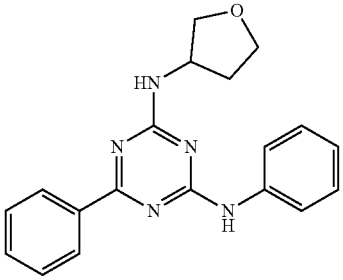 [SMILES: c1ccc(Nc2nc(NC3CCOC3)nc(-c3ccccc3)n2)cc1] |
| 175 | 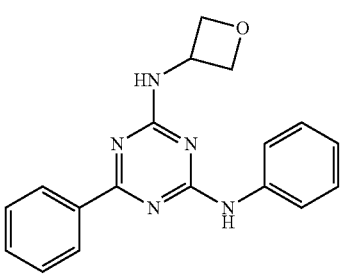 [SMILES: c1ccc(Nc2nc(NC3COC3)nc(-c3ccccc3)n2)cc1] |
| 176 | 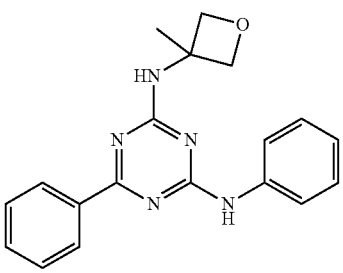 [SMILES: CC1(Nc2nc(Nc3ccccc3)nc(-c3ccccc3)n2)COC1] |
| 177 | 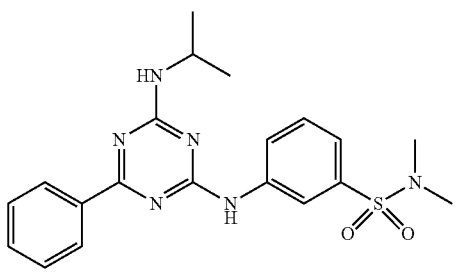 [SMILES: CC(C)Nc1nc(Nc2cccc(S(=O)(=O)N(C)C)c2)nc(-c2ccccc2)n1] |
| 178 | 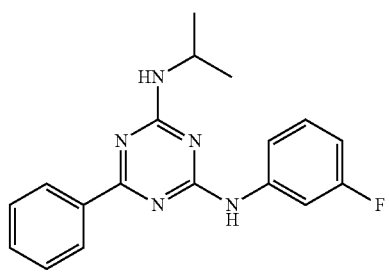 [SMILES: CC(C)Nc1nc(Nc2cccc(F)c2)nc(-c2ccccc2)n1] |
| 179 | 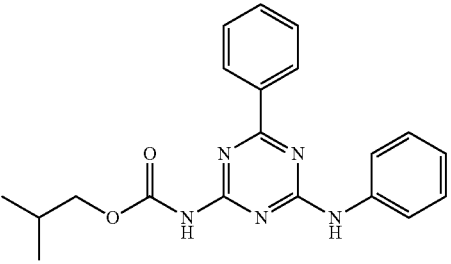 [SMILES: CC(C)COC(=O)Nc1nc(Nc2ccccc2)nc(-c2ccccc2)n1] |
| 181 | 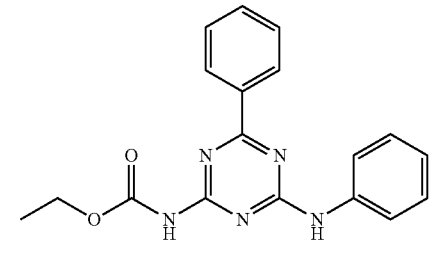 [SMILES: CCOC(=O)Nc1nc(Nc2ccccc2)nc(-c2ccccc2)n1] |
| 182 | 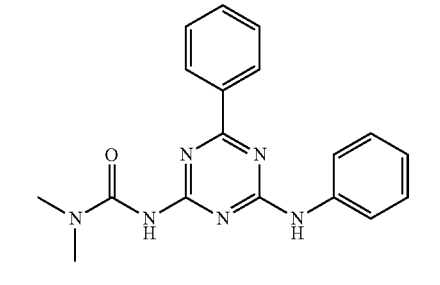 [SMILES: CN(C)C(=O)Nc1nc(Nc2ccccc2)nc(-c2ccccc2)n1] |
| 183 | 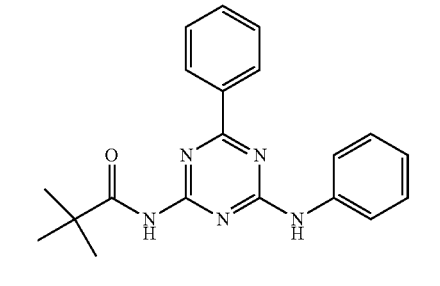 [SMILES: CC(C)(C)C(=O)Nc1nc(Nc2ccccc2)nc(-c2ccccc2)n1] |
| 184 | 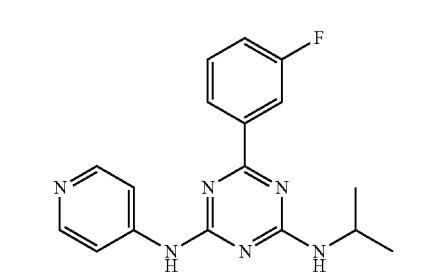 |

TABLE 1-continued

Representative Compounds

| Cmpd No | Structure |
|---|---|
| 185 | 3-chlorophenyl-substituted triazine with pyridin-4-ylamino and isopropylamino groups |
| 186 | phenyl-substituted triazine with pyridin-4-ylamino and sec-butylamino groups |
| 187 | phenyl-substituted triazine with pyridin-4-ylamino and cyclopentylamino groups |
| 188 | phenyl-substituted triazine with pyridin-4-ylamino and cyclobutylamino groups |
| 189 | phenyl-substituted triazine with pyridin-4-ylamino and tert-butylamino groups |
| 190 | phenyl-substituted triazine with pyridin-4-ylamino and isobutylamino groups |
| 191 | phenyl-substituted triazine with pyridin-4-ylamino and neopentylamino groups |
| 193 | phenyl-substituted triazine with (5-fluoropyridin-3-yl)amino and isopropylamino groups |
| 194 | phenyl-substituted triazine with (5-chloropyridin-3-yl)amino and isopropylamino groups |
| 195 | phenyl-substituted triazine with (3-(methoxymethyl)phenyl)amino and isopropylamino groups |
| 196 | phenyl-substituted triazine with (6-fluoropyridin-3-yl)amino and isopropylamino groups |
| 197 | phenyl-substituted triazine with (2-cyanopyridin-4-yl)amino and isopropylamino groups |

TABLE 1-continued

Representative Compounds

| Cmpd No | Structure |
|---|---|
| 198 | 3-(cyanomethyl)phenyl-NH-[4-phenyl-6-(isopropylamino)-1,3,5-triazin-2-yl] |
| 199 | 2-chloropyridin-4-yl-NH-[4-phenyl-6-(isopropylamino)-1,3,5-triazin-2-yl] |
| 200 | 2-ethoxypyridin-4-yl-NH-[4-phenyl-6-(isopropylamino)-1,3,5-triazin-2-yl] |
| 201 | 3-(2-hydroxypropan-2-yl)phenyl-NH-[4-phenyl-6-(isopropylamino)-1,3,5-triazin-2-yl] |
| 202 | 2-(trifluoromethyl)pyridin-4-yl-NH-[4-phenyl-6-(isopropylamino)-1,3,5-triazin-2-yl] |
| 203 | PhNH-[4-phenyl-6-((2-hydroxy-2-methylpropyl)amino)-1,3,5-triazin-2-yl] |
| 204 | 3-(N-ethylsulfamoyl)phenyl-NH-[4-phenyl-6-(isopropylamino)-1,3,5-triazin-2-yl] |
| 205 | 3-(ethylsulfonyl)phenyl-NH-[4-phenyl-6-(isopropylamino)-1,3,5-triazin-2-yl] |
| 206 | 3-(isopropylsulfonyl)phenyl-NH-[4-phenyl-6-(isopropylamino)-1,3,5-triazin-2-yl] |
| 207 | PhNH-[4-phenyl-6-(3-ethylureido)-1,3,5-triazin-2-yl] |

TABLE 1-continued

Representative Compounds

| Cmpd No | Structure |
|---|---|
| 208 | 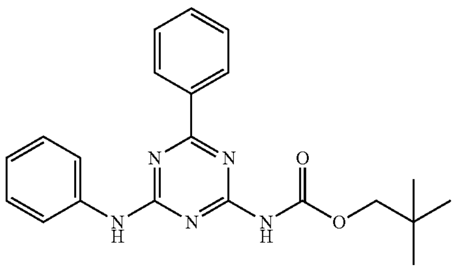 [SMILES: CC(C)(C)COC(=O)Nc1nc(Nc2ccccc2)nc(-c2ccccc2)n1] |
| 209 | 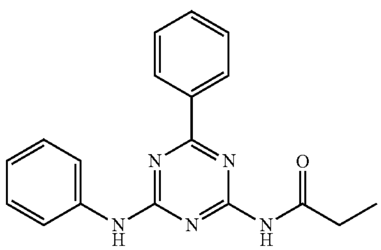 [SMILES: CCC(=O)Nc1nc(Nc2ccccc2)nc(-c2ccccc2)n1] |
| 210 | 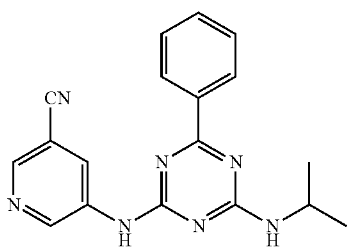 |
| 211 | 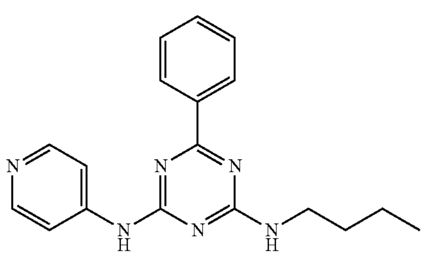 [SMILES: CCCCNc1nc(Nc2ccncc2)nc(-c2ccccc2)n1] |
| 212 | 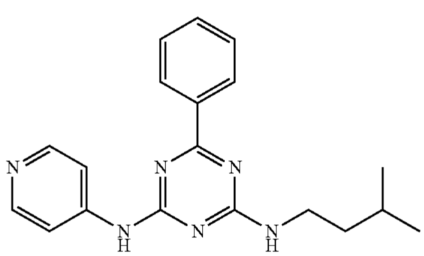 [SMILES: CC(C)CCNc1nc(Nc2ccncc2)nc(-c2ccccc2)n1] |
| 213 | |
| 214 | |
| 215 | |
| 216 | |
| 217 | |

TABLE 1-continued

Representative Compounds

| Cmpd No | Structure |
|---|---|
| 218 | (pyridin-4-yl)NH-triazine(phenyl)-NH(1-methylcyclopropyl) |
| 219 | (pyridin-4-yl)NH-triazine(phenyl)-NH(cyclopropyl-methyl) |
| 220 | (pyridin-4-yl)NH-triazine(phenyl)-NH(2-methylbutyl) |
| 221 | (pyridin-4-yl)NH-triazine(phenyl)-NH-CH2(2-methyltetrahydrofuran-2-yl) |
| 222 | (pyridin-4-yl)NH-triazine(phenyl)-NH-CH2(tetrahydrofuran-2-yl) |
| 223 | (2-fluoropyridin-4-yl)NH-triazine(phenyl)-NH(isopropyl) |
| 224 | (2-ethylaminopyridin-4-yl)NH-triazine(phenyl)-NH(isopropyl) |
| 225 | (phenyl)NH-triazine(phenyl)-NH(2-methoxyethyl) |
| 226 | (pyridin-4-yl)NH-triazine(2-chlorophenyl)-NH(isopropyl) |
| 227 | (pyridin-4-yl)NH-triazine(2-fluorophenyl)-NH(isopropyl) |
| 228 | (4-chloropyridin-2-yl)-triazine-(pyridin-4-yl)NH-NH(isopropyl) |

TABLE 1-continued

Representative Compounds

| Cmpd No | Structure |
|---|---|
| 229 | 6-(6-chloropyridin-2-yl)-N2-isopropyl-N4-phenyl-1,3,5-triazine-2,4-diamine |
| 230 | 6-(3-chloropyridin-2-yl)-N2-isopropyl-N4-phenyl-1,3,5-triazine-2,4-diamine |
| 231 | 2-(4-(isopropylamino)-6-(phenylamino)-1,3,5-triazin-2-yl)pyridin-3-ol |
| 232 | cyclopropylmethyl (4-phenyl-6-(phenylamino)-1,3,5-triazin-2-yl)carbamate |
| 233 | N-(4-phenyl-6-(phenylamino)-1,3,5-triazin-2-yl)cyclopropanecarboxamide |
| 234 | N2-(morpholin-2-ylmethyl)-6-phenyl-N4-(pyridin-4-yl)-1,3,5-triazine-2,4-diamine |
| 235 | 6-phenyl-N2-(pyridin-4-yl)-N4-(tetrahydrofuran-3-yl)-1,3,5-triazine-2,4-diamine |
| 236 | N2-(oxetan-3-yl)-6-phenyl-N4-(pyridin-4-yl)-1,3,5-triazine-2,4-diamine |
| 237 | N2-(oxetan-2-ylmethyl)-6-phenyl-N4-phenyl-1,3,5-triazine-2,4-diamine |
| 238 | 2-((4-phenyl-6-(phenylamino)-1,3,5-triazin-2-yl)amino)ethan-1-ol |

TABLE 1-continued

Representative Compounds

| Cmpd No | Structure |
|---|---|
| 239 | 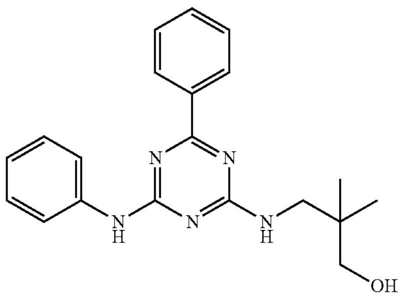 [SMILES: CC(C)(CO)CNc1nc(Nc2ccccc2)nc(-c2ccccc2)n1] |
| 240 | 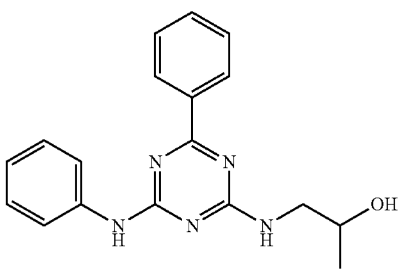 [SMILES: CC(O)CNc1nc(Nc2ccccc2)nc(-c2ccccc2)n1] |
| 241 | 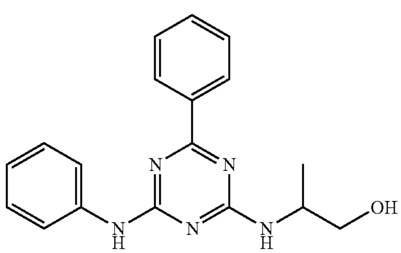 |
| 242 | 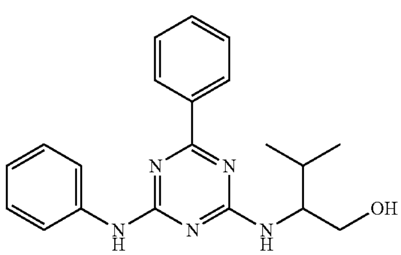 [SMILES: CC(C)C(CO)Nc1nc(Nc2ccccc2)nc(-c2ccccc2)n1] |
| 243 | 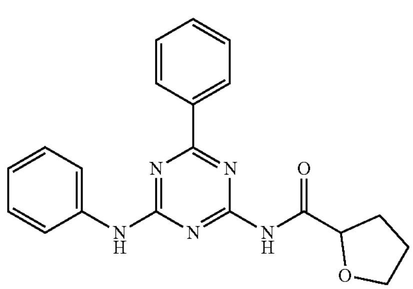 [SMILES: O=C(Nc1nc(Nc2ccccc2)nc(-c2ccccc2)n1)C1CCCO1] |
| 244 | |
| 245 | |
| 246 | |
| 247 | |
| 248 | |

TABLE 1-continued

Representative Compounds

| Cmpd No | Structure |
|---|---|
| 249 | N-propyl, N-(pyridin-4-yl)-6-phenyl-1,3,5-triazine-2,4-diamine |
| 250 | N-(cyclobutylmethyl), N-(pyridin-4-yl)-6-phenyl-1,3,5-triazine-2,4-diamine |
| 251 | N-(3-methyloxetan-3-yl), N-(pyridin-4-yl)-6-phenyl-1,3,5-triazine-2,4-diamine |
| 252 | N-(3-methoxy-2,2-dimethylpropyl), N-(pyridin-4-yl)-6-phenyl-1,3,5-triazine-2,4-diamine |
| 253 | N-(3,3-difluorocyclobutyl), N-(pyridin-4-yl)-6-phenyl-1,3,5-triazine-2,4-diamine |
| 254 | N-(4,4-difluorocyclohexyl), N-(pyridin-4-yl)-6-phenyl-1,3,5-triazine-2,4-diamine |
| 255 | N-(3,3-dimethylbutan-2-yl), N-(pyridin-4-yl)-6-phenyl-1,3,5-triazine-2,4-diamine |
| 256 | N-(4-hydroxycyclohexyl), N-(pyridin-4-yl)-6-phenyl-1,3,5-triazine-2,4-diamine |
| 257 | N-(1-cyclopropylethyl), N-(pyridin-4-yl)-6-phenyl-1,3,5-triazine-2,4-diamine |
| 258 | N-(tetrahydro-2H-pyran-4-yl), N-(pyridin-4-yl)-6-phenyl-1,3,5-triazine-2,4-diamine |

TABLE 1-continued

Representative Compounds

| Cmpd No | Structure |
|---|---|
| 259 | 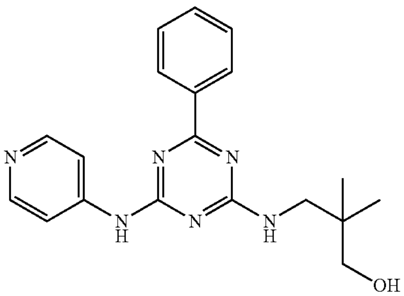 [SMILES: CC(C)(CO)CNc1nc(Nc2ccncc2)nc(-c2ccccc2)n1] |
| 260 | 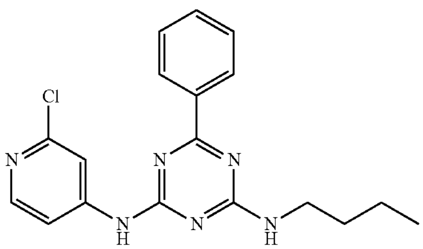 [SMILES: CCCCNc1nc(Nc2ccnc(Cl)c2)nc(-c2ccccc2)n1] |
| 261 | 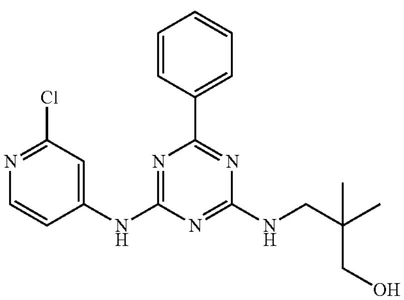 [SMILES: CC(C)(CO)CNc1nc(Nc2ccnc(Cl)c2)nc(-c2ccccc2)n1] |
| 262 | 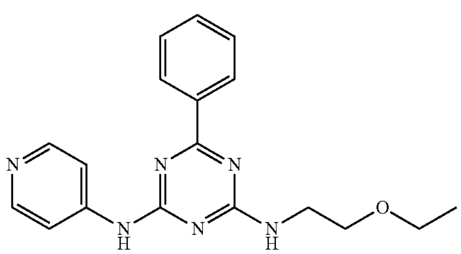 |
| 263 | 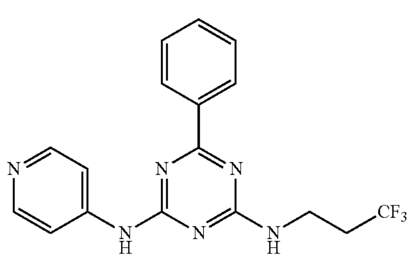 [SMILES: FC(F)(F)CCNc1nc(Nc2ccncc2)nc(-c2ccccc2)n1] |
| 264 | 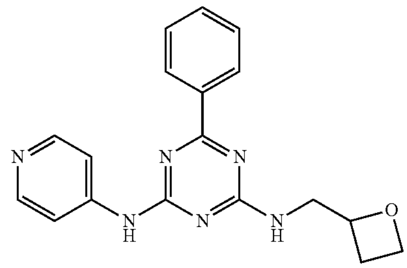 |
| 265 | 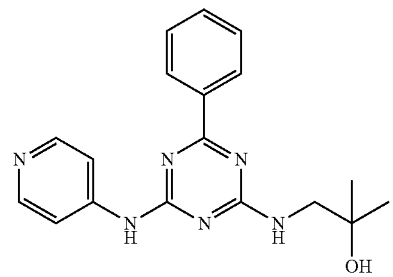 [SMILES: CC(C)(O)CNc1nc(Nc2ccncc2)nc(-c2ccccc2)n1] |
| 266 | 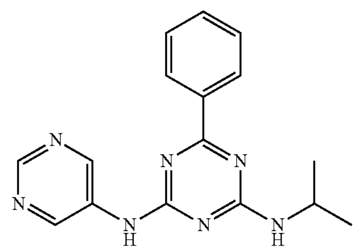 [SMILES: CC(C)Nc1nc(Nc2cncnc2)nc(-c2ccccc2)n1] |
| 267 | 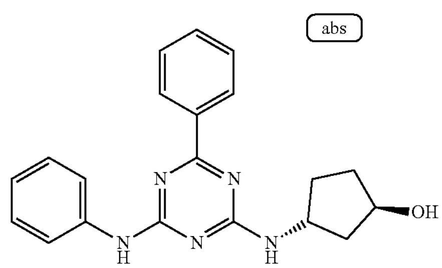 |
| 268 | 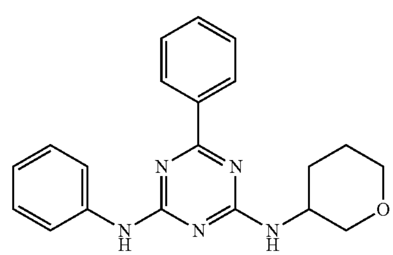 [SMILES: c1ccc(Nc2nc(NC3CCCOC3)nc(-c3ccccc3)n2)cc1] |

TABLE 1-continued

Representative Compounds

| Cmpd No | Structure |
|---|---|
| 269 | (triazine with phenyl, NH-phenyl, and NH-CH(CH3)CH2-OMe substituents) |
| 270 | (triazine with 4-CF3-pyridin-2-yl, NH-phenyl, and NH-isopropyl substituents) |
| 271 | (triazine with phenyl, NH-pyridin-4-yl, and NH-CH2-CH(OH)CH3 substituents) |
| 272 | (triazine with phenyl, NH-pyridin-4-yl, and NH-CH(CH3)CH2-OMe substituents) |
| 273 | (triazine with phenyl, NH-pyridin-4-yl, and NH-(tetrahydropyran-3-yl) substituents) |
| 274 | (triazine with phenyl, NH-pyridin-4-yl, and NH-CH2-CH(OMe)CH3 substituents) |
| 275 | (triazine with phenyl, NH-pyridin-4-yl, and NH-(CH2)3-OMe substituents) |
| 276 | (triazine with phenyl, NH-pyridin-4-yl, and NH-(3-oxocyclobutyl) substituents) |
| 277 | (triazine with 2-(ethylsulfinyl)pyridin-4-yl, NH-isopropyl, and additional NH substituents) |
| 278 | (triazine with phenyl, NH-pyridin-4-yl, and NH-CH(CH3)CH2OH substituents) |

TABLE 1-continued

Representative Compounds

| Cmpd No | Structure |
|---|---|
| 279 | |
| 280 | |
| 281 | |
| 282 | |
| 283 | |
| 284 | 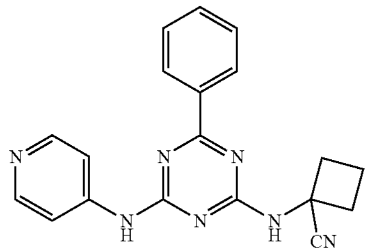 [SMILES: N#CC1(Nc2nc(Nc3ccncc3)nc(-c3ccccc3)n2)CCC1] |
| 285 | 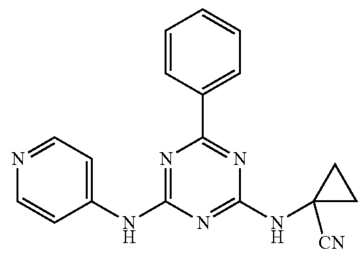 [SMILES: N#CC1(Nc2nc(Nc3ccncc3)nc(-c3ccccc3)n2)CC1] |
| 286 | 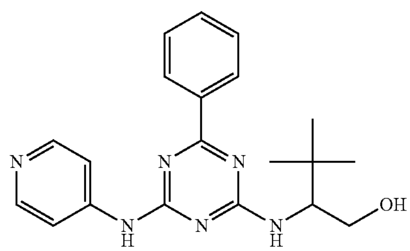 [SMILES: CC(C)(C)C(CO)Nc1nc(Nc2ccncc2)nc(-c2ccccc2)n1] |
| 287 | 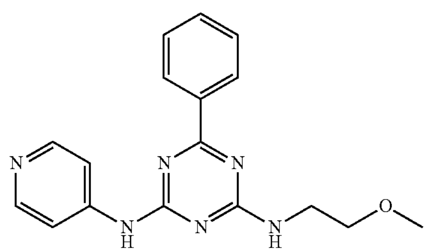 |
| 288 | 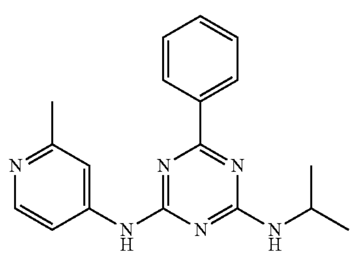 [SMILES: Cc1cc(Nc2nc(NC(C)C)nc(-c3ccccc3)n2)ccn1] |
| 289 | 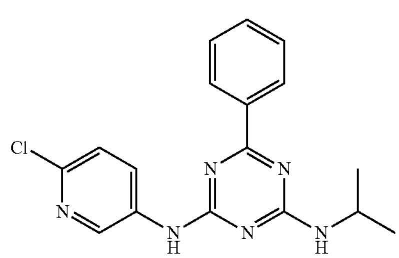 [SMILES: CC(C)Nc1nc(Nc2ccc(Cl)nc2)nc(-c2ccccc2)n1] |

TABLE 1-continued

Representative Compounds

| Cmpd No | Structure |
|---|---|
| 290 | 2-amino-pyridin-2-yl triazine with NHPh and NH-isopropyl |
| 291 | 6-phenyl triazine with NH-(pyridin-4-yl) and NH-CH(Et)CH2OH |
| 292 | 6-phenyl triazine with NH-(3-fluoropyridin-4-yl) and NH-isopropyl |
| 293 | 6-phenyl triazine with NH-(2-(dimethylamino)pyridin-4-yl) and NH-isopropyl |
| 294 | 6-phenyl triazine with NH-(pyridin-4-yl) and NH-CH2CH2OH |
| 295 | 6-phenyl triazine with NH-(pyridin-4-yl) and NH-norbornyl |
| 296 | 6-phenyl triazine with NHPh and NH-norbornyl |
| 297 | 6-phenyl triazine with NH-(pyridin-4-yl) and NH-(3-oxabicyclo[3.1.0]hexyl) |
| 298 | 6-phenyl triazine with NH-(2-morpholinopyridin-4-yl) and NH-isopropyl |
| 299 | 6-phenyl triazine with NH-(2-(azetidin-1-yl)pyridin-4-yl) and NH-isopropyl |

TABLE 1-continued

Representative Compounds

| Cmpd No | Structure |
|---|---|
| 300 | 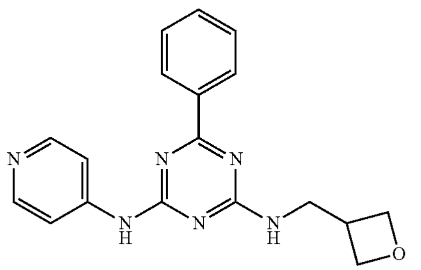 [SMILES: c1ccc(-c2nc(NCC3COC3)nc(Nc3ccncc3)n2)cc1] |
| 301 | 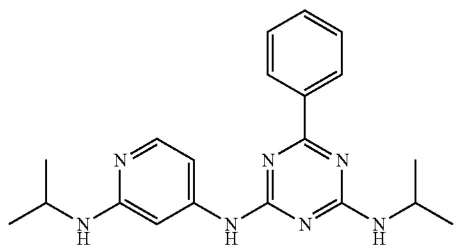 [SMILES: CC(C)Nc1cc(Nc2nc(NC(C)C)nc(-c3ccccc3)n2)ccn1] |
| 302 | 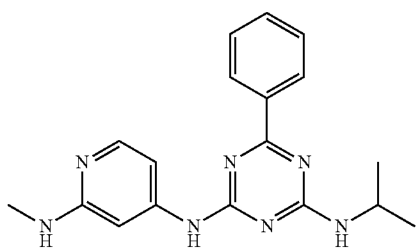 [SMILES: CNc1cc(Nc2nc(NC(C)C)nc(-c3ccccc3)n2)ccn1] |
| 303 | 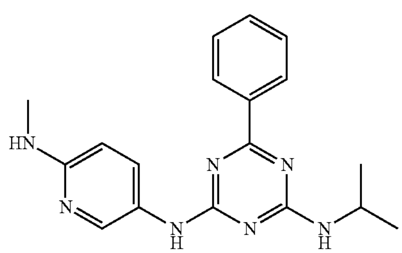 [SMILES: CNc1ccc(Nc2nc(NC(C)C)nc(-c3ccccc3)n2)cn1] |
| 304 | 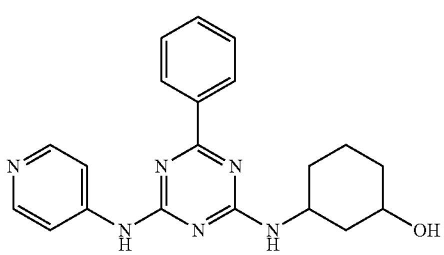 [SMILES: OC1CCCC(Nc2nc(Nc3ccncc3)nc(-c3ccccc3)n2)C1] |
| 305 | 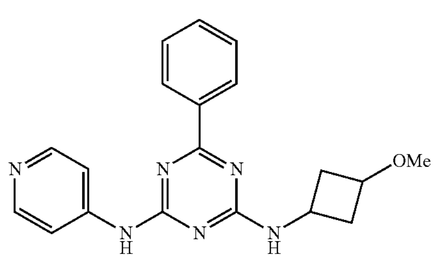 [SMILES: COC1CC(Nc2nc(Nc3ccncc3)nc(-c3ccccc3)n2)C1] |
| 306 | |
| 308 | |
| 309 | |
| 310 | |
| 311 | |
| 312 | |

TABLE 1-continued

Representative Compounds

| Cmpd No | Structure |
|---|---|
| 313 | 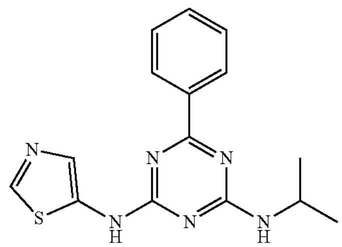 [SMILES: CC(C)Nc1nc(Nc2cncs2)nc(-c2ccccc2)n1] |
| 314 | 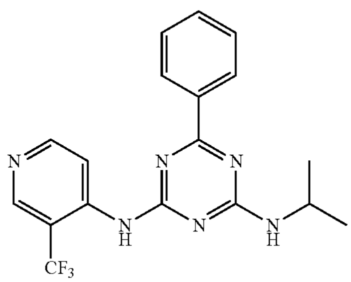 [SMILES: CC(C)Nc1nc(Nc2ccncc2C(F)(F)F)nc(-c2ccccc2)n1] |
| 315 | 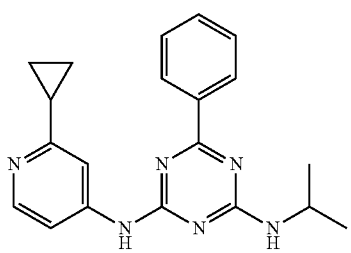 [SMILES: CC(C)Nc1nc(Nc2ccnc(C3CC3)c2)nc(-c2ccccc2)n1] |
| 316 | 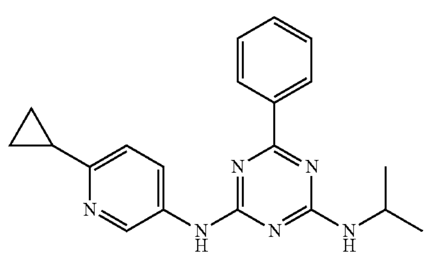 [SMILES: CC(C)Nc1nc(Nc2ccc(C3CC3)nc2)nc(-c2ccccc2)n1] |
| 317 | 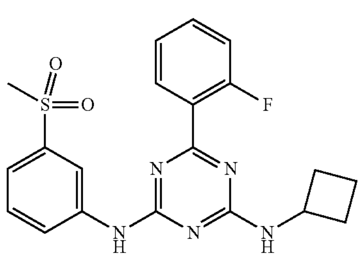 [SMILES: CS(=O)(=O)c1cccc(Nc2nc(NC3CCC3)nc(-c3ccccc3F)n2)c1] |
| 318 | |
| 319 | |
| 320 | |
| 321 | |
| 322 | |

TABLE 1-continued

Representative Compounds

| Cmpd No | Structure |
|---|---|
| 323 | (structure) |
| 324 | (structure) |
| 325 | (structure) |
| 326 | (structure) |
| 327 | (structure) |
| 328 | (structure) |
| 329 | (structure) |
| 330 | (structure) |
| 331 | (structure) |
| 332 | (structure) |
| 334 | (structure) |

TABLE 1-continued
Representative Compounds
| Cmpd No | Structure |
|---|---|
| 335 | 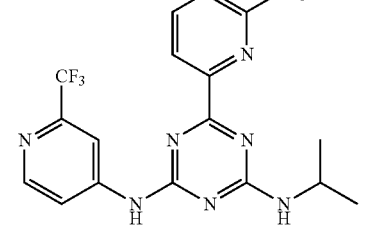 |
| 336 | 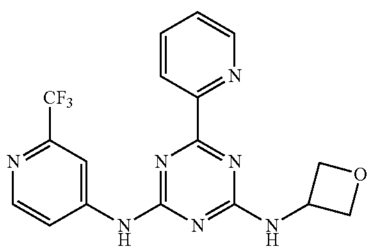 [SMILES: FC(F)(F)c1cc(Nc2nc(NC3COC3)nc(-c3ccccn3)n2)ccn1] |
| 337 | 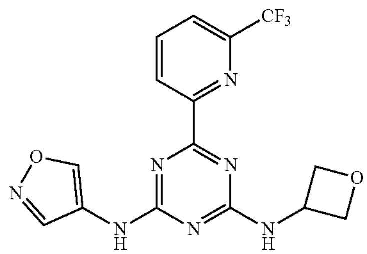 [SMILES: FC(F)(F)c1cccc(-c2nc(Nc3cnoc3)nc(NC3COC3)n2)n1] |
| 340 | 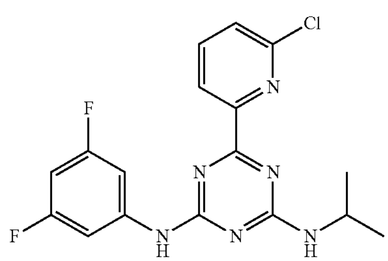 [SMILES: CC(C)Nc1nc(Nc2cc(F)cc(F)c2)nc(-c2cccc(Cl)n2)n1] |
| 341 | 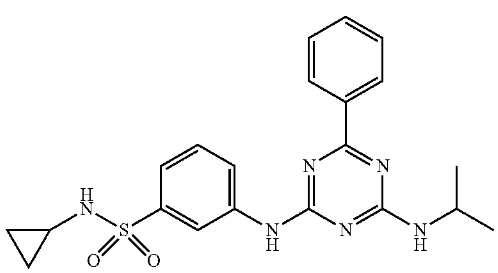 [SMILES: CC(C)Nc1nc(Nc2cccc(S(=O)(=O)NC3CC3)c2)nc(-c2ccccc2)n1] |
| 342 | 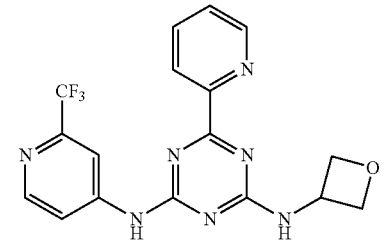 |
| 343 | |
| 344 | |
| 345 | |
| 346 | |

TABLE 1-continued
Representative Compounds
| Cmpd No | Structure |
|---|---|
| 347 | 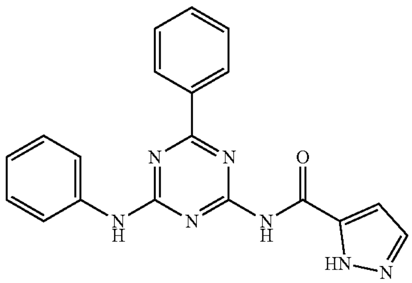 [SMILES: O=C(Nc1nc(Nc2ccccc2)nc(-c2ccccc2)n1)c1ccn[nH]1] |
| 348 | 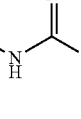 |
| 350 | 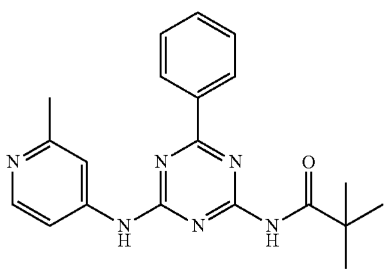 [SMILES: Cc1cc(Nc2nc(NC(=O)C(C)(C)C)nc(-c3ccccc3)n2)ccn1] |
| 351 | 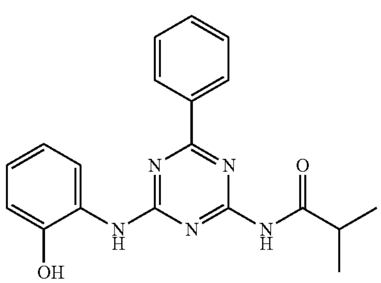 [SMILES: CC(C)C(=O)Nc1nc(Nc2ccccc2O)nc(-c2ccccc2)n1] |
| 352 | 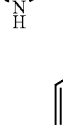 |
| 353 | 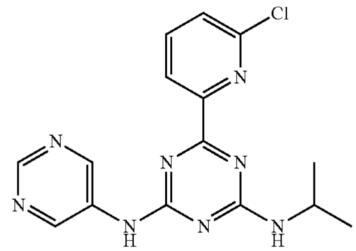 [SMILES: CC(C)Nc1nc(Nc2cncnc2)nc(-c2cccc(Cl)n2)n1] |
| 354 | 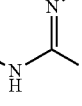 |
| 355 | 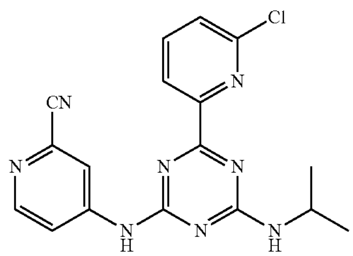 |
| 356 | 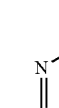 |
| 357 | 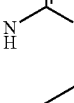 |
| 358 | 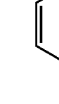 |

TABLE 1-continued

Representative Compounds

| Cmpd No | Structure |
|---|---|
| 359 | (structure) |
| 360 | (structure) |
| 361 | (structure) |
| 362 | (structure) |
| 363 | (structure) |
| 364 | (structure) |
| 365 | (structure) |
| 366 | (structure) |
| 367 | (structure) |
| 368 | (structure) |

TABLE 1-continued

Representative Compounds

| Cmpd No | Structure |
|---|---|
| 369 | 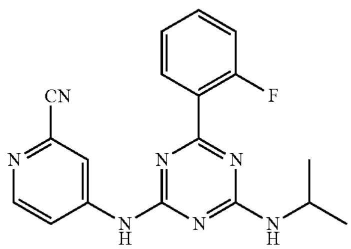 [SMILES: CC(C)Nc1nc(Nc2ccnc(C#N)c2)nc(-c2ccccc2F)n1] |
| 370 | 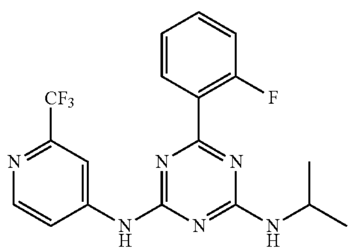 [SMILES: CC(C)Nc1nc(Nc2ccnc(C(F)(F)F)c2)nc(-c2ccccc2F)n1] |
| 371 | 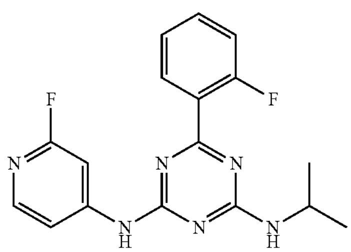 [SMILES: CC(C)Nc1nc(Nc2ccnc(F)c2)nc(-c2ccccc2F)n1] |
| 372 | 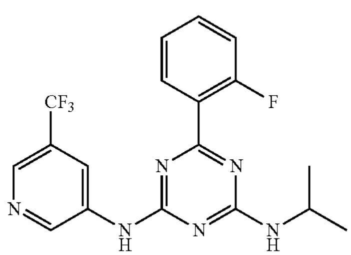 |
| 374 | 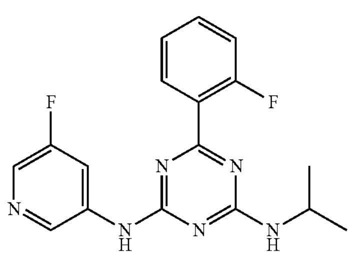 |
| 376 | 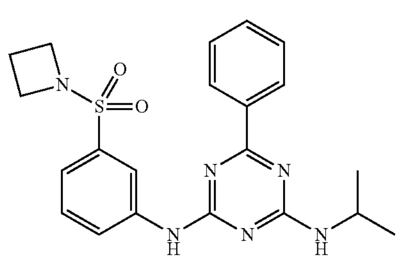 [SMILES: CC(C)Nc1nc(Nc2cccc(S(=O)(=O)N3CCC3)c2)nc(-c2ccccc2)n1] |
| 377 | 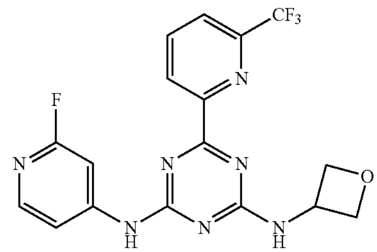 |
| 378 | 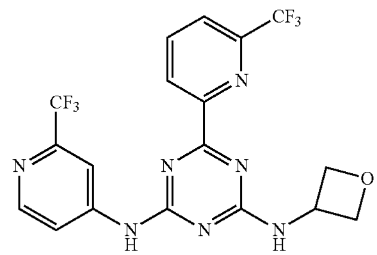 [SMILES: FC(F)(F)c1cc(Nc2nc(NC3COC3)nc(-c3cccc(C(F)(F)F)n3)n2)ccn1] |
| 379 | 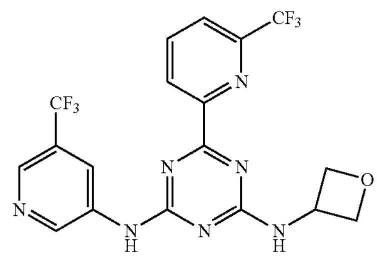 [SMILES: FC(F)(F)c1cncc(Nc2nc(NC3COC3)nc(-c3cccc(C(F)(F)F)n3)n2)c1] |
| 380 | 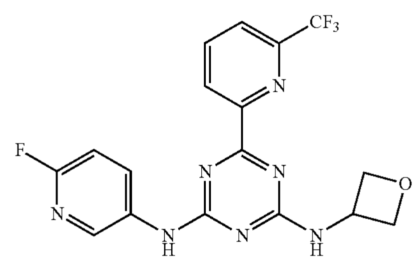 |
| 381 | 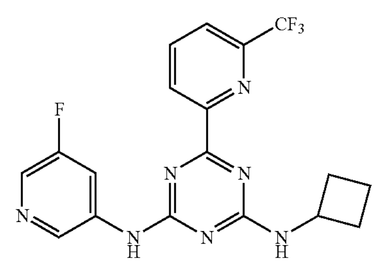 [SMILES: Fc1cncc(Nc2nc(NC3CCC3)nc(-c3cccc(C(F)(F)F)n3)n2)c1] |
| 382 | 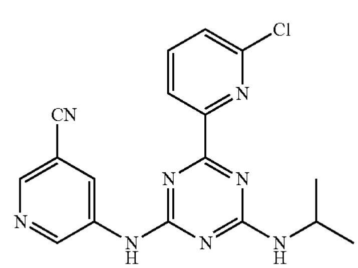 [SMILES: CC(C)Nc1nc(Nc2cncc(C#N)c2)nc(-c2cccc(Cl)n2)n1] |

TABLE 1-continued
Representative Compounds
| Cmpd No | Structure |
|---|---|
| 383 | 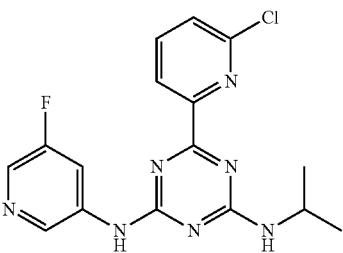 |
| 384 | 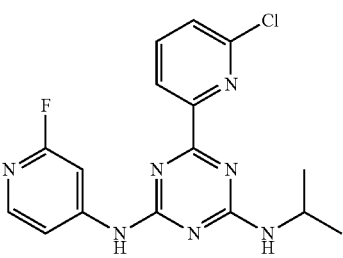 |
| 385 | 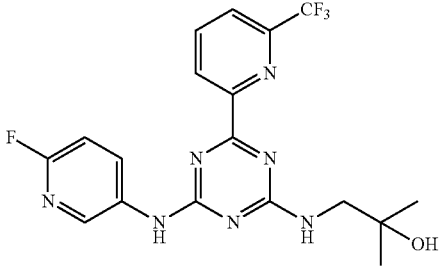 [SMILES: CC(C)(O)CNc1nc(Nc2ccc(F)nc2)nc(-c2cccc(C(F)(F)F)n2)n1] |
| 386 | 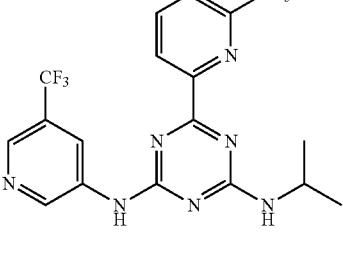 |
| 387 | 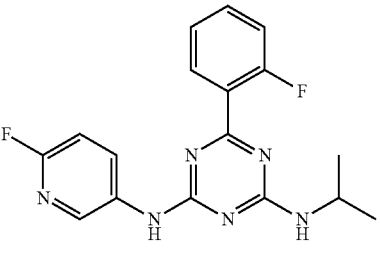 [SMILES: CC(C)Nc1nc(Nc2ccc(F)nc2)nc(-c2ccccc2F)n1] |
| 388 | 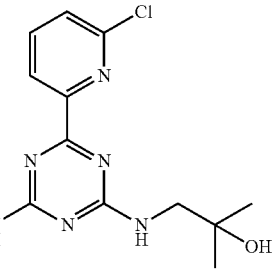 |
| 389 | 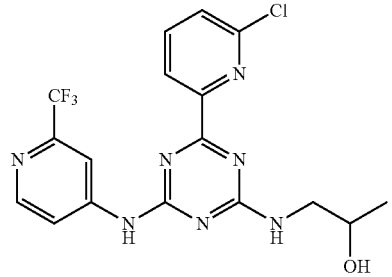 [SMILES: CC(O)CNc1nc(Nc2ccnc(C(F)(F)F)c2)nc(-c2cccc(Cl)n2)n1] |
| 390 | 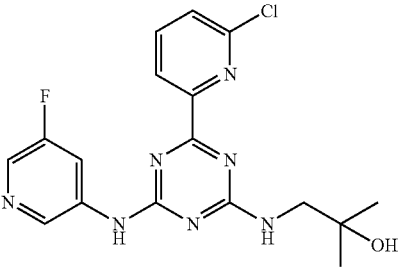 [SMILES: CC(C)(O)CNc1nc(Nc2cncc(F)c2)nc(-c2cccc(Cl)n2)n1] |
| 391 | 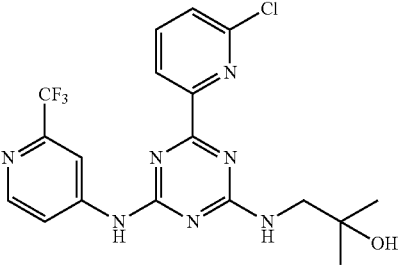 [SMILES: CC(C)(O)CNc1nc(Nc2ccnc(C(F)(F)F)c2)nc(-c2cccc(Cl)n2)n1] |
| 392 | 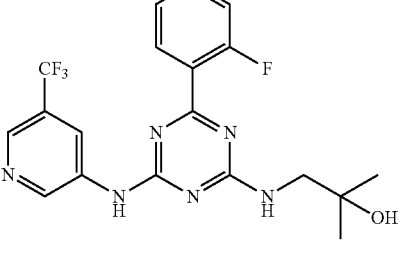 |

TABLE 1-continued

Representative Compounds

| Cmpd No | Structure |
|---|---|
| 393 | 6-chloropyridin-2-yl triazine with 2-fluoropyridin-4-ylamino and oxetan-3-ylamino substituents |
| 394 | 6-chloropyridin-2-yl triazine with 5-(trifluoromethyl)pyridin-3-ylamino and isopropylamino substituents |
| 395 | 6-(1,1-difluoroethyl)pyridin-2-yl triazine with 3-(methylsulfonyl)phenylamino and isopropylamino substituents |
| 396 | 6-chloropyridin-2-yl triazine with 2-(trifluoromethyl)pyridin-4-ylamino and isopropylamino substituents |
| 397 | 6-cyclopropylpyridin-2-yl triazine with 3-(methylsulfonyl)phenylamino and isopropylamino substituents |
| 398 | 6-aminopyridin-2-yl triazine with 3,5-difluorophenylamino and isopropylamino substituents |
| 399 | 6-chloropyridin-2-yl triazine with 5-fluoropyridin-3-ylamino and isobutylamino substituents |
| 400 | 6-chloropyridin-2-yl triazine with 3-(azetidin-1-ylsulfonyl)phenylamino and isopropylamino substituents |
| 401 | 6-(trifluoromethyl)pyridin-2-yl triazine with 5-cyanopyridin-3-ylamino and isopropylamino substituents |
| 402 | 6-(trifluoromethyl)pyridin-2-yl triazine with 2-fluoropyridin-4-ylamino and (tetrahydrofuran-2-ylmethyl)amino substituents |

TABLE 1-continued

Representative Compounds

| Cmpd No | Structure |
|---|---|
| 403 | (structure) |
| 404 | (structure) |
| 405 | (structure) |
| 406 | (structure) |
| 407 | (structure) |
| 408 | (structure) |
| 409 | (structure) |
| 410 | (structure) |
| 411 | (structure) |
| 412 | (structure) |

TABLE 1-continued

Representative Compounds

| Cmpd No | Structure |
|---|---|
| 413 | 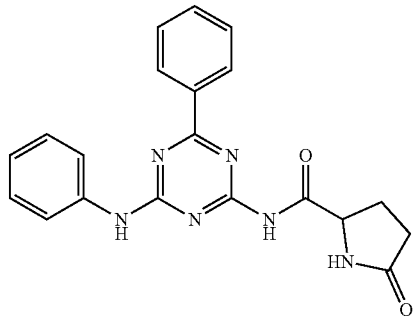 [SMILES: O=C1CCC(C(=O)Nc2nc(Nc3ccccc3)nc(-c3ccccc3)n2)N1] |
| 414 | 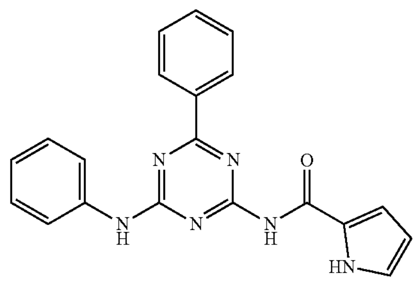 [SMILES: O=C(Nc1nc(Nc2ccccc2)nc(-c2ccccc2)n1)c1ccc[nH]1] |
| 415 | 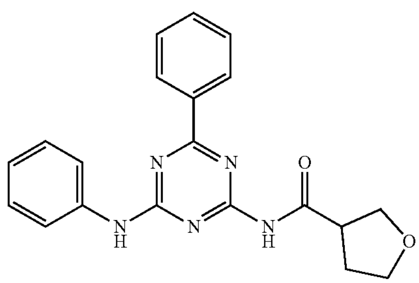 [SMILES: O=C(Nc1nc(Nc2ccccc2)nc(-c2ccccc2)n1)C1CCOC1] |
| 416 | 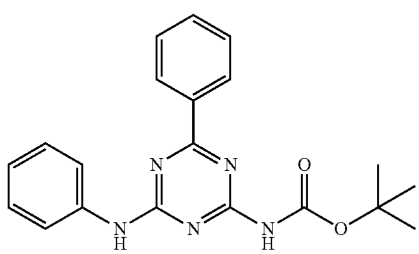 [SMILES: CC(C)(C)OC(=O)Nc1nc(Nc2ccccc2)nc(-c2ccccc2)n1] |
| 450 | 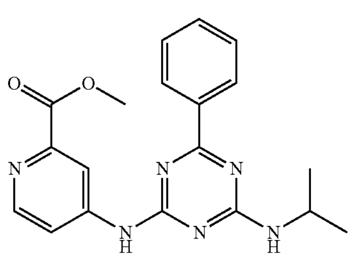 [SMILES: COC(=O)c1cc(Nc2nc(NC(C)C)nc(-c3ccccc3)n2)ccn1] |
| 451 | |
| 452 | |
| 454 | |
| 455 | |
| 456 | |

TABLE 1-continued

Representative Compounds

| Cmpd No | Structure |
|---|---|
| 458 | 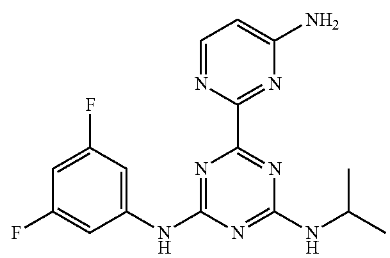 |
| 459 | 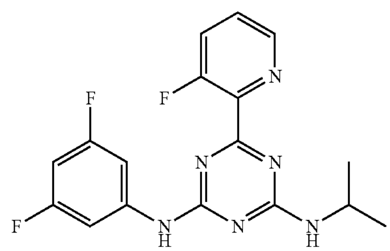 [SMILES: CC(C)Nc1nc(Nc2cc(F)cc(F)c2)nc(-c2ncccc2F)n1] |
| 460 | 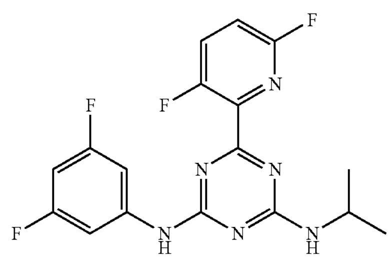 [SMILES: CC(C)Nc1nc(Nc2cc(F)cc(F)c2)nc(-c2nc(F)ccc2F)n1] |
| 461 | 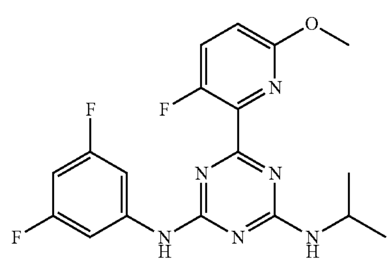 [SMILES: COc1ccc(F)c(-c2nc(Nc3cc(F)cc(F)c3)nc(NC(C)C)n2)n1] |
| 462 | 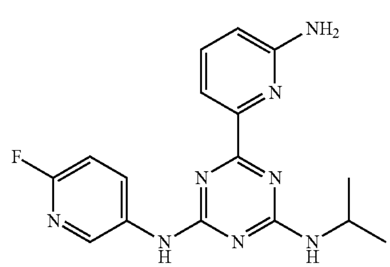 [SMILES: CC(C)Nc1nc(Nc2ccc(F)nc2)nc(-c2cccc(N)n2)n1] |
| 463 | |
| 464 | |
| 465 | |
| 466 | |
| 467 | |

TABLE 1-continued

Representative Compounds

| Cmpd No | Structure |
|---|---|
| 468 | 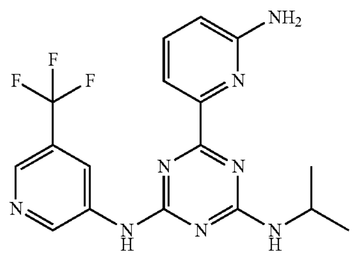 [SMILES: CC(C)Nc1nc(Nc2cncc(C(F)(F)F)c2)nc(-c2cccc(N)n2)n1] |
| 469 | 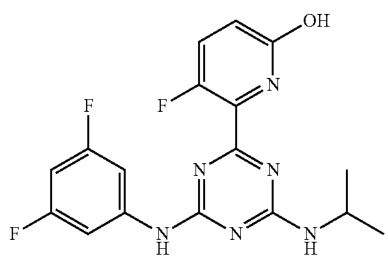 [SMILES: CC(C)Nc1nc(Nc2cc(F)cc(F)c2)nc(-c2nc(O)ccc2F)n1] |
| 470 | 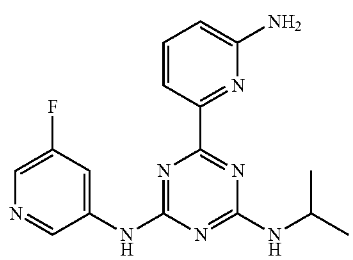 |
| 471 | 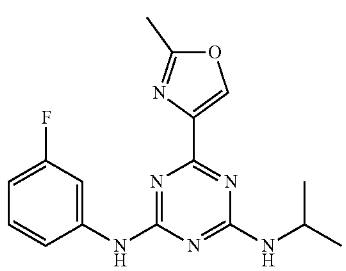 [SMILES: Cc1nc(-c2nc(Nc3cccc(F)c3)nc(NC(C)C)n2)co1] |
| 472 | 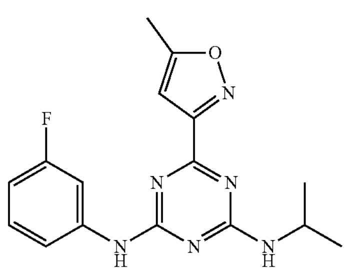 [SMILES: Cc1cc(-c2nc(Nc3cccc(F)c3)nc(NC(C)C)n2)no1] |
| 473 | |
| 474 | |
| 475 | |
| 476 | |
| 477 | |

TABLE 1-continued

Representative Compounds

| Cmpd No | Structure |
|---|---|
| 478 | [chemical structure: 2-(4-amino-pyrimidin-2-yl)-N-(3,5-difluorophenyl)-N'-(cyclopropylmethyl)-1,3,5-triazine-2,4-diamine] |
| 479 | [chemical structure: 2-(4-amino-pyrimidin-2-yl)-N-(3,5-difluorophenyl)-N'-tert-butyl-1,3,5-triazine-2,4-diamine] |
| 480 | [chemical structure: 2-(4-amino-pyrimidin-2-yl)-N-(3,5-difluorophenyl)-N'-(2,2,2-trifluoroethyl)-1,3,5-triazine-2,4-diamine] |
| 481 | [chemical structure: 2-(4-amino-6-trifluoromethyl-pyrimidin-2-yl)-N-(3,5-difluorophenyl)-N'-isopropyl-1,3,5-triazine-2,4-diamine] |
| 482 | [chemical structure: 2-(2-amino-pyrimidin-4-yl)-N-(3,5-difluorophenyl)-N'-isopropyl-1,3,5-triazine-2,4-diamine] |
| 483 | [chemical structure: 2-(4,6-dichloropyridin-2-yl)-N-(3-(methylsulfonyl)phenyl)-N'-isopropyl-1,3,5-triazine-2,4-diamine] |
| 484 | [chemical structure: 2-(3-fluoro-6-trifluoromethylpyridin-2-yl)-N-(3-(methylsulfonyl)phenyl)-N'-isopropyl-1,3,5-triazine-2,4-diamine] |
| 485 | [chemical structure: 2-(6-amino-4-chloropyridin-2-yl)-N-(3,5-difluorophenyl)-N'-isopropyl-1,3,5-triazine-2,4-diamine] |
| 486 | [chemical structure: 2-(4-chloro-6-methoxypyridin-2-yl)-N-(3,5-difluorophenyl)-N'-isopropyl-1,3,5-triazine-2,4-diamine] |
| 487 | [chemical structure: 2-(4-hydroxymethyl-6-trifluoromethylpyridin-2-yl)-N-(3,5-difluorophenyl)-N'-isopropyl-1,3,5-triazine-2,4-diamine] |

TABLE 1-continued

Representative Compounds

| Cmpd No | Structure |
|---|---|
| 488 | (structure) |
| 489 | (structure) |
| 490 | (structure) |
| 491 | (structure) |
| 492 | (structure) |
| 493 | (structure) |
| 494 | (structure) |
| 495 | (structure) |
| 496 | (structure) |
| 497 | (structure) |

| Cmpd No | Structure |
|---|---|
| 498 | 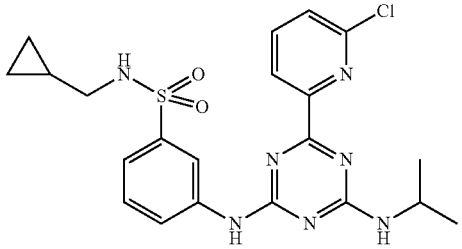 [SMILES: CC(C)Nc1nc(Nc2cccc(S(=O)(=O)NCC3CC3)c2)nc(-c2cccc(Cl)n2)n1] |
| 499 | 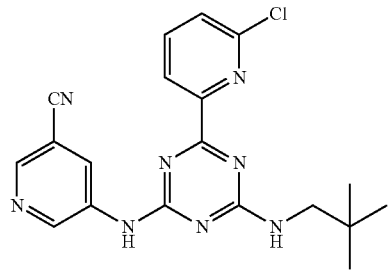 [SMILES: CC(C)(C)CNc1nc(Nc2cncc(C#N)c2)nc(-c2cccc(Cl)n2)n1] |
| 500 | 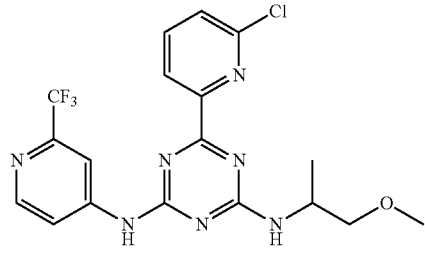 [SMILES: COCC(C)Nc1nc(Nc2ccnc(C(F)(F)F)c2)nc(-c2cccc(Cl)n2)n1] |
| 501 | 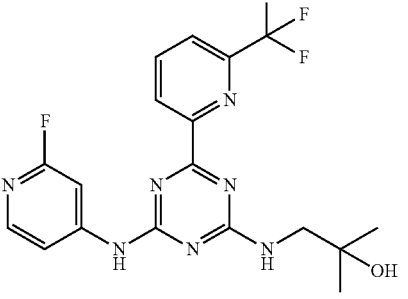 |
| 502 | 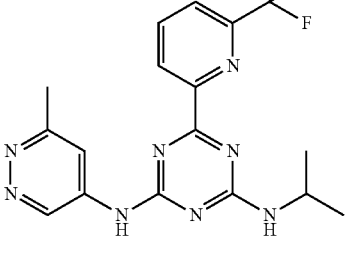 |
| 503 | 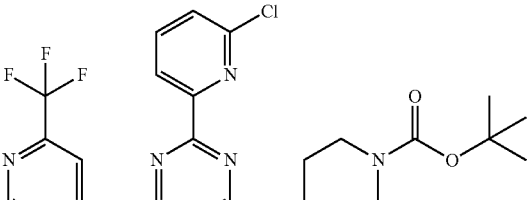 |
| 504 | 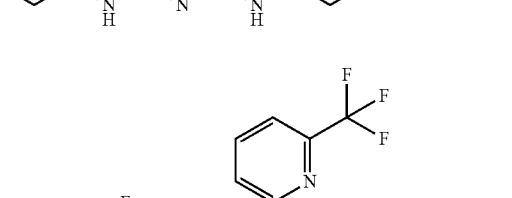 |
| 505 | 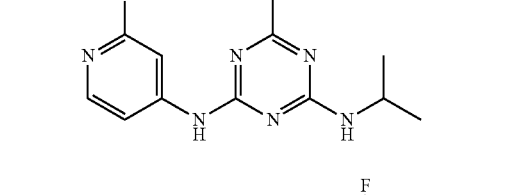 |
| 506 | 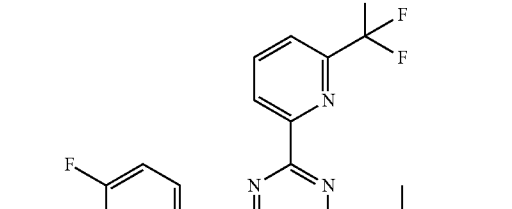 |
| 507 | 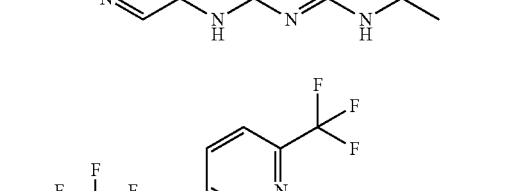 |

TABLE 1-continued

Representative Compounds

| Cmpd No | Structure |
|---|---|
| 508 | |
| 509 | |
| 510 | |
| 511 | |
| 512 | |
| 513 | 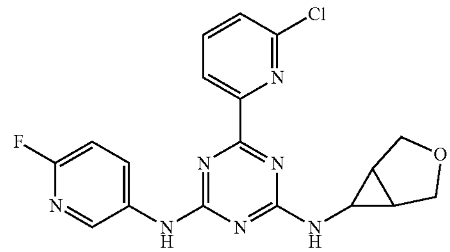 [SMILES: Fc1ccc(Nc2nc(NC3C4COCC43)nc(-c3cccc(Cl)n3)n2)cn1] |
| 514 | 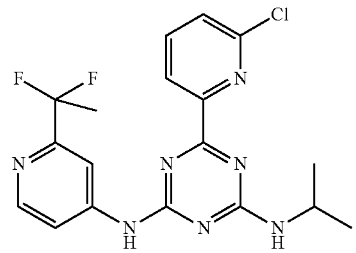 [SMILES: CC(C)Nc1nc(Nc2ccnc(C(C)(F)F)c2)nc(-c2cccc(Cl)n2)n1] |
| 515 | 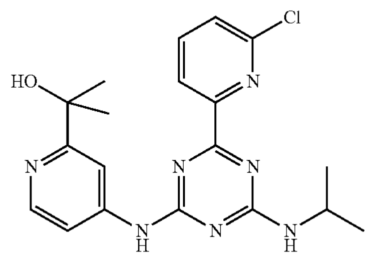 [SMILES: CC(C)Nc1nc(Nc2ccnc(C(C)(C)O)c2)nc(-c2cccc(Cl)n2)n1] |
| 516 | 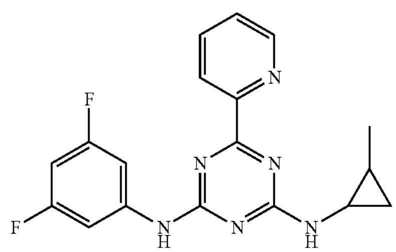 [SMILES: CC1CC1Nc1nc(Nc2cc(F)cc(F)c2)nc(-c2ccccn2)n1] |
| 517 | 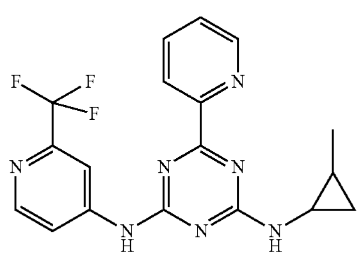 [SMILES: CC1CC1Nc1nc(Nc2ccnc(C(F)(F)F)c2)nc(-c2ccccn2)n1] |
| 518 | 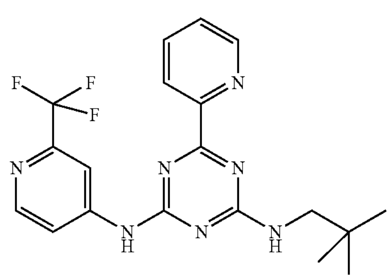 [SMILES: CC(C)(C)CNc1nc(Nc2ccnc(C(F)(F)F)c2)nc(-c2ccccn2)n1] |

TABLE 1-continued

Representative Compounds

| Cmpd No | Structure |
|---|---|
| 519 | 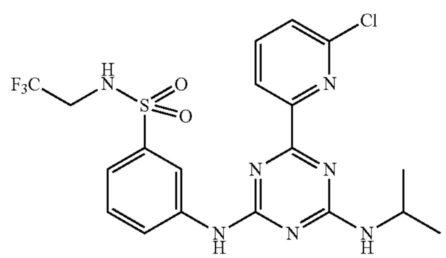 [SMILES: CC(C)Nc1nc(Nc2cccc(S(=O)(=O)NCC(F)(F)F)c2)nc(-c2cccc(Cl)n2)n1] |
| 521 | 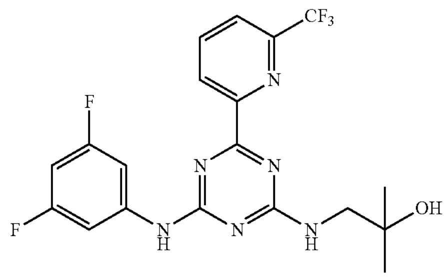 [SMILES: CC(C)(O)CNc1nc(Nc2cc(F)cc(F)c2)nc(-c2cccc(C(F)(F)F)n2)n1] |
| 522 | 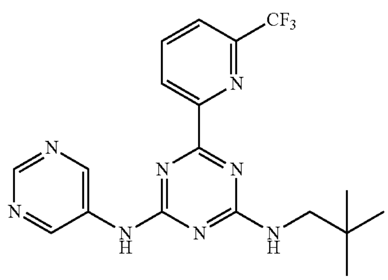 [SMILES: CC(C)(C)CNc1nc(Nc2cncnc2)nc(-c2cccc(C(F)(F)F)n2)n1] |
| 523 | 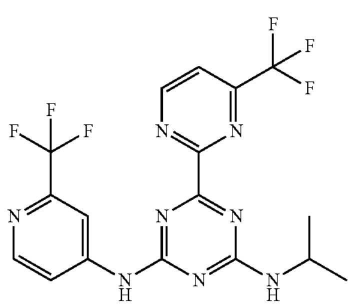 [SMILES: CC(C)Nc1nc(Nc2ccnc(C(F)(F)F)c2)nc(-c2nccc(C(F)(F)F)n2)n1] |
| 524 | 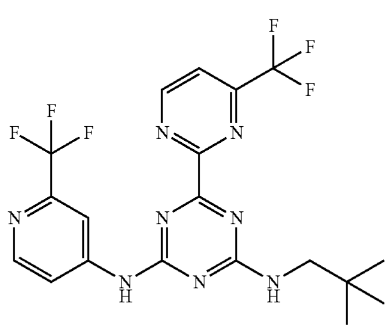 [SMILES: CC(C)(C)CNc1nc(Nc2ccnc(C(F)(F)F)c2)nc(-c2nccc(C(F)(F)F)n2)n1] |
| 526 | 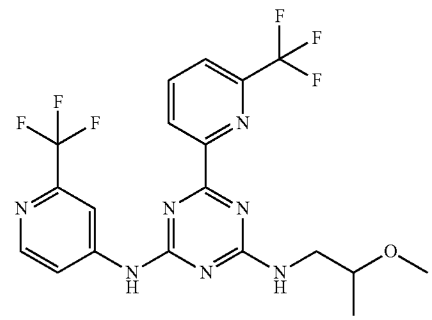 [SMILES: COC(C)CNc1nc(Nc2ccnc(C(F)(F)F)c2)nc(-c2cccc(C(F)(F)F)n2)n1] |
| 527 | 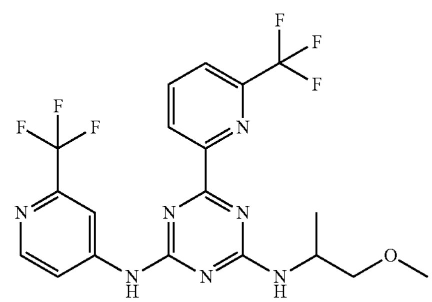 [SMILES: COCC(C)Nc1nc(Nc2ccnc(C(F)(F)F)c2)nc(-c2cccc(C(F)(F)F)n2)n1] |
| 528 | 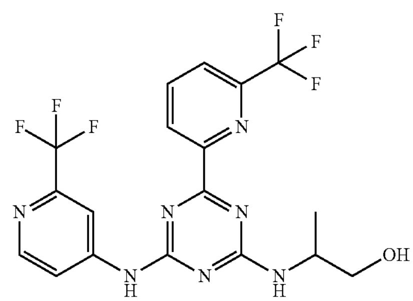 |
| 529 | 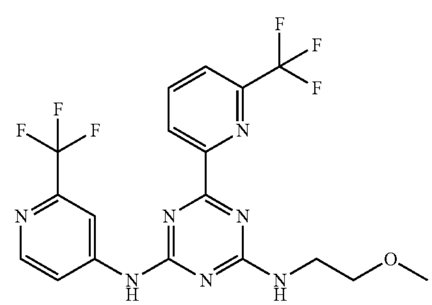 [SMILES: COCCNc1nc(Nc2ccnc(C(F)(F)F)c2)nc(-c2cccc(C(F)(F)F)n2)n1] |
| 530 | 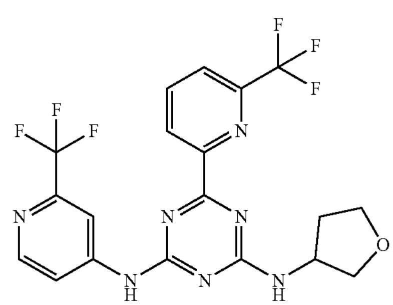 [SMILES: FC(F)(F)c1cc(Nc2nc(NC3CCOC3)nc(-c3cccc(C(F)(F)F)n3)n2)ccn1] |

TABLE 1-continued

Representative Compounds

| Cmpd No | Structure |
|---|---|
| 531 | (structure) |
| 532 | (structure) |
| 533 | (structure) |
| 534 | (structure) |
| 535 | (structure) |
| 536 | (structure) |
| 537 | (structure) |
| 538 | (structure) |
| 540 | (structure) |

TABLE 1-continued
Representative Compounds
| Cmpd No | Structure |
|---|---|
| 541 | 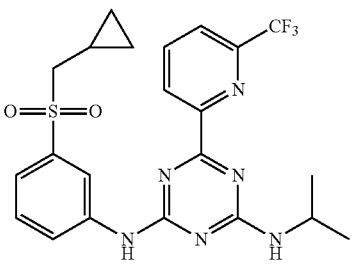 [SMILES: CC(C)Nc1nc(Nc2cccc(S(=O)(=O)CC3CC3)c2)nc(-c2cccc(C(F)(F)F)n2)n1] |
| 542 | 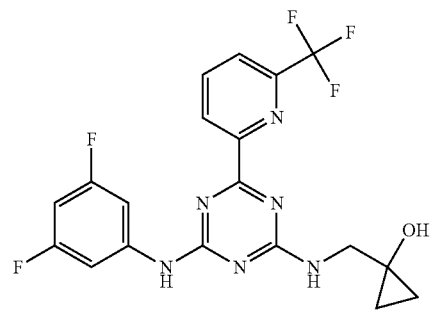 [SMILES: OC1(CNc2nc(Nc3cc(F)cc(F)c3)nc(-c3cccc(C(F)(F)F)n3)n2)CC1] |
| 543 | 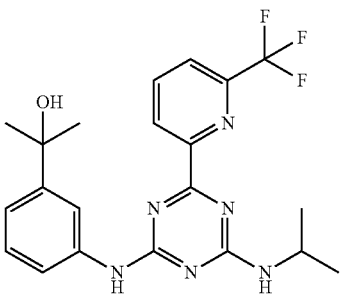 [SMILES: CC(C)Nc1nc(Nc2cccc(C(C)(C)O)c2)nc(-c2cccc(C(F)(F)F)n2)n1] |
| 544 | 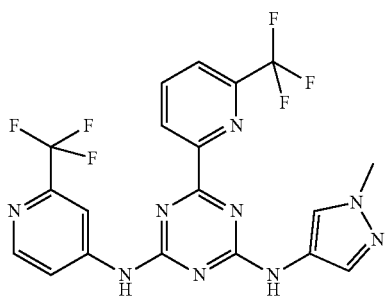 [SMILES: Cn1cc(Nc2nc(Nc3ccnc(C(F)(F)F)c3)nc(-c3cccc(C(F)(F)F)n3)n2)cn1] |
| 545 | 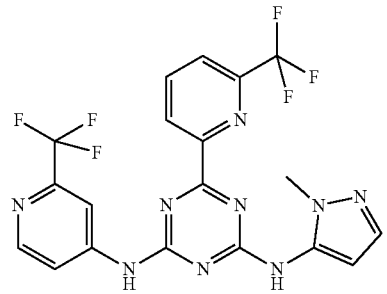 [SMILES: Cn1nccc1Nc1nc(Nc2ccnc(C(F)(F)F)c2)nc(-c2cccc(C(F)(F)F)n2)n1] |
| 546 | 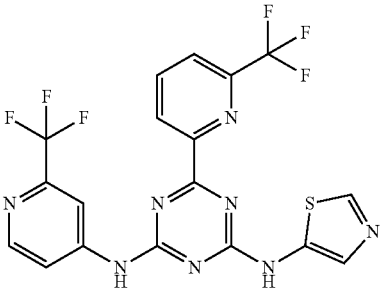 [SMILES: FC(F)(F)c1cc(Nc2nc(Nc3cncs3)nc(-c3cccc(C(F)(F)F)n3)n2)ccn1] |
| 547 | 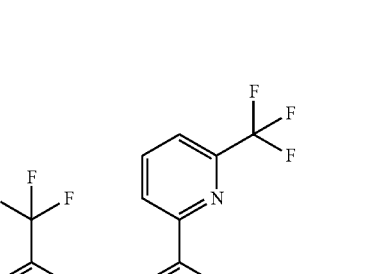 |
| 548 | 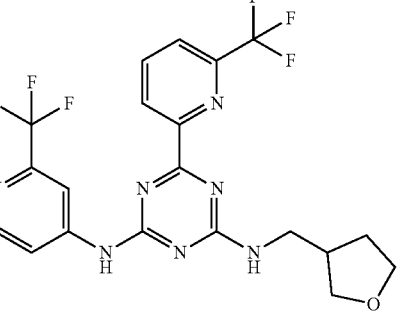 |
| 549 | 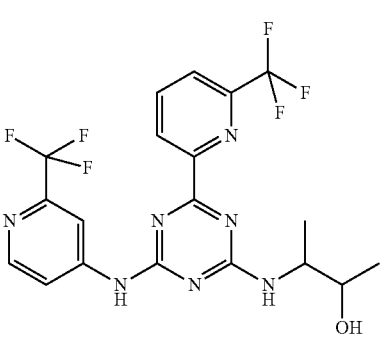 [SMILES: CC(O)C(C)Nc1nc(Nc2ccnc(C(F)(F)F)c2)nc(-c2cccc(C(F)(F)F)n2)n1] |

TABLE 1-continued

Representative Compounds

| Cmpd No | Structure |
|---|---|
| 550 | (structure) |
| 551 | (structure) |
| 552 | (structure) |
| 554 | (structure) |
| 555 | (structure) |
| 556 | (structure) |
| 557 | (structure) |
| 558 | (structure) |
| 559 | (structure) |

TABLE 1-continued

Representative Compounds

| Cmpd No | Structure |
|---|---|
| 560 | (structure) |
| 561 | (structure) |
| 562 | (structure) |
| 563 | (structure) |
| 564 | (structure) |
| 565 | (structure) |
| 566 | (structure) |
| 567 | (structure) |
| 568 | (structure) |
| 569 | (structure) |

TABLE 1-continued

Representative Compounds

| Cmpd No | Structure |
|---|---|
| 570 | (structure) |
| 571 | (structure) |
| 572 | (structure) |
| 573 | (structure) |
| 574 | (structure) |
| 576 | (structure) |
| 577 | (structure) |
| 578 | (structure) |
| 580 | (structure) |
| 581 | (structure) |

TABLE 1-continued

Representative Compounds

| Cmpd No | Structure |
|---|---|
| 582 | (structure) |
| 583 | (structure) |
| 584 | (structure) |
| 585 | (structure) |
| 586 | (structure) |
| 587 | (structure) |
| 588 | (structure) |
| 589 | (structure) |
| 590 | (structure) |

TABLE 1-continued

Representative Compounds

| Cmpd No | Structure |
|---|---|
| 591 | (structure) |
| 592 | (structure) |
| 593 | (structure) |
| 594 | (structure) |
| 595 | (structure) |
| 596 | (structure) |
| 597 | (structure) |
| 598 | (structure) |
| 599 | (structure) |

TABLE 1-continued

Representative Compounds

| Cmpd No | Structure |
|---|---|
| 600 | (structure) |
| 601 | (structure) |
| 602 | (structure) |
| 603 | (structure) |
| 604 | (structure) |
| 605 | (structure) |
| 606 | (structure) |
| 607 | (structure) |
| 608 | (structure) |
| 609 | (structure) |

TABLE 1-continued

Representative Compounds

| Cmpd No | Structure |
|---|---|
| 610 | |
| 611 | |
| 612 | |
| 613 | |
| 614 | 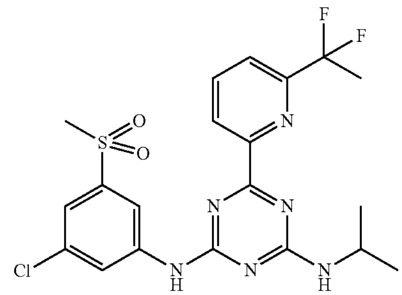 [SMILES: CC(C)Nc1nc(Nc2cc(Cl)cc(S(C)(=O)=O)c2)nc(-c2cccc(C(C)(F)F)n2)n1] |
| 615 | 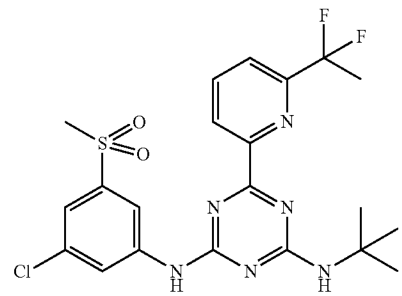 [SMILES: CC(C)(C)Nc1nc(Nc2cc(Cl)cc(S(C)(=O)=O)c2)nc(-c2cccc(C(C)(F)F)n2)n1] |
| 616 | 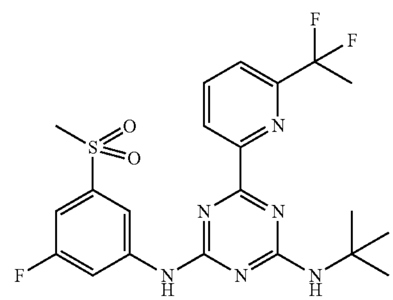 [SMILES: CC(C)(C)Nc1nc(Nc2cc(F)cc(S(C)(=O)=O)c2)nc(-c2cccc(C(C)(F)F)n2)n1] |
| 617 | 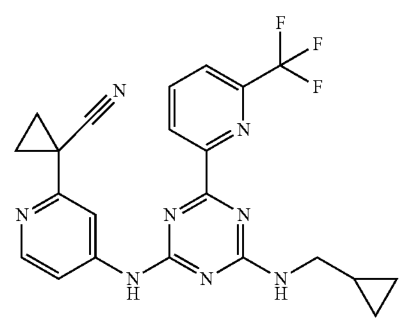 [SMILES: N#CC1(c2cc(Nc3nc(NCC4CC4)nc(-c4cccc(C(F)(F)F)n4)n3)ccn2)CC1] |
| 618 | 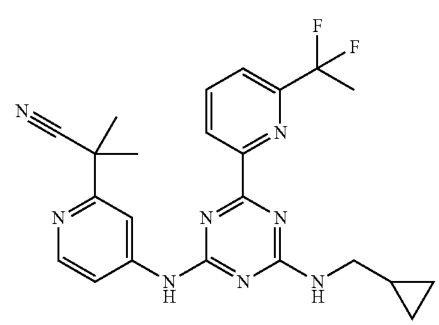 [SMILES: CC(F)(F)c1cccc(-c2nc(NCC3CC3)nc(Nc3ccnc(C(C)(C)C#N)c3)n2)n1] |

TABLE 1-continued
Representative Compounds
| Cmpd No | Structure |
|---|---|
| 619 | 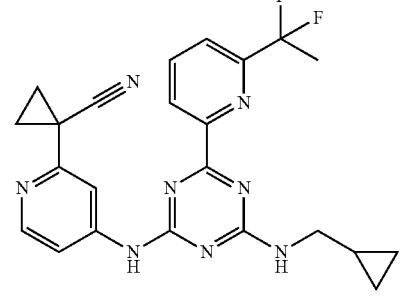 |
| 621 | 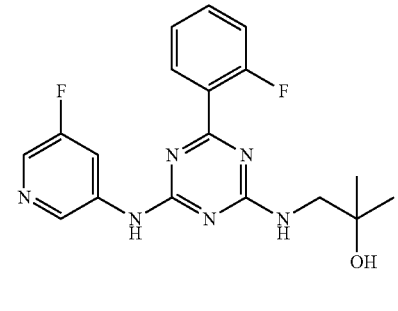 [SMILES: CC(C)(O)CNc1nc(Nc2cncc(F)c2)nc(-c2ccccc2F)n1] |
| 622 | 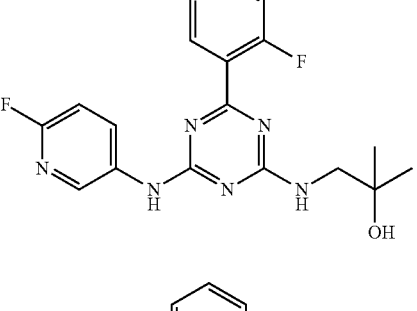 |
| 623 | 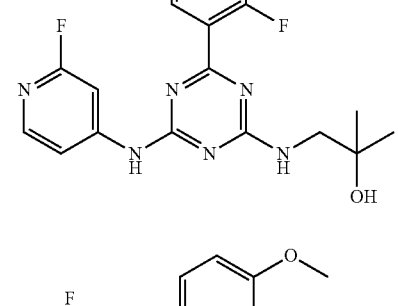 |
| 624 | 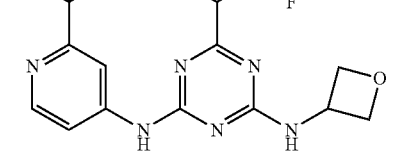 |
| 625 | 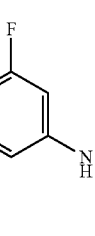 |
| 626 | 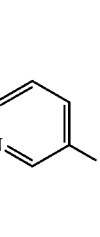 |
| 627 | 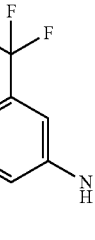 |
| 628 | 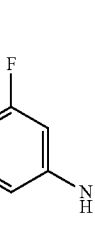 |
| 629 | 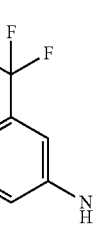 |
| 630 | 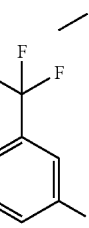 |

TABLE 1-continued
Representative Compounds
| Cmpd No | Structure |
|---|---|
| 631 | 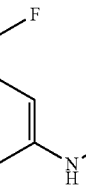 |
| 632 | 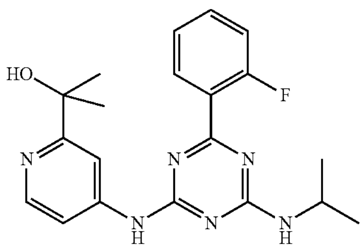 [SMILES: CC(C)Nc1nc(Nc2ccnc(C(C)(C)O)c2)nc(-c2ccccc2F)n1] |
| 633 | 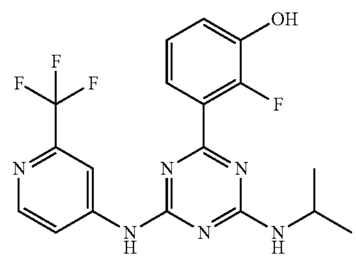 [SMILES: CC(C)Nc1nc(Nc2ccnc(C(F)(F)F)c2)nc(-c2cccc(O)c2F)n1] |
| 634 | 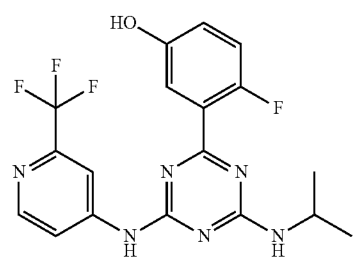 [SMILES: CC(C)Nc1nc(Nc2ccnc(C(F)(F)F)c2)nc(-c2cc(O)ccc2F)n1] |
| 635 | 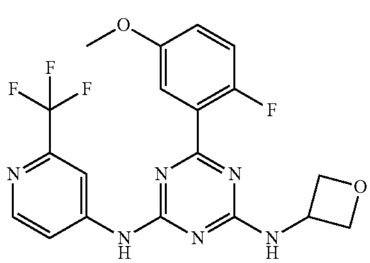 [SMILES: COc1ccc(F)c(-c2nc(Nc3ccnc(C(F)(F)F)c3)nc(NC3COC3)n2)c1] |
| 636 | 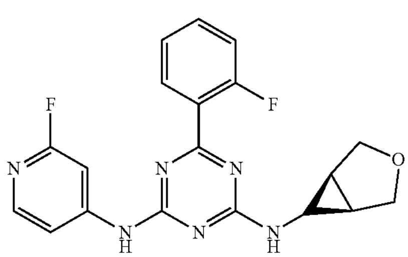 |
TABLE 1-continued
Representative Compounds
| Cmpd No | Structure |
|---|---|
| 637 | 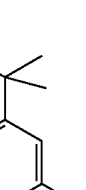 |
| 638 | 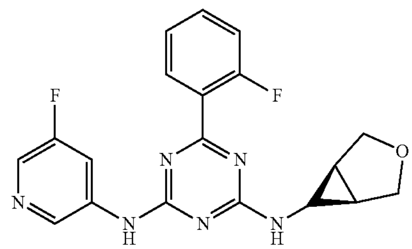 |
| 639 | 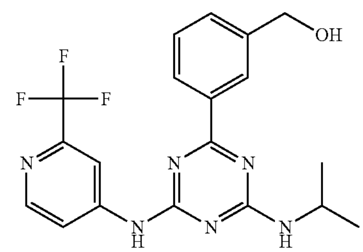 [SMILES: CC(C)Nc1nc(Nc2ccnc(C(F)(F)F)c2)nc(-c2cccc(CO)c2)n1] |
| 640 | 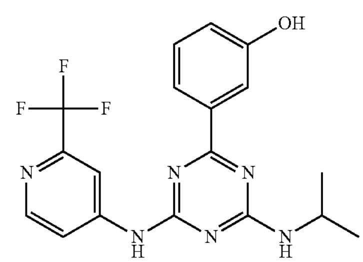 [SMILES: CC(C)Nc1nc(Nc2ccnc(C(F)(F)F)c2)nc(-c2cccc(O)c2)n1] |
| 641 | 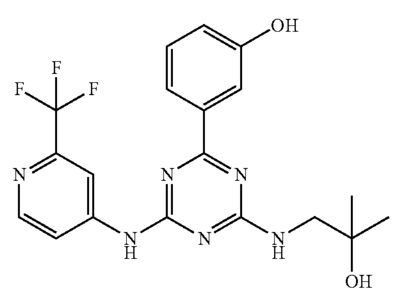 [SMILES: CC(C)(O)CNc1nc(Nc2ccnc(C(F)(F)F)c2)nc(-c2cccc(O)c2)n1] |

TABLE 1-continued

Representative Compounds

| Cmpd No | Structure |
|---|---|
| 642 | (structure) |
| 644 | (structure) |
| 645 | (structure) |
| 646 | (structure) |
| 647 | (structure) |
| 648 | (structure) |
| 649 | (structure) |
| 650 | (structure) |
| 651 | (structure) |
| 652 | (structure) |

TABLE 1-continued
Representative Compounds
| Cmpd No | Structure |
|---|---|
| 653 | 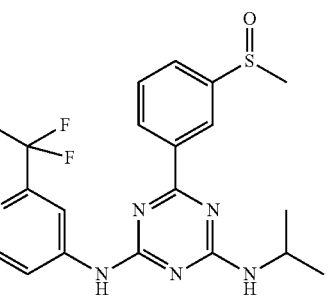 |
| 654 | 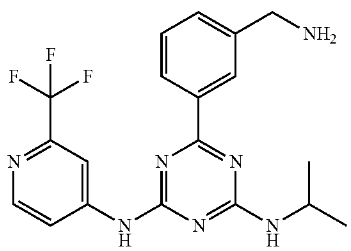 [SMILES: CC(C)Nc1nc(Nc2ccnc(C(F)(F)F)c2)nc(-c2cccc(CN)c2)n1] |
| 655 | 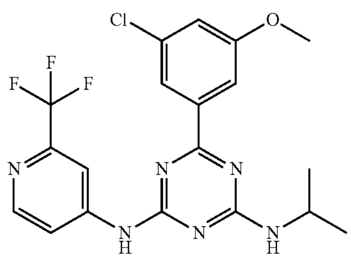 [SMILES: COc1cc(Cl)cc(-c2nc(Nc3ccnc(C(F)(F)F)c3)nc(NC(C)C)n2)c1] |
| 657 | 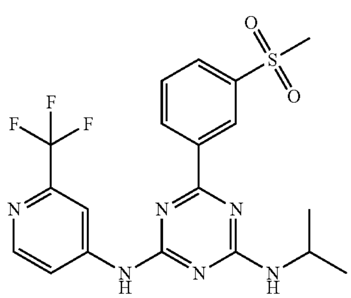 [SMILES: CC(C)Nc1nc(Nc2ccnc(C(F)(F)F)c2)nc(-c2cccc(S(C)(=O)=O)c2)n1] |
| 658 | 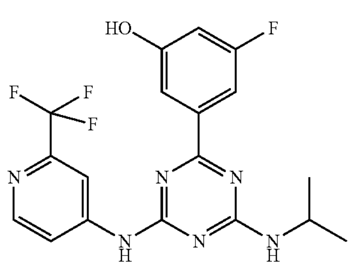 [SMILES: CC(C)Nc1nc(Nc2ccnc(C(F)(F)F)c2)nc(-c2cc(O)cc(F)c2)n1] |
| 660 | |
| 662 | |
| 663 | |
| 664 | |
| 665 | |

TABLE 1-continued

Representative Compounds

| Cmpd No | Structure |
|---|---|
| 667 | 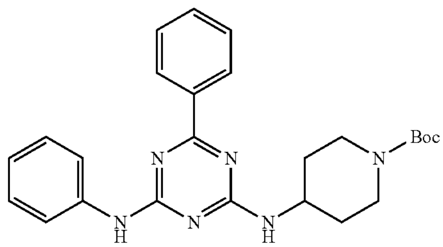 [SMILES: CC(C)(C)OC(=O)N1CCC(Nc2nc(Nc3ccccc3)nc(-c3ccccc3)n2)CC1] |
| 669 | 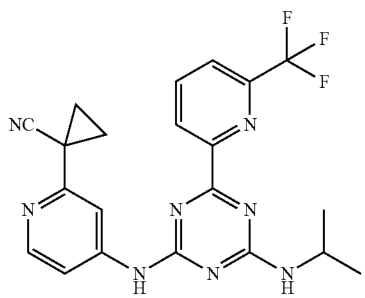 [SMILES: CC(C)Nc1nc(Nc2ccnc(C3(C#N)CC3)c2)nc(-c2cccc(C(F)(F)F)n2)n1] |
| 670 | 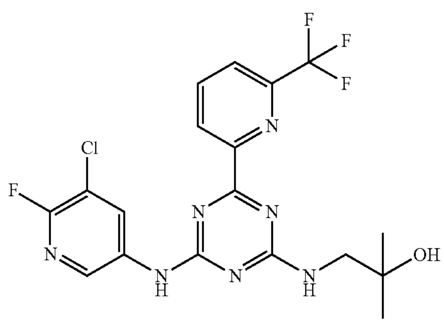 [SMILES: CC(C)(O)CNc1nc(Nc2cnc(F)c(Cl)c2)nc(-c2cccc(C(F)(F)F)n2)n1] |
| 671 | 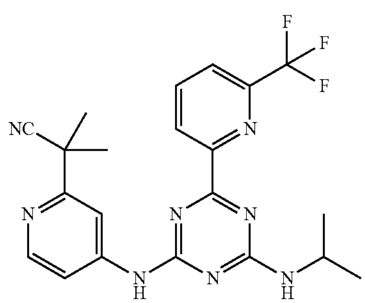 [SMILES: CC(C)Nc1nc(Nc2ccnc(C(C)(C)C#N)c2)nc(-c2cccc(C(F)(F)F)n2)n1] |
| 672 | 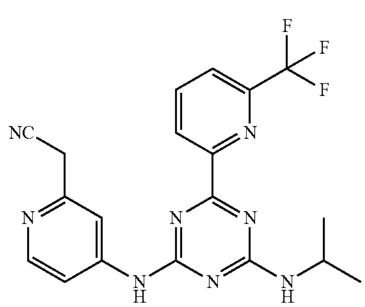 [SMILES: CC(C)Nc1nc(Nc2ccnc(CC#N)c2)nc(-c2cccc(C(F)(F)F)n2)n1] |
| 673 | |
| 674 | |
| 675 | |
| 676 | |
| 677 | |

TABLE 1-continued

Representative Compounds

| Cmpd No | Structure |
|---|---|
| 678 | 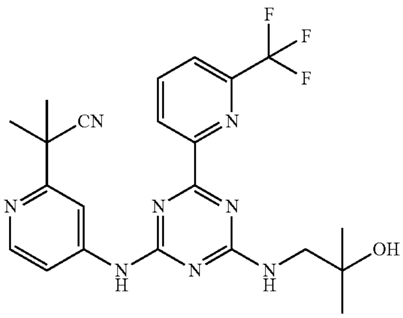 [SMILES: CC(C)(O)CNc1nc(Nc2ccnc(C(C)(C)C#N)c2)nc(-c2cccc(C(F)(F)F)n2)n1] |
| 679 | 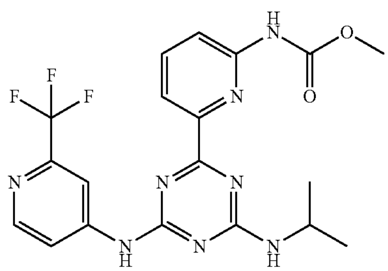 [SMILES: COC(=O)Nc1cccc(-c2nc(Nc3ccnc(C(F)(F)F)c3)nc(NC(C)C)n2)n1] |
| 680 | 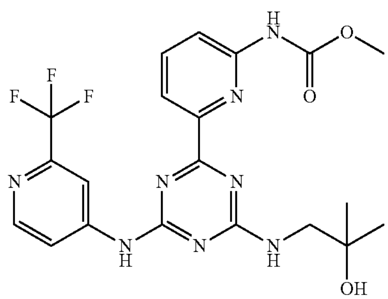 [SMILES: COC(=O)Nc1cccc(-c2nc(NCC(C)(C)O)nc(Nc3ccnc(C(F)(F)F)c3)n2)n1] |
| 681 | 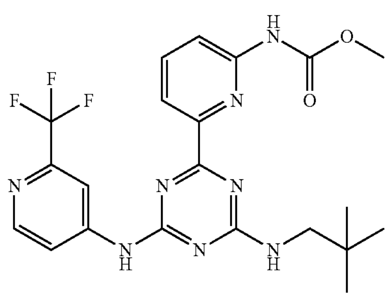 [SMILES: COC(=O)Nc1cccc(-c2nc(NCC(C)(C)C)nc(Nc3ccnc(C(F)(F)F)c3)n2)n1] |
| 682 | 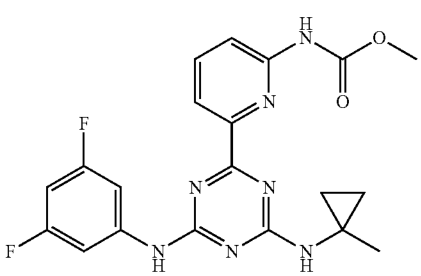 [SMILES: COC(=O)Nc1cccc(-c2nc(Nc3cc(F)cc(F)c3)nc(NC3(C)CC3)n2)n1] |
| 683 | |
| 684 | |
| 685 | |
| 686 | |
| 687 | |

TABLE 1-continued

Representative Compounds

| Cmpd No | Structure |
|---|---|
| 689 | 2-amino-6-[2-(trifluoromethyl)pyridin-4-ylamino]-N-neopentyl-1,3,5-triazine-2,4-diamine derivative |
| 690 | 2-amino-6-[2-(trifluoromethyl)pyridin-4-ylamino]-N-isobutyl-1,3,5-triazine-2,4-diamine derivative |
| 691 | 2-(6-aminopyridin-2-yl)-N-(3,5-difluorophenyl)-N'-(2-hydroxy-2-methylpropyl)-1,3,5-triazine-2,4-diamine derivative |
| 692 | 2-amino-6-[2-(trifluoromethyl)pyridin-4-ylamino]-N-(1-methylcyclopropyl)-1,3,5-triazine-2,4-diamine derivative |
| 693 | 2-(6-aminopyridin-2-yl)-N-(3,5-difluorophenyl)-N'-(1-methylcyclopropyl)-1,3,5-triazine-2,4-diamine derivative |
| 694 | 2-amino-6-[2-(trifluoromethyl)pyridin-4-ylamino]-N-(1,1,1-trifluoropropan-2-yl)-1,3,5-triazine-2,4-diamine derivative |
| 695 | 2-amino-6-[2-(trifluoromethyl)pyridin-4-ylamino]-N-tert-butyl-1,3,5-triazine-2,4-diamine derivative |
| 696 | 2-amino-6-[2-(difluoromethyl)pyridin-4-ylamino]-N-isopropyl-1,3,5-triazine-2,4-diamine derivative |
| 697 | N-acetyl derivative of 2-amino-6-[2-(trifluoromethyl)pyridin-4-ylamino]-N-isopropyl-1,3,5-triazine-2,4-diamine |
| 698 | 2-(6-aminopyridin-2-yl)-N-(3,5-difluorophenyl)-N'-tert-butyl-1,3,5-triazine-2,4-diamine derivative |

TABLE 1-continued

Representative Compounds

| Cmpd No | Structure |
|---|---|
| 699 | 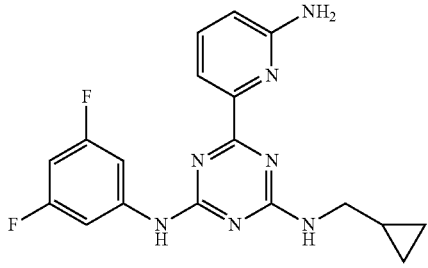 [SMILES: Nc1cccc(-c2nc(NCC3CC3)nc(Nc3cc(F)cc(F)c3)n2)n1] |

Included herein are also methods for making compounds of Formula I or a compound of any one of the embodiments described herein comprising reacting

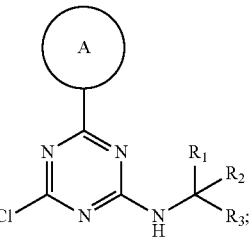

with

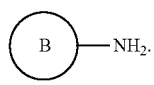

In some embodiments, the preceding methods comprise step (1) reacting

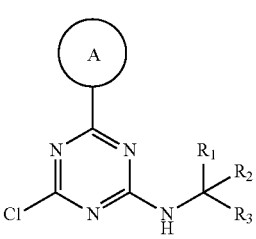

with

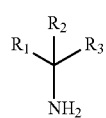

to give

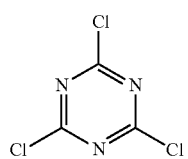

and step (2) reacting

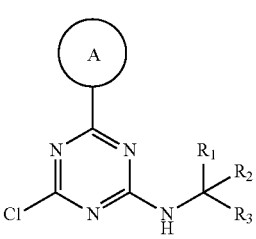

with

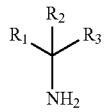

In other embodiments, the preceding methods comprise step (1) reacting

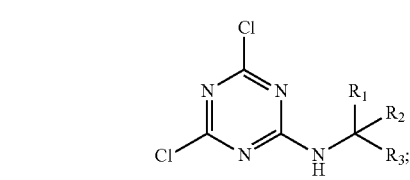

with

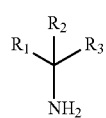

to give

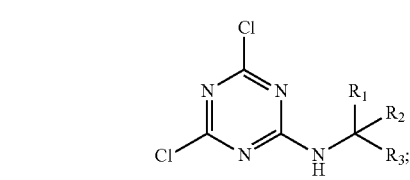

121
step (2) reacting
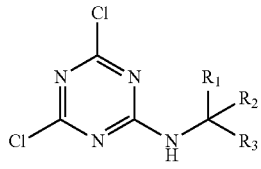
with
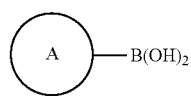
to give
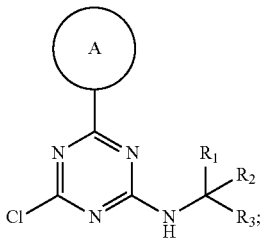
and step (3) reacting
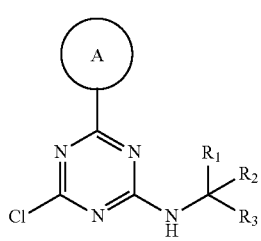
with
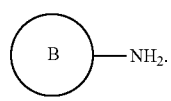
Also included are methods for making compounds of Formula I or a compound of any one of the embodiments described herein comprising reacting
122
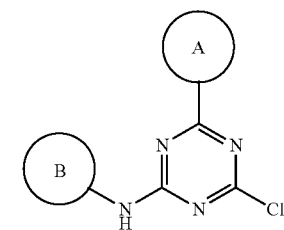
with
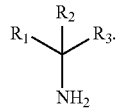
In some embodiments, the preceding methods comprise step (1) reacting
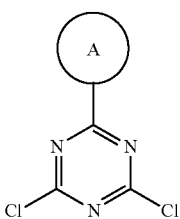
with
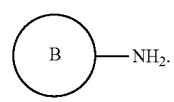
to give
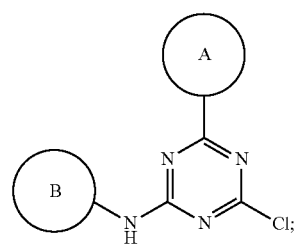

and step (2) reacting

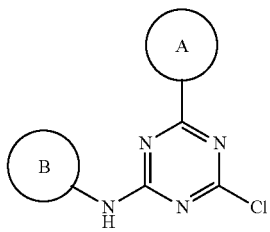

with

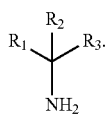

In other embodiments, the preceding methods wherein $R^1$ and $R^3$ are taken together with the carbon atom to form C(=O), comprise step (1) reacting

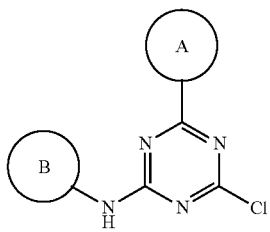

with $NH_3$ to give

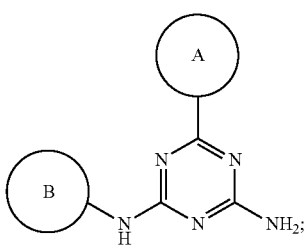

and step (2) reacting

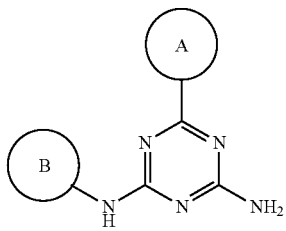

with $R^2C(O)Cl$ or $R^2C(O)OMe$.

Also included are methods for making compounds of Formula I or a compound of any one of the embodiments described herein comprising reacting

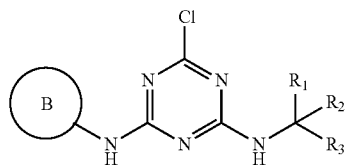

with

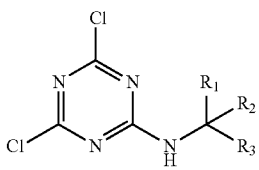

In some embodiments, the preceding methods comprise step (1) reacting

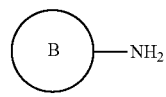

with

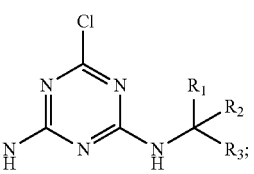

to give

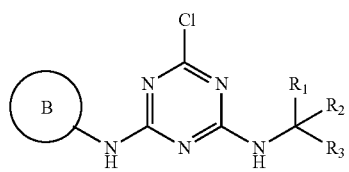

and step (2) reacting

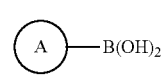

with

Also included are methods for making compounds of Formula I or a compound of any one of the embodiments described herein comprising reacting

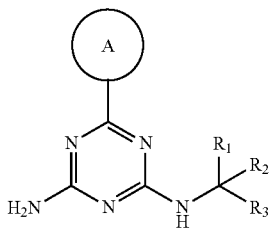

with

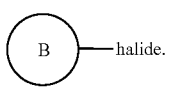

In some embodiments, the preceding methods comprise step (1) reacting

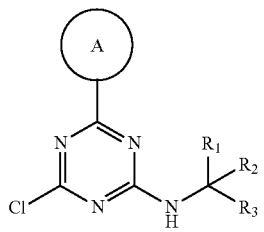

with NH₃ to give

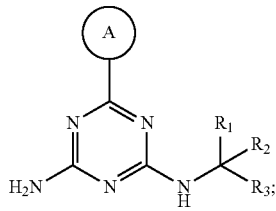

and step (2) reacting

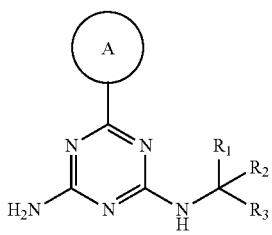

with

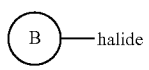

Also included are methods for making compounds of Formula I or a compound of any one of the embodiments described herein comprising reacting

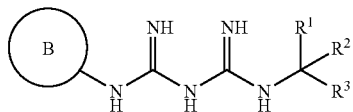

with

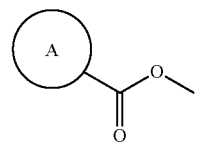

In some embodiments, the preceding methods comprise step (1) reacting

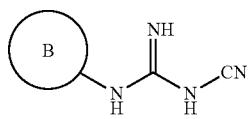

with

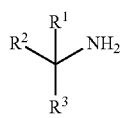

to give

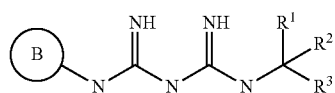

and step (2) reacting

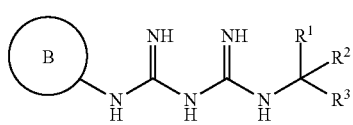

with

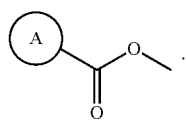

In other embodiments, the preceding methods comprise step (1) converting

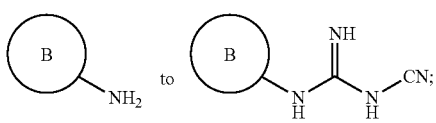

step (2) reacting with

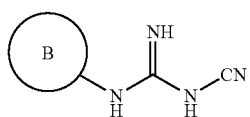

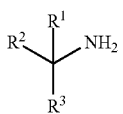

to give

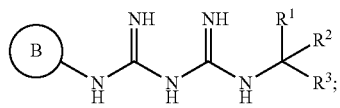

and step (3) reacting

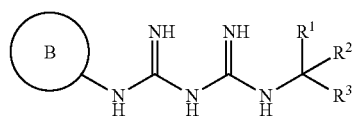

with

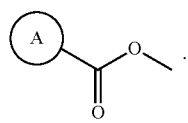

The compounds of one aspect of this invention may contain one or more asymmetric centers and thus occur as racemates, racemic mixtures, scalemic mixtures, and diastereomeric mixtures, as well as single enantiomers or individual stereoisomers that are substantially free from another possible enantiomer or stereoisomer. The term "substantially free of other stereoisomers" as used herein means a preparation enriched in a compound having a selected stereochemistry at one or more selected stereocenters by at least about 60%, 65%, 70%, 75%, 80%, 85%, 90%, 95%, 96%, 97%, 98%, or 99%. The term "enriched" means that at least the designated percentage of a preparation is the compound having a selected stereochemistry at one or more selected stereocenters. Methods of obtaining or synthesizing an individual enantiomer or stereoisomer for a given compound are known in the art and may be applied as practicable to final compounds or to starting material or intermediates.

In certain embodiments, the compound of Formula I or II is enriched for a structure or structures having a selected stereochemistry at one or more carbon atoms. For example, the compound is enriched in the specific stereoisomer by at least about 60%, 65%, 70%, 75%, 80%, 85%, 90%, 95%, 96%, 97%, 98%, or 99%.

The compounds of Formula I or II may also comprise one or more isotopic substitutions. For example, H may be in any isotopic form, including $^1H$, $^2H$ (D or deuterium), and $^3H$ (T or tritium); C may be in any isotopic form, including $^{12}C$, $^{13}C$, and $^{14}C$; O may be in any isotopic form, including $^{16}O$ and $^{18}O$; and the like. For example, the compound is enriched in a specific isotopic form of H, C and/or O by at least about 60%, 65%, 70%, 75%, 80%, 85%, 90%, 95%, 96%, 97%, 98%, or 99%.

Unless otherwise indicated when a disclosed compound is named or depicted by a structure without specifying the stereochemistry and has one or more chiral centers, it is understood to represent all possible stereoisomers of the compound.

The compounds of one aspect of this invention may also be represented in multiple tautomeric forms, in such instances, one aspect of the invention expressly includes all tautomeric forms of the compounds described herein, even though only a single tautomeric form may be represented (e.g., alkylation of a ring system may result in alkylation at multiple sites, one aspect of the invention expressly includes all such reaction products; and keto-enol tautomers). All such isomeric forms of such compounds are expressly included herein.

It may be convenient or desirable to prepare, purify, and/or handle a corresponding salt of the active compound, for example, a pharmaceutically-acceptable salt. Examples of pharmaceutically acceptable salts are discussed in Berge et al., 1977, "Pharmaceutically Acceptable Salts." J. Pharm. Sci. Vol. 66, pp. 1-19.

For example, if the compound is anionic, or has a functional group which may be anionic (e.g., —COOH may be —COO$^-$), then a salt may be formed with a suitable cation. Examples of suitable inorganic cations include, but are not limited to, alkali metal ions such as Na$^+$ and K$^+$, alkaline earth cations such as Ca$^{2+}$ and Mg$^{2+}$, and other cations such as Al$^{3+}$. Examples of suitable organic cations include, but are not limited to, ammonium ion (i.e., NH$_4^+$) and substituted ammonium ions (e.g., NH$_3$R$^+$, NH$_2$R$_2^+$, NHR$_3^+$, NR$_4^+$) Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH$_3$)$_4^+$.

If the compound is cationic, or has a functional group that may be cationic (e.g., —NH$_2$ may be —NH$_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucoheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Mesylates of each compound in Table 1 are explicitly included herein. Examples of suitable polymeric organic anions include, but are not limited to, those derived from the following polymeric acids: tannic acid, carboxymethyl cellulose.

The compounds provided herein therefore include the compounds themselves, as well as their salts, hydrates and their prodrugs, if applicable. The compounds provided herein may be modified and converted to prodrugs by appending appropriate functionalities to enhance selected biological properties, e.g., targeting to a particular tissue. Such modifications (i.e., prodrugs) are known in the art and include those which increase biological penetration into a given biological compartment (e.g., blood, lymphatic system, central nervous system), increase oral availability, increase solubility to allow administration by injection, alter metabolism and alter rate of excretion. Examples of prodrugs include esters (e.g., phosphates, amino acid (e.g., valine) esters), carbamates and other pharmaceutically acceptable derivatives, which, upon administration to a subject, are capable of providing active compounds. Calcium and sodium phosphates of each compound in Table 1, if applicable, are explicitly included herein. Amino acid (e.g., valine) esters of each compound in Table 1, if applicable, are explicitly included herein.

Compositions and Routes of Administration

The compounds utilized in the methods described herein may be formulated together with a pharmaceutically acceptable carrier or adjuvant into pharmaceutically acceptable compositions prior to be administered to a subject. In another embodiment, such pharmaceutically acceptable compositions further comprise additional therapeutic agents in amounts effective for achieving a modulation of disease or disease symptoms, including those described herein.

The term "pharmaceutically acceptable carrier or adjuvant" refers to a carrier or adjuvant that may be administered to a subject, together with a compound of one aspect of this invention, and which does not destroy the pharmacological activity thereof and is nontoxic when administered in doses sufficient to deliver a therapeutic amount of the compound.

Pharmaceutically acceptable carriers, adjuvants and vehicles that may be used in the pharmaceutical compositions of one aspect of this invention include, but are not limited to, ion exchangers, alumina, aluminum stearate, lecithin, self-emulsifying drug delivery systems (SEDDS) such as d-α-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives may also be advantageously used to enhance delivery of compounds of the formulae described herein.

The pharmaceutical compositions of one aspect of this invention may be administered orally, parenterally, by inhalation spray, topically, rectally, nasally, buccally, vaginally or via an implanted reservoir, preferably by oral administration or administration by injection. The pharmaceutical compositions of one aspect of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

The pharmaceutical compositions of one aspect of this invention may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

The pharmaceutical compositions of one aspect of this invention may also be administered in the form of suppositories for rectal administration. These compositions can be prepared by mixing a compound of one aspect of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions of one aspect of this invention is useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of one aspect of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier with suitable emulsifying agents. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of one aspect of this invention may also be topically applied to the lower intestinal tract by rectal suppository formulation or in a suitable enema formulation.

Topically-transdermal patches are also included in one aspect of this invention.

The pharmaceutical compositions of one aspect of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

When the compositions of one aspect of this invention comprise a combination of a compound of the formulae described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds of one aspect of this invention. Alternatively, those agents may be part of a single dosage form, mixed together with the compounds of one aspect of this invention in a single composition.

The compounds described herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.5 to about 100 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions of one aspect of this invention will be administered from about 1 to about 6 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Alternatively, such preparations contain from about 20% to about 80% active compound.

Lower or higher doses than those recited above may be required. Specific dosage and treatment regimens for any particular subject will depend upon a variety of factors, including the activity of the specific compound employed, the age, body weight, general health status, sex, diet, time of administration, rate of excretion, drug combination, the severity and course of the disease, condition or symptoms, the subject's disposition to the disease, condition or symptoms, and the judgment of the treating physician.

Upon improvement of a subject's condition, a maintenance dose of a compound, composition or combination of one aspect of this invention may be administered, if necessary. Subsequently, the dosage or frequency of administration, or both, may be reduced, as a function of the symptoms, to a level at which the improved condition is retained when the symptoms have been alleviated to the desired level. Subjects may, however, require intermittent treatment on a long-term basis upon any recurrence of disease symptoms.

The pharmaceutical compositions described above comprising a compound of Structural Formula I or II or a compound described in any one of the embodiments herein, may further comprise another therapeutic agent useful for treating cancer.

Methods of Use

The inhibitory activities of the compounds provided herein against IDH2 mutants (e.g., IDH2R140Q and IDH2R172K) can be tested by methods described in Example 12 or analogous methods.

Provided is a method for inhibiting a mutant IDH2 activity comprising contacting a subject in need thereof with a compound of Structural Formula I or II, a compound described in any one of the embodiments herein, or a pharmaceutically acceptable salt thereof. In one embodiment, the cancer to be treated is characterized by a mutant allele of IDH2 wherein the IDH2 mutation results in a new ability of the enzyme to catalyze the NADPH-dependent reduction of α-ketoglutarate to R(−)-2-hydroxyglutarate in a subject. In one aspect of this embodiment, the mutant IDH2 has an R140X mutation. In another aspect of this embodiment, the R140X mutation is a R140Q mutation. In another aspect of this embodiment, the R140X mutation is a R140W mutation. In another aspect of this embodiment, the R140X mutation is a R140L mutation. In another aspect of this embodiment, the mutant IDH2 has an R172X mutation. In another aspect of this embodiment, the R172X mutation is a R172K mutation. In another aspect of this embodiment, the R172X mutation is a R172G mutation.

Also provided are methods of treating a cancer characterized by the presence of a mutant allele of IDH2 comprising the step of administering to subject in need thereof (a) a compound of Structural Formula I or II, a compound described in any one of the embodiments herein, or a pharmaceutically acceptable salt thereof, or (b) a pharmaceutical composition comprising (a) and a pharmaceutically acceptable carrier.

In one embodiment, the cancer to be treated is characterized by a mutant allele of IDH2 wherein the IDH2 mutation results in a new ability of the enzyme to catalyze the NADPH-dependent reduction of α-ketoglutarate to R(−)-2-hydroxyglutarate in a patient. In one aspect of this embodiment, the mutant IDH2 has an R140X mutation. In another aspect of this embodiment, the R140X mutation is a R140Q mutation. In another aspect of this embodiment, the R140X mutation is a R140W mutation. In another aspect of this embodiment, the R140X mutation is a R140L mutation. In another aspect of this embodiment, the mutant IDH2 has an R172X mutation. In another aspect of this embodiment, the R172X mutation is a R172K mutation. In another aspect of this embodiment, the R172X mutation is a R172G mutation. A cancer can be analyzed by sequencing cell samples to determine the presence and specific nature of (e.g., the changed amino acid present at) a mutation at amino acid 140 and/or 172 of IDH2.

Without being bound by theory, applicants believe that mutant alleles of IDH2 wherein the IDH2 mutation results in a new ability of the enzyme to catalyze the NADPH-dependent reduction of α-ketoglutarate to R(−)-2-hydroxyglutarate, and in particular R140Q and/or R172K mutations of IDH2, characterize a subset of all types of cancers, without regard to their cellular nature or location in the body. Thus, the compounds and methods of one aspect of this invention are useful to treat any type of cancer that is characterized by the presence of a mutant allele of IDH2 imparting such activity and in particular an IDH2 R140Q and/or R172K mutation.

In one aspect of this embodiment, the efficacy of cancer treatment is monitored by measuring the levels of 2HG in the subject. Typically levels of 2HG are measured prior to treatment, wherein an elevated level is indicated for the use of the compound of Formula I or II or a compound described in any one of the embodiments described herein to treat the cancer. Once the elevated levels are established, the level of 2HG is determined during the course of and/or following termination of treatment to establish efficacy. In certain embodiments, the level of 2HG is only determined during the course of and/or following termination of treatment. A reduction of 2HG levels during the course of treatment and following treatment is indicative of efficacy. Similarly, a determination that 2HG levels are not elevated during the course of or following treatment is also indicative of efficacy. Typically, the these 2HG measurements will be utilized together with other well-known determinations of efficacy of cancer treatment, such as reduction in number and size of tumors and/or other cancer-associated lesions, improvement in the general health of the subject, and alterations in other biomarkers that are associated with cancer treatment efficacy.

2HG can be detected in a sample by LC/MS. The sample is mixed 80:20 with methanol, and centrifuged at 3,000 rpm for 20 minutes at 4 degrees Celsius. The resulting supernatant can be collected and stored at −80 degrees Celsius prior to LC-MS/MS to assess 2-hydroxyglutarate levels. A variety of different liquid chromatography (LC) separation methods can be used. Each method can be coupled by negative electrospray ionization (ESI, −3.0 kV) to triple-quadrupole mass spectrometers operating in multiple reaction monitoring (MMR) mode, with MS parameters optimized on infused metabolite standard solutions. Metabolites can be separated by reversed phase chromatography using 10 mM tributyl-amine as an ion pairing agent in the aqueous mobile phase, according to a variant of a previously reported method (Luo et al. *J Chromatogr A* 1147, 153-64, 2007). One method allows resolution of TCA metabolites: t=0, 50% B; t=5, 95% B; t=7, 95% B; t=8, 0% B, where B refers to an organic mobile phase of 100% methanol. Another method is specific for 2-hydroxyglutarate, running a fast linear gradient from 50%-95% B (buffers as defined above) over 5 minutes. A Synergi Hydro-RP, 100 mm×2 mm, 2.1 μm particle size (Phenomonex) can be used as the column, as described above. Metabolites can be quantified by comparison of peak areas with pure metabolite standards at known concentration. Metabolite flux studies from $^{13}$C-glutamine can be performed as described, e.g., in Munger et al. *Nat Biotechnol* 26, 1179-86, 2008.

In one embodiment 2HG is directly evaluated.

In another embodiment a derivative of 2HG formed in process of performing the analytic method is evaluated. By way of example such a derivative can be a derivative formed in MS analysis. Derivatives can include a salt adduct, e.g., a Na adduct, a hydration variant, or a hydration variant which is also a salt adduct, e.g., a Na adduct, e.g., as formed in MS analysis.

In another embodiment a metabolic derivative of 2HG is evaluated. Examples include species that build up or are elevated, or reduced, as a result of the presence of 2HG, such as glutarate or glutamate that will be correlated to 2HG, e.g., R-2HG.

Exemplary 2HG derivatives include dehydrated derivatives such as the compounds provided below or a salt adduct thereof:

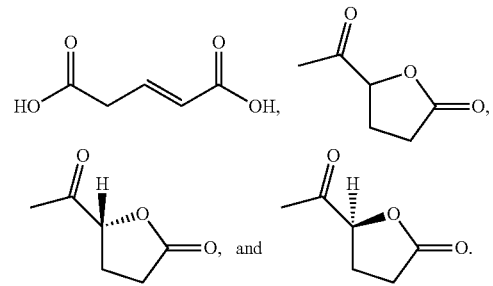

In one embodiment the cancer is a tumor wherein at least 30, 40, 50, 60, 70, 80 or 90% of the tumor cells carry an IDH2 mutation, and in particular an IDH2 R140Q, R140W, or R140L and/or R172K or R172G mutation, at the time of diagnosis or treatment.

In another embodiment, one aspect of the invention provides a method of treating a cancer selected from glioblastoma (glioma), myelodysplastic syndrome (MDS), myeloproliferative neoplasm (MPN), acute myelogenous leukemia (AML), sarcoma, melanoma, non-small cell lung cancer, chondrosarcoma, cholangiocarcinomas or angioimmunoblastic lymphoma in a patient by administering to the patient a compound of Formula I or Formula II in an amount effective to treat the cancer. In a more specific embodiment the cancer to be treated is glioma, myelodysplastic syndrome (MDS), myeloproliferative neoplasm (MPN), acute myelogenous leukemia (AML), melanoma, chondrosarcoma, or angioimmunoblastic non-Hodgkin's lymphoma (NHL).

2HG is known to accumulate in the inherited metabolic disorder 2-hydroxyglutaric aciduria. This disease is caused by deficiency in the enzyme 2-hydroxyglutarate dehydrogenase, which converts 2HG to α-KG (Struys, E. A. et al. Am J Hum Genet 76, 358-60 (2005)). Patients with 2-hydroxyglutarate dehydrogenase deficiencies accumulate 2HG in the brain as assessed by MRI and CSF analysis, develop leukoencephalopathy, and have an increased risk of developing brain tumors (Aghili, M., Zahedi, F. & Rafiee, J Neurooncol 91, 233-6 (2009); Kolker, S., Mayatepek, E. & Hoffmann, G. F. Neuropediatrics 33, 225-31 (2002); Wajner, M., Latini, A., Wyse, A. T. & Dutra-Filho, C. S. J Inherit Metab Dis 27, 427-48 (2004)). Furthermore, elevated brain levels of 2HG result in increased ROS levels (Kolker, S. et al. Eur J Neurosci 16, 21-8 (2002); Latini, A. et al. Eur J Neurosci 17, 2017-22 (2003)), potentially contributing to an increased risk of cancer. The ability of 2HG to act as an NMDA receptor agonist may contribute to this effect (Kolker, S. et al. Eur J Neurosci 16, 21-8 (2002)). 2HG may also be toxic to cells by competitively inhibiting glutamate and/or αKG utilizing enzymes. These include transaminases which allow utilization of glutamate nitrogen for amino and nucleic acid biosynthesis, and αKG-dependent prolyl hydroxylases such as those which regulate Hif1-alpha levels.

Thus, according to another embodiment, one aspect of the invention provides a method of treating 2-hydroxyglutaric aciduria, particularly D-2-hydroxyglutaric aciduria, in a patient by administering to the patient a compound of Structural Formula I or II or a compound described in any one of the embodiments described herein.

Treatment methods described herein can additionally comprise various evaluation steps prior to and/or following treatment with a compound of Structural Formula I or II or a compound described in any one of the embodiments described herein.

In one embodiment, prior to and/or after treatment with a compound of Structural Formula I or II or a compound described in any one of the embodiments described herein, the method further comprises the step of evaluating the growth, size, weight, invasiveness, stage and/or other phenotype of the cancer.

In one embodiment, prior to and/or after treatment with a compound of Formula I or II or a compound described in any one of the embodiments described herein, the method further comprises the step of evaluating the IDH2 genotype of the cancer. This may be achieved by ordinary methods in the art, such as DNA sequencing, immuno analysis, and/or evaluation of the presence, distribution or level of 2HG.

In one embodiment, prior to and/or after treatment with a compound of Formula I or II or a compound described in any one of the embodiments described herein, the method further comprises the step of determining the 2HG level in the subject. This may be achieved by spectroscopic analysis, e.g., magnetic resonance-based analysis, e.g., MRI and/or MRS measurement, sample analysis of bodily fluid, such as serum or spinal cord fluid analysis, or by analysis of surgical material, e.g., by mass-spectroscopy.

Combination Therapies

In some embodiments, the methods described herein comprise the additional step of co-administering to a subject in need thereof a second therapy e.g., an additional cancer therapeutic agent or an additional cancer treatment. Exemplary additional cancer therapeutic agents include for example, chemotherapy, targeted therapy, antibody therapies, immunotherapy, and hormonal therapy. Additional cancer treatments include, for example: surgery, and radiation therapy. Examples of each of these treatments are provided below.

The term "co-administering" as used herein with respect to an additional cancer therapeutic agents means that the additional cancer therapeutic agent may be administered together with a compound of one aspect of this invention as part of a single dosage form (such as a composition of one aspect of this invention comprising a compound of one aspect of the invention and an second therapeutic agent as described above) or as separate, multiple dosage forms. Alternatively, the additional cancer therapeutic agent may be administered prior to, consecutively with, or following the administration of a compound of one aspect of this invention. In such combination therapy treatment, both the compounds of one aspect of this invention and the second therapeutic agent(s) are administered by conventional methods. The administration of a composition of one aspect of this invention, comprising both a compound of one aspect of the invention and a second therapeutic agent, to a subject does not preclude the separate administration of that same therapeutic agent, any other second therapeutic agent or any compound of one aspect of this invention to said subject at another time during a course of treatment. The term "co-administering" as used herein with respect to an additional cancer treatment means that the additional cancer treatment may occur prior to, consecutively with, concurrently with or following the administration of a compound of one aspect of this invention.

In some embodiments, the additional cancer therapeutic agent is a chemotherapy agent. Examples of chemotherapeutic agents used in cancer therapy include, for example, antimetabolites (e.g., folic acid, purine, and pyrimidine derivatives), alkylating agents (e.g., nitrogen mustards, nitrosoureas, platinum, alkyl sulfonates, hydrazines, triazenes, aziridines, spindle poison, cytotoxic agents, topoisomerase inhibitors and others), and hypomethylating agents (e.g., decitabine (5-aza-deoxycytidine), zebularine, isothiocyanates, azacitidine (5-azacytidine), 5-flouro-2'-deoxycytidine, 5,6-dihydro-5-azacytidine and others). Exemplary agents include Aclarubicin, Actinomycin, Alitretinoin, Altretamine, Aminopterin, Aminolevulinic acid, Amrubicin, Amsacrine, Anagrelide, Arsenic trioxide, Asparaginase, Atrasentan, Belotecan, Bexarotene, bendamustine, Bleomycin, Bortezomib, Busulfan, Camptothecin, Capecitabine, Carboplatin, Carboquone, Carmofur, Carmustine, Celecoxib, Chlorambucil, Chlormethine, Cisplatin, Cladribine, Clofarabine, Crisantaspase, Cyclophosphamide, Cytarabine, Dacarbazine, Dactinomycin, Daunorubicin, Decitabine, Demecolcine, Docetaxel, Doxorubicin, Efaproxiral, Elesclomol, Elsamitrucin, Enocitabine, Epirubicin, Estramustine, Etoglucid, Etoposide, Floxuridine, Fludarabine, Fluorouracil (5FU), Fotemustine, Gemcitabine, Gliadel implants, Hydroxycarbamide, Hydroxyurea, Idarubicin, Ifosfamide, Irinotecan, Irofulven, Ixabepilone, Larotaxel, Leucovorin, Liposomal doxorubicin, Liposomal daunorubicin, Lonidamine, Lomustine, Lucanthone, Mannosulfan, Masoprocol, Melphalan, Mercaptopurine, Mesna, Methotrexate, Methyl aminolevulinate, Mitobronitol, Mitoguazone, Mitotane, Mitomycin, Mitoxantrone, Nedaplatin, Nimustine, Oblimersen, Omacetaxine, Ortataxel, Oxaliplatin, Paclitaxel, Pegaspargase, Pemetrexed, Pentostatin, Pirarubicin, Pixantrone, Plicamycin, Porfimer sodium, Prednimustine, Procarbazine, Raltitrexed, Ranimustine, Rubitecan, Sapacitabine, Semustine, Sitimagene ceradenovec, Strataplatin, Streptozocin, Talaporfin, Tegafur-uracil, Temoporfin, Temozolomide, Teniposide, Tesetaxel, Testolactone, Tetranitrate, Thiotepa, Tiazofurine, Tioguanine, Tipifarnib, Topotecan, Trabectedin, Triaziquone, Triethylenemelamine, Triplatin, Tretinoin, Treosulfan, Trofosfamide, Uramustine, Valrubicin, Verteporfin, Vinblastine, Vincristine, Vindesine, Vinflunine, Vinorelbine, Vorinostat, Zorubicin, and other cytostatic or cytotoxic agents described herein.

Because some drugs work better together than alone, two or more drugs are often given at the same time. Often, two or more chemotherapy agents are used as combination chemotherapy.

In some embodiments, the additional cancer therapeutic agent is a differentiation agent. Such differentiation agent includes retinoids (such as all-trans-retinoic acid (ATRA), 9-cis retinoic acid, 13-cis-retinoic acid (13-cRA) and 4-hydroxy-phenretinamide (4-HPR)); arsenic trioxide; histone deacetylase inhibitors HDACs (such as azacytidine (Vidaza) and butyrates (e.g., sodium phenylbutyrate)); hybrid polar compounds (such as hexamethylene bisacetamide ((HMBA)); vitamin D; and cytokines (such as colony-stimulating factors including G-CSF and GM-CSF, and interferons).

In some embodiments the additional cancer therapeutic agent is a targeted therapy agent. Targeted therapy constitutes the use of agents specific for the deregulated proteins of cancer cells. Small molecule targeted therapy drugs are generally inhibitors of enzymatic domains on mutated, overexpressed, or otherwise critical proteins within the cancer cell. Prominent examples are the tyrosine kinase inhibitors such as Axitinib, Bosutinib, Cediranib, dasatinib, erlotinib, imatinib, gefitinib, lapatinib, Lestaurtinib, Nilotinib, Semaxanib, Sorafenib, Sunitinib, and Vandetanib, and also cyclin-dependent kinase inhibitors such as Alvocidib and Seliciclib.

Monoclonal antibody therapy is another strategy in which the therapeutic agent is an antibody which specifically binds to a protein on the surface of the cancer cells. Examples include the anti-HER2/neu antibody trastuzumab (HERCEPTIN®) typically used in breast cancer, and the anti-CD20 antibody rituximab and Tositumomab typically used in a variety of B-cell malignancies. Other exemplary antibodies include Cetuximab, Panitumumab, Trastuzumab, Alemtuzumab, Bevacizumab, Edrecolomab, and Gemtuzumab. Exemplary fusion proteins include Aflibercept and Denileukin diftitox. In some embodiments, the targeted therapy can be used in combination with a compound described herein, e.g., a biguanide such as metformin or phenformin, preferably phenformin.

Targeted therapy can also involve small peptides as "homing devices" which can bind to cell surface receptors or affected extracellular matrix surrounding the tumor. Radionuclides which are attached to these peptides (e.g., RGDs) eventually kill the cancer cell if the nuclide decays in the vicinity of the cell. An example of such therapy includes BEXXAR®.

In some embodiments, the additional cancer therapeutic agent is an immunotherapy agent. Cancer immunotherapy refers to a diverse set of therapeutic strategies designed to induce the subject's own immune system to fight the tumor. Contemporary methods for generating an immune response against tumors include intravesicular BCG immunotherapy for superficial bladder cancer, and use of interferons and other cytokines to induce an immune response in renal cell carcinoma and melanoma subjects.

Allogeneic hematopoietic stem cell transplantation can be considered a form of immunotherapy, since the donor's immune cells will often attack the tumor in a graft-versus-tumor effect. In some embodiments, the immunotherapy agents can be used in combination with a compound or composition described herein.

In some embodiments, the additional cancer therapeutic agent is a hormonal therapy agent. The growth of some cancers can be inhibited by providing or blocking certain hormones. Common examples of hormone-sensitive tumors include certain types of breast and prostate cancers. Removing or blocking estrogen or testosterone is often an important additional treatment. In certain cancers, administration of hormone agonists, such as progestogens may be therapeutically beneficial. In some embodiments, the hormonal therapy agents can be used in combination with a compound or a composition described herein.

Other possible additional therapeutic modalities include imatinib, gene therapy, peptide and dendritic cell vaccines, synthetic chlorotoxins, and radiolabeled drugs and antibodies.

Examples
ABBREVIATIONS

| | |
|---|---|
| anhy.—anhydrous | dt—doublet of triplets |
| aq.—aqueous | $CHCl_3$—chloroform |
| min—minute(s) | DCM—dichloromethane |
| mL—milliliter | DMF—dimethylformamide |
| mmol—millimole(s) | $Et_2O$—diethyl ether |
| mol—mole(s) | EtOH—ethyl alcohol |
| MS—mass spectrometry | EtOAc—ethyl acetate |
| NMR—nuclear magnetic resonance | MeOH—methyl alcohol |
| TLC—thin layer chromatography | MeCN—acetonitrile |
| HPLC—high-performance liquid chromatography | PE—petroleum ether |
| | THF—tetrahydrofuran |
| Hz—hertz | AcOH—acetic acid |
| δ—chemical shift | HCl—hydrochloric acid |
| J—coupling constant | $H_2SO_4$—sulfuric acid |
| s—singlet | $NH_4Cl$—ammonium chloride |
| d—doublet | KOH—potassium hydroxide |
| t—triplet | NaOH—sodium hydroxide |
| q—quartet | $K_2CO_3$—potassium carbonate |
| m—multiplet | $Na_2CO_3$—sodium carbonate |
| br—broad | TFA—trifluoroacetic acid |
| qd—quartet of doublets | $Na_2SO_4$—sodium sulfate |
| dquin—doublet of quintets | $NaBH_4$—sodium borohydride |
| dd—doublet of doublets | $NaHCO_3$—sodium bicarbonate |
| LiHMDS—lithium hexamethyldisilylamide | |
| NaHMDS—sodium hexamethyldisilylamide | |
| LAH—lithium aluminum hydride | |
| $NaBH_4$—sodium borohydride | |
| LDA—lithium diisopropylamide | |
| $Et_3N$—triethylamine | |
| DMAP—4-(dimethylamino)pyridine | |
| DIPEA—N,N-diisopropylethylamine | |
| $NH_4OH$—ammonium hydroxide | |
| EDCI—1-ethyl-3-(3-dimethylaminopropyl)carbodiimide | |
| HOBt—1-hydroxybenzotriazole | |
| HATU—O-(7-azabenzotriazol-1-yl)-N,N,N',N'-tetra-methyluronium | |
| BINAP—2,2'-bis(diphenylphosphanyl)-1,1'-binaphthyl | |

In the following examples, reagents were purchased from commercial sources (including Alfa, Acros, Sigma Aldrich, TCI and Shanghai Chemical Reagent Company), and used without further purification. Nuclear magnetic resonance (NMR) spectra were obtained on a Brucker AMX-400 NMR (Brucker, Switzerland). Chemical shifts were reported in parts per million (ppm, δ) downfield from tetramethylsilane. Mass spectra were run with electrospray ionization (ESI) from a Waters LCT TOF Mass Spectrometer (Waters, USA).

For exemplary compounds disclosed in this section, the specification of a stereoisomer (e.g., an (R) or (S) stereoisomer) indicates a preparation of that compound such that the compound is enriched at the specified stereocenter by at least about 90%, 95%, 96%, 97%, 98%, or 99%. The chemical name of each of the exemplary compound described below is generated by ChemDraw software.

Example 1. Preparation of Compounds of Formula I Wherein Ring a is Phenyl, and —$C(R^1)(R^2)(R^3)$ is Isopropyl The compounds of this Example are prepared by general Scheme 1, set forth below.

Scheme 1

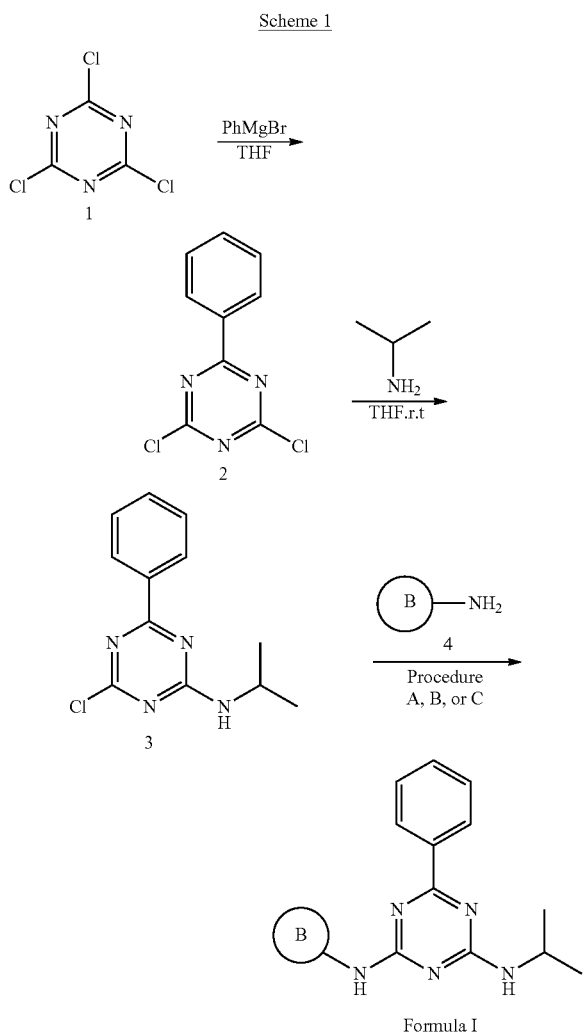

Example 1, Step 1: Preparation of 2,4-dichloro-6-phenyl-1,3,5-triazine (2)

To a solution of 2,4,6-trichloro-[1,3,5]triazine (1, 120 g, 0.652 mol) in anhydrous THF (1200 mL) was added phenylmagnesium bromide (217 mL, 0.651 mol, 3 M in ether) dropwise at −10 to −0° C. under $N_2$ protection. After the addition, the mixture was warmed to room temperature and stirred for 2 hrs. The reaction was cooled to 0° C. and quenched by addition of saturated $NH_4Cl$ (200 mL), then extracted with ethyl acetate. The organic layer was dried, concentrated and purified via column chromatography (eluted with petroleum ether) to afford 2,4-dichloro-6-phenyl-1,3,5-triazine as a white solid. $^1$H NMR (CDCl$_3$) δ 7.51-7.55 (m, 2H), 7.64-7.67 (m, 1H), 8.49-8.63 (m, 2H).

Example 1, Step 2: Preparation of 4-chloro-N-isopropyl-6-phenyl-1,3,5-triazin-2-amine (3)

To a solution of 2,4-dichloro-6-phenyl-1,3,5-triazine (2; 20 g, 0.089 mol) in anhydrous THF (150 mL) was added dropwise a solution of isopropylamine (5.25 g, 0.089 mol) in THF (10 mL) at room temperature via syringe under $N_2$. After the addition, the mixture was stirred at room temperature under $N_2$ for 16 hrs. The reaction was quenched by water (150 mL) and extracted with ethyl acetate. The organic layer was dried, concentrated and purified via SiO$_2$ chromatography to afford 4-chloro-N-isopropyl-6-phenyl-1,3,5-triazin-2-amine (3) as white solid.

$^1$H NMR (CDCl$_3$) δ 1.17-1.24 (m, 6H), 4.16-4.35 (m, 1H), 5.46-5.54 (m, 1H), 7.18-7.50 (m, 3H0, 8.31 (dd, $J_1$=8.4 Hz, $J_2$=34.4 Hz, 2H).

Example 1, Step 3 (Procedure A). Preparation of Compound 178—N-(3-Fluoro-phenyl)-N'-isopropyl-6-phenyl-[1,3,5]triazine-2,4-diamine A mixture of (4-chloro-6-phenyl-[1,3,5]triazin-2-yl)-isopropyl-amine (3; 200 mg, 0.806 mmol) and 3-fluoro-phenylamine (135 mg, 1.215 mmol) in anhydrous THF was stirred at room temperature for 16 hrs. The reaction was quenched by water and extracted with ethyl acetate. The organic layer was washed with brine, dried over $Na_2SO_4$, concentrated and purified by a standard method to give N-(3-fluoro-phenyl)-N'-isopropyl-6-phenyl-[1,3,5]triazine-2,4-diamine.

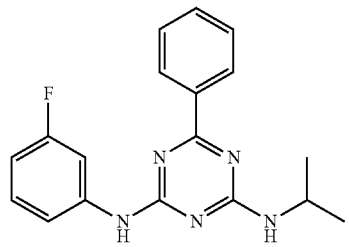 [SMILES: CC(C)Nc1nc(Nc2cccc(F)c2)nc(-c2ccccc2)n1]

$^1$H NMR (METHANOL-d$_4$) δ 8.37-8.33 (m, 2H), 7.87-7.84 (m, 1H), 7.52-7.48 (m, 5H), 7.27-7.25 (m, 1H), 6.73-6.69 (m, 1H), 4.24 (m, 1H), 1.16 (d, J=6.4 Hz, 6H). LC-MS: m/z 323.9 (M+H)$^+$. Other compounds produced by Step 3, Procedure A of this example using the appropriate reagent 4 are set forth below.

Compound 195—$N^2$-isopropyl-$N^4$-(3-(methoxymethyl)phenyl)-6-phenyl-1,3,5-triazine-2,4-diamine

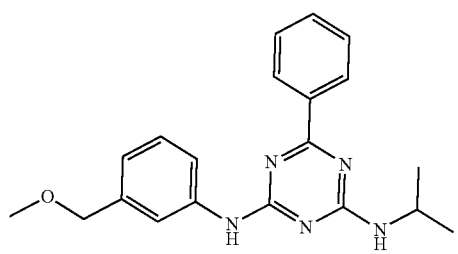 [SMILES: COCc1cccc(Nc2nc(NC(C)C)nc(-c3ccccc3)n2)c1]

$^1$H NMR (METHANOL-d$_4$) 8.40-8.34 (m, 2H) 7.99-7.83 (m, 1H), 7.62-7.60 (m, 1H), 7.53-7.44 (m, 3H), 7.31-7.27 (m, 1H), 7.00-6.99 (m, 1H), 4.48 (s, 2H) 4.29-4.27 (m, 1H), 3.41 (s, 3H), 1.16 (d, J=6.8 Hz, 6H). LC-MS: m/z 350.3 (M+H)$^+$.

141

Compound 198—2-(3-(4-(isopropylamino)-6-phenyl-1,3,5-triazin-2-ylamino)phenyl)acetonitrile

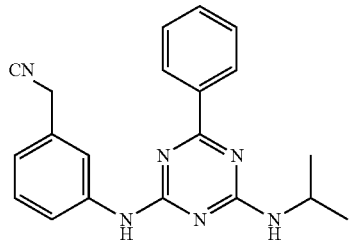 [SMILES: CC(C)Nc1nc(Nc2cccc(CC#N)c2)nc(-c2ccccc2)n1]

$^1$H NMR (METHANOL-d$_4$) 8.42-8.38 (m, 2H) 8.18-8.11 (m, 1H), 7.61-7.60 (m, 1H), 7.52-7.45 (m, 3H), 7.35-7.31 (m, 1H), 7.02-7.00 (m, 1H), 4.34 (m, 1H), 3.92 (s, 2H), 1.16 (d, J=6.8 Hz, 6H). LC-MS: m/z 345.2 (M+H)$^+$.

Compound 201—2-(3-(4-(isopropylamino)-6-phenyl-1,3,5-triazin-2-ylamino)phenyl)propan-2-ol

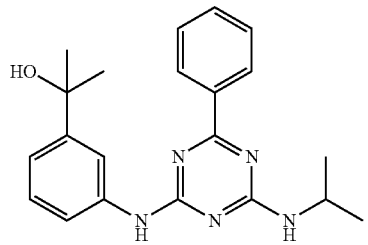 [SMILES: CC(C)Nc1nc(Nc2cccc(C(C)(C)O)c2)nc(-c2ccccc2)n1]

$^1$H NMR (METHANOL-d$_4$) 8.36-8.35 (m, 2H), 8.06-8.01 (m, 1H), 7.55-7.44 (m, 4H), 7.29-7.25 (m, 1H), 7.20-7.18 (m, 1H), 4.46-4.41 (m, 1H), 1.58 (s, 6H), 1.16 (d, J=6.8 Hz, 6H). LC-MS: m/z 364.1 (M+H)$^+$.

Compound 204—N-ethyl-3-(4-(isopropylamino)-6-phenyl-1,3,5-triazin-2-ylamino)benzenesulfonamide

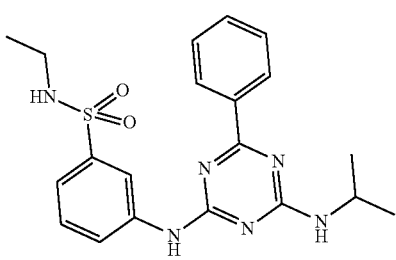 [SMILES: CCNS(=O)(=O)c1cccc(Nc2nc(NC(C)C)nc(-c3ccccc3)n2)c1]

$^1$H NMR (METHANOL-d$_4$) δ 8.86-8.64 (m, 1H), 8.44-8.38 (m, 2H), 7.82-7.72 (m, 1H), 7.53-7.44 (m, 5H), 4.37-4.35 (m, 1H), 2.97-2.92 (m, 2H), 1.299-1.282 (d, J=6.8 Hz, 6H), 1.09-1.05 (t, 3H). LC-MS: m/z 413.1 (M+H)$^+$.

142

Compound 205—N$^2$-(3-(ethylsulfonyl)phenyl)-N$^4$-isopropyl-6-phenyl-1,3,5-triazine-2,4-diamine

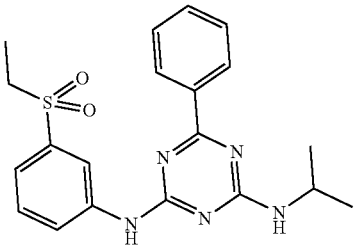 [SMILES: CCS(=O)(=O)c1cccc(Nc2nc(NC(C)C)nc(-c3ccccc3)n2)c1]

$^1$H NMR (METHANOL-d$_4$) δ 8.81-8.79 (m, 1H), 8.28-8.26 (m, 2H), 7.82-7.63 (m, 6H), 4.45-4.42 (m, 1H), 3.26-3.23 (m, 2H), 1.386-1.369 (d, J=6.8 Hz, 6H), 1.27-1.24 (t, 3H). LC-MS: m/z 398.0 (M+H)$^+$.

Compound 206—N$^2$-isopropyl-N$^4$-(3-(isopropylsulfonyl)phenyl)-6-phenyl-1,3,5-triazine-2,4-diamine

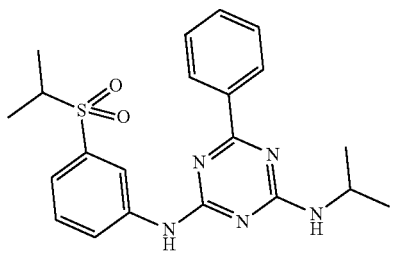 [SMILES: CC(C)Nc1nc(Nc2cccc(S(=O)(=O)C(C)C)c2)nc(-c2ccccc2)n1]

$^1$H NMR (METHANOL-d$_4$) δ 9.00-8.97 (m, 1H) 8.45-8.39 (m, 2H), 7.78-7.76 (m, 1H), 7.58-7.44 (m, 5H), 4.36-4.31 (m, 1H), 3.32-3.31 (m, 1H), 1.31-1.29 (m, 6H). LC-MS: m/z 412.0 (M+H)$^+$.

Compound 341—N-cyclopropyl-3-(4-(isopropylamino)-6-phenyl-1,3,5-triazin-2-ylamino)benzenesulfonamide

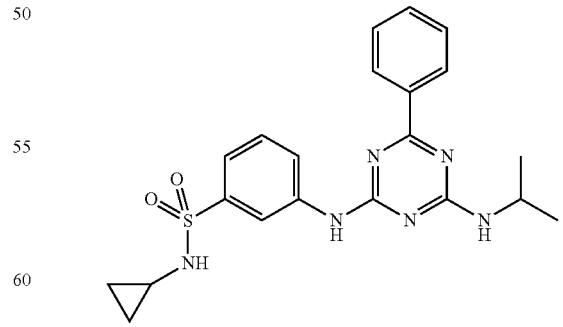

$^1$H NMR (METHANOL-d$_4$) δ 8.77-8.72 (m, 1H), 8.24-8.22 (m, 2H), 7.67-7.62 (m, 6H), 4.48-4.45 (m, 1H), 2.24-2.16 (m, 1H), 1.378-1.362 (d, J=6.4 Hz, 6H), 0.53-0.51 (m, 4H). LC-MS: m/z 425.3 (M+H)$^+$.

Compound 342—N-tert-butyl-3-(4-(isopropylamino)-6-phenyl-1,3,5-triazin-2-ylamino)benzenesulfonamide

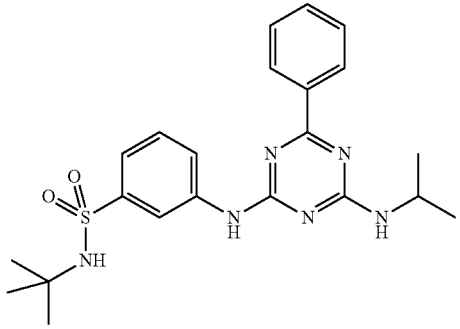 [SMILES: CC(C)Nc1nc(Nc2cccc(S(=O)(=O)NC(C)(C)C)c2)nc(-c2ccccc2)n1]

$^1$H NMR (METHANOL-d$_4$) δ 8.88-8.69 (m, 1H), 8.45-8.49 (m, 2H), 7.77-7.70 (m, 1H), 7.53-7.44 (m, 5H), 4.40-4.37 (m, 1H), 1.304-1.288 (d, J=6.4 Hz, 6H), 1.21 (s, 9H). LC-MS: m/z 441.3 (M+H)$^+$.

Compound 351—2-(4-(isopropylamino)-6-phenyl-1,3,5-triazin-2-ylamino)phenol

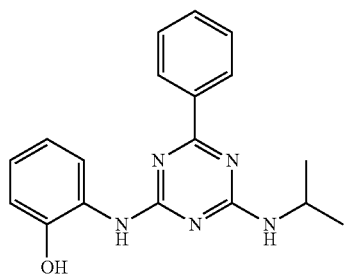 [SMILES: CC(C)Nc1nc(Nc2ccccc2O)nc(-c2ccccc2)n1]

$^1$H NMR (METHANOL-d$_4$) δ 8.40-8.32 (m, 2H), 8.00-7.99 (m, 1H), 7.57-7.47 (m, 3H), 6.97-6.87 (m, 3H), 4.45-4.21 (m, 1H), 1.31 (d, J=6.8 Hz, 6H). LC-MS: m/z 321.9 (M+H).

Example 1, Step 3 (Procedure B). Preparation of Compound 288—N$^2$-isopropyl-N$^4$-(2-methylpyridin-4-yl)-6-phenyl-1,3,5-triazine-2,4-diamine To a solution of (4-chloro-6-phenyl-[1,3,5]triazin-2-yl)-isopropyl-amine (3; 150 mg, 0.6 mmol) in DMSO (2 mL) was added 2-methylpyridin-4-amin (78.4 mg, 0.73 mmol), CsF (310 mg, 1.21 mmol) and DIPEA (230 mg, 1.81 mmol). The mixture was stirred at 80° C. for 2 h. The mixture was cooled down to rt and filtered to remove the solid. The filtrate was purified by a standard method to give N$^2$-isopropyl-N$^4$-(2-methylpyridin-4-yl)-6-phenyl-1,3,5-triazine-2,4-diamine (110 mg, 57.9%).

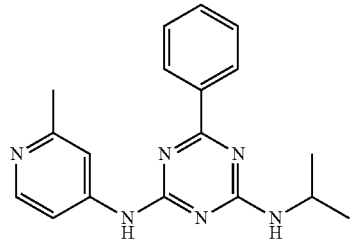

$^1$H NMR (METHANOL-d$_4$) δ 8.19-8.40 (m, 5H), 7.53-7.58 (m, 3H), 4.30-4.43 (m, 1H), 2.66-2.77 (m, 3H), 1.33 (d, J=4.4 Hz, 6H). LC-MS: m/z 321.1 (M+H)$^+$.

Additional compounds of Formula I were made using the appropriate reagent 4 and following Step 3, Procedure B.

Compound 292—N$^2$-(3-fluoropyridin-4-yl)-N'-isopropyl-6-phenyl-1,3,5-triazine-2,4-diamine

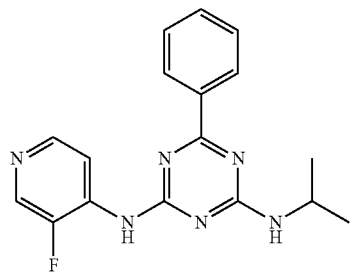 [SMILES: CC(C)Nc1nc(Nc2ccncc2F)nc(-c2ccccc2)n1]

$^1$H NMR (METHANOL-d$_4$) δ 1.34-1.39 (m, 6H), 4.43-4.51 (m, 1H), 7.19-7.25 (m, 1H), 7.53-7.65 (m, 3H), 8.53-8.58 (m, 2H), 9.40-9.45 (m, 1H), 9.56-9.60 (m, 1H). LC-MS: m/z 325.0 (M+H)$^+$.

Compound 298—N$^2$-isopropyl-N$^4$-(2-morpholinopyridin-4-yl)-6-phenyl-1,3,5-triazine-2,4-diamine

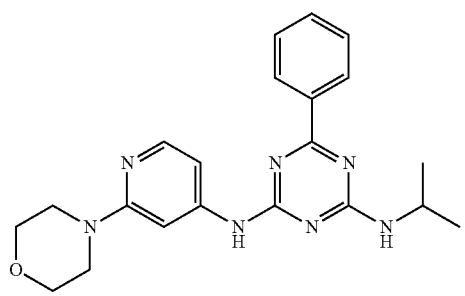 [SMILES: CC(C)Nc1nc(Nc2ccnc(N3CCOCC3)c2)nc(-c2ccccc2)n1]

$^1$H NMR (METHANOL-d$_4$) δ 8.35-8.37 (m, 2H), 7.76-7.90 (m, 2H), 7.51-7.52 (m, 3H), 7.45-7.47 (m, 1H), 4.23-4.49 (m, 1H), 3.82-3085 (m, 4H), 3.50-3.51 (m, 4H), 1.30 (d, J=6.4 Hz, 6H). LC-MS: m/z 392.1 (M+H)$^+$.

Compound 299—N²-(2-(azetidin-1-yl)pyridin-4-yl)-N⁴-isopropyl-6-phenyl-1,3,5-triazine-2,4-diamine

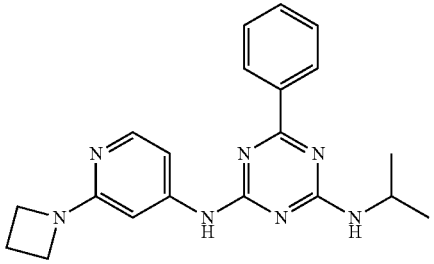 [SMILES: CC(C)Nc1nc(Nc2ccnc(N3CCC3)c2)nc(-c2ccccc2)n1]

¹H NMR (METHANOL-d₄) δ 8.38-8.43 (m, 2H), 7.46-7.74 (m, 5H), 6.88-6.90 (m, 1H), 4.21-4.25 (m, 4H), 2.53-2.56 (m, 2H), 1.30 (d, J=6.4 Hz, 6H). LC-MS: m/z 362.0 (M+H)⁺.

Example 1, Step 3 (Procedure C). Preparation of Compound 146—N-(6-fluoro-pyridin-3-yl)-N'-isopropyl-6-phenyl-[1,3,5]triazine-2,4-diamine

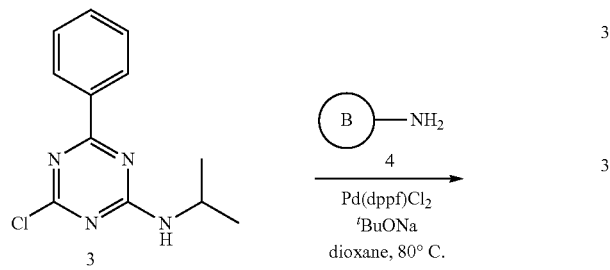

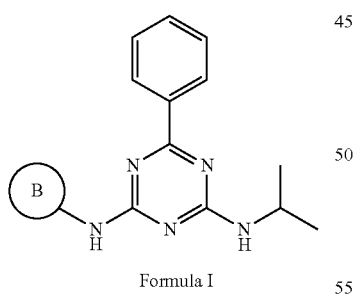

Formula I

A mixture of (4-chloro-6-phenyl-[1,3,5]triazin-2-yl)-isopropyl-amine (3; 400 mg, 1.61 mmol), 6-fluoro-pyridin-3-ylamine (272 mg, 2.43 mmol) Pd(dppf)Cl₂ (120 mg, 0.164 mmol) and t-BuONa (310 mg, 3.23 mmol) was stirred at 80° C. under N₂ for 2 hrs. The mixture was cooled to room temperature and quenched by water, then extracted with ethyl acetate. The organic layer was washed with brine, dried over Na₂SO₄, concentrated and purified by a standard method to give N-(6-fluoro-pyridin-3-yl)-N'-isopropyl-6-phenyl-[1,3,5]triazine-2,4-diamine.

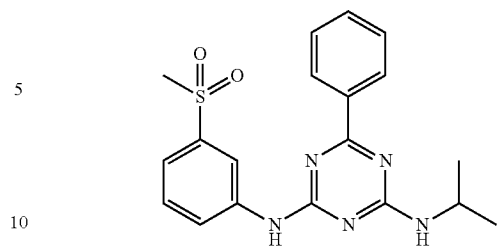

1H NMR (METHANOL-d₄) δ 8.41-8.39 (m, 2H), 7.91-7.88 (m, 5H), 7.62-7.45 (m, 3H), 5.55-5.20 (m, 1H), 4.44-4.20 (m., 1H), 3.05 (s., 1H), 1.31 (dd, J=4, 400 MHz, 6H). LC-MS: m/z 384.2 (M+H)+

Additional compounds of Formula 1 in the example that were prepared according to Example 1, Step 3, Procedure C using the appropriate reagent 4 are set forth below.

Compound 177—3-(4-(isopropylamino)-6-phenyl-1,3,5-triazin-2-ylamino)-N,N-dimethylbenzenesulfonamide

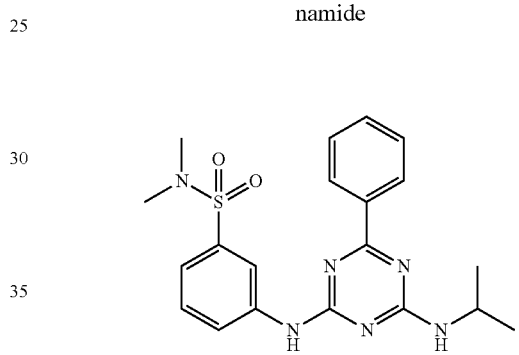

¹H NMR (METHANOL-d₄) δ 8.99-8.78 (m, 1H), 8.39-8.37 (m, 2H), 7.99-7.97 (m, 1H), 7.91-7.65 (m, 1H), 7.54-7.38 (m. 5H), 4.41-4.38 (m, 1H), 2.71 (s, 6H), 1.293-1.277 (d, J=6.4 Hz, 6H). LC-MS: m/z 413.1 (M+H)⁺.

Compound 193—N²-(5-fluoropyridin-3-yl)-N'-isopropyl-6-phenyl-1,3,5-triazine-2,4-diamine

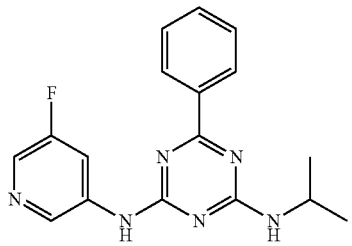 [SMILES: CC(C)Nc1nc(Nc2cncc(F)c2)nc(-c2ccccc2)n1]

1H NMR (METHANOL-d₄) δ 8.47-8.15 (m, 5H), 7.52-7.44 (m, 3H), 7.24-7.17 (m, 1H), 5.37-5.16 (m, 1H), 4.44-4.19 (m., 1H), 3.05 (s., 1H), 1.16 (dd, J=4, 400 MHz, 6H). LC-MS: m/z 325.1 (M+H)⁺

Compound 194—N²-(5-chloropyridin-3-yl)-N'-isopropyl-6-phenyl-1,3,5-triazine-2,4-diamine

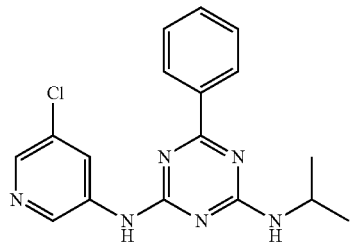

1H NMR (METHANOL-d₄) δ 8.59-8.25 (m, 5H), 7.52-7.45 (m, 3H), 7.39-7.26 (m, 1H), 5.44-5.23 (m, 1H), 4.45-4.20 (m., 1H), 3.05 (s., 1H), 1.31 (dd, J=4, 400 MHz, 6H). LC-MS: m/z 340.9 (M+H)⁺

Compound 196—N²-(6-fluoropyridin-3-yl)-N'-isopropyl-6-phenyl-1,3,5-triazine-2,4-diamine

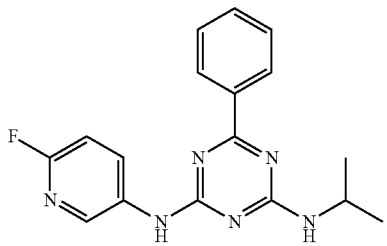 [SMILES: CC(C)Nc1nc(Nc2ccc(F)nc2)nc(-c2ccccc2)n1]

¹H NMR (METHANOL-d₄) δ 8.63-8.57 (m, 1H), 8.38-8.35 (m, 3H), 7.51-7.45 (m, 3H), 7.05-7.01 (m. 1H), 4.40-4.23 (m, 1H), 1.286-1.273 (d, J=5.2 Hz, 6H). LC-MS: m/z 325.2 (M+H)⁺.

Compound 197—4-(4-(isopropylamino)-6-phenyl-1,3,5-triazin-2-ylamino)picolinonitrile

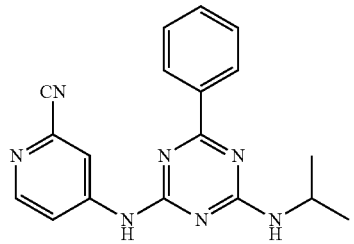

¹H NMR (METHANOL-d₄) δ 8.56-8.32 (m, 4H), 8.03-8.02 (m, 1H), 7.67-7.57 (m. 3H), 4.42-4.33 (m, 1H), 1.36-1.28 (br, 6H). LC-MS: m/z 332.1 (M+H)⁺.

Compound 199—N²-(2-chloropyridin-4-yl)-N⁴-isopropyl-6-phenyl-1,3,5-triazine-2,4-diamine

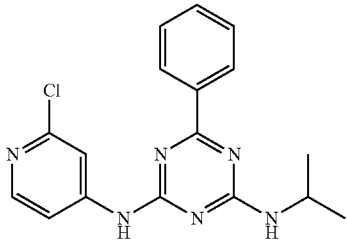

¹H NMR (METHANOL-d₄) δ 8.43-8.37 (m, 2H), 8.23-8.10 (m, 2H), 7.67-7.66 (m, 1H), 7.55-7.45 (m. 3H), 4.27-4.24 (m, 1H), 1.327-1.311 (d, J=6.4 Hz, 6H). LC-MS: m/z 341.2 (M+H)⁺.

Compound 200—N²-(2-ethoxypyridin-4-yl)-N⁴-isopropyl-6-phenyl-1,3,5-triazine-2,4-diamine

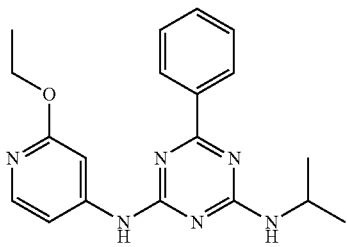 [SMILES: CCOc1cc(Nc2nc(NC(C)C)nc(-c3ccccc3)n2)ccn1]

¹H NMR (METHANOL-d₄) δ 8.41-8.36 (m, 2H), 7.91-7.88 (m, 1H), 7.52-7.45 (m. 4H), 7.30-7.29 (m, 1H), 4.30-4.25 (m, 1H), 1.42-1.38 (t, 3H), 1.308-1.292 (d, J=6.4 Hz, 6H). LC-MS: m/z 351.2 (M+H)⁺.

Compound 202—N²-isopropyl-6-phenyl-N⁴-(2-(trifluoromethyl)pyridin-4-yl)-1,3,5-triazine-2,4-diamine

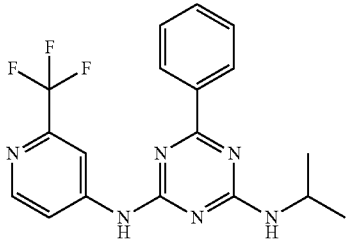

¹H NMR (METHANOL-d₄) δ 10.45-10.27 (m, 1H), 8.68-8.28 (m, 4H), 7.99-7.51 (m, 5H), 4.17-4.16 (m., 1H), 3.25 (s, 6H), 1.24 (dd, J=4, 400 MHz, 6H). LC-MS: m/z 375.1 (M+H)⁺.

Compound 210—5-(4-(isopropylamino)-6-phenyl-1,3,5-triazin-2-ylamino)nicotinonitrile

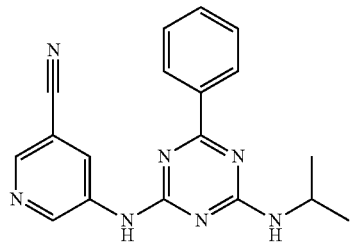 [SMILES: CC(C)Nc1nc(Nc2cncc(C#N)c2)nc(-c2ccccc2)n1]

$^1$H NMR (METHANOL-$d_4$) δ 8.75-9.25 (m, 2H), 8.34-8.48 (m, 3H), 7.76-7.51 (m, 3H), 4.0-4.58 (m, 1H), 1.30 (d, J=6.8 Hz, 6H). LC-MS: m/z 331.9 (M+H)$^+$.

Compound 223—N$^2$-(2-fluoropyridin-4-yl)-N'-isopropyl-6-phenyl-1,3,5-triazine-2,4-diamine

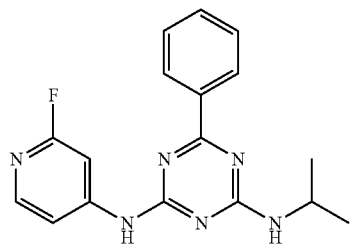 [SMILES: CC(C)Nc1nc(Nc2ccnc(F)c2)nc(-c2ccccc2)n1]

$^1$H NMR (METHANOL-$d_4$) δ 8.43-8.37 (m, 2H), 7.99-7.97 (m, 1H), 7.86-7.80 (m, 1H), 7.65-7.45 (m, 4H), 4.28-4.22 (m, 1H), 1.315-1.299 (d, J=6.4 Hz, 6H). LC-MS: m/z 325.1 (M+H)$^+$.

Compound 224—N$^2$-(2-(ethylamino)pyridin-4-yl)-N'-isopropyl-6-phenyl-1,3,5-triazine-2,4-diamine

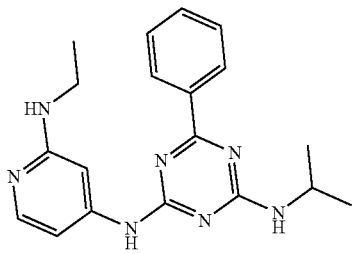 [SMILES: CCNc1cc(Nc2nc(NC(C)C)nc(-c3ccccc3)n2)ccn1]

$^1$H NMR (METHANOL-$d_4$) δ 8.53-8.49 (m, 1H), 8.42-8.36 (m, 2H), 7.74-7.72 (m, 2H), 7.53-7.46 (m, 3H), 7.03-6.99 (m, 1H), 4.42-4.24 (m, 1H), 3.36-3.31 (m, 2H), 1.34-1.16 (m, 9H). LC-MS: m/z 350.0 (M+H)$^+$.

Compound 266—N$^2$-isopropyl-6-phenyl-N$^4$-(pyrimidin-5-yl)-1,3,5-triazine-2,4-diamine

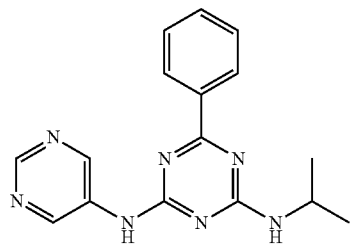 [SMILES: CC(C)Nc1nc(Nc2cncnc2)nc(-c2ccccc2)n1]

$^1$H NMR (METHANOL-$d_4$) δ 9.25-9.30 (m, 2H), 8.78-8.79 (m, 1H), 8.36-8.43 (m, 2H), 7.45-7.53 (m, 3H), 4.25-4.62 (m, 1H), 1.31 (d, J=6.4 Hz, 6H). LC-MS: m/z 308.2 (M+H)$^+$.

Compound 277—N$^2$-(3-(ethylsulfinyl)phenyl)-N'-isopropyl-6-phenyl-1,3,5-triazine-2,4-diamine

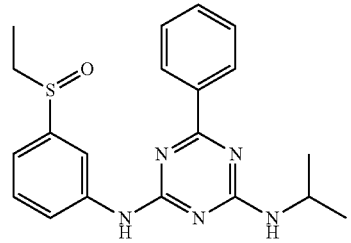 [SMILES: CCS(=O)c1cccc(Nc2nc(NC(C)C)nc(-c3ccccc3)n2)c1]

$^1$H NMR (METHANOL-$d_4$) δ 8.51-8.32 (m, 3H), 7.76-7.52 (m, 4H), 7.35-7.27 (m, 1H), 4.50-4.32 (m, 1H), 3.14-3.03 (m, 1H), 2.94-2.89 (m, 1H), 1.33 (d, J=6.0 Hz, 6H), 1.23 (t, J=7.2 Hz, 3H). LC-MS: m/z 382.1 (M+H)$^+$.

Compound 281—N$^2$-isopropyl-N$^4$-(6-methylpyridin-3-yl)-6-phenyl-1,3,5-triazine-2,4-diamine

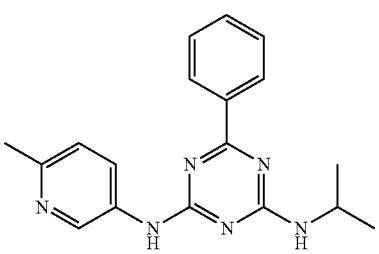 [SMILES: Cc1ccc(Nc2nc(NC(C)C)nc(-c3ccccc3)n2)cn1]

$^1$H NMR (METHANOL-$d_4$) δ 8.99-8.83 (m, 1H), 8.40-8.35 (m, 2H), 8.32-8.13 (m, 1H), 7.55-7.45 (m, 3H), 7.30-7.28 (m, 1H), 4.46-4.22 (m, 1H), 2.52 (s, 3H), 1.30 (d, J=6.8 Hz, 6H). LC-MS: m/z 321.2 (M+H)$^+$.

Compound 289—N²-(6-chloropyridin-3-yl)-N⁴-isopropyl-6-phenyl-1,3,5-triazine-2,4-diamine

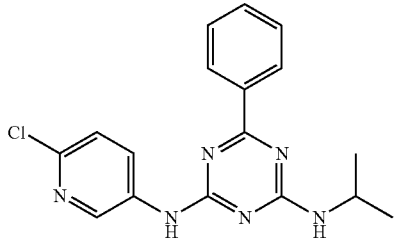 [SMILES: CC(C)Nc1nc(Nc2ccc(Cl)nc2)nc(-c2ccccc2)n1]

¹H NMR (METHANOL-d₄) δ 8.79-8.86 (m, 1H), 8.25-8.40 (m, 3H), 7.37-7.53 (m, 4H), 4.40-4.61 (m, 1H), 1.30 (d, J=6.4 Hz, 6H). LC-MS: m/z 340.9 (M+H)⁺.

Compound 293—N²-(2-(dimethylamino)pyridin-4-yl)-N⁴-isopropyl-6-phenyl-1,3,5-triazine-2,4-diamine

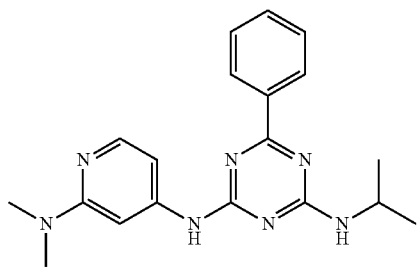 [SMILES: CC(C)Nc1nc(Nc2ccnc(N(C)C)c2)nc(-c2ccccc2)n1]

¹H NMR (METHANOL-d₄) δ 8.44-8.38 (m, 2H), 7.86-7.79 (m, 2H), 7.54-7.45 (m, 3H), 7.02-7.00 (m, 1H), 4.30 (m., 1H), 3.25 (s, 6H), 1.30 (dd, J=8, 400 MHz, 6H). LC-MS: m/z 350.1 (M+H)⁺.

Compound 301—N²-isopropyl-N⁴-(2-(isopropylamino)pyridin-4-yl)-6-phenyl-1,3,5-triazine-2,4-diamine

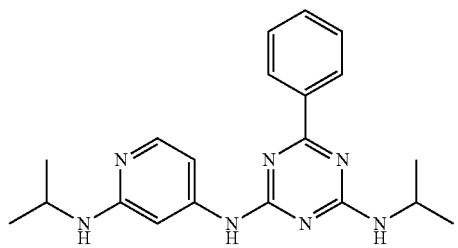 [SMILES: CC(C)Nc1cc(Nc2nc(NC(C)C)nc(-c3ccccc3)n2)ccn1]

¹H NMR (DMSO-d₄) δ 1.03-1.09 (m, 12H), 3.57-3.74 (m 1H), 3.99-4.18 (m, 1H), 7.00 (br, 1H), 7.34-8.35 (m, 9H), 10.7 (d, 1H). LC-MS: m/z 364 (M+H)⁺.

Compound 302—N²-isopropyl-N⁴-(2-(methylamino)pyridin-4-yl)-6-phenyl-1,3,5-triazine-2,4-diamine

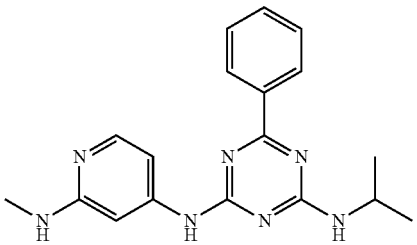 [SMILES: CNc1cc(Nc2nc(NC(C)C)nc(-c3ccccc3)n2)ccn1]

¹H NMR (METHANOL-d₄) δ 8.42-8.35 (m, 2H), 7.79-7.54 (m, 5H), 7.12-7.10 (m, 1H), 4.35 (m., 1H), 3.03 (s, 3H), 1.30 (dd, J=16, 400 MHz, 6H). LC-MS: m/z 336.2 (M+H)⁺.

Compound 303—N²-isopropyl-N⁴-(6-(methylamino)pyridin-3-yl)-6-phenyl-1,3,5-triazine-2,4-diamine

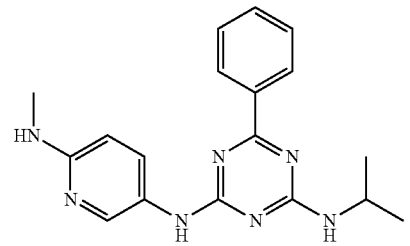 [SMILES: CNc1ccc(Nc2nc(NC(C)C)nc(-c3ccccc3)n2)cn1]

¹H NMR (METHANOL-d₄) δ 8.50 (m, 1H), 8.25-8.24 (m, 2H), 8.07-8.05 (m, 1H), 7.75-7.63 (m, 3H), 7.14-7.11 (m, 1H), 4.35 (m., 1H), 3.07 (s, 3H), 1.35 (dd, J=8, 400 MHz, 6H). LC-MS: m/z 336.2 (M+H)⁺.

Compound 308—N²-isopropyl-N⁴-(1-methyl-1H-pyrazol-4-yl)-6-phenyl-1,3,5-triazine-2,4-diamine

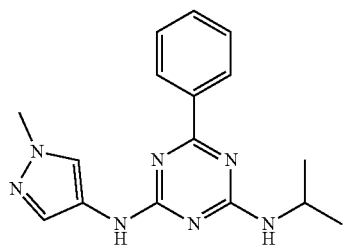 [SMILES: CC(C)Nc1nc(Nc2cnn(C)c2)nc(-c2ccccc2)n1]

¹H NMR (METHANOL-d₄) δ 8.49-8.20 (m, 2H), 8.21-8.15 (m, 1H), 7.70-7.50 (m, 4H), 4.49-4.25 (m, 1H), 3.91 (s, 3H), 1.33 (d, J=6.8 Hz, 6H). LC-MS: m/z 310.2 (M+H).

Compound 309—N²-isopropyl-N⁴-(isoxazol-4-yl)-6-phenyl-1,3,5-triazine-2,4-diamine

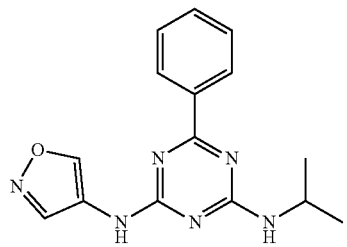 [SMILES: CC(C)Nc1nc(Nc2cnoc2)nc(-c2ccccc2)n1]

¹H NMR (METHANOL-d₄) δ 9.30-9.12 (m, 1H), 8.57 (s, 1H), 8.39-8.34 (m, 2H), 7.53-7.47 (m, 3H), 4.41-4.25 (m, 1H), 1.31 (d, J=5.2 Hz, 6H). LC-MS: m/z 297.2 (M+H).

Compound 310—N²-(2,6-dimethylpyridin-4-yl)-N⁴-isopropyl-6-phenyl-1,3,5-triazine-2,4-diamine

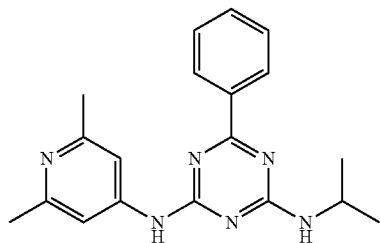 [SMILES: Cc1cc(Nc2nc(NC(C)C)nc(-c3ccccc3)n2)cc(C)n1]

¹H NMR (METHANOL-d₄) δ 8.46-8.40 (m, 2H), 8.08-8.06 (m, 2H), 7.57-7.48 (m, 3H), 4.47-4.20 (m, 1H), 2.66 (s, 6H), 1.34 (d, J=6.4 Hz, 6H). LC-MS: m/z 335.3 (M+H)⁺.

Compound 311—N²-(6-(cyclopropylmethoxy)pyridin-3-yl)-N⁴-isopropyl-6-phenyl-1,3,5-triazine-2,4-diamine

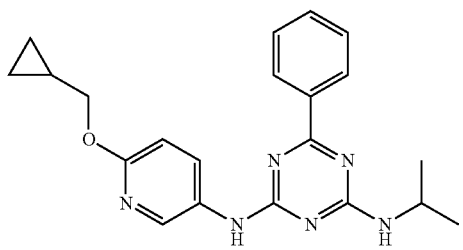 [SMILES: CC(C)Nc1nc(Nc2ccc(OCC3CC3)nc2)nc(-c2ccccc2)n1]

¹H NMR (METHANOL-d₄) δ 8.56-8.34 (m, 3H), 8.09-8.07 (m, 1H), 7.53-7.45 (m, 3H), 6.84-6.81 (m, 1H), 4.41-4.25 (m, 1H), 4.10 (d, J=6.8 Hz, 1H), 1.30 (d, J=6.4 Hz, 1H), 1.21-1.20 (m, 1H), 0.65-0.61 (m, 2H), 0.39-0.36 (m, 2H). LC-MS: m/z 377.3 (M+H)⁺.

Compound 312—N²-(6-isopropoxypyridin-3-yl)-N⁴-isopropyl-6-phenyl-1,3,5-triazine-2,4-diamine

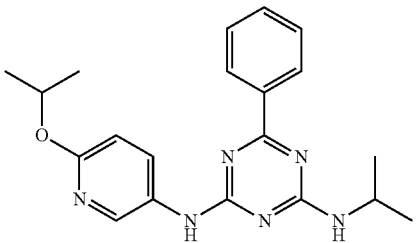 [SMILES: CC(C)Nc1nc(Nc2ccc(OC(C)C)nc2)nc(-c2ccccc2)n1]

¹H NMR (METHANOL-d₄) δ 8.59-8.42 (m, 3H), 8.07-8.04 (m, 1H), 7.53-7.45 (m, 3H), 6.77-6.75 (m, 1H), 5.19-5.16 (m, 1H), 4.43-4.21 (m, 1H), 1.35 (d, J=6.0 Hz, 6H), 1.29 (d, J=6.4 Hz, 6H). LC-MS: m/z 365.2 (M+H)⁺.

Compound 313—N²-isopropyl-6-phenyl-N⁴-(thiazol-5-yl)-1,3,5-triazine-2,4-diamine

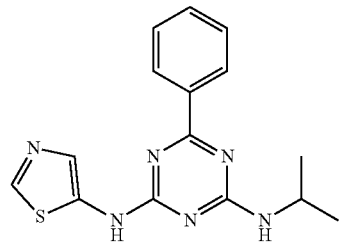 [SMILES: CC(C)Nc1nc(Nc2cncs2)nc(-c2ccccc2)n1]

¹H NMR (METHANOL-d₄) δ 8.59-8.38 (m, 3H), 7.69-7.48 (m, 4H), 4.45-4.23 (m, 1H), 1.22 (d, J=6.8 Hz, 6H). LC-MS: m/z 313.1 (M+H)⁺.

Compound 314—N²-isopropyl-6-phenyl-N⁴-(3-(trifluoromethyl)pyridin-4-yl)-1,3,5-triazine-2,4-diamine

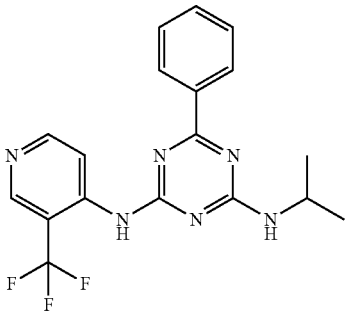 [SMILES: CC(C)Nc1nc(Nc2ccncc2C(F)(F)F)nc(-c2ccccc2)n1]

¹H NMR (METHANOL-d₄) δ 9.58 (s, 1H), 9.35 (s, 1H), 8.45-8.40 (m, 2H), 7.56-7.42 (m, 3H), 7.11 (s, 1H), 4.28-4.25 (m, 1H), 1.25 (d, J=6.4 Hz, 6H). LC-MS: m/z 375.2 (M+H)⁺.

Compound 315—N²-(2-cyclopropylpyridin-4-yl)-N⁴-isopropyl-6-phenyl-1,3,5-triazine-2,4-diamine

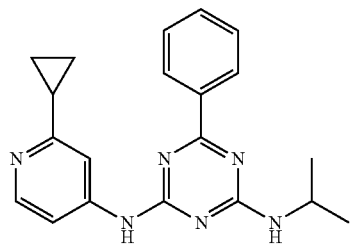 [SMILES: CC(C)Nc1nc(Nc2ccnc(C3CC3)c2)nc(-c2ccccc2)n1]

¹H NMR (METHANOL-d₄) δ 8.43-8.34 (m, 2H), 8.21-8.18 (m, 1H), 7.93-7.16 (m, 2H), 7.54-7.45 (m. 3H), 4.29-4.26 (m, 1H), 2.15-2.12 (m, 1H), 1.319-1.303 (d, J=6.4 Hz, 6H), 1.19-1.18 (m, 2H) 1.03-1.02 (m, 2H). LC-MS: m/z 347.3 (M+H)⁺.

Compound 316—N²-(6-cyclopropylpyridin-3-yl)-N⁴-isopropyl-6-phenyl-1,3,5-triazine-2,4-diamine

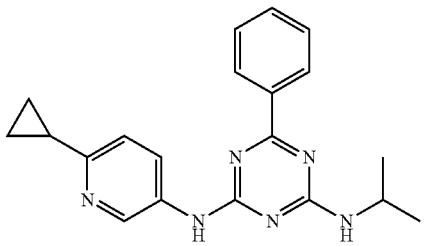 [SMILES: CC(C)Nc1nc(Nc2ccc(C3CC3)nc2)nc(-c2ccccc2)n1]

¹H NMR (METHANOL-d₄) δ 9.01-8.98 (m, 1H), 8.40-8.34 (m, 2H), 8.16-8.13 (m, 1H), 7.54-7.44 (m, 3H), 7.27-7.25 (m. 1H), 4.27-4.24 (m, 1H), 1.299-1.282 (d, J=6.8 Hz, 6H), 1.11-1.06 (m, 2H) 0.97-0.96 (m, 2H). LC-MS: m/z 347.3 (M+H)⁺.

Compound 329—N²-isopropyl-6-phenyl-N⁴-(5-(trifluoromethyl)pyridin-3-yl)-1,3,5-triazine-2,4-diamine

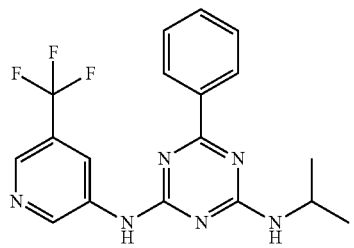

¹H NMR (METHANOL-d₄) δ 8.99-9.03 (m, 2H), 8.36-8.47 (m, 3H), 7.45-7.52 (m, 3H), 4.18-4.57 (m, 1H), 1.30 (d, J=6.4 Hz, 6H). LC-MS: m/z 375.2 (M+H)⁺.

Compound 332—N²-isopropyl-N⁴-(1-methyl-1H-imidazol-4-yl)-6-phenyl-1,3,5-triazine-2,4-diamine

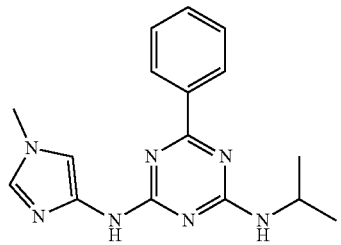 [SMILES: CC(C)Nc1nc(Nc2cn(C)cn2)nc(-c2ccccc2)n1]

¹H NMR (METHANOL-d₄) δ 8.51-8.22 (m, 3H), 7.48-7.38 (m, 3H), 7.28 (s, 1H), 4.38-4.12 (m, 1H), 3.83 (s, 3H), 1.18 (d, J=6.4 Hz, 6H). LC-MS: m/z 309.9 (M+H).

Compound 129—N²-isopropyl-6-phenyl-N⁴-(pyridin-4-yl)-1,3,5-triazine-2,4-diamine

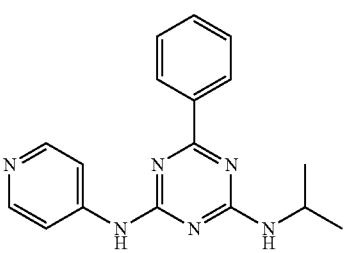 [SMILES: CC(C)Nc1nc(Nc2ccncc2)nc(-c2ccccc2)n1]

¹H NMR (METHANOL-d₄) δ 14.92 (br. s., 1H), 112.-11.13 (m, 1H), 8.68-8.63 (m, 2H), 8.41-8.36 (m, 4H), 8.24-8.10 (m, 1H), 7.63-7.53 (m, 3H), 4.34-4.17 (m., 1H), 1.17 (dd, J=4, 400 MHz, 6H). LC-MS: m/z 307.2 (M+H)⁺.

Compound 343—N²-isopropyl-N⁴-(2-methylpyrimidin-5-yl)-6-phenyl-1,3,5-triazine-2,4-diamine

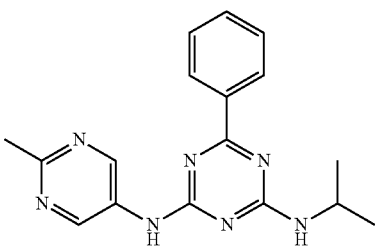 [SMILES: Cc1ncc(Nc2nc(NC(C)C)nc(-c3ccccc3)n2)cn1]

¹H NMR (METHANOL-d₄) 9.17-9.11 (m, 2H), 8.42-8.35 (m, 2H), 7.55-7.44 (m. 3H), 4.26-4.23 (m, 1H), 2.66 (s, 3H), 1.308-1.292 (d, J=6.4 Hz, 6H). LC-MS: m/z 322.2 (M+H)⁺.

Compound 376—N²-(3-(azetidin-1-ylsulfonyl)phenyl)-N⁴-isopropyl-6-phenyl-1,3,5-triazine-2,4-diamine

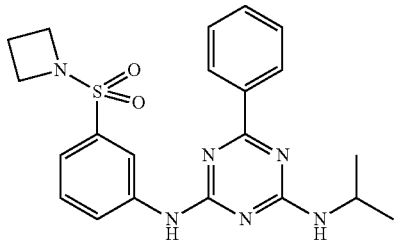 [SMILES: CC(C)Nc1nc(Nc2cccc(S(=O)(=O)N3CCC3)c2)nc(-c2ccccc2)n1]

¹H NMR (METHANOL-d₄) 8.99-8.86 (m, 1H), 8.44-8.38 (m, 2H), 7.77-7.75 (m, 1H), 7.60-7.44 (m. 5H), 4.35-4.32 (m, 1H), 3.82-3.78 (m, 4H), 2.10-2.02 (m, 2H), 1.300-1.284 (d, J=6.4 Hz, 6H). LC-MS: m/z 425.2 (M+H)⁺.

Example 2. Preparation of Compounds of Formula I Wherein Ring A is Optionally Substituted Pyridin-2-yl or Pyrimidin-2-yl The compounds of this Example are prepared by general Scheme 2, set forth below.

Scheme 2

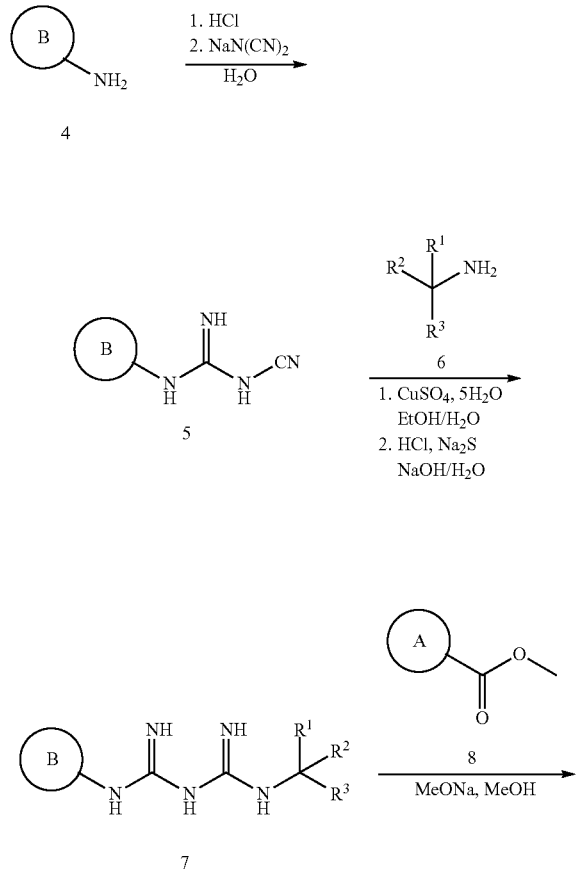

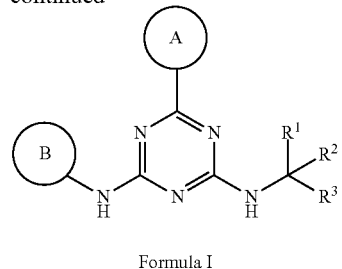

Formula I

Example 2, Step 1: Preparation of 1-phenyl-2-cyanoguanidine (5)

To a solution of NaN(CN)₂ (50 g, 0.5618 mol) in water (430 mL) at 80° C. was added a solution of aniline (26.2 g, 0.28 mol) in water and conc. HCl (132 mL/23.5 mL). The mixture was heated to 90° C. for 16 hours. The mixture was cooled to room temperature and quenched by adding saturated sodium bicarbonate (317 mL). The mixture was filtered and the filter cake was dried via vacuum to afford 1-phenyl-2-cyanoguanidine as a white solid.

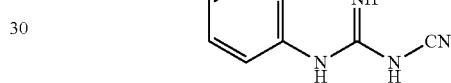

¹H NMR (DMSO-d₄) δ 6.95 (s, 2H), 7.02-7.06 (m, 1H), 7.26-7.32 (m, 4H), 9.00 (s, 1H).

The procedure set forth in Example 2, step 1 was used to produce the following intermediates (5) using the appropriate starting material 4.

1-(3-cyanophenyl-2-cyanoguanidine as a brown solid.

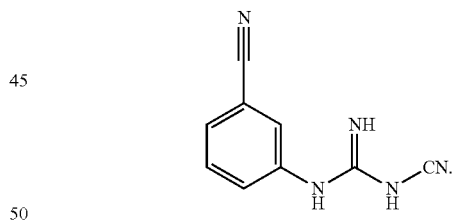

LC-MS: m/z 185.9 (M+H)⁺.

1-methanesulfonyl-benzenyl-2-cyanoguanidine as a pale gray solid.

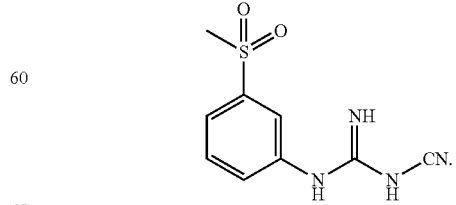

LC-MS: m/z 238.8 (M+H)⁺.

1-3-fluoro-pyridin-2-cyanoguanidine as a pale solid.

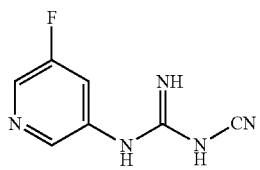 [SMILES: N#CNC(=N)Nc1cncc(F)c1]

¹H NMR (DMSO-d₄) δ 7.42 (s, 2H), 7.85-8.01 (m, 1H), 8.24 (s, 1H), 8.38 (s, 1H).

1-3-chloro-pyridin-2-cyanoguanidine as a pale gray solid.

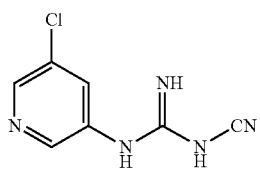 [SMILES: N#CNC(=N)Nc1cncc(Cl)c1]

¹H NMR (DMSO-d₄) δ 8.06 (s, 1H), 8.29 (s, 1H), 8.47 (s, 1H).

1-2-fluoro-pyridin-2-cyanoguanidine as a brown solid.

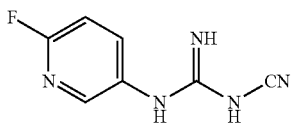 [SMILES: N#CNC(=N)Nc1ccc(F)nc1]

¹H NMR (DMSO-d₄) δ 7.10-7.20 (m, 1H), 7.95-7.99 (m, 1H), 8.15 (s, 1H).

1-3,5-difluoro-phenyl-2-cyano-guanidine as white solid, which was directly used in the next step without further purification.

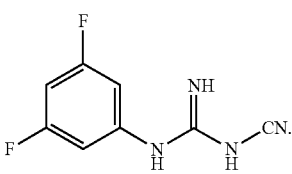 [SMILES: N#CNC(=N)Nc1cc(F)cc(F)c1]

LC-MS: m/z 196.8 (M+H)⁺.

Example 2, Step 2: Preparation of 1-phenyl-2-isopropylamine-diguanidine(7)

To a mixture of 1-phenyl-2-cyanoguanidine (5.0 g, 0.031 mol) in ethanol/water (46 mL/18.4 mL) was added CuSO₄·5H₂O (3.91 g, 0.01563 mol), followed by isopropyl amine (5.53 g, 0.03975 mol). The mixture was heated to reflux for 16 hours. To the mixture was added water (137 mL) and aq.HCl (15.5 mL in 93 mL of water) at 25-30° C. The resultant mixture was stirred at r.t. for 30 min. Then Na₂S (12.4 g in 62 mL of water) was added and stirred for another 30 min. The insoluble CuS was filtered off. The filtrate was cooled to 10° C. and added aqueous NaOH (7 g NaOH in 50 mL water) dropwise. The mixture was extracted with dichloromethane (100 mL×3). The organic layer was combined, dried over Na₂SO₄ and concentrated to give 1-phenyl-2-isopropylamine-diguanidine as a brown solid.

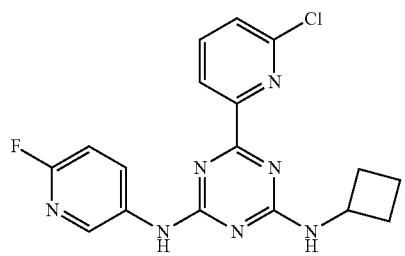 [SMILES: Fc1ccc(Nc2nc(NC3CCC3)nc(-c3cccc(Cl)n3)n2)cn1]

¹H NMR (DMSO-d4) δ 1.25 (d, J=4.8 Hz, 6H), 4.91-4.97 (m, 1H), 7.17-7.39 (m, 5H).

The procedure set forth in Example 2, step 2 was used to produce the following intermediates (7) using the appropriate intermediate 5 and the appropriate amine 6.

1-3-cyanophenyl-2-isopropylamine-diguanidine as a brown solid.

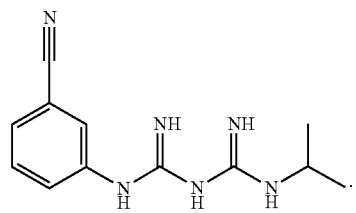 [SMILES: CC(C)NC(=N)NC(=N)Nc1cccc(C#N)c1]

LC-MS: m/z 245 (M+H)⁺.

1-methanesulfonyl-2-isopropyl-diguanidine as a pale solid.

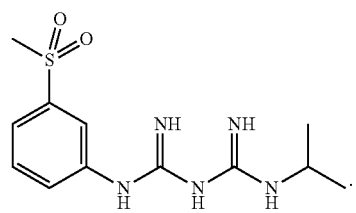 [SMILES: CC(C)NC(=N)NC(=N)Nc1cccc(S(C)(=O)=O)c1]

LC-MS: m/z 298 (M+H)⁺.

1-3-fluoro-pyridin-2-cyclobutyl-diguanidine as a red solid.

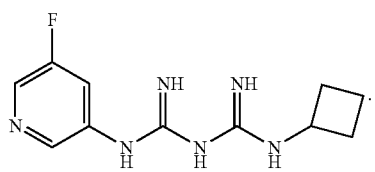 [SMILES: N=C(NC(=N)NC1CCC1)Nc1cncc(F)c1]

LC-MS: m/z 251 (M+H)⁺.

1-3-chloro-pyridin-2-cyclobutyl-diguanidine as a red solid.

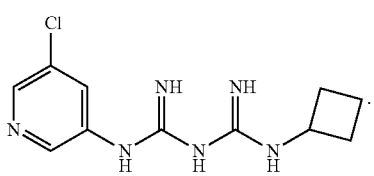

LC-MS: m/z 267 (M+H)$^+$.

1-2-fluoro-pyridin-2-cyclobutyl-diguanidine as a red solid.

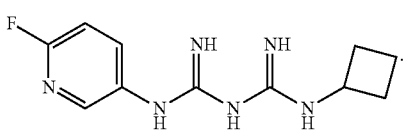 [SMILES: N=C(NC(=N)NC1CCC1)Nc1ccc(F)nc1]

LC-MS: m/z 250.8 (M+H)$^+$.

1-3,5-difluoropneyl-2-isopropyl-diguanidine as a brown solid, which was used in the next step without further purification.

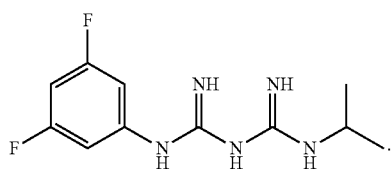 [SMILES: CC(C)NC(=N)NC(=N)Nc1cc(F)cc(F)c1]

LC-MS: m/z 256 (M+H)$^+$.

Example 2, Step 3: Preparation of Compound 214—N-Isopropyl-N'-phenyl-6-pyridin-2-yl-[1,3,5]triazine-2,4-diamine To a mixture of N-isopropyl-N'-phenyl-6-pyridin-2-yl-[1,3,5]triazine-2,4-diamine (0.5 g, 2.28 mmol) and pyridine-2-carboxylic acid methyl ester (0.312 g, 2.28 mmol) in methanol (7 mL) was added NaOMe (0.25 g, 4.56 mmol). The mixture was stirred at r.t. for 16 hours. The mixture was poured into water and extracted with ethyl acetate (50 mL), dried over Na$_2$SO$_4$, concentrated and purified by a standard method to afford N-isopropyl-N'-phenyl-6-pyridin-2-yl-[1,3,5]triazine-2,4-diamine.

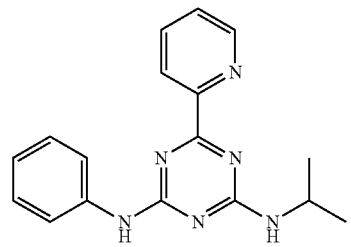 [SMILES: CC(C)Nc1nc(Nc2ccccc2)nc(-c2ccccn2)n1]

$^1$H NMR (METHANOL-d$_4$) δ 8.72-8.73 (d, 1H), 8.47-8.49 (d, 1H), 7.97-8.01 (t, 1H), 7.77-7.79 (d, 2H), 7.56-7.59 (t, 1H), 7.31-7.35 (t, 2H), 7.04-7.07 (t, 1H), 4.40-4.45 (m, 1H), 1.30-1.31 (d, 6H). LC-MS: m/z 307.0 (M+H)$^+$.

Additional compounds of Formula I set forth below were similarly produced following Scheme 2 utilizing the appropriate intermediates and reagents.

Compound 228—6-(4-chloropyridin-2-yl)-N$^2$-isopropyl-N$^4$-phenyl-1,3,5-triazine-2,4-diamine

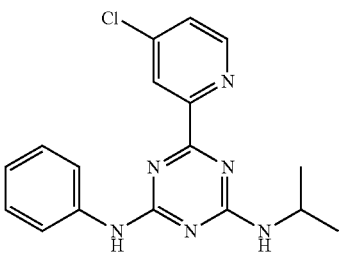 [SMILES: CC(C)Nc1nc(Nc2ccccc2)nc(-c2cc(Cl)ccn2)n1]

$^1$H NMR (METHANOL-d$_4$) δ 8.63-8.64 (d, 1H), 8.48 (s, 1H), 7.73-7.75 (d, 2H), 7.63 (s, 1H), 7.29-7.31 (t, 2H), 7.05-7.10 (t, 1H), 4.21-4.24 (m, 1H), 1.27-1.29 (d, 6H). LC-MS: m/z 341.0 (M+H)$^+$.

Compound 229—6-(6-chloropyridin-2-yl)-N$^2$-isopropyl-N$^4$-phenyl-1,3,5-triazine-2,4-diamine

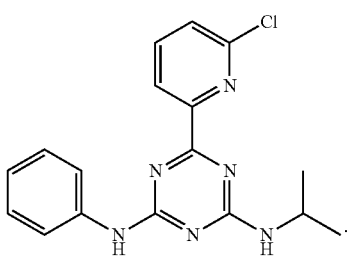 [SMILES: CC(C)Nc1nc(Nc2ccccc2)nc(-c2cccc(Cl)n2)n1]

$^1$H NMR (METHANOL-d$_4$) δ 8.37-8.39 (d, 1H), 7.91-7.95 (t, 1H), 7.72-7.74 (d, 2H), 7.56-7.58 (d, 1H), 7.29-7.32 (t, 2H), 7.02-7.04 (t, 1H), 4.23-4.29 (m, 1H), 1.27-1.28 (d, 6H). LC-MS: m/z 341.0 (M+H)$^+$.

Compound 230—6-(3-chloropyridin-2-yl)-N$^2$-isopropyl-N$^4$-phenyl-1,3,5-triazine-2,4-diamine

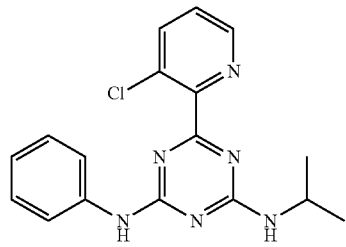 [SMILES: CC(C)Nc1nc(Nc2ccccc2)nc(-c2ncccc2Cl)n1]

$^1$H NMR (METHANOL-d$_4$) δ 8.54-8.55 (d, 1H), 8.01-8.03 (d, 1H), 7.70-7.72 (d, 1H), 7.50-7.53 (m, 1H), 7.27-7.31 (t, 2H), 7.04 (s, 1H), 4.32-4.40 (m, 1H), 1.21-1.30 (m, 6H). LC-MS: m/z 340.9 (M+H)$^+$.

163

Compound 231—6-(4-(isopropylamino)-6-(phenylamino)-1,3,5-triazin-2-yl)pyridin-2-ol

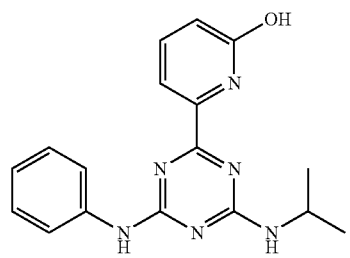 [SMILES: CC(C)Nc1nc(Nc2ccccc2)nc(-c2cccc(O)n2)n1]

¹H NMR (METHANOL-d₄) δ 7.70-7.75 (m, 3H), 7.43-7.47 (d, 1H), 7.28-7.33 (t, 2H), 7.02-7.07 (t, 1H), 6.68-6.72 (m, 1H), 4.28-4.39 (m, 1H), 1.33-1.35 (d, 6H). LC-MS: m/z 323.0 (M+H)⁺.

Compound 246—3-(4-(isopropylamino)-6-(pyridin-2-yl)-1,3,5-triazin-2-ylamino)benzonitrile

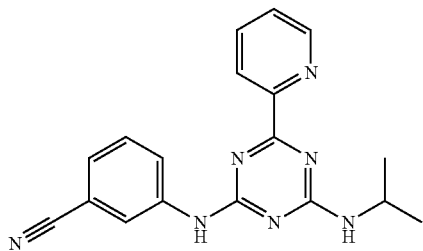 [SMILES: CC(C)Nc1nc(Nc2cccc(C#N)c2)nc(-c2ccccn2)n1]

¹H NMR (METHANOL-d₄) δ 8.71-8.72 (d, 1H), 8.41-8.51 (m, 2H), 7.90-8.00 (m, 2H), 7.44-7.58 (m, 2H), 7.33-7.37 (t, 1H), 4.22-4.27 (m, 1H), 1.27-1.33 (m, 6H). LC-MS: m/z 332.0 (M+H)⁺.

Compound 247—N²-isopropyl-N⁴-phenyl-6-(6-(trifluoromethyl)pyridin-2-yl)-1,3,5-triazine-2,4-diamine

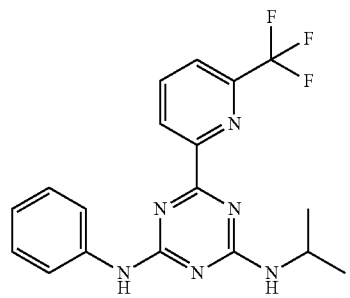 [SMILES: CC(C)Nc1nc(Nc2ccccc2)nc(-c2cccc(C(F)(F)F)n2)n1]

¹H NMR (DMSO-d₆) δ 8.64-8.66 (m, 1H), 8.19 (m, 1H), 7.94 (m, 1H), 7.77 (m, 2H), 7.27-7.34 (m, 2H), 7.05 (m, 1H), 4.24-4.49 (m, 1H), 1.30 (d, 6H). LC-MS: m/z 375.0 (M+H)⁺.

164

Compound 270—N²-isopropyl-N⁴-phenyl-6-(4-(trifluoromethyl)pyridin-2-yl)-1,3,5-triazine-2,4-diamine

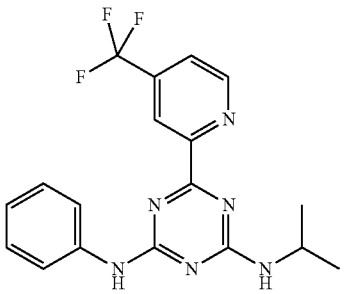 [SMILES: CC(C)Nc1nc(Nc2ccccc2)nc(-c2cc(C(F)(F)F)ccn2)n1]

¹H NMR (METHANOL-d₄) δ 8.99 (d, 1H), 8.76 (m, 1H), 7.89 (m, 1H), 7.79 (m, 2H), 7.29-7.39 (m, 2H), 7.05 (m, 1H), 4.21-4.52 (m, 1H), 1.29-1.33 (m, 6H). LC-MS: m/z 375 (M+H)⁺.

Compound 290—6-(6-aminopyridin-2-yl)-N²-isopropyl-N⁴-phenyl-1,3,5-triazine-2,4-diamine

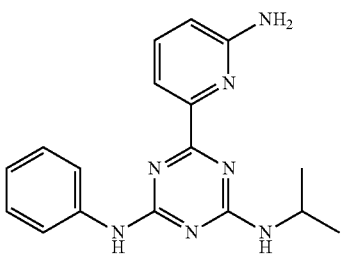 [SMILES: CC(C)Nc1nc(Nc2ccccc2)nc(-c2cccc(N)n2)n1]

¹H NMR (METHANOL-d₄) δ 7.92-8.03 (m, 1H), 7.72-7.83 (m, 1H), 7.69 (m, 2H), 7.29-7.33 (m, 2H), 7.14 (m., 1H), 7.06 (m, 1H), 4.15-4.51 (m, 1H), 1.25 (d, 6H). LC-MS: m/z 322.1 (M+H)⁺.

Compound 322—N²-cyclobutyl-N⁴-(5-fluoropyridin-3-yl)-6-(pyridin-2-yl)-1,3,5-triazine-2,4-diamine

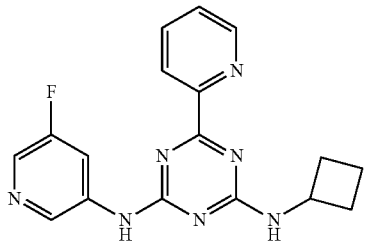 [SMILES: Fc1cncc(Nc2nc(NC3CCC3)nc(-c3ccccn3)n2)c1]

¹H NMR (DMSO-d₆) δ 10.3 (s, 1H), 8.69-8.85 (m, 2H), 8.34-8.59 (m, 2H), 8.17-8.29 (m, 2H), 7.99 (m, 1H), 7.55 (m, 1H), 4.35-4.70 (m, 1H), 2.31 (m, 2H), 2.05 (m, 2H), 1.72 (m, 2H). LC-MS: m/z 337.9 (M+H)⁺.

Compound 323—6-(6-chloropyridin-2-yl)-N²-cyclobutyl-N⁴-(5-fluoropyridin-3-yl)-1,3,5-triazine-2,4-diamine

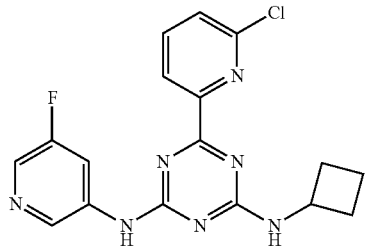 [SMILES: Fc1cncc(Nc2nc(NC3CCC3)nc(-c3cccc(Cl)n3)n2)c1]

¹H NMR (DMSO-d₆) δ 10.4 (s, 1H), 8.80 (s, 1H), 8.52-8.62 (m, 1H), 8.27-8.42 (m, 2H), 8.22 (m, 1H), 8.09 (m, 1H), 7.70 (m, 1H), 4.35-4.69 (m, 1H), 2.31 (m, 2H), 2.09 (m, 2H), 1.72 (m, 2H). LC-MS: m/z 372.2 (M+H)⁺.

Compound 325—6-(6-chloropyridin-2-yl)-N²-cyclobutyl-N⁴-(6-fluoropyridin-3-yl)-1,3,5-triazine-2,4-diamine

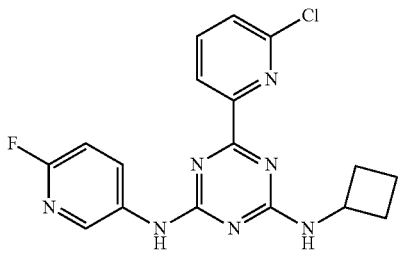

¹H NMR (DMSO-d₆) δ 10.22 (s, 1H), 8.59-8.69 (d, 1H), 8.12-8.51 (m, 3H), 8.07 (m, 1H), 7.69 (m., 1H), 7.11-7.24 (m, 1H), 4.32-4.66 (m, 1H), 2.33 (m, 2H), 2.06 (m, 2H), 1.72 (m, 2H). LC-MS: m/z 371.9 (M+H)⁺.

Compound 330—N²-(5-chloropyridin-3-yl)-N⁴-cyclobutyl-6-(pyridin-2-yl)-1,3,5-triazine-2,4-diamine

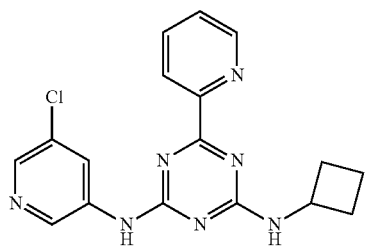 [SMILES: Clc1cncc(Nc2nc(NC3CCC3)nc(-c3ccccn3)n2)c1]

¹H NMR (DMSO-d₆) δ 10.33 (s, 1H), 8.83-9.98 (m, 1H), 8.76 (m, 1H), 8.55-8.69 (m, 1H), 8.31-8.52 (m., 1H), 8.18-8.29 (m, 2H), 8.01 (m, 1H), 7.57 (m, 1H), 4.35-4.69 (m, 1H), 2.33 (m, 2H), 2.06 (m, 2H), 1.72 (m, 2H). LC-MS: m/z 354.2 (M+H)⁺.

Compound 331—N²-isopropyl-6-(6-(methylamino)pyridin-2-yl)-N⁴-phenyl-1,3,5-triazine-2,4-diamine

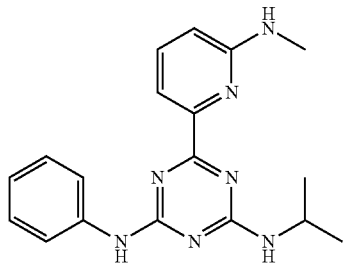 [SMILES: CNc1cccc(-c2nc(Nc3ccccc3)nc(NC(C)C)n2)n1]

¹H NMR (METHANOL-d₄) δ 7.76 (m, 2H), 7.60 (m, 2H), 7.31 (m, 2H), 7.04 (m, 1H), 6.64 (m, 1H), 4.19-4.48 (m, 1H), 2.96 (s, 3H), 1.27 (m, 6H). LC-MS: m/z 336.2 (M+H)⁺.

Compound 344—6-(6-chloropyridin-2-yl)-N²-(6-fluoropyridin-3-yl)-N'-isopropyl-1,3,5-triazine-2,4-diamine

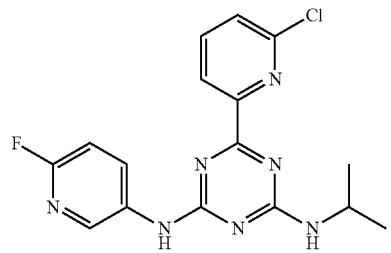 [SMILES: CC(C)Nc1nc(Nc2ccc(F)nc2)nc(-c2cccc(Cl)n2)n1]

¹H NMR (DMSO-d₆) δ 10.21-10.81 (d, 1H), 8.61-8.79 (d, 1H), 8.04-8.51 (m, 4H), 7.69-7.81 (m, 1H), 7.12-7.24 (m, 1H), 4.05-4.32 (m, 1H), 1.22 (d, 6H). LC-MS: m/z 359.9 (M+H)⁺. 381.9 (M+Na)⁺.

Compound 326—6-(6-chloropyridin-2-yl)-N²-isopropyl-N⁴-(3-(methylsulfonyl)phenyl)-1,3,5-triazine-2,4-diamine

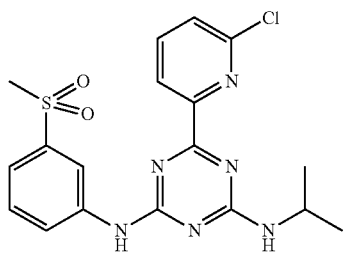

¹H NMR (METHANOL-d₄) δ 8.99 (s, 1H), 8.46-8.47 (d, 1H), 7.96-7.99 (m, 1H), 7.74-7.77 (m, 1H), 7.55-7.62 (m, 3H), 4.32-4.50 (m, 1H), 3.18 (s, 3H), 1.28-1.32 (d, 6H). LC-MS: m/z 418.9 (M+H)⁺.

Compound 340—6-(6-chloropyridin-2-yl)-$N^2$-(3,5-difluorophenyl)-$N^4$-isopropyl-1,3,5-triazine-2,4-diamine

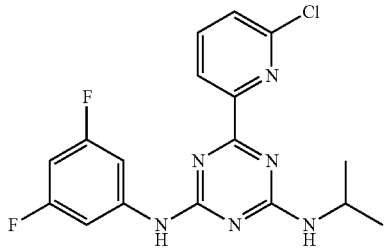

$^1$H NMR (METHANOL-$d_4$) δ 8.41-8.45 (t, 1H), 8.00-8.04 (t, 1H), 7.63-7.69 (m, 1H), 6.64-6.69 (t, 1H), 4.22-4.27 (m, 1H), 1.29-1.35 (d, 6H). LC-MS: m/z 377.2 (M+H)$^+$.

Compound 358—$N^2$-isopropyl-$N^4$-(3-(methylsulfonyl)phenyl)-6-(6-(trifluoromethyl)pyridin-2-yl)-1,3,5-triazine-2,4-diamine

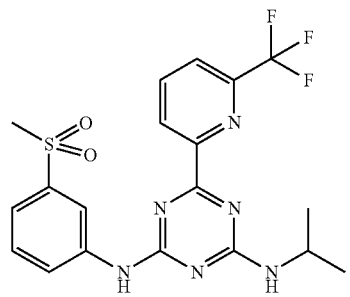 [SMILES: CC(C)Nc1nc(Nc2cccc(S(C)(=O)=O)c2)nc(-c2cccc(C(F)(F)F)n2)n1]

$^1$H NMR (METHANOL-$d_4$) δ 8.99 (s, 1H), 8.60-8.72 (m, 1H), 8.19 (t, 1H), 7.81 (d, 1H), 7.77-7.78 (m, 1H), 7.55-7.62 (m, 2H), 4.35-4.47 (m, 1H), 3.11-3.18 (m, 3H), 1.33 (d, 6H). LC-MS: m/z 453.2 (M+H)$^+$.

Compound 359—$N^2$-isopropyl-6-(6-methylpyridin-2-yl)-$N^4$-(3-(methylsulfonyl)phenyl)-1,3,5-triazine-2,4-diamine

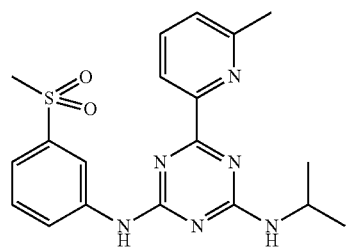 [SMILES: Cc1cccc(-c2nc(Nc3cccc(S(C)(=O)=O)c3)nc(NC(C)C)n2)n1]

$^1$H NMR (METHANOL-$d_4$) δ 8.60-9.03 (m, 1H), 8.31 (m, 1H), 7.70-8.05 (m, 2H), 7.81 (d, 1H), 7.57-7.63 (m, 2H), 7.45-7.47 (m, 1H), 4.39 (m, 1H), 3.12-3.19 (m, 3H), 2.67 (s, 3H), 1.34 (d, 6H). LC-MS: m/z 399.2 (M+H)$^+$.

Compound 360—6-(6-ethynylpyridin-2-yl)-$N^2$-isopropyl-$N^4$-(3-(methylsulfonyl)phenyl)-1,3,5-triazine-2,4-diamine

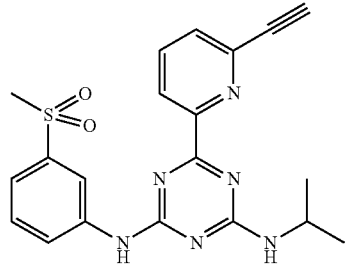 [SMILES: C#Cc1cccc(-c2nc(Nc3cccc(S(C)(=O)=O)c3)nc(NC(C)C)n2)n1]

$^1$H NMR (METHANOL-$d_4$) δ 8.89 (s, 1H), 8.56 (d, 1H), 8.15-8.19 (m, 1H), 7.71-7.95 (m, 4H), 4.45 (br., 1H), 4.03 (s, 1H), 3.18 (s, 3H), 1.39 (d, 6H). LC-MS: m/z 409.2 (M+H)$^+$.

Compound 361—$N^2$-isopropyl-6-(6-methoxypyridin-2-yl)-$N^4$-(3-(methylsulfonyl)phenyl)-1,3,5-triazine-2,4-diamine

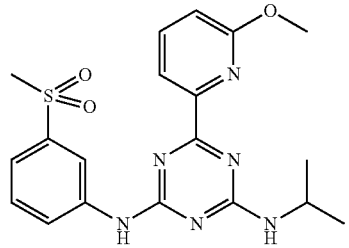 [SMILES: COc1cccc(-c2nc(Nc3cccc(S(C)(=O)=O)c3)nc(NC(C)C)n2)n1]

$^1$H NMR (METHANOL-$d_4$) δ 8.55-8.99 (m, 1H), 7.82-8.13 (m, 3H), 7.57-7.64 (m, 2H), 6.98 (d, 1H), 4.37-4.41 (m., 1H), 4.07 (s, 3H), 3.16 (s, 3H), 1.34 (d, 6H). LC-MS: m/z 414.9 (M+H)$^+$., 436.9 (M+Na)$^+$.

Compound 363—$N^2$-(6-fluoropyridin-3-yl)-$N^4$-neopentyl-6-(pyridin-2-yl)-1,3,5-triazine-2,4-diamine

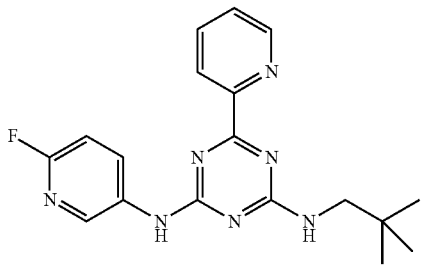 [SMILES: CC(C)(C)CNc1nc(Nc2ccc(F)nc2)nc(-c2ccccn2)n1]

$^1$H NMR (METHANOL-$d_4$) δ 8.82 (d, 1H), 8.47-8.54 (m, 1H), 8.40 (d, 1H), 8.14-8.17 (m, 1H), 7.83-7.88 (m., 1H), 7.45-7.52 (m, 1H), 7.10-7.20 (m, 1H), 6.93-6.99 (m, 1H), 5.40-5.77 (m, 1H), 3.31-3.49 (m, 2H), 1.00 (s, 9H). LC-MS: m/z 354.2 (M+H)$^+$.

Compound 364—N²-isopropyl-6-(6-(methylamino)pyridin-2-yl)-N⁴-(3-(methylsulfonyl)phenyl)-1,3,5-triazine-2,4-diamine

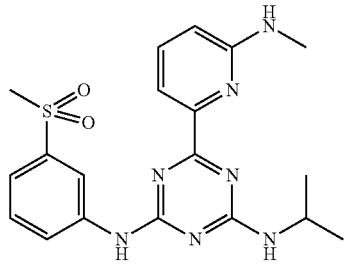 [SMILES: CNc1cccc(-c2nc(Nc3cccc(S(C)(=O)=O)c3)nc(NC(C)C)n2)n1]

¹H NMR (CDCl₃) δ 10.00-10.31 (br., 1H), 8.61-8.82 (m, 1H), 7.53-8.82 (m, 5H), 6.95-7.02 (m, 1H), 4.34 (m., 1H), 3.07 (d, 6H), 1.31-1.37 (m, 6H). LC-MS: m/z 414.2 (M+H)⁺.

Compound 365—N²-isopropyl-N⁴-(3-(methylsulfonyl)phenyl)-6-(6-(prop-1-ynyl)pyridin-2-yl)-1,3,5-triazine-2,4-diamine

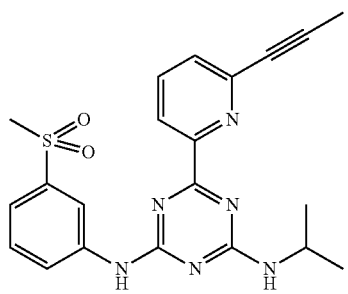 [SMILES: CC#Cc1cccc(-c2nc(Nc3cccc(S(C)(=O)=O)c3)nc(NC(C)C)n2)n1]

¹H NMR (Methanol-d4) δ 8.89 (s, 1H), 8.49 (d, 1H), 8.11 (t, 1H), 7.80-7.86 (m, 3H), 7.71-7.75 (m., 1H), 4.45 (m, 1H), 3.19 (s, 3H), 2.17 (d, 3H), 1.40 (d, 6H). LC-MS: m/z 423.0 (M+H)⁺.

Compound 366—6-(6-(difluoromethyl)pyridin-2-yl)-N²-isopropyl-N⁴-(3-(methylsulfonyl)phenyl)-1,3,5-triazine-2,4-diamine

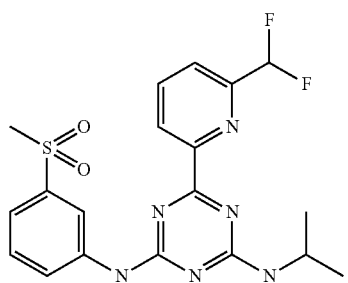

¹H NMR (Methanol-d4) δ 8.88 (s, 1H), 8.78 (m, 1H), 8.35 (s, 1H), 8.10 (m, 1H), 7.82 (t, 2H), 7.71 (t, 1H), 6.70-7.10 (m., 1H), 4.30-4.50 (m, 1H), 3.17 (s, 3H), 1.39 (d, 6H). LC-MS: m/z 434.9 (M+H)⁺.

Compound 395—6-(6-(1,1-difluoroethyl)pyridin-2-yl)-N²-isopropyl-N⁴-(3-(methylsulfonyl)phenyl)-1,3,5-triazine-2,4-diamine

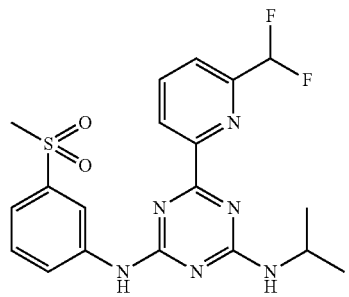 [SMILES: CC(C)Nc1nc(Nc2cccc(S(C)(=O)=O)c2)nc(-c2cccc(C(F)F)n2)n1]

¹H NMR (Methanol-d4) δ 8.98 (s, 1H), 8.57 (d, 1H), 8.09 (t, 1H), 7.85 (d, 1H), 7.80 (m, 1H), 7.55-7.62 (m, 1H), 4.36-4.39 (m, 1H), 3.14-3.17 (m, 3H), 2.11 (t, 3H), 1.32 (d, 6H). LC-MS: m/z 449.3 (M+H)⁺. 471.3 (M+Na)⁺.

Compound 397—6-(6-cyclopropylpyridin-2-yl)-N²-isopropyl-N⁴-(3-(methylsulfonyl)phenyl)-1,3,5-triazine-2,4-diamine

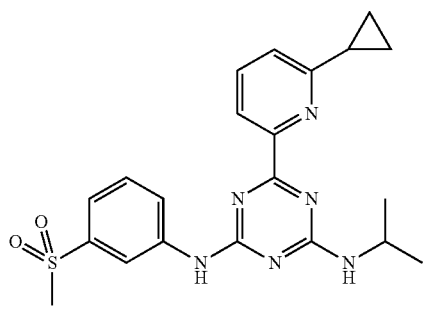 [SMILES: CC(C)Nc1nc(Nc2cccc(S(C)(=O)=O)c2)nc(-c2cccc(C3CC3)n2)n1]

¹H NMR (METHANOL-d₄) δ 8.97 (s, 1H), 8.21-8.2 (d, 1H), 7.76-7.80 (t, 2H), 7.55-7.61 (m, 2H), 7.25-7.27 (d, 1H), 4.35-4.38 (m, 1H), 3.13 (s, 3H), 2.23-2.28 (m, 1H), 1.31-1.32 (d, 6H), 1.02-1.12 (m, 4H). LC-MS: m/z 425.3 (M+H)⁺.

Compound 398—6-(6-aminopyridin-2-yl)-N²-(3,5-difluorophenyl)-N⁴-isopropyl-1,3,5-triazine-2,4-diamine

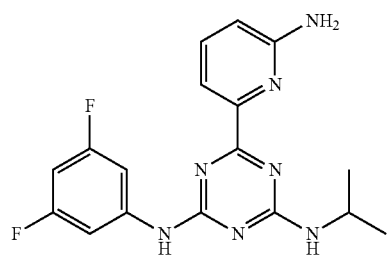

$^1$H NMR (METHANOL-$d_4$) δ 7.66-7.70 (t, 1H), 7.56-7.60 (t, 1H), 7.49-7.51 (d, 2H), 6.70-6.73 (d, 1H), 6.53-6.57 (t, 1H), 4.21-4.24 (m, 1H), 1.18-1.31 (m, 6H). LC-MS: m/z 358.3 (M+H)$^+$.

Example 3. Preparation of Additional Compounds of Formula I Wherein Ring A is Substituted Pyridin-2-yl The compounds of this Example are prepared by general Scheme 3, set forth below.

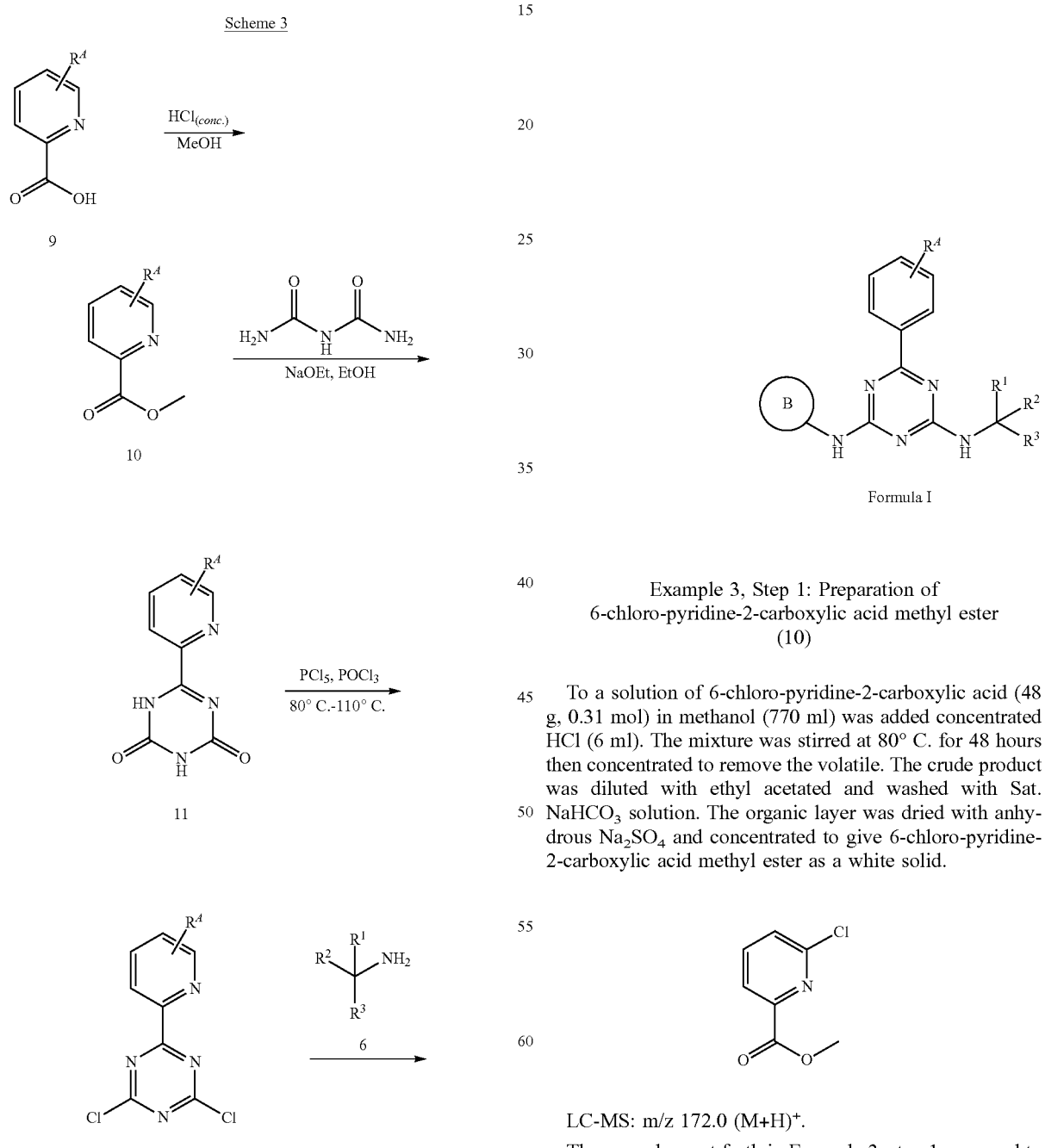

Example 3, Step 1: Preparation of 6-chloro-pyridine-2-carboxylic acid methyl ester (10)

To a solution of 6-chloro-pyridine-2-carboxylic acid (48 g, 0.31 mol) in methanol (770 ml) was added concentrated HCl (6 ml). The mixture was stirred at 80° C. for 48 hours then concentrated to remove the volatile. The crude product was diluted with ethyl acetated and washed with Sat. NaHCO$_3$ solution. The organic layer was dried with anhydrous Na$_2$SO$_4$ and concentrated to give 6-chloro-pyridine-2-carboxylic acid methyl ester as a white solid.

LC-MS: m/z 172.0 (M+H)$^+$.

The procedure set forth in Example 3, step 1 was used to produce the following intermediates (10) using the appropriate starting material 9.

6-trifluoromethyl-pyridine-2-carboxylic acid methyl ester

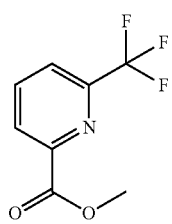

LC-MS: m/z 206 (M+H)$^+$.

Example 3, Step 2: Preparation of 6-(6-chloropyridin-2-yl)-1,3,5-triazine-2,4-dione To a solution of Na (32 g, 0.16 mol) in ethanol (500 mL) was added methyl 6-chloropicolinate (32 g, 0.16 mol) and biuret (5.3 g, 0.052 mol). The mixture was heated to reflux for 1 hour. Then concentrated to give residue which was poured to water and added Sat.NaHCO$_3$ solution to adjust pH to 7, the precipitated solid was collected by filtration and dried to give 6-(6-chloropyridin-2-yl)-1,3,5-triazine-2,4-dione as a white solid.

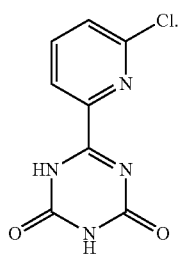 [SMILES: O=c1nc(-c2cccc(Cl)n2)[nH]c(=O)[nH]1]

LC-MS: m/z 225 (M+H)$^+$.

The procedure set forth in Example 3, step 2 was used to produce the following intermediates (11) starting with appropriate intermediate 10.

6-(6-trifluoromethyl-pyridin-2-yl)-1H-1,3,5-triazine-2,4-dione as a pale white solid.

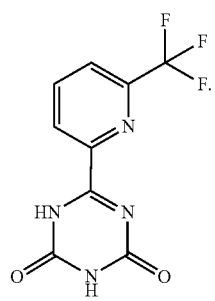 [SMILES: O=c1nc(-c2cccc(C(F)(F)F)n2)[nH]c(=O)[nH]1]

LC-MS: m/z 259 (M+H)$^+$.

6-pyridin-2-yl-1H-1,3,5-triazine-2,4-dione

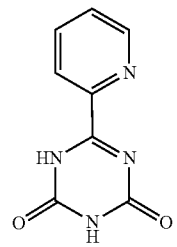 [SMILES: O=c1nc(-c2ccccn2)[nH]c(=O)[nH]1]

$^1$H NMR (DMSO-d4). δ 11.9-12.5 (s, 1H), 11.3-11.6 (s, 1H), 8.7-8.9 (m, 1H), 8.2-8.4 (m, 1H), 8.0-8.2 (m, 1H), 7.6-7.8 (m, 1H).

Example 3, Step 3: Preparation of 2,4-dichloro-6-(6-chloropyridin-2-yl)-1,3,5-triazine To a solution of 6-(pyridin-2-yl)-1,3,5-triazine-2,4(1H, 3H)-dione (3.0 g, 013 mol) in POCl$_3$ (48 mL) was added PCl$_5$ (23 g, 0.1 mol). The mixture was stirred at 100° C. for 2 hours then concentrated to remove the volatile. The residue was diluted with ethyl acetated and washed with Sat.NaHCO$_3$ solution. The organic layer was dried over anhydrous Na$_2$SO$_4$ and concentrated to give 2,4-dichloro-6-(6-chloropyridin-2-yl)-1,3,5-triazine as a brown solid.

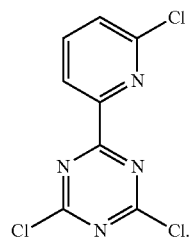

LC-MS: m/z 260.9 (M+H)$^+$.

The procedure set forth in Example 3, step 3 together with the appropriate starting intermediate 11 was used to produce the following intermediates (12).

2,4-dichloro-6-(6-trifluoromethyl-pyridin-2-yl)-1,3,5-triazine as light yellow solid.

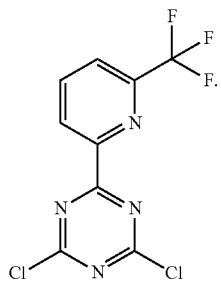 [SMILES: FC(F)(F)c1cccc(-c2nc(Cl)nc(Cl)n2)n1]

LC-MS: m/z 294.9 (M+H)$^+$.

2,4-Dichloro-6-pyridin-2-yl-[1,3,5]triazine (1.0 g, 80%) as brown solid.

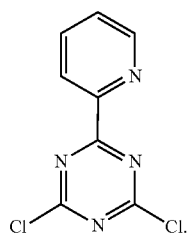 [SMILES: Clc1nc(Cl)nc(-c2ccccn2)n1]

LC-MS: m/z 227.0 (M+H)+.

Example 3, Step 4: Preparation of 4-chloro-6-(6-chloropyridin-2-yl)-N-isopropyl-1, 3, 5-triazin-2-amine To a solution of 2,4-dichloro-6-(pyridin-2-yl)-1,3,5-triazine (2.0 g, 0.0077 mol) in anhydrous THF (20 mL) was added isopropyl amine (0.45 g, 0.0077 mol). The mixture was stirred at room temperature for 1 hour. The mixture was quenched by water and extracted with ethyl acetate. The organic layer was dried over anhydrous Na₂SO₄ and concentrated to give 4-chloro-6-(6-chloropyridin-2-yl)-N-isopropyl-1,3,5-triazin-2-amine which was used directly in the next step.

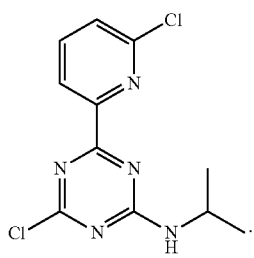 [SMILES: CC(C)Nc1nc(Cl)nc(-c2cccc(Cl)n2)n1]

LC-MS: m/z 221.1 (M+H)+.

The procedure set forth in Step 4 using the appropriate intermediate 12 and amine 6 was used to produce the following intermediates (13).

4-Chloro-6-(6-trifluoromethyl-pyridin-2-yl)-1, 3, 5 triazin-2-y]-isopropyl-amine

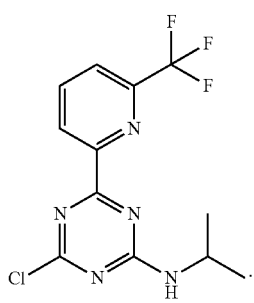 [SMILES: CC(C)Nc1nc(Cl)nc(-c2cccc(C(F)(F)F)n2)n1]

LC-MS: m/z 318.1 (M+H)+.

(4-Chloro-6-pyridin-2-yl-[1,3,5]triazin-2-yl)-isopropyl-amine

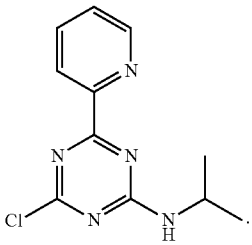 [SMILES: CC(C)Nc1nc(Cl)nc(-c2ccccn2)n1]

LC-MS: m/z 249.9 (M+H)+.

4-chloro-6-(6-chloropyridin-2-yl)-N-(oxetan-3-yl)-1,3,5-triazin-2-amine, which was used directly in the next step.

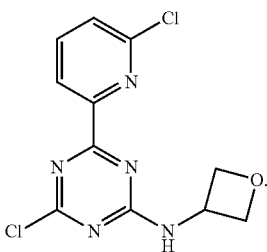 [SMILES: Clc1cccc(-c2nc(Cl)nc(NC3COC3)n2)n1]

LC-MS: m/z 298.2 (M+H)+.

4-Chloro-6-(6-trifluoromethyl-pyridin-2-yl)-1,3,5 triazin-2-y]-oxetan-3-yl-amine, which was used directly in the next step.

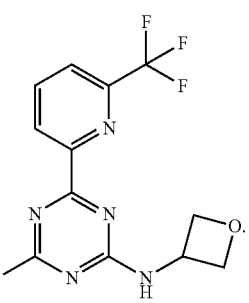

LC-MS: m/z 332.1 (M+H)+.

4-chloro-N-((tetrahydrofuran-2-yl)-methyl)-6-(6-(trifluoromethyl)pyridin-2-yl)-1,3,5-triazin-2-amine which was used directly in the next step.

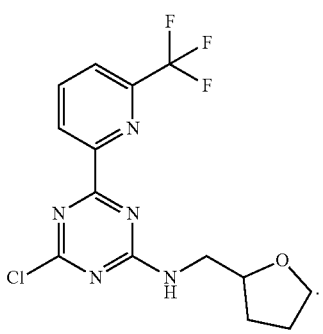 [SMILES: FC(F)(F)c1cccc(-c2nc(Cl)nc(NCC3CCCO3)n2)n1]

LC-MS: 360.1 (M+H)+.

[4-Chloro-6-(6-trifluoromethyl-pyridin-2-yl)-[1,3,5]triazin-2-yl]-(3-oxa-bicyclo[3.1.0]hex-6-yl)-amine, which was used directly in the next step.

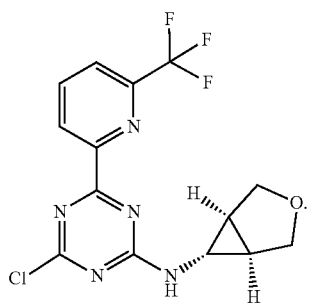 [SMILES: FC(F)(F)c1cccc(-c2nc(Cl)nc(N[C@H]3[C@@H]4COC[C@@H]43)n2)n1]

LC-MS: m/z 358.1 (M+H)+.

1-[4-Chloro-6-(6-trifluoromethyl-pyridin-2-yl)-[1,3,5]triazin-2-ylamino]-2-methyl-propan-2-ol.

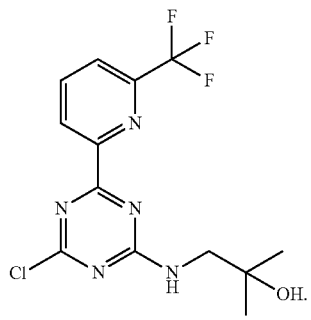 [SMILES: CC(C)(O)CNc1nc(Cl)nc(-c2cccc(C(F)(F)F)n2)n1]

LC-MS: 348.0 (M+H)+.

Example 3, Step 5: Preparation of 6-(6-Chloropyridin-2-yl)-N-oxetan-3-yl-N'-(2-trifluoromethyl-pyridin-4-yl)-[1,3,5]triazine-2,4-diamine-Compound 356

To a solution of 4-chloro-6-(6-chloropyridin-2-yl)-N-(oxetan-3-yl)-1,3,5-triazin-2-amine (0.23 g, 0.78 mmol) in anhydrous dioxane (3 mL) was added 2-trifluoromethyl-pyridin-4-ylamine (0.13 g, 0.78 mmol), t-BuONa (0.15 g, 1.56 mmol) and Pd(dppf)Cl₂ (0.057 g, 0.078 mmol). The mixture was stirred at 80° C. under N₂ for 1 hour. The mixture was quenched by water and extracted with ethyl acetate. The organic layer was dried with anhydrous Na₂SO₄, concentrated and purified by a standard method to give 6-(6-chloro-pyridin-2-yl)-N-oxetan-3-yl-N'-(2-trifluoromethyl-pyridin-4-yl)-[1,3,5]triazine-2,4-diamine.

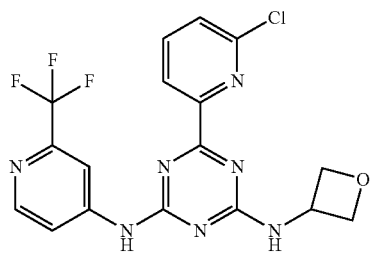 [SMILES: FC(F)(F)c1cc(Nc2nc(NC3COC3)nc(-c3cccc(Cl)n3)n2)ccn1]

¹H NMR (METHANOL-d₄): δ 8.5 (m, 2H), 8.4 (m, 1H), 8.3-8.1 (m, 0.5H), 7.96 (m, 1H), 7.85 (m, 0.6H), 7.6 (m, 1H), 5.1-5.5 (m, 1H), 5.0 (m, 2H), 4.7 (m, 2H). LC-MS: m/z 424.2 (M+H)+.

Additional compounds of Formula I set forth below were similarly produced following Scheme 3 utilizing the appropriate intermediates and reagents.

Compound 334—N²-isopropyl-6-phenyl-N⁴-(2-(trifluoromethyl)pyridin-4-yl)-1,3,5-triazine-2,4-diamine

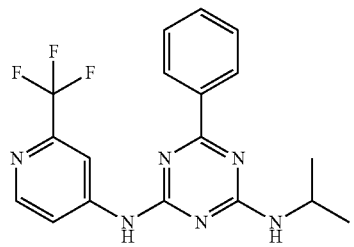 [SMILES: CC(C)Nc1nc(Nc2ccnc(C(F)(F)F)c2)nc(-c2ccccc2)n1]

¹H NMR (METHANOL-d₄): δ 8.65-8.75 (m, 2H), 8.5 (m, 2H), 8.15-8.3 (m, 0.5H), 8.0 (m, 1H), 7.82 (m, 0.6H), 4.2-4.6 (m, 1H), 1.3 (d, J=6.4 Hz, 6H). LC-MS: m/z 375.0 (M+H)+.

Compound 335—N²-isopropyl-6-(6-(trifluoromethyl)pyridin-2-yl)-N⁴-(2-(trifluoromethyl)pyridin-4-yl)-1,3,5-triazine-2,4-diamine

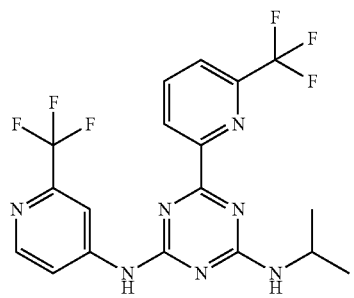

¹H NMR (METHANOL-d₄): δ 8.6 (m, 2H), 8.5 (m, 1H), 8.1-8.2 (m, 1H), 7.78 (m, 0.7H), 4.24-4.27 (m, 1H), 1.3 (d, J=6.8 Hz, 6H). LC-MS: m/z 444.3 (M+H)+.

Compound 336—N²-(oxetan-3-yl)-6-(pyridin-2-yl)-N⁴-(2-(trifluoromethyl)pyridin-4-yl)-1,3,5-triazine-2,4-diamine

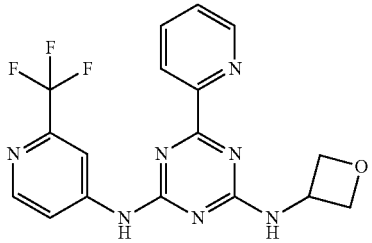

¹H NMR (METHANOL-d₄): δ 8.7 (m, 1H), 8.46-8.52 (m, 3H), 7.89-8.23 (m, 2H), 7.6 (m, 1H), 5.15-5.55 (m, 1H), 5.0 (m, 2H), 4.7 (m, 2H). LC-MS: m/z 390.2 (M+H)⁺.

Compound 337—N²-(isoxazol-4-yl)-N⁴-(oxetan-3-yl)-6-(6-(trifluoromethyl)pyridin-2-yl)-1,3,5-triazine-2,4-diamine

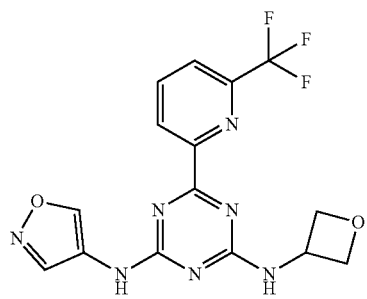 [SMILES: FC(F)(F)c1cccc(-c2nc(Nc3cnoc3)nc(NC3COC3)n2)n1]

¹H NMR (METHANOL-d₄): δ 9.35-9.05 (m, 1H), 8.6-8.7 (m, 2H), 8.2 (m, 1H), 8.0 (m, 1H), 5.2-5.4 (m, 1H), 5.0 (m, 2H), 4.7-4.8 (d, J=6.4 Hz, 6H). LC-MS: m/z 343.2 (M+H)⁺.

Compound 345—N²-cyclobutyl-N⁴-(6-fluoropyridin-3-yl)-6-(pyridin-2-yl)-1,3,5-triazine-2,4-diamine

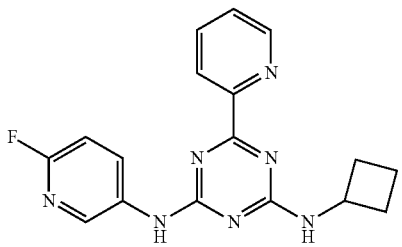 [SMILES: Fc1ccc(Nc2nc(NC3CCC3)nc(-c3ccccn3)n2)cn1]

¹H NMR (DMSO-d₆) δ 10.11 (br.s., 1H), 8.75-8.69 (m, 2H), 8.38-8.32 (m, 2H), 8.26-8.06 (m, 1H), 7.98-7.94 (m, 1H), 7.56-7.52 (m, 1H), 7.19-7.11 (m, 1H), 4.65-4.39 (m, 1H), 2.31-2.27 (m, 2H), 2.09-2.02 (m, 2H), 1.70-1.67 (m, 2H). LC-MS: m/z 338.2 (M+H)⁺.

Compound 363—N²-(6-fluoropyridin-3-yl)-N⁴-neopentyl-6-(pyridin-2-yl)-1,3,5-triazine-2,4-diamine

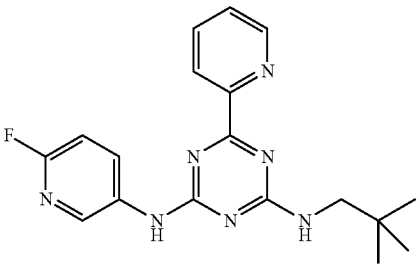

¹H NMR (CDCl₃) δ 8.82 (s., 1H), 8.53-8.41 (m, 1H), 8.41-8.39 (m, 1H), 8.17-8.09 (m, 1H), 7.88-7.83 (m, 1H), 7.49-7.42 (m, 1H), 7.25-7.15 (m, 1H), 6.99-6.92 (m, 1H), 5.76-4.90 (m, 1H), 3.48-3.31 (m, 2H), 1.01 (s, 9H). LC-MS: m/z 354.2 (M+H)⁺.

Compound 353—6-(6-chloropyridin-2-yl)-N²-isopropyl-N⁴-(pyrimidin-5-yl)-1,3,5-triazine-2,4-diamine

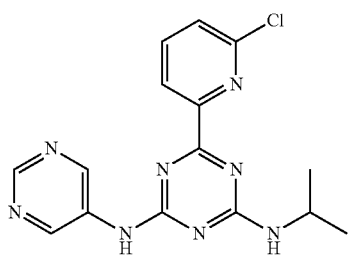

¹H NMR (METHANOL-d₄): δ 9.37 (m, 1H), 8.8 (m, 1H), 8.4 (m, 1H), 7.97 (m, 1H), 7.6 (m, 1H), 4.2-4.5 (m, 2H), 1.3 (m, 2H). LC-MS: m/z 390.2 (M+H)⁺.

Compound 354—6-(6-chloropyridin-2-yl)-N²-(2-chloropyridin-4-yl)-N'-isopropyl-1,3,5-triazine-2,4-diamine

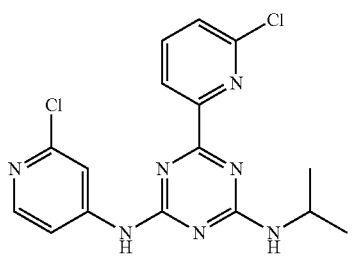 [SMILES: CC(C)Nc1nc(Nc2ccnc(Cl)c2)nc(-c2cccc(Cl)n2)n1]

¹H NMR (METHANOL-d₄): δ 8.41-8.44 (m, 1H), 8.17-8.22 (m, 2H), 7.96-8.0 (m, 1H), 7.62-7.66 (m, 2H), 4.2-4.6 (m, 1H), 1.35 (d, J=6.8 Hz, 6H). LC-MS: m/z 376.2 (M+H)⁺.

Compound 355—4-(4-(6-chloropyridin-2-yl)-6-(iso-propylamino)-1,3,5-triazin-2-ylamino)picolinonitrile

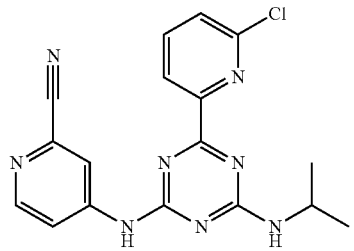 [SMILES: CC(C)Nc1nc(Nc2ccnc(C#N)c2)nc(-c2cccc(Cl)n2)n1]

$^1$H NMR (METHANOL-d$_4$): δ 8.55-8.7 (m, 3H), 8.0 (m, 2H), 7.65 (m, 1H), 4.6-4.25 (m, 1H), 1.35 (d, J=6.4 Hz, 6H). LC-MS: m/z 367.2 (M+H)$^+$.

Compound 357—N$^2$-(oxetan-3-yl)-N$^4$-(thiazol-5-yl)-6-(6-(trifluoromethyl)pyridin-2-yl)-1,3,5-triazine-2,4-diamine

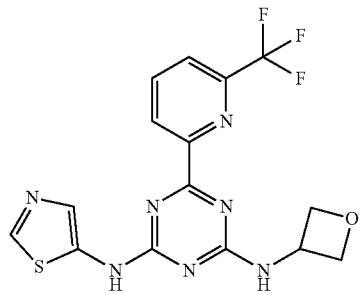 [SMILES: FC(F)(F)c1cccc(-c2nc(Nc3cncs3)nc(NC3COC3)n2)n1]

$^1$H NMR (METHANOL-d$_4$): δ 9.19-8.79 (m, 2H), 8.50-8.40 (m, 1H), 8.25-8.19 (m, 1H), 7.93-7.81 (m, 1H), 5.21-5.06 (m, 1H), 5.02-4.90 (m, 1H), 4.44-4.38 (m, 1H), 3.83-3.72 (m, 2H). LC-MS: m/z 396.1 (M+H)$^+$.

Compound 367—1-(4-(6-chloropyridin-2-yl)-6-(5-(trifluoromethyl)pyridin-3-ylamino)-1,3,5-triazin-2-ylamino)-2-methylpropan-2-ol

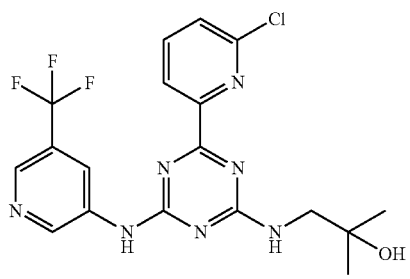 [SMILES: CC(C)(O)CNc1nc(Nc2cncc(C(F)(F)F)c2)nc(-c2cccc(Cl)n2)n1]

$^1$H NMR (METHANOL-d$_4$) δ 8.98 (s, 1H), 8.94 (s, 1H), 8.49 (s, 1H), 8.41-8.39 (m, 1H), 7.98-7.94 (s, 1H), 7.62-7.60 (m., 1H), 3.53 (s, 2H), 1.26 (s., 6H). LC-MS: m/z 440.2 (M+H)

Compound 368—1-(4-(6-chloropyridin-2-yl)-6-(2-fluoropyridin-4-ylamino)-1,3,5-triazin-2-ylamino)-2-methylpropan-2-ol

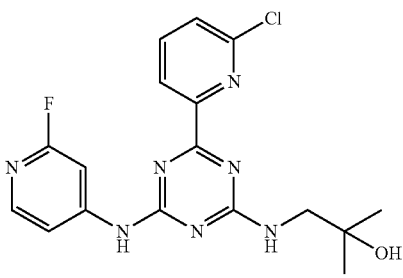 [SMILES: CC(C)(O)CNc1nc(Nc2ccnc(F)c2)nc(-c2cccc(Cl)n2)n1]

$^1$H NMR (METHANOL-d$_4$) δ 8.37-8.33 (m, 1H), 7.94-7.90 (m, 2H), 7.68 (s, 1H), 7.54-7.42 (m, 2H), 3.46 (s, 2H), 1.19 (s., 6H). LC-MS: m/z 390.2 (M+H)

Compound 377—N$^2$-(2-fluoropyridin-4-yl)-N$^4$-(oxetan-3-yl)-6-(6-(trifluoromethyl)pyridin-2-yl)-1,3,5-triazine-2,4-diamine

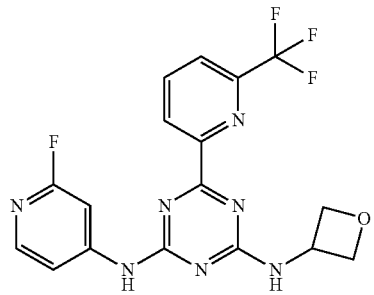 [SMILES: Fc1cc(Nc2nc(NC3COC3)nc(-c3cccc(C(F)(F)F)n3)n2)ccn1]

$^1$H NMR (METHANOL-d$_4$): δ 8.67 (m, 1H), 8.2 (m, 1H), 7.8-8.05 (m, 3H), 7.5 (m, 1H), 5.15-5.4 (m, 1H), 5.0 (m, 2H), 4.75 (m, 2H). LC-MS: m/z 408 (M+H)$^+$.

Compound 378—N$^2$-(oxetan-3-yl)-6-(6-(trifluoromethyl)pyridin-2-yl)-N$^4$-(2-(trifluoromethyl)pyridin-4-yl)-1,3,5-triazine-2,4-diamine

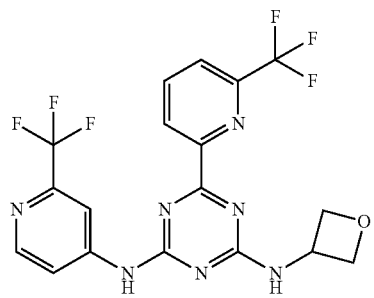 [SMILES: FC(F)(F)c1cc(Nc2nc(NC3COC3)nc(-c3cccc(C(F)(F)F)n3)n2)ccn1]

$^1$H NMR (METHANOL-d$_4$): δ 8.7 (m, 1H), 8.6-8.35 (m, 2H), 8.1-8.3 (m, 1.4H), 7.85-8.0 (m, 1.7H), 5.4-5.15 (m, 1H), 5.02 (m, 2H), 4.75 (m, 2H). LC-MS: m/z 458.2 (M+H)$^+$.

Compound 379—N²-(oxetan-3-yl)-6-(6-(trifluoromethyl)pyridin-2-yl)-N⁴-(5-(trifluoromethyl)pyridin-3-yl)-1,3,5-triazine-2,4-diamine

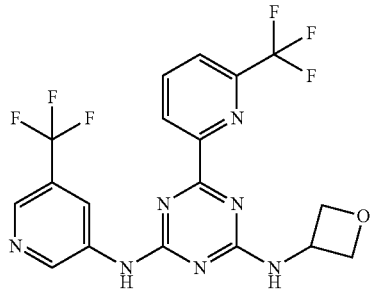 [SMILES: FC(F)(F)c1cncc(Nc2nc(NC3COC3)nc(-c3cccc(C(F)(F)F)n3)n2)c1]

¹H NMR (DMSO-d₆): δ 10.2-10.8 (m, 1H), 9.0-9.4 (m, 2H), 8.5-8.9 (m, 3H), 8.3 (m, 1H), 8.1 (m, 1H), 5.0-5.2 (m, 1H), 4.7 (m, 2H), 4.6 (m, 2H). LC-MS: m/z 458.2 (M+H)⁺.

Compound 380—N²-(6-fluoropyridin-3-yl)-N⁴-(oxetan-3-yl)-6-(6-(trifluoromethyl)pyridin-2-yl)-1,3,5-triazine-2,4-diamine

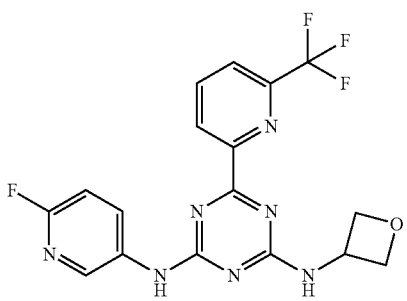 [SMILES: Fc1ccc(Nc2nc(NC3COC3)nc(-c3cccc(C(F)(F)F)n3)n2)cn1]

¹H NMR (METHANOL-d₄): δ 8.5-8.7 (m, 2H), 8.3-8.55 (m, 2H), 8.2 (m, 1H), 7.97 (m, 1H), 7.0-7.15 (m, 1H), 5.1-5.4 (m, 1H), 5.0 (m, 2H), 4.7 (m, 2H). LC-MS: m/z 407 (M+H)⁺.

Compound 381—N²-(5-fluoropyridin-3-yl)-N⁴-(oxetan-3-yl)-6-(6-(trifluoromethyl)pyridin-2-yl)-1,3,5-triazine-2,4-diamine

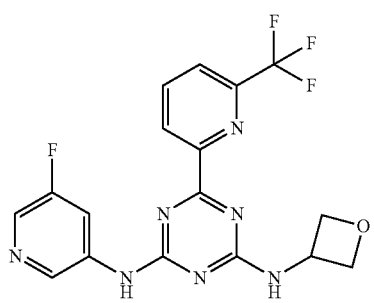

¹H NMR (METHANOL-d₄): δ 8.6-8.7 (m, 3H), 8.1-8.22 (m, 2H), 7.95 (m, 1H), 5.1-5.4 (m, 1H), 5.0 (m, 2H), 4.72 (m, 2H). LC-MS: m/z 407 (M+H)⁺.

Compound 382—5-(4-(6-chloropyridin-2-yl)-6-(isopropylamino)-1,3,5-triazin-2-ylamino)nicotinonitrile

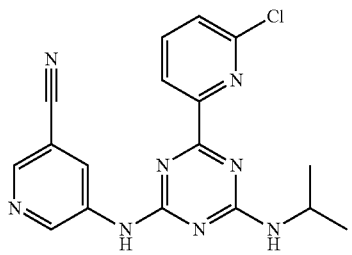

¹H NMR (METHANOL-d₄) δ 9.12 (s, 1H), 8.95-8.77 (m, 2H), 8.71-8.67 (m, 1H), 8.56-8.51 (m, 1H), 8.19-8.15 (m, 1H), 7.88-7.86 (m, 1H), 4.60-4.29 (m, 1H), 1.40 (d, J=6.4 Hz, 6H) LC-MS: m/z 367.2 (M+H)⁺.

Compound 383—6-(6-chloropyridin-2-yl)-N²-(5-fluoropyridin-3-yl)-N'-isopropyl-1,3,5-triazine-2,4-diamine

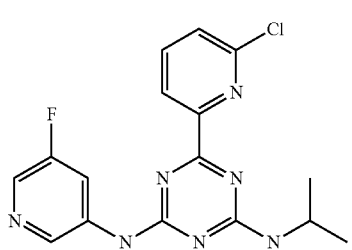

¹H NMR (METHANOL-d₄) δ 8.88 (s, 1H), 8.52-8.49 (m, 2H), 8.32-8.30 (m, 1H), 8.20-8.16 (m, 1H), 7.89-7.87 (m, 1H), 4.35-4.31 (m, 1H), 1.40 (d, J=6.4 Hz, 6H). LC-MS: m/z 360.1 (M+H)⁺.

Compound 384—6-(6-chloropyridin-2-yl)-N²-(2-fluoropyridin-4-yl)-N⁴-isopropyl-1,3,5-triazine-2,4-diamine

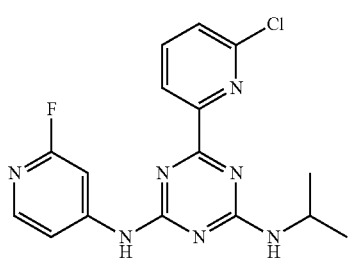 [SMILES: CC(C)Nc1nc(Nc2ccnc(F)c2)nc(-c2cccc(Cl)n2)n1]

¹H NMR (METHANOL-d₄) δ 8.45-8.41 (m, 1H), 8.02-7.96 (m, 2H), 7.79 (s, 1H), 7.63-7.61 (m, 1H), 7.54-7.49 (m, 1H), 4.47-4.24 (m, 1H), 1.32 (d, J=6.4 Hz, 6H). LC-MS: m/z 360.1 (M+H)⁺.

Compound 385—1-(4-(6-fluoropyridin-3-ylamino)-6-(6-(trifluoromethyl)pyridin-2-yl)-1,3,5-triazin-2-ylamino)-2-methylpropan-2-ol

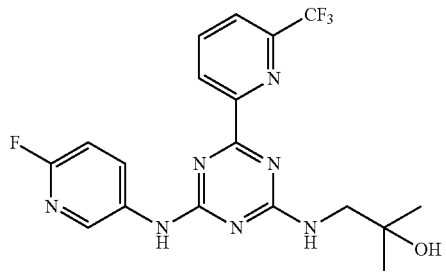 [SMILES: CC(C)(O)CNc1nc(Nc2ccc(F)nc2)nc(-c2cccc(C(F)(F)F)n2)n1]

$^1$H NMR (METHANOL-d$_4$) δ 8.63-8.75 (m, 2H), 8.42-8.56 (m, 1H), 8.26-8.30 (q, J=8, 1H), 8.04-8.06 (d, J=7.2 Hz, 1H), 7.16-7.19 (m, 1H), 3.60-3.68 (d, J=32.4 Hz, 2H), 1.35 (s., 6H). LC-MS: m/z 424.2 (M+H)$^+$.

Compound 386—N$^2$-isopropyl-6-(6-(trifluoromethyl)pyridin-2-yl)-N$^4$-(5-(trifluoromethyl)pyridin-3-yl)-1,3,5-triazine-2,4-diamine

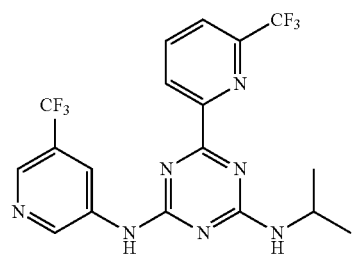 [SMILES: CC(C)Nc1nc(Nc2cncc(C(F)(F)F)c2)nc(-c2cccc(C(F)(F)F)n2)n1]

$^1$H NMR (METHANOL-d$_4$) δ 9.04-8.96 (m, 2H), 8.68-8.64 (m, 1H), 8.49-8.47 (m, 1H), 8.20-8.16 (m, 1H), 7.96-7.94 (d, J=8.0 Hz, 1H), 4.60-4.20 (m, 1H), 1.31 (d, J=6.4 Hz, 6H). LC-MS: m/z 444.2 (M+H)$^+$.

Compound 388—1-(4-(6-chloropyridin-2-yl)-6-(6-fluoropyridin-3-ylamino)-1,3,5-triazin-2-ylamino)-2-methylpropan-2-ol

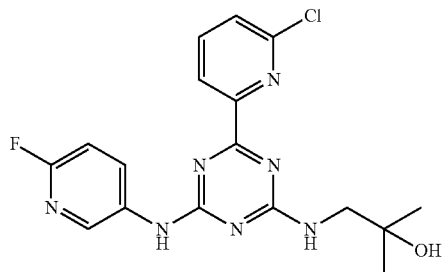

$^1$H NMR (METHANOL-d$_4$) δ 8.58 (s, 1H), 8.42-8.31 (m, 2H), 8.00-7.98 (m, 1H), 7.63-7.61 (m, 1H), 7.09-7.08 (m, 1H), 3.52 (s., 2H), 1.27 (s., 6H). LC-MS: m/z 390.2 (M+H)

Compound 389—1-(4-(6-chloropyridin-2-yl)-6-(2-(trifluoromethyl)pyridin-4-ylamino)-1,3,5-triazin-2-ylamino)propan-2-ol

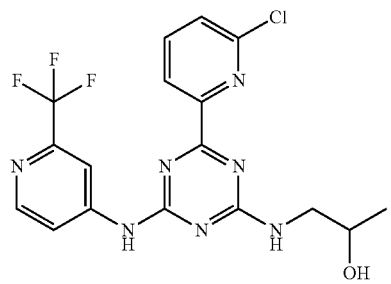

$^1$H NMR (METHANOL-d$_4$) δ 8.46-7.92 (m, 3H), 7.91-7.52 (m, 3H), 3.98-3.88 (m, 1H), 3.52-3.33 (m, 2H), 1.16 (t, J=8.0 Hz, 6H). LC-MS: m/z 426.2 (M+H).

Compound 390—1-(4-(6-chloropyridin-2-yl)-6-(5-fluoropyridin-3-ylamino)-1,3,5-triazin-2-ylamino)-2-methylpropan-2-ol

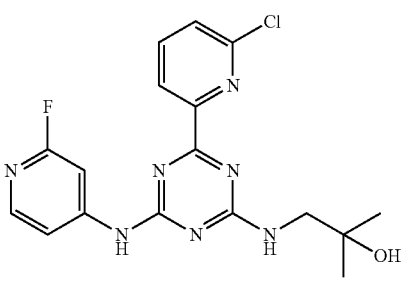 [SMILES: CC(C)(O)CNc1nc(Nc2ccnc(F)c2)nc(-c2cccc(Cl)n2)n1]

$^1$H NMR (METHANOL-d$_4$) δ 8.72 (s, 1H), 8.63-8.43 (m, 2H), 8.16-8.16 (m, 1H), 8.03-7.99 (m, 1H), 7.65-7.64 (m, 1H), 3.57 (s, 2H), 1.30 (s, 6H). LC-MS: m/z 390.2 (M+H).

Compound 391—1-(4-(6-chloropyridin-2-yl)-6-(2-(trifluoromethyl)pyridin-4-ylamino)-1,3,5-triazin-2-ylamino)-2-methylpropan-2-ol

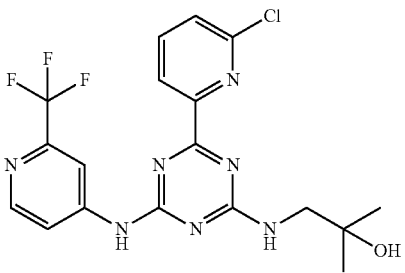 [SMILES: CC(C)(O)CNc1nc(Nc2ccnc(C(F)(F)F)c2)nc(-c2cccc(Cl)n2)n1]

$^1$H NMR (METHANOL-d$_4$) δ 8.62-8.17 (m, 3H), 8.00-7.95 (m, 1H), 7.84-7.83 (m, 1H), 7.63-7.61 (m, 1H), 3.56 (s, 2H), 1.28 (s, 6H). LC-MS: m/z 440.3 (M+H).

187

Compound 393—6-(6-chloropyridin-2-yl)-N²-(2-fluoropyridin-4-yl)-N⁴-(oxetan-3-yl)-1,3,5-triazine-2,4-diamine

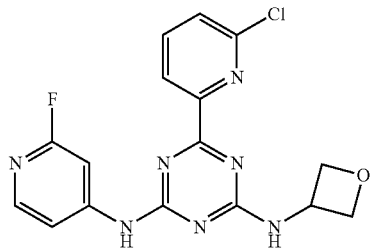

¹H NMR (DMSO-d₆): δ 10.6-10.8 (m, 2H), 8.8-9.2 (m, 1H), 8.3-8.5 (m, 1H), 7.9-8.2 (m, 2.4H), 7.6-7.8 (m, 2.5H), 5.0-5.2 (m, 1H), 4.75 (m, 2H), 4.6 (m, 2H). LC-MS: m/z 373 (M+H)⁺.

Compound 394—6-(6-chloropyridin-2-yl)-N²-isopropyl-N⁴-(5-(trifluoromethyl)pyridin-3-yl)-1,3,5-triazine-2,4-diamine

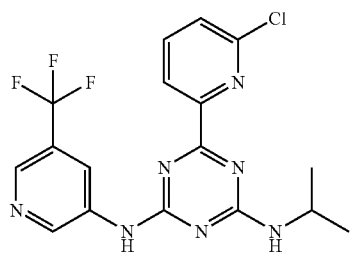 [SMILES: CC(C)Nc1nc(Nc2cncc(C(F)(F)F)c2)nc(-c2cccc(Cl)n2)n1]

¹H NMR (METHANOL-d₄) δ 9.15-8.70 (s, 2H), 8.49 (s, 1H), 8.43-8.38 (m, 1H), 7.98-7.93 (m, 1H), 7.60-7.58 (m, 1H), 4.50-4.18 (m, 1H), 1.30 (d, J=8 Hz, 6H). LC-MS: m/z 410.2 (M+H)⁺.

Compound 396—6-(6-chloropyridin-2-yl)-N²-isopropyl-N⁴-(2-(trifluoromethyl)pyridin-4-yl)-1,3,5-triazine-2,4-diamine

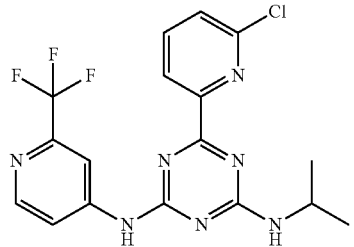 [SMILES: CC(C)Nc1nc(Nc2ccnc(C(F)(F)F)c2)nc(-c2cccc(Cl)n2)n1]

¹H NMR (METHANOL-d₄) δ 8.86-8.67 (br.s, 1H), 8.48-8.42 (m, 2H), 8.23-7.61 (m, 3H), 4.53-4.13 (m, 1H), 1.32 (s, 6H). LC-MS: m/z 410.2 (M+H)⁺.

188

Compound 399—6-(6-chloropyridin-2-yl)-N²-(5-fluoropyridin-3-yl)-N⁴-isobutyl-1,3,5-triazine-2,4-diamine

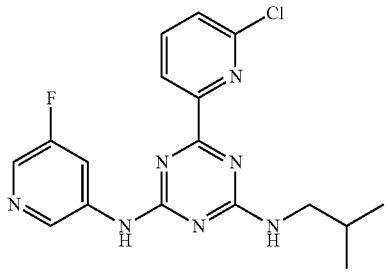 [SMILES: CC(C)CNc1nc(Nc2cncc(F)c2)nc(-c2cccc(Cl)n2)n1]

1H NMR (METHANOL-d₄) δ 8.67-8.41 (m, 3H), 8.13-8.10 (m, 1H), 8.00-7.97 (m, 1H), 7.96-7.62 (m, 1H), 3.42-3.31 (m., 2H), 2.04-2.01 (m., 1H), 1.00 (dd, J=4, 400 MHz, 6H). LC-MS: m/z 374.2 (M+H)⁺.

Compound 400—N²-(3-(azetidin-1-ylsulfonyl)phenyl)-6-(6-chloropyridin-2-yl)-N⁴-isopropyl-1,3,5-triazine-2,4-diamine

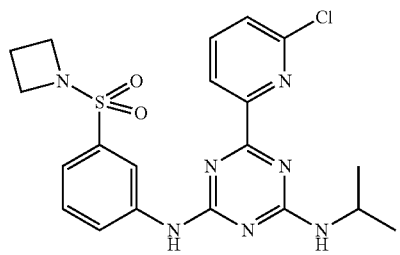 [SMILES: CC(C)Nc1nc(Nc2cccc(S(=O)(=O)N3CCC3)c2)nc(-c2cccc(Cl)n2)n1]

¹H NMR (METHANOL-d₄) δ 8.93 (s, 1H), 8.47-8.45 (m, 1H), 7.98 (m, 1H), 7.63-7.61 (m, 1H), 7.56 (m, 2H), 7.50-7.48 (m, 1H), 4.35 (m, 1H), 3.82-3.78 (m., 4H), 2.1-2.06 (m., 2H), 1.32-1.30 (d, J=8 Hz, 6H). LC-MS: m/z 459.9 (M+H)⁺.

Compound 401—5-(4-(isopropylamino)-6-(6-(trifluoromethyl)pyridin-2-yl)-1,3,5-triazin-2-ylamino)nicotinonitrile

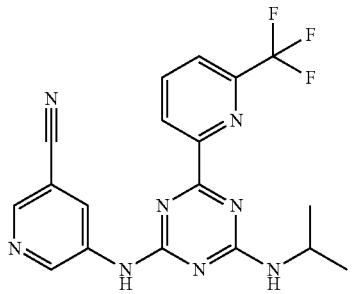 [SMILES: CC(C)Nc1nc(Nc2cncc(C#N)c2)nc(-c2cccc(C(F)(F)F)n2)n1]

¹H NMR (METHANOL-d₄) δ: 8.96-8.84 (m, 2H), 8.59-8.54 (m, 1H), 8.42-8.397 (m, 1H), 8.11-8.07 (m, 1H), 7.87-7.85 (d, J=8.0 Hz, 1H), 4.47-4.12 (m, 1H), 1.21 (d, J=6.8 Hz, 6H). LC-MS: m/z 401.2 (M+H)+.

Compound 402—N²-(2-fluoropyridin-4-yl)-N⁴-((tetrahydrofuran-2-yl)methyl)-6-(6-(trifluoromethyl)pyridin-2-yl)-1,3,5-triazine-2,4-diamine

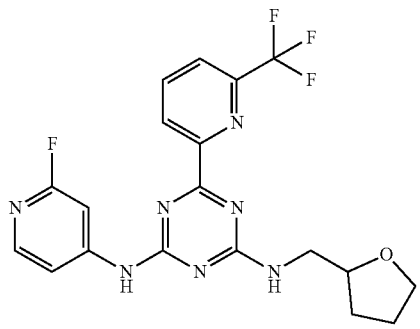 [SMILES: Fc1cc(Nc2nc(NCC3CCCO3)nc(-c3cccc(C(F)(F)F)n3)n2)ccn1]

¹H NMR (METHANOL-d₄) δ: 8.69 (t, J=7.4 Hz, 1H), 8.22 (t, J=8.0 Hz, 1H), 8.04-7.98 (m, 2H), 7.84 (s, 1H), 7.53 (dd, J=10.8 Hz, 5.2 Hz, 1H), 4.23-4.19 (m, 1H), 3.99-3.96 (m, 1H), 3.83-3.78 (m, 1H), 3.70-3.63 (m, 2H), 2.12-2.08 (m, 1H), 2.04-1.95 (m, 2H), 1.79-1.72 (m, 1H). LC-MS: m/z 436.2 (M+H)+.

Compound 403—4-(4-((tetrahydrofuran-2-yl)methylamino)-6-(6-(trifluoromethyl)pyridin-2-yl)-1,3,5-triazin-2-ylamino)picolinonitrile

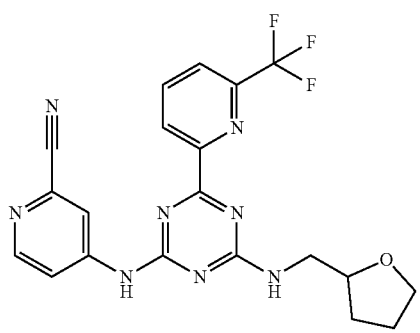 [SMILES: N#Cc1cc(Nc2nc(NCC3CCCO3)nc(-c3cccc(C(F)(F)F)n3)n2)ccn1]

¹H NMR (METHANOL-d₄) δ: 8.68 (t, J=7.2 Hz, 1H), 8.59 (d, J=16.8 Hz, 1H), 8.46 (dd, J=14.0 Hz, 5.8 Hz, 2H), 8.21 (t, J=7.8 Hz, 1H), 7.99-7.95 (m, 2H), 4.23-4.20 (m, 1H), 3.99-3.93 (m, 1H), 3.84-3.78 (m, 1H), 3.69-3.62 (m, 2H), 2.13-2.09 (m, 1H), 2.05-1.98 (m, 2H), 1.79-1.73 (m, 1H). LC-MS: m/z 443.3 (M+H)+.

Compound 404—4-(4-(isopropylamino)-6-(6-(trifluoromethyl)pyridin-2-yl)-1,3,5-triazin-2-ylamino)picolinonitrile

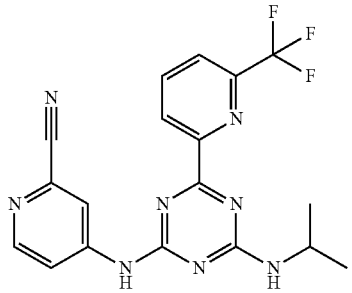 [SMILES: CC(C)Nc1nc(Nc2ccnc(C#N)c2)nc(-c2cccc(C(F)(F)F)n2)n1]

¹H NMR (METHANOL-d₄) δ: 8.72-8.65 (m, 1H), 8.59 (s, 1H), 8.48 (dd, J=10.4 Hz, 6.0 Hz, 1H), 8.22 (t, J=7.8 Hz, 1H), 7.99-7.94 (m, 2H), 4.49-4.25 (m, 1H), 1.31 (d, J=7.6 Hz, 6H). LC-MS: m/z 401.2 (M+H)+.

Compound 405—5-(4-(2-hydroxy-2-methylpropylamino)-6-(6-(trifluoromethyl)pyridin-2-yl)-1,3,5-triazin-2-ylamino)nicotinonitrile

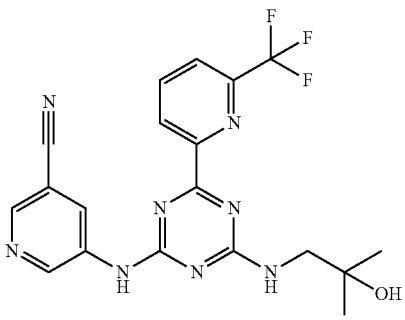 [SMILES: CC(C)(O)CNc1nc(Nc2cncc(C#N)c2)nc(-c2cccc(C(F)(F)F)n2)n1]

¹H NMR (METHANOL-d₄) δ 9.03-9.12 (m, 1H), 8.70-8.78 (m, 3H), 8.37-8.45 (m, 1H), 8.18-8.25 (d, J=7.2 Hz, 1H), 3.62 (s, 2H), 1.35 (s, 6H). LC-MS: m/z 431.1 (M+H)+.

Compound 406—2-methyl-1-(4-(6-(trifluoromethyl)pyridin-2-yl)-6-(5-(trifluoromethyl)pyridin-3-ylamino)-1,3,5-triazin-2-ylamino)propan-2-ol

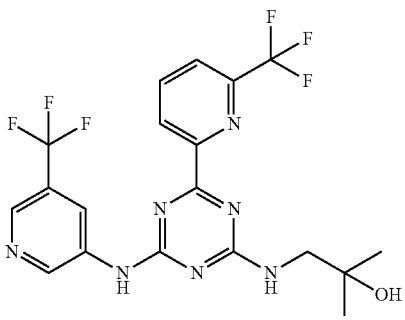 [SMILES: CC(C)(O)CNc1nc(Nc2cncc(C(F)(F)F)c2)nc(-c2cccc(C(F)(F)F)n2)n1]

¹H NMR (METHANOL-d₄) δ 9.00-9.18 (m, 2H), 8.69-8.71 (m, 1H), 8.51-8.54 (m, 1H), 8.20-8.22 (m, 1H), 7.98-8.00 (m, 1H), 3.57-3.65 (d, J=30.8 Hz, 2H), 1.30 (s, 6H). LC-MS: m/z 474.2 (M+H)⁺.

Compound 407—1-(4-(5-fluoropyridin-3-ylamino)-6-(6-(trifluoromethyl)pyridin-2-yl)-1,3,5-triazin-2-ylamino)-2-methylpropan-2-ol

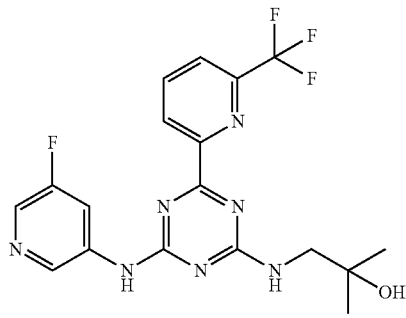 [SMILES: CC(C)(O)CNc1nc(Nc2cncc(F)c2)nc(-c2cccc(C(F)(F)F)n2)n1]

¹H NMR (METHANOL-d₄) δ 8.92 (s, 1H), 8.81-8.83 (m, 1H), 8.53-8.58 (m, 3H), 8.26-8.28 (m, 1H), 3.64 (s, 2H), 1.35 (s, 6H). LC-MS: m/z 424.2 (M+H)⁺.

Compound 408—4-(4-(isobutylamino)-6-(6-(trifluoromethyl)pyridin-2-yl)-1,3,5-triazin-2-ylamino)picolinonitrile

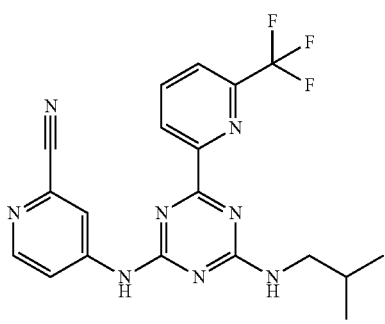 [SMILES: CC(C)CNc1nc(Nc2ccnc(C#N)c2)nc(-c2cccc(C(F)(F)F)n2)n1]

¹H NMR (DMSO-d₄) δ 10.7 (s, 1H), 8.52-8.70 (m, 4H), 8.30-8.34 (m, 1H), 8.11-8.13 (m, 1H), 7.93-8.05 (m, 1H), 3.21-3.24 (q, J=6.4 Hz, 2H), 1.95-2.00 (m, 1H), 0.96-0.98 (q, J=3.6 Hz, 6H). LC-MS: m/z 415.3 (M+H)⁺.

Compound 409—2-methyl-1-(4-(6-(trifluoromethyl)pyridin-2-yl)-6-(2-(trifluoromethyl)pyridin-4-ylamino)-1,3,5-triazin-2-ylamino)propan-2-ol

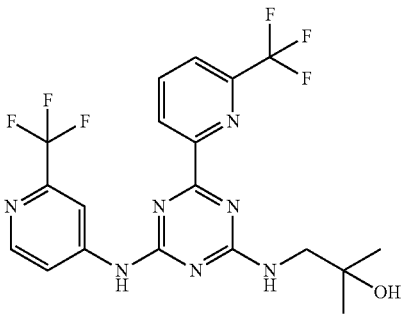 [SMILES: CC(C)(O)CNc1nc(Nc2ccnc(C(F)(F)F)c2)nc(-c2cccc(C(F)(F)F)n2)n1]

¹H NMR (METHANOL-d₄) δ 8.62-8.68 (m, 2H), 847-8.50 (m, 1H), 8.18-8.21 (m, 1H), 7.96-7.98 (m, 1H), 7.82-7.84 (m, 1H), 3.56-3.63 (d, J=28 Hz, 2H), 1.30 (s, 6H). LC-MS: m/z 474.3 (M+H)⁺.

Compound 410—6-(6-chloropyridin-2-yl)-N²-(6-fluoropyridin-3-yl)-N⁴-(oxetan-3-yl)-1,3,5-triazine-2,4-diamine

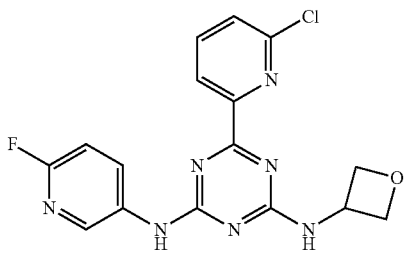 [SMILES: Fc1ccc(Nc2nc(NC3COC3)nc(-c3cccc(Cl)n3)n2)cn1]

1H NMR (METHANOL-d₄) δ 8.50-8.31 (m, 3H), 7.89-7.86 (m, 1H), 7.53-7.51 (m, 1H), 7.02-7.00 (m, 1H), 5.02-4.90 (m., 1H), 4.88-4.84 (m., 2H), 4.61-4.59 (m, 2H) LC-MS: m/z 374.2 (M+H)⁺.

Compound 411—N²-(3-oxabicyclo[3.1.0]hexan-6-yl)-N⁴-(5-fluoropyridin-3-yl)-6-(6-(trifluoromethyl)pyridin-2-yl)-1,3,5-triazine-2,4-diamine

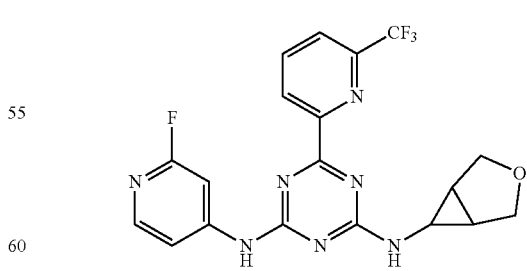

1H NMR (DMSO-d₆) δ 10.04-10.06 (m, 1H), 8.69-8.91 (m, 1H), 8.47-8.58 (m, 2H), 8.32 (t, J=8.0 Hz, 1H), 8.19-8.24 (m., 1H), 8.10-8.12 (m, 1H), 3.98 (d., J=8.0 Hz, 2H), 3.69 (d., J=8.0 Hz, 2H), 2.57-2.61 (m, 1H), 1.97 (s, 2H). LC-MS: m/z 434.2 (M+H)⁺.

Example 4. Preparation of Compounds of Formula I Wherein Ring A is Substituted Phenyl The compounds of this Example are prepared by general Scheme 4, set forth below.

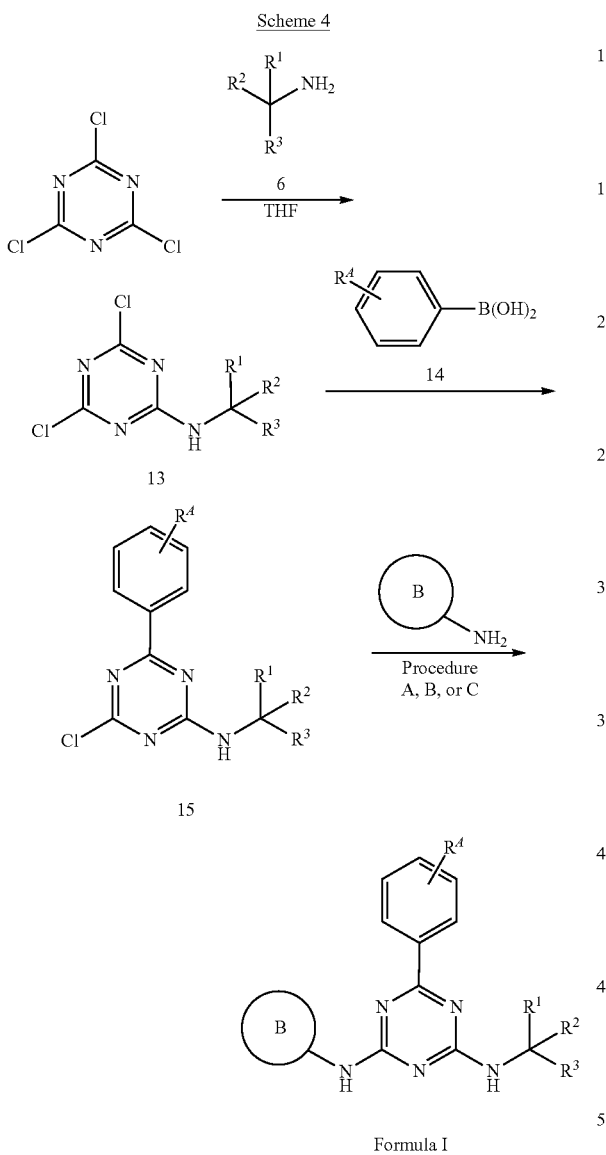

Scheme 4

Formula I

Example 4, Step 1: Preparation of 4,6-dichloro-N-isopropyl-1,3,5-triazin-2-amine To a solution of 2,4,6-trichloro-1,3,5-triazine (4.0 g, 0.0217 mol) in THF (25 mL) was added isopropyl amine (1.27 g, 0.0217 mmol) at 0° C. The mixture was stirred at room temperature for 12 hours. The mixture was adjusted pH 7 by aq NaHCO$_3$ and extracted with ethyl acetate (100 mL*2). The combined organic layer was dried over Na$_2$SO$_4$, concentrated and purified by column chromatography to give 4,6-dichloro-N-isopropyl-1,3,5-triazin-2-amine as a colorless oil.

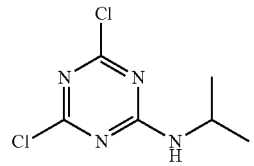

$^1$H NMR (CDCl$_3$) δ 1.24-1.27 (m, 6H), 4.21-4.26 (m, 1H), 5.68 (br s, 1H).

The following intermediates (13) were prepared following the procedure of Step 1 using the appropriate amine 6.

4,6-dichloro-N-(oxetan-3-yl)-1,3,5-triazin-2-amine, which was directly used in the next step.

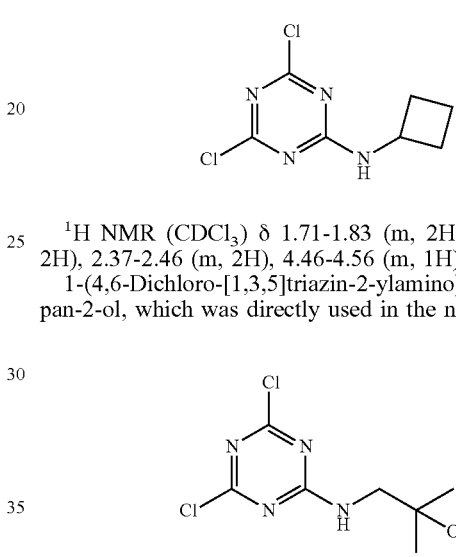

$^1$H NMR (CDCl$_3$) δ 1.71-1.83 (m, 2H), 1.90-2.04 (m, 2H), 2.37-2.46 (m, 2H), 4.46-4.56 (m, 1H), 6.04 (br. 1H).

1-(4,6-Dichloro-[1,3,5]triazin-2-ylamino)-2-methyl-propan-2-ol, which was directly used in the next step.

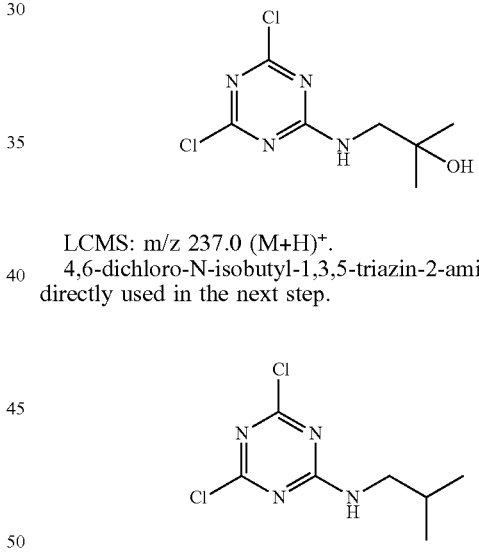

LCMS: m/z 237.0 (M+H)$^+$.

4,6-dichloro-N-isobutyl-1,3,5-triazin-2-amine, which was directly used in the next step.

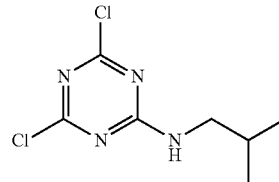

$^1$H NMR (CDCl$_3$) δ 0.85 (d, J=8.6 Hz, 6H), 1.75-1.94 (m, 1H), 3.30-3.33 (m, 2H), 6.29 (br, 1H).

Example 4, Step 2: Preparation of 1-[4-chloro-6-(2-fluoro-phenyl)-[1,3,5] triazin-2-ylamino]-2-methyl-propan-2-ol To a mixture of 4,6-dichloro-N-isopropyl-1,3,5-triazin-2-amine (1.0 g, 4.83 mmol), 3-fluorophenylboronic acid (0.671 g, 0.00483 mol) and Cs$_2$CO$_3$ (3.15 g, 0.00966 mol) in dioxane/water (12 mL/2.4 mL) was added Pd(PPh$_3$)$_4$ (0.56 g, 483 mmol). The mixture was heated to 80° C. for 2 hours. The mixture was concentrated and purified by SiO$_2$ chromatography to give 1-[4-chloro-6-(2-fluoro-phenyl)-[1,3,5] triazin-2-ylamino]-2-methyl-propan-2-ol as a white solid.

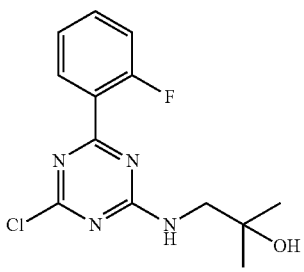 [SMILES: CC(C)(O)CNc1nc(Cl)nc(-c2ccccc2F)n1]

LCMS: m/z 297.1 (M+H)+.

Additional intermediates 15 were prepared by the method of Example 4, step 2 using the appropriate boronic acid 14 and the appropriate starting intermediate 13.

[4-chloro-6-(3-chloro-phenyl)-[1,3,5]triazin-2-yl]-isopropyl-amine

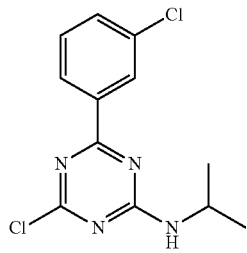 [SMILES: CC(C)Nc1nc(Cl)nc(-c2cccc(Cl)c2)n1]

LCMS: m/z 282.9 (M+H)+.

4-chloro-6-(2-fluorophenyl)-N-isopropyl-1,3,5-triazin-2-amine

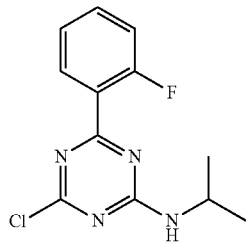 [SMILES: CC(C)Nc1nc(Cl)nc(-c2ccccc2F)n1]

LCMS: m/z 266.8 (M+H)+.

4-chloro-6-(2-chlorophenyl)-N-isopropyl-1,3,5-triazin-2-amine

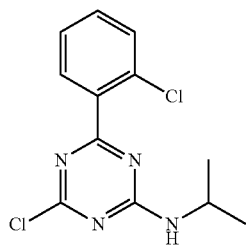 [SMILES: CC(C)Nc1nc(Cl)nc(-c2ccccc2Cl)n1]

LCMS: m/z 282.8 (M+H)+.

4-chloro-6-(3-fluorophenyl)-N-isopropyl-1,3,5-triazin-2-amine

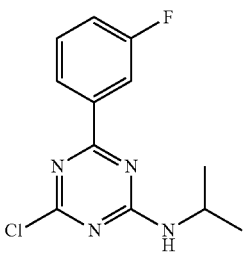 [SMILES: CC(C)Nc1nc(Cl)nc(-c2cccc(F)c2)n1]

LCMS: m/z 266.9 (M+H)+.

[3-(4-Chloro-6-isopropylamino-[1,3,5] triazin-2-yl)-phenyl]-carbamic acid tert-butyl ester

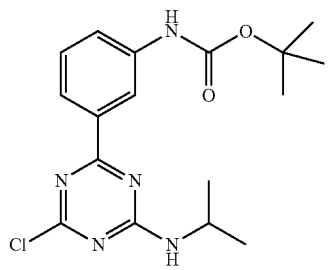 [SMILES: CC(C)Nc1nc(Cl)nc(-c2cccc(NC(=O)OC(C)(C)C)c2)n1]

LCMS: m/z 364.2 (M+H)+.

[4-Chloro-6-(3-methoxy-phenyl)-[1,3,5]triazin-2-yl]-isopropyl-amine

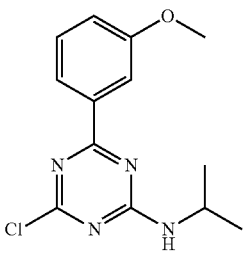 [SMILES: COc1cccc(-c2nc(Cl)nc(NC(C)C)n2)c1]

LCMS: m/z 279.1 (M+H)+.

Example 4, Step 3 (Procedure A): Preparation of Compound 227—6-(2-fluorophenyl)-N²-isopropyl-N⁴-(pyridin-4-yl)-1,3,5-triazine-2,4-diamine A mixture of 4-chloro-6-(2-fluorophenyl)-N-isopropyl-1,3,5-triazin-2-amine (290 mg, 1.1 mmol), pyridine-4-amine (103 mg, 1.1 mmol), CsF (554 mg, 2.2 mmol) and DIPEA (0.425 g, 3.3 mmol) in DMSO (4 mL) was heated to 80° C. for 2 hours. The mixture was filtered and purified by a standard method to give 6-(2-fluorophenyl)-N²-isopropyl-N⁴-(pyridin-4-yl)-1,3,5-triazine-2,4-diamine.

¹H NMR (METHANOL-d₄) δ: 8.32 (t, J=6.2 Hz, 2H), 8.12-8.03 (m, 1H), 7.89 (t, J=6.2 Hz, 2H), 7.54-7.49 (m, 1H), 7.27 (t, J=7.6 Hz, 1H), 7.23-7.18 (m, 1H), 4.35-4.23 (m, 1H), 1.30-1.26 (m, 6H). LC-MS: m/z 325.0 (M+H)⁺.

The following compound was also made using the procedure of Step 3 and the appropriate amine 4.

Compound 226—6-(2-chlorophenyl)-N²-isopropyl-N⁴-(pyridin-4-yl)-1,3,5-triazine-2,4-diamine ¹H NMR (METHANOL-d₄) δ: 8.31 (t, J=6.2 Hz, 2H), 7.87 (t, J=6.2 Hz, 2H), 7.74-7.65 (m, 1H), 7.50-7.37 (m, 3H), 4.31-4.26 (m, 1H), 1.30-1.24 (m, 6H). LC-MS: m/z 341.0 (M+H)⁺.

Example 4, Step 3 (Procedure B): Compound 317—N²-cyclobutyl-6-(2-fluorophenyl)-N⁴-(3-(methylsulfonyl)phenyl)-1,3,5-triazine-2,4-diamine A mixture of [4-chloro-6-(2-fluoro-phenyl)-[1,3,5]triazin-2-yl]-cyclobutyl-amine (150 mg, 0.538 mmol) and 3-methanesulfonyl-phenylamine (111 mg, 0.648 mmol) in anhydrous THF (10 mL) was stirred at 80° C. for 8 hrs. TLC (petroleum ether/ethyl acetate 10/1) indicated the reaction was complete and water was added. The mixture was extracted with ethyl acetate and the organic layer was washed with brine, dried over sodium sulfate. Filtered and the filtrate was concentrated in vacuo to give crude N-cyclobutyl-6-(2-fluoro-phenyl)-N'-(3-methane-sulfonyl-phenyl)-[1,3,5]triazine-2,4-diamine, which was purified a standard method to give pure N-cyclobutyl-6-(2-fluoro-phenyl)-N'-(3-methanesulfonyl-phenyl)-[1,3,5]triazine-2,4-diamine.

¹H NMR (METHANOL-d₄) δ: 9.00-8.61 (m, 1H), 8.16-7.76 (m, 1H), 7.62-7.52 (m, 3H), 7.30-7.18 (m, 2H), 4.67-4.61 (m, 1H), 3.16 (s, 3H), 2.52-2.38 (m, 2H), 2.10-2.01 (m, 2H), 1.88-1.76 (m, 2H). LC-MS: m/z 414.3 (M+H)⁺.

Example 4, Step 3 (Procedure C): Synthesis of Compound 318—N-Cyclobutyl-6-(2-fluoro-phenyl)-N'-(5-fluoro-pyridin-3-yl)-[1,3,5]triazine-2,4-diamine A mixture of [4-chloro-6-(2-fluoro-phenyl)-[1,3,5]triazin-2-yl]-cyclobutyl-amine (300 mg, 1.08 mmol), 5-fluoro-pyridin-3-ylamine (145 mg, 1.29 mmol) Pd(dppf)Cl₂ (80 mg, 0.11 mmol) and t-BuONa (208 mg, 2.17 mmol) in dioxane (15 mL) was stirred at 80° C. under N₂ for 2 hrs. Cooled to room temperature and water was added. Extracted with ethyl acetate and the organic layer was washed with brine, dried over sodium sulfate and filtered. The filtrate was concentrated in vacuo and the residue was purified by a standard method to obtain N-cyclobutyl-6-(2-fluoro-phenyl)-N'-(5-fluoro-pyridin-3-yl)-[1,3,5]triazine-2,4-diamine.

¹H NMR (METHANOL-d₄) δ: 8.73-8.44 (m, 2H), 8.08 (d, J=13.1 Hz, 2H), 7.53 (br.s., 1H), 7.28-7.19 (m, 2H), 4.58-4.51 (m, 1H), 2.42 (br.s., 2H), 2.09 (t, J=9.6 Hz, 2H), 1.80 (br.s., 2H). LC-MS: m/z 355.2 (M+H)⁺.

The following compounds were analogously made according to Example 4, step 3 (procedure C) using the appropriate intermediate 15 and the appropriate amine 4

Compound 184—6-(3-fluorophenyl)-N²-isopropyl-N⁴-(pyridin-4-yl)-1,3,5-triazine-2,4-diamine ¹H NMR (METHANOL-d₄) δ: 8.35-8.31 (m, 2H), 8.26-8.20 (m, 1H), 8.10 (t, J=8.9 Hz, 1H), 7.90 (t, J=6.9 Hz, 2H), 7.55-7.47 (m, 1H), 7.30-7.24 (m, 1H), 4.43-4.24 (m, 1H), 1.30 (d, J=6.9 Hz, 6H). LC-MS: m/z 325.0 (M+H)⁺.

Compound 185—6-(3-chlorophenyl)-$N^2$-isopropyl-$N^4$-(pyridin-4-yl)-1,3,5-triazine-2,4-diamine

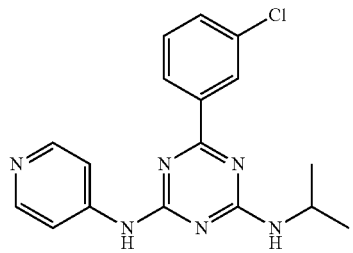 [SMILES: CC(C)Nc1nc(Nc2ccncc2)nc(-c2cccc(Cl)c2)n1]

$^1$H NMR (METHANOL-$d_4$) δ: 8.38-8.30 (m, 4H), 7.91-7.87 (m, 2H), 7.53-7.43 (m, 2H), 4.41-4.23 (m, 1H), 1.30 (d, J=6.2 Hz, 6H). LC-MS: m/z 340.9 (M+H)$^+$.

Compound 319—1-(4-(2-fluorophenyl)-6-(2-(trifluoromethyl)pyridin-4-ylamino)-1,3,5-triazin-2-ylamino)-2-methylpropan-2-ol

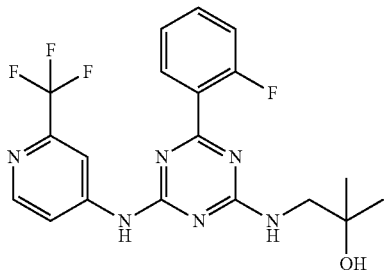 [SMILES: CC(C)(O)CNc1nc(Nc2ccnc(C(F)(F)F)c2)nc(-c2ccccc2F)n1]

$^1$H NMR (METHANOL-$d_4$) δ: 8.65 (s, 1H), 8.49-8.38 (m, 1H), 8.19-7.85 (m, 2H), 7.62-7.52 (m, 1H), 7.32-7.22 (m, 2H), 3.58-3.56 (m, 2H), 1.29-1.27 (m, 6H). LC-MS: m/z 423.3 (M+H)$^+$.

Compound 392—1-(4-(2-fluorophenyl)-6-(5-(trifluoromethyl)pyridin-3-ylamino)-1,3,5-triazin-2-ylamino)-2-methylpropan-2-ol

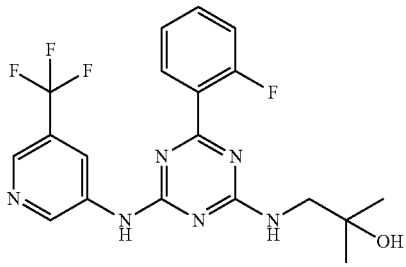 [SMILES: CC(C)(O)CNc1nc(Nc2cncc(C(F)(F)F)c2)nc(-c2ccccc2F)n1]

$^1$H NMR (METHANOL-$d_4$): δ 8.8-9.1 (m, 2H), 8.48 (m, 1H), 8.1 (m, 1H), 7.5 (m, 1H), 7.2-7.3 (m, 2H), 3.5 (m, 2H), 1.25 (m, 6H). LC-MS: m/z 428.3 (M+H)$^+$.

Compound 320—6-(2-fluorophenyl)-$N^2$-(5-fluoropyridin-3-yl)-$N^4$-isobutyl-1,3,5-triazine-2,4-diamine

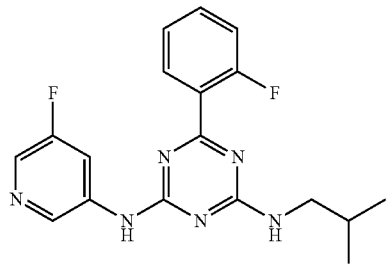 [SMILES: CC(C)CNc1nc(Nc2cncc(F)c2)nc(-c2ccccc2F)n1]

$^1$H NMR (METHANOL-$d_4$) δ: 8.64-8.48 (m, 2H), 8.10-8.04 (m, 2H), 7.55-7.51 (m, 1H), 7.29 (t, J=7.6, 1H), 7.29 (t, J=11.0, 1H), 3.32 (br.s., 2H), 2.03-1.96 (m, 1H), 1.03-0.96 (m, 6H). LC-MS: m/z 357.2 (M+H)$^+$.

Compound 321—5-(4-(2-fluorophenyl)-6-(isopropylamino)-1,3,5-triazin-2-ylamino)nicotinonitrile

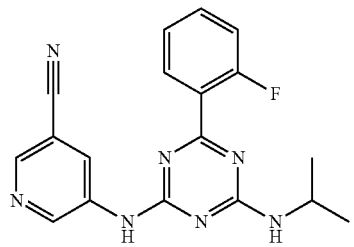 [SMILES: CC(C)Nc1nc(Nc2cncc(C#N)c2)nc(-c2ccccc2F)n1]

$^1$H NMR (DMSO-$d_6$) δ: 10.25-10.14 (m, 1H), 9.14 (t, J=2.40, 1H), 8.89-8.79 (m, 1H), 8.62-8.61 (m, 1H), 8.04-7.97 (m, 2H), 7.59-7.56 (m, 1H), 7.36-7.31 (m, 1H), 4.25-4.13 (m, 1H), 1.24-1.21 (m, 6H). LC-MS: m/z 350.2 (M+H)$^+$.

Compound 369—4-(4-(2-fluorophenyl)-6-(isopropylamino)-1,3,5-triazin-2-ylamino)picolinonitrile

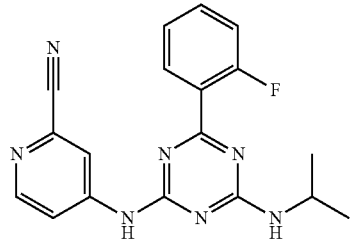 [SMILES: CC(C)Nc1nc(Nc2ccnc(C#N)c2)nc(-c2ccccc2F)n1]

$^1$H NMR (METHANOL-$d_4$) δ 8.61-8.59 (m, 1H), 8.48-8.44 (m, 1H), 8.16-8.13 (m, 1H), 7.98-7.96 (m, 1H), 7.57-7.54 (m, 1H), 7.32-7.23 (m., 2H), 4.29-4.27 (m., 2H), 3.05 (s., 1H), 1.16 (dd, J=4, 400 MHz, 6H). LC-MS: m/z 350.2 (M+H)$^+$.

Compound 370—6-(2-fluorophenyl)-N²-isopropyl-N⁴-(2-(trifluoromethyl)pyridin-4-yl)-1,3,5-triazine-2,4-diamine

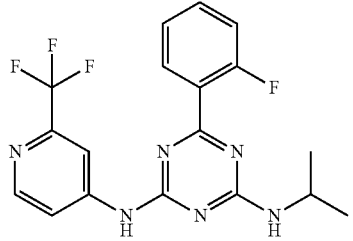 [SMILES: CC(C)Nc1nc(Nc2ccnc(C(F)(F)F)c2)nc(-c2ccccc2F)n1]

¹H NMR (METHANOL-d₄) δ 8.65-8.64 (m, 2H), 8.22-8.18 (m, 1H), 7.90-7.89 (m, 1H), 7.72 (m, 2H), 7.45-7.35 (m., 2H), 4.38-4.35 (m., 1H), 1.39 (dd, J=4, 400 MHz, 6H). LC-MS: m/z 393.0 (M+H)⁺.

Compound 371—6-(2-fluorophenyl)-N²-(2-fluoropyridin-4-yl)-N'-isopropyl-1,3,5-triazine-2,4-diamine

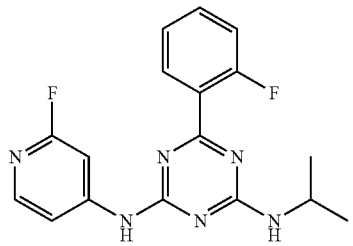

¹H NMR (METHANOL-d₄) δ 8.20-8.15 (m, 2H), 7.75-7.59 (m, 2H), 7.45-7.38 (m, 3H), 4.37-4.35 (m., 1H), 1.37 (dd, J=4, 400 MHz, 6H). LC-MS: m/z 342.9 (M+H)⁺.

Compound 372—6-(2-fluorophenyl)-N²-isopropyl-N⁴-(5-(trifluoromethyl)pyridin-3-yl)-1,3,5-triazine-2,4-diamine

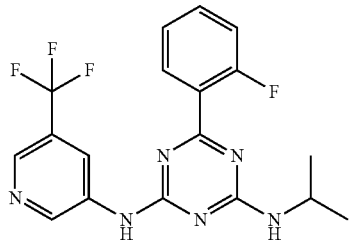 [SMILES: CC(C)Nc1nc(Nc2cncc(C(F)(F)F)c2)nc(-c2ccccc2F)n1]

¹H NMR (METHANOL-d₄) δ 9.31-8.77 (m, 3H), 8.21 (m, 1H), 7.79 (m, 1H), 7.47-7.41 (m., 2H), 4.33-4.32 (m, 1H), 1.37 (dd, J=4, 400 MHz, 6H). LC-MS: m/z 393.0 (M+H)⁺.

Compound 374—6-(2-fluorophenyl)-N²-(5-fluoropyridin-3-yl)-N⁴-isopropyl-1,3,5-triazine-2,4-diamine

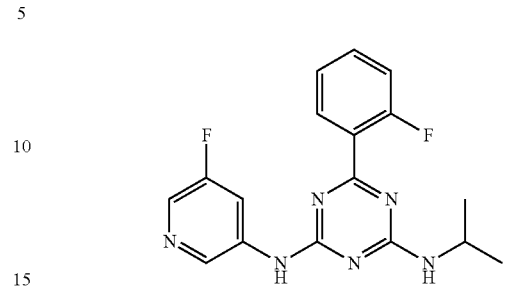

¹H NMR (METHANOL-d₄) δ 8.69-8.61 (m, 2H), 8.12-8.05 (m, 2H), 7.57-7.52 (m, 1H), 7.31-7.21 (m., 2H), 4.28-4.25 (m, 1H), 1.31 (dd, J=4, 400 MHz, 6H). LC-MS: m/z 343.2 (M+H)⁺.

Compound 387—6-(2-fluorophenyl)-N²-(6-fluoropyridin-3-yl)-N'-isopropyl-1,3,5-triazine-2,4-diamine

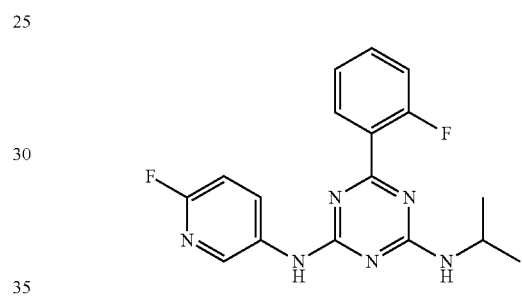

¹H NMR (METHANOL-d₄) δ 8.61-8.57 (m, 1H), 8.42-8.37 (m, 1H), 8.04-8.00 (m, 1H), 7.55-7.51 (m., 1H), 7.30-7.05 (m, 3H), 4.26-4.23 (m, 1H), 1.29 (dd, J=4, 400 MHz, 6H). LC-MS: m/z 342.9 (M+H)⁺.

Preparation of 1-[4-(3-Amino-phenyl)-6-(pyridin-4-ylamino)-[1,3,5]triazin-2-yl-amino]-2-methyl-propan-2-ol Compound 327—

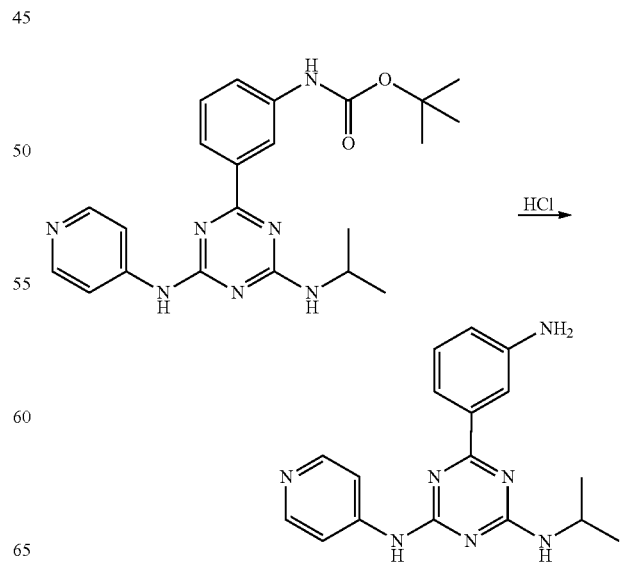

To a mixture of 1-[4-(3-N—(BOC-amino)-phenyl)-6-(pyridin-4-ylamino)-[1,3,5]triazin-2-ylamino]-2-methyl-propan-2-ol (100.2 mg, 0.24 mmol) in ethyl acetate (1 mL) was added HCl/ethyl acetate (4 mL) at 0° C. under $N_2$. The mixture was stirred at r.t. for 2 hours. TLC (petroleum ether/ethyl acetate=3:1) showed that the reaction was complete. The mixture was concentrated to give a residue, which was purified by a standard method to give 1-[4-(3-amino-phenyl)-6-(pyridin-4-ylamino)-[1,3,5]triazin-2-ylamino]-2-methyl-propan-2-ol. $^1$H NMR (METHANOL-$d_4$) δ: 8.44-8.40 (m, 2H), 8.17-8.12 (m, 2H), 7.83-7.72 (m, 2H), 7.22 (t, J=7.6 Hz, 2H), 6.92 (d, J=7.6 Hz, 2H), 4.45-4.26 (m, 1H), 1.31 (d, J=6.5 Hz, 6H). LC-MS: m/z 322.2 (M+H)$^+$.

Preparation of 3-[4-Isopropylamino-6-(pyridin-4-ylamino)-[1,3,5]triazin-2-yl]-phenol Compound 328—

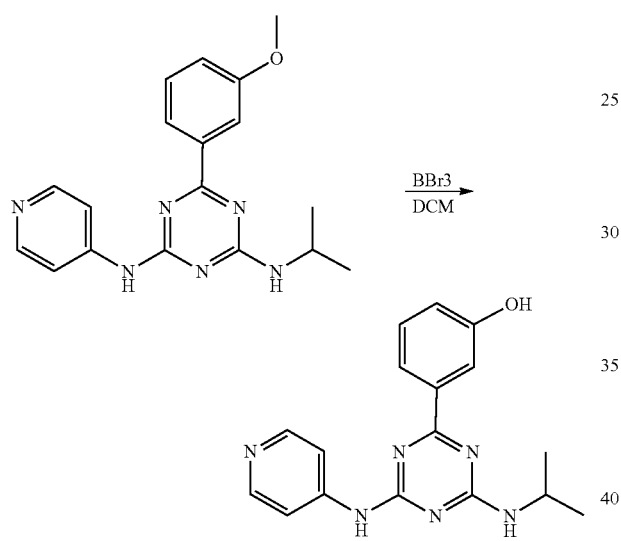

To a mixture of N-isopropyl-6-(3-methoxy-phenyl)-N'-pyridin-4-yl-[1,3,5]triazine-2,4-diamine (200 mg, 0.6 mmol) in DCM (10 mL) was added BBr$_3$ (60 mg, 0.6 mol) at −78° C. under $N_2$. The mixture was allowed to warm to r.t. and stirred for 90 min. before pouring to water (2 mL). After stirring for 20 min. to the mixture was added NaHCO$_3$ to adjust pH to 7 and extracted with ethyl acetate. The organic layer was dried over sodium sulphate and concentrated to give a residue, which was purified by a standard method to give 3-[4-isopropylamino-6-(pyridin-4-ylamino)-[1,3,5]triazin-2-yl]-phenol.

$^1$H NMR (DMSO-$d_6$) δ: 11.12-11.05 (m, 1H), 9.72 (br.s., 1H), 8.67-8.60 (m, 2H), 8.38-8.31 (m, 2H), 8.15-8.00 (m, 1H), 7.82-7.74 (m, 2H), 7.32 (t, J=8.2 Hz, 1H), 7.00 (d, J=8.2 Hz, 1H), 4.433-4.17 (m, 1H), 1.26-1.22 (m, 6H). LC-MS: m/z 323.2 (M+H)$^+$.

Example 5. Preparation of Compounds of Formula I Wherein Ring A and Ring B are Phenyl The compounds of this Example are prepared by general Scheme 5, set forth below.

Scheme 5

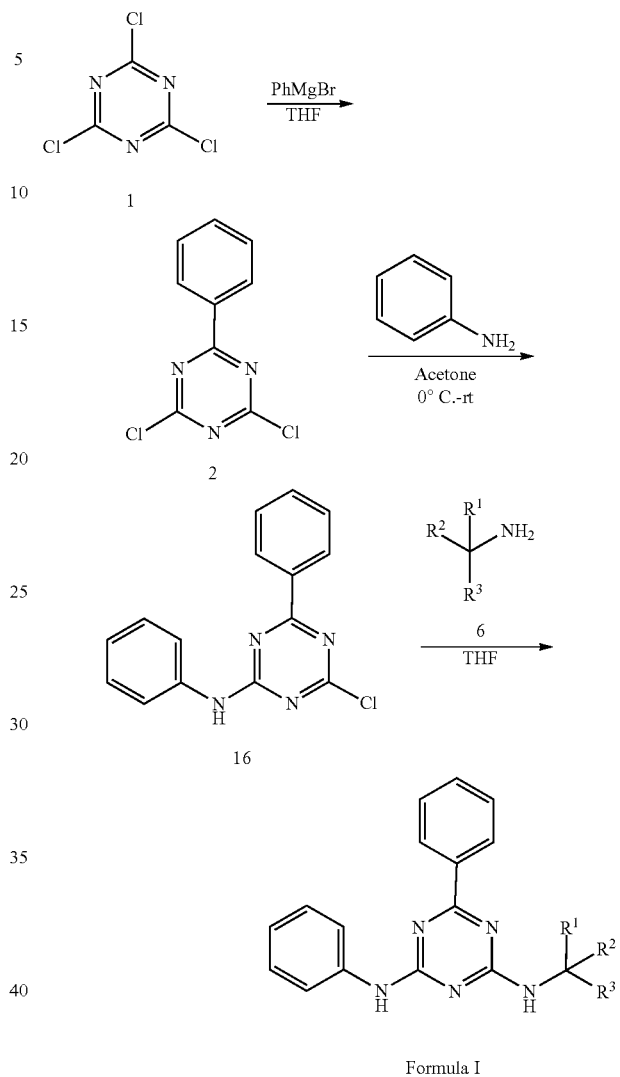

Formula I

Example 5 Step 2: Preparation of 4-chloro-N,6-diphenyl-1,3,5-triazin-2-amine

To a solution of 2,4-dichloro-6-phenyl-1,3,5-triazine (1 g, 4.4 mol) in acetone (10 mL) was added dropwise a solution of aniline (0.41 g, 4.4 mol) in acetone (2 mL) at 0° C. via syringe under $N_2$. After the addition, the mixture was stirred at 0° C. under $N_2$ for 4 hrs. The reaction mixture was adjusted to pH 7 with saturated NaHCO$_3$. The cake was dissolved in ethyl acetate (500 ml), dried over anhydrous Na$_2$SO$_4$, concentrated and purified via silica gel chromatography to give 4-chloro-N,6-diphenyl-1,3,5-triazin-2-amine as a white solid.

$^1$H NMR (CDCl$_3$) δ: 8.42 (d, J=7.6 Hz, 1H), 8.33 (d, J=7.6 Hz, 1H), 7.57-7.43 (m, 3H), 5.57-5.49 (m, 1H), 4.42-4.24 (m, 1H), 1.31-1.23 (m, 6H).

Example Step 3: Preparation of 2,6-diphenyl-N$^4$-(tetrahydrofuran-3-yl)-1,3,5-triazine-2,4-diamine tetrahydrofuran-3-amine Compound 203—

To a solution of (4-chloro-6-phenyl-[1,3,5]triazin-2-yl)-phenyl-amine (150 mg, 0.532 mmol) in anhydrous THF (5 mL) was added a solution of 1-amino-2-methyl-propan-2-ol (71 mg, 0.796 mmol) in THF (2 mL) via syringe at room temperature and the result mixture was stirred at room temperature for 16 hrs. The reaction was quenched by water (15 mL) and extracted with ethyl acetate. The organic layer was dried over $Na_2SO_4$, concentrated and purified by a standard method to give pure 2-methyl-1-(4-phenyl-6-phenylamino-[1,3,5]triazin-2-yl-amino)-propan-2-ol.

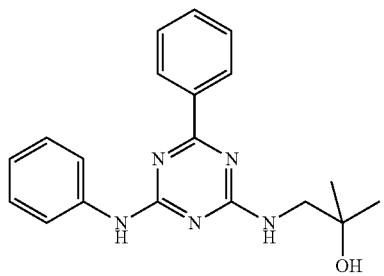 [SMILES: CC(C)(O)CNc1nc(Nc2ccccc2)nc(-c2ccccc2)n1]

$^1$H NMR (METHANOL-$d_4$) δ: 8.35 (t, J=9.6 Hz, 2H), 7.74 (d, J=8.2 Hz, 2H), 7.53-7.43 (m, 3H), 7.31 (t, J=5.5 Hz, 2H), 7.03 (t, J=7.6 Hz, 1H), 3.56-3.47 (m, 2H), 1.26 (s, 6H). LC-MS: m/z 336.2 $(M+H)^+$.

Other compounds were produced following Example 5, step 3 using the appropriate amine 6.

Compound 174—$N^2$,6-diphenyl-$N^4$-(tetrahydrofuran-3-yl)-1,3,5-triazine-2,4-diamine

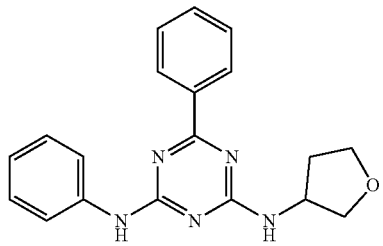 [SMILES: c1ccc(Nc2nc(NC3CCOC3)nc(-c3ccccc3)n2)cc1]

$^1$H NMR (METHANOL-$d_4$) δ: 8.39 (br.s., 1H), 8.35 (d, J=6.9 Hz, 1H), 7.75 (d, J=7.6 Hz, 3H), 7.52-7.43 (m, 3H), 7.31 (br.s., 2H), 7.02 (t, J=7.6 Hz, 1H), 4.60 (br.s., 1H), 4.05-3.95 (m, 2H), 3.89-3.83 (m, 1H), 3.76 (dd, J=8.9, 3.4 Hz, 1H), 2.34-2.29 (m, 1H), 2.04-1.97 (m, 1H). LC-MS: m/z 333.9 $(M+H)^+$.

Compound 175—$N^2$-(oxetan-3-yl)-$N^4$,6-diphenyl-1,3,5-triazine-2,4-diamine

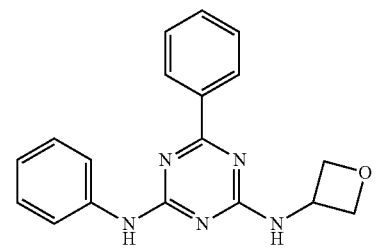 [SMILES: c1ccc(Nc2nc(NC3COC3)nc(-c3ccccc3)n2)cc1]

$^1$H NMR (METHANOL-$d_4$) δ: 8.35 (d, J=7.2 Hz, 2H), 7.71 (br.s., 2H), 7.51-7.41 (m, 3H), 7.30 (br.s., 2H), 7.02 (t, J=7.2 Hz, 1H), 5.25-5.10 (m, 1H), 4.93 (br.s., 2H), 4.69 (br.s., 2H). LC-MS: m/z 320.0 $(M+H)^+$.

Compound 176—$N^2$-(3-methyloxetan-3-yl)-$N^4$,6-diphenyl-1,3,5-triazine-2,4-diamine

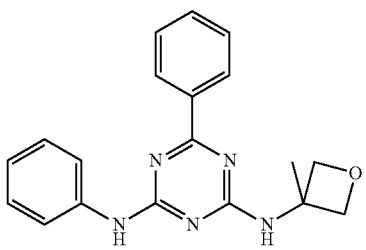 [SMILES: CC1(Nc2nc(Nc3ccccc3)nc(-c3ccccc3)n2)COC1]

$^1$H NMR (METHANOL-$d_4$) δ: 8.35 (d, J=7.6 Hz, 2H), 7.70 (br, 2H), 7.52-7.42 (m, 3H), 7.31 (t, J=7.6 Hz, 2H), 7.06 (br.s., 1H), 4.88 (br.s., 2H), 4.52-4.88 (br.s., 2H), 1.77 (s, 3H). LC-MS: m/z 334.0 $(M+H)^+$.

Compound 225—$N^2$-(2-methoxyethyl)-$N^4$,6-diphenyl-1,3,5-triazine-2,4-diamine

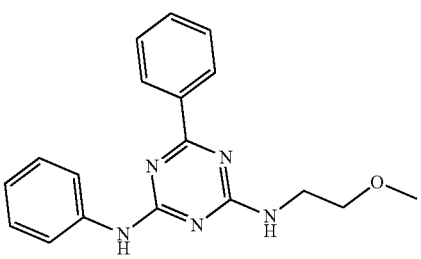 [SMILES: COCCNc1nc(Nc2ccccc2)nc(-c2ccccc2)n1]

$^1$H NMR (METHANOL-$d_4$) δ: 8.42-8.34 (m, 2H), 7.75 (d, J=6.9 Hz, 2H), 7.54-7.44 (m, 3H), 7.32 (t, J=7.6 Hz, 2H), 7.04 (t, J=7.1 Hz, 1H), 3.7-3.58 (m, 4H), 3.41 (s, 3H). LC-MS: m/z 322.0 $(M+H)^+$.

Compound 237—$N^2$-(oxetan-2-ylmethyl)-$N^4$,6-diphenyl-1,3,5-triazine-2,4-diamine

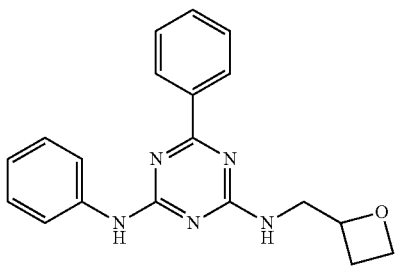 [SMILES: c1ccc(Nc2nc(NCC3CCO3)nc(-c3ccccc3)n2)cc1]

$^1$H NMR (METHANOL-$d_4$) δ: 8.40-8.33 (m, 2H), 7.74 (d, J=8.2 Hz, 2H), 7.52-7.43 (m, 3H), 7.31 (t, J=8.2 Hz, 2H), 7.02 (t, J=7.6 Hz, 1H), 5.1-5.04 (m, 1H), 4.72-4.66 (m, 1H), 4.62-4.57 (m, 2H), 3.89-3.68 (m, 2H), 2.71-2.67 (m, 1H), 2.61-2.52 (m, 1H). LC-MS: m/z 333.9 (M+H)$^+$.

Compound 238—2-(4-phenyl-6-(phenylamino)-1,3,5-triazin-2-ylamino)ethanol

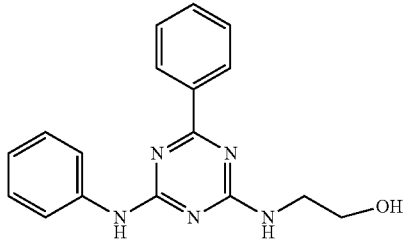 [SMILES: OCCNc1nc(Nc2ccccc2)nc(-c2ccccc2)n1]

$^1$H NMR (METHANOL-d$_4$) δ: 8.39-8.31 (m, 2H), 7.75 (d, J=7.6 Hz, 2H), 7.52-7.43 (m, 3H), 7.31 (t, J=7.6 Hz, 2H), 7.02 (t, J=6.9 Hz, 1H), 3.76 (t, J=5.5 Hz, 2H), 3.65-3.59 (m, 2H). LC-MS: m/z 308.0 (M+H)$^+$.

Compound 239—2,2-dimethyl-3-(4-phenyl-6-(phenylamino)-1,3,5-triazin-2-ylamino)propan-1-ol

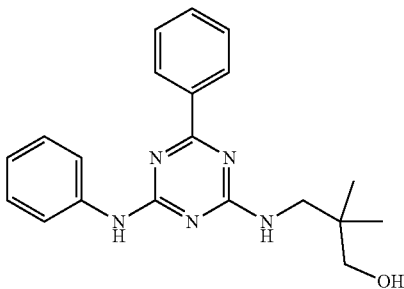 [SMILES: CC(C)(CO)CNc1nc(Nc2ccccc2)nc(-c2ccccc2)n1]

$^1$H NMR (METHANOL-d$_4$) δ: 8.35-8.29 (m, 2H), 7.74 (t, J=6.5 Hz, 2H), 7.54-7.44 (m, 3H), 7.32 (q, J=7.6 Hz, 2H), 7.06-7.01 (m, 1H), 3.39 (d, J=9.5 Hz, 2H), 3.22 (s, 2H), 0.94 (s, 6H). LC-MS: m/z 350.1 (M+H)$^+$.

Compound 240—1-(4-phenyl-6-(phenylamino)-1,3,5-triazin-2-ylamino)propan-2-ol

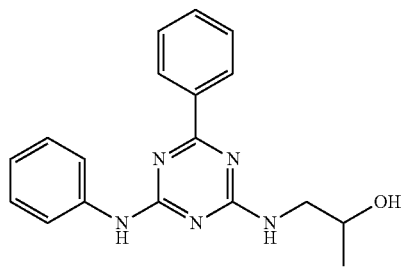 [SMILES: CC(O)CNc1nc(Nc2ccccc2)nc(-c2ccccc2)n1]

$^1$H NMR (METHANOL-d$_4$) δ: 8.39-8.32 (m, 2H), 7.74 (d, J=7.8 Hz, 2H), 7.52-7.43 (m, 3H), 7.31 (t, J=7.8 Hz, 2H), 7.02 (t, J=7.1 Hz, 1H), 4.06-3.98 (m, 1H), 3.56-3.33 (m, 2H), 1.22 (d, J=6.4 Hz, 3H). LC-MS: m/z 321.9 (M+H)$^+$.

Compound 241—2-(4-phenyl-6-(phenylamino)-1,3,5-triazin-2-ylamino)propan-1-ol

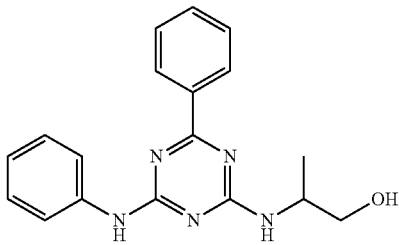 [SMILES: CC(CO)Nc1nc(Nc2ccccc2)nc(-c2ccccc2)n1]

$^1$H NMR (METHANOL-d$_4$) δ: 8.39-8.32 (m, 2H), 7.74 (d, J=7.6 Hz, 2H), 7.52-7.42 (m, 3H), 7.30 (t, J=7.6 Hz, 2H), 7.02 (t, J=7.6 Hz, 1H), 4.37-4.25 (m, 1H), 3.65-3.58 (m, 2H), 1.27 (d, J=6.9 Hz, 3H). LC-MS: m/z 322.0 (M+H)$^+$.

Compound 242—3-methyl-2-(4-phenyl-6-(phenylamino)-1,3,5-triazin-2-ylamino)butan-1-ol

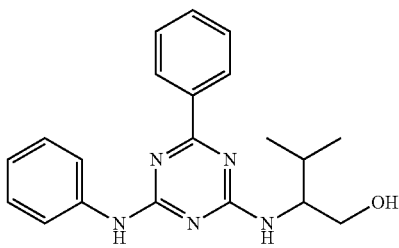 [SMILES: CC(C)C(CO)Nc1nc(Nc2ccccc2)nc(-c2ccccc2)n1]

$^1$H NMR (METHANOL-d$_4$) δ: 8.41-8.33 (m, 2H), 7.75 (d, J=8.0 Hz, 2H), 7.52-7.44 (m, 3H), 7.31 (t, J=7.6 Hz, 2H), 7.03 (t, J=7.6 Hz, 1H), 4.25-4.05 (m, 1H), 3.73 (d, J=4.8 Hz, 2H), 2.12-2.02 (m, 1H), 1.04-1.00 (m, 3H). LC-MS: m/z 350.1 (M+H)$^+$.

Compound 267—(1R,3R)-3-(4-phenyl-6-(phenylamino)-1,3,5-triazin-2-ylamino)cyclopentanol

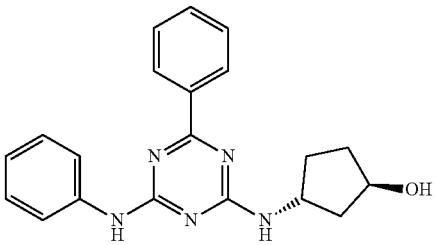

$^1$H NMR (METHANOL-d$_4$) δ: 8.42-8.32 (m, 2H), 7.80-7.75 (m, 2H), 7.52-7.42 (m, 3H), 7.33-7.29 (m, 2H), 7.01 (t, J=7.2 Hz, 1H), 4.63-4.58 (m, 1H), 4.39-4.36 (m, 1H), 2.32-2.25 (m, 1H), 2.10-2.03 (m, 2H), 1.84-1.78 (m, 1H), 1.69-1.52 (m, 2H). LC-MS: m/z 348.1 (M+H)$^+$.

209

Compound 268—$N^2$,6-diphenyl-$N^4$-(tetrahydro-2H-pyran-3-yl)-1,3,5-triazine-2,4-diamine

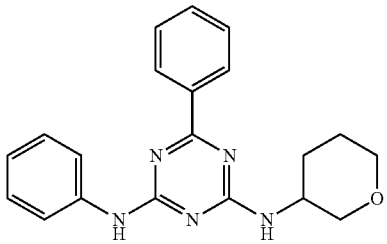 [SMILES: c1ccc(Nc2nc(NC3CCCOC3)nc(-c3ccccc3)n2)cc1]

$^1$H NMR (METHANOL-$d_4$) δ: 8.43-8.36 (m, 2H), 7.77 (t, J=7.6 Hz, 2H), 7.55-7.45 (m, 3H), 7.34 (t, J=7.6 Hz, 2H), 7.05 (t, J=7.2 Hz, 1H), 4.26-4.05 (m, 2H), 3.86-3.83 (m, 1H), 3.55-3.50 (m, 1H), 3.40-3.33 (m, 1H), 2.15-2.06 (m, 1H), 1.87-1.66 (m, 3H). LC-MS: m/z 348.1 (M+H)$^+$.

Compound 269—$N^2$-(1-methoxypropan-2-yl)-$N^4$,6-diphenyl-1,3,5-triazine-2,4-diamine

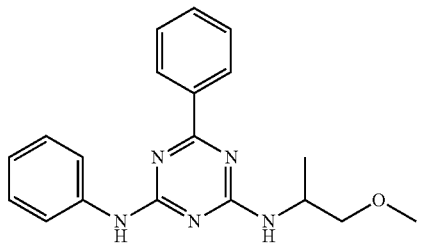 [SMILES: COCC(C)Nc1nc(Nc2ccccc2)nc(-c2ccccc2)n1]

$^1$H NMR (METHANOL-$d_4$) δ: 8.41-8.35 (m, 2H), 7.78 (d, J=7.2 Hz, 2H), 7.55-7.45 (m, 3H), 7.33 (t, J=7.6 Hz, 2H), 7.05 (t, J=7.2 Hz, 1H), 4.54-4.37 (m, 1H), 3.58-3.55 (m, 1H), 3.46-3.41 (m, 1H), 3.41 (s, 3H), 1.30 (d, J=6.9 Hz, 3H). LC-MS: m/z 336.1 (M+H)$^+$.

Compound 296—$N^2$-((1S,2R,4R)-bicyclo[2.2.1]hept-2-yl)-$N^4$,6-diphenyl-1,3,5-triazine-2,4-diamine

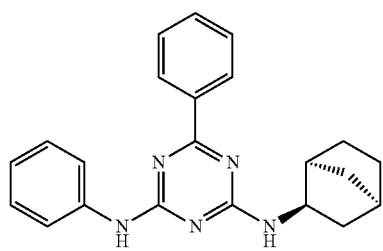 [SMILES: c1ccc(Nc2nc(N[C@@H]3C[C@@H]4CC[C@H]3C4)nc(-c3ccccc3)n2)cc1]

$^1$H NMR (DMSO-$d_6$) δ: 9.60-9.47 (m, 1H), 8.36-8.30 (m, 2H), 7.89-7.84 (m, 2H), 7.80-7.61 (m, 1H), 7.56-7.50 (m, 3H), 7.31 (t, J=7.6 Hz, 2H), 6.70 (t, J=6.9 Hz, 1H), 4.30-4.15 (m, 1H), 2.32-2.25 (m, 1H), 2.07-1.90 (m, 1H), 1.65-1.1 (m, 8H). LC-MS: m/z 358.1 (M+H)$^+$.

210

Compound 352—(1S,2R)-2-(4-phenyl-6-(phenylamino)-1,3,5-triazin-2-ylamino)cyclopentanol

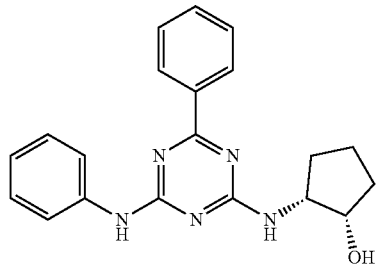 [SMILES: O[C@H]1CCC[C@H]1Nc1nc(Nc2ccccc2)nc(-c2ccccc2)n1]

$^1$H NMR (METHANOL-$d_4$) δ: 8.42-8.32 (m, 2H), 7.77 (t, J=7.9 Hz, 2H), 7.56-7.46 (m, 3H), 7.34 (t, J=7.6 Hz, 2H), 7.05 (t, J=7.2 Hz, 1H), 4.42-4.23 (m, 2H), 2.17-2.10 (m, 1H), 1.99-1.87 (m, 2H), 1.80-1.70 (m, 3H). LC-MS: m/z 348.2 (M+H)$^+$.

Compound 362—3-(4-phenyl-6-(phenylamino)-1,3,5-triazin-2-ylamino)cyclohex-2-enone

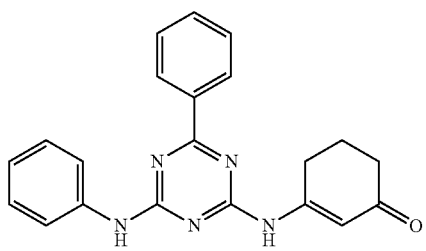 [SMILES: O=C1C=C(Nc2nc(Nc3ccccc3)nc(-c3ccccc3)n2)CCC1]

$^1$H NMR (METHANOL-$d_4$) δ: 8.47 (d, J=7.6 Hz, 1H), 7.78 (br.s., 2H), 7.60-7.50 (m, 3H), 7.39 (t, J=8.2 Hz, 2H), 7.23 (br.s., 1H), 7.12 (t, J=7.6 Hz, 1H), 2.75 (t, J=6.2 Hz, 2H), 2.43 (t, J=6.2 Hz, 2H), 2.12-2.03 (m, 2H). LC-MS: m/z 358.2 (M+H)$^+$.

Example 6. Preparation of Additional Compounds of Formula I Wherein Ring A is Phenyl The compounds of this Example are prepared by general Scheme 6, set forth below.

Scheme 6

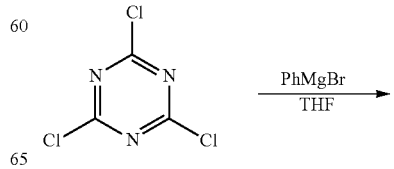

-continued

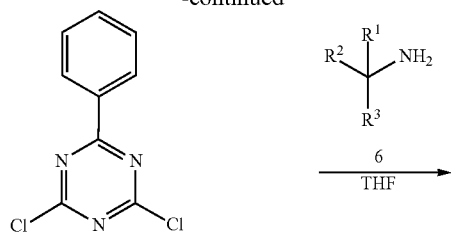

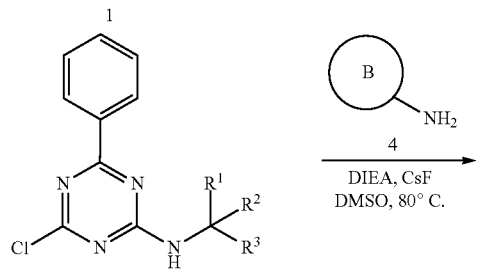

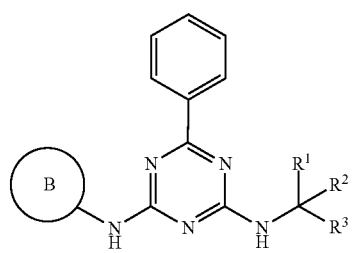

Formula I

Example 6, Step 2: Preparation of tert-Butyl-(4-chloro-6-phenyl-[1,3,5]triazin-2-yl)-amine To a solution of 2,4-dichloro-6-phenyl-1,3,5-triazine (500 mg, 2.212 mmol) in anhydrous THF (4 mL) was added dropwise a solution of tert-butylamine (194.1 mg, 2.654 mol) in THF (1 mL) at room temperature via syringe under $N_2$. After the addition, the mixture was stirred at room temperature under $N_2$ for 2 hrs. The reaction was quenched by water (5 mL) and extracted with ethyl acetate. The organic layer was dried, concentrated to afford tert-butyl-(4-chloro-6-phenyl-[1,3, and 5]-triazin-2-yl)-amine as a white solid, which was used the directly in the next step without purification.

Other amines 6 were also employed using the standard procedure described above to give the desired intermediates and were also used in the next step directly without further purification.

Example 6, Step 3: Preparation of Compound 227 6-(2-fluorophenyl)-$N^2$-isopropyl-$N^4$-(pyridin-4-yl)-1,3,5-triazine-2,4-diamine A mixture of tert-butyl-(4-chloro-6-phenyl-[1, 3, and 5] triazin-2-yl)-amine (186.1 mg, 0.71 mmol), pyridine-4-amine (80 mg, 0.85 mmol), CsF (107.85 mg, 0.71 mmol) and DIEA (275.30 mg, 2.13 mmol) in DMSO (4 mL) was heated to 80° C. for 2 hours. The mixture was filtered and purified by a standard method to give 6-(2-fluorophenyl)-$N^2$-isopropyl-$N^4$-(pyridin-4-yl)-1,3,5-triazine-2,4-diamine. This compound was also produced by Step 3, procedure A of Example 4.

Additional compounds of one aspect of the invention are produced according to Scheme 6 and the methods set forth in this example using the appropriate amine 6 and the appropriate amine 4.

Compound 186—$N^2$-sec-butyl-6-phenyl-$N^4$-(pyridin-4-yl)-1,3,5-triazine-2,4-diamine

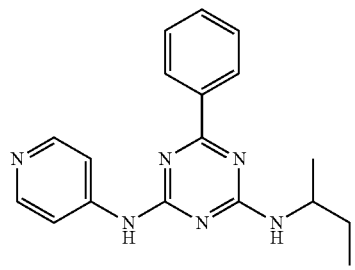 [SMILES: CCC(C)Nc1nc(Nc2ccncc2)nc(-c2ccccc2)n1]

$^1$H NMR (METHANOL-d4) δ: 8.44-8.33 (m, 4H), 7.92 (m, 2H), 7.54 (t, J=7.14 Hz, 1H), 7.48 (t, J=7.14 Hz, 2H), 4.30-4.09 (m, 1H), 1.66 (m, 2H), 1.28 (d, J=6.56 Hz, 3H), 1.02 (t, J=7.29 Hz, 3H). LC-MS: m/z 321.1 (M+H)$^+$.

Compound 287—$N^2$-cyclopentyl-6-phenyl-$N^4$-(pyridin-4-yl)-1,3,5-triazine-2,4-diamine

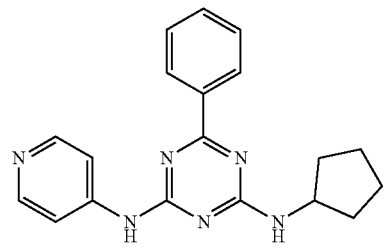 [SMILES: c1ccc(-c2nc(Nc3ccncc3)nc(NC3CCCC3)n2)cc1]

$^1$H NMR (DMSO-d$_6$) δ: 8.43-8.37 (m, 4H), 8.06-8.02 (m, 2H), 7.52-7.46 (m, 3H), 4.52-4.36 (m, 1H), 2.08 (m, 2H), 1.80-1.62 (m, 6H). LC-MS: m/z 333.1 (M+H)$^+$.

Compound 188—$N^2$-cyclobutyl-6-phenyl-$N^4$-(pyridin-4-yl)-1,3,5-triazine-2,4-diamine

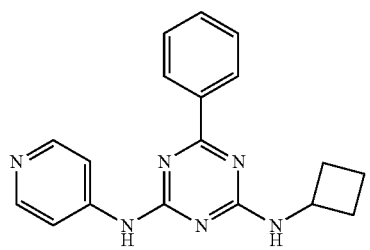 [SMILES: c1ccc(-c2nc(Nc3ccncc3)nc(NC3CCC3)n2)cc1]

¹H NMR (DMSO-d₆) δ: 8.50-8.30 (m, 4H), 8.00-7.90 (m, 2H), 7.60-7.40 (m, 3H), 4.55 (m, 1H), 2.45 (m, 2H), 2.10 (m, 2H), 1.80 (m, 2H). LC-MS: m/z 319.1 (M+H)⁺.

Compound 189—N²-tert-butyl-6-phenyl-N⁴-(pyridin-4-yl)-1,3,5-triazine-2,4-diamine

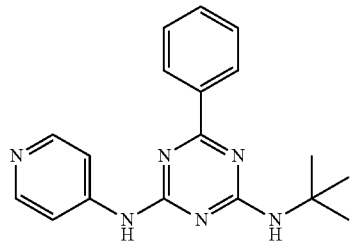 [SMILES: CC(C)(C)Nc1nc(Nc2ccncc2)nc(-c2ccccc2)n1]

¹H NMR (DMSO-d₆) δ: 8.50-8.30 (m, 4H), 8.00-7.90 (m, 2H), 7.60-7.40 (m, 3H), 1.56 (m, 9H). LC-MS: m/z 321.1 (M+H)⁺.

Compound 190—N²-isobutyl-6-phenyl-N⁴-(pyridin-4-yl)-1,3,5-triazine-2,4-diamine

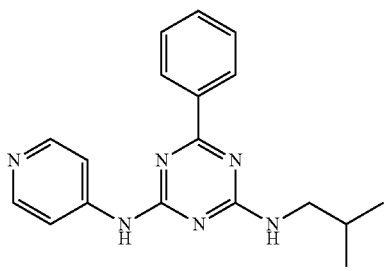 [SMILES: CC(C)CNc1nc(Nc2ccncc2)nc(-c2ccccc2)n1]

¹H NMR (METHANOL-d₄) δ: 8.35-8.21 (m, 4H), 7.84-7.78 (m, 2H), 7.48-7.34 (m, 3H), 3.30 (d, J=2.0 Hz, 2H), 1.96-1.87 (m, 1H), 0.92 (d, J=6.8 Hz, 6H). LC-MS: m/z 321.0 (M+H)⁺.

Compound 191—N²-neopentyl-6-phenyl-N⁴-(pyridin-4-yl)-1,3,5-triazine-2,4-diamine

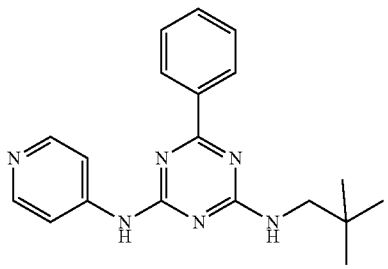 [SMILES: CC(C)(C)CNc1nc(Nc2ccncc2)nc(-c2ccccc2)n1]

¹H NMR (METHANOL-d₄) δ: 8.57-8.52 (m, 1H), 8.43-8.28 (m, 4H), 7.60-7.37 (m, 3H), 3.36 (d, J=2.0 Hz, 2H), 0.94 (d, J=9.6 Hz, 9H). LC-MS: m/z 335.1 (M+H)⁺.

Compound 211—N²-butyl-6-phenyl-N⁴-(pyridin-4-yl)-1,3,5-triazine-2,4-diamine

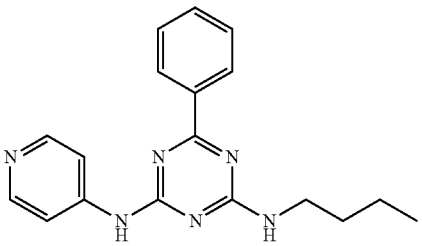 [SMILES: CCCCNc1nc(Nc2ccncc2)nc(-c2ccccc2)n1]

¹H NMR (METHANOL-d₄) δ: 8.37-8.25 (m, 4H), 7.84 (d, J=6.41 Hz, 2H), 7.46 (t, J=7.12 Hz, 1H), 7.40 (t, J=7.12 Hz, 2H), 3.50-3.41 (m, 2H), 1.61 (m, 2H), 1.40 (m, 2H), 0.93 (t, J=7.23 Hz, 3H). LC-MS: m/z 321.0 (M+H)⁺.

Compound 212—N²-isopentyl-6-phenyl-N⁴-(pyridin-4-yl)-1,3,5-triazine-2,4-diamine

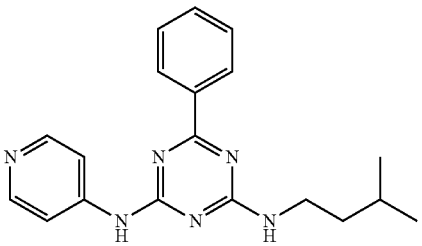 [SMILES: CC(C)CCNc1nc(Nc2ccncc2)nc(-c2ccccc2)n1]

¹H NMR (METHANOL-d4) δ: 8.30-8.18 (m, 4H), 7.77 (d, J=5.98 Hz, 2H), 7.41-7.31 (m, 3H), 3.45-3.36 (m, 2H), 1.60 (m, 1H), 1.45 (m, 2H), 0.86 (d, J=6.52 Hz, 3H). LC-MS: m/z 335.1 (M+H)⁺.

Compound 213—N²-(3-methylbutan-2-yl)-6-phenyl-N⁴-(pyridin-4-yl)-1,3,5-triazine-2,4-diamine

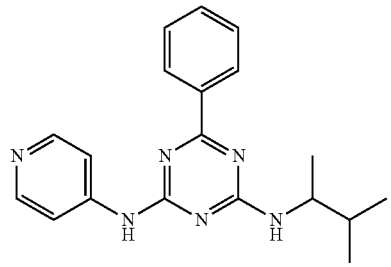 [SMILES: CC(C)C(C)Nc1nc(Nc2ccncc2)nc(-c2ccccc2)n1]

¹H NMR (METHANOL-d4) δ: 8.33-8.23 (m, 4H), 7.85-7.80 (m, 2H), 7.44 (t, J=7.03 Hz, 1H), 7.38 (t, J=7.03 Hz, 2H), 4.14-3.97 (m, 1H), 1.83 (m, 1H), 1.14 (d, J=6.69 Hz, 3H), 0.94-0.90 (m, 6H). LC-MS: m/z 335.1 (M+H)⁺.

Compound 215—6-phenyl-N²-(pyridin-4-yl)-N⁴-(2,2,2-trifluoroethyl)-1,3,5-triazine-2,4-diamine

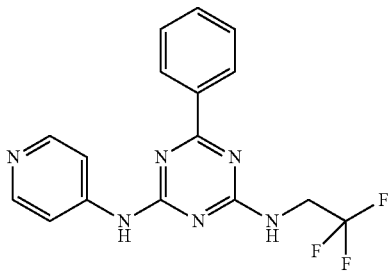 [SMILES: FC(F)(F)CNc1nc(Nc2ccncc2)nc(-c2ccccc2)n1]

¹H NMR (METHANOL-d4) δ: 8.44 (m, 2H), 8.36 (m, 2H), 7.90 (m, 2H), 7.55 (t, J=7.32 Hz, 1H), 7.48 (t, J=7.32 Hz, 2H), 4.35-4.20 (m, 2H). LC-MS: m/z 346.9 (M+H)⁺.

Compound 216—N²-(cyclopropylmethyl)-6-phenyl-N⁴-(pyridin-4-yl)-1,3,5-triazine-2,4-diamine

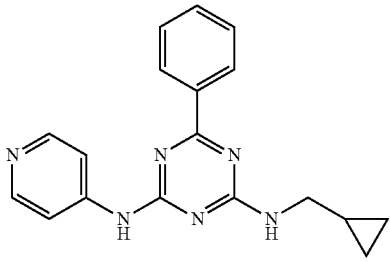 [SMILES: c1ccc(-c2nc(NCC3CC3)nc(Nc3ccncc3)n2)cc1]

¹H NMR (METHANOL-d4) δ: 8.43-8.32 (m, 4H), 7.91 (m, 2H), 7.53 (t, J=7.21 Hz, 1H), 7.47 (t, J=7.21 Hz, 2H), 3.43-3.36 (m, 2H), 1.18 (m, 1H), 0.54 (m, 2H), 0.32 (m, 2H). LC-MS: m/z 319.0 (M+H)⁺.

Compound 217—N²-cyclopropyl-6-phenyl-N⁴-(pyridin-4-yl)-1,3,5-triazine-2,4-diamine

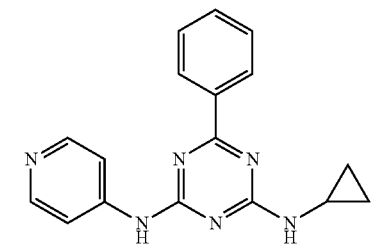 [SMILES: c1ccc(-c2nc(Nc3ccncc3)nc(NC3CC3)n2)cc1]

¹H NMR (METHANOL-d4) δ: 8.46-8.33 (m, 4H), 8.01-7.91 (m, 2H), 7.54-7.44 (m, 3H), 2.88-2.99 (m, 1H), 0.87 (m, 2H), 0.64 (m, 2H). LC-MS: m/z 305.0 (M+H)⁺.

Compound 218—N²-(1-methylcyclopropyl)-6-phenyl-N⁴-(pyridin-4-yl)-1,3,5-triazine-2,4-diamine

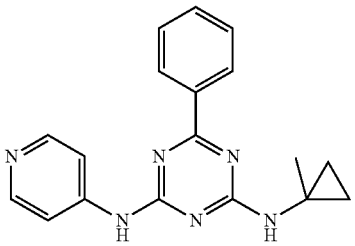

¹H NMR (METHANOL-d4) δ: 8.51-8.33 (m, 4H), 8.05-7.90 (m, 2H), 7.54-7.44 (m, 3H), 1.54 (s, 3H), 0.91-0.77 (m, 4H). LC-MS: m/z 319.0 (M+H)⁺.

Compound 219—N²-(2-methylcyclopropyl)-6-phenyl-N⁴-(pyridin-4-yl)-1,3,5-triazine-2,4-diamine

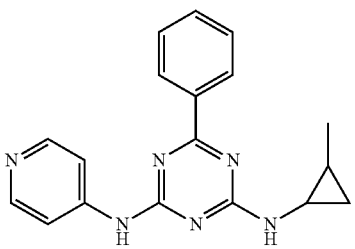

¹H NMR (METHANOL-d4) δ: 8.57-8.40 (m, 4H), 7.98-8.09 (m, 2H), 7.59 (t, J=7.23 Hz, 1H), 7.53 (t, J=7.23 Hz, 2H), 2.66 (m, 1H), 1.29 (d, J=5.43 Hz, 3H), 1.05 (m, 1H), 0.91 (m, 1H), 0.70 (m, 1H). LC-MS: m/z 319.2 (M+H)⁺.

Compound 220—N²-(2-methylbutyl)-6-phenyl-N⁴-(pyridin-4-yl)-1,3,5-triazine-2,4-diamine

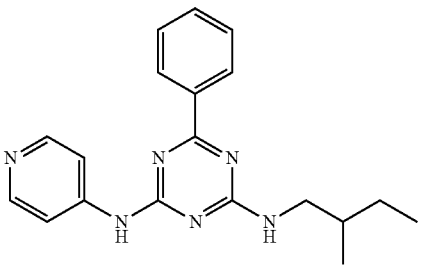 [SMILES: CCC(C)CNc1nc(Nc2ccncc2)nc(-c2ccccc2)n1]

¹H NMR (METHANOL-d4) δ: 8.47 (m, 2H), 8.39 (d, J=5.80 Hz, 2H), 7.97 (m, 2H), 7.59 (t, J=6.44 Hz, 1H), 7.53 (t, J=6.44 Hz, 2H), 3.58-3.29 (m, 2H), 1.85 (m, 1H), 1.60 (m, 1H), 1.32 (m, 1H), 1.06-1.02 (m, 6H). LC-MS: m/z 335.2 (M+H)⁺.

Compound 221—N²-((2-methyltetrahydrofuran-2-yl)methyl)-6-phenyl-N'-(pyridin-4-yl)-1,3,5-triazine-2,4-diamine

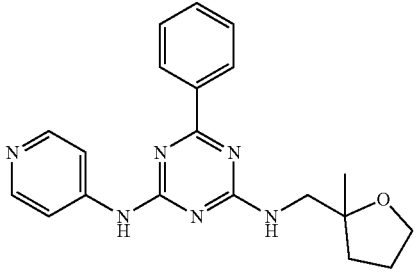 [SMILES: CC1(CNc2nc(Nc3ccncc3)nc(-c3ccccc3)n2)CCCO1]

¹H NMR (METHANOL-d4) δ: 8.51-8.41 (m, 4H), 7.99 (m, 2H), 7.61 (t, J=7.22 Hz, 1H), 7.55 (t, J=7.22 Hz, 2H), 3.98 (m, 2H), 3.78-3.65 (m, 2H), 2.10-1.80 (m, 4H), 1.36 (s, 3H). LC-MS: m/z 363.1 (M+H)⁺.

Compound 222—6-phenyl-N²-(pyridin-4-yl)-N⁴-((tetrahydrofuran-2-yl)methyl)-1,3,5-triazine-2,4-diamine

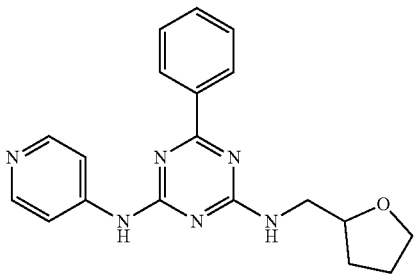 [SMILES: c1ccc(-c2nc(NCC3CCCO3)nc(Nc3ccncc3)n2)cc1]

¹H NMR (METHANOL-d4) δ: 8.53-8.42 (m, 4H), 8.02 (m, 2H), 7.62 (t, J=7.21 Hz, 1H), 7.56 (t, J=7.21 Hz, 2H), 4.27 (m, 1H), 4.01 (m, 1H), 3.86 (q, J=7.23 Hz, 1H), 3.75 (m, 1H), 3.68 (m, 1H), 2.17-1.83 (m, 4H). LC-MS: m/z 349.2 (M+H)⁺.

Compound 234—N²-(morpholin-2-ylmethyl)-6-phenyl-N⁴-(pyridin-4-yl)-1,3,5-triazine-2,4-diamine

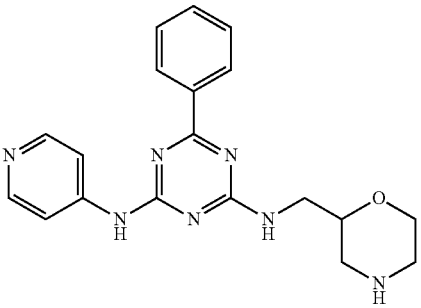 [SMILES: c1ccc(-c2nc(NCC3CNCCO3)nc(Nc3ccncc3)n2)cc1]

¹H NMR (METHANOL-d₄) δ 8.42 (d, J=7.2 Hz, 1H), 8.39-8.32 (m, 3H), 7.89 (d, J=4.8 Hz, 2H), 7.51 (d, J=6.8 Hz, 1H), 7.48-7.44 (m, 2H), 3.90-3.87 (m, 1H), 3.76-3.74 (m, 1H), 3.63-3.52 (m, 3H), 2.99-2.96 (m, 1H), 2.81-2.78 (m, 2H), 2.62-2.53 (m, 1H). LC-MS: m/z 364.0 (M+H)⁺.

Compound 235—6-phenyl-N²-(pyridin-4-yl)-N⁴-(tetrahydrofuran-3-yl)-1,3,5-triazine-2,4-diamine

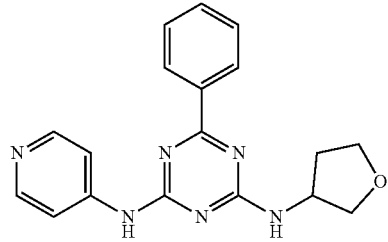 [SMILES: c1ccc(-c2nc(Nc3ccncc3)nc(NC3CCOC3)n2)cc1]

¹H NMR (DMSO-d₆) δ: 9.8-10.0 (m, 1H), 8.1-8.4 (m, 4H), 7.9-8.1 (m, 1H), 7.6-7.8 (m, 2H), 7.3-7.5 (m, 3H), 4.3-4.6 (m, 1H), 3.75-3.85 (m, 1H), 3.7-3.75 (m, 1H), 3.55-3.65 (m, 1H), 3.45-3.55 (m, 1H), 2.0-2.15 (m, 1H), 61.75-1.85 (m, 1H). LC-MS: m/z 335.1 (M+H)⁺.

Compound 236—N²-(oxetan-3-yl)-6-phenyl-N⁴-(pyridin-4-yl)-1,3,5-triazine-2,4-diamine

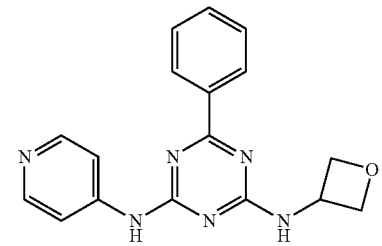 [SMILES: c1ccc(-c2nc(Nc3ccncc3)nc(NC3COC3)n2)cc1]

¹H NMR (METHANOL-d₄) δ: 8.3-8.5 (m, 4H), 7.8-8.0 (m, 2H), 7.45-7.6 (m, 3H), 5.15-5.4 (m, 1H), 5.03 (t, J=6.8 Hz, 2H), 4.76 (t, J=6.4 Hz, 2H). LC-MS: m/z 320.9 (M+H)⁺.

Compound 248—N²-ethyl-6-phenyl-N⁴-(pyridin-4-yl)-1,3,5-triazine-2,4-diamine

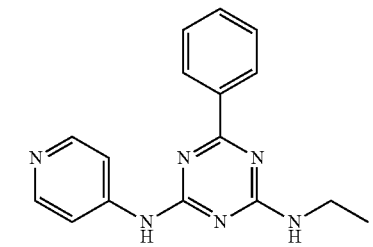 [SMILES: CCNc1nc(Nc2ccncc2)nc(-c2ccccc2)n1]

¹H NMR (CDCl₃) δ: 8.50 (m, 2H), 8.43-8.32 (m, 2H), 7.65 (m, 2H), 7.55-7.46 (m, 3H), 7.20-7.08 (m, 1H), 5.45-5.29 (m, 1H), 3.66-3.54 (m, 2H), 1.32 (t, J=7.25 Hz, 3H). LC-MS: m/z 292.9 (M+H)⁺.

Compound 249—6-phenyl-$N^2$-propyl-$N^4$-(pyridin-4-yl)-1,3,5-triazine-2,4-diamine

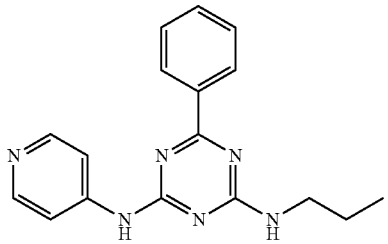 [SMILES: CCCNc1nc(Nc2ccncc2)nc(-c2ccccc2)n1]

$^1$H NMR (METHANOL-d4) δ: 8.46-8.35 (m, 4H), 7.96 (m, 2H), 7.55 (t, J=7.25 Hz, 1H), 7.49 (t, J=7.25 Hz, 2H), 3.56-3.45 (m, 2H), 1.73 (m, 2H), 1.05 (t, J=7.35 Hz, 3H). LC-MS: m/z 307.0 (M+H)$^+$.

Compound 250—$N^2$-(cyclobutylmethyl)-6-phenyl-$N^4$-(pyridin-4-yl)-1,3,5-triazine-2,4-diamine

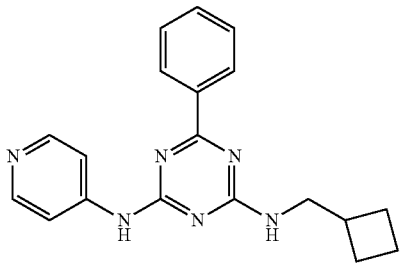

$^1$H NMR (METHANOL-d$_4$) δ: 8.29-8.48 (m, 4H), 7.88-7.95 (m, 2H), 7.49-7.51 (m, 3H), 3.48-3.61 (m, 2H), 2.60-2.75 (m, 1H), 2.08-2.18 (m, 2H), 1.75-2.00 (m, 4H). LC-MS: m/z 332.4 (M+H)$^+$.

Compound 251—$N^2$-(3-methyloxetan-3-yl)-6-phenyl-$N^4$-(pyridin-4-yl)-1,3,5-triazine-2,4-diamine

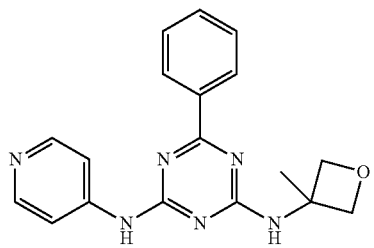 [SMILES: CC1(Nc2nc(Nc3ccncc3)nc(-c3ccccc3)n2)COC1]

$^1$H NMR (METHANOL-d$_4$) δ: 8.3-8.5 (m, 4H), 7.8-8.0 (m, 2H), 7.4-7.6 (m, 3H), 4.96 (d, J=6.4 Hz, 2H), 4.60 (d, J=6.0 Hz, 2H), 1.81 (s, 3H). LC-MS: m/z 334.9 (M+H)$^+$.

Compound 252—$N^2$-(2-methoxy-2-methylpropyl)-6-phenyl-$N^4$-(pyridin-4-yl)-1,3,5-triazine-2,4-diamine

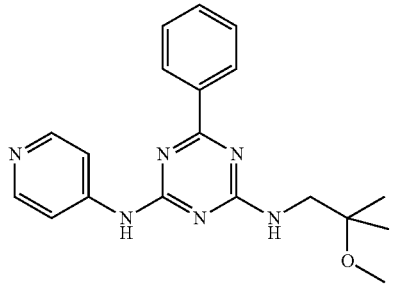 [SMILES: COC(C)(C)CNc1nc(Nc2ccncc2)nc(-c2ccccc2)n1]

$^1$H NMR (METHANOL-d$_4$) δ: 8.30-8.49 (m, 4H), 7.88-7.98 (m, 2H), 7.46-7.51 (m, 3H), 3.62 (s, 1H), 3.70 (s, 2H), 3.30 (s, 3H), 1.25 (s, 6H). LC-MS: m/z 350.43 (M+H)$^+$.

Compound 253—$N^2$-(3,3-difluorocyclobutyl)-6-phenyl-$N^4$-(pyridin-4-yl)-1,3,5-triazine-2,4-diamine

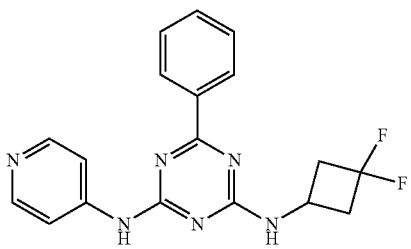 [SMILES: FC1(F)CC(Nc2nc(Nc3ccncc3)nc(-c3ccccc3)n2)C1]

$^1$H NMR (METHANOL-d4) δ: 8.27-8.18 (m, 4H), 7.73 (m, 2H), 7.37 (t, J=6.92 Hz, 1H), 7.31 (t, J=6.92 Hz, 2H), 4.34-4.26 (m, 1H), 2.89 (m, 2H), 2.53 (m, 2H). LC-MS: m/z 354.9 (M+H)$^+$.

Compound 254—$N^2$-(4,4-difluorocyclohexyl)-6-phenyl-$N^4$-(pyridin-4-yl)-1,3,5-triazine-2,4-diamine

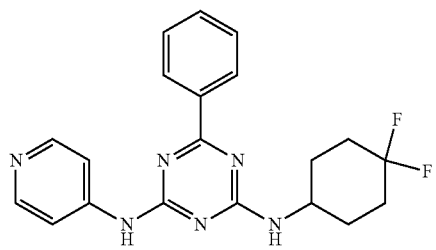 [SMILES: FC1(F)CCC(Nc2nc(Nc3ccncc3)nc(-c3ccccc3)n2)CC1]

$^1$H NMR (METHANOL-d4) δ: 8.47-8.35 (m, 4H), 7.93 (m, 2H), 7.56 (t, J=7.19 Hz, 1H), 7.50 (t, J=7.19 Hz, 2H), 4.28-4.12 (m, 1H), 1.76-2.18 (m, 8H). LC-MS: m/z 383.1 (M+H)$^+$.

Compound 255—N²-(3,3-dimethylbutan-2-yl)-6-phenyl-N⁴-(pyridin-4-yl)-1,3,5-triazine-2,4-diamine

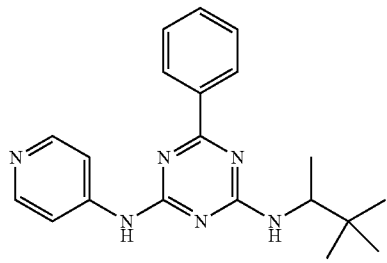 [SMILES: CC(Nc1nc(Nc2ccncc2)nc(-c2ccccc2)n1)C(C)(C)C]

$^1$H NMR (METHANOL-d$_4$) δ: 8.33-8.42 (m, 4H), 7.91-7.96 (m, 2H), 7.46-7.53 (m, 3H), 1.36 (d, J=6.4 Hz, 1H), 1.21 (d, J=6.8 Hz, 2H), 1.01 (s, 9H). LC-MS: m/z 349.1 (M+H)⁺.

Compound 256—4-(4-phenyl-6-(pyridin-4-ylamino)-1,3,5-triazin-2-ylamino)cyclohexanol

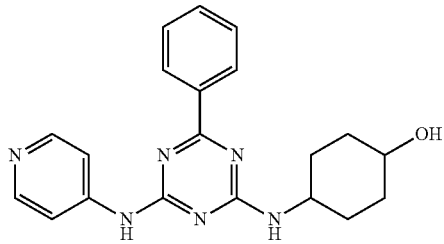 [SMILES: OC1CCC(Nc2nc(Nc3ccncc3)nc(-c3ccccc3)n2)CC1]

$^1$H NMR (METHANOL-d$_4$) δ: 8.56-8.30 (m, 4H), 7.90 (d, J=5.5 Hz, 2H), 7.53-7.44 (m, 3H), 3.85-4.1 (m, 1H), 3.62 (s, 1H), 2.15 (s, 2H), 2.03 (s, 2H), 1.46-1.35 (m, 4H). LC-MS: m/z 363.2 (M+H)⁺.

Compound 257—N²-(1-cyclopropylethyl)-6-phenyl-N⁴-(pyridin-4-yl)-1,3,5-triazine-2,4-diamine

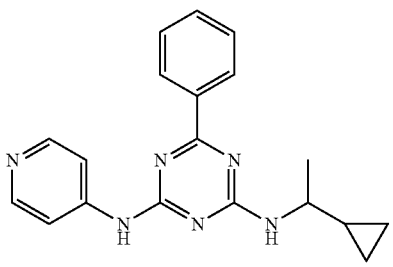 [SMILES: CC(Nc1nc(Nc2ccncc2)nc(-c2ccccc2)n1)C1CC1]

$^1$H NMR (METHANOL-d$_4$) δ: 8.40-8.34 (m, 4H), 7.94-7.90 (d, J=16 Hz, 3H), 7.53-7.45 (m, 3H), 4.59 (br.s., 1H), 3.75-3.68 (m, 1H), 1.36-1.35 (d, J=4 Hz, 1H), 1.05 (br.s., 1H), 0.59-0.47 (m, 3H), 0.3 (br.s., 1H). LC-MS: m/z 333.2 (M+H)⁺.

Compound 258—6-phenyl-N²-(pyridin-4-yl)-N⁴-(tetrahydro-2H-pyran-4-yl)-1,3,5-triazine-2,4-diamine

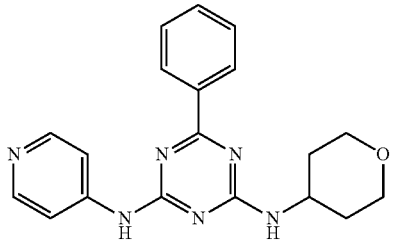 [SMILES: c1ccc(-c2nc(Nc3ccncc3)nc(NC3CCOCC3)n2)cc1]

$^1$H NMR (METHANOL-d4) δ: 9.38 (m, 2H), 8.54 (m, 2H), 7.65-7.53 (m, 3H), 7.03 (m, 2H), 4.39-4.30 (m, 1H), 4.05 (m, 2H), 3.64 (m, 2H), 2.06 (m, 2H), 1.73 (m, 2H). LC-MS: m/z 349.2 (M+H)⁺.

Compound 259—2,2-dimethyl-3-(4-phenyl-6-(pyridin-4-ylamino)-1,3,5-triazin-2-ylamino)propan-1-ol

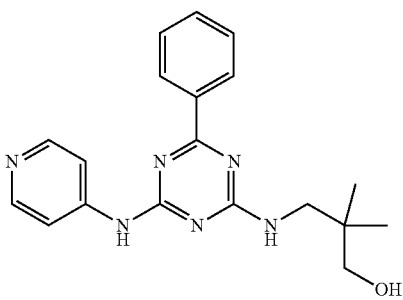 [SMILES: CC(C)(CO)CNc1nc(Nc2ccncc2)nc(-c2ccccc2)n1]

$^1$H NMR (METHANOL-d4) δ: 9.38 (m, 2H), 8.54 (m, 2H), 7.65-7.53 (m, 3H), 7.03 (m, 2H), 4.39-4.30 (m, 1H), 4.05 (m, 2H), 3.64 (m, 2H), 2.06 (m, 2H), 1.73 (m, 2H). LC-MS: m/z 349.2 (M+H)⁺.

Compound 262—N²-(2-ethoxyethyl)-6-phenyl-N⁴-(pyridin-4-yl)-1,3,5-triazine-2,4-diamine

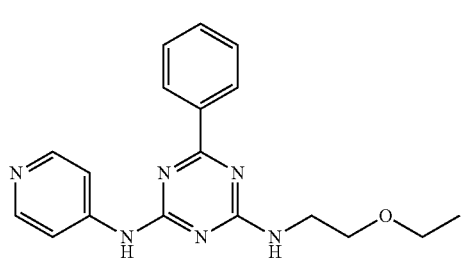

$^1$H NMR (METHANOL-d$_4$) δ: 8.46-8.35 (m, 4H), 7.93-7.91 (d, J=6 Hz, 2H), 7.55-7.47 (m, 3H), 4.93-4.63 (m, 3H), 4.63 (br.s., 1H), 3.77-3.70 (m, 4H), 3.62-3.57 (m, 2H), 1.23 (t, J=6.8 Hz, 3H). LC-MS: m/z 336.9 (M+H)⁺.

223

Compound 263—6-phenyl-N²-(pyridin-4-yl)-N⁴-(3,3,3-trifluoropropyl)-1,3,5-triazine-2,4-diamine

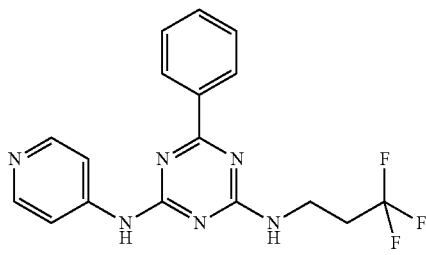 [SMILES: FC(F)(F)CCNc1nc(Nc2ccncc2)nc(-c2ccccc2)n1]

¹H NMR (METHANOL-d₄) δ: 8.35-8.47 (m, 4H), 7.90-7.93 (m, 2H), 7.46-7.56 (m, 3H), 3.75-3.82 (m, 2H), 2.57-2.65 (m, 2H). LC-MS: m/z 361.0 (M+H)⁺.

Compound 264—N²-(oxetan-2-ylmethyl)-6-phenyl-N⁴-(pyridin-4-yl)-1,3,5-triazine-2,4-diamine

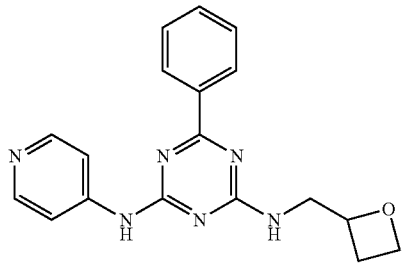 [SMILES: c1ccc(-c2nc(NCC3CCO3)nc(Nc3ccncc3)n2)cc1]

¹H NMR (CDCl3) δ: 8.47 (d, J=5.41 Hz, 2H), 8.36 (m, 2H), 7.63 (m, 2H), 7.52 (t, J=6.84 Hz, 1H), 7.46 (t, J=6.84 Hz, 2H), 7.18 (m, 1H), 6.25-5.92 (m, 1H), 5.09 (m, 1H), 4.65 (m, 2H), 3.87-3.67 (m, 2H), 2.62 (m, 2H). LC-MS: m/z 335.2 (M+H)⁺.

Compound 265—2-methyl-1-(4-phenyl-6-(pyridin-4-ylamino)-1,3,5-triazin-2-ylamino)propan-2-ol

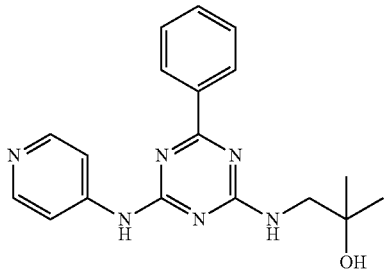 [SMILES: CC(C)(O)CNc1nc(Nc2ccncc2)nc(-c2ccccc2)n1]

¹H NMR (CDCl3) δ: 8.51 (m, 2H), 8.36 (d, J=7.70 Hz, 2H), 7.65 (d, J=4.74 Hz, 2H), 7.55 (t, J=7.70 Hz, 1H), 7.48 (t, J=7.70 Hz, 2H), 7.21 (m, 1H), 5.86 (m, 1H), 3.59 (m, 2H), 1.33 (s, 6H). LC-MS: m/z 337.3 (M+H)⁺.

224

Compound 271—1-(4-phenyl-6-(pyridin-4-ylamino)-1,3,5-triazin-2-ylamino)propan-2-ol

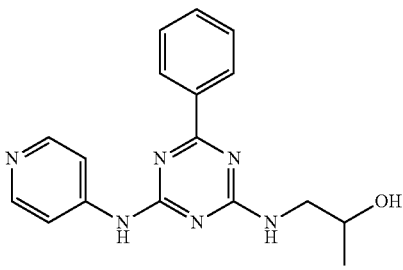 [SMILES: CC(O)CNc1nc(Nc2ccncc2)nc(-c2ccccc2)n1]

¹H NMR (METHANOL-d₄) δ: 9.38-9.44 (m, 2H), 8.54-8.59 (m, 2H), 7.55-7.64 (m, 3H), 7.01-7.05 (m, 2H), 4.00-4.06 (m, 1H), 3.59-3.67 (m, 2H), 1.29-1.30 (d, J=6.4 Hz, 3H). LC-MS: m/z 323.1 (M+H)⁺.

Compound 272—N²-(1-methoxypropan-2-yl)-6-phenyl-N⁴-(pyridin-4-yl)-1,3,5-triazine-2,4-diamine

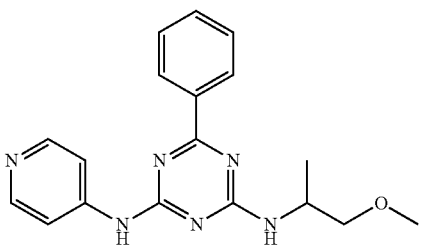 [SMILES: COCC(C)Nc1nc(Nc2ccncc2)nc(-c2ccccc2)n1]

¹H NMR (METHANOL-d₄) δ: 8.39-8.45 (m, 4H), 7.97-8.01 (m, 2H), 7.48-7.50 (m, 3H), 4.35-4.62 (m, 1H), 3.57-3.61 (m, 2H), 3.43 (s, 3H), 1.32-1.33 (d, J=4.0 Hz, 3H). LC-MS: m/z 337.1 (M+H)⁺.

Compound 273—6-phenyl-N²-(pyridin-4-yl)-N⁴-(tetrahydro-2H-pyran-3-yl)-1,3,5-triazine-2,4-diamine

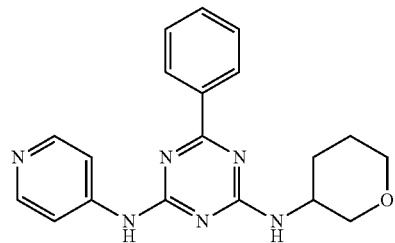 [SMILES: c1ccc(-c2nc(Nc3ccncc3)nc(NC3CCCOC3)n2)cc1]

¹H NMR (METHANOL-d₄) δ: 9.36-9.41 (m, 2H), 8.53-8.57 (m, 2H), 7.53-7.66 (m, 3H), 7.01-7.05 (m, 2H), 4.17-4.39 (m, 1H), 4.02-4.11 (m, 1H), 3.83-3.91 (m, 1H), 2.10-2.20 (m, 1H), 1.77-1.80 (m, 3H). LC-MS: m/z 349.2 (M+H)⁺.

Compound 274—N²-(2-methoxypropyl)-6-phenyl-N⁴-(pyridin-4-yl)-1,3,5-triazine-2,4-diamine

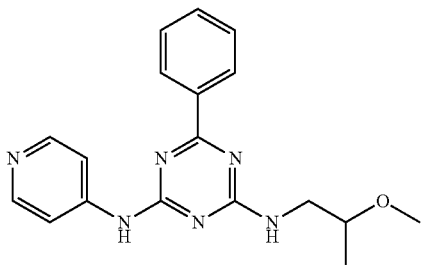 [SMILES: COC(C)CNc1nc(Nc2ccncc2)nc(-c2ccccc2)n1]

¹H NMR (METHANOL-d₄) δ: 9.29-9.33 (m, 2H), 8.48-8.52 (m, 2H), 7.52-7.61 (m, 3H), 6.98-7.01 (m, 2H), 3.55-3.78 (m, 3H), 3.44 (s, 3H), 1.26-1.27 (d, J=4.0 Hz, 3H). LC-MS: m/z 337.2 (M+H)⁺.

Compound 275—N²-(3-methoxypropyl)-6-phenyl-N⁴-(pyridin-4-yl)-1,3,5-triazine-2,4-diamine

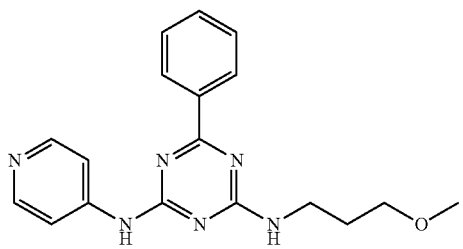 [SMILES: COCCCNc1nc(Nc2ccncc2)nc(-c2ccccc2)n1]

¹H NMR (METHANOL-d₄) δ: 8.36-8.41 (m, 4H), 7.93-7.95 (m, 2H), 7.49-7.51 (m, 3H), 3.54-3.60 (m, 4H), 3.38 (s, 3H), 1.95-1.98 (m, 2H). LC-MS: m/z 337.1 (M+H)⁺.

Compound 276—3-(4-phenyl-6-(pyridin-4-ylamino)-1,3,5-triazin-2-ylamino)cyclobutanone

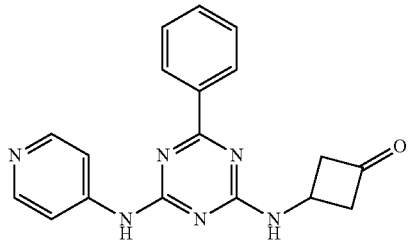 [SMILES: O=C1CC(Nc2nc(Nc3ccncc3)nc(-c3ccccc3)n2)C1]

¹H NMR (METHANOL-d₄) δ: 8.39-8.44 (m, 4H), 7.97 (s, 2H), 7.48-7.56 (m, 3H), 4.70-4.80 (m, 1H), 3.51-3.58 (m, 2H), 3.20-3.30 (m, 2H). LC-MS: m/z 333.0 (M+H)⁺.

Compound 278—2-(4-phenyl-6-(pyridin-4-ylamino)-1,3,5-triazin-2-ylamino)propan-1-ol

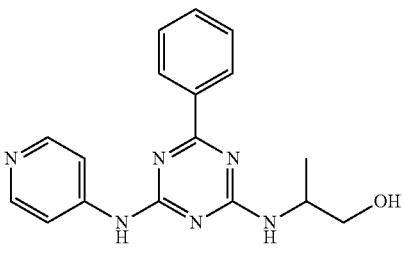 [SMILES: CC(CO)Nc1nc(Nc2ccncc2)nc(-c2ccccc2)n1]

¹H NMR (METHANOL-d₄) δ: 9.28-9.33 (m, 2H), 8.46-8.51 (m, 2H), 7.49-7.54 (m, 3H), 6.95-6.99 (m, 2H), 4.30-4.55 (m, 1H), 3.68-3.72 (m, 2H), 1.34 (t, J=6.8 Hz, 1H). LC-MS: m/z 323.0 (M+H)⁺.

Compound 279—3-methyl-2-(4-phenyl-6-(pyridin-4-ylamino)-1,3,5-triazin-2-ylamino)butan-1-ol

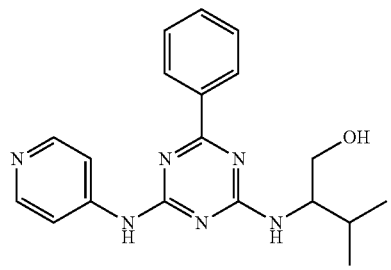 [SMILES: CC(C)C(CO)Nc1nc(Nc2ccncc2)nc(-c2ccccc2)n1]

¹H NMR (METHANOL-d₄) δ: 9.23-9.26 (m, 2H), 8.4 (d, J=8.0 Hz, 2H), 7.41-7.5 (m, 3H), 6.89 (t, J=8.0 Hz, 2H), 4.1-4.3 (m, 1H), 3.6-3.8 (m, 1H), 1.9-2.1 (m, 1H), 0.9-1.1 (m. 6H). LC-MS: m/z 351.1 (M+H)⁺.

Compound 280—N²-cyclohexyl-6-phenyl-N⁴-(pyridin-4-yl)-1,3,5-triazine-2,4-diamine

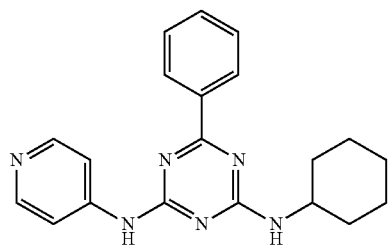 [SMILES: c1ccc(-c2nc(Nc3ccncc3)nc(NC3CCCCC3)n2)cc1]

¹H NMR (METHANOL-d₄) δ: 9.34 (t, J=8.0 Hz, 2H), 8.51 (t, J=8.0 Hz, 2H), 7.50-7.63 (m, 3H), 6.98-7.03 (m, 2H), 4.0-4.2 (m, 1H), 2.08 (t, J=12 Hz, 2H), 1.85-1.87 (m, 2H), 1.52-1.53 (m, 1H), 1.28-1.51 (m, 5H). LC-MS: m/z 347.1 (M+H)⁺.

Compound 282—2-(4-phenyl-6-(pyridin-4-ylamino)-1,3,5-triazin-2-ylamino)cyclohexanol

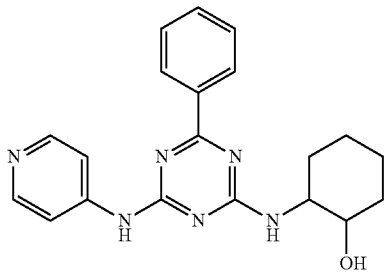 [SMILES: OC1CCCCC1Nc1nc(Nc2ccncc2)nc(-c2ccccc2)n1]

$^1$H NMR (METHANOL-d4) δ: 9.18 (m 2H), 8.32 (m, 3H), 7.46-7.32 (m, 3H), 6.82 (m, 2H), 4.13-4.02 (m, 1H), 3.96-3.90 (m, 1H), 1.71-1.30 (m, 8H). LC-MS: m/z 363.0 (M+H)$^+$.

Compound 283—(1S,3R)-3-(4-phenyl-6-(pyridin-4-ylamino)-1,3,5-triazin-2-ylamino)cyclopentanol

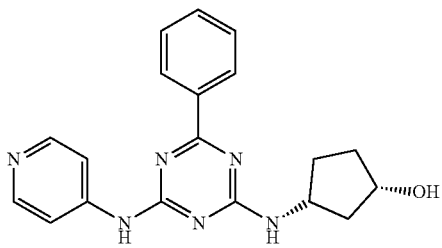

$^1$H NMR (DMSO-d6) δ: 9.37-9.22 (m, 2H), 9.18 (m, 2H), 8.88-8.69 (m, 1H), 8.54-8.44 (m, 2H), 7.71-7.57 (m, 3H), 7.04 (d, J=7.85 Hz, 2H), 4.44 (m, 1H), 4.18 (m, 1H), 2.33-1.54 (m, 6H). LC-MS: m/z 49.1 (M+H)$^+$.

Compound 284—1-(4-phenyl-6-(pyridin-4-ylamino)-1,3,5-triazin-2-ylamino)cyclobutanecarbonitrile

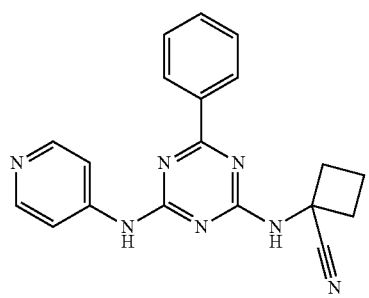 [SMILES: N#CC1(Nc2nc(Nc3ccncc3)nc(-c3ccccc3)n2)CCC1]

$^1$H NMR (METHANOL-d4) δ: 8.47 (m, 2H), 8.38 (m, 2H), 7.95 (m, 2H), 7.57 (t, J=6.74 Hz, 1H), 7.50 (t, J=6.74 Hz, 2H), 2.88 (m, 2H), 2.57 (m, 2H), 2.22 (m, 2H). LC-MS: m/z 344.0 (M+H)$^+$.

Compound 285—1-(4-phenyl-6-(pyridin-4-ylamino)-1,3,5-triazin-2-ylamino)cyclopropanecarbonitrile

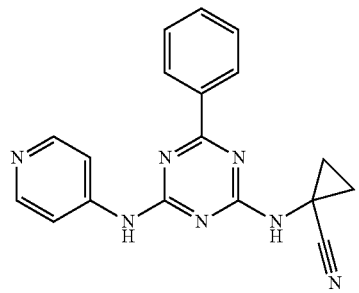 [SMILES: N#CC1(Nc2nc(Nc3ccncc3)nc(-c3ccccc3)n2)CC1]

$^1$H NMR (METHANOL-d4) δ: 9.46-9.35 (m, 2H), 8.71-8.55 (m, 2H), 7.70-7.54 (m, 3H), 7.09-7.01 (m, 2H), 1.75 (m, 2H), 1.46 (m, 2H). LC-MS: m/z 330.0 (M+H)$^+$.

Compound 286—3,3-dimethyl-2-(4-phenyl-6-(pyridin-4-ylamino)-1,3,5-triazin-2-ylamino)butan-1-ol

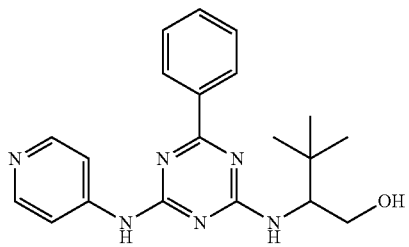 [SMILES: CC(C)(C)C(CO)Nc1nc(Nc2ccncc2)nc(-c2ccccc2)n1]

$^1$H NMR (METHANOL-d$_4$) δ: 9.43 (m, 2H), 8.59 (m, 2H), 7.67-7.55 (m, 3H), 7.05 (m, 2H), 4.53-4.30 (m, 1H), 4.01 (m, 1H), 3.68 (m, 1H), 1.09 (s, 9H). LC-MS: m/z 365.1 (M+H)$^+$.

Compound 291—2-(4-phenyl-6-(pyridin-4-ylamino)-1,3,5-triazin-2-ylamino)butan-1-ol

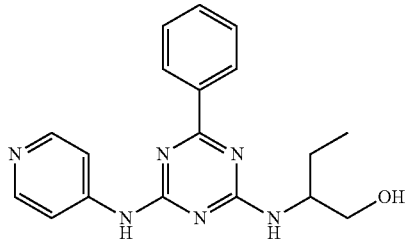 [SMILES: CCC(CO)Nc1nc(Nc2ccncc2)nc(-c2ccccc2)n1]

$^1$H NMR (METHANOL-d4) δ: 9.38 (m, 2H), 8.54 (m, 2H), 7.65-7.51 (m, 3H), 7.01 (m, 2H), 4.37-4.22 (m, 1H), 3.71 (m, 2H), 1.73 (m, 2H), 1.04 (m, 3H). LC-MS: m/z 337.1 (M+H)$^+$.

Compound 294—2-(4-phenyl-6-(pyridin-4-ylamino)-1,3,5-triazin-2-ylamino)ethanol

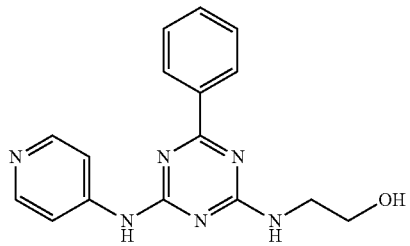 [SMILES: OCCNc1nc(Nc2ccncc2)nc(-c2ccccc2)n1]

$^1$H NMR (METHANOL-d4) δ: 9.40 (m, 2H), 8.56 (m, 2H), 7.65-7.53 (m, 3H), 7.03 (m, 2H), 3.84-3.72 (m, 4H). LC-MS: m/z 309.0 (M+H)$^+$.

Compound 295—N$^2$-((1S,2R,4R)-bicyclo[2.2.1]heptan-2-yl)-6-phenyl-N$^4$-(pyridin-4-yl)-1,3,5-triazine-2,4-diamine

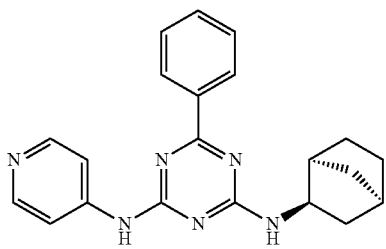 [SMILES: c1ccc(-c2nc(Nc3ccncc3)nc(N[C@@H]3C[C@@H]4CC[C@H]3C4)n2)cc1]

$^1$H NMR (DMSO-d$_6$) δ: 10.03 (br.s., 1H), 8.41-8.31 (m, 4H), 8.03-7.85 (m, 3H), 7.59-7.52 (m, 3H), 4.30-4.10 (m, 1H), 2.33-2.09 (m, 1H), 2.05-1.90 (m, 1H), 1.66-1.19 (m, 8H). LC-MS: m/z 359.2 (M+H)$^+$.

Compound 297—N$^2$-(3-oxabicyclo[3.1.0]hexan-6-yl)-6-phenyl-N$^4$-(pyridin-4-yl)-1,3,5-triazine-2,4-diamine

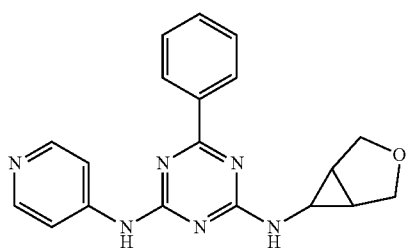 [SMILES: c1ccc(-c2nc(Nc3ccncc3)nc(NC3C4COCC43)n2)cc1]

$^1$H NMR (DMSO-d$_6$) δ: 10.10 (br.s., 1H), 8.41-8.38 (m, 4H), 8.32-8.00 (m, 1H), 7.95-7.85 (m, 2H), 7.58-7.53 (m, 3H), 3.97 (m, 2H), 3.73 (m, 2H), 2.70-2.55 (m, 1H), 1.96 (m, 2H). LC-MS: m/z 347.0 (M+H)$^+$.

Compound 300—N$^2$-(oxetan-3-ylmethyl)-6-phenyl-N$^4$-(pyridin-4-yl)-1,3,5-triazine-2,4-diamine

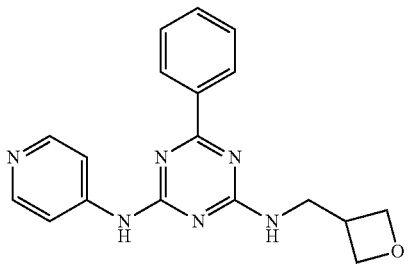

$^1$H NMR (METHANOL-d4) δ: 8.38-8.30 (m, 4H), 7.89 (m, 2H), 7.53-7.44 (m, 3H), 4.83 (m, 2H), 4.56 (m, 2H), 3.83 (m, 2H), 3.35 (m, 1H). LC-MS: m/z 335.0 (M+H)$^+$.

Compound 304—3-(4-phenyl-6-(pyridin-4-ylamino)-1,3,5-triazin-2-ylamino)cyclohexanol

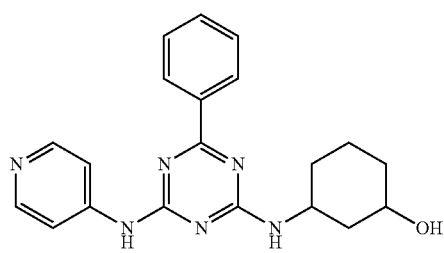 [SMILES: OC1CCCC(Nc2nc(Nc3ccncc3)nc(-c3ccccc3)n2)C1]

$^1$H NMR (METHANOL-d$_4$) δ: 8.33-8.44 (m, 4H), 7.90-7.93 (m, 2H), 7.46-7.54 (m, 3H), 3.9-4.2 (m, 1H), 3.6-3.8 (m, 1H), 2.35-2.38 (m, 1H), 1.87-2.06 (m, 3H), 1.26-1.36 (m, 4H). LC-MS: m/z 363.2 (M+H)$^+$.

Compound 305—N$^2$-(3-methoxycyclobutyl)-6-phenyl-N'-(pyridin-4-yl)-1,3,5-triazine-2,4-diamine

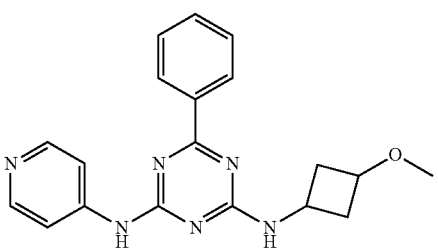 [SMILES: COC1CC(Nc2nc(Nc3ccncc3)nc(-c3ccccc3)n2)C1]

$^1$H NMR (METHANOL-d$_4$) δ: 9.32-9.38 (m, 2H), 8.49-8.54 (m, 2H), 7.49-7.62 (m, 3H), 6.98-7.01 (m, 2H), 4.2-4.6 (m, 1H), 3.7-4.1 (m, 1H), 3.3 (br. s., 1H), 2.83-2.84 (m, 1H), 2.47-2.50 (m, 1H), 2.36-2.38 (m, 1H), 2.0-2.04 (m, 1H). LC-MS: m/z 349.2 (M+H)$^+$.

Example 7. Preparation of Compounds of Formula I Wherein R$^1$ and R$^3$ are Taken Together with the Carbon Atom to which they are Attached to Form C(=O)

The compounds of this Example are prepared by general Scheme 7, Procedure 1 or 2, as set forth below.

Scheme 7

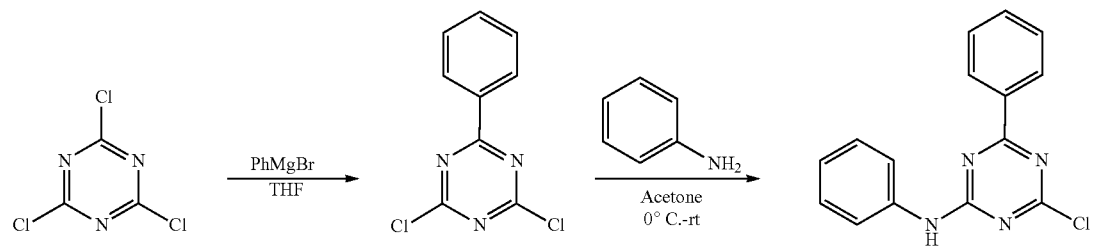

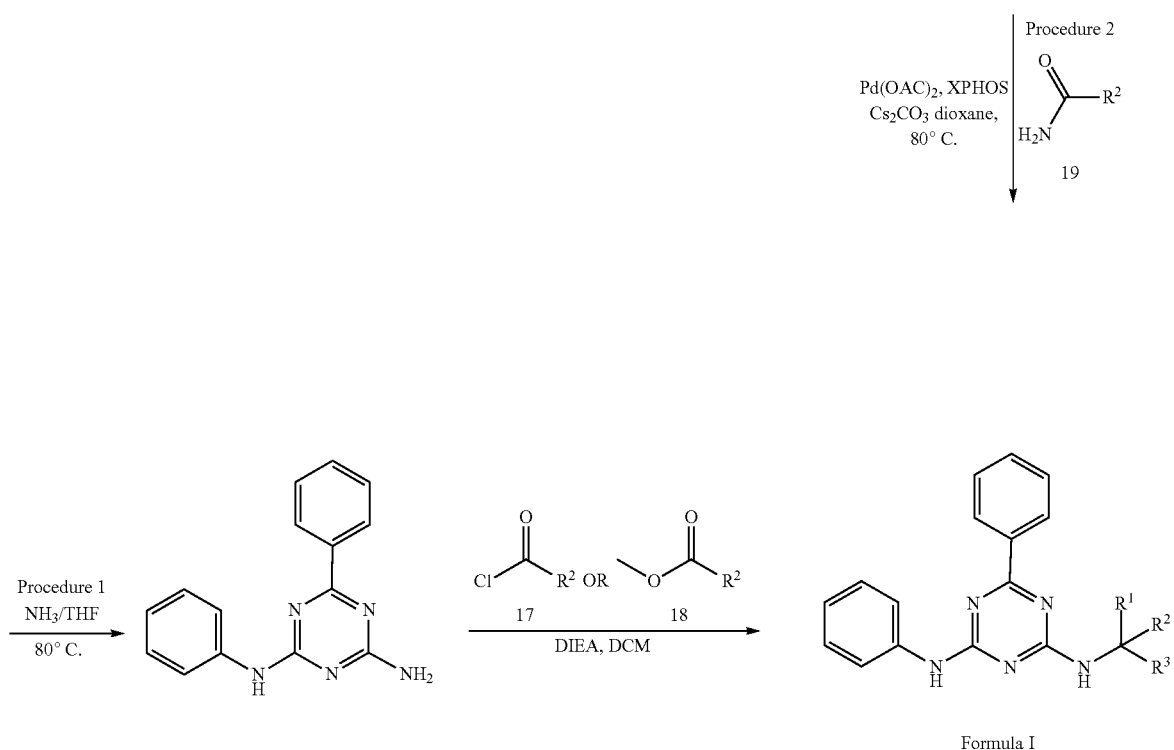

Formula I

Example 7, Step 3 (Procedure 1): Preparation of N²,6-diphenyl-1,3,5-triazine-2,4-diamine A mixture of 4-chloro-N,6-diphenyl-1,3,5-triazin-2-amine (4.0 g, 0.14 mol) and NH₃.H₂O (40 mL) in THF (12 mL) was added in a sealed tube. The reaction mixture was stirred at 80° C. for 16 hours. The mixture was extracted with ethyl acetate (50 mL×3). The organic layer was dried over anhydrous Na₂SO₄ and concentrated to give N²,6-diphenyl-1,3,5-triazine-2,4-diamine as a white solid, which was used in the next step directly without further purification.

Preparation of Compound 179—Isobutyl 4-phenyl-6-(phenyl-amino)-1,3,5-triazin-2-ylcarbamate (Procedure 1, Step 4, Reagent 17)

Pyridine (60 mg, 0.76 mmol) was added dropwise to a solution of N²,6-diphenyl-1,3,5-triazine-2,4-diamine (100 mg, 0.38 mmol) in DCM (4 mL) under ice-bath cooling. The mixture was then stirred 0° C. for 15 min, then isobutyl carbonochloridate (63 mg, 0.46 mmol) was added dropwise and the resultant mixture was stirred at rt for 1 hours. The reaction mixture was concentrated and purified by a standard method to give isobutyl 4-phenyl-6-(phenyl-amino)-1,3,5-triazin-2-ylcarbamate.

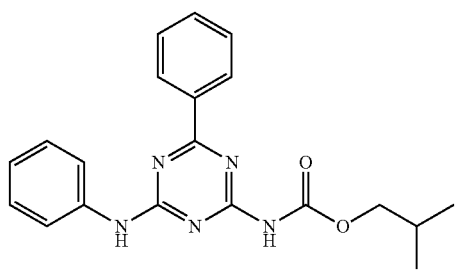 [SMILES: CC(C)COC(=O)Nc1nc(Nc2ccccc2)nc(-c2ccccc2)n1]

¹H NMR (METHANOL-d₄) δ: 8.48 (d, J=7.2 Hz, 2H), 7.82 (br.s., 2H), 7.55-7.46 (m, 3H), 7.36 (br.s., 2H), 7.07 (br.s., 1H), 4.01 (d, J=6.8 Hz, 2H), 2.06-2.00 (m, 1H), 1.01 (d, J=6.8 Hz, 6H). LC-MS: m/z 364.0 (M+H)⁺

Other compounds of one aspect of the invention were similarly prepared using Example 7, Procedure 1, Step 4 of this example and the appropriate chloridate 17.

233

Compound 160—isopropyl 4-phenyl-6-(phenylamino)-1,3,5-triazin-2-ylcarbamate

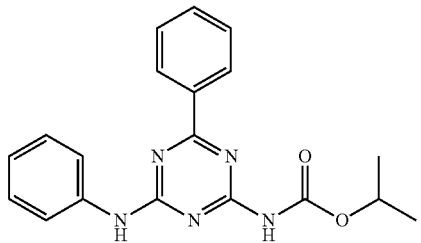 [SMILES: CC(C)OC(=O)Nc1nc(Nc2ccccc2)nc(-c2ccccc2)n1]

$^1$H NMR (DMSO-$d_6$) δ: 10.48 (br.s., 1H), 10.12 (br.s., 1H), 8.38 (d, J=7.2 Hz, 2H), 8.02 (br.s., 2H), 7.61-7.53 (m, 3H), 7.33 (br.s., 2H), 7.04 (t, J=7.2 Hz, 1H), 4.98 (t, J=6.4 Hz, 1H), 1.30 (d, J=6.0 Hz, 6H). LC-MS: m/z 350.1 (M+H)$^+$

Compound 183—N-(4-phenyl-6-(phenylamino)-1,3,5-triazin-2-yl)pivalamide

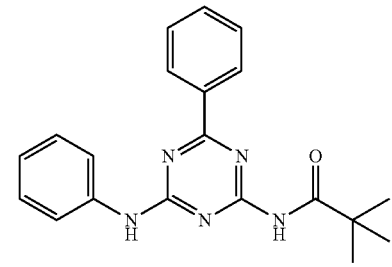 [SMILES: CC(C)(C)C(=O)Nc1nc(Nc2ccccc2)nc(-c2ccccc2)n1]

$^1$H NMR (DMSO-$d_6$) δ: 10.14 (br.s., 1H), 9.95 (br.s., 1H), 8.40 (d, J=6.4 Hz, 2H), 8.02 (br.s., 2H), 7.60-7.55 (m, 3H), 7.33 (br.s., 2H), 7.03 (br.s., 1H), 1.27 (s, 9H). LC-MS: m/z 348.0 (M+H)$^+$

Compound 208—Neopentyl 4-phenyl-6-(phenylamino)-1,3,5-triazin-2-ylcarbamate

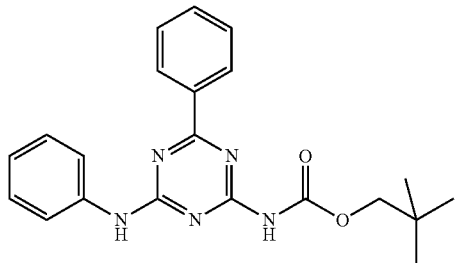 [SMILES: CC(C)(C)COC(=O)Nc1nc(Nc2ccccc2)nc(-c2ccccc2)n1]

$^1$H NMR (DMSO-$d_6$) δ: 10.57 (br.s., 1H), 10.12 (br.s., 1H), 8.38 (d, J=7.2 Hz, 2H), 8.02 (br.s., 2H), 7.62-7.52 (m, 3H), 7.32 (t, J=7.2 Hz, 2H), 7.03 (t, J=7.2 Hz, 1H), 3.85 (s, 2H), 0.96 (s, 9H). LC-MS: m/z 378.0 (M+H)$^+$

234

Compound 232—cyclopropylmethyl 4-phenyl-6-(phenylamino)-1,3,5-triazin-2-ylcarbamate

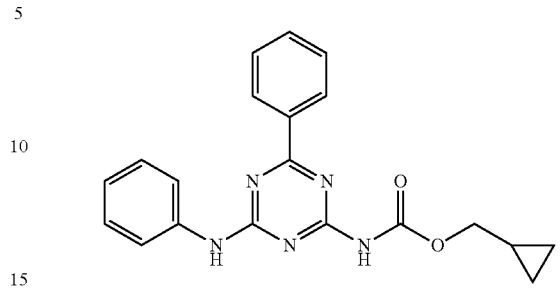

$^1$H NMR (DMSO-$d_6$) δ: 10.46. (br.s., 1H), 10.12 (br.s., 1H), 8.38 (d, J=7.2 Hz, 2H), 8.02 (br.s., 2H), 7.70-7.54 (m, 3H), 7.31 (br.s., 2H), 7.02 (br.s., 1H), 4.00 (d, J=7.2 Hz, 2H), 0.88-0.85 (m, 1H), 0.56 (d, J=7.2 Hz, 2H), 0.35 (d, J=7.2 Hz, 2H). LC-MS: m/z 362.0 (M+H)$^+$

Compound 233—N-(4-phenyl-6-(phenylamino)-1,3,5-triazin-2-yl)cyclopropanecarboxamide

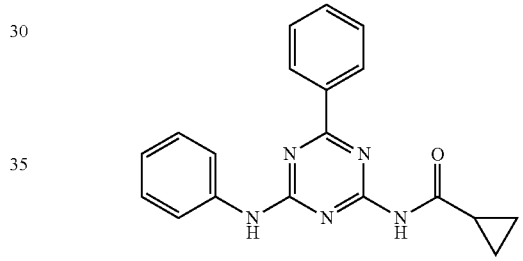

$^1$H NMR (DMSO-$d_6$) δ: 10.89. (br.s., 1H), 10.13 (br.s., 1H), 8.37 (d, J=7.2 Hz, 2H), 7.97 (br.s., 2H), 7.62-7.53 (m, 3H), 7.32 (br.s., 2H), 7.04 (t, J=6.8 Hz, 1H), 2.32 (br.s., 1H), 0.90-0.84 (m., 4H). LC-MS: m/z 332.1 (M+H)$^+$

Compound 347—N-(4-phenyl-6-(phenylamino)-1,3,5-triazin-2-yl)-1H-pyrazole-5-carboxamide

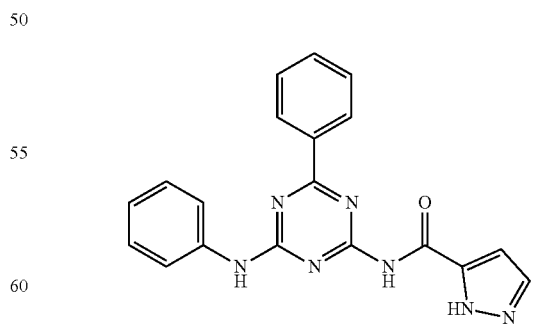

$^1$H NMR (METHANOL-$d_4$) δ: 8.37 (d, J=7.2 Hz, 2H), 7.75 (br.s., 2H), 7.72 (s, 1H), 7.51-7.42 (m, 3H), 7.31 (t, J=7.6 Hz, 2H), 7.03 (t, J=7.2 Hz, 1H), 6.89 (s, 1H). LC-MS: m/z 358.1 (M+H)$^+$

Compound 412—1-hydroxy-N-(4-phenyl-6-(phenylamino)-1,3,5-triazin-2-yl)cyclopropanecarboxamide

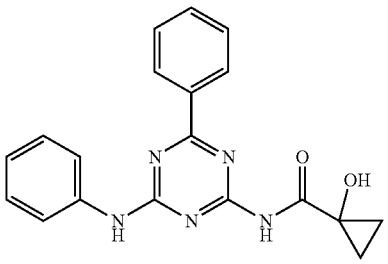 [SMILES: O=C(Nc1nc(Nc2ccccc2)nc(-c2ccccc2)n1)C1(O)CC1]

$^1$H NMR (METHANOL-d$_4$) δ: 8.36 (d, J=7.2 Hz, 2H), 7.60-7.89 (m, 2H), 7.48-7.39 (m, 3H), 7.29 (br.s., 2H), 7.25 (br.s., 2H), 1.29 (q, J=4.8 Hz, 2H), 1.06 (q, J=4.4 Hz, 2H). LC-MS: m/z 347.9 (M+H)$^+$

Compound 413—5-oxo-N-(4-phenyl-6-(phenylamino)-1,3,5-triazin-2-yl)pyrrolidine-2-carboxamide

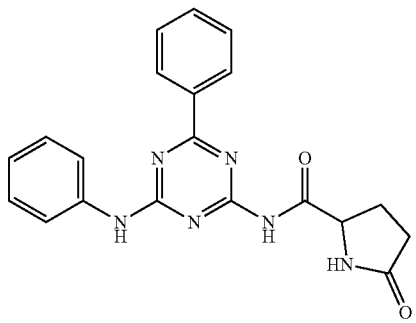 [SMILES: O=C1CCC(C(=O)Nc2nc(Nc3ccccc3)nc(-c3ccccc3)n2)N1]

H NMR (METHANOL-d$_4$) δ: 8.33 (d, J=7.6 Hz, 2H), 7.73 (d, J=8.2 Hz, 2H), 7.53-7.43 (m, 3H), 7.31 (t, J=7.6 Hz, 2H), 7.03 (t, J=6.9 Hz, 1H), 4.12-4.08 (m, 1H), 2.44-2.25 (m, 3H), 2.18-2.10 (m, 1H). LC-MS: m/z 375.2 (M+H)$^+$

Compound 415—N-(4-phenyl-6-(phenylamino)-1,3,5-triazin-2-yl)tetrahydrofuran-3-carboxamide

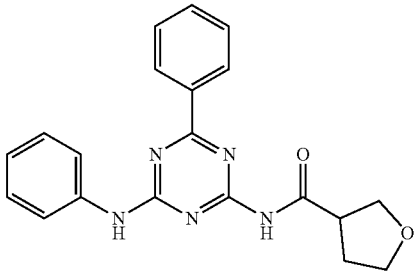 [SMILES: O=C(Nc1nc(Nc2ccccc2)nc(-c2ccccc2)n1)C1CCOC1]

$^1$H NMR (METHANOL-d$_4$) δ: 8.24 (d, J=7.6 Hz, 2H), 7.55-7.37 (m, 6H), 7.25 (d, J=7.2 Hz, 2H), 4.13-4.06 (m, 3H), 3.96 (q, J=8.0 Hz, 1H), 3.36 (q, J=7.26 Hz, 1H), 2.40-2.20 (m, 2H). LC-MS: m/z 362.2 (M+H)$^+$

Preparation of Compound 414—1H-Pyrrole-2-carboxylic acid (4-phenyl-6-phenylamino-[1,3,5]triazin-2-yl)-amide (Procedure 1, Step 4 Reagent 18)

To a solution of (4-amino-6-phenyl-[1,3,5]-triazin-2-yl)-phenyl-amine (210.6 mg, 0.8 mmol) in DCE (4 mL) was added Me$_3$Al (1 mL, 2.0 mmol) at 0° C. The mixture was stirred for 50 mins, warmed up to room temperature and 1H-Pyrrole-2-carboxylic acid methyl ester (50 mg, 0.4 mmol) was added. The mixture was stirred for 48 hr at 80° C. The reaction mixture was diluted with H$_2$O (5 mL) and extracted with EtOAc (5 mL×3). The combined organic layers were dried over Na$_2$SO$_4$ and concentrated to give a crude residue, which was purified by a standard method to give 1H-pyrrole-2-carboxylic acid (4-phenyl-6-phenylamino-[1,3,5]triazin-2-yl)-amide.

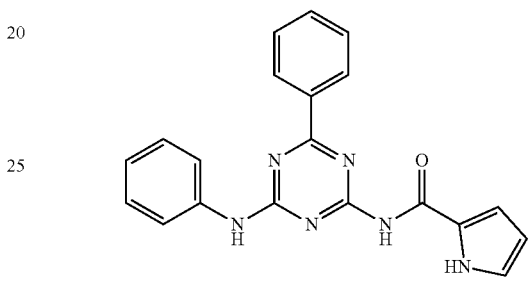

$^1$H NMR (METHANOL-d$_4$) δ: 8.39 (d, J=7.2 Hz, 1H), 7.75 (br.s., 2H), 7.48-7.40 (m, 3H), 7.29 (t, J=7.2 Hz, 2H), 7.07 (d, J=2.8 Hz, 1H), 6.99 (s, 2H), 6.18 (t, J=3.6 Hz, 1H). LC-MS: m/z 357.0 (M+H)$^+$

Other compounds of one aspect of the invention were similarly prepared using Example 7, Procedure 1, step 4 of this example, trimethylaluminum, and the appropriate ester 18.

2-oxo-N-(4-phenyl-6-(phenylamino)-1,3,5-triazin-2-yl)propanamide

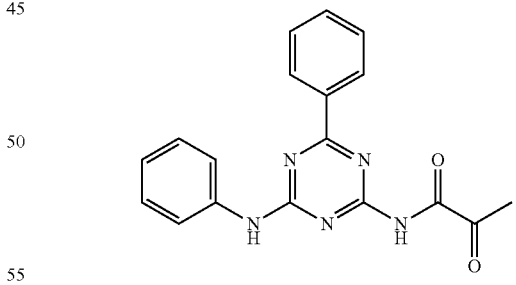

$^1$H NMR (DMSO-d$_6$) δ: 11.30 (s, 1H), 10.34 (s, 1H), 8.24 (d, J=6.4 Hz, 2H), 7.82 (d, J=8.4 Hz, 2H), 7.65-7.50 (m, 3H), 7.38 (br.s., 2H), 7.11 (t, J=7.2 Hz, 1H), 2.39 (br.s., 3H). LC-MS: m/z 334.2 (M+H)$^+$.

Preparation of Compound 416—Tert-butyl 4-phenyl-6-(phenylamino)-1,3,5-triazin-2-ylcarbamate Example 7, (Procedure 2)

A mixture of 4-chloro-N,6-diphenyl-1,3,5-triazin-2-amine (141 mg, 0.5 mmol), tert-butyl carbamate (69.6 mg, 0.6 mmol), Pd(AcO)₂ (24 mg, 0.05 mmol), X-phos (67.3 mg, 0.1 mmol) and Cs₂CO₃ (326 mg, 1 mmol) in dioxane (5 mL) was purged with N₂ for 5 minutes. Then the mixture was heated to 80° C. for 2 hours. The reaction mixture was filtered. The filtrate was concentrated and purified by a standard method to give ter-butyl 4-phenyl-6-(phenylamino)-1,3,5-triazin-2-ylcarbamate.

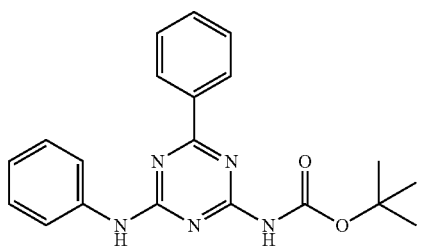 [SMILES: CC(C)(C)OC(=O)Nc1nc(Nc2ccccc2)nc(-c2ccccc2)n1]

¹H NMR (DMSO-d₆) δ: 10.24. (br.s., 1H), 10.07 (br.s., 1H), 8.38 (d, J=6.8 Hz, 2H), 7.99 (br.s., 2H), 7.62-7.53 (m, 3H), 7.31 (br.s., 2H), 7.04 (t, J=6.8 Hz, 1H), 1.51 (s, 9H). LC-MS: m/z 364.2 (M+H)⁺.

Other compounds of one aspect of the invention were similarly prepared using Example 7, Procedure 2 of this example and the appropriate amine 19.

Compound 181—ethyl 4-phenyl-6-(phenylamino)-1,3,5-triazin-2-ylcarbamate

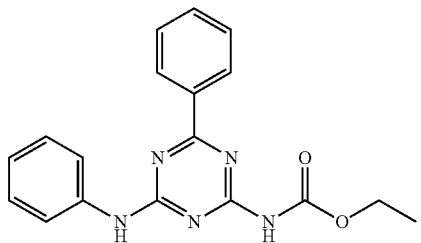 [SMILES: CCOC(=O)Nc1nc(Nc2ccccc2)nc(-c2ccccc2)n1]

¹H NMR (DMSO-d₆) δ: 10.58. (br.s., 1H), 10.12 (br.s., 1H), 8.37 (d, J=6.8 Hz, 2H), 8.05. (br.s., 2H), 7.60-7.52 (m, 3H), 7.32 (br.s., 2H), 7.04 (t, J=7.6 Hz, 1H), 4.20 (q, J=6.8 Hz, 2H), 1.27 (t, J=6.8 Hz, 1H). LC-MS: m/z 336.2 (M+H)⁺.

Compound 182—1,1-dimethyl-3-(4-phenyl-6-(phenylamino)-1,3,5-triazin-2-yl)urea

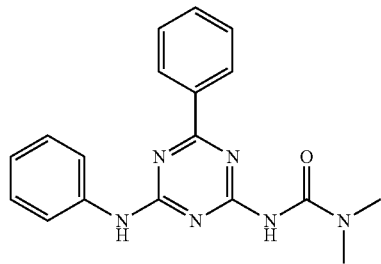 [SMILES: CN(C)C(=O)Nc1nc(Nc2ccccc2)nc(-c2ccccc2)n1]

¹H NMR (DMSO-d₆) δ: 9.59. (br.s., 1H), 9.35 (br s., 1H), 8.34 (d, J=7.2 Hz, 2H), 7.86 (d, J=8.0 Hz, 2H), 7.58-7.51 (m, 3H), 7.31 (t, J=7.2 Hz, 2H), 7.02 (t, J=7.2 Hz, 1H), 2.97 (s, 6H). LC-MS: m/z 335.0 (M+H)⁺

Compound 207—1-ethyl-3-(4-phenyl-6-(phenylamino)-1,3,5-triazin-2-yl)urea

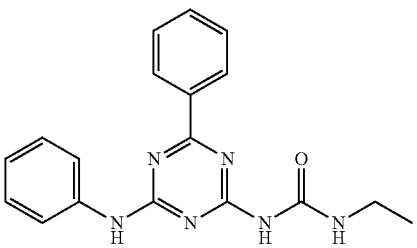 [SMILES: CCNC(=O)Nc1nc(Nc2ccccc2)nc(-c2ccccc2)n1]

¹H NMR (DMSO-d₆) δ: 10.10. (br.s., 1H), 9.84 (br.s., 1H), 8.30 (d, J=6.9 Hz, 2H), 7.73 (br.s., 2H), 7.63-7.53 (m, 3H), 7.38 (br.s., 2H), 7.11 (t, J=7.2 Hz, 1H), 3.33 (br.s., 2H), 1.11 (br.s., 3H). LC-MS: m/z 335.2 (M+H)⁺

Compound 209—N-(4-phenyl-6-(phenylamino)-1,3,5-triazin-2-yl)propionamide

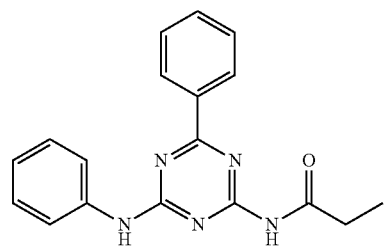 [SMILES: CCC(=O)Nc1nc(Nc2ccccc2)nc(-c2ccccc2)n1]

¹H NMR (DMSO-d₆) δ: 10.53. (br.s., 1H), 10.10 (br.s., 1H), 8.36 (d, J=6.9 Hz, 2H), 7.96 (br.s., 2H), 7.62-7.53 (m, 3H), 7.33 (t, J=7.2 Hz, 2H), 7.04 (t, J=7.2 Hz, 1H), 2.66-2.62 (m, 2H), 1.08 (t, J=7.6 Hz, 3H). LC-MS: m/z 320.2 (M+H)⁺

Compound 243—N-(4-phenyl-6-(phenylamino)-1,3,5-triazin-2-yl)tetrahydrofuran-2-carboxamide

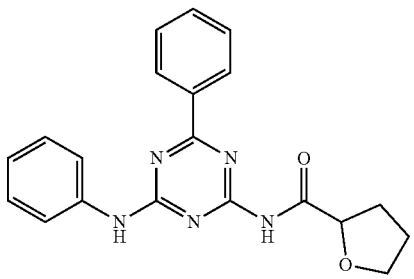 [SMILES: O=C(Nc1nc(Nc2ccccc2)nc(-c2ccccc2)n1)C1CCCO1]

¹H NMR (DMSO-d₆) δ: 10.21. (br.s., 2H), 8.38 (d, J=7.6 Hz, 2H), 8.00 (br.s., 2H), 7.63-7.53 (m, 3H), 7.34 (br.s., 2H), 7.06 (t, J=7.2 Hz, 1H), 4.69 (br.s., 1H), 3.95-3.82 (m., 1H), 4.01-3.97 (m., 1H), 2.32-2.19 (m., 1H), 2.03-1.85 (m., 3H). LC-MS: m/z 362.0 (M+H)⁺

Compound 244—2-isopropoxy-N-(4-phenyl-6-(phenylamino)-1,3,5-triazin-2-yl)acetamide

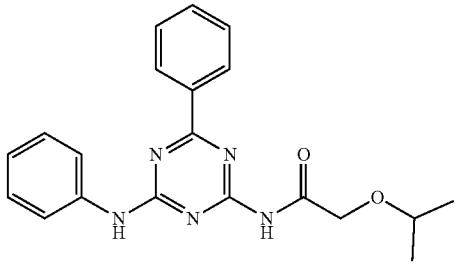 [SMILES: CC(C)OCC(=O)Nc1nc(Nc2ccccc2)nc(-c2ccccc2)n1]

¹H NMR (DMSO-d₆) δ: 10.35. (br.s., 1H), 10.20 (br.s., 1H), 8.37 (d, J=7.2 Hz, 2H), 7.92 (br.s., 2H), 7.62-7.54 (m, 3H), 7.35 (br.s., 2H), 7.08 (t, J=7.2 Hz, 1H), 4.37 (s, 2H), 3.70-3.67 (m., 1H), 1.15 (d, J=6.0 Hz, 6H). LC-MS: m/z 364.0 (M+H)⁺

Compound 324—2-hydroxy-N-(4-phenyl-6-(phenylamino)-1,3,5-triazin-2-yl)propanamide

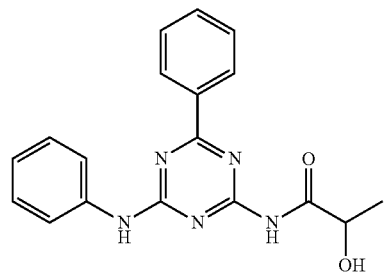 [SMILES: CC(O)C(=O)Nc1nc(Nc2ccccc2)nc(-c2ccccc2)n1]

¹H NMR (DMSO-d₆) δ: 10.28. (br.s., 1H), 10.05. (br.s., 1H), 8.39 (d, J=7.2 Hz, 2H), 8.09 (br.s., 2H), 7.63-7.55 (m, 3H), 7.36 (br.s., 2H), 7.05 (br.s., 1H), 5.88 (br.s., 1H), 4.38-4.35 (m, 1H), 1.35 (d, J=6.8 Hz, 3H). LC-MS: m/z 335.9 (M+H)⁺

Compound 348—2-hydroxy-N-(4-phenyl-6-(phenylamino)-1,3,5-triazin-2-yl)acetamide

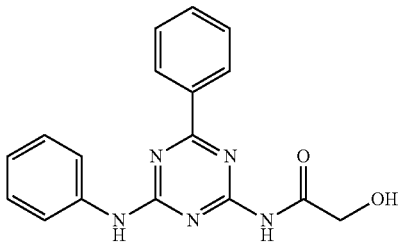 [SMILES: O=C(CO)Nc1nc(Nc2ccccc2)nc(-c2ccccc2)n1]

¹H NMR (METHANOL-d₄) δ: 8.44 (d, J=7.6 Hz, 2H), 7.74 (br.s., 2H), 7.60-7.49 (m, 3H), 7.38 (t, J=7.6 Hz, 2H), 7.12 (t, J=7.6 Hz, 1H), 4.94 (s, 2H). LC-MS: m/z 322.1 (M+H)⁺

Additional compounds of Formula I that were prepared according to Example 1, step 3, Procedure C using the appropriate reagent 4 are as follows:

Compound 450—methyl 4-((4-(isopropylamino)-6-phenyl-1,3,5-triazin-2-yl)amino)picolinate

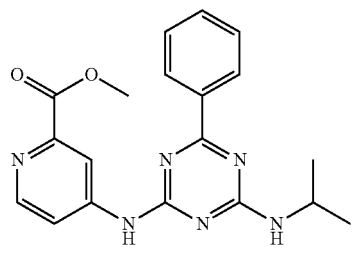 [SMILES: COC(=O)c1cc(Nc2nc(NC(C)C)nc(-c3ccccc3)n2)ccn1]

¹H NMR (METHANOL-d₄) δ 9.08-8.74 (d, 1H), 8.49-8.43 (m, 3H), 8.13-7.83 (m, 1H), 7.56-7.48 (m, 3H), 4.37-4.34 (m, 1H), 4.02 (s, 3H0, 1.35-1.30 (m, 6H). LC-MS: m/z 365.2 (M+H)⁺

Compound 451—2-(4-((4-(isopropylamino)-6-phenyl-1,3,5-triazin-2-yl)amino)pyridin-2-yl)propan-2-ol

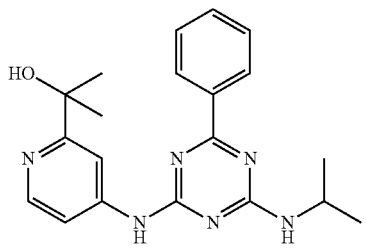

¹H NMR (METHANOL-d₄) δ 8.48-8.23 (m, 4H), 7.72-7.63 (m, 1H), 7.56-7.44 (m, 3H), 4.48-4.28 (m, 1H), 1.57 (s, 6H), 1.30 (d, 6H). LC-MS: m/z 365.2 (M+H)⁺

Compound 452—N2-isopropyl-N4-(4-(methylsulfonyl)phenyl)-6-phenyl-1,3,5-triazine-2,4-diamine

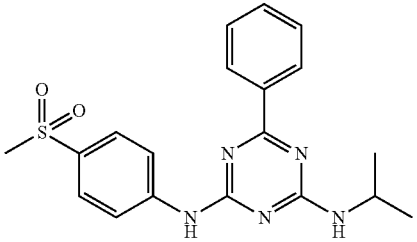 [SMILES: CC(C)Nc1nc(Nc2ccc(S(C)(=O)=O)cc2)nc(-c2ccccc2)n1]

¹H NMR (METHANOL-d₄) δ 8.41-8.31 (m, 2H), 7.91-7.88 (m, 4H), 7.63-7.45 (m, 4H), 5.51-5.08 (m, 1H), 4.48-4.19 (m, 1H), 3.05 (s, 3H), 1.30 (d, 6H). LC-MS: m/z 384.2 (M+H)⁺

Additional compounds of Formula I were prepared according to Scheme 2 using the appropriate reagents are as follows:

Compound 453—6-(3,6-Difluoro-pyridin-2-yl)-N-isopropyl-N'-(3-methanesulfonyl-phenyl)-[1,3,5]triazine-2,4-diamine

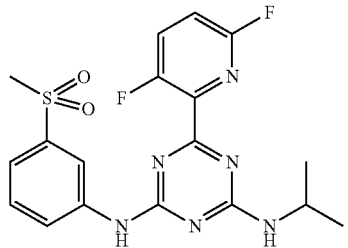 [SMILES: CC(C)Nc1nc(Nc2cccc(S(C)(=O)=O)c2)nc(-c2nc(F)ccc2F)n1]

¹H NMR (METHANOL-d₄) δ 8.90-8.40 (m, 1H), 8.13-8.11 (m, 1H), 7.82-7.80 (m, 2H), 7.71-7.67 (m, 1H), 7.59-7.57 (m, 1H), 4.42 (m, 1H), 3.16 (s, 1H), 1.37-1.36 (d, J=6.8 Hz, 6H). LC-MS: m/z 421.2 (M+H)⁺.

Compound 455—N-(3,5-Difluoro-phenyl)-N'-isopropyl-6-(4-trifluoromethyl-pyrimidin-2-yl)-[1,3,5]triazine-2,4-diamine

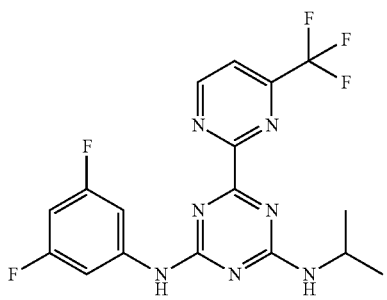

¹H NMR (DMSO-d₆) δ 10.39-10.42 (m, 1H), 9.36-9.38 (m, 1H), 8.19-8.34 (m, 2H), 7.68-7.71 (m, 2H), 6.79-6.84 (m, 1H), 4.10-4.15 (m, 1H), 1.18-1.23 (m, 6H). LC-MS: m/z 412.3 (M+H)⁺.

Compound 456—N-(5-Fluoro-pyridin-3-yl)-6-(3-fluoro-pyridin-2-yl)-N'-isopropyl-[1,3,5]triazine-2,4-diamine

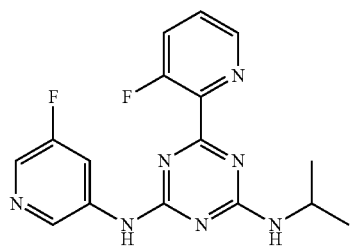 [SMILES: CC(C)Nc1nc(Nc2cncc(F)c2)nc(-c2ncccc2F)n1]

¹H NMR (METHANOL-d₄) δ 8.70 (s, 1H), 8.61-8.40 (m, 1H), 8.15-8.10 (m, 2H), 7.87-7.83 (m, 1H), 7.71-7.67 (m, 1H), 4.31-4.27 (m, 1H), 1.35-1.27 (m, 6H). LC-MS: m/z 344.2 (M+H)⁺.

Compound 458—6-(4-Amino-pyrimidin-2-yl)-N-(3,5-difluoro-phenyl)-N'-isopropyl-[1,3,5]triazine-2,4-diamine

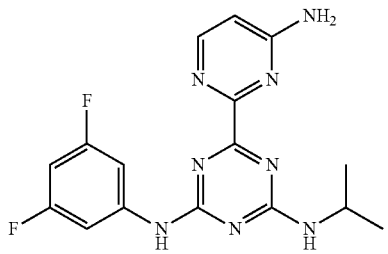

¹H NMR (METHANOL-d₄) δ (s, 1H), 7.50-7.52 (d, J=8.8 Hz, 2H), 6.58-6.67 (m, 2H), 4.23-4.55 (m, 1H), 1.25-1.34 (m, 6H). LC-MS: m/z 359.0 (M+H)⁺.

Compound 459—N-(3,5-Difluoro-phenyl)-6-(3-fluoro-pyridin-2-yl)-N'-isopropyl-[1,3,5]triazine-2,4-diamine

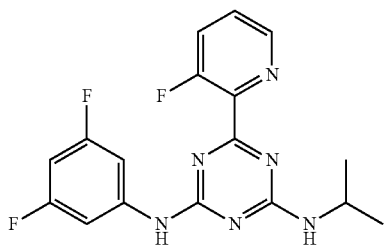

¹H NMR (METHANOL-d₄) δ 8.54-8.53 (d, 1H), 7.82-7.78 (m, 1H), 7.66-7.61 (m, 1H), 7.55-7.50 (m, 2H), 6.60-6.53 (m, 1H), 4.39-4.24 (m, 1H), 1.34-1.23 (m, 6H). LC-MS: m/z 361.2 (M+H)⁺.

Compound 460—N-(3,5-Difluoro-phenyl)-6-(3,6-difluoro-pyridin-2-yl)-N'-isopropyl-[1,3,5]triazine-2,4-diamine

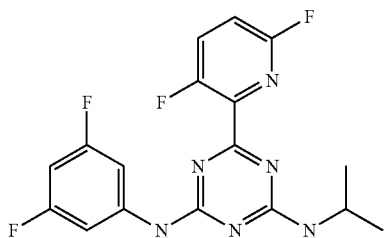

¹H NMR (METHANOL-d₄) δ 8.03-7.97 (m, 1H), 7.51-7.49 (m, 2H), 7.41-7.30 (m, 1H), 6.68-6.64 (m, 1H), 4.31-4.24 (m, 1H), 1.35-1.27 (m, 6H). LC-MS: m/z 379.1 (M+H)⁺.

243

Compound 461—N-(3,5-Difluoro-phenyl)-6-(3-fluoro-6-methoxy-pyridin-2-yl)-N'-isopropyl-[1,3,5]triazine-2,4-diamine

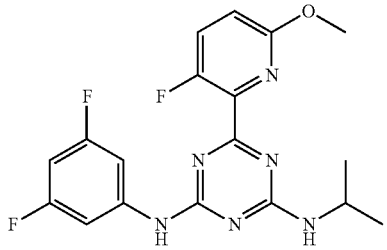 [SMILES: COc1ccc(F)c(-c2nc(Nc3cc(F)cc(F)c3)nc(NC(C)C)n2)n1]

$^1$H NMR (METHANOL-d$_4$) δ 7.83-7.79 (m, 1H), 7.54-7.51 (m, 2H), 7.22-7.19 (m, 1H), 6.78 (m, 1H), 4.35-4.31 (m, 1H), 4.08 (s, 3H), 1.39-1.31 (m, 6H). LC-MS: m/z 391.3 (M+H)$^+$.

Compound 462—6-(6-Amino-pyridin-2-yl)-N-(6-fluoro-pyridin-3-yl)-N'-isopropyl-[1,3,5]triazine-2,4-diamine

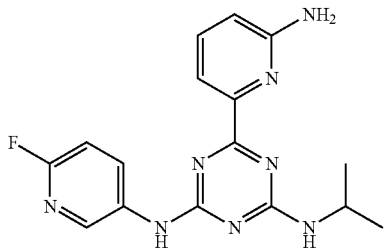 [SMILES: CC(C)Nc1nc(Nc2ccc(F)nc2)nc(-c2cccc(N)n2)n1]

$^1$H NMR (METHANOL-d$_4$) δ 8.65-8.58 (m, 1H), 8.50-8.30 (m, 1H), 8.20-7.61 (m, 2H), 7.20-6.90 (m, 2H), 4.60-4.20 (m, 1H), 1.30 (d, 6H). LC-MS: m/z 340.9 (M+H)$^+$.

Compound 463—N-(3,5-Difluoro-phenyl)-N'-isopropyl-6-(6-prop-1-ynyl-pyridin-2-yl)-[1,3,5]triazine-2,4-diamine

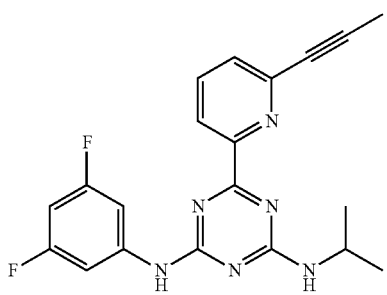 [SMILES: CC#Cc1cccc(-c2nc(Nc3cc(F)cc(F)c3)nc(NC(C)C)n2)n1]

$^1$H NMR (METHANOL-d$_4$) δ 8.39-8.34 (m, 1H), 7.94-7.90 (t, 1H), 7.60-7.52 (m, 3H), 6.62-6.57 (m, 1H), 4.50-4.24 (m, 1H), 2.12 (s, 3H), 1.34-1.29 (m, 6H). LC-MS: m/z 380.9 (M+H)$^+$.

244

Compound 464—N-(3,5-Difluoro-phenyl)-N'-isopropyl-6-(6-methylamino-pyridin-2-yl)-[1,3,5]triazine-2,4-diamine

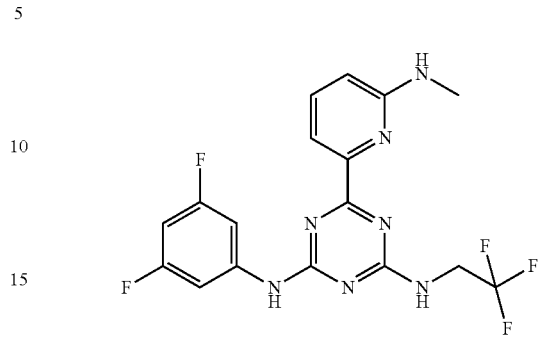

$^1$H NMR (METHANOL-d$_4$) δ 7.72-7.67 (m, 1H), 7.63-7.52 (m, 3H), 6.68-6.65 (d, 1H), 6.60-6.56 (m, 1H), 4.36-4.16 (m, 2H), 2.98 (s, 3H). LC-MS: m/z 441.9 (M+H)$^+$.

Compound 465—N-(3,5-Difluoro-phenyl)-6-(6-methylamino-pyridin-2-yl)-N'-(2,2,2-trifluoro-ethyl)-[1,3,5]triazine-2,4-diamine

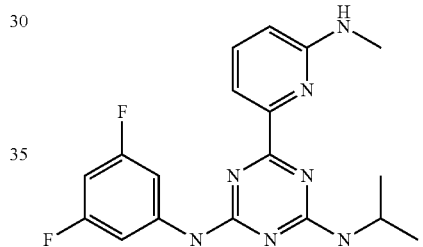

$^1$H NMR (METHANOL-d$_4$) δ 8.00-7.85 (m, 1H), 7.84-7.78 (m, 1H), 7.50-7.45 (m, 1H), 7.19-7.17 (m, 1H), 6.68-6.60 (m, 1H), 4.26-4.23 (m, 1H), 3.14-3.12 (d, 3H), 1.33-1.28 (m, 6H). LC-MS: m/z 372.3 (M+H)$^+$.

Compound 466—6-(2,6-difluorophenyl)-N2-isopropyl-N4-(3-(methylsulfonyl)phenyl)-1,3,5-triazine-2,4-diamine

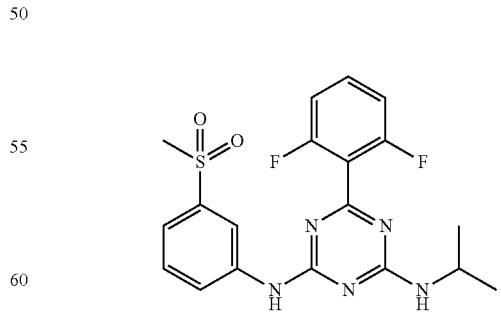

$^1$H NMR (METHANOL-d$_4$): δ 9.0-8.4 (m, 1.0H), 8.05-7.75 (m, 1H), 7.75-7.4 (m, 3H), 7.15-7.05 (m, 2H), 4.45-4.1 (m, 1H), 3.15 (s, 3H), 1.3 (d, J=6.4, 6H).
LC-MS: m/z 419.8 (M+H)$^+$.

Compound 467—N-(3-Fluoro-phenyl)-N'-isopropyl-6-(6-prop-1-ynyl-pyridin-2-yl)-[1,3,5]triazine-2,4-diamine

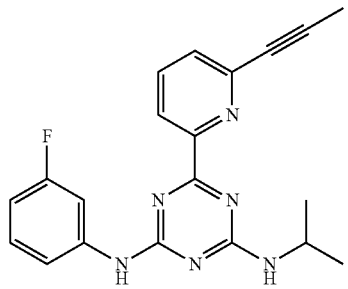 [SMILES: CC#Cc1cccc(-c2nc(Nc3cccc(F)c3)nc(NC(C)C)n2)n1]

¹H NMR (METHANOL-d₄) δ 8.33-8.31 (m, 1H), 7.92-7.82 (m, 2H), 7.58-7.56 (m, 1H), 7.40-7.30 (m, 2H), 6.78-6.76 (m, 1H), 4.25-4.22 (m, 1H), 2.10 (s, 3H), 1.33-1.28 (m, 6H). LC-MS: m/z 363.2 (M+H)⁺.

Compound 468—6-(6-Amino-pyridin-2-yl)-N-isopropyl-N'-(5-trifluoromethyl-pyridin-3-yl)-[1,3,5]triazine-2,4-diamine

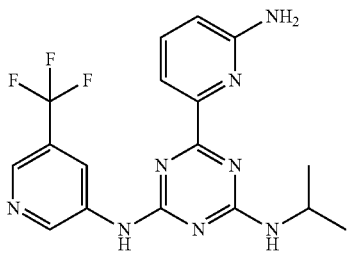 [SMILES: CC(C)Nc1nc(Nc2cncc(C(F)(F)F)c2)nc(-c2cccc(N)n2)n1]

¹H NMR (METHANOL-d₄) δ 9.21 (s, 2H), 8.48 (s, 1H), 7.70-7.58 (m, 2H), 6.74-6.72 (m, 1H), 4.22 (m, 1H), 1.31-1.29 (d, J=8.0 Hz, 6H). LC-MS: m/z 391.3 (M+H)⁺.

Compound 469—6-[4-(3,5-Difluoro-phenylamino)-6-isopropylamino-[1,3,5]triazin-2-yl]-5-fluoro-pyridin-2-ol

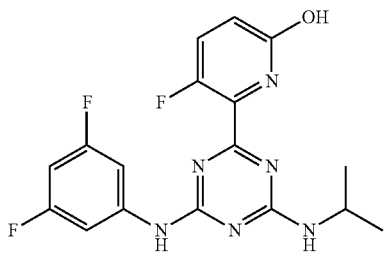

¹H NMR (METHANOL-d₄) δ 7.71-7.65 (m, 2H), 7.49-7.47 (m, 2H), 6.77-6.72 (m, 1H), 6.55-6.53 (m, 1H), 4.40-4.18 (m, 1H), 1.30-1.25 (m, 6H). LC-MS: m/z 377.2 (M+H)⁺.

Compound 470—6-(6-Amino-pyridin-2-yl)-N-(5-fluoro-pyridin-3-yl)-N'-isopropyl-[1,3,5]triazine-2,4-diamine

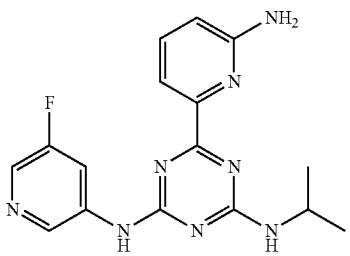 [SMILES: CC(C)Nc1nc(Nc2cncc(F)c2)nc(-c2cccc(N)n2)n1]

¹H NMR (METHANOL-d₄) δ 9.38-9.35 (m, 1H), 8.77-8.63 (m, 2H), 8.09-7.86 (m, 2H), 7.25-7.22 (m, 1H), 4.28-4.25 (m, 1H), 1.34 (dd, 6H) LC-MS: m/z 341.1 (M+H)⁺.

Compound 471—N-(3-Fluoro-phenyl)-N'-isopropyl-6-(2-methyl-oxazol-4-yl)-[1,3,5]triazine-2,4-diamine

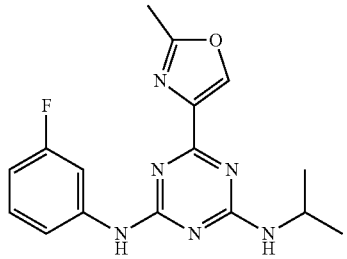 [SMILES: Cc1nc(-c2nc(Nc3cccc(F)c3)nc(NC(C)C)n2)co1]

¹H NMR (METHANOL-d₄) δ 8.46-8.43 (m, 1H), 7.85-7.82 (m, 1H), 7.40-7.27 (m, 2H), 6.78-6.74 (m, 1H), 4.25-4.22 (m, 1H), 2.57 (s, H), 1.29 (dd, J=13.2 Hz, 6.4 Hz, 6H). LC-MS: m/z 329.2 (M+H)⁺.

Compound 472—N-(3-Fluoro-phenyl)-N'-isopropyl-6-(5-methyl-isoxazol-3-yl)-[1,3,5]triazine-2,4-diamine

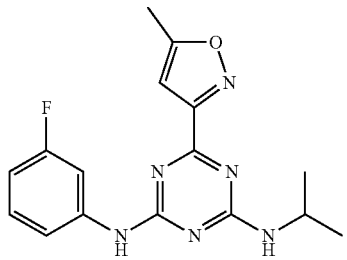 [SMILES: Cc1cc(-c2nc(Nc3cccc(F)c3)nc(NC(C)C)n2)no1]

¹H NMR (METHANOL-d₄) δ 7.87-7.82 (m, 1H), 7.41-7.38 (m, 1H), 7.34-7.26 (m, 1H), 6.77-6.68 (m, 2H), 4.38-4.21 (m, 1H), 2.53 (s, H), 1.29 (dd, J=10.8 Hz, 6.8 Hz, 6H). LC-MS: m/z 329.3 (M+H)⁺.

Compound 473—6-(2,6-Difluoro-phenyl)-N-(3-fluoro-phenyl)-N'-isopropyl-[1,3,5]triazine-2,4-diamine

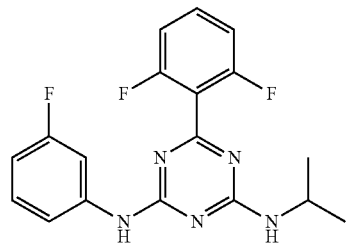 [SMILES: CC(C)Nc1nc(Nc2cccc(F)c2)nc(-c2c(F)cccc2F)n1]

$^1$H NMR (METHANOL-d$_4$) δ 6.98-6.97 (m, 1H), 6.69-6.54 (m, 3H), 6.28-6.23 (m, 2H), 5.92 (m, 1H), 3.47-3.44 (m, 1H), 0.49 (d, 6H) LC-MS: m/z 359 (M+H)$^+$.

Compound 474—6-(2,6-Difluoro-phenyl)-N-(5-fluoro-pyridin-3-yl)-N'-isopropyl-[1,3,5]triazine-2,4-diamine

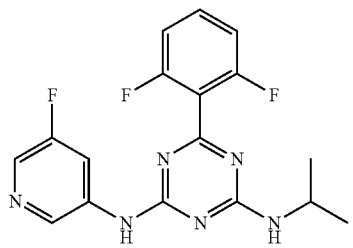

$^1$H NMR (METHANOL-d$_4$) δ 9.23-9.01 (m, 1H), 8.78-8.43 (m, 2H), 7.63-7.61 (m, 1H), 7.20-7.16 (m, 2H), 4.31-4.20 (m, 1H), 1.33 (d, 6H) LC-MS: m/z 361.1 (M+H)$^+$.

Compound 475—N-(3-Fluoro-phenyl)-N'-isopropyl-6-(4-trifluoromethyl-thiazol-2-yl)-[1,3,5]triazine-2,4-diamine

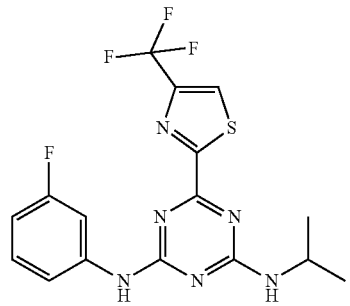 [SMILES: CC(C)Nc1nc(Nc2cccc(F)c2)nc(-c2nc(C(F)(F)F)cs2)n1]

$^1$H NMR (METHANOL-d$_4$) δ 8.71 (s, 1H), 8.24 (d, J=7.6 Hz, 1H), 8.00-7.86 (m, 1H), 7.52-7.50 (m, 1H), 7.36-7.27 (m, 1H), 4.25-4.08 (m, 1H), 1.21 (d, J=6.4 Hz, 6H). LC-MS: m/z 399.0 (M+H)$^+$.

Compound 476—N-(3,5-Difluoro-phenyl)-N'-isopropyl-6-(2-methyl-oxazol-4-yl)-[1,3,5]triazine-2,4-diamine

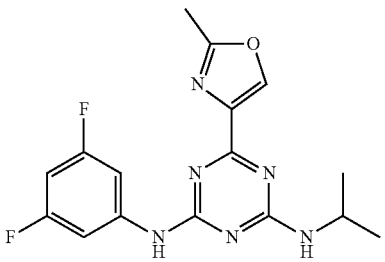 [SMILES: Cc1nc(-c2nc(Nc3cc(F)cc(F)c3)nc(NC(C)C)n2)co1]

$^1$H NMR (METHANOL-d$_4$) δ 8.67 (br, 1H), 7.42 (d, J=9.2 Hz, 2H), 6.77-6.72 (m, 1H), 4.28-4.23 (m, 1H), 2.56 (s, 3H), 1.28 (d, J=9.6 Hz, 6H). LC-MS: m/z 347.1 (M+H)$^+$.

Compound 477—6-(6-amino-3-fluoropyridin-2-yl)-N2-(3,5-difluorophenyl)-N4-isopropyl-1,3,5-triazine-2,4-diamine

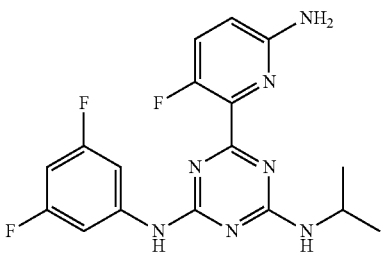

$^1$H NMR (METHANOL-d$_4$) δ 7.55-7.45 (m, 2H), 7.45-7.35 (m, 1H), 7.0-6.9 (m, 1H), 6.65-6.5 (m, 1H), 4.4-4.15 (m, 1H), 1.4-1.25 (m, 6H). LC-MS: m/z 376.2 (M+H)$^+$.

Compound 478—6-(4-Amino-pyrimidin-2-yl)-N-cyclopropylmethyl-N'-(3,5-difluoro-phenyl)-[1,3,5]triazine-2,4-diamine

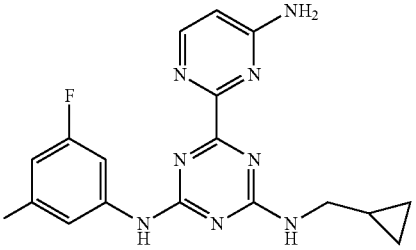

$^1$H NMR (METHANOL-d$_4$) δ 8.26-8.25 (d, J=5.6 Hz, 1H), 7.532-7.490 (m, 2H), 6.66-6.57 (m, 2H), 3.43-3.23 (m, 2H), 1.16-1.18 (m, 1H), 0.58-0.51 (m, 2H), 0.34-0.29 (m, 2H). LC-MS: m/z 371.2 (M+H)$^+$.

Compound 479—6-(4-Amino-pyrimidin-2-yl)-N-tert-butyl-N'-(3,5-difluoro-phenyl)-[1,3,5]triazine-2,4-diamine

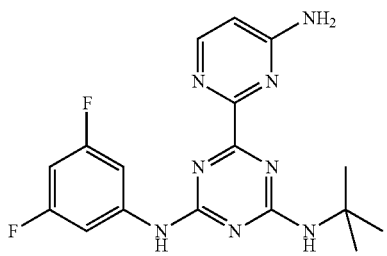 [SMILES: CC(C)(C)Nc1nc(Nc2cc(F)cc(F)c2)nc(-c2nccc(N)n2)n1]

$^1$H NMR (METHANOL-d$_4$) δ 8.28-8.26 (d, J=5.2 Hz, 1H), 7.49-7.47 (d, J=8 Hz, 2H), 6.66-6.60 (m, 2H), 1.54 (s, 9H). LC-MS: m/z 373.2 (M+H)$^+$.

Compound 480—6-(4-Amino-pyrimidin-2-yl)-N-(3,5-difluoro-phenyl)-N'-(2,2,2-trifluoro-ethyl)-[1,3,5]triazine-2,4-diamine

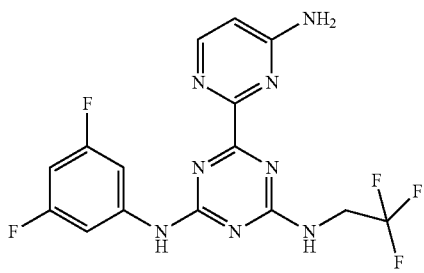 [SMILES: Nc1ccnc(-c2nc(NCC(F)(F)F)nc(Nc3cc(F)cc(F)c3)n2)n1]

$^1$H NMR (METHANOL-d$_4$) δ 8.29-8.26 (m, 1H), 7.55-7.44 (m, 2H), 6.67-6.59 (m, 2H), 4.44-4.20 (m, 2H). LC-MS: m/z 399.2 (M+H)$^+$.

Compound 481—6-(4-amino-6-(trifluoromethyl)pyrimidin-2-yl)-N2-(3,5-difluorophenyl)-N4-isopropyl-1,3,5-triazine-2,4-diamine

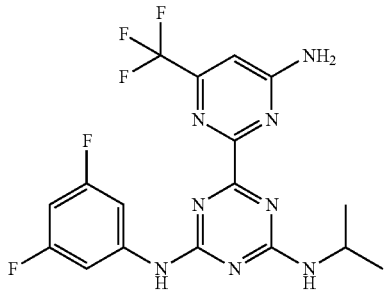 [SMILES: CC(C)Nc1nc(Nc2cc(F)cc(F)c2)nc(-c2nc(N)cc(C(F)(F)F)n2)n1]

$^1$H NMR (METHANOL-d$_4$) δ 7.53 (d, J=8.0 Hz, 2H), 6.98 (s, 1H), 6.63-6.55 (m, 1H), 4.50-4.23 (m, 1H), 1.34 (d, J=6.2 Hz, 6H). LC-MS: m/z 427.1 (M+H)$^+$.

Compound 482—6-(2-Amino-pyrimidin-4-yl)-N-(3,5-difluoro-phenyl)-N'-isopropyl-[1,3,5]triazine-2,4-diamine

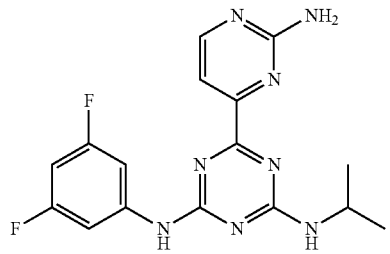

$^1$H NMR (METHANOL-d4) δ 8.47-8.46 (m, 1H), 7.60-7.48 (m, 3H), 4.26-4.22 (m, 1H), 1.33-1.26 (m, 6H). LC-MS: m/z 372.3 (M+H)$^+$.

Compound 483—6-(4,6-dichloropyridin-2-yl)-N2-isopropyl-N4-(3-(methylsulfonyl)phenyl)-1,3,5-triazine-24-diamine

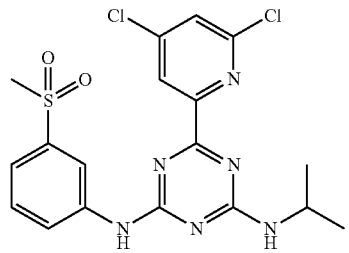 [SMILES: CC(C)Nc1nc(Nc2cccc(S(C)(=O)=O)c2)nc(-c2cc(Cl)cc(Cl)n2)n1]

$^1$H NMR (DMSO-d6) δ 10.40 (br, 1H), 8.88 (s, 1H), 8.34-8.18 (m, 2H), 7.99 (s, 1H), 7.81-7.79 (m, 1H), 7.56-7.53 (m, 2H), 4.23 (br, 1H), 3.18 (m, 3H), 1.20 (s, 6H). LC-MS: m/z 475.0 (M+H)$^+$.

Compound 484—6-(3-fluoro-6-(trifluoromethyl)pyridin-2-yl)-N2-isopropyl-N4-(3-(methylsulfonyl)phenyl)-1,3,5-triazine-2,4-diamine

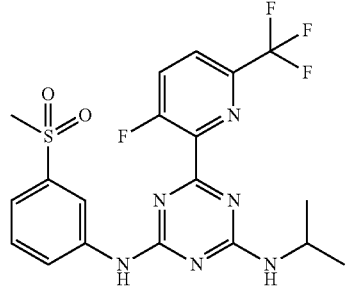 [SMILES: CC(C)Nc1nc(Nc2cccc(S(C)(=O)=O)c2)nc(-c2nc(C(F)(F)F)ccc2F)n1]

$^1$H NMR (METHANOL-d4) δ 8.52 (s, 1H), 8.03-7.95 (m, 2H), 7.79 (br, 1H), 7.61-7.53 (m, 2H), 4.36-4.28 (m, 1H), 3.11 (d, 3H), 1.31-1.21 (m, 6H). LC-MS: m/z 471.1 (M+H)$^+$.

251

Compound 485—6-(6-amino-4-chloropyridin-2-yl)-N²-(3,5-difluorophenyl)-N⁴-isopropyl-1,3,5-triazine-2,4-diamine

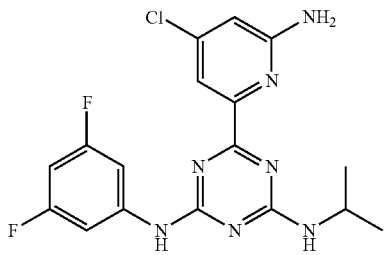 [SMILES: CC(C)Nc1nc(Nc2cc(F)cc(F)c2)nc(-c2cc(Cl)cc(N)n2)n1]

¹H NMR (METHANOL-d₄) δ 7.66 (s, 1H), 7.49-7.47 (d, 2H), 6.73 (s, 1H), 6.57-6.50 (m, 1H), 4.47-4.09 (m, 1H), 1.35-1.26 (m, 6H). LC-MS: m/z 392.1 (M+H)⁺.

Compound 486—6-(4-chloro-6-methoxypyridin-2-yl)-N²-(3,5-difluorophenyl)-N⁴-isopropyl-1,3,5-triazine-2,4-diamine

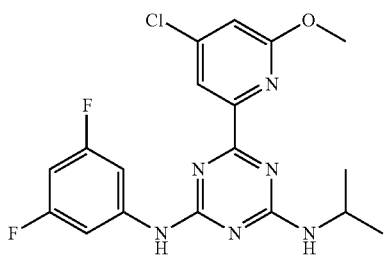 [SMILES: COc1cc(Cl)cc(-c2nc(Nc3cc(F)cc(F)c3)nc(NC(C)C)n2)n1]

¹H NMR (METHANOL-d₄) δ 8.05 (s, 1H), 7.52 (br, 2H), 7.00 (s, 1H), 6.58-6.52 (m, 1H), 4.40-4.21 (m, 1H), 4.07 (s, 3H), 1.31-1.29 (d, 6H). LC-MS: m/z 407.1 (M+H)⁺.

Compound 487—(2-(4-((3,5-difluorophenyl)amino)-6-(isopropylamino)-1,3,5-triazin-2-yl)-6-(trifluoromethyl)pyridin-4-yl)methanol

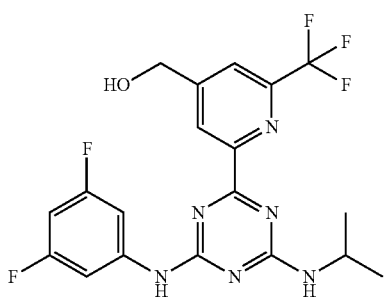 [SMILES: CC(C)Nc1nc(Nc2cc(F)cc(F)c2)nc(-c2cc(CO)cc(C(F)(F)F)n2)n1]

¹H NMR (METHANOL-d₄) δ 8.66 (s, 1H), 7.92 (s, 1H), 7.54-7.52 (d, J=8 Hz, 2H), 6.60-6.54 (m, 1H), 4.83 (s, 2H), 4.47-4.22 (m, 1H), 1.33-1.31 (d, J=6.4 Hz, 6H). LC-MS: m/z 441.1 (M+H)⁺.

252

Compound 488—6-(6-(1,1-difluoroethyl)-4-fluoropyridin-2-yl)-N²-isopropyl-N⁴-(3-(methylsulfonyl)phenyl)-1,3,5-triazine-2,4-diamine

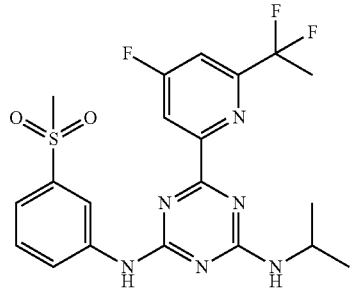 [SMILES: CC(C)Nc1nc(Nc2cccc(S(C)(=O)=O)c2)nc(-c2cc(F)cc(C(C)(F)F)n2)n1]

¹H NMR (METHANOL-d₄) δ 8.95 (m, 1H), 8.3 (m, 1H), 7.75 (m, 1H), 7.6-7.5 (m, 3H), 4.4 (m, 1H), 3.15 (s, 3H), 2.2-2.0 (m, 3H), 1.4-1.3 (m, 6H).

Compound 489—6-(6-amino-4-fluoropyridin-2-yl)-N-(3,5-difluorophenyl)-N'-isopropyl-1,3,5-triazine-2,4-diamine

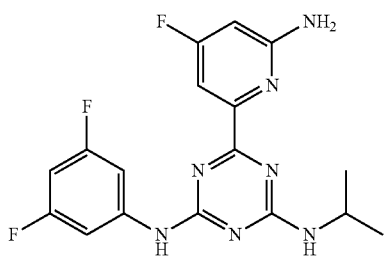 [SMILES: CC(C)Nc1nc(Nc2cc(F)cc(F)c2)nc(-c2cc(F)cc(N)n2)n1]

¹H NMR (DMSO) δ 10.15 (m, 1H), 8.0 (m, 1H), 7.7-7.5 (m, 2H), 7.2 (m, 1H), 6.75 (m, 1H) 6.36 (m, 1H), 6.26 (m, 2H), 4.4-4.0 (m, 1H), 1.2 (m, 6H).

Compound 490—(2-chloro-6-(4-((3,5-difluorophenyl)amino)-6-(isopropylamino)-1,3,5-triazin-2-yl)pyridin-4-yl)methanol

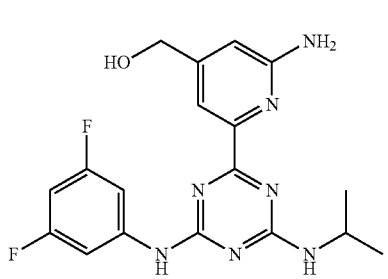

¹H NMR (METHANOL-d₄) δ 10.28-10.24 (m, 1H), 8.29 (s, 1H), 8.16-7.88 (m, 1H), 7.71-7.54 (m, 2H), 7.54-7.53 (d, 1H), 6.80-6.72 (m, 1H), 5.63-5.60 (q, 2H), 4.63-4.61 (m, 1H), 4.33-4.05 (m, 1H), 1.21-1.19 (d, 6H). LC-MS: m/z 407.1 (M+H)⁺.

Compound 491—6-(6-aminopyridin-2-yl)-N2-(3,5-difluorophenyl)-N4-(2,2,2-trifluoroethyl)-1,3,5-triazine-2,4-diamine

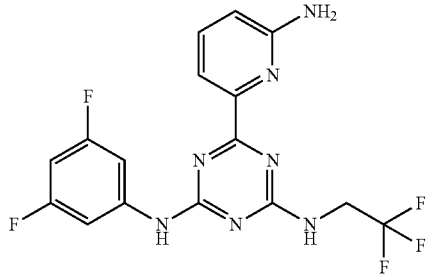 [SMILES: Nc1cccc(-c2nc(NCC(F)(F)F)nc(Nc3cc(F)cc(F)c3)n2)n1]

¹H NMR (METHANOL-d₄) δ 8.10-8.07 (m, 1H), 7.93-7.86 (m, 1H), 7.54-7.41 (m, 2H), 7.25-7.22 (m, 1H), 6.69-6.65 (m, 1H), 4.42-4.25 (m, 2H). LC-MS: m/z 398.2 (M+H)$^+$.

Compound 492—6-(6-aminopyridin-2-yl)-N2-(3-fluorophenyl)-N4-isopropyl-1,3,5-triazine-2,4-diamine

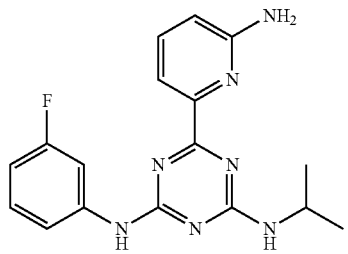

¹H NMR (METHANOL-d₄) δ 8.04-8.00 (m, 1H), 7.83 (br, 2H), 7.40-7.37 (m, 1H), 7.33-7.28 (m, 1H), 7.18-7.16 (m, 1H), 6.79 (t, 1H), 4.51-4.25 (m, 1H), 1.29 (d, 6H). LC-MS: m/z 340.2 (M+H)$^+$.

Compound 493—6-(6-amino-3-fluoropyridin-2-yl)-N2-(tert-butyl)-N4-(2-(trifluoromethyl)pyridin-4-yl)-1,3,5-triazine-2,4-diamine Step 1: Preparation of (E)-2-(tert-butyl)-1-(diaminomethylene)guanidine To a mixture of 1-phenyl-2-cyanoguanidine (10 g, 0.119 mol) in ethanol/water (176.5 mL/70.6 mL) was added CuSO₄:5H₂O (14.9 g, 0.059 mol), followed by 2-methylpropan-2-amine (11.3 g, 0.155 mol). The mixture was heated to reflux for 16 hours. To the mixture was added water (137 mL) and aq.HCl (59.5 mL in 100 mL of water) at 25-30° C. The resultant mixture was stirred at r.t. for 30 min. Then Na₂S (47.6 g in 100 mL of water) was added and stirred for another 30 min. The insoluble CuS was filtered off. The filtrate was cooled to 10° C. and added aqueous NaOH (27 g NaOH in 100 mL water) dropwise. The mixture was extracted with dichloromethane (100 mL×3). The aqueous layer was concentrated and the residue was added dichloromethane (200 mL) and the mixture was stirred for 1 hour and the mixture was filtrated. The filtrated was concentrated to give (E)-2-(tert-butyl)-1-(diaminomethylene)guanidine as a brown solid.

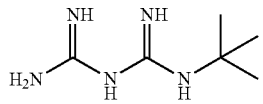

¹H NMR (CDCl₃) δ 1.32-1.37 (m, 9H).

Step 2: Preparation of N2-(tert-butyl)-6-(3,6-difluoropyridin-2-yl)-1,3,5-triazine-2,4-diamine The mixture of (E)-2-(tert-butyl)-1-(diaminomethylene)guanidine (1.2 g, 7.6 mmol), methyl 3,6-difluoropicolinate (1.3 g, 7.6 mol) and MeONa (0.9 g, 15.2 mol) in MeOH (25 mL) was stirred for 5 hours at r.t. TLC showed the reaction was completed. The mixture was poured into water (15 mL), extracted with EA (50 mL) for 3 times. The combine organic layer was dried, concentrated and purified by Prep-HPLC to give N2-(tert-butyl)-6-(3,6-difluoropyridin-2-yl)-1,3,5-triazine-2,4-diamine as a white solid.

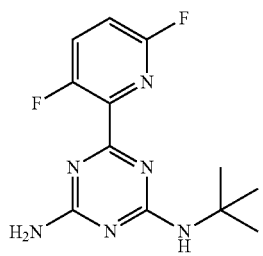 [SMILES: CC(C)(C)Nc1nc(N)nc(-c2nc(F)ccc2F)n1]

¹H NMR (CDCl₃) δ 7.5 (m, 1H), 7.0 (m, 1H), 5.4 (B, 1H), 5.1-5.2 (br s, 2H), 4.4 (m, 9H).

Step 3: Preparation of N²-(tert-butyl)-6-(3,6-difluoropyridin-2-yl)-N4-(2-(trifluoromethyl) pyridin-4-yl)-1,3,5-triazine-2,4-diamine

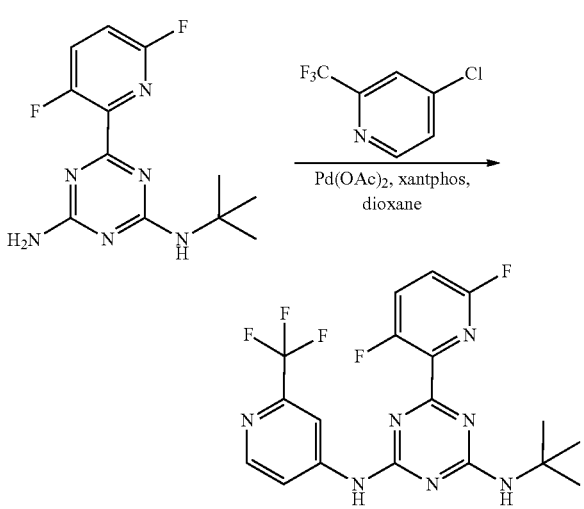

To the mixture of N²-(tert-butyl)-6-(3,6-difluoropyridin-2-yl)-1,3,5-triazine-2,4-diamine (0.4 g, 1.4 mmol), 4-chloro- 2-(trifluoromethyl)pyridine (0.31 g, 1.7 mmol), Cs2CO3 (0.7 g, 2.1 mmol) and X-phos (0.048 g, 0.07 mmol) in dioxane (10 mL) was added Pd(OAc)2 under N₂ protection. The reaction mixture was heated to 80 deg and stirred for 2 hours. TLC showed the reaction was completed. the reaction mixture was added water (10 mL), extracted with EA (100 mL) for 3 times. The combine organic layer was dried and concentrated. The residue was purified by a standard method to give N²-(tert-butyl)-6-(3,6-difluoropyridin-2-yl)-N⁴-(2-(trifluoromethyl)pyridin-4-yl)-1,3,5-triazine-2,4-diamine.

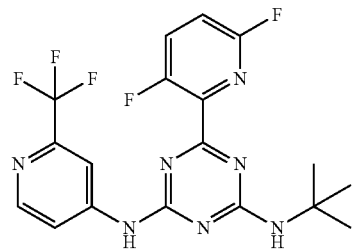 [SMILES: CC(C)(C)Nc1nc(Nc2ccnc(C(F)(F)F)c2)nc(-c2nc(F)ccc2F)n1]

$^1$H NMR (CDCl₃) δ 8.6-8.4 (m, 2H), 7.65 (m, 1H), 7.5-7.4 (m, 2H), 7.1 (m, 1H), 5.7 (m, 1H), 1.45 (m, 9H).

Step 4: Preparation of 6-(6-amino-3-fluoropyridin-2-yl)-N2-(tert-butyl)-N4-(2-(trifluoromethyl) pyridin-4-yl)-1,3,5-triazine-2,4-diamine—Compound 494

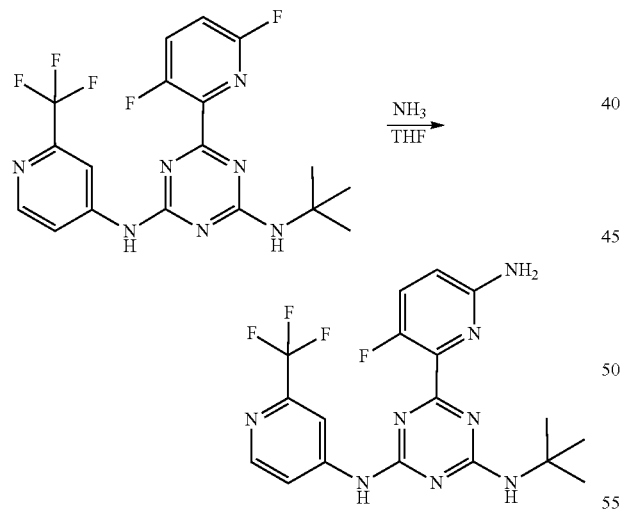

To the solution of N²-(tert-butyl)-6-(3,6-difluoropyridin-2-yl)-N⁴-(2-(trifluoromethyl)pyridine-4-yl)-1,3,5-triazine-2,4-diamine (300 mg, 0.7 mmol) and CuI (134 mg, 0.7 mmol) in THF (5 mL) was added sat.NH₃/EtOH (15 mL) solution. The reaction mixture was stirred in a seal reactor at 130 deg for 10 hours. LCMS showed the reaction was completed. The solvent was removed and the residue was purified by a standard method to give 6-(6-amino-3-fluoropyridin-2-yl)-N²-(tert-butyl)-N⁴-(2-(trifluoromethyl)pyridin-4-yl)-1,3,5-triazine-2,4-diamine.

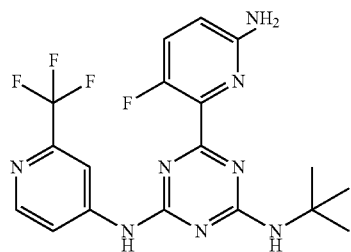 [SMILES: CC(C)(C)Nc1nc(Nc2ccnc(C(F)(F)F)c2)nc(-c2nc(N)ccc2F)n1]

$^1$H NMR (CDCl₃) δ 8.63 (m, 1H), 8.45 (m, 1H), 7.85 (m, 1H), 7.5-7.4 (m, 1H), 6.75 (m, 1H), 1.5 (m, 9H).

According to the general strategy outlined in Scheme 3, step 2, the following intermediates were prepared:

6-(4-(trifluoromethyl)pyrimidin-2-yl)-1,3,5-triazine-2,4(1H,3H)-dione

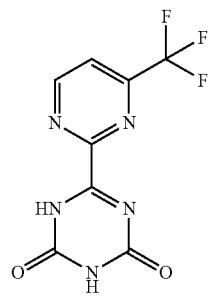 [SMILES: O=c1nc(-c2nccc(C(F)(F)F)n2)[nH]c(=O)[nH]1]

LCMS: m/z 260.1 (M+H)⁺.

Methyl 6-(4,6-dioxo-1,4,5,6-tetrahydro-1,3,5-triazin-2-yl)pyridin-2-ylcarbamate

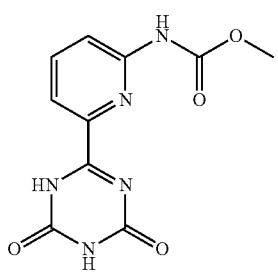 [SMILES: COC(=O)Nc1cccc(-c2nc(=O)[nH]c(=O)[nH]2)n1]

LCMS: m/z 264.2 (M+H)⁺.

257

6-(4-methoxypyridin-2-yl)-1,3,5-triazine-2,4(1H,3H)-dione

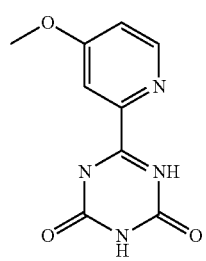 [SMILES: COc1ccnc(-c2nc(=O)[nH]c(=O)[nH]2)c1]

LCMS: m/z 221.1 (M+H)⁺.

According to the general strategy outlined in Scheme 3, step 3, the following intermediates were prepared:

2,4-dichloro-6-(4-(trifluoromethyl)-pyrimidin-2-yl)-1,3,5-triazine

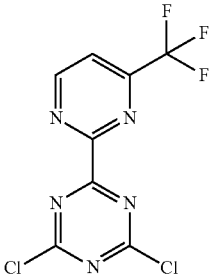 [SMILES: FC(F)(F)c1ccnc(-c2nc(Cl)nc(Cl)n2)n1]

LCMS: m/z 296.0 (M+H)⁺.

2,4-Dichloro-6-(6-difluoromethyl-pyridin-2-yl)-[1,3,5]triazine

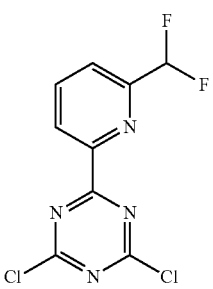 [SMILES: FC(F)c1cccc(-c2nc(Cl)nc(Cl)n2)n1]

LCMS: m/z 277.0 (M+H)⁺.

258

2,4-Dichloro-6-[6-(1,1-difluoroethyl)-pyridin-2-yl]-[1,3,5]triazine

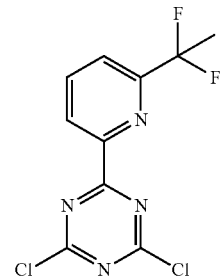 [SMILES: CC(F)(F)c1cccc(-c2nc(Cl)nc(Cl)n2)n1]

LCMS: m/z 290.9 (M+H)⁺.

Methyl 6-(4,6-dichloro-1,3,5-triazin-2-yl)-pyridin-2-ylcarbamate

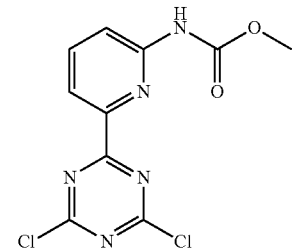 [SMILES: COC(=O)Nc1cccc(-c2nc(Cl)nc(Cl)n2)n1]

LCMS: m/z 300.1 (M+H)⁺.

2,4-Dichloro-6-(4-methoxypyridin-2-yl)-1,3,5-triazine

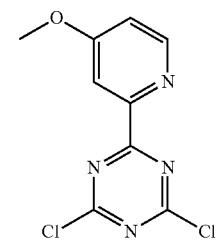 [SMILES: COc1ccnc(-c2nc(Cl)nc(Cl)n2)c1]

LCMS: m/z 257.1 (M+H)⁺.

According to the general strategy outlined in Scheme 3, steps 4-5, the following compounds were prepared from appropriate reagents and intermediates:

Compound 494—N-[2-(1, 1-Difluoro-ethyl)-pyridin-4-yl]-N'-isopropyl-6-(6-trifluoromethyl-pyridin-2-yl)-[1,3,5] triazine-2,4-diamine

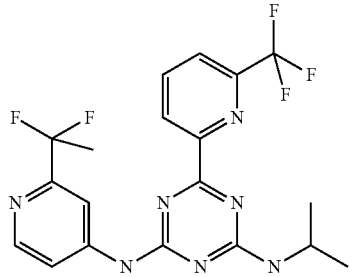 [SMILES: CC(C)Nc1nc(Nc2ccnc(C(C)(F)F)c2)nc(-c2cccc(C(F)(F)F)n2)n1]

$^1$H NMR (METHANOL-d$_4$) δ 8.67 (s, 1H), 8.51-8.18 (m, 3H), 7.97-7.73 (m, 2H), 4.51-4.32 (m, 1H), 1.97 (t, J=18.8 Hz, 2H), 1.32 (d, J=6.4 Hz, 6H). LC-MS: m/z 440.3 (M+H)$^+$.

Compound 495—3-[4-(6-Chloro-pyridin-2-yl)-6-(2-trifluoromethyl-pyridin-4-ylamino)-[1,3,5]triazin-2-ylamino]-2,2-dimethyl-propan-1-ol

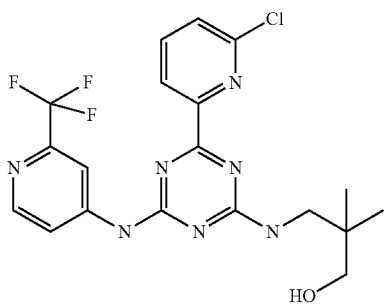 [SMILES: CC(C)(CO)CNc1nc(Nc2ccnc(C(F)(F)F)c2)nc(-c2cccc(Cl)n2)n1]

$^1$H NMR (METHANOL-d$_4$) δ 8.63-8.45 (m, 3H), 8.44-7.99 (m, 2H), 7.97-7.62 (m, 1H), 3.49 (s, 1H), 3.43 (s., 1H), 3.40 (s, 1H), 3.23 (s., 1H), 0.98 (d., J=6.4 Hz, 6H). LC-MS: m/z 454.3 (M+H)$^+$.

Compound 496—2-{4-[4-Isopropylamino-6-(6-trifluoromethyl-pyridin-2-yl)-[1,3,5]triazin-2-ylamino]-pyridin-2-yl}-propan-2-ol

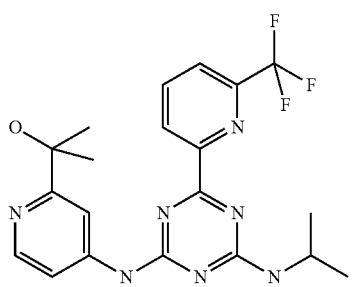 [SMILES: CC(C)Nc1nc(Nc2ccnc(C(C)(C)O)c2)nc(-c2cccc(C(F)(F)F)n2)n1]

$^1$H NMR (METHANOL-d$_4$) δ 8.66 (s, 1H), 8.29-8.11 (m, 3H), 7.88 (s, 1H), 7.58-7.56 (m, 1H), 4.40-4.29 (m., 1H), 1.49 (s, 6H), 1.25 (d., J=6.4 Hz, 6H). LC-MS: m/z 434.3 (M+H)$^+$.

Compound 497—3-[4-(6-Chloro-pyridin-2-yl)-6-isopropylamino-[1,3,5]triazin-2-ylamino]-N-cyclopropylmethyl-benzenesulfonamide

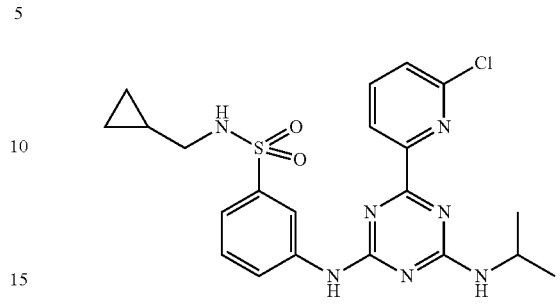

$^1$H NMR (METHANOL-d$_4$) δ 8.70 (s, 1H), 8.50 (m, 1H), 8.14-8.10 (m, 1H), 7.82-7.80 (m, 1H), 7.69-7.67 (m., 2H), 7.58 (m, 1H), 4.42 (m, 1H), 2.78-2.76 (d., J=6.8 Hz, 2H), 1.36-1.28 (d, J=10 Hz, 6H), 0.87-0.81 (m, 1H), 0.43-0.38 (m, 2H), 0.10-0.07 (m, 2H). LC-MS: m/z 474.3 (M+H)$^+$.

Compound 498—5-[4-(6-Chloro-pyridin-2-yl)-6-(2,2-dimethyl-propylamino)-[1,3,5]triazin-2-ylamino]-nicotinonitrile

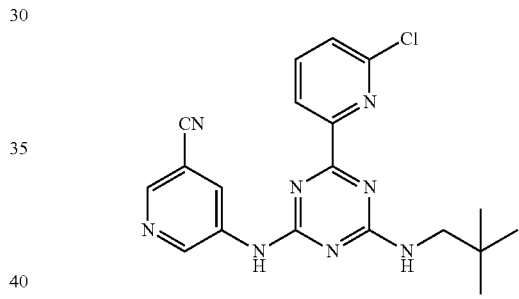

1H NMR (METHANOL-d$_4$) δ 9.01-8.94 (m, 2H), 8.53-8.41 (m, 2H), 8.00-7.96 (m, 1H), 7.62-7.60 (m, 1H), 3.35 (s, 3H), 1.00 (s, 9H). LC-MS: m/z 395.2 (M+H)$^+$.

Compound 499—6-(6-Chloro-pyridin-2-yl)-N-(2-methoxy-1-methyl-ethyl)-N'-(2-trifluoromethyl-pyridin-4-yl)-[1,3,5]triazine-2,4-diamine

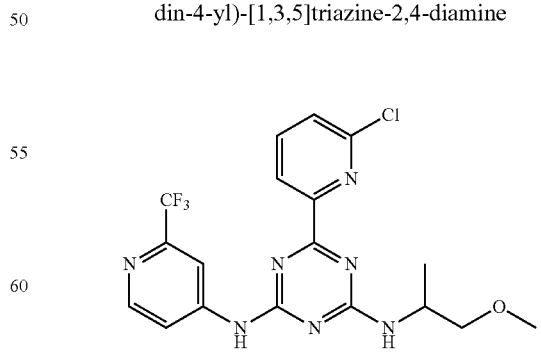

$^1$H NMR (METHANOL-d$_4$) δ 8.62-8.43 (m, 3H), 8.25-8.61 (m, 3H), 4.40-4.36 (m, 1H), 3.56-3.48 (m, 2H), 3.47 (s, 3H), 1.32-1.26 (s, 3H). LC-MS: m/z 440.3 (M+H)$^+$.

Compound 500—1-[4-(2-Fluoro-pyridin-4-ylamino)-6-(6-trifluoromethyl-pyridin-2-yl)-[1,3,5]triazin-2-ylamino]-2-methyl-propan-2-ol Using the standard procedure described above except replacing t-BuONa by Cs₂CO₃ yielded the title compound.

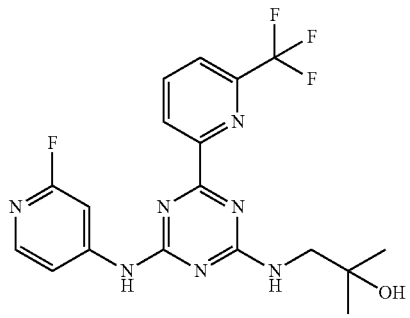 [SMILES: CC(C)(O)CNc1nc(Nc2ccnc(F)c2)nc(-c2cccc(C(F)(F)F)n2)n1]

¹H NMR (METHANOL-d₄) δ 8.79-8.81 (d, J=8 Hz, 1H), 8.37-8.43 (m, 1H), 8.20-8.24 (m, 2H), 7.56-7.72 (m, 2H), 3.65 (s, 2H), 1.36 (s, 6H). LC-MS: m/z 424.2 (M+H)⁺.

Compound 501—N-Isopropyl-N'-(6-methyl-pyridazin-4-yl)-6-(6-trifluoromethyl-pyridin-2-yl)-[1,3,5]triazine-2,4-diamine Using the standard procedure described above except replacing t-BuONa by Cs₂CO₃ yielded the title compound.

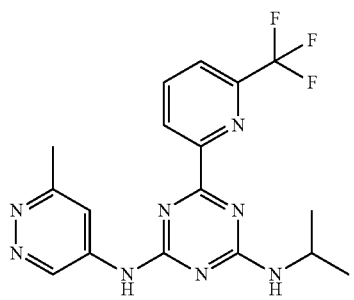 [SMILES: Cc1cc(Nc2nc(NC(C)C)nc(-c3cccc(C(F)(F)F)n3)n2)cnn1]

¹H NMR (METHANOL-d₄) δ 9.30-8.85 (m, 2H), 8.78-8.80 (d, J=8 Hz, 1H), 8.29-8.28 (m, 1H), 8.07-8.15 (m, 1H), 4.36-4.55 (m, 1H), 2.87 (s, 3H), 1.38-1.41 (m, 6H). LC-MS: m/z 391.2 (M+H)⁺.

Compound 502—4-[4-(6-Chloro-pyridin-2-yl)-6-(2-trifluoromethyl-pyridin-4-ylamino)-[1,3,5]triazin-2-ylamino]-piperidine-1-carboxylic acid tert-butyl ester

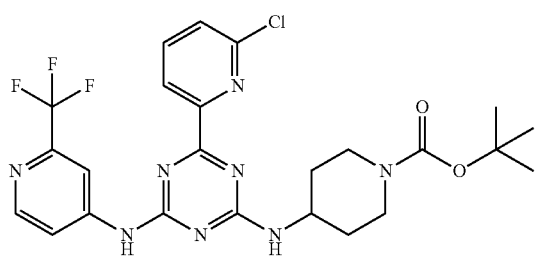 [SMILES: CC(C)(C)OC(=O)N1CCC(Nc2nc(Nc3ccnc(C(F)(F)F)c3)nc(-c3cccc(Cl)n3)n2)CC1]

¹H NMR (CDCl3-d₆) δ 8.51-8.55 (m, 2H), 8.27 (d, J=7.6 Hz, 1H), 7.77 (t, J=8 Hz, 1H), 7.45-7.50 (m, 2H), 7.28-7.33 (m., 1H), 5.65 (d, J=7.6 Hz, 1H), 3.95-4.11 (m, 3H), 2.88-2.93 (m., 2H), 2.02 (d, J=11.2 Hz, 2H), 1.41-1.51 (m, 11H). LC-MS: m/z 552.0 (M+H)⁺.

Compound 503—N-(5-Fluoro-pyridin-3-yl)-N'-isopropyl-6-(6-trifluoromethyl-pyridin-2-yl)-[1,3,5]triazine-2,4-diamine

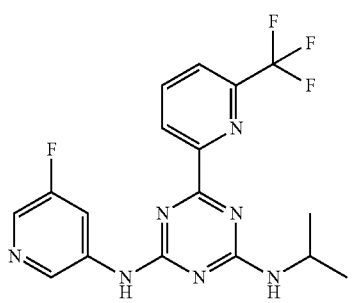 [SMILES: CC(C)Nc1nc(Nc2cncc(F)c2)nc(-c2cccc(C(F)(F)F)n2)n1]

¹H NMR (METHANOL-d₄) δ 8.66-8.62 (m, 2H), 8.54 (br, 1H), 8.17 (t, J=7.8 Hz, 1H), 8.09-8.05 (m, 1H), 7.93 (d, J=7.6 Hz, 1H), 4.24-4.21 (m, 1H), 1.26 (d, J=4.2 Hz, 6H). LC-MS: m/z 394.2 (M+H)⁺.

N-(6-Fluoro-pyridin-3-yl)-N'-isopropyl-6-(6-trifluoromethyl-pyridin-2-yl)-[1,3,5]triazine-2,4-diamine

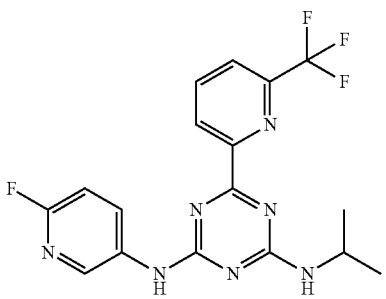 [SMILES: CC(C)Nc1nc(Nc2ccc(F)nc2)nc(-c2cccc(C(F)(F)F)n2)n1]

¹H NMR (METHANOL-d₄) δ 8.53-8.50 (m, 2H), 8.46-8.24 (m, 1H), 8.07 (t, J=7.8 Hz, 1H), 7.84 (d, J=7.6 Hz, 1H), 6.97-6.94 (m, 1H), 4.35-4.13 (m, 1H), 1.19 (d, J=6.4 Hz, 6H). LC-MS: m/z 394.1 (M+H)⁺.

Compound 504—N-(3-Oxa-bicyclo[3.1.0]hex-6-yl)-N'-(2-trifluoromethyl-pyridin-4-yl)-6-(6-trifluoromethyl-pyridin-2-yl)-[1,3,5]triazine-2,4-diamine

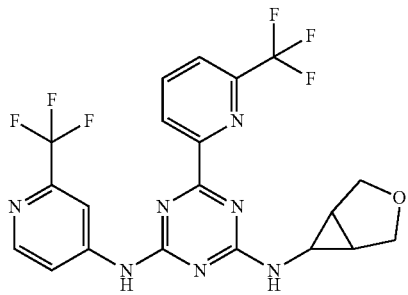

$^1$H NMR (METHANOL-$d_4$) δ 8.60 (dd, J=8.0 Hz, 2.0, 1H) 8.53 (dd, J=5.6 Hz, 1.6, 1H), 8.34 (s, 1H), 8.26-8.21 (m, 2H), 8.01-7.97 (m, 1H), 4.10 (d, J=7.4 Hz, 2H), 3.80 (d, J=8.4 Hz, 2H), 2.80-2.77 (m, 1H), 2.06 (s, 2H). LC-MS: m/z 484.3 (M+H)$^+$.

Compound 505—4-[4-(3-Oxa-bicyclo[3.1.0]hex-6-ylamino)-6-(6-trifluoromethyl-pyridin-2-yl)-[1,3,5]triazin-2-ylamino]-pyridine-2-carbonitrile Using the standard procedure described above except replacing t-BuONa by Cs$_2$CO$_3$ to yield the title compound.

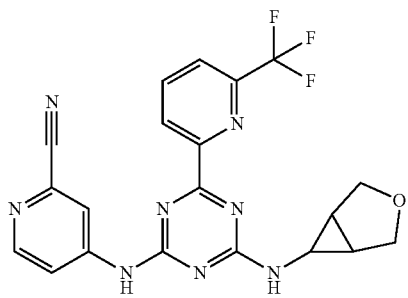 [SMILES: N#Cc1cc(Nc2nc(NC3C4COCC43)nc(-c3cccc(C(F)(F)F)n3)n2)ccn1]

$^1$H NMR (METHANOL-$d_4$) δ 8.69-8.51 (m, 3H), 8.24-8.20 (m, 1H), 8.09-7.98 (m, 2H), 4.12 (d, J=9.2 Hz, 2H), 3.84 (d, J=8.4 Hz, 2H). 2.75 (s, 1H), 2.02 (s, 2H). LC-MS: m/z 441.3 (M+H)$^+$.

Compound 506—N-(6-Fluoro-pyridin-3-yl)-N'-(3-oxa-bicyclo[3.1.0]hex-6-yl)-6-(6-trifluoromethyl-pyridin-2-yl)-[1,3,5]triazine-2,4-diamine

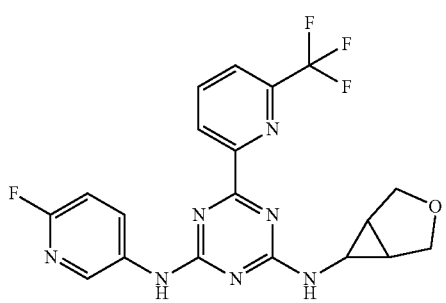 [SMILES: Fc1ccc(Nc2nc(NC3C4COCC43)nc(-c3cccc(C(F)(F)F)n3)n2)cn1]

$^1$H NMR (METHANOL-$d_4$) δ 8.69-8.61 (m, 2H), 8.38 (br, 1H), 8.16 (t, J=8.0 Hz, 1H), 7.92 (d, J=8.4 Hz, 1H), 7.05 (dd, J=6.4 Hz, 2.4, 1H), 4.04 (d, J=8.4 Hz, 2H), 3.78 (d, J=8.4 hz, 2H), 2.64 (s, 1H), 1.94 (s, 1H). LC-MS: m/z 433.9 (M+H)$^+$.

N-(2-Fluoro-pyridin-4-yl)-N'-(3-oxa-bicyclo[3.1.0]hex-6-yl)-6-(6-trifluoromethyl-pyridin-2-yl)-[1,3,5]triazine-2,4-diamine

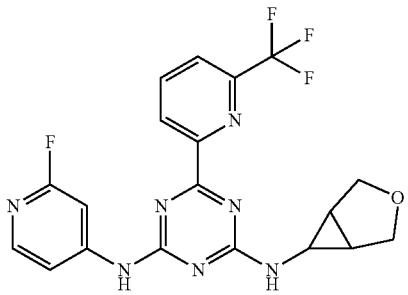 [SMILES: Fc1cc(Nc2nc(NC3C4COCC43)nc(-c3cccc(C(F)(F)F)n3)n2)ccn1]

$^1$H NMR (METHANOL-$d_4$) δ 8.68-8.66 (m, 1H), 8.24-7.97 (m, 4H), 7.50 (d, J=5.2 Hz, 1H), 4.12 (d, J=8.4 Hz, 2H), 3.83 (d, J=8.0 Hz, 2H), 2.71 (s, 1H), 2.05-1.99 (m, 2H). LC-MS: m/z 433.9 (M+H)$^+$.

Compound 507—N-(3-Oxa-bicyclo[3.1.0]hex-6-yl)-N'-(5-trifluoromethyl-pyridin-3-yl)-6-(6-trifluoromethyl-pyridin-2-yl)-[1,3,5]triazine-2,4-diamine

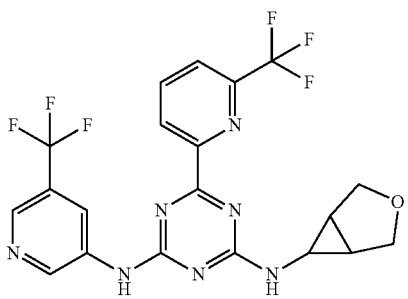

$^1$H NMR (METHANOL-$d_4$) δ 9.38 (br, 1H), 8.82-8.42 (m, 4H), 8.24 (d, J=8.4 Hz, 1H), 4.05 (d, J=8.4 Hz, 2H), 3.79 (d, J=8.4 Hz, 2H), 2.81 (s, 1H), 2.15 (s, 2H). LC-MS: m/z 484.3 (M+H)$^+$.

Compound 508—N-(2-Fluoro-pyridin-4-yl)-N'-(3-oxa-bicyclo[3.1.0]hex-6-yl)-6-(6-trifluoromethyl-pyridin-2-yl)-[1,3,5]triazine-2,4-diamine Using the standard procedure described above except replacing t-BuONa by Cs$_2$CO$_3$ to yield the title compound.

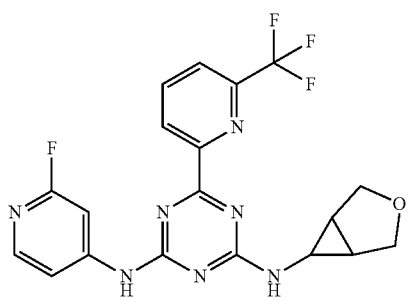 [SMILES: Fc1cc(Nc2nc(NC3C4COCC43)nc(-c3cccc(C(F)(F)F)n3)n2)ccn1]

¹H NMR (METHANOL-d₄) δ 8.48-8.50 (d, J=7.2 Hz, 1H), 7.97-8.15 (m, 3H), 7.79-7.96 (m, 1H), 7.48-7.54 (m, 1H), 4.13-4.15 (d, J=8.8 Hz, 2H), 3.83-3.85 (d, J=8 Hz, 2H), 2.78 (s, 1H), 2.07-2.10 (d, J=13.2 Hz, 2H). LC-MS: m/z 400.1 (M+H)⁺.

Compound 509—N-(3-Oxa-bicyclo[3.1.0]hex-6-yl)-N'-(2-trifluoromethyl-pyridin-4-yl)-6-(6-trifluoromethyl-pyridin-2-yl)-[1,3,5]triazine-2,4-diamine Using the standard procedure described above except replacing t-BuONa by Cs₂CO₃ to yield the title compound.

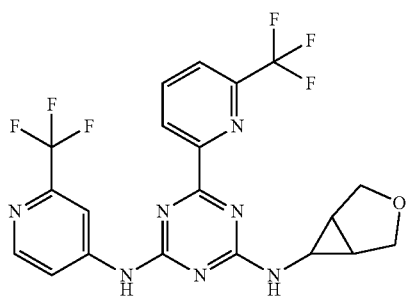

¹H NMR (METHANOL-d₄) δ 8.47-8.66 (m, 2H), 8.07-8.28 (m, 3H), 7.76-7.78 (d, J=8 Hz, 1H), 4.06-4.14 (m, 2H), 3.80-3.82 (d, J=8.4 Hz, 2H), 2.82 (s, 1H), 2.04-2.16 (m, 2H). LC-MS: m/z 450.1 (M+H)⁺.

Compound 510—N-(3-Oxa-bicyclo[3.1.0]hex-6-yl)-N'-(5-trifluoromethyl-pyridin-3-yl)-6-(6-trifluoromethyl-pyridin-2-yl)-[1,3,5]triazine-2,4-diamine Using the standard procedure described above except replacing t-BuONa by Cs₂CO₃ to yield the title compound.

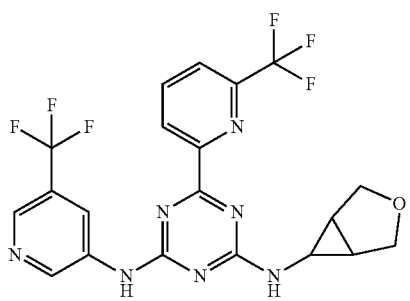

¹H NMR (METHANOL-d₄) δ 9.05-9.20 (m, 1H), 8.36-8.45 (m, 3H), 7.96-7.97 (m, 1H), 7.57-7.60 (d, J=7.6 Hz, 1H), 4.04-4.06 (d, J=8.4 Hz, 2H), 3.75-3.77 (d, J=8.4 Hz, 2H), 2.78 (s, 1H), 1.94 (s, 2H). LC-MS: m/z 450.1 (M+H)⁺.

Compound 511—6-(6-Chloro-pyridin-2-yl)-N-(5-fluoro-pyridin-3-yl)-N'-(3-oxa-bicyclo[3.1.0]hex-6-yl)-[1,3,5]triazine-2,4-diamine

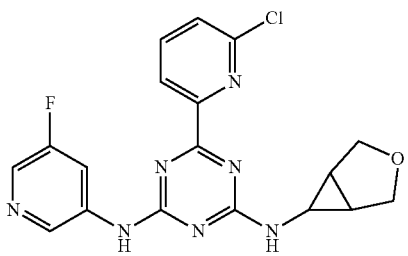 [SMILES: Fc1cncc(Nc2nc(NC3C4COCC43)nc(-c3cccc(Cl)n3)n2)c1]

¹H NMR (DMSO-d₆) δ 10.50-10.60 (m, 1H), 8.79-8.91 (m, 1H), 8.43-8.48 (m, 2H), 8.19-8.29 (m., 2H), 8.05-8.11 (m, 1H), 7.67-7.73 (m, 1H), 3.95-4.06 (m, 2H), 3.68-3.70 (m, 2H), 3.32-3.33 (m, 1H), 1.95 (s, 2H). LC-MS: m/z 400.2 (M+H)⁺.

Compound 512—6-(6-Chloro-pyridin-2-yl)-N-(6-fluoro-pyridin-3-yl)-N'-(3-oxa-bicyclo[3.1.0]hex-6-yl)-[1,3,5]triazine-2,4-diamine

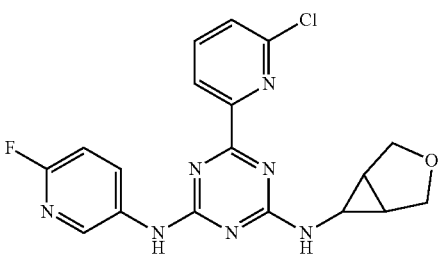 [SMILES: Fc1ccc(Nc2nc(NC3C4COCC43)nc(-c3cccc(Cl)n3)n2)cn1]

¹H NMR (DMSO-d₆) δ 10.36 (br, 1H), 8.76-8.93 (m, 1H), 8.30-8.43 (m, 3H), 8.04-8.10 (m., 1H), 7.70-7.72 (m, 1H), 7.13-7.20 (m, 1H), 3.96-3.94 (m, 2H), 3.65-3.70 (m, 2H), 3.32-3.33 (m, 1H), 2.09 (s, 2H). LC-MS: m/z 400.2 (M+H)⁺.

Compound 513—6-(6-Chloro-pyridin-2-yl)-N-[2-(1,1-difluoro-ethyl)-pyridin-4-yl]-N'-isopropyl-[1,3,5]triazine-2,4-diamine

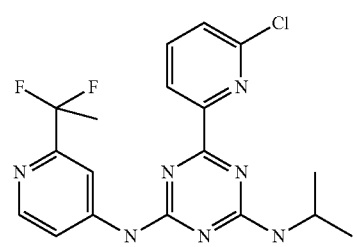 [SMILES: CC(C)Nc1nc(Nc2ccnc(C(C)(F)F)c2)nc(-c2cccc(Cl)n2)n1]

¹H NMR (METHANOL-d₄) δ 8.51-8.14 (m, 3H), 7.96-7.59 (m, 3H), 4.52-4.26 (m, 1H), 1.97 (t, J=18.8 Hz, 2H), 1.31 (t., J=6.4 Hz, 6H). LC-MS: m/z 406.3 (M+H)⁺.

267

Compound 514—2-{4-[4-(6-Chloro-pyridin-2-yl)-6-isopropylamino-[1,3,5]triazin-2-ylamino]-pyridin-2-yl}-propan-2-ol

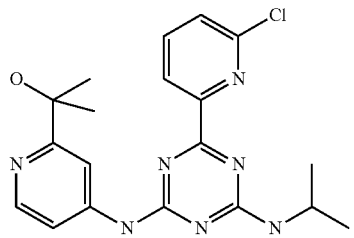 [SMILES: CC(C)Nc1nc(Nc2ccnc(C(C)(C)O)c2)nc(-c2cccc(Cl)n2)n1]

¹H NMR (METHANOL-d₄) δ 8.48-8.30 (m, 3H), 7.99-7.95 (m, 1H), 7.77-7.61 (m, 2H), 4.51-4.37 (m, 1H), 1.57 (s., 6H), 1.30 (d., J=6.4 Hz, 6H). LC-MS: m/z 400.3 (M+H)⁺.

Compound 515—N-(3,5-Difluoro-phenyl)-N'-(2-methyl-cyclopropyl)-6-pyridin-2-yl-[1,3,5]triazine-2,4-diamine

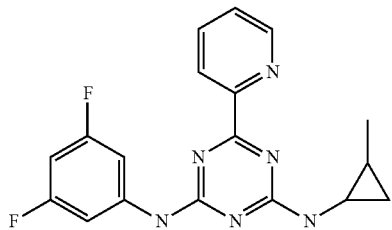 [SMILES: CC1CC1Nc1nc(Nc2cc(F)cc(F)c2)nc(-c2ccccn2)n1]

¹H NMR (METHANOL-d₄) δ 8.72-8.48 (m, 2H), 8.08-7.57 (m, 4H), 6.58 (s, 1H), 2.27-2.57 (m, 1H), 1.20 (s., 3H), 0.99-0.75 (m, 2H), 0.64-0.51 (s, H). LC-MS: m/z 455.2 (M+H)⁺.

Compound 516—N-(2-Methyl-cyclopropyl)-6-pyridin-2-yl-N'-(2-trifluoromethyl-pyridin-4-yl)-[1,3,5]triazine-2,4-diamine

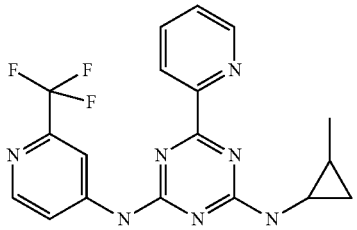 [SMILES: CC1CC1Nc1nc(Nc2ccnc(C(F)(F)F)c2)nc(-c2ccccn2)n1]

¹H NMR (METHANOL-d₄) δ 8.73-7.98 (m, 6H), 7.61-7.58 (m, 1H), 2.79-2.54 (m, 1H), 1.20 (d, J=6.0 Hz, 3H), 0.85-0.81 (m., 1H), 0.71-0.67 (m, 2H). LC-MS: m/z 388.3 (M+H)⁺.

268

Compound 517—N-(2,2-Dimethyl-propyl)-6-pyridin-2-yl-N'-(2-trifluoromethyl-pyridin-4-yl)-[1,3,5]triazine-2,4-diamine

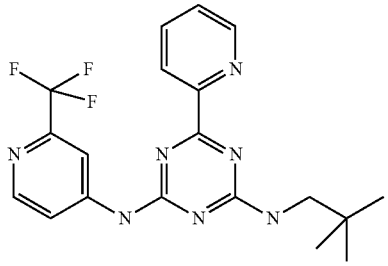 [SMILES: CC(C)(C)CNc1nc(Nc2ccnc(C(F)(F)F)c2)nc(-c2ccccn2)n1]

¹H NMR (METHANOL-d₄) δ 8.75-8.49 (m, 4H), 8.03-7.76 (m, 1H), 7.62-7.59 (m, 2H), 3.41 (s, 2H), 0.99 (s., 9H). LC-MS: m/z 404.3 (M+H)⁺.

Compound 518—3-[4-(6-Chloro-pyridin-2-yl)-6-isopropylamino-[1,3,5]triazin-2-ylamino]-N-(2,2,2-trifluoro-ethyl)-benzenesulfonamide

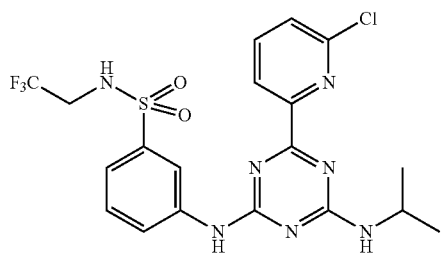 [SMILES: CC(C)Nc1nc(Nc2cccc(S(=O)(=O)NCC(F)(F)F)c2)nc(-c2cccc(Cl)n2)n1]

¹H NMR (DMSO-d₆) δ 8.74 (s, 1H), 8.70-8.40 (m, 1H), 8.37-8.30 (m, 1H), 8.30-8.11 (m, 1H), 8.09-8.01 (m., 1H), 7.84-7.82 (m, 1H), 7.69 (m, 1H), 7.54 (m, 1H), 7.48-7.44 (m, 1H), 4.33-4.22 (m, 1H), 3.72-3.62 (m, 2H), 1.23-1.20 (d, J=12 Hz, 6H). LC-MS: m/z 501.8 (M+H)⁺.

Compound 520—1-[4-(3,5-Difluoro-phenylamino)-6-(6-trifluoromethyl-pyridin-2-yl)-[1,3,5]triazin-2-ylamino]-propan-2-ol

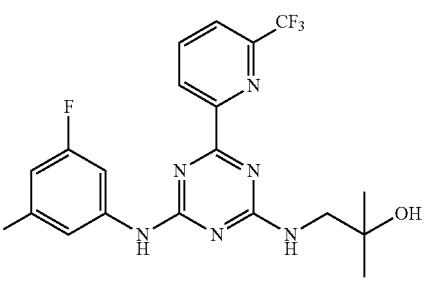

¹H NMR (METHANOL-d₄) δ 8.66-8.68 (m, 1H), 8.19-8.23 (m, 1H), 7.96-7.98 (m, 1H), 7.51-7.57 (m., 2H), 6.57-6.60 (m, 1H), 3.56-3.61 (d, J=20 Hz, 2H), 1.29 (s, 6H). LC-MS: m/z 441.2 (M+H)⁺.

Compound 521—N-(2,2-Dimethyl-propyl)-N'-pyrimidin-5-yl-6-(6-trifluoromethyl-pyridin-2-yl)-[1,3,5]triazine-2,4-diamine

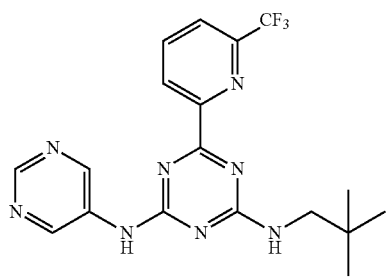 [SMILES: CC(C)(C)CNc1nc(Nc2cncnc2)nc(-c2cccc(C(F)(F)F)n2)n1]

¹H NMR (METHANOL-d₄) δ 9.28-9.31 (m, 2H), 8.79-8.82 (m, 1H), 8.67-8.69 (m, 1H), 8.19-8.23 (m, 1H), 7.96-7.98 (m, 1H), 3.37-3.45 (m, 1H), 3.30-3.37 (m, 1H), 1.01 (s, 9H). LC-MS: m/z 405.3 (M+H)⁺.

Compound 522—N2-isopropyl-N4-(2-(trifluoromethyl)pyridin-4-yl)-6-(4-(trifluoromethyl)pyrimidin-2-yl)-1,3,5-triazine-2,4-diamine Using the standard procedure described above except replace t-BuONa by Cs₂CO₃ to give the title compound.

$^1$H NMR (DMSO-d$_6$): δ 10.63-10.81-10.95 (m, 1H), 9.36-9.39 (m, 1H), 8.73 (s, 1H), 8.08-8.56 (m, 3H), 7.84-7.85 (m, 1H), 4.14-4.19 (m, 1H), 1.20-1.24 (m, 6H). LC-MS: m/z 444.8 (M+H)⁺.

Compound 523—N2-neopentyl-N4-(2-(trifluoromethyl)pyridin-4-yl)-6-(4-(trifluoromethyl)pyrimidin-2-yl)-1,3,5-triazine-2,4-diamine Using the standard procedure described above except replace t-BuONa by Cs₂CO₃ to yield the title compound.

$^1$H NMR (DMSO-d$_6$): δ 10.70-10.95 (m, 1H), 9.23 (d, J=6.0 Hz, 1H), 8.86 (s, 1H), 8.36-8.76 (m, 3H), 7.64-7.66 (m, 1H), 3.29-3.35 (m, 2H), 0.90-1.0.95 (m, 9H). LC-MS: m/z 473.2 (M+H)⁺.

Compound 524—N-(2-Methoxy-propyl)-6-(6-trifluoromethyl-pyridin-2-yl)-N'-(2-trifluoromethyl-pyridin-4-yl)-[1,3,5]triazine-2,4-diamine

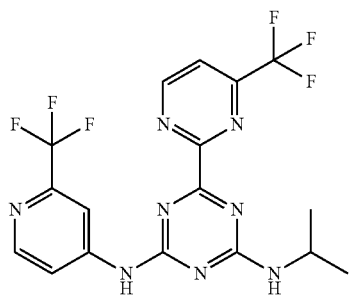 [SMILES: CC(C)Nc1nc(Nc2ccnc(C(F)(F)F)c2)nc(-c2nccc(C(F)(F)F)n2)n1]

1H NMR (METHANOL-d₄) δ 8.75-8.77 (m, 1H), 8.66-8.67 (m, 1H), 8.50-8.52 (m, 1H), 8.36-8.38 (m, 1H), 8.1.7-8.18 (m, 1H), 7.91-7.92 (m., 1H), 3.52-3.80 (m, 3H), 3.45 (s., 3H), 1.27-1.255 (d., J=6.0 Hz, 2H). LC-MS: m/z 474.2 (M+H)⁺.

Compound 526—N-(2-Methoxy-1-methyl-ethyl)-6-(6-trifluoromethyl-pyridin-2-yl)-N'-(2-trifluoromethyl-pyridin-4-yl)-[1,3,5]triazine-2,4-diamine $^1$H NMR (METHANOL-d₄) δ 8.69-8.67 (m, 1H), 8.61-8.29 (m, 2H), 8.22-7.87 (m, 3H), 4.62-4.37 (m, 1H), 3.57-3.46 (m., 2H), 3.31 (s, 3H), 1.33-1.30 (m, 3H). LC-MS: m/z 473.9 (M+H)⁺.

Compound 527—2-[4-(6-Trifluoromethyl-pyridin-2-yl)-6-(2-trifluoromethyl-pyridin-4-ylamino)-[1,3,5]triazin-2-ylamino]-propan-1-ol

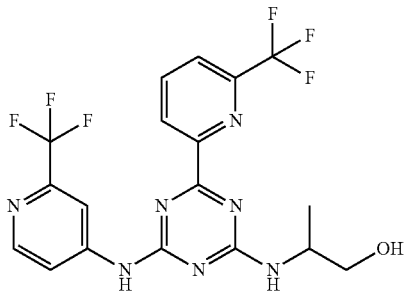 [SMILES: CC(CO)Nc1nc(Nc2ccnc(C(F)(F)F)c2)nc(-c2cccc(C(F)(F)F)n2)n1]

¹H NMR (METHANOL-d₄) δ 8.73-8.48 (m, 3H), 8.23-7.92 (m, 3H), 4.62-4.29 (m, 1H), 3.70-3.67 (m, 2H), 1.335-1.319 (d, J=6.4 Hz, 3H). LC-MS: m/z 459.9 (M+H)⁺.

Compound 528—N-(3-Methoxy-propyl)-N'-(2-trifluoromethyl-pyridin-4-yl)-6-(6-trifluoromethyl-pyridin-2-yl)-[1,3,5]triazine-2,4-diamine

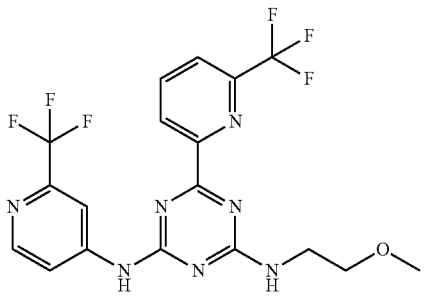 [SMILES: COCCNc1nc(Nc2ccnc(C(F)(F)F)c2)nc(-c2cccc(C(F)(F)F)n2)n1]

¹H NMR (METHANOL-d₄) δ 8.67-8.69 (m, 1H), 8.50-8.61 (m, 2H), 8.19-8.23 (m, 1H), 7.93-7.99 (m, 2H), 3.61-3.69 (m, 2H), 3.54-3.56 (m, 2H), 3.30-3.37 (m, 1H), 1.93-1.99 (m, 2H). LC-MS: m/z 474.3 (M+H)⁺.

Compounds 529—N-(Tetrahydro-furan-3-yl)-N'-(2-trifluoromethyl-pyridin-4-yl)-6-(6-rifluoromethyl-pyridin-2-yl)-[1,3,5]triazine-2,4-diamine

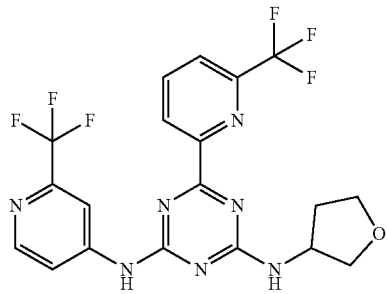 [SMILES: FC(F)(F)c1cc(Nc2nc(NC3CCOC3)nc(-c3cccc(C(F)(F)F)n3)n2)ccn1]

¹H NMR (METHANOL-d₄) δ 8.66-8.68 (m, 1H), 8.62-8.66 (m, 1H), 8.49-8.51 (m, 1H), 8.18-8.22 (m, 2H), 7.95-7.97 (m, 1H), 4.60-4.66 (m, 1H), 3.99-4.05 (m, 2H), 3.79-3.82 (m, 2H), 2.04-2.39 (m, 2H). LC-MS: m/z 472.3 (M+H)⁺.

Compounds 530—2,2-Dimethyl-3-[4-(6-trifluoromethyl-pyridin-2-yl)-6-(2-trifluoromethyl-pyridin-4-ylamino)-[1,3,5]triazin-2-ylamino]-propan-1-ol

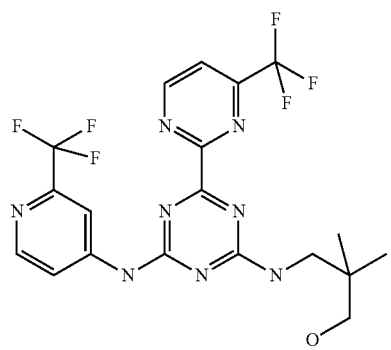 [SMILES: CC(C)(CO)CNc1nc(Nc2ccnc(C(F)(F)F)c2)nc(-c2nccc(C(F)(F)F)n2)n1]

¹H NMR (METHANOL-d₄) δ 8.74-8.70 (m, 1H), 8.67-8.52 (m, 2H), 8.29-7.90 (m, 3H), 3.51-3.41 (m, 2H), 3.34-3.33 (m., 1H), 3.23 (s, 1H), 1.03-0.92 (m, 6H). LC-MS: m/z 488.3 (M+H)⁺.

Compound 531—N-(2-Methyl-tetrahydro-furan-2-ylmethyl)-6-(6-trifluoromethyl-pyridin-2-yl)-N'-(2-trifluoromethyl-pyridin-4-yl)-[1,3,5]triazine-2,4-diamine

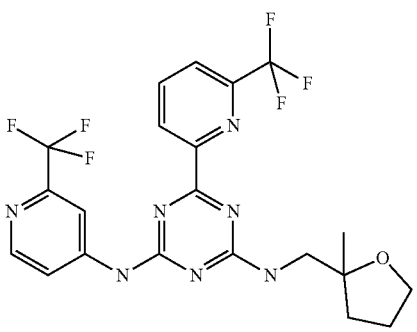 [SMILES: CC1(CNc2nc(Nc3ccnc(C(F)(F)F)c3)nc(-c3cccc(C(F)(F)F)n3)n2)CCCO1]

¹H NMR (METHANOL-d₄) δ 8.71-8.24 (m, 3H), 8.23-7.84 (m, 3H), 3.97-3.90 (m, 2H), 3.78-3.58 (m, 2H), 2.03-1.97 (m., 2H), 1.78-1.74 (m, 1H), 1.31 (s, 3H). LC-MS: m/z 500.3 (M+H)⁺.

Compound 532—N-(2-Methyl-cyclopropyl)-6-(6-trifluoromethyl-pyridin-2-yl)-N'-(2-trifluoromethyl-pyridin-4-yl)-[1,3,5]triazine-2,4-diamine

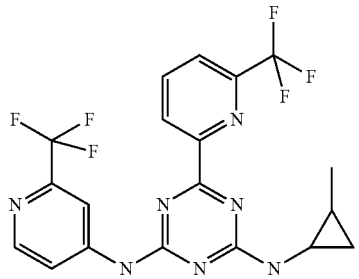 [SMILES: CC1CC1Nc1nc(Nc2ccnc(C(F)(F)F)c2)nc(-c2cccc(C(F)(F)F)n2)n1]

¹H NMR (METHANOL-d₄) δ 8.70-8.19 (m, 3H), 8.06-7.98 (m, 3H), 2.67-2.64 (m, 1H), 1.25-1.21 (m, 3H), 1.21-0.98 (m., 1H), 0.88-0.80 (m, 1H), 0.62-0.51 (m, 1H). LC-MS: m/z 456.2 (M+H)⁺.

Compound 533—N-(1-Methyl-cyclopropyl)-6-(6-trifluoromethyl-pyridin-2-yl)-N'-(2-trifluoromethyl-pyridin-4-yl)-[1,3,5]triazine-2,4-diamine

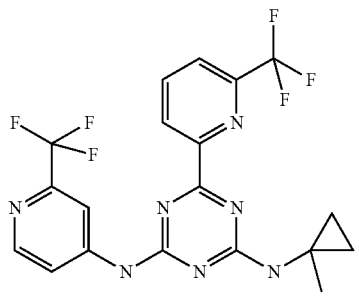 [SMILES: CC1(Nc2nc(Nc3ccnc(C(F)(F)F)c3)nc(-c3cccc(C(F)(F)F)n3)n2)CC1]

¹H NMR (METHANOL-d₄) δ 8.85-8.65 (m, 2H), 8.48 (s, 1H), 8.20-8.16 (m, 1H), 7.96-7.82 (m, 2H), 1.55 (s, 3H), 0.93-0.90 (m, 2H), 0.85-0.82 (m, 2H). LC-MS: m/z 456.2 (M+H)⁺.

Compound 534—4-[4-Isopropylamino-6-(4-trifluoromethyl-pyrimidin-2-yl)-[1,3,5]triazin-2-ylamino]-pyridine-2-carbonitrile Using the standard procedure described above except replacing t-BuONa by Cs₂CO₃ to yield the title compound.

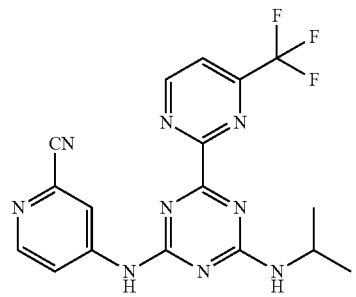 [SMILES: CC(C)Nc1nc(Nc2ccnc(C#N)c2)nc(-c2nccc(C(F)(F)F)n2)n1]

¹H NMR (METHANOL-d₄) δ 9.33-9.31 (m, 1H), 8.65 (d, J=6.4 Hz, 1H), 8.47 (dd, J=7.2 Hz, 5.6 Hz, 1H), 8.07 (d, J=4.8 Hz, 1H), 7.96-7.95 (m, 1H), 4.30-4.27 (m, 1H), 1.32 (dd, J=12 Hz, 6.0 Hz, 6H). LC-MS: m/z 402.2 (M+H)⁺.

Compound 535—N-(6-Fluoro-pyridin-3-yl)-N'-isopropyl-6-(4-trifluoromethyl-pyrimidin-2-yl)-[1,3,5]triazine-2,4-diamine

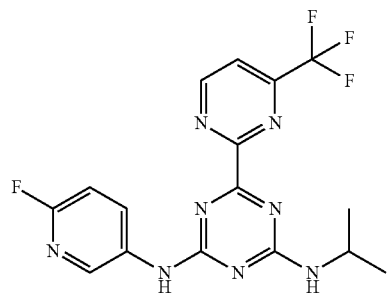 [SMILES: CC(C)Nc1nc(Nc2ccc(F)nc2)nc(-c2nccc(C(F)(F)F)n2)n1]

¹H NMR (METHANOL-d₄) δ 9.30 (d, J=4.8 Hz, 1H), 8.62-8.53 (m, 2H), 8.05 (d, J=5.2 Hz, 1H), 7.08-7.07 (m, 1H), 4.25-4.22 (m, 1H), 1.28 (dd, J=10.8 Hz, 6.4 Hz, 6H). LC-MS: m/z 395.2 (M+H)⁺.

Compound 536—N-Isopropyl-N'-(5-trifluoromethyl-pyridin-3-yl)-6-(4-trifluoromethyl-pyrimidin-2-yl)-[1,3,5]triazine-2,4-diamine Using the standard procedure described above except replacing t-BuONa by Cs₂CO₃ to yield the title compound.

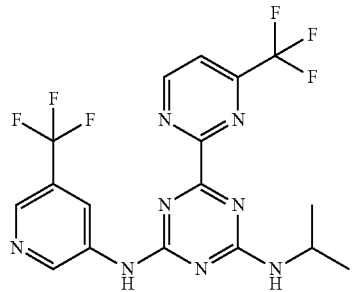 [SMILES: CC(C)Nc1nc(Nc2cncc(C(F)(F)F)c2)nc(-c2nccc(C(F)(F)F)n2)n1]

¹H NMR (METHANOL-d₄) δ 9.31-9.33 (d, J=4.8 Hz, 1H), 8.98-9.11 (m, 1H), 8.52 (s, 1H), 8.06-8.07 (d, J=4 Hz, 1H), 4.26-4.63 (m, 2H), 1.28-1.34 (m, 6H). LC-MS: m/z 445.3 (M+H)⁺.

Compound 537—N-(2-Fluoro-pyridin-4-yl)-N'-isopropyl-6-(4-trifluoromethyl-pyrimidin-2-yl)-[1,3,5]triazine-2,4-diamine Using the standard procedure described above except replacing t-BuONa by Cs₂CO₃ to yield the title compound.

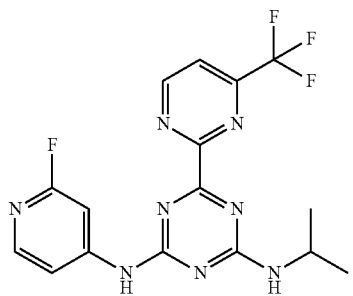 [SMILES: CC(C)Nc1nc(Nc2ccnc(F)c2)nc(-c2nccc(C(F)(F)F)n2)n1]

¹H NMR (METHANOL-d₄) δ 9.41-9.42 (m, 1H), 8.14-8.20 (m, 2H), 7.59-7.82 (m, 1H), 4.35-4.38 (m, 2H), 1.32-1.41 (m, 6H). LC-MS: m/z 395.2 (M+H)⁺.

Compound 539—1-(4-(5,6-difluoropyridin-3-ylamino)-6-(6-(trifluoromethyl)pyridin-2-yl)-1,3,5-triazin-2-ylamino)-2-methylpropan-2-ol

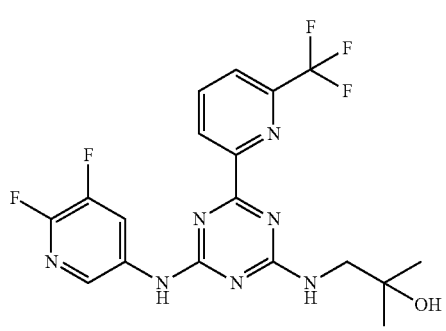 [SMILES: CC(C)(O)CNc1nc(Nc2cnc(F)c(F)c2)nc(-c2cccc(C(F)(F)F)n2)n1]

¹H NMR (METHANOL-d₄) δ 8.61-8.75 (m, 1H), 8.01-8.43 (m, 4H), 3.48 (s, 2H), 1.21 (s, 6H). LC-MS: m/z 442.2 (M+H)⁺.

Compound 540—1-[4-(6-Fluoro-5-methyl-pyridin-3-ylamino)-6-(6-trifluoromethyl-pyridin-2-yl)-[1,3,5]triazin-2-ylamino]-2-methyl-propan-2-ol

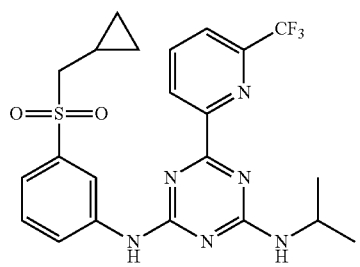 [SMILES: CC(C)Nc1nc(Nc2cccc(S(=O)(=O)CC3CC3)c2)nc(-c2cccc(C(F)(F)F)n2)n1]

¹H NMR (METHANOL-d₄) δ 8.94 (s, 1H), 8.78 (d, J=7.6 Hz, 1H), 8.35 (t, J=8.0 Hz, 1H), 8.14 (d, J=7.6 Hz, 1H), 7.65-7.86 (m, 3H), 4.41-4.48 (m, 1H), 3.20 (d, J=7.2 Hz, 2H), 1.37 (d, J=6.4 Hz, 6H), 0.98-1.06 (m, 1H), 0.53-0.57 (m, 2H), 0.17-0.21 (m, 2H). LC-MS: m/z 493.1 (M+H)⁺.

Compound 541—1-{[4-(3,5-Difluoro-phenylamino)-6-(6-trifluoromethyl-pyridin-2-yl)-[1,3,5]triazin-2-ylamino]-methyl}-cyclopropanol

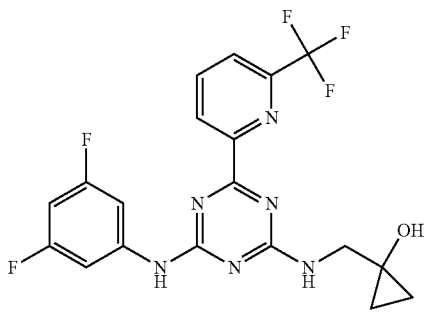 [SMILES: OC1(CNc2nc(Nc3cc(F)cc(F)c3)nc(-c3cccc(C(F)(F)F)n3)n2)CC1]

¹H NMR (DMSO-d₆) δ 8.628-8.543 (m, 1H), 8.336-8.281 (m, 1H), 8.107-8.088 (d, J=7.6 Hz, 2H), 7.788-7.767 (d, J=8.4 Hz, 1H), 1.30 (d, J=6.2 Hz, 1H), 6.842-6.797 (m, 1H), 5.503-5.428 (d, J=30 Hz, 1H), 3.629-3.567 (m, 2H), 0.666-0.584 (m, 2H). LC-MS: m/z 439.0 (M+H)⁺.

Compound 542—2-{3-[4-Isopropylamino-6-(6-trifluoromethyl-pyridin-2-yl)-[1,3,5]triazin-2-ylamino]-phenyl}-propan-2-ol

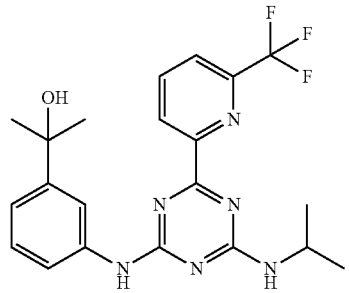 [SMILES: CC(C)Nc1nc(Nc2cccc(C(C)(C)O)c2)nc(-c2cccc(C(F)(F)F)n2)n1]

¹H NMR (METHANOL-d₄) δ 8.82-8.79 (m, 1H), 8.77-8.75 (m, 1H), 8.48-8.42 (m, 1H), 8.23-8.20 (m, 1H), 7.63-7.57 (m, 3H), 4.43-4.26 (m, 1H), 1.656-1.573 (d, J=33.2 Hz, 3H), 1.288-1.188 (d, J=40 Hz 3H). LC-MS: m/z 433.1 (M+H)⁺.

Compound 543—N-(1-Methyl-1H-pyrazol-4-yl)-6-(6-trifluoromethyl-pyridin-2-yl)-N'-(2-trifluoromethyl-pyridin-4-yl)-[1,3,5]triazine-2,4-diamine

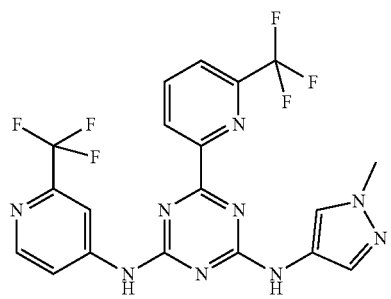 [SMILES: Cn1cc(Nc2nc(Nc3ccnc(C(F)(F)F)c3)nc(-c3cccc(C(F)(F)F)n3)n2)cn1]

¹H NMR (METHANOL-d₄) δ 8.71-8.69 (m, 1H), 8.58-8.31 (m, 4H), 8.19-7.99 (m, 2H), 7.70-7.65 (m, 1H), 3.92 (s, 3H). LC-MS: m/z 481.37 (M+H)⁺.

Compound 544—N-(2-Methyl-2H-pyrazol-3-yl)-6-(6-trifluoromethyl-pyridin-2-yl)-N'-(2-trifluoromethyl-pyridin-4-yl)-[1,3,5]triazine-2,4-diamine

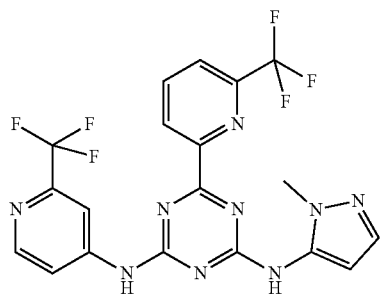 [SMILES: Cn1nccc1Nc1nc(Nc2ccnc(C(F)(F)F)c2)nc(-c2cccc(C(F)(F)F)n2)n1]

¹H NMR (METHANOL-d₄) δ 8.75-8.32 (m, 4H), 8.25-8.00 (m, 2H), 7.53 (s, 1H), 6.44 (s, 1H), 3.83 (s, 3H). LC-MS: m/z 482.3 (M+H)⁺.

Compound 546—N2-(thiazol-5-yl)-6-(6-(trifluoromethyl)pyridin-2-yl)-N4-(2-(trifluoromethyl)pyridin-4-yl)-1,3,5-triazine-2,4-diamine

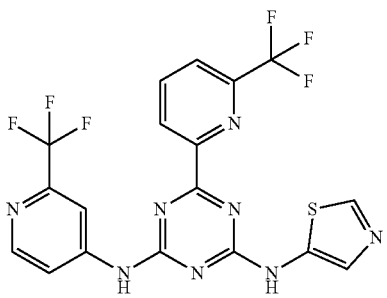 [SMILES: FC(F)(F)c1cc(Nc2nc(Nc3cncs3)nc(-c3cccc(C(F)(F)F)n3)n2)ccn1]

¹H NMR (METHANOL-d₄) δ 8.7-8.9 (m, 1H), 8.65 (m, 1H), 8.35-8.55 (m, 1H), 8.05-8.3 (m, 2H), 8.0 (m, 1H), 7.75 (m, 1H). LC-MS: m/z 485.2 (M+H)⁺.

Compound 547—N-(Tetrahydro-furan-3-ylmethyl)-N'-(2-trifluoromethyl-pyridin-4-yl)-6-(6-trifluoromethyl-pyridin-2-yl)-[1,3,5]triazine-2,4-diamine

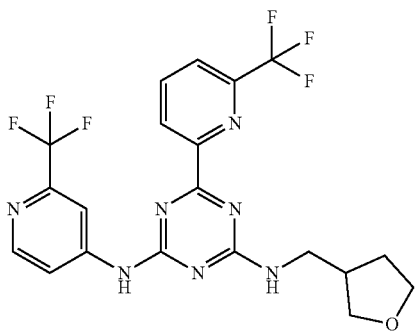 [SMILES: FC(F)(F)c1cc(Nc2nc(NCC3CCOC3)nc(-c3cccc(C(F)(F)F)n3)n2)ccn1]

¹H NMR (METHANOL-d₄) δ 8.78-8.76 (d, J=8 Hz 1H), 8.70-8.68 (d, J=5.6 Hz 1H), 8.53-8.52 (m, 1H), 8.43-8.37 (m, 1H), 8.22-8.20 (m, 1H), 7.92-7.91 (m, 1H), 3.95-3.93 (m, 1H), 3.92-3.88 (m, 1H), 3.86-3.85 (m, 1H), 3.78-3.77 (m, 3H), 2.73-2.71 (m, 1H), 2.18-2.15 (m, 1H), 1.77-1.75 (m, 1H). LC-MS: m/z 486.2 (M+H)⁺.

Compound 548—3-[4-(6-Trifluoromethyl-pyridin-2-yl)-6-(2-trifluoromethyl-pyridin-4-ylamino)-[1,3,5]triazin-2-ylamino]-butan-2-ol

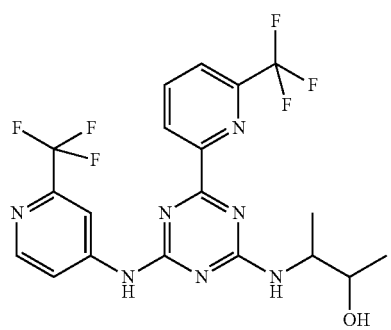 [SMILES: CC(O)C(C)Nc1nc(Nc2ccnc(C(F)(F)F)c2)nc(-c2cccc(C(F)(F)F)n2)n1]

¹H NMR (METHANOL-d₄) δ 8.60-8.40 (m, 3H), 8.13-7.80 (m, 3H), 4.32-4.05 (m, 1H), 3.88-3.79 (m, 1H), 1.23-1.12 (m, 6H). LC-MS: m/z 474.3 (M+H)⁺

Compound 549—N-(3-Methyl-oxetan-3-yl)-6-(6-trifluoromethyl-pyridin-2-yl)-N'-(2-trifluoromethyl-pyridin-4-yl)-[1,3,5]triazine-2,4-diamine

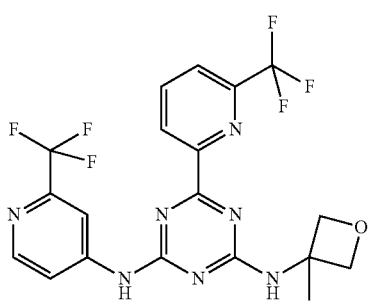 [SMILES: CC1(Nc2nc(Nc3ccnc(C(F)(F)F)c3)nc(-c3cccc(C(F)(F)F)n3)n2)COC1]

¹H NMR (METHANOL-d₄) δ 8.71-8.54 (m, 1H), 8.49-8.52 (m, 2H), 8.25-8.21 (m, 1H), 8.14-7.89 (m, 2H), 4.65-4.64 (m, 2H), 1.85 (s, 3H). LC-MS: m/z 472.3 (M+H)⁺

Compound 550—N-(3-Methyl-oxetan-3-ylmethyl)-6-(6-trifluoromethyl-pyridin-2-yl)-N'-(2-trifluoromethyl-pyridin-4-yl)-[1,3,5]triazine-2,4-diamine

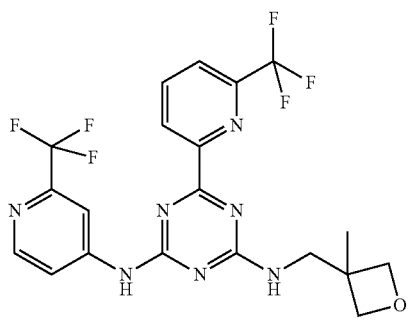 [SMILES: CC1(CNc2nc(Nc3ccnc(C(F)(F)F)c3)nc(-c3cccc(C(F)(F)F)n3)n2)COC1]

¹H NMR (METHANOL-d₄) δ 8.72-8.52 (m, 3H), 8.26-7.99 (m, 3H), 4.74-4.67 (m, 2H), 4.45-4.42 (m, 2H), 3.87-3.82 (m, 2H), 1.43 (s, 3H). LC-MS: m/z 486.3 (M+H)⁺

Compound 551—N-(2-Difluoromethyl-pyridin-4-yl)-N'-isopropyl-6-(6-trifluoromethyl-pyridin-2-yl)-[1,3,5]triazine-2,4-diamine

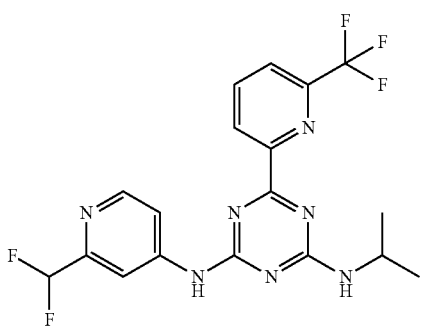 [SMILES: CC(C)Nc1nc(Nc2ccnc(C(F)F)c2)nc(-c2cccc(C(F)(F)F)n2)n1]

¹H NMR (METHANOL-d₄) δ 8.71-8.68 (m, 1H), 8.53 (s, 1H), 8.44 (m, 1H), 8.23-7.78 (m, 3H), 6.84-6.56 (m., 1H), 4.31 (m, 1H), 1.36-1.34 (d, J=8 Hz, 6H). LC-MS: m/z 426.2 (M+H)⁺

Compound 552—2-Methyl-3-[4-(6-trifluoromethyl-pyridin-2-yl)-6-(2-trifluoromethyl-pyridin-4-ylamino)-[1,3,5]triazin-2-ylamino]-propan-1-ol

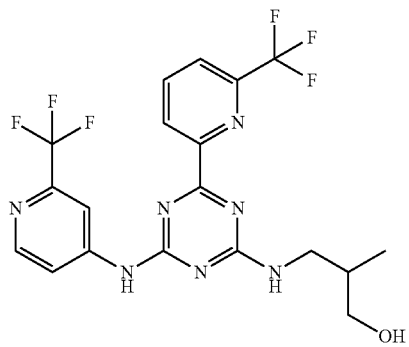 [SMILES: CC(CO)CNc1nc(Nc2ccnc(C(F)(F)F)c2)nc(-c2cccc(C(F)(F)F)n2)n1]

¹H NMR (METHANOL-d₄) δ 8.72-8.69 (m, 1H), 8.56-8.49 (m, 2H), 8.28-7.96 (m, 3H), 4.64-3.29 (m, 4H), 2.07-2.03 (m, 1H), 1.04-0.998 (m, 3H). LC-MS: m/z 474.2 (M+H)⁺

Compound 554—5-[4-(2,2-Dimethyl-propylamino)-6-(4-trifluoromethyl-pyrimidin-2-yl)-[1,3,5]triazin-2-ylamino]-nicotinonitrile Using the standard procedure described above except replacing t-BuONa by Cs₂CO₃ yielded the title compound.

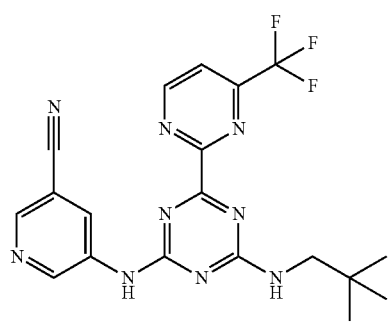 [SMILES: CC(C)(C)CNc1nc(Nc2cncc(C#N)c2)nc(-c2nccc(C(F)(F)F)n2)n1]

¹H NMR (MeOH-d₄) δ 9.42-9.46 (m, 1H), 8.73-9.25 (m, 3H), 8.21-8.26 (m, 1H), 3.49-3.51 (m, 2H), 1.00-1.07 (m, 9H). LC-MS: m/z 430.3 (M+H)⁺.

Compound 555—N-Isopropyl-N'-(1-propyl-1H-pyrazol-4-yl)-6-(6-trifluoromethyl-pyridin-2-yl)-[1,3,5]triazine-2,4-diamine

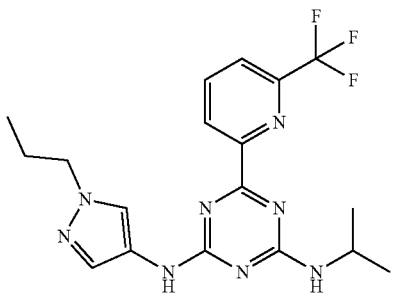 [SMILES: CCCn1cc(Nc2nc(NC(C)C)nc(-c3cccc(C(F)(F)F)n3)n2)cn1]

¹H NMR (METHANOL-d₄) δ 8.67-8.65 (m, 1H), 8.30-7.98 (m, 3H), 7.70-7.60 (m, 1H), 4.50-4.20 (m, 1H), 4.13-4.10 (m., 2H), 1.92-1.89 (m, 2H), 1.35-1.29 (m, 6H), 0.96-0.93 (t, 3H). LC-MS: m/z 407.3 (M+H)⁺

Compound 556—N-(7-Oxa-bicyclo[2.2.1]hept-2-yl)-6-(6-trifluoromethyl-pyridin-2-yl)-N'-(2-trifluoromethyl-pyridin-4-yl)-[1,3,5]triazine-2,4-diamine

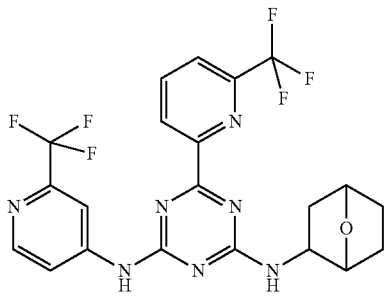 [SMILES: FC(F)(F)c1cc(Nc2nc(NC3CC4CCC3O4)nc(-c3cccc(C(F)(F)F)n3)n2)ccn1]

$^1$H NMR (METHANOL-d$_4$) δ 8.71-8.48 (m, 3H), 8.24-7.93 (m, 3H), 4.87-4.86 (m, 1H), 4.70-4.605 (m, 1H), 4.43-4.18 (m, 1H), 2.35-1.99 (m, 2H), 1.78-1.23 (m, 4H). LC-MS: m/z 498.2 (M+H)$^+$

Compound 557—N$^2$-((tetrahydrofuran-3-yl)methyl)-N4-(2-(trifluoromethyl)pyridin-4-yl)-6-(4-(trifluoromethyl)pyrimidin-2-yl)-1,3,5-triazine-2,4-diamine

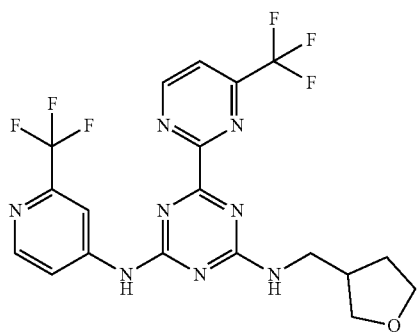 [SMILES: FC(F)(F)c1cc(Nc2nc(NCC3CCOC3)nc(-c3nccc(C(F)(F)F)n3)n2)ccn1]

$^1$H NMR (MeOH-d$_4$) δ 9.36-9.42 (m, 1H), 8.50-8.69 (m, 2H), 8.20-8.21 (m, 1H), 7.93-8.13 (m, 1H), 3.64-3.98 (m, 6H), 2.71-2.77 (m, 1H), 2.12-2.27 (m, 1H), 1.73-1.81 (m, 1H). LC-MS: m/z 487.3 (M+H)$^+$.

Compound 558—N$^2$-(1-methoxypropan-2-yl)-N4-(2-(trifluoromethyl)pyridin-4-yl)-6-(4-(trifluoromethyl)pyrimidin-2-yl)-1,3,5-triazine-2,4-diamine

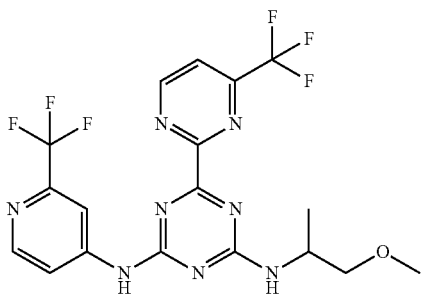 [SMILES: COCC(C)Nc1nc(Nc2ccnc(C(F)(F)F)c2)nc(-c2nccc(C(F)(F)F)n2)n1]

$^1$H NMR (MeOH-d$_4$) δ 9.31 (d, J=4.8 Hz, 1H), 8.30-8.66 (m, 2H), 7.87-8.21 (m, 2H), 4.36-4.67 (m, 1H), 3.49 (s, 3H), 1.28-1.34 (m, 3H). LC-MS: m/z 475.3 (M+H)$^+$.

Compound 559—N-Isopropyl-N'-[2-(1-methoxy-cyclopropyl)-pyridin-4-yl]-6-(6-trifluoromethyl-pyridin-2-yl)-[1,3,5]triazine-2,4-diamine

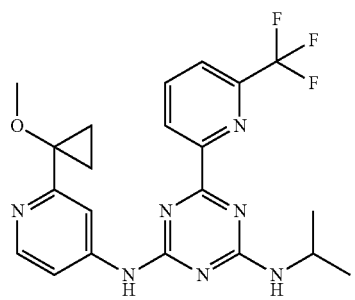 [SMILES: COC1(c2cc(Nc3nc(NC(C)C)nc(-c4cccc(C(F)(F)F)n4)n3)ccn2)CC1]

$^1$H NMR (METHANOL-d$_4$) δ 8.69-8.71 (d, J=8 Hz, 1H), 8.18-8.31 (m, 3H), 7.93-7.98 (m, 1.3H), 7.58-7.59 (d, J=3.6 Hz, 0.7H), 4.34-4.62 (m, 1H), 3.39 (s, 3H), 1.33-1.34 (d, J=6 Hz, 1H), 1.23-1.28 (m, 4H). LC-MS: m/z 446.2 (M+H)$^+$

Compound 560—1-[4-[6-(1,1-Difluoro-ethyl)-pyridin-2-yl]-6-(3,5-difluoro-phenylamino)-[1,3,5]triazin-2-ylamino]-2-methyl-propan-2-ol

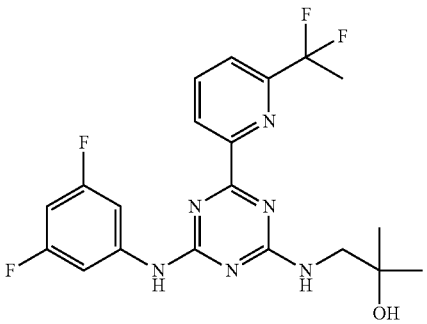 [SMILES: CC(C)(O)CNc1nc(Nc2cc(F)cc(F)c2)nc(-c2cccc(C(C)(F)F)n2)n1]

$^1$H NMR (METHANOL-d$_4$) δ 8.65-8.88 (d, J=7.6 Hz, 1H) 8.30-8.35 (d, J=20 Hz, 1H), 8.10-8.12 (d, J=8 Hz, 1H), 7.50-7.58 (m, 2H), 6.86-6.90 (m, 1H), 3.58-3.64 (d, J=24 Hz, 1H), 2.13-2.25 (m, 3H), 1.35-1.37 (d, J=6.8 Hz, 6H). LC-MS: m/z 437.1 (M+H)$^+$

283

Compound 561—N-(3-Chloro-5-methanesulfonyl-phenyl)-N'-isopropyl-6-(6-trifluoromethyl-pyridin-2-yl)-[1,3,5]triazine-2,4-diamine

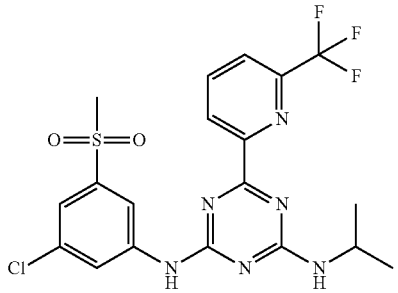 [SMILES: CC(C)Nc1nc(Nc2cc(Cl)cc(S(C)(=O)=O)c2)nc(-c2cccc(C(F)(F)F)n2)n1]

1H NMR (METHANOL-$d_4$) δ 8.70-8.67 (m, 2H), 8.24-8.17 (m, 1H), 8.04 (m, 1H), 7.97-7.95 (m, 1H), 7.58-7.55 (s., 1H), 4.34-4.28 (m, 1H), 3.19 (s, 3H), 1.33-1.31 (d, J=6.4 Hz, 6H). LC-MS: m/z 487.2 (M+H)$^+$

Compound 562—2-Methyl-2-[4-(6-trifluoromethyl-pyridin-2-yl)-6-(2-trifluoromethyl-pyridin-4-ylamino)-[1,3,5]triazin-2-ylamino]-propan-1-ol

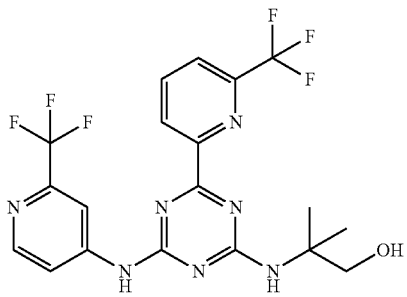 [SMILES: CC(C)(CO)Nc1nc(Nc2ccnc(C(F)(F)F)c2)nc(-c2cccc(C(F)(F)F)n2)n1]

$^1$H NMR (METHANOL-$d_4$) δ 8.70-8.68 (d, J=8 Hz 1H), 8.64-7.88 (m, 5H), 8.53-8.52 (m, 1H), 3.83 (s, 3H), 1.523-1.496 (d, J=10.8 Hz 6H). LC-MS: m/z 474.3 (M+H)$^+$.

Compound 563—N-(2-Cyclopropyl-pyridin-4-yl)-N'-isopropyl-6-(6-trifluoromethyl-pyridin-2-yl)-[1,3,5]triazine-2,4-diamine

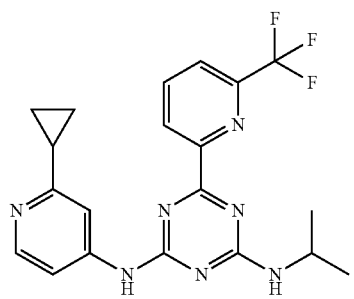 [SMILES: CC(C)Nc1nc(Nc2ccnc(C3CC3)c2)nc(-c2cccc(C(F)(F)F)n2)n1]

$^1$H NMR (METHANOL-$d_4$) δ 8.78-8.76 (m, 1H), 8.48-8.35 (m, 2H), 8.17-8.06 (m, 3H), 4.39-4.36 (m, 1H), 1.49-1.38 (m, 8H), 1.21-1.19 (m, 2H). LC-MS: m/z 416.1 (M+H)$^+$.

284

Compound 564—N-tert-Butyl-N'-(2-cyclopropyl-pyridin-4-yl)-6-(6-trifluoromethyl-pyridin-2-yl)-[1,3,5]triazine-2,4-diamine

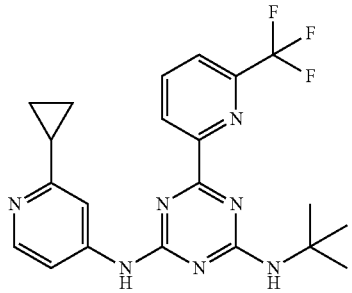 [SMILES: CC(C)(C)Nc1nc(Nc2ccnc(C3CC3)c2)nc(-c2cccc(C(F)(F)F)n2)n1]

$^1$H NMR (METHANOL-$d_4$) δ 8.68-8.66 (m, 1H), 8.21-8.19 (m, 2H), 7.98-7.64 (m, 3H), 2.15-2.11 (m, 1H), 1.59 (s, 9H), 1.11-1.01 (m, 4H). LC-MS: m/z 430.1 (M+H)$^+$.

Compound 565—N-(2-Cyclopropyl-pyridin-4-yl)-N'-(1-methyl-cyclopropyl)-6-(6-trifluoromethyl-pyridin-2-yl)-[1,3,5]triazine-2,4-diamine

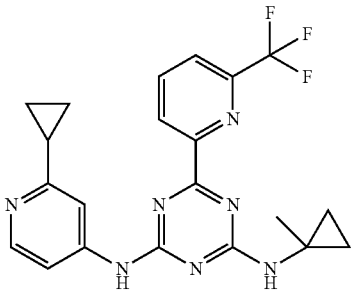 [SMILES: CC1(Nc2nc(Nc3ccnc(C4CC4)c3)nc(-c3cccc(C(F)(F)F)n3)n2)CC1]

$^1$H NMR (METHANOL-$d_4$) δ 8.69-8.67 (m, 1H), 8.25-8.19 (m, 2H), 8.01-7.86 (m, 3H), 2.15-2.11 (m, 1H), 1.57-1.56 (m, 1H), 1.17-1.12 (m, 2H), 1.08-1.02 (m, 2H), 0.94-0.90 (m, 2H), 0.87-0.85 (m, 2H). LC-MS: m/z 428.1 (M+H)$^+$.

Compound 566—{1-[4-(6-Trifluoromethyl-pyridin-2-yl)-6-(2-trifluoromethyl-pyridin-4-ylamino)-[1,3,5]triazin-2-ylamino]-cyclopropyl}-methanol

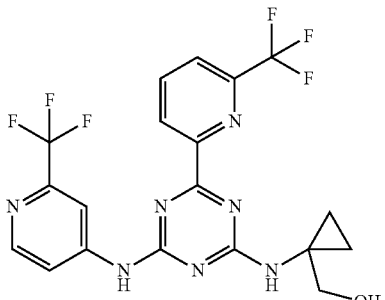

¹H NMR (METHANOL-d₄) δ 8.74-8.69 (m, 2H), 8.52-8.48 (m, 1H), 8.25-7.58 (m, 3H), 3.79 (s, 2H), 1.02-0.95 (m, 4H). LC-MS: m/z 494.2 (M+H)⁺.

Compound 567—N-tert-Butyl-N'-[2-(1,1-difluoroethyl)-pyridin-4-yl]-6-(6-trifluoromethyl-pyridin-2-yl)-[1,3,5]triazine-2,4-diamine

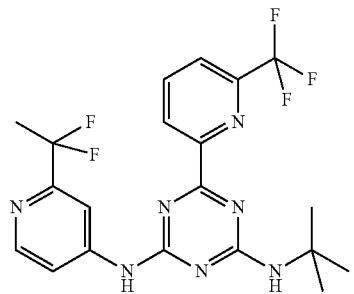 [SMILES: CC(C)(C)Nc1nc(Nc2ccnc(C(C)(F)F)c2)nc(-c2cccc(C(F)(F)F)n2)n1]

¹H NMR (METHANOL-d₄) δ 8.72-8.44 (m, 3H), 8.25-7.77 (m, 3H), 2.05-1.95 (m, 3H), 1.58 (s, 9H). LC-MS: m/z 454.1 (M+H)⁺.

Compound 568—2-[4-(6-Trifluoromethyl-pyridin-2-yl)-6-(2-trifluoromethyl-pyridin-4-ylamino)-[1,3,5]triazin-2-ylamino]-cyclopropanol

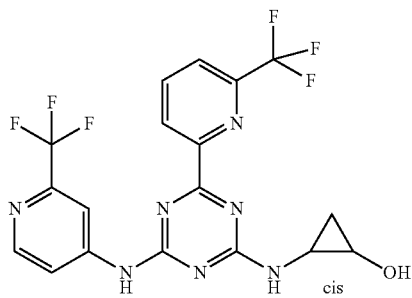 [SMILES: OC1CC1Nc1nc(Nc2ccnc(C(F)(F)F)c2)nc(-c2cccc(C(F)(F)F)n2)n1]

¹H NMR (METHANOL-d₄) δ 8.31-8.90 (m, 3H), 8.15-8.30 (m, 2H), 7.93-8.05 (m, 1H), 3.43-3.55 (m, 1H), 2.90-3.10 (m, 1H), 1.10-1.25 (m, 1H), 0.89-0.99 (m, 1H). LC-MS: m/z 458.2 (M+H)⁺.

Compound 569—2-[4-(6-Trifluoromethyl-pyridin-2-yl)-6-(2-trifluoromethyl-pyridin-4-ylamino)-[1,3,5]triazin-2-ylamino]-cyclopropanol

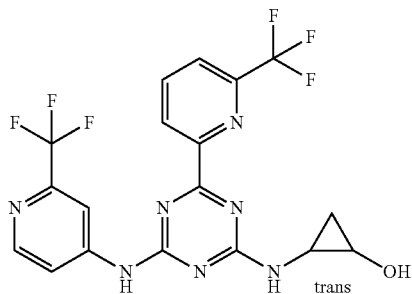 [SMILES: OC1CC1Nc1nc(Nc2ccnc(C(F)(F)F)c2)nc(-c2cccc(C(F)(F)F)n2)n1]

¹H NMR (METHANOL-d₄) δ 8.35-8.90 (m, 3H), 8.13-8.34 (m, 2H), 7.97-8.05 (m, 1H), 3.47-3.55 (m, 1H), 2.72-3.01 (m, 1H), 1.08-1.25 (m, 1H), 0.90-0.99 (m, 1H). LC-MS: m/z 458.2 (M+H)⁺.

Compound 570—N2-(3-fluoro-5-(methylsulfonyl)phenyl)-N4-isopropyl-6-(6-(trifluoromethyl)pyridin-2-yl)-1,3,5-triazine-2,4-diamine

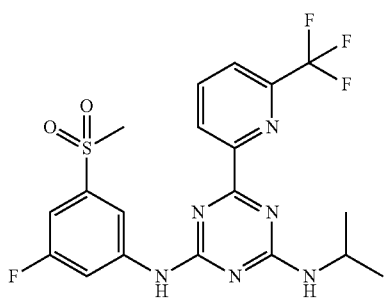 [SMILES: CC(C)Nc1nc(Nc2cc(F)cc(S(C)(=O)=O)c2)nc(-c2cccc(C(F)(F)F)n2)n1]

¹H NMR (METHANOL-d₄) δ 8.70-8.62 (m, 2H), 8.21-7.84 (m, 3H), 7.35-7.33 (m, 1H), 4.34-4.31 (m, 1H), 3.16 (s, 3H), 1.31 (dd, 6H). LC-MS: m/z 470.0 (M+H)⁺.

Compound 571—N2-isobutyl-N4-(3-(methylsulfonyl)phenyl)-6-(6-(trifluoromethyl)pyridin-2-yl)-1,3,5-triazine-2,4-diamine

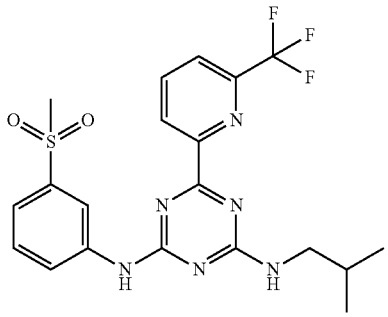 [SMILES: CC(C)CNc1nc(Nc2cccc(S(C)(=O)=O)c2)nc(-c2cccc(C(F)(F)F)n2)n1]

¹H NMR (METHANOL-d₄): δ 8.7-8.9 (m, 2H), 8.3-8.5 (m, 1H), 8.0-8.2 (m, 1H), 7.6-7.86 (m, 3H), 3.5 (m, 2H), 3.15 (S, 3H), 1.0-1.1 (d, J=16 Hz, 6H). LC-MS: m/z 467.1 (M+H)⁺.

Compound 572—N2-(2-chloropyridin-4-yl)-N4-isopropyl-6-(6-(trifluoromethyl)pyridin-2-yl)-1,3,5-triazine-2,4-diamine

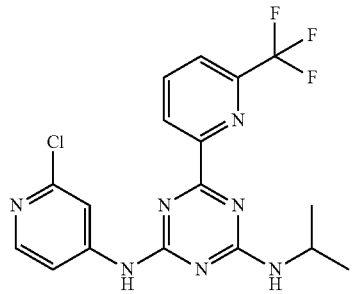 [SMILES: CC(C)Nc1nc(Nc2ccnc(Cl)c2)nc(-c2cccc(C(F)(F)F)n2)n1]

¹H NMR (DMSO-d₄) δ 10.2-10.5 (m, 1.0H), 8.85-8.65 (m, 1H), 8.6 (m, 1H), 8.25-8.45 (m, 3H), 8.1 (m, 1H), 7.2 (m, 1H), 4.1-4.4 (m, 1H), 1.2 (d, J=6.4 Hz, 6H). LC-MS: m/z 410.1 (M+H)⁺.

Compound 573—1-[4-[2-(1,1-Difluoro-ethyl)-pyridin-4-ylamino]-6-(6-trifluoromethyl-pyridin-2-yl)-[1,3,5]triazin-2-ylamino]-2-methyl-propan-2-ol

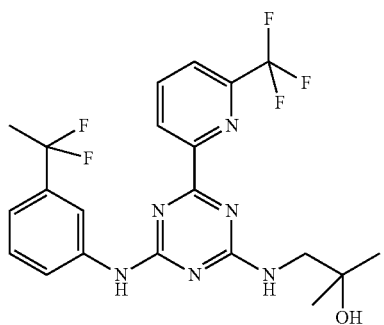 [SMILES: CC(C)(O)CNc1nc(Nc2cccc(C(C)(F)F)c2)nc(-c2cccc(C(F)(F)F)n2)n1]

¹H NMR (METHANOL-d₄) δ 8.72-8.42 (m, 3H), 8.24-7.74 (m, 3H), 3.64-3.60 (m, 2H), 2.05-1.94 (m, 3H), 2.34-1.91 (m, 4H), 1.30-1.29 (m, 6H). LC-MS: m/z 492.1 (M+Na)⁺.

Compound 574—1-{4-[4-Isopropylamino-6-(6-trifluoromethyl-pyridin-2-yl)-[1,3,5]triazin-2-ylamino]-pyridin-2-yl}-propan-1-one

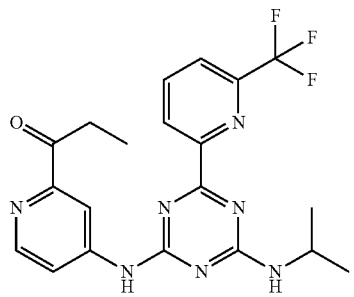 [SMILES: CCC(=O)c1cc(Nc2nc(NC(C)C)nc(-c3cccc(C(F)(F)F)n3)n2)ccn1]

¹H NMR (METHANOL-d₄) δ 8.69 (s, 0.7H), 8.63-8.64 (d, J=8 Hz, 1H), 8.38-8.40 (dd, J₁=5.2 Hz, J₂=9.2 Hz, 1H), 8.13-8.18 (q, J=8 Hz, 1H), 7.78-8.03 (m, 2H), 4.22-4.36 (m, 1H), 3.12-3.16 (m, 2H), 1.25-1.29 (m, 6H), 1.11-1.14 (m, 3H). LC-MS: m/z 375.1 (M+H)⁺.

Compound 576—6-[6-(1,1-Difluoro-ethyl)-pyridin-2-yl]-N-[2-(1,1-difluoro-ethyl)-pyridin-4-yl]-N'-isopropyl-[1,3,5]triazine-2,4-diamine

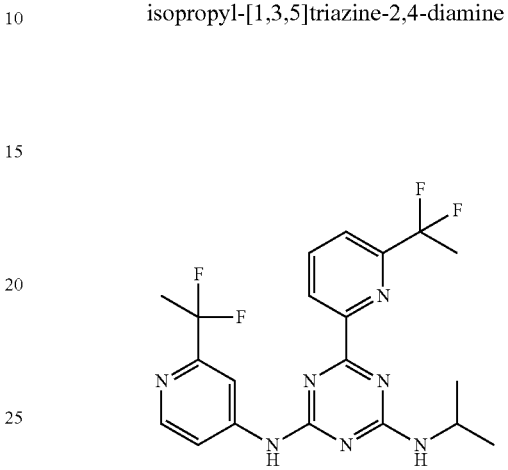

¹H NMR (METHANOL-d₄) δ 8.78-8.80 (d, J=6 Hz, 1H), 8.69-8.71 (d, J=8.4 Hz, 2H), 8.26-8.53 (m, 1H), 8.05-8.19 (m, 2H), 4.39-4.60 (m, 1H), 2.10-2.24 (m, 6H), 1.40-1.46 (m, 6H). LC-MS: m/z 436.3 (M+H)⁺.

Compound 577—4-[4-(6-Trifluoromethyl-pyridin-2-yl)-6-(2-trifluoromethyl-pyridin-4-ylamino)-[1,3,5]triazin-2-ylamino]-piperidine-1-carboxylic acid methyl ester

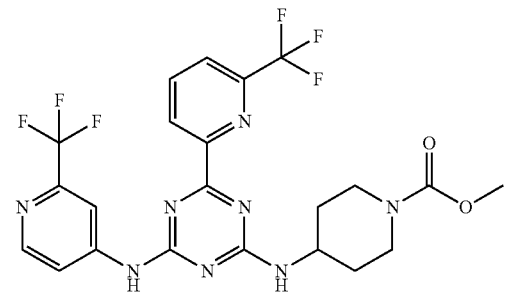 [SMILES: COC(=O)N1CCC(Nc2nc(Nc3ccnc(C(F)(F)F)c3)nc(-c3cccc(C(F)(F)F)n3)n2)CC1]

¹H NMR (METHANOL-d₄) δ 8.30-8.78 (m, 3H), 7.82-8.29 (m, 3H), 4.10-4.39 (m, 3H), 3.73 (s, 3H), 2.99-3.18 (m, 2H), 2.02-2.16 (m, 2H), 1.53-1.65 (m, 2H). LC-MS: m/z 543.3 (M+H)⁺.

Compound 578—1-{4-[4-(6-Trifluoromethyl-pyridin-2-yl)-6-(2-trifluoromethyl-pyridin-4-ylamino)-[1,3,5]triazin-2-ylamino]-piperidin-1-yl}-ethanone

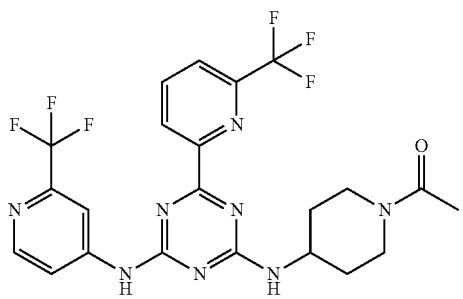 [SMILES: CC(=O)N1CCC(Nc2nc(Nc3ccnc(C(F)(F)F)c3)nc(-c3cccc(C(F)(F)F)n3)n2)CC1]

$^1$H NMR (METHANOL-d$_4$) δ 8.62-8.87 (m, 2H), 8.30-8.60 (m, 2H), 7.88-8.29 (m, 2H), 4.31-4.60 (m, 2H), 3.95-4.10 (m, 1H), 3.37-3.43 (m, 1H), 2.90-3.19 (m, 1H), 2.10-2.30 (m, 5H), 1.58-1.83 (m, 2H). LC-MS: m/z 527.2 (M+H)$^+$.

Compound 580—N-(1-Methanesulfonyl-piperidin-4-yl)-6-(6-trifluoromethyl-pyridin-2-yl)-N'-(2-trifluoromethyl-pyridin-4-yl)-[1,3,5]triazine-2,4-diamine

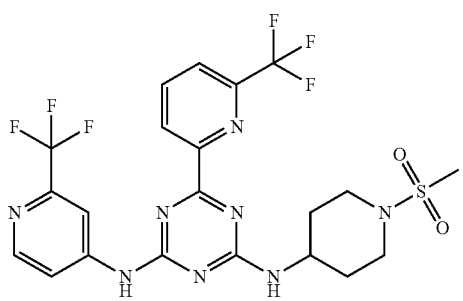 [SMILES: CS(=O)(=O)N1CCC(Nc2nc(Nc3ccnc(C(F)(F)F)c3)nc(-c3cccc(C(F)(F)F)n3)n2)CC1]

$^1$H NMR (METHANOL-d$_4$) δ 8.67-8.93 (m, 2H), 8.38-8.59 (m, 2H), 7.92-8.31 (m, 2H), 4.19-4.52 (m, 1H), 3.70-3.88 (m, 2H), 3.08 (t, J=10.4 Hz, 6H), 2.93 (s, 3H), 2.18-2.32 (m, 2H), 1.77-1.98 (m, 2H). LC-MS: m/z 563.3 (M+H)$^+$.

Compound 581—N-Isopropyl-N'-[2-(1-methyl-cyclopropyl)-pyridin-4-yl]-6-(6-trifluoromethyl-pyridin-2-yl)-[1,3,5]triazine-2,4-diamine

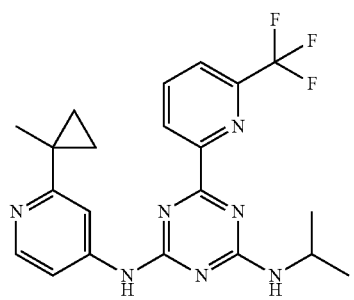 [SMILES: CC(C)Nc1nc(Nc2ccnc(C3(C)CC3)c2)nc(-c2cccc(C(F)(F)F)n2)n1]

$^1$H NMR (DMSO-d$_6$) δ 8.73-8.69 (d, J=17.6 Hz 1H), 8.26-8.16 (m, 3H), 8.06-7.97 (m, 1H), 7.63-7.62 (m, 1H), 4.38-4.34 (m, 1H), 1.54-1.52 (s, 3H), 1.35-1.26 (m, 6H), 1.18-1.16 (m, 2H), 0.90-0.97 (m, 2H). LC-MS: m/z 430.1 (M+H)$^+$.

Compound 582—6-[6-(1,1-Difluoro-ethyl)-pyridin-2-yl]-N-isopropyl-N'-(2-trifluoromethyl-pyridin-4-yl)-[1,3,5]triazine-2,4-diamine

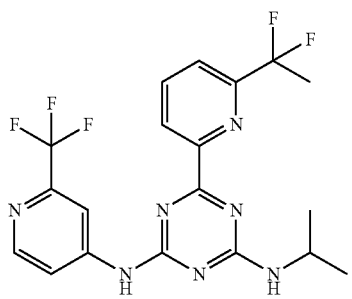

$^1$H NMR (METHANOL-d$_4$) δ 8.63-8.50 (m, 3H), 8.26-8.09 (m, 1H), 7.97-7.87 (m, 2H), 4.50-4.29 (m, 1H), 2.14 (t, J=13.2 Hz, 3H), 1.35 (d, J=8.8 Hz, 6H). LC-MS: m/z 440.1 (M+H)$^+$.

Compound 583—6-(6-(1,1-difluoroethyl)pyridin-2-yl)-N2-(3,5-difluorophenyl)-N4-isopropyl-1,3,5-triazine-2,4-diamine

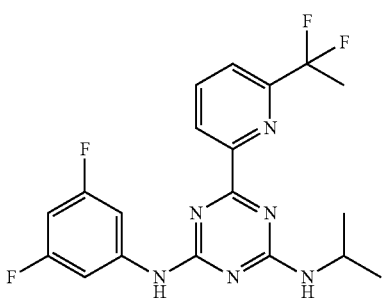

$^1$H NMR (METHANOL-d$_4$) δ 8.53 (t, 1H), 8.09 (t, 1H), 7.86-7.84 (m, 1H), 7.58-7.56 (m, 1H), 6.60-6.56 (m, 1H), 4.28-4.25 (m, 1H), 2.17-2.04 (m, 3H), 1.33-1.29 (m, 6H). LC-MS: m/z 407.2 (M+H)$^+$.

Compound 584—N2-(cyclopropylmethyl)-6-(6-(1,1-difluoroethyl)pyridin-2-yl)-N4-(3,5-difluorophenyl)-1,3,5-triazine-2,4-diamine

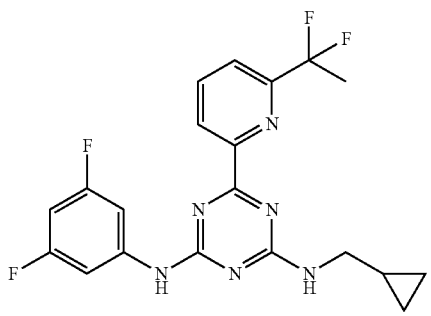

$^1$H NMR (METHANOL-d$_4$) δ 8.51 (t, 1H), 8.01 (t, 1H), 7.84 (t, 1H), 7.56-7.54 (m, 1H), 6.56 (t, 1H), 3.42-3.36 (1H), 2.10 (t, 3H), 1.18-1.16 (m, 1H), 0.57-0.51 (m, 2H), 0.33-0.29 (m, 2H). LC-MS: m/z 419.2 (M+H)$^+$.

Compound 585—N2-(tert-butyl)-6-(6-(1,1-difluoroethyl)pyridin-2-yl)-N4-(3,5-difluorophenyl)-1,3,5-triazine-2,4-diamine

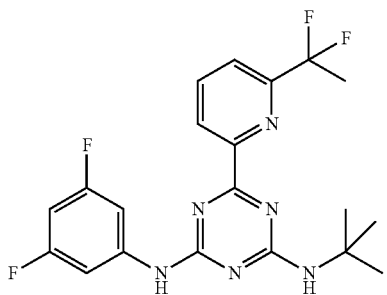 [SMILES: CC(C)(C)Nc1nc(Nc2cc(F)cc(F)c2)nc(-c2cccc(C(C)(F)F)n2)n1]

$^1$H NMR (METHANOL-d$_4$) δ 8.85-8.49 (m, 1H), 8.09-8.06 (m, 1H), 7.83 (d, 1H), 7.52-7.48 (m, 2H), 6.61-6.56 (m, 1H), 2.10 (t, 3H), 1.53 (s, 9H). LC-MS: m/z 421.1 (M+H)$^+$.

Compound 586—1-(4-((4-(((cyclopropylmethyl)amino)-6-(6-(1,1-difluoroethyl)pyridin-2-yl)-1,3,5-triazin-2-yl)amino)pyridin-2-yl)cyclopropanecarbonitrile

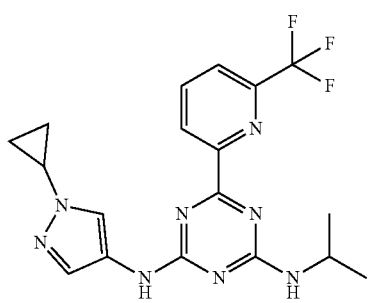 [SMILES: CC(C)Nc1nc(Nc2cnn(C3CC3)c2)nc(-c2cccc(C(F)(F)F)n2)n1]

$^1$H NMR (METHANOL-d$_4$) δ 8.62 (d, 1H), 8.16-7.56 (m, 4H), 4.47-4.23 (m, 1H), 3.62-3.61 (m, 1H), 1.34-1.04 (m, 10H). LC-MS: m/z 405.2 (M+H)$^+$.

Compound 587—N2-(tetrahydro-2H-pyran-4-yl)-6-(6-(trifluoromethyl)pyridin-2-yl)-N4-(2-(trifluoromethyl)pyridin-4-yl)-1,3,5-triazine-2,4-diamine

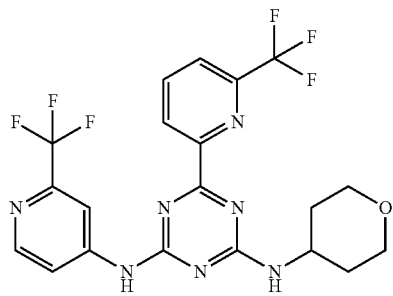 [SMILES: FC(F)(F)c1cc(Nc2nc(NC3CCOCC3)nc(-c3cccc(C(F)(F)F)n3)n2)ccn1]

1H NMR (METHANOL-d$_4$) δ 8.7-8.25 (m, 3H), 8.25-7.7 (m, 3H), 4.4-4.1 (m, 1H), 4.0 (m, 2H), 3.65-3.5 (m, 2H), 2.1-2.0 (m, 2H), 1.8-1.6 (m, 2H). LC-MS: m/z 486.3 (M+H)$^+$.

Compound 588—2-((4-(6-(trifluoromethyl)pyridin-2-yl)-6-((2-(trifluoromethyl)pyridin-4-yl)amino)-1,3,5-triazin-2-yl)amino)cyclopentanol

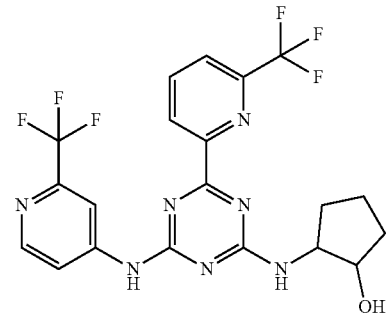 [SMILES: OC1CCCC1Nc1nc(Nc2ccnc(C(F)(F)F)c2)nc(-c2cccc(C(F)(F)F)n2)n1]

$^1$H NMR (METHANOL-d$_4$) δ 8.85-8.6 (m, 2.0H), 8.5-8.0 (m, 4H), 4.4-4.15 (m, 2H), 2.4-1.6 (m, 6H). LC-MS: m/z 486.0 (M+H)$^+$.

Preparation of 3-[4-(6-Chloro-pyridin-2-yl)-6-isopropylamino-[1,3,5]triazin-2-ylamino]-N-cyclopropyl-benzamide Step 1: Preparation of methyl 3-(4-(6-chloropyridin-2-yl)-6-(isopropylamino)-1,3,5-triazin-2-ylamino) benzoate To a solution of 4-chloro-6-(6-chloropyridin-2-yl)-N-isopropyl-1,3,5-triazin-2-amine (134 mg, 0.47 mmol) in toluene (4 mL) was added methyl 3-aminobenzoate (85.6 mg, 0.57 mmol), Cs$_2$CO$_3$ (306.9 mg, 0.94 mmol), BINAP (29.33 mg, 0.047 mmol) and Pd$_2$(dba)$_3$ (43.13 mg, 0.047 mmol). The mixture was purged with nitrogen three times and stirred at 110° C. for 40 min under M.W. irradiation. TLC (PE:EA=1:1) showed the reaction was complete. The mixture was partitioned between H₂O (150 mL) and EA (50 mL). The organic layer was separated, dried over Na₂SO₄, filtered and concentrated in vacuo. The residue was purified by combi flash to give methyl 3-(4-(6-chloropyridin-2-yl)-6-(isopropylamino)-1,3,5-triazin-2-yl amino)benzoate as a yellow solid.

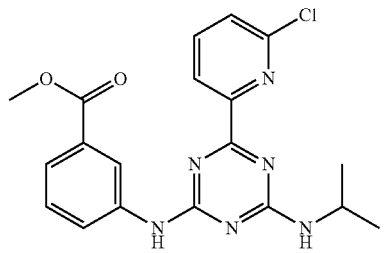 [SMILES: COC(=O)c1cccc(Nc2nc(NC(C)C)nc(-c3cccc(Cl)n3)n2)c1]

Step 2: Preparation of 3-(4-(6-chloropyridin-2-yl)-6-(isopropylamino)-1,3,5-triazin-2-ylamino)benzoic acid To a solution of methyl 3-(4-(6-chloropyridin-2-yl)-6-(isopropylamino)-1,3,5-triazin-2-y-1 amino)benzoate (112 mg, 0.28 mmol) in MeOH (2 mL) was added NaOH (0.28 mL, 3 N). The mixture was stirred at room temperature for 3 h. TLC (PE:EA=1:1) showed the reaction was complete. The mixture was concentrated in vacuo. The residue was acidified with 1 N HCl to pH=6 and extracted with CH₂Cl₂ (50 mL*3). The combined extracts were concentrated to give 3-(4-(6-chloropyridin-2-yl)-6-(isopropylamino)-1,3,5-triazin-2-ylamino) benzoic acid as a yellow solid.

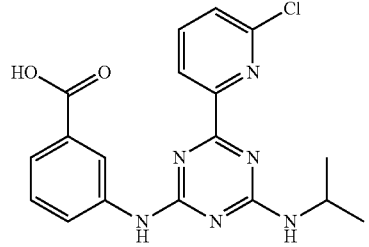 [SMILES: CC(C)Nc1nc(Nc2cccc(C(=O)O)c2)nc(-c2cccc(Cl)n2)n1]

Step 3: 3-[4-(6-Chloro-pyridin-2-yl)-6-isopropylamino-[1,3,5]triazin-2-ylamino]-N-cyclopropyl-benzamide To a solution of 3-(4-(6-chloropyridin-2-yl)-6-(isopropylamino)-1,3,5-triazin-2-ylamino) benzoic acid (104 mg, 0.27 mmol) in DMF (4 mL) was added HATU (205 mg, 0.54 mmol), NMM (81.93 mg, 0.81 mmol). The mixture was purged with nitrogen and stirred at room temperature overnight. LCMS showed the reaction was complete. The mixture was poured into brine (150 mL) and extracted with EA (50 mL*2). The combined extracts were dried over Na₂SO₄, filtered and concentrated in vacuo. The residue was purified by a standard method to give the title compound.

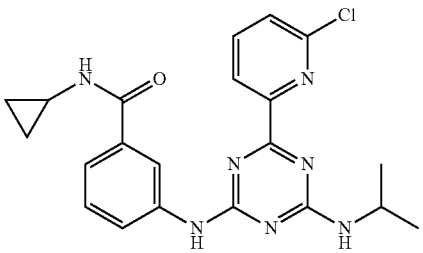 [SMILES: CC(C)Nc1nc(Nc2cccc(C(=O)NC3CC3)c2)nc(-c2cccc(Cl)n2)n1]

¹H NMR (METHANOL-d₄) δ 8.57-8.40 (m, 2H), 8.01 (t, J=7.9 Hz, 1H), 7.82 (d, J=8.0 Hz, 1H), 7.64 (d, J=8.0 Hz, 1H), 7.48-7.40 (m, 2H), 4.33-4.30 (m, 1H), 2.89-2.87 (m, 1H), 1.32 (d, J=6.4 Hz, 6H), 0.87-0.82 (m, 2H), 0.68-0.64 (m, 2H). LC-MS. m/z 424.2 (M+H)⁺.

Example 8. Preparation of Compounds of Formula I Wherein Ring A is Substituted Aryl or Heteroaryl The compounds of this Example are prepared by the general method in Scheme 8, set forth below.

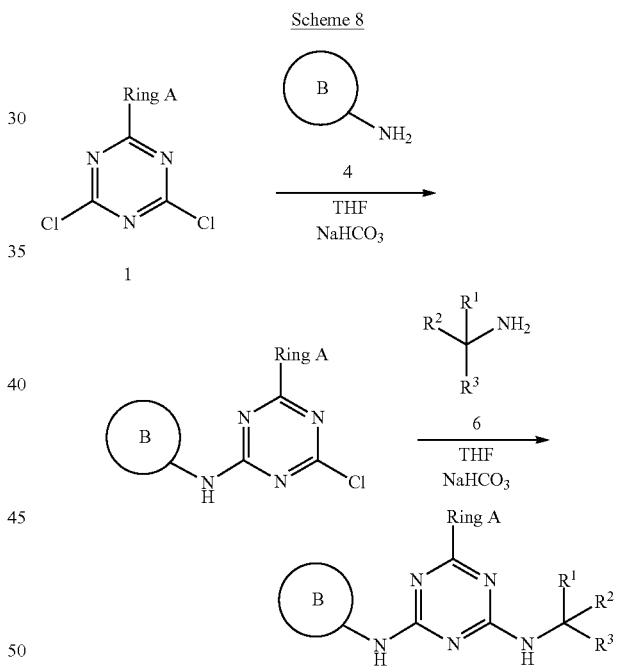

Preparation of 2-Methyl-1-[4-(2-trifluoromethyl-pyridin-4-ylamino)-6-(4-trifluoromethyl-pyrimidin-2-yl)-[1,3,5]triazin-2-ylamino]-propan-2-ol Example 8, Step 1: Preparation of 4-chloro-6-(4-trifluoromethyl-pyrimidin-2-yl)-[1,3,5]triazin-2-yl]-(2-trifluoromethyl-pyridin-4-yl)-amine To a solution of 2,4-dichloro-6-(4-(trifluoromethyl)pyrimidin-2-yl)-1,3,5-triazine (1) (981 mg, 3.31 mmol) in THF (80 mL) was added 2-(trifluoromethyl)pyridin-4-amine (4) (590 mg, 3.64 mmol) and NaHCO₃ (556 mg, 6.6 mmol). The mixture was stirred at refluxing for 18 hours. The mixture was concentrated and poured to water, extracted with ethyl acetate, dried over sodium sulphate, filtered and concentrated to give a residue, which was purified by SiO₂ chromatography to give 4-chloro-6-(4-trifluoromethyl-pyrimidin-2-yl)-[1,3,5]triazin-2-yl]-(2-trifluoromethyl-pyridin-4-yl)-amine (0.45 g, 32%) as a yellow solid.

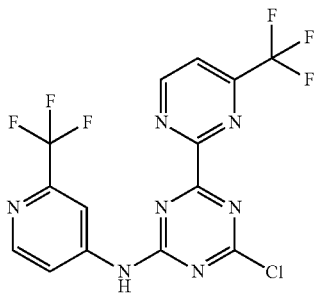 [SMILES: FC(F)(F)c1cc(Nc2nc(Cl)nc(-c3nccc(C(F)(F)F)n3)n2)ccn1]

LCMS: m/z 422.2 (M+H)⁺

The following intermediate was similarly prepared according to Example 8, step 1:

4-chloro-6-(6-(trifluoromethyl)pyridin-2-yl)-N-(2-(trifluoromethyl)pyridin-4-yl)-1,3,5-triazin-2-amine

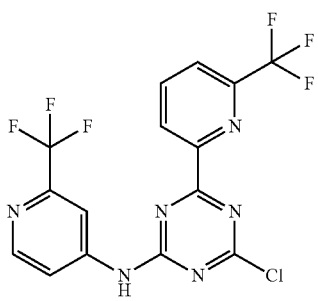

LCMS: m/z 421.2 (M+H)⁺

4-chloro-6-(6-(1,1-difluoroethyl)pyridin-2-yl)-N-(2-(trifluoromethyl)pyridin-4-yl)-1,3,5-triazin-2-amine

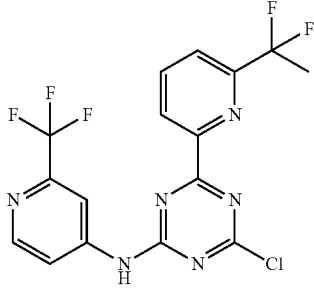 [SMILES: CC(F)(F)c1cccc(-c2nc(Cl)nc(Nc3ccnc(C(F)(F)F)c3)n2)n1]

LCMS: m/z 416.3 (M+H)⁺

Example 8, Step 2: 2-Methyl-1-[4-(2-trifluoromethyl-pyridin-4-ylamino)-6-(4-trifluoromethyl-pyrimidin-2-yl)-[1,3,5]triazin-2-ylamino]-propan-2-ol To a solution of [4-chloro-6-(4-trifluoromethyl-pyrimidin-2-yl)-[1,3,5]triazin-2-yl]-(2-trifluoromethyl-pyridin-4-yl)-amine (90 mg, 0.21 mmol) in anhydrous THF (2 mL) was added 1-amino-2-methyl-propan-2-ol (28.5 mg, 0.32 mmol). The mixture was stirred at ambient temperature for 4 hour. After concentration, the residue was purified by a standard method to give 2-methyl-1-[4-(2-trifluoromethyl-pyridin-4-ylamino)-6-(4-trifluoromethyl-pyrimidin-2-yl)-[1,3,5]triazin-2-ylamino]-propan-2-ol.

Compound 589—2-methyl-1-((4-((2-(trifluoromethyl)pyridin-4-yl)amino)-6-(4-(trifluoromethyl)pyrimidin-2-yl)-1,3,5-triazin-2-yl)amino)propan-2-ol

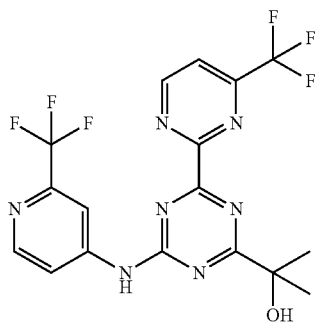 [SMILES: CC(C)(O)c1nc(Nc2ccnc(C(F)(F)F)c2)nc(-c2nccc(C(F)(F)F)n2)n1]

¹H NMR (MeOH-d₄) δ 9.41-9.48 (m, 1H), 8.49-8.72 (m, 2H), 7.92-8.27 (m, 2H), 3.65-3.69 (m, 2H), 1.37 (s, 6H). LC-MS: m/z 475.3 (M+H)⁺.

The following compounds were prepared in a similar manner to the synthetic sequence in Scheme 8, Steps 1 and 2, using appropriate reagents and synthetic intermediates:

Compound 590—2-((4-((2-(trifluoromethyl)pyridin-4-yl)amino)-6-(4-(trifluoromethyl)pyrimidin-2-yl)-1,3,5-triazin-2-yl)amino)propan-1-ol

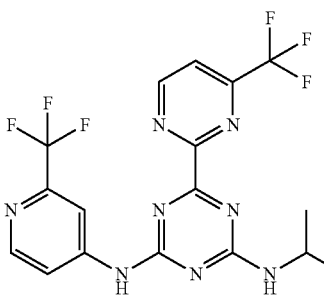

¹H NMR (MeOH-d₄) δ 9.35-9.41 (m, 1H), 8.39-8.64 (m, 2H), 8.18-8.21 (m, 1H), 7.93-8.13 (m, 1H), 4.34-4.46 (m, 1H), 3.67-3.80 (m, 2H), 1.31-1.39 (m, 3H). LC-MS: m/z 461.3 (M+H)⁺.

Compound 591—2-Methyl-3-[4-(6-trifluoromethyl-pyridin-2-yl)-6-(2-trifluoromethyl-pyridin-4-ylamino)-[1,3,5]triazin-2-ylamino]-butan-2-ol

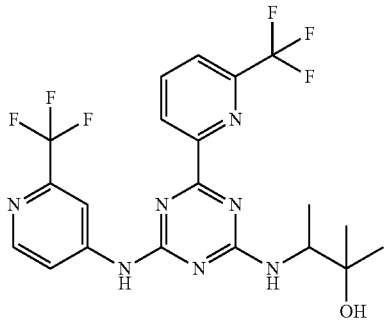 [SMILES: CC(Nc1nc(Nc2ccnc(C(F)(F)F)c2)nc(-c2cccc(C(F)(F)F)n2)n1)C(C)(C)O]

¹H NMR (METHANOL-d₄) δ 8.71-8.66 (m, 2H), 8.25-8.61 (m, 1H), 8.24-7.84 (m, 3H), 4.24-4.22 (m, 1H), 1.31-1.28 (s, 3H). LC-MS: m/z 488.0 (M+H)⁺.

Compound 592—N-tert-Butyl-N'-(3-fluoro-5-methanesulfonyl-phenyl)-6-(6-trifluoromethyl-pyridin-2-yl)-[1,3,5]triazine-2,4-diamine

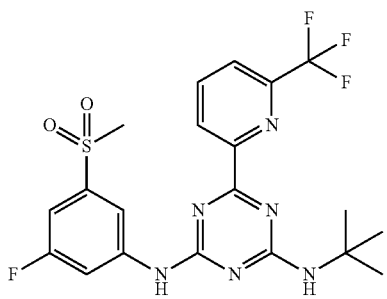 [SMILES: CC(C)(C)Nc1nc(Nc2cc(F)cc(S(C)(=O)=O)c2)nc(-c2cccc(C(F)(F)F)n2)n1]

¹H NMR (METHANOL-d₄) δ 8.75-8.73 (m, 1H), 8.24-8.21 (m, 2H), 7.99-7.92 (m, 2H), 7.39-7.37 (m, 1H), 3.20 (s, 3H), 1.57 (s, 9H). LC-MS: m/z 485.1 (M+H)⁺.

Compound 593—N-Cyclopropylmethyl-N'-(3-fluoro-5-methanesulfonyl-phenyl)-6-(6-trifluoromethyl-pyridin-2-yl)-[1,3,5]triazine-2,4-diamine

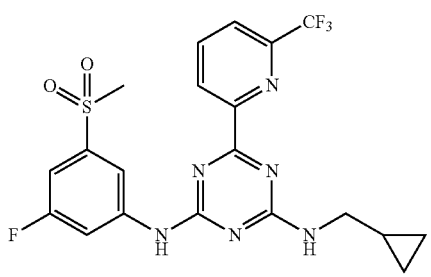 [SMILES: CS(=O)(=O)c1cc(F)cc(Nc2nc(NCC3CC3)nc(-c3cccc(C(F)(F)F)n3)n2)c1]

¹H NMR (METHANOL-d₄) δ 8.71-8.60 (m, 2H), 8.22-7.95 (m, 3H), 7.34-7.33 (m, 1H), 3.44-3.39 (m, 2H), 3.20 (s, 3H), 1.23 (m, 1H), 0.36-0.10 (m, 2H). LC-MS: m/z 483.1 (M+H)⁺.

Compound 594—1-((4-(6-(1,1-difluoroethyl)pyridin-2-yl)-6-((2-(trifluoromethyl)pyridin-4-yl)amino)-1,3,5-triazin-2-yl)amino)-2-methylpropan-2-ol

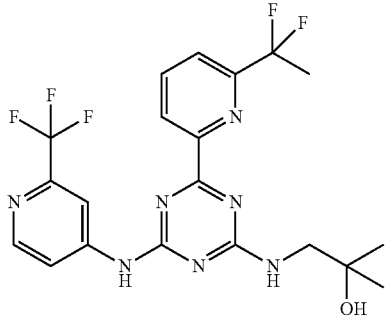 [SMILES: CC(C)(O)CNc1nc(Nc2ccnc(C(F)(F)F)c2)nc(-c2cccc(C(C)(F)F)n2)n1]

¹H NMR (METHANOL-d₄) δ 8.61-8.21 (m, 3H), 8.15-7.85 (m, 3H), 3.59 (d, 2H), 2.11 (t, 3H), 1.27 (d, 6H). LC-MS: m/z 470.2 (M+H)⁺.

Compound 595—N2-(cyclopropylmethyl)-6-(6-(1,1-difluoroethyl)pyridin-2-yl)-N4-(2-(trifluoromethyl)pyridin-4-yl)-1,3,5-triazine-2,4-diamine

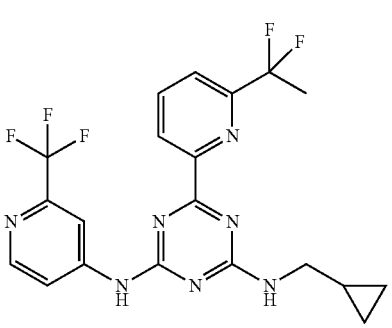 [SMILES: CC(F)(F)c1cccc(-c2nc(NCC3CC3)nc(Nc3ccnc(C(F)(F)F)c3)n2)n1]

¹H NMR (METHANOL-d₄) δ 8.66-8.28 (m, 3H), 8.22-7.85 (m, 3H), 3.42 (dd, 2H), 2.11 (t, 3H), 1.21 (br, 1H), 0.59-0.55 (m, 2H), 0.36-0.31 (m, 2H). LC-MS: m/z 452.2 (M+H)⁺.

Compound 596—N2-(tert-butyl)-6-(6-(1,1-difluoroethyl)pyridin-2-yl)-N4-(2-(1,1-difluoroethyl)pyridin-4-yl)-1,3,5-triazine-2,4-diamine

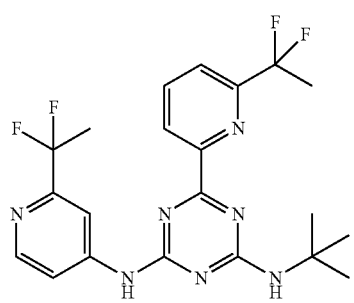 [SMILES: CC(C)(C)Nc1nc(Nc2ccnc(C(C)(F)F)c2)nc(-c2cccc(C(C)(F)F)n2)n1]

¹H NMR (METHANOL-d₄) δ 8.55-8.41 (m, 3H), 8.11-8.07 (m, 1H), 7.86-7.76 (m, 2H), 2.14-1.93 (m, 6H), 1.56 (s, 9H). LC-MS: m/z 450.2 (M+H)⁺.

Compound 597—N2-(cyclopropylmethyl)-6-(6-(trifluoromethyl)pyridin-2-yl)-N4-(2-(trifluoromethyl)pyridin-4-yl)-1,3,5-triazine-2,4-diamine

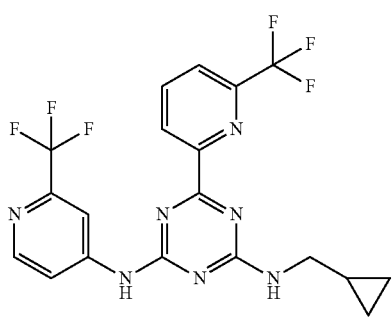 [SMILES: FC(F)(F)c1cc(Nc2nc(NCC3CC3)nc(-c3cccc(C(F)(F)F)n3)n2)ccn1]

¹H NMR (METHANOL-d₄) δ 8.75-8.73 (d, 2H), 8.55-8.38 (m, 1H), 8.28-8.22 (m, 1H), 8.02 (d, 1H), 7.88 (br, 1H), 3.53-3.41 (dd, 2H), 1.21 (br, 1H), 0.64-0.58 (m, 2H), 0.46-0.33 (m, 2H). LC-MS: m/z 456.2 (M+H)⁺.

Compound 598—N2-(cyclopropylmethyl)-N4-(3,5-difluorophenyl)-6-(6-(trifluoromethyl)pyridin-2-yl)-1,3,5-triazine-2,4-diamine

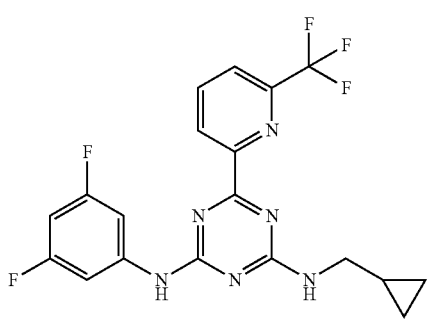 [SMILES: Fc1cc(F)cc(Nc2nc(NCC3CC3)nc(-c3cccc(C(F)(F)F)n3)n2)c1]

¹H NMR (METHANOL-d₄) δ 8.68-865 (m, 1H), 8.22-8.18 (m, 1H), 7.97-7.95 (m, 1H), 7.56-7.52 (m, 2H), 6.61-6.56 (m, 1H), 3.44-3.38 (m, 2H), 1.20-1.18 (m, 1H), 0.57-0.55 (m, 2H), 0.34-0.33 (m, 2H). LC-MS: m/z 423.2 (M+H)⁺.

Compound 599—N2-(3-chloro-5-(methylsulfonyl)phenyl)-N4-(cyclopropylmethyl)-6-(6-(trifluoromethyl)pyridin-2-yl)-1,3,5-triazine-2,4-diamine

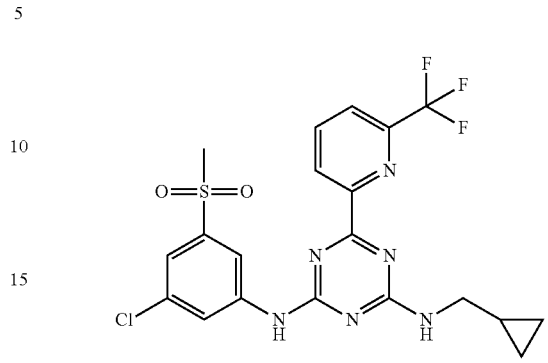

¹H NMR (METHANOL-d₄) δ 8.73-8.71 (m, 2H), 8.24-8.20 (t, J=8 Hz, 1H), 8.10 (s, 1H), 7.99-7.97 (d, J=8 Hz, 1H), 7.61 (s, 1H), 3.49-3.43 (m, 2H), 3.19 (s, 1H), 1.23-1.19 (m, 1H), 0.58-0.55 (m, 2H), 0.39-0.35 (m, 2H). LC-MS: m/z 499.2 (M+H)⁺.

Compound 600—N2-(tert-butyl)-N4-(3-chloro-5-(methylsulfonyl)phenyl)-6-(6-(trifluoromethyl)pyridin-2-yl)-1,3,5-triazine-2,4-diamine

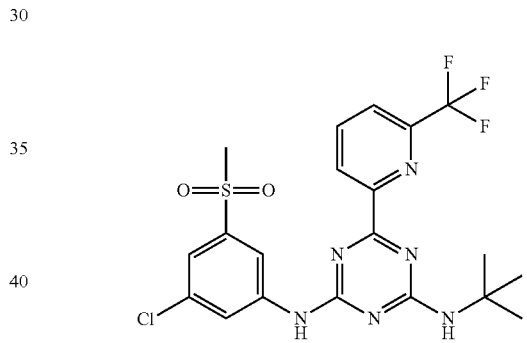

¹H NMR (METHANOL-d₄) δ 8.68-8.66 (m, 2H), 8.43-8.28 (m, 1H), 8.18-8.14 (m, 2H), 7.94-7.92 (d, J=7.6 Hz, 1H), 7.58-7.53 (m, 1H), 3.16 (s, 3H), 1.53 (s, 9H). LC-MS: m/z 501.2 (M+H)⁺.

Compound 601—N2-(tert-butyl)-N4-(3,5-difluorophenyl)-6-(6-(trifluoromethyl)pyridin-2-yl)-1,3,5-triazine-2,4-diamine

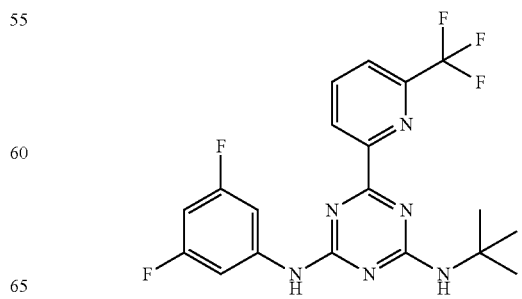

¹H NMR (METHANOL-d₄) δ 8.64-8.62 (m, 1H), 8.20-8.16 (m, 1H), 7.95-7.93 (m, 1H), 7.50-7.48 (m, 2H), 6.60-6.53 (m, 1H), 1.53 (s, 9H). LC-MS: m/z 425.5 (M+H)⁺.

Compound 602—N2-(tert-butyl)-6-(6-(trifluoromethyl)pyridin-2-yl)-N4-(2-(trifluoromethyl)pyridin-4-yl)-1,3,5-triazine-2,4-diamine

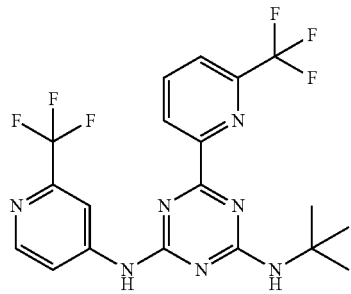 [SMILES: CC(C)(C)Nc1nc(Nc2ccnc(C(F)(F)F)c2)nc(-c2cccc(C(F)(F)F)n2)n1]

¹H NMR (METHANOL-d₄) δ 8.67-8.64 (m, 1H), 8.49-8.48 (m, 1H), 8.21-8.17 (m., 2H), 7.96-7.94 (m, 1H), 7.81 (br.s., 1H). 1.55 (s, 9H). LC-MS: m/z 458.2 (M+H)⁺.

Compound 603—N2-(3,5-difluorophenyl)-N4-isopropyl-6-(6-(trifluoromethyl)pyridin-2-yl)-1,3,5-triazine-2,4-diamine

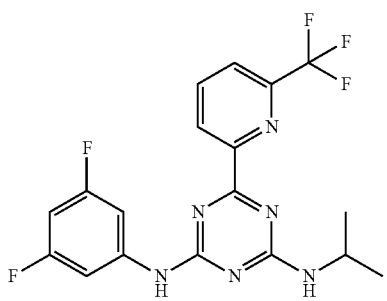

¹H NMR (METHANOL-d₄) δ 8.35-8.16 (d, 1H), 7.79-7.65 (m, 1H), 7.58-7.56 (s, 2H), 7.30-7.20 (d, 1H), 6.10-6.0 (s, 1H), 4.50-4.27 (m, 1H), 1.33-1.31 (d, 6H). LC-MS: m/z 411.1 (M+H)⁺.

Compound 604—N2-(cyclopropylmethyl)-N4-(2-(1,1-difluoroethyl)pyridin-4-yl)-6-(6-(trifluoromethyl)pyridin-2-yl)-1,3,5-triazine-2,4-diamine

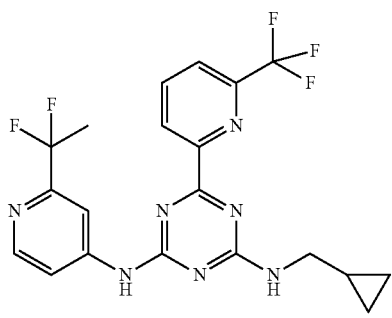 [SMILES: CC(F)(F)c1cc(Nc2nc(NCC3CC3)nc(-c3cccc(C(F)(F)F)n3)n2)ccn1]

¹H NMR (METHANOL-d₄) δ 8.68 (d, 1H), 8.50-8.18 (m, 3H), 8.02-7.73 (m, 2H), 3.42 (dd, 2H), 2.01 (t, 2H), 1.24-1.16 (m, 1H), 0.58-0.55 (m, 2H), 0.35-0.33 (m, 2H). LC-MS: m/z 452.1 (M+H)⁺.

Compound 605—1-((4-(6-(1,1-difluoroethyl)pyridin-2-yl)-6-((2-(1,1-difluoroethyl)pyridin-4-yl)amino)-1,3,5-triazin-2-yl)amino)-2-methylpropan-2-ol

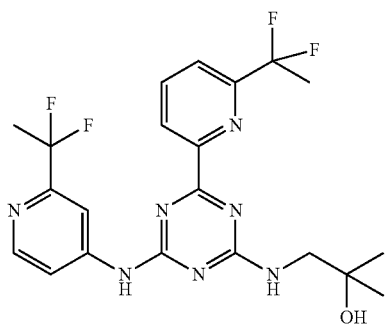 [SMILES: CC(C)(O)CNc1nc(Nc2ccnc(C(C)(F)F)c2)nc(-c2cccc(C(C)(F)F)n2)n1]

¹H NMR (METHANOL-d₄) δ 8.58-8.13 (m 3H), 8.11-7.76 (m, 3H), 3.60 (d, 2H), 2.17-1.93 (m, 6H), 1.28 (d, 6H). LC-MS: m/z 466.1 (M+H)⁺.

Compound 606—1-(4-((4-((tert-butylamino)-6-(6-(1,1-difluoroethyl)pyridin-2-yl)-1,3,5-triazin-2-yl)amino)pyridin-2-yl)cyclopropanecarbonitrile

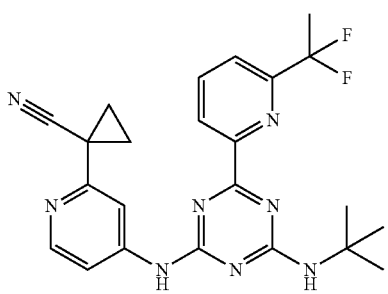 [SMILES: CC(C)(C)Nc1nc(Nc2ccnc(C3(C#N)CC3)c2)nc(-c2cccc(C(C)(F)F)n2)n1]

¹H NMR (METHANOL-d₄) δ 8.71-8.5 (m, 1H), 8.4-8.2 (m, 1H), 8.1 (m, 1H), 7.9 (m, H), 7.6 (m, 1H), 2.15-2.06 (t, J=18 Hz, 3H), 1.78-1.74 (d, J=16 Hz, 4H), 1.55 (s, 9H). LC-MS: m/z 450.2 (M+H)⁺.

Compound 607—N2-(cyclopropylmethyl)-N4-(3-(methylsulfonyl)phenyl)-6-(6-(trifluoromethyl)pyridin-2-yl)-1,3,5-triazine-2,4-diamine

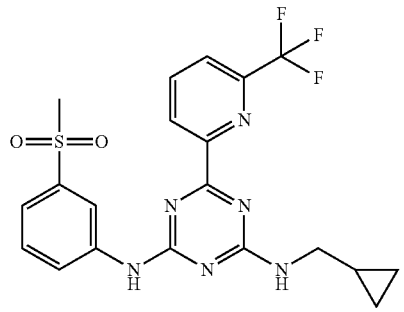 [SMILES: CS(=O)(=O)c1cccc(Nc2nc(NCC3CC3)nc(-c3cccc(C(F)(F)F)n3)n2)c1]

¹H NMR (DMSO, T=273+80K) δ 10.03 (s, 1H), 8.78 (s, 1H), 8.59-8.57 (m, 1H), 8.28-8.24 (m, 1H), 8.04-7.97 (m, 2H), 7.59-7.84 (m, 3H), 3.35 (br.s., 2H), 3.17 (S, 3H), 1.15-1.14 (m, 1H), 0.48-0.46 (m, 2H), 0.32-0.31 (m, 2H). LC-MS: m/z 465.2 (M+H)⁺.

Compound 608—1-(4-((4-(tert-butylamino)-6-(6-(trifluoromethyl)pyridin-2-yl)-1,3,5-triazin-2-yl)amino)pyridin-2-yl)cyclopropanecarbonitrile

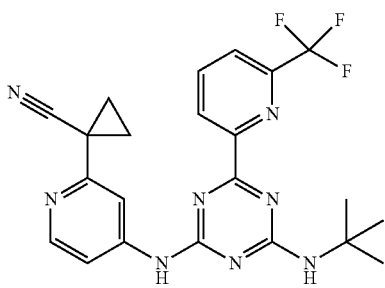 [SMILES: CC(C)(C)Nc1nc(Nc2ccnc(C3(C#N)CC3)c2)nc(-c2cccc(C(F)(F)F)n2)n1]

¹H NMR (METHANOL-d₄) δ 8.87-8.85 (m, 1H), 8.7-8.11 (m, 2H), 7.96-7.87 (m, 1H), 7.585-7.583 (m, 1H) 1.8-1.70 (d, 4H), 1.59-1.54 (m, 6H). LC-MS: m/z 455.1 (M+H)⁺.

Compound 609—N2-(3-chloro-5-(methylsulfonyl)phenyl)-N4-(cyclopropylmethyl)-6-(6-(1,1-difluoroethyl)pyridin-2-yl)-1,3,5-triazine-2,4-diamine

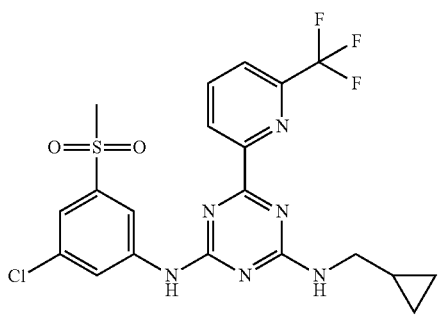 [SMILES: CS(=O)(=O)c1cc(Cl)cc(Nc2nc(NCC3CC3)nc(-c3cccc(C(F)(F)F)n3)n2)c1]

¹H NMR (METHANOL-d₄) δ 8.65 (s, 1H), 8.54-8.51 (m, 1H), 8.06-8.04 (t, J=7.8 Hz, 2H), 7.84-7.82 (d, J=7.6 Hz, 1H), 7.57-7.56 (m, 1H), 3.39-3.37 (m, 2H), 3.14 (s, 3H), 2.13-20.3 (t, J=19.2 Hz, 1H), 1.18-1.13 (m, 1H), 0.54-0.50 (m, 2H), 0.32-0.31 (m, 2H). LC-MS: m/z 501.2 (M+H)⁺.

Compound 610—N2-(cyclopropylmethyl)-6-(6-(1,1-difluoroethyl)pyridin-2-yl)-N4-(2-(1,1-difluoroethyl)pyridin-4-yl)-1,3,5-triazine-2,4-diamine

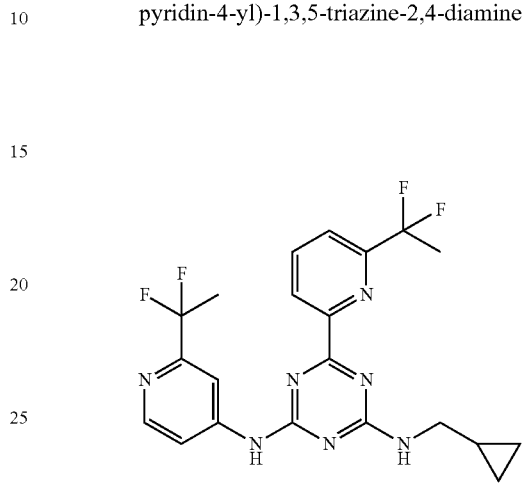

¹H NMR (METHANOL-d₄) δ 8.56-8.13 (m, 3H), 8.11-7.77 (m, 3H), 3.45-3.40 (m, 2H), 2.15-1.94 (m, 6H), 1.22-1.18 (m, 1H), 0.58-1.19 (m, 1H), 0.59-0.54 (m, 2H), 0.36-0.31 (m, 2H). LC-MS: m/z 448.2 (M+H)⁺.

Compound 611—N2-(cyclopropylmethyl)-6-(6-(1,1-difluoroethyl)pyridin-2-yl)-N4-(3-(methylsulfonyl)phenyl)-1,3,5-triazine-2,4-diamine

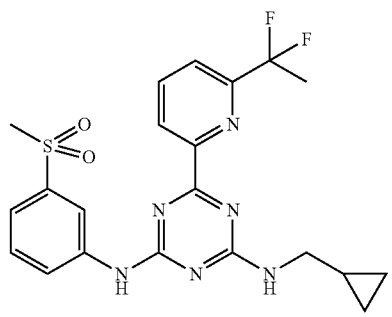 [SMILES: CC(F)(F)c1cccc(-c2nc(NCC3CC3)nc(Nc3cccc(S(C)(=O)=O)c3)n2)n1]

¹H NMR (METHANOL-d₄) δ 8.96 (s, 1H), 8.58-8.55 (m, 1H), 8.10-7.78 (m, 3H), 7.62-7.55 (m, 2H), 3.44-3.41 (m, 2H), 3.14 (d, 3H), 2.11 (t, 3H), 1.20-1.17 (m, 1H), 0.57-0.52 (m, 2H), 0.36-0.33 (m, 2H). LC-MS: m/z 461.2 (M+H)⁺.

Compound 612—N2-(cyclopropylmethyl)-6-(6-(1,1-difluoroethyl)pyridin-2-yl)-N4-(3-fluoro-5-(methylsulfonyl)phenyl)-1,3,5-triazine-2,4-diamine

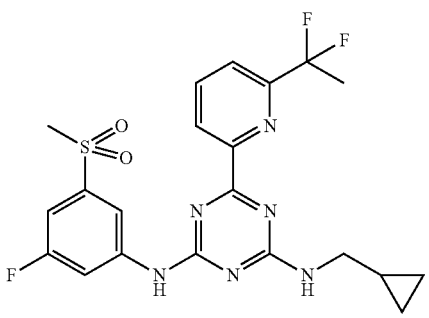 [SMILES: CC(F)(F)c1cccc(-c2nc(NCC3CC3)nc(Nc3cc(F)cc(S(C)(=O)=O)c3)n2)n1]

¹H NMR (METHANOL-d₄) δ 8.58-8.13 (m, 2H), 8.12-7.86 (m, 2H), 7.36-7.32 (m, 1H), 3.46-3.41 (m, 2H), 3.19 (d, 3H), 2.13 (t, 3H), 1.24-1.18 (m, 1H), 0.59-0.56 (m, 2H), 0.37-0.35 (m, 2H). LC-MS: m/z 479.2 (M+H)⁺.

Compound 613—6-(6-(1,1-difluoroethyl)pyridin-2-yl)-N2-(3-fluoro-5-(methylsulfonyl)phenyl)-N4-isopropyl-1,3,5-triazine-2,4-diamine

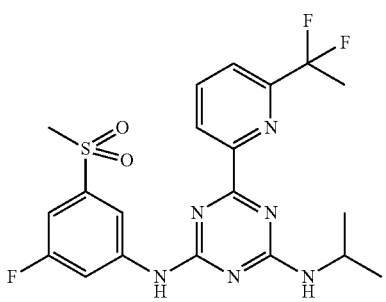 [SMILES: CC(C)Nc1nc(Nc2cc(F)cc(S(C)(=O)=O)c2)nc(-c2cccc(C(C)(F)F)n2)n1]

¹H NMR (METHANOL-d₄) δ 8.57 (d, 2H), 8.13-7.86 (m, 3H), 7.37-7.32 (m, 1H), 4.37-4.34 (m, 1H), 3.19 (d, 3H), 2.18-2.06 (m, 3H), 1.35-1.32 (m, 6H). LC-MS: m/z 467.2 (M+H)⁺.

Compound 614—N2-(3-chloro-5-(methylsulfonyl)phenyl)-6-(6-(1,1-difluoroethyl)pyridin-2-yl)-N4-isopropyl-1,3,5-triazine-2,4-diamine

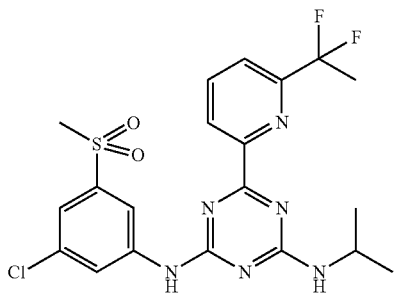 [SMILES: CC(C)Nc1nc(Nc2cc(Cl)cc(S(C)(=O)=O)c2)nc(-c2cccc(C(C)(F)F)n2)n1]

¹H NMR (METHANOL-d₄) δ 8.73-8.33 (m, 2H), 8.11 (t, 2H), 7.87 (d, 1H), 7.61 (s, 1H), 4.48-4.28 (m, 1H), 3.20 (d, 3H), 2.13 (t, 3H), 1.34 (t, 6H). LC-MS: m/z 488.2 (M+H)⁺.

Compound 615—N2-(tert-butyl)-N4-(3-chloro-5-(methylsulfonyl)phenyl)-6-(6-(1,1-difluoroethyl)pyridin-2-yl)-1,3,5-triazine-2,4-diamine

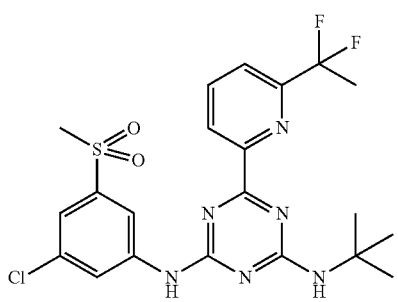

¹H NMR (METHANOL-d₄) δ 8.57-8.56 (m, 1H), 8.43-8.25 (m, 2H), 8.12-8.06 (m, 1H), 7.85 (d, 1H), 7.61 (s, 1H), 3.17 (s, 3H), 2.11 (t, 3H), 1.56 (s, 9H). LC-MS: m/z 497.2 (M+H)⁺.

Compound 616—N2-(tert-butyl)-6-(6-(1,1-difluoroethyl)pyridin-2-yl)-N4-(3-fluoro-5-(methylsulfonyl)phenyl)-1,3,5-triazine-2,4-diamine

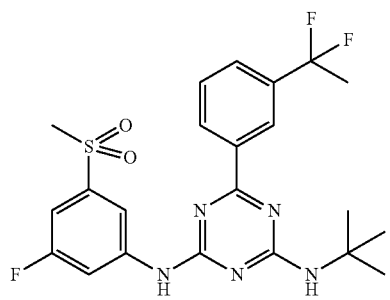 [SMILES: CC(C)(C)Nc1nc(Nc2cc(F)cc(S(C)(=O)=O)c2)nc(-c2cccc(C(C)(F)F)c2)n1]

¹H NMR (METHANOL-d₄) δ 8.59-8.42, 8.13-8.05 (m, 2H), 7.87 (d, 1H), 7.39-7.34 (m, 1H), 3.19 (s, 3H), 2.18-2.06 (m, 3H), 1.57 (s, 9H). LC-MS: m/z 481.2 (M+H)⁺.

Compound 617—1-(4-((4-((cyclopropylmethyl)amino)-6-(6-(trifluoromethyl)pyridin-2-yl)-1,3,5-triazin-2-yl)amino)pyridin-2-yl)cyclopropanecarbonitrile

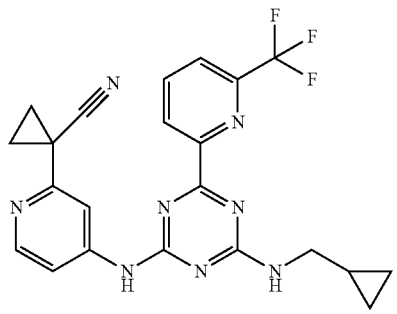 [SMILES: N#CC1(c2cc(Nc3nc(NCC4CC4)nc(-c4cccc(C(F)(F)F)n4)n3)ccn2)CC1]

¹H NMR (METHANOL-d₄) δ 8.87-8.85 (m, 1H), 8.7-8.11 (m, 2H), 7.96-7.87 (m, 1H), 7.585-7.583 (m, 1H), 3.35 (br.s., 2H), 1.15-1.14 (m, 1H), 0.48-0.46 (m, 2H), 0.32-0.31 (m, 2H). LC-MS: m/z 453.1 (M+H)⁺.

Compound 618—(4-((4-((cyclopropylmethyl)amino)-6-(6-(1,1-difluoroethyl)pyridin-2-yl)-1,3,5-triazin-2-yl)amino)pyridin-2-yl)-2-methylpropanenitrile

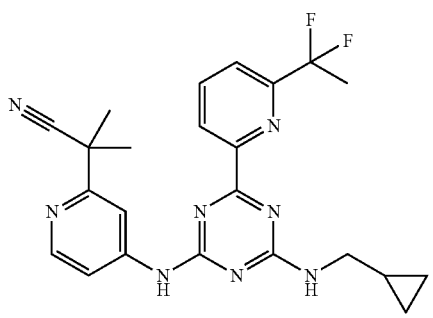 [SMILES: CC(F)(F)c1cccc(-c2nc(NCC3CC3)nc(Nc3ccnc(C(C)(C)C#N)c3)n2)n1]

¹H NMR (METHANOL-d₄) δ 8.60-8.56 (m, 1H), 8.44-8.37 (m, 2H), 8.11-8.03 (m, 1H), 7.87-7.85 (m, 1H), 7.62-7.60 (m, 1H), 3.45-3.43 (d, 2H), 2.15-2.06 (t, 3H), 1.78 (s, 6H), 1.21-1.16 (m, 1H), 0.57-0.54 (m, 2H), 0.36-0.33 (m, 2H). LC-MS: m/z 451.2 (M+H)⁺.

Compound 619—1-(4-((4-((cyclopropylmethyl)amino)-6-(6-(1,1-difluoroethyl)pyridin-2-yl)-1,3,5-triazin-2-yl)amino)pyridin-2-yl)cyclopropanecarbonitrile

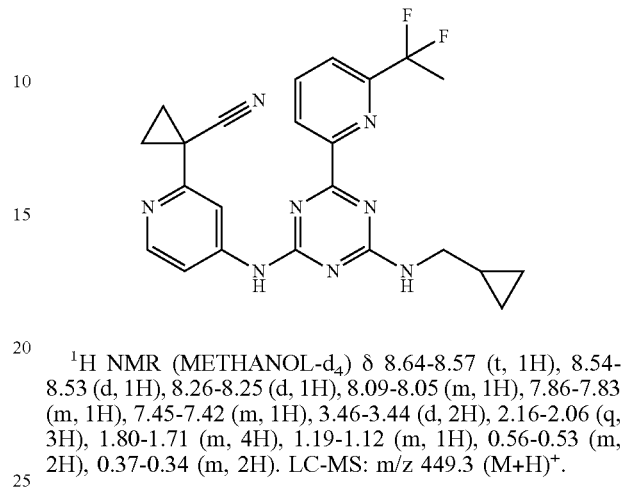

¹H NMR (METHANOL-d₄) δ 8.64-8.57 (t, 1H), 8.54-8.53 (d, 1H), 8.26-8.25 (d, 1H), 8.09-8.05 (m, 1H), 7.86-7.83 (m, 1H), 7.45-7.42 (m, 1H), 3.46-3.44 (d, 2H), 2.16-2.06 (q, 3H), 1.80-1.71 (m, 4H), 1.19-1.12 (m, 1H), 0.56-0.53 (m, 2H), 0.37-0.34 (m, 2H). LC-MS: m/z 449.3 (M+H)⁺.

N2-isopropyl-6-(6-(2,2,2-trifluoroethylamino)pyridin-2-yl)-N4-(2-(trifluoromethyl)pyridin-4-yl)-1,3,5-triazine-2,4-diamine

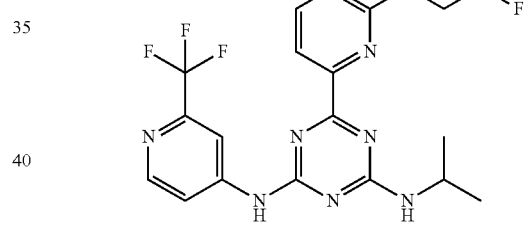

¹H NMR (DMSO-d₄): δ 10.6-10.2 (m, 1H), 8.7-8.4 (m, 2H), 8.4-7.8 (m, 2H), 7.8-7.5 (m, 2H), 7.4-7.2 (m, 1H), 6.8 (m, 1H), 4.5-4.0 (m, 3H), 1.2 (d, J=4.8 Hz, 1H). LC-MS: m/z 473.2 (M+H)⁺.

The following compounds were prepared according to the general procedure shown in Scheme 4:

The following intermediates prepared according to Example 4, step 1, using appropriate reagents:

Preparation of (4,6-Dichloro-[1,3,5]triazin-2-yl)-oxetan-3-yl-amine

Using the standard procedure described above yielded the title compound which was directly used in the next step.

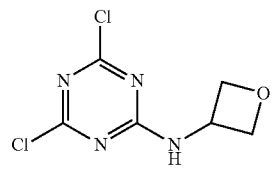 [SMILES: Clc1nc(Cl)nc(NC2COC2)n1]

Preparation of (4,6-Dichloro-[1,3,5]triazin-2-yl)-(3-oxa-bicyclo[3.1.0]hex-6-yl)-amine Using the standard procedure described above except DIPEA (1 eq) was added to give (4,6-Dichloro-[1,3,5]triazin-2-yl)-(3-oxa-bicyclo[3.1.0]hex-6-yl-amine as a white solid.

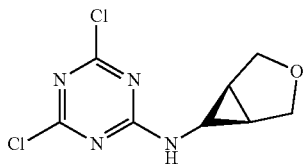

LCMS: m/z 247.1 (M+H)$^+$.

The following intermediates were prepared according to Example 4, step 2:

Preparation of 4-chloro-6-(2-fluoro-3-methoxyphenyl)-N-(oxetan-3-yl)-1,3,5-triazin-2-amine Using the standard procedure described above yielded the title compound

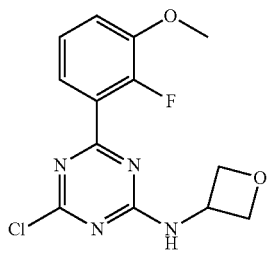 [SMILES: COc1cccc(-c2nc(Cl)nc(NC3COC3)n2)c1F]

LCMS: m/z 311.0 (M+H)$^+$.

Step 2-9: Preparation of 4-chloro-6-(2-fluoro-5-methoxyphenyl)-N-(oxetan-3-yl)-1,3,5-triazin-2-amine Using the standard procedure described above yielded the title compound.

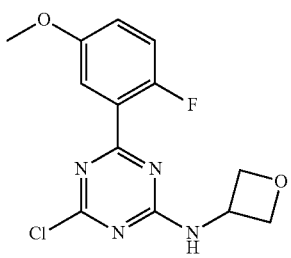 [SMILES: COc1ccc(F)c(-c2nc(Cl)nc(NC3COC3)n2)c1]

LCMS: m/z 311.1 (M+H)$^+$.

Preparation of N-((1R,5S,6r)-3-oxabicyclo[3.1.0]hexan-6-yl)-4-chloro-6-(2-fluoro phenyl)-1,3,5-triazin-2-amine Using the standard procedure described above yielded the title compound

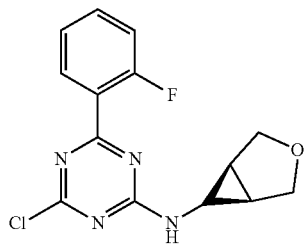

LCMS: m/z 306.9 (M+H)$^+$.

Preparation of 4-chloro-6-(2-fluorophenyl)-N-isobutyl-1,3,5-triazin-2-amine

Using the standard procedure described yielded the title compound

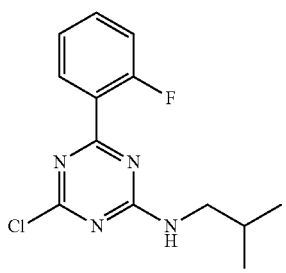 [SMILES: CC(C)CNc1nc(Cl)nc(-c2ccccc2F)n1]

LCMS: m/z 281.1 (M+H)$^+$.

Preparation of 4-Chloro-6-(6-fluoro-5-methoxyphenyl)-N-isopropyl-1,3,5-triazin-2-amine Using the standard procedure described above yielded the title compound as a white solid.

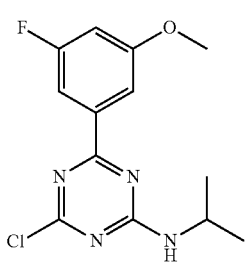 [SMILES: COc1cc(F)cc(-c2nc(Cl)nc(NC(C)C)n2)c1]

LCMS: m/z 297.1 (M+H)$^+$.

Preparation of 4-(3-(1-((tert-butyldimethylsilyl)oxy)cyclopropyl)phenyl)-6-chloro-N-isopropyl-1,3,5-triazin-2-amine Using the standard procedure described above yielded the title compound as a colorless oil.

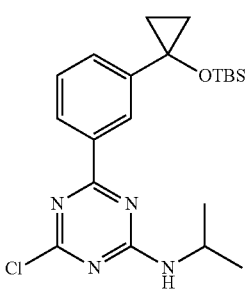 [SMILES: CC(C)Nc1nc(Cl)nc(-c2cccc(C3(O[Si](C)(C)C(C)(C)C)CC3)c2)n1]

The following compounds were synthesized using Example 4, step 3 (Procedure C), utilizing appropriate intermediates and reagents:

Compound 621—1-(4-(2-fluorophenyl)-6-(5-fluoro-pyridin-3-ylamino)-1,3,5-triazin-2-ylamino)-2-methylpropan-2-ol

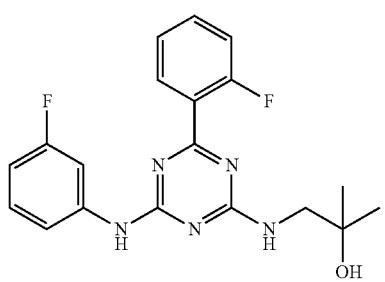 [SMILES: CC(C)(O)CNc1nc(Nc2cccc(F)c2)nc(-c2ccccc2F)n1]

$^1$H NMR (METHANOL-d$_4$) δ 8.68-9.01 (m, 1H), 8.44-8.51 (m, 2H), 8.20-8.23 (m, 1H), 8.76-8.77 (m, 1H), 7.38-7.47 (m, 2H), 7.76-7.81 (m, 2H), 3.56-3.61 (m, 2H), 1.27-1.31 (m, 6H). LC-MS: m/z 373.3 (M+H)$^+$.

Compound 622—1-(4-(2-fluorophenyl)-6-(6-fluoro-pyridin-3-ylamino)-1,3,5-triazin-2-ylamino)-2-methylpropan-2-ol

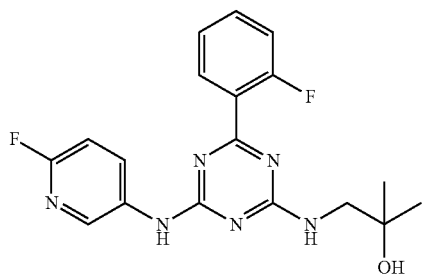 [SMILES: CC(C)(O)CNc1nc(Nc2ccc(F)nc2)nc(-c2ccccc2F)n1]

$^1$H NMR (METHANOL-d$_4$) δ 8.08-8.15 (m, 1H), 7.96-7.97 (m, 2H), 7.83-7.89 (m, 1H), 7.51-7.54 (m, 2H), 7.21-7.31 (m, 2H), 3.53-3.55 (m, 2H), 3.56-3.61 (m, 2H), 1.25-1.27 (m, 6H). LC-MS: m/z 373.2 (M+H)$^+$.

Compound 623—1-(4-(2-fluorophenyl)-6-(2-fluoro-pyridin-4-ylamino)-1,3,5-triazin-2-ylamino)-2-methylpropan-2-ol

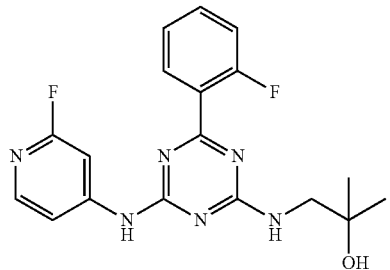 [SMILES: CC(C)(O)CNc1nc(Nc2ccnc(F)c2)nc(-c2ccccc2F)n1]

$^1$H NMR (METHANOL-d$_4$) δ 8.27-8.55 (m, 1H), 8.25-8.27 (m, 2H), 7.77-7.78 (m, 1H), 7.39-7.47 (m, 2H), 7.16-7.19 (m, 1H), 3.51-3.53 (m, 2H), 1.28 (m, 6H). LC-MS: m/z 373.2 (M+H)$^+$.

Compound 624—6-(2-Fluoro-3-methoxy-phenyl)-N-oxetan-3-yl-N'-(2-trifluoromethyl-pyridin-4-yl)-[1,3,5]triazine-2,4-diamine

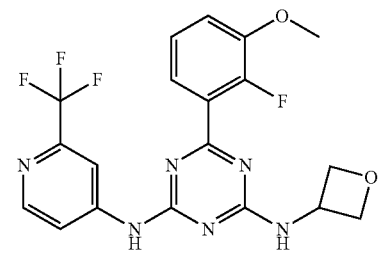 [SMILES: COc1cccc(-c2nc(Nc3ccnc(C(F)(F)F)c3)nc(NC3COC3)n2)c1F]

$^1$H NMR (DMSO-d$_6$) δ 10.53-10.43 (m, 1H), 8.89-7.92 (m, 4H), 7.55-7.48 (m, 1H), 7.39-7.34 (m, 1H), 7.25 (t, J=8.25 Hz, 1H), 5.07-5.01 (m, 1H), 4.83-4.77 (m, 2H), 4.61 (t, J=6.18 Hz, 2H), 3.88 (s, 3H). LC-MS: m/z 437.2 (M+H)$^+$.

Compound 625—6-(2-Fluoro-phenyl)-N-(5-fluoro-pyridin-3-yl)-N'-oxetan-3-yl-[1,3,5]triazine-2,4-diamine

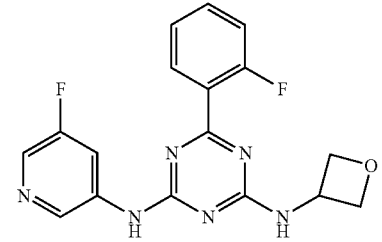 [SMILES: Fc1cncc(Nc2nc(NC3COC3)nc(-c3ccccc3F)n2)c1]

$^1$H NMR (DMSO-d$_6$) δ 10.17-10.12 (m, 1H), 8.77-7.98 (m, 5H), 7.61-7.59 (m, 1H), 7.37-7.34 (m., 2H), 5.09-5.06 (m, 1H), 4.81-4.80 (m, 2H), 4.62-4.61 (m, 2H). LC-MS: m/z 357.1 (M+H)$^+$.

Compound 626—6-(2-Fluoro-phenyl)-N-(6-fluoro-pyridin-3-yl)-N'-oxetan-3-yl-[1,3,5]triazine-2,4-diamine

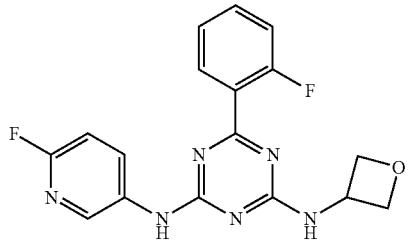 [SMILES: Fc1ccc(Nc2nc(NC3COC3)nc(-c3ccccc3F)n2)cn1]

¹H NMR (DMSO-d₆) δ 10.06-9.59 (m, 1H), 8.71-8.29 (m, 3H), 8.07-7.95 (m, 1H), 7.61-7.56 (m., 1H), 7.34-7.28 (m, 2H), 7.16-7.15 (m, 1H), 5.06-4.95 (m, 1H), 4.77-4.76 (m, 2H), 4.59-4.56 (m, 2H). LC-MS: m/z 357.1 (M+H)⁺.

Compound 627—6-(2-Fluoro-phenyl)-N-oxetan-3-yl-N'-(2-trifluoromethyl-pyridin-4-yl)-[1,3,5]triazine-2,4-diamine

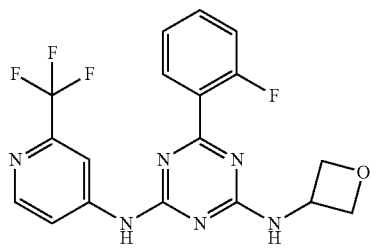 [SMILES: Fc1ccccc1-c1nc(Nc2ccnc(C(F)(F)F)c2)nc(NC2COC2)n1]

¹H NMR (METHANOL-d₄) δ 8.56-8.47 (m, 2H), 8.17-7.89 (m, 2H), 7.58-7.53 (m, 1H), 7.31-7.21 (m., 2H), 5.34-5.24 (m, 1H), 5.01-4.99 (m, 2H), 4.80-4.73 (m, 2H). LC-MS: m/z 407.2 (M+H)⁺.

Compound 628—6-(2-Fluoro-phenyl)-N-(2-fluoro-pyridin-4-yl)-N'-oxetan-3-yl-[1,3,5]triazine-2,4-diamine

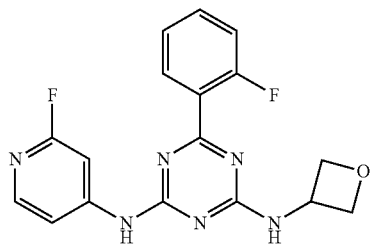 [SMILES: Fc1cc(Nc2nc(NC3COC3)nc(-c3ccccc3F)n2)ccn1]

¹H NMR (DMSO-d₆) δ 10.45-10.39 (m, 1H), 8.86-8.68 (m, 1H), 8.08-7.69 (m, 5H), 7.37-7.33 (m., 2H), 5.11-5.09 (m, 1H), 4.85-4.80 (m, 2H), 4.64-4.59 (m, 2H). LC-MS: m/z 357.1 (M+H)⁺.

Compound 629—6-(2-Fluoro-phenyl)-N-oxetan-3-yl-N'-(5-trifluoromethyl-pyridin-3-yl)-[1,3,5]triazine-2,4-diamine

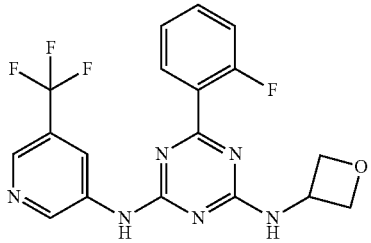 [SMILES: Fc1ccccc1-c1nc(Nc2cncc(C(F)(F)F)c2)nc(NC2COC2)n1]

¹H NMR (DMSO-d₆) δ 10.34-10.20 (m, 1H), 9.25-8.50 (m, 3H), 8.06-8.00 (m, 1H), 7.77-7.72 (m., 1H), 7.39-7.25 (m, 2H), 5.10-4.99 (m, 1H), 4.79-4.56 (m, 2H), 4.59-4.52 (m, 2H). LC-MS: m/z 407.3 (M+H)⁺.

Compound 630—6-(2-Fluoro-5-methoxy-phenyl)-N-isopropyl-N'-(2-trifluoromethyl-pyridin-4-yl)-[1,3,5]triazine-2,4-diamine

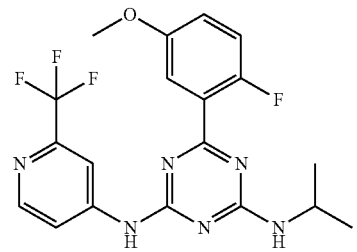 [SMILES: COc1ccc(F)c(-c2nc(Nc3ccnc(C(F)(F)F)c3)nc(NC(C)C)n2)c1]

¹H NMR (METHANOL-d₄) δ 8.70-7.82 (m, 3H), 7.67-7.61 (m, 1H), 7.16-7.06 (m, 2H), 4.30-4.25 (m., 1H), 3.84 (s, 3H), 4.26-4.23 (m, 1H), 1.317-1.279 (d, J=15.2 MHz, 3H). LC-MS: m/z 422.9 (M+H)⁺.

Compound 631—6-(2-Fluoro-3-methoxy-phenyl)-N-isopropyl-N'-(2-trifluoromethyl-pyridin-4-yl)-[1,3,5]triazine-2,4-diamine

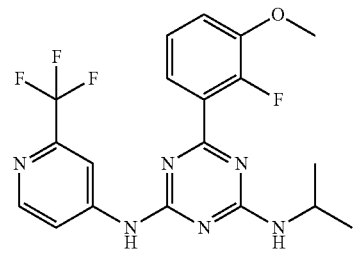 [SMILES: COc1cccc(-c2nc(Nc3ccnc(C(F)(F)F)c3)nc(NC(C)C)n2)c1F]

¹H NMR (METHANOL-d₄) δ 8.65-7.83 (m, 3H), 7.59-7.56 (m, 1H), 7.24-7.16 (m, 2H), 4.28-4.25 (m., 1H), 3.92 (s, 3H), 1.315-1.272 (d, J=17.2 MHz, 3H). LC-MS: m/z 423.0 (M+H)⁺.

Compound 632—2-(4-((4-(2-fluorophenyl)-6-(iso-propylamino)-1,3,5-triazin-2-yl)amino)pyridin-2-yl)propan-2-ol

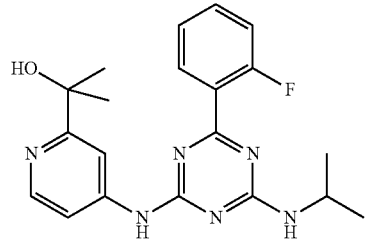 [SMILES: CC(C)Nc1nc(Nc2ccnc(C(C)(C)O)c2)nc(-c2ccccc2F)n1]

¹H NMR (DMSO-d₆) δ 8.30-8.08 (m, 3H), 7.70-7.51 (m, 2H), 7.29 (t, 1H), 7.24-7.19 (dd, 1H), 4.36-4.34 (m, 1H), 1.57 (s, 6H), 1.32-1.28 (m, 6H). LC-MS: m/z 383.3 (M+H)⁺.

Compound 633—2-Fluoro-3-[4-isopropylamino-6-(2-trifluoromethyl-pyridin-4-ylamino)-[1,3,5]triazin-2-yl]-phenol

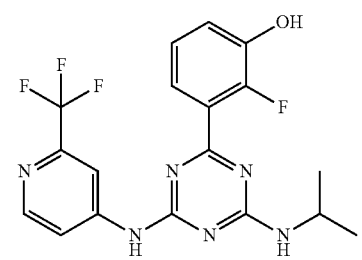 [SMILES: CC(C)Nc1nc(Nc2ccnc(C(F)(F)F)c2)nc(-c2cccc(O)c2F)n1]

¹H NMR (METHANOL-d₄) δ 8.70-8.68 (d, J=6 Hz, 1H), 8.56-8.49 (m, 1H), 7.90-7.89 (m, 1H), 7.59-7.57 (m., 1H), 7.33-7.23 (m, 2H), 4.39-4.35 (m, 1H), 1.407-1.391 (d, J=6.4 Hz, 3H). LC-MS: m/z 409.3 (M+H)⁺.

Compound 634—4-Fluoro-3-[4-isopropylamino-6-(2-trifluoromethyl-pyridin-4-ylamino)-[1,3,5]triazin-2-yl]-phenol

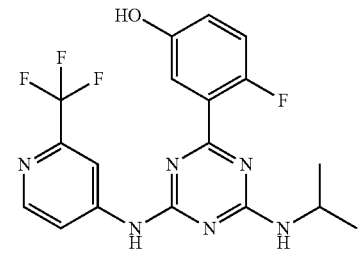 [SMILES: CC(C)Nc1nc(Nc2ccnc(C(F)(F)F)c2)nc(-c2cc(O)ccc2F)n1]

¹H NMR (METHANOL-d₄) δ 8.70-8.68 (d, J=5.6 MHz, 1H), 8.56-8.53 (m, 1H), 7.91-7.89 (m, 1H), 7.58-7.55 (m., 1H), 7.27-7.15 (m, 2H), 4.40-4.35 (m, 1H), 1.40-1.39 (d, J=6.4 MHz, 3H). LC-MS: m/z 409.1 (M+H)⁺.

Compound 635—6-(2-Fluoro-5-methoxy-phenyl)-N-oxetan-3-yl-N'-(2-trifluoromethyl-pyridin-4-yl)-[1,3,5]triazine-2,4-diamine

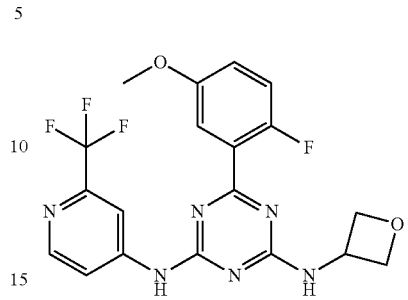

¹H NMR (DMSO-d₆) δ 10.73-10.63 (m, 1H), 9.11-8.11 (m, 4H), 7.82-7.69 (m, 1H), 7.47 (t, J=9.62 Hz, 1H), 7.35 (brs., 1H), 5.34-5.20 (m, 1H), 5.04-5.00 (m, 2H), 4.83-4.80 (m, 2H), 3.80 (s, 3H). LC-MS: m/z 437.3 (M+H)⁺.

Compound 636—6-(2-Fluoro-phenyl)-N-(2-fluoro-pyridin-4-yl)-N'-(3-oxa-bicyclo[3.1.0]hex-6-yl)-[1,3,5]triazine-2,4-diamine

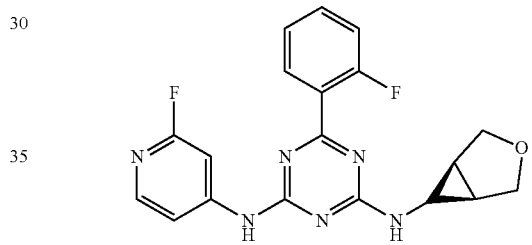

¹H NMR (DMSO-d₆) δ 10.50-10.21 (m, 1H), 8.35-7.85 (m, 4H), 7.62-7.52 (m, 2H), 7.37-7.29 (m, 2H), 3.96-3.88 (m., 2H), 3.69-3.61 (m, 2H), 2.66-2.49 (m, 1H), 1.94-1.87 (m, 2H). LC-MS: m/z 383.1 (M+H)⁺.

Compound 637—6-(2-Fluoro-phenyl)-N-(6-fluoro-pyridin-3-yl)-N'-(3-oxa-bicyclo[3.1.0]hex-6-yl)-[1,3,5]triazine-2,4-diamine

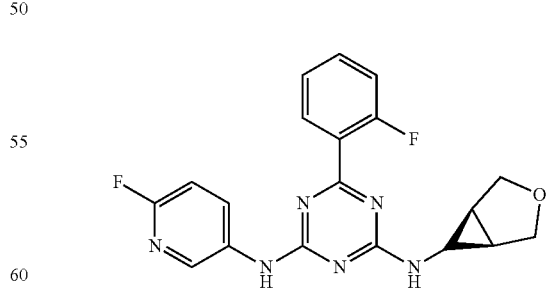

¹H NMR (METHANOL-d₄) δ 8.71-8.57 (m, 1H), 8.30 (brs. 1H), 8.18 (brs. 1H), 7.81 (brs. 1H), 7.50-7.43 (m., 2H), 7.21 (brs. 1H), 4.12-4.02 (m, 2H), 3.81-3.75 (m, 2H), 2.80-2.68 (m, 2H), 2.14-2.09 (m, 2H). LC-MS: m/z 383.2 (M+H)⁺.

317

Compound 638—6-(2-Fluoro-phenyl)-N-(5-fluoro-pyridin-3-yl)-N'-(3-oxa-bicyclo[3.1.0]hex-6-yl)-[1,3,5]triazine-2,4-diamine

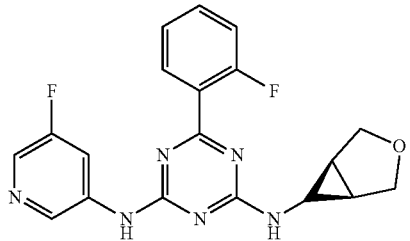

¹H NMR (METHANOL-d₄) δ 8.67 (brs., 2H), 8.20-8.07 (m, 2H), 7.56 (brs., 1H), 7.32-7.21 (m, 2H), 4.14-4.05 (m., 2H), 3.83-3.78 (m, 2H), 2.71-2.68 (m, 1H), 2.00-1.96 (m, 2H). LC-MS: m/z 383.1 (M+H)⁺.

Compound 639—{3-[4-Isopropylamino-6-(2-trifluoromethyl-pyridin-4-ylamino)-[1,3,5]triazin-2-yl]-phenyl}-methanol

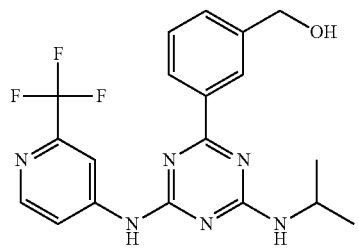

¹H NMR (METHANOL-d₄) δ 8.37-8.41 (m, 3H), 8.31-8.28 (m, 2H), 7.53-7.53 (d, J=6 Hz, 1H), 7.46-7.45 (m, 1H), 4.685 (s, 2H), 4.52-4.18 (m, 1H), 1.31-1.30 (d, J=6.4 Hz, 6H). LC-MS: m/z 405.1 (M+H)⁺.

Compound 640—3-[4-Isopropylamino-6-(2-trifluoromethyl-pyridin-4-ylamino)-[1,3,5]triazin-2-yl]-phenol

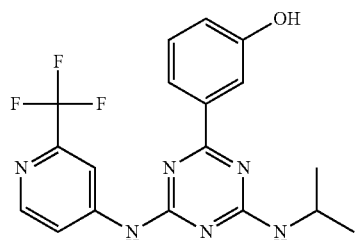

¹H NMR (METHANOL-d₄) δ 8.679-8.245 (m, 2H), 7.95-7.83 (m, 2H), 7.32-7.282 (m, 1H), 7.00-6.98 (d, J=8 Hz, 1H), 4.31-4.28 (m, 1H), 1.34-1.25 (m, 6H). LC-MS: m/z 391.2 (M+H)⁺.

318

Compound 641—3-(4-((2-hydroxy-2-methylpropyl)amino)-6-((2-(trifluoromethyl)pyridin-4-yl)amino)-1,3,5-triazin-2-yl)phenol

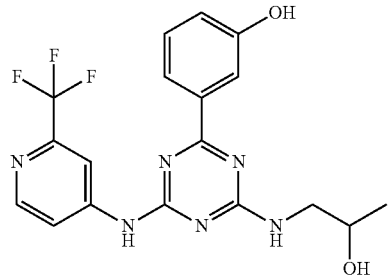

¹H NMR (METHANOL-d₄) δ 8.72-8.70 (m, 1H), 8.68-8.38 (m, 1H), 8.28-7.96 (m, 1H), 7.79-7.70 (m, 2H), 7.51-7.44 (m, 1H), 7.23-7.17 (m, 1H), 3.65 (d, 2H), 1.36 (d, 6H). LC-MS: m/z 421.2 (M+H)⁺.

Compound 642—5-(4-((3,5-difluorophenyl)amino)-6-(isopropylamino)-1,3,5-triazin-2-yl)benzene-1,3-diol

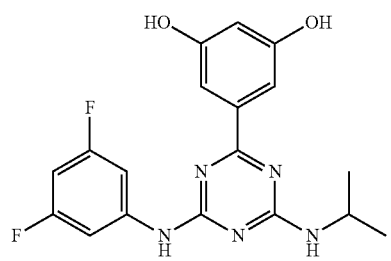 [SMILES: CC(C)Nc1nc(Nc2cc(F)cc(F)c2)nc(-c2cc(O)cc(O)c2)n1]

¹H NMR (METHANOL-d₄) δ 7.51-7.48 (m, 2H), 7.30 (d, 2H), 6.52-6.41 (m, 2H), 4.23-4.21 (m, 1H), 1.35-1.27 (m, 6H). LC-MS: m/z 374.1 (M+H)⁺.

Compound 644—6-(3-Chloro-5-trifluoromethyl-phenyl)-N-isopropyl-N'-(2-trifluoromethyl-pyridin-4-yl)-[1,3,5]triazine-2,4-diamine

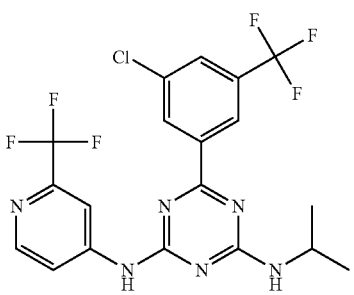 [SMILES: CC(C)Nc1nc(Nc2ccnc(C(F)(F)F)c2)nc(-c2cc(Cl)cc(C(F)(F)F)c2)n1]

¹H NMR (METHANOL-d₄) δ 8.79-8.50 (m, 3H), 8.49-7.86 (m, 2H), 7.77-7.76 (m, 1H), 4.26-4.23 (m, 1H), 1.32-1.30 (d, 6H). LC-MS: m/z 477.1 (M+H)⁺.

319

Compound 645—6-(6-aminopyridin-3-yl)-N2-(3,5-difluorophenyl)-N4-isopropyl-1,3,5-triazine-2,4-diamine

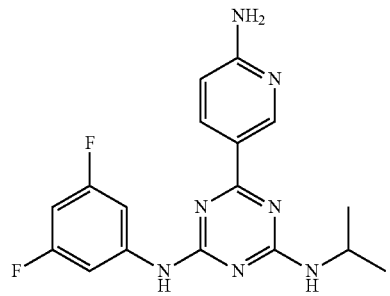 [SMILES: CC(C)Nc1nc(Nc2cc(F)cc(F)c2)nc(-c2ccc(N)nc2)n1]

¹H NMR (DMSO-d₆) δ 9.80 (d, 1H), 8.87 (d, 1H), 8.52-7.29 (m, 5H), 6.78-6.50 (m, 3H), 4.29-4.11 (m, 1H), 1.20 (d, 6H). LC-MS: m/z 358.2 (M+H)⁺.

Compound 646—3-(4-(tert-butylamino)-6-((3-fluoro-5-(methylsulfonyl)phenyl)amino)-1,3,5-triazin-2-yl)phenol

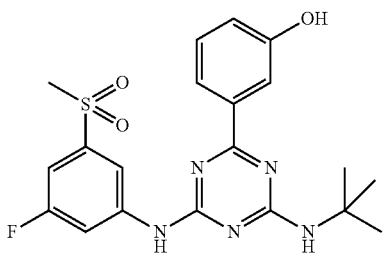 [SMILES: CC(C)(C)Nc1nc(Nc2cc(F)cc(S(C)(=O)=O)c2)nc(-c2cccc(O)c2)n1]

¹H NMR (METHANOL-d₄) δ 8.37-7.74 (m, 4H), 7.25 (br, 2H), 6.92 (br, 1H), 3.13 (s, 3H), 1.51 (s, 6H). LC-MS: m/z 432.0 (M+H)⁺.

Compound 647—6-(3-chloro-5-fluorophenyl)-N2-isopropyl-N4-(2-(trifluoromethyl)pyridin-4-yl)-1,3,5-triazine-2,4-diamine

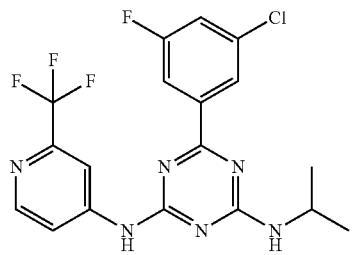 [SMILES: CC(C)Nc1nc(Nc2ccnc(C(F)(F)F)c2)nc(-c2cc(F)cc(Cl)c2)n1]

1H NMR (DMSO-d₆) δ 10.39-10.56 (m, 1H), 8.16-8.70 (m, 4H), 7.71-8.00 (m, 3H), 4.16-4.35 (m, 1H), 1.25 (dd, J=6.4, 6H). LC-MS: m/z 427.1 (M+H)⁺.

320

Compound 648—N2-isopropyl-6-(2-methoxypyridin-3-yl)-N4-(2-(trifluoromethyl)pyridin-4-yl)-1,3,5-triazine-2,4-diamine

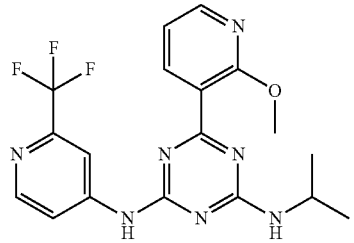 [SMILES: COc1ncccc1-c1nc(Nc2ccnc(C(F)(F)F)c2)nc(NC(C)C)n1]

¹H NMR (METHANOL-d₄) δ 8.61-8.27 (m, 3H), 8.23-7.88 (m, 2H), 7.09-7.06 (m, 1H), 4.28-4.25 (m, 1H), 4.01 (s, 3H), 1.31-1.28 (m, 6H). LC-MS: m/z 406.1 (M+H)⁺.

Example 9. Preparation of Compounds of Formula I Wherein Ring A is Substituted Aryl or Heteroaryl The compounds of this Example are prepared by the general method in Scheme 9, set forth below.

Scheme 9

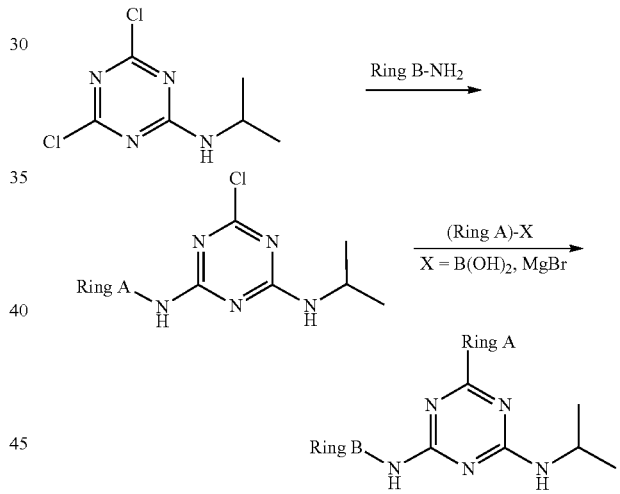

Compound 649—6-(2-aminopyrimidin-5-yl)-N2-(3,5-difluorophenyl)-N4-isopropyl-1,3,5-triazine-2,4-diamine

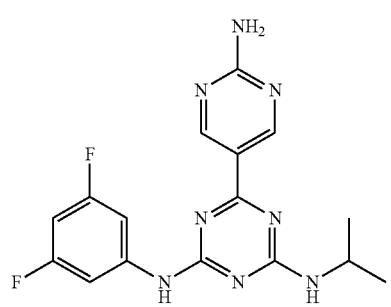 [SMILES: CC(C)Nc1nc(Nc2cc(F)cc(F)c2)nc(-c2cnc(N)nc2)n1]

Example 9, Step 1

Preparation of 6-chloro-N²-(3,5-difluorophenyl)-N4-isopropyl-1,3,5-triazine-2,4-diamine To a solution of 4,6-dichloro-N-isopropyl-1,3,5-triazin-2-amine (1 g, 4.83 mmol) in THF (10 mL) was added 3,5-difluoro aniline (0.62 g, 4.83 mmol), ′BuONa (0.93 g, 9.66 mol) and Pd(dppf)Cl₂ (0.35 g, 0.48 mmol). The mixture was stirred at 80° C. under N₂ protection fro 2 hrs. The reaction was quenched by water and extracted by EtOAc. The organic layer was dried, concentrated and purified to afford 6-chloro-N2-(3,5-difluorophenyl)-N4-isopropyl-1,3,5-triazine-2,4-diamine as white solid.

Example 9, Step 2

To a mixture of 5-chloro-N1-(3,5-difluorophenyl)-N3-isopropylbenzene-1,3-diamine (50 mg, 0.17 mmol), 5-(4,4,5,5-tetramethyl-1,3,2-dioxaborolan-2-yl)pyrimidin-2-amine (37 mg, 0.17 mmol) and Cs₂CO₃ (108 mg, 0.34 mmol) in dioxane/water (0.8 mL/0.16 mL) was added Pd(PPh₃)₄ (19 mg, 0.017 mmol). The mixture was heated to 80° C. for 2 hours. The mixture was concentrated and purified by a standard method to give 6-(2-aminopyrimidin-5-yl)-N2-(3,5-difluoro-phenyl)-N4-isopropyl-1,3,5-triazine-2,4-diamine.

¹H NMR (METHANOL-d₄): δ 9.11-9.17 (m, 2H), 7.49-7.50 (m, 2H), 6.51-6.55 (m, 1H), 4.22-4.34 (m, 1H), 1.35 (d, J=6.8 Hz, 6H). LC-MS: m/z 359.2 (M+H)⁺.

The following compounds were prepared according Example 8, method B, using appropriate intermediates and reagents.

Compound 650—6-(4-(isopropylamino)-6-((2-(trifluoromethyl)pyridin-4-yl)amino)-1,3,5-triazin-2-yl)pyridin-2(1H)-one

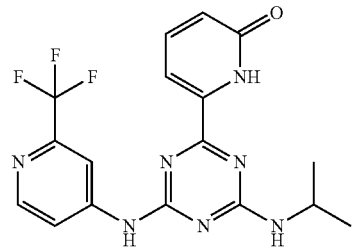 [SMILES: CC(C)Nc1nc(Nc2ccnc(C(F)(F)F)c2)nc(-c2cccc(=O)[nH]2)n1]

¹H NMR (METHANOL-d₄) δ 8.70-8.25 (m, 2H), 8.15-8.06 (m, 1H), 7.81-7.50 (m, 1H), 6.89 (br, 1H), 4.31-4.23 (m, 1H), 1.34-1.29 (m, 6H). LC-MS: m/z 392.1 (M+H)⁺.

Compound 651—6-(4-(isopropylamino)-6-((2-(trifluoromethyl)pyridin-4-yl)amino)-1,3,5-triazin-2-yl)picolinamide

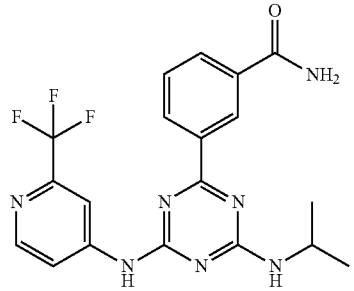 [SMILES: CC(C)Nc1nc(Nc2ccnc(C(F)(F)F)c2)nc(-c2cccc(C(N)=O)c2)n1]

¹H NMR (DMSO-d₆) δ 10.56 (br, 1H), 8.87-8.85 (m, 1H), 8.68-8.04 (m, 6H), 7.92-7.96 (m, 1H), 7.63-7.59 (m, 1H), 7.58-7.48 (m, 1H), 4.20-4.15 (m, 1H), 1.25 (d, 6H). LC-MS: m/z 418.2 (M+H)⁺.

Compound 652—2,2,2-trifluoro-1-(3-(4-(isopropylamino)-6-((2-(trifluoromethyl)pyridin-4-yl)amino)-1,3,5-triazin-2-yl)phenyl)ethanol

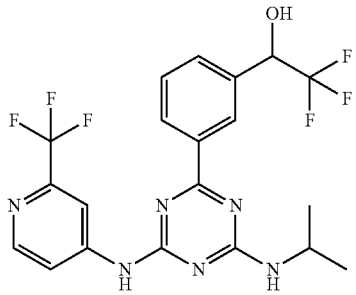 [SMILES: CC(C)Nc1nc(Nc2ccnc(C(F)(F)F)c2)nc(-c2cccc(C(O)C(F)(F)F)c2)n1]

¹H NMR (METHANOL-d₄) δ 8.76-8.40 (m, 4H), 8.32-7.52 (m, 3H), 5.16-5.11 (m, 1H), 4.51-4.28 (m, 1H), 1.34 (d, 6H). LC-MS: m/z 473.2 (M+H)⁺.

Compound 653—N-Isopropyl-6-(3-methanesulfinyl-phenyl)-N'-(2-trifluoromethyl-pyridin-4-yl)-[1,3,5]triazine-2,4-diamine

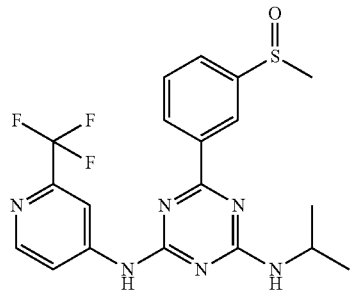 [SMILES: CC(C)Nc1nc(Nc2ccnc(C(F)(F)F)c2)nc(-c2cccc(S(C)=O)c2)n1]

¹H NMR (METHANOL-d₄) δ 8.81-8.28 (m, 4H), 7.91-7.71 (m, 3H), 4.51-4.28 (m, 1H), 2.88 (s, 3H), 1.36-1.33 (m, 6H). LC-MS: m/z 437.2 (M+H)⁺.

Compound 654—6-(3-(aminomethyl)phenyl)-N2-isopropyl-N4-(2-(trifluoromethyl)pyridin-4-yl)-1,3,5-triazine-2,4-diamine

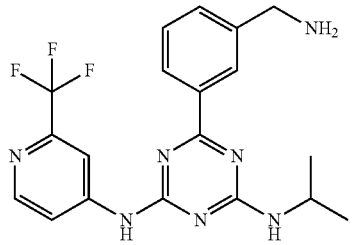 [SMILES: CC(C)Nc1nc(Nc2ccnc(C(F)(F)F)c2)nc(-c2cccc(CN)c2)n1]

¹H NMR (METHANOL-d₄) δ 8.66-8.40 (m, 4H), 7.96 (br, 1H), 7.77-7.67 (m, 2H), 4.52-4.31 (m, 1H), 4.24 (s, 2H), 1.34 (d, 6H). LC-MS: m/z 404.2 (M+H)⁺.

Compound 655—6-(3-chloro-5-methoxyphenyl)-N2-isopropyl-N4-(2-(trifluoromethyl)pyridin-4-yl)-1,3,5-triazine-2,4-diamine

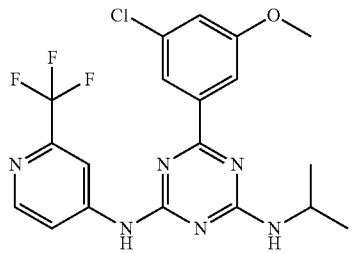

¹H NMR (DMSO-d₆) δ 10.44 (d, 1H), 8.71 (s, 1H), 8.57-8.55 (m, 1H), 8.30-8.08 (m, 1H), 7.92-7.79 (m, 3H), 6.97 (s, 1H), 4.35-4.13 (m, 1H), 3.86 (s, 3H), 1.24 (d, 6H). LC-MS: m/z 439.2 (M+H)⁺.

Compound 657—N-Isopropyl-6-(3-methanesulfonyl-phenyl)-N'-(2-trifluoromethyl)pyridin-4-yl)-[1,3,5]triazine-2,4-diamine

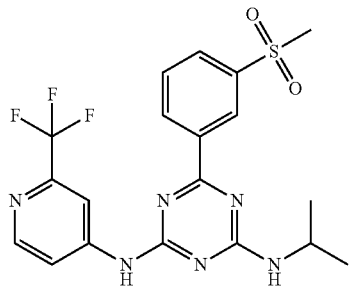 [SMILES: CC(C)Nc1nc(Nc2ccnc(C(F)(F)F)c2)nc(-c2cccc(S(C)(=O)=O)c2)n1]

¹H NMR (METHANOL-d₄) δ 8.95 (s, 1H), 8.76-7.98 (m, 5H), 7.80-7.76 (m, 1H), 4.49-4.22 (m, 1H), 3.17 (s, 3H), 1.34-1.27 (m, 6H). LC-MS: m/z 453.2 (M+H)⁺.

Compound 658—3-Fluoro-5-[4-isopropylamino-6-(2-trifluoromethyl-pyridin-4-ylamino)-[1,3,5]triazin-2-yl]-phenol

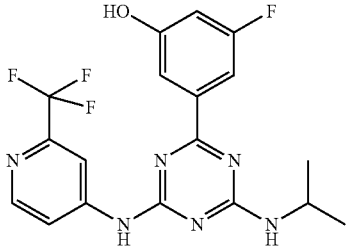

¹H NMR (METHANOL-d₄) δ 8.63-8.63 (m, 2H), 7.95 (s, 1H), 7.56-7.49 (m, 2H), 6.80-6.78 (d, J=8.8 Hz, 1H), 4.31 (s, 1H), 1.36-1.34 (d, J=6 Hz, 6H). LC-MS: m/z 409.1 (M+H)⁺.

Compound 660—6-(3-fluoro-5-(trifluoromethyl)phenyl)-N2-isopropyl-N4-(3-(methylsulfonyl)phenyl)-1,3,5-triazine-2,4-diamine

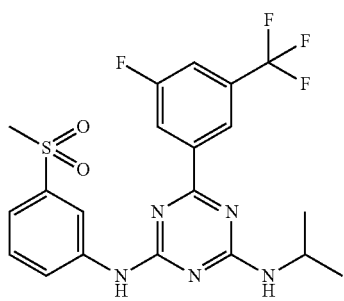 [SMILES: CC(C)Nc1nc(Nc2cccc(S(C)(=O)=O)c2)nc(-c2cc(F)cc(C(F)(F)F)c2)n1]

¹H NMR (Methanol-d₄) δ 8.98 (s, 1H), 8.55 (s, 1H), 8.37 (d, 1H), 7.99-7.75 (m, 1H), 7.61-7.53 (m, 3H), 4.37-4.34 (m, 1H), 3.15 (d, 3H), 1.30 (d, 6H). LC-MS: m/z 470.0 (M+H)⁺.

Compound 662—6-(3-fluoro-5-methoxyphenyl)-N2-isopropyl-N4-(2-(trifluoromethyl)pyridin-4-yl)-1,3,5-triazine-2,4-diamine

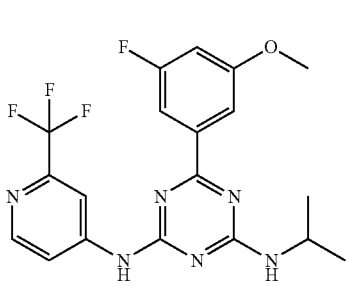

¹H NMR (DMSO-d₆) δ 10.30 (d, 1H), 8.67-8.04 (m, 3H), 8.04-7.58 (m, 3H), 7.08-7.03 (m, 1H), 4.35-4.10 (m, 1H), 3.83 (s, 3H), 1.21 (d, 3H). LC-MS: m/z 423.2 (M+H)⁺.

325

Compound 663—1-(3-(4-(isopropylamino)-6-((2-(trifluoromethyl)pyridin-4-yl)amino)-1,3,5-triazin-2-yl)phenyl)ethanol

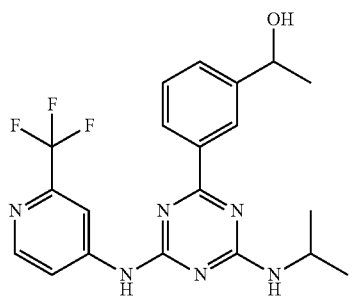 [SMILES: CC(C)Nc1nc(Nc2ccnc(C(F)(F)F)c2)nc(-c2cccc(C(C)O)c2)n1]

¹H NMR (METHANOL-d₄) δ 8.74-8.29 (m, 4H), 8.28-7.80 (m, 1H), 7.57-7.43 (m, 2H), 4.48-4.26 (m, 1H), 1.49 (d, 3H), 1.31 (d, 6H). LC-MS: m/z 419.2 (M+H)⁺.

6-(3-(1-((tert-butyldimethylsilyl)oxy)cyclopropyl)phenyl)-N2-isopropyl-N⁴-(2-(trifluoromethyl)pyridin-4-yl)-1,3,5-triazine-2,4-diamine

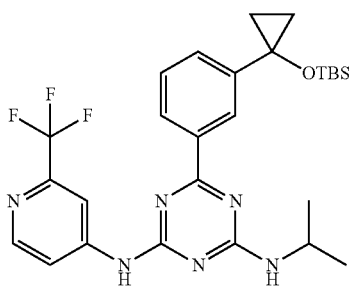 [SMILES: CC(C)Nc1nc(Nc2ccnc(C(F)(F)F)c2)nc(-c2cccc(C3(O[Si](C)(C)C(C)(C)C)CC3)c2)n1]

LCMS: m/z 545.3 (M+H)⁺.

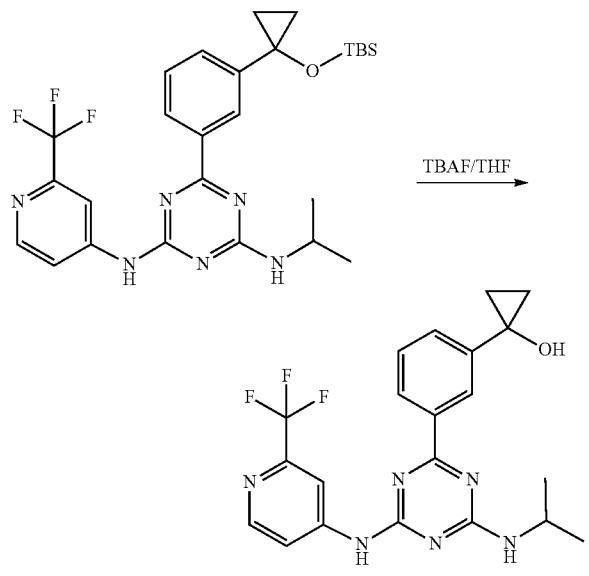

To a solution of 6-(3-(1-((tert-butyldimethylsilyl)oxy)cyclopropyl) phenyl)-N2-isopropyl-N4-(2-(trifluoromethyl)

326 pyridin-4-yl)-1,3,5-triazine-2,4-diamine (510 mg, 0.936 mmol) in anhydrous THF (15 mL) was TBAF (490 mg, 1.872 mmol) at room temperature. The mixture was stirred at r.t. for 2 hours. The mixture was partitioned between EtOAc and water. The organic layer was washed with brine, dried over Na₂SO₄, then concentrated. The crude product was purified by a standard method to give 1-(3-(4-(isopropylamino)-6-((2-(trifluoromethyl)pyridin-4-yl)amino)-1,3,5-triazin-2-yl)phenyl)cyclopropanol.

Compound 664—1-(3-(4-(isopropylamino)-6-((2-(trifluoromethyl)pyridin-4-yl)amino)-1,3,5-triazin-2-yl)phenyl)cyclopropanol

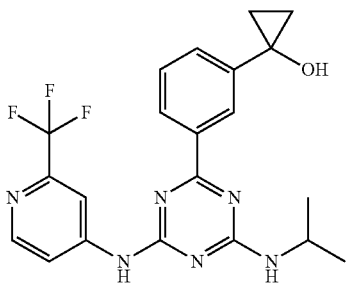 [SMILES: CC(C)Nc1nc(Nc2ccnc(C(F)(F)F)c2)nc(-c2cccc(C3(O)CC3)c2)n1]

¹H NMR (METHANOL-d₄) δ 8.67-8.46 (m, 2H), 8.31-8.21 (m, 2H), 7.84-7.83 (m, 1H), 7.52-7.39 (m, 2H), 4.45-4.23 (m, 1H), 1.32-1.30 (d, J=8.0 Hz, 6H), 1.23-1.22 (m, 2H), 1.09-1.06 (m, 2H). LC-MS: m/z 431.2 (M+H)⁺.

Compound 665—3-(hydroxymethyl)-5-(4-(isopropylamino)-6-((2-(trifluoromethyl)pyridin-4-yl)amino)-1,3,5-triazin-2-yl)phenol

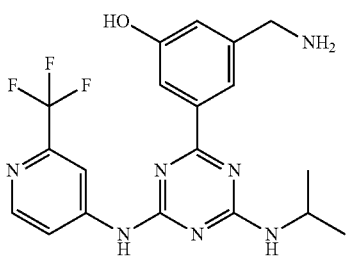 [SMILES: CC(C)Nc1nc(Nc2ccnc(C(F)(F)F)c2)nc(-c2cc(O)cc(CN)c2)n1]

¹H NMR (CDCl₃) δ 10.40-10.24 (m, 1H), 9.56 (s, 1H), 8.68-8.26 (m, 2H), 7.93-7.59 (m, 3H), 6.94 (s, 1H), 5.23-5.20 (m, 1H), 4.50-4.49 (d, J=5.6, 2H), 4.20-4.12 (m, 1H) 1.26-1.23 (m, 6H). LC-MS: m/z 421.2 (M+H)⁺.

The following compounds were prepared according to Scheme 5 using appropriate intermediates and reagents:

Compound 667—4-(4-Phenyl-6-phenylamino-[1,3,5]triazin-2-ylamino)-piperidine-1-carboxylic acid tert-butyl ester

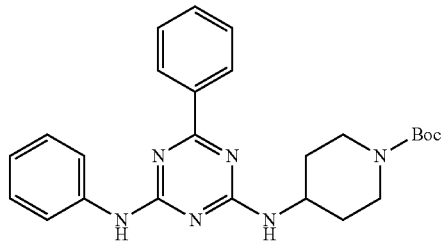 [SMILES: CC(C)(C)OC(=O)N1CCC(Nc2nc(Nc3ccccc3)nc(-c3ccccc3)n2)CC1]

¹H NMR (CDCl3) δ: 8.23-8.82 (m, 2H), 8.53-7.66 (m., 2H), 7.33-7.48 (m, 3H), 7.25-7.31 (m, 2H), 6.98-7.09 (m., 2H), 5.05-5.29 (m, 1H), 3.95-4.20 (m, 3H), 2.85-2.97 (m, 2H), 2.03 (d, J=12 Hz, 2H), 1.37-1.42 (m, 11H). LC-MS: m/z 447.0 (M+H)⁺.

Example 10: Preparation of Compounds of Formula 1 Via N-Arylation of Triazine-Amine Cross-Coupling Scheme 10

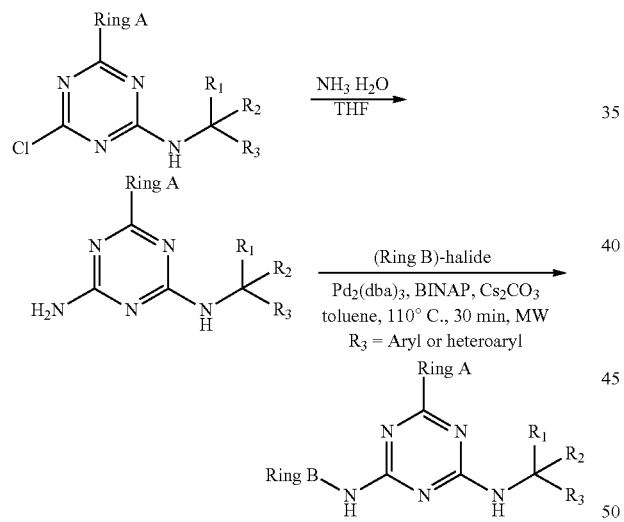

Example 10, Step 1: Preparation of N2-isopropyl-6-(6-(trifluoromethyl)pyridin-2-yl)-1,3,5-triazine-2,4-diamine To the solution of 4-chloro-N-isopropyl-6-(6-(trifluoromethyl)pyridin-2-yl)-1,3,5-triazin-2-amine (300 mg, 0.94 mmol) in THF (5 mL) was added NH₃/H₂O (8 mL). The mixture was stirred at 80° C. overnight. TLC (PE:EA=1:1) showed the reaction was complete. The mixture was washed with H₂O and ethyl acetate. The organic layer was dried over Na₂SO₄, filtered, concentrated to give N2-isopropyl-6-(6-(trifluoromethyl)pyridin-2-yl)-1,3,5-triazine-2,4-diamine as a yellow solid which was used without further purification. LC-MS: m/z 299.8 (M+H)⁺.

The following intermediates were prepared using the procedure in Example 10, Step 1:

6-[6-(1,1-Difluoro-ethyl)-pyridin-2-yl]-N-isopropyl-[1,3,5]triazine-2,4-diamine

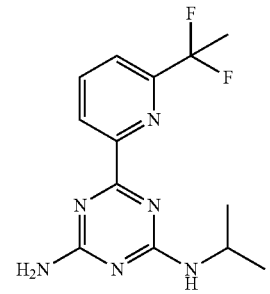 [SMILES: CC(C)Nc1nc(N)nc(-c2cccc(C(C)(F)F)n2)n1]

LC-MS: m/z 295.2 (M+H)⁺.

6-(6-Difluoromethyl-pyridin-2-yl)-N-isopropyl-[1,3,5]triazine-2,4-diamine

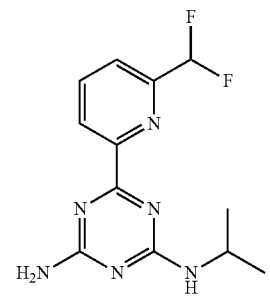 [SMILES: CC(C)Nc1nc(N)nc(-c2cccc(C(F)F)n2)n1]

LC-MS: m/z 281.1 (M+H)⁺.

1-(4-amino-6-(6-(trifluoromethyl) pyridin-2-yl)-1,3,5-triazin-2-ylamino)-2-methylpropan-2-ol

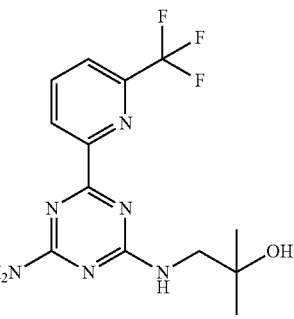

LC-MS: m/z 329.0 (M+H)⁺.

Step 2: Preparation of 1-(4-(4-(isopropylamino)-6-(6-(trifluoromethyl)pyridin-2-yl)-1,3,5-triazin-2-ylamino)pyridin-2-yl)cyclopropanecarbonitrile To a solution of N2-isopropyl-6-(6-(trifluoromethyl)pyridin-2-yl)-1,3,5-triazine-2,4-diamine (120 mg, 0.4 mmol) in anhydrous toluene (5 mL) was added 1-(4-chloro-pyridin-2-yl)cyclopropanecarbonitrile (89 mg, 0.48 mmol), Cs$_2$CO$_3$ (262 mg, 0.8 mmol), BINAP (24.9 mg, 0.04 mmol), and Pd$_2$(dba)$_3$ (36.6 mg, 0.04 mmol) under N$_2$. The mixture was stirred at 110° C. for 30 min under M.W. irradiation. The mixture was quenched by water and extracted with ethyl acetate. The organic layer was dried with anhydrous Na$_2$SO$_4$, concentrated and purified by a standard method to give 1-(4-(4-(isopropylamino)-6-(6-(trifluoromethyl)-pyridin-2-yl)-1,3,5-triazin-2-ylamino)pyridin-2-yl)cyclopropanecarbonitrile. The following compounds were prepared from the appropriate intermediates using the procedure in Example 10, Step 2:

Compound 669—1-{4-[4-Isopropylamino-6-(6-trifluoromethyl-pyridin-2-yl)-[1,3,5]triazin-2-ylamino]-pyridin-2-yl}-cyclopropanecarbonitrile

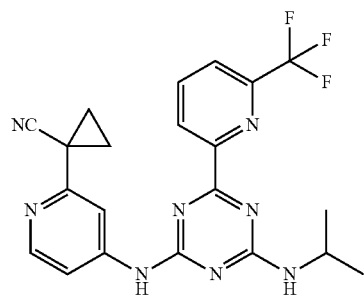 [SMILES: CC(C)Nc1nc(Nc2ccnc(C3(C#N)CC3)c2)nc(-c2cccc(C(F)(F)F)n2)n1]

$^1$H NMR (METHANOL-d$_4$) δ 8.79-8.78 (m, 2H), 8.27 (d, J=5.6 Hz, 1H), 8.20 (t, J=8.2 Hz, 1H), 7.36 (dd, J=3.6 Hz, 2.0 Hz, 1H), 4.47 (m, 1H), 1.82-1.73 (m, 4H), 1.31 (d, J=4.0 Hz, 6H). LC-MS: m/z 441.2 (M+H)$^+$.

Compound 670—1-[4-(5-Chloro-6-fluoro-pyridin-3-ylamino)-6-(6-trifluoromethyl-pyridin-2-yl)-[1,3,5]triazin-2-ylamino]-2-methyl-propan-2-ol Using the standard procedure described in except replacing BINAP with X-Phos and Cs$_2$CO$_3$ with t-BuONa to give 670.

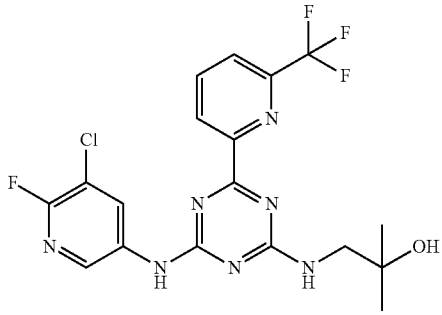 [SMILES: CC(C)(O)CNc1nc(Nc2cnc(F)c(Cl)c2)nc(-c2cccc(C(F)(F)F)n2)n1]

$^1$H NMR (METHANOL-d$_4$) δ 8.82-8.63 (m, 2H), 8.39-8.38 (m, 1H), 8.22 (t, J=7.9 Hz, 1H), 7.98 (d, J=7.6 Hz, 1H), 3.63 (s, 1H), 3.55 (s, 1H), 1.30 (d, J=4.0 Hz, 6H). LC-MS: m/z 458.2 (M+H)$^+$.

Compound 671—2-{4-[4-Isopropylamino-6-(6-trifluoromethyl-pyridin-2-yl)-[1,3,5]triazin-2-ylamino]-pyridin-2-yl}-2-methyl-propionitrile

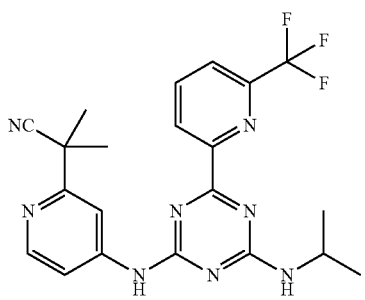 [SMILES: CC(C)Nc1nc(Nc2ccnc(C(C)(C)C#N)c2)nc(-c2cccc(C(F)(F)F)n2)n1]

$^1$H NMR (METHANOL-d$_4$) δ 8.77-8.73 (m, 1H), 8.50 (s, 1H), 8.40 (d, J=4.4 Hz, 1H), 8.23 (t, J=6.6 Hz, 1H), 8.00 (d, J=8.0 Hz, 1H), 7.57 (dd, J=3.6 Hz, 2.0 Hz, 1H), 4.49-4.41 (m, 1H), 1.74 (s, 6H), 1.34 (d, J=6.4 Hz, 6H). LC-MS: m/z 443.2 (M+H)$^+$.

Compound 672—{4-[4-Isopropylamino-6-(6-trifluoromethyl-pyridin-2-yl)-[1,3,5]triazin-2-ylamino]-pyridin-2-yl}-acetonitrile

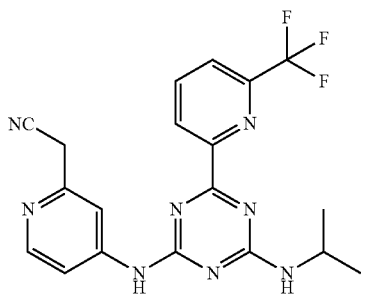 [SMILES: CC(C)Nc1nc(Nc2ccnc(CC#N)c2)nc(-c2cccc(C(F)(F)F)n2)n1]

$^1$H NMR (METHANOL-d$_4$) δ 10.41 (s, 1H), 8.62 (dd, J=9.6 Hz, 8.0 Hz, 1H), 8.37 (d, J=2.4 Hz, 1H), 8.29 (dd, J=8.4 Hz, 1.9 Hz, 2H), 8.28 (s, 1H), 8.11 (d, J=7.6 Hz, 1H), 7.97-7.67 (m, 1H), 4.35-4.28 (m, 1H), 4.17 (s, 1H), 4.13 (s, 1H), 1.25 (d, J=6.8 Hz, 6H). LC-MS: m/z 415.3 (M+H)$^+$.

Compound 673—6-(6-Difluoromethyl-pyridin-2-yl)-N-(2-difluoromethyl-pyridin-4-yl)-N'-isopropyl-[1,3,5]triazine-2,4-diamine Using the standard procedure described in Example 10 Step 2 except replacing Cs$_2$CO$_3$ by t-BuONa yielded 673.

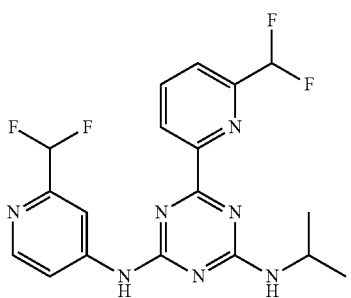 [SMILES: CC(C)Nc1nc(Nc2ccnc(C(F)F)c2)nc(-c2cccc(C(F)F)n2)n1]

¹H NMR (METHANOL-d₄) δ 8.64-7.77 (m, 6H), 6.98-6.58 (m, 2H), 4.33-4.30 (m, 1H), 1.34 (d, J=6.4 Hz, 6H). LC-MS: m/z 408.2 (M+H)⁺.

Compound 674—1-{4-[4-Isopropylamino-6-(6-trifluoromethyl-pyridin-2-yl)-[1,3,5]triazin-2-ylamino]-pyridin-2-yl}-cyclopropanol

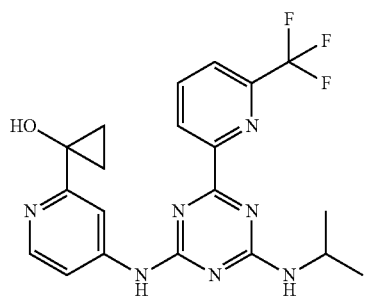 [SMILES: CC(C)Nc1nc(Nc2ccnc(C3(O)CC3)c2)nc(-c2cccc(C(F)(F)F)n2)n1]

¹H NMR (METHANOL-d₄) δ 8.61-8.64 (q, J=7.6 Hz, 1H), 8.38 (s, 1H), 8.09-8.16 (m, 2H), 7.86-7.88 (d, J=7.6 Hz, 1H), 7.44-7.62 (m, 1H), 4.26-4.30 (m, 1H), 1.76-1.23 (m, 8H), 1.10-1.12 (q, J=4 Hz, 2H). LC-MS: m/z 432.2 (M+H)⁺.

Compound 675—6-[6-(1,1-Difluoro-ethyl)-pyridin-2-yl]-N-(2-difluoromethyl-pyridin-4-yl)-N'-isopropyl-[1,3,5]triazine-2,4-diamine Using the standard procedure described in Example 10 Step 2 except replacing Cs₂CO₃ by t-BuONa yielded 675.

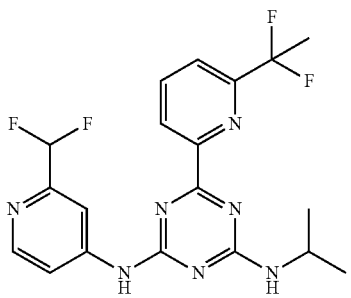 [SMILES: CC(C)Nc1nc(Nc2ccnc(C(F)F)c2)nc(-c2cccc(C(C)(F)F)n2)n1]

¹H NMR (METHANOL-d₄) δ 8.58-8.46 (m, 2H), 8.18-8.11 (m, 2H), 7.90-7.88 (m, 2H), 6.86-6.58 (m, 1H), 4.34-4.32 (m, 1H), 2.17-2.05 (m, 3H), 1.35 (d, J=7.2 Hz, 6H). LC-MS: m/z 422.2 (M+H)⁺.

Compound 676—N-(2-Fluoromethyl-pyridin-4-yl)-N'-isopropyl-6-(6-trifluoromethyl-pyridin-2-yl)-[1,3,5]triazine-2,4-diamine Using the standard procedure described in Example 10 Step 2 except replacing Cs₂CO₃ by t-BuONa yielded 676.

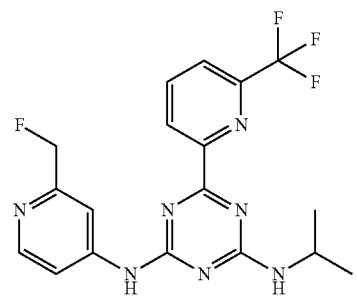 [SMILES: CC(C)Nc1nc(Nc2ccnc(CF)c2)nc(-c2cccc(C(F)(F)F)n2)n1]

¹H NMR (METHANOL-d₄) δ 8.72-8.70 (m, 1H), 8.40-7.98 (m, 5H), 5.55 (s, 1H), 5.43 (s, 1H), 4.52-4.33 (m, 1H), 1.34 (d, J=8.4 Hz, 6H). LC-MS: m/z 408.1 (M+H)⁺.

Compound 677—2-(4-{4-[6-(1,1-Difluoro-ethyl)-pyridin-2-yl]-6-isopropylamino-[1,3,5]triazin-2-ylamino}-pyridin-2-yl)-2-methyl-propionitrile

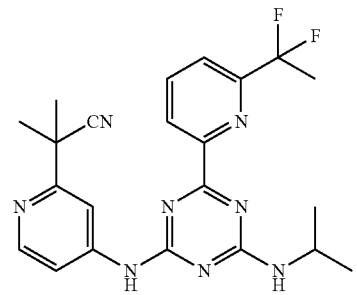 [SMILES: CC(C)Nc1nc(Nc2ccnc(C(C)(C)C#N)c2)nc(-c2cccc(C(C)(F)F)n2)n1]

¹H NMR (METHANOL-d₄) δ 8.61 (d, J=6.8 Hz, 1H), 8.45 (s, 1H), 8.40 (d, J=5.2 Hz, 1H), 8.11 (t, J=7.6 Hz, 1H), 7.88 (d, J=8.0 Hz, 1H), 7.62 (s, 1H), 2.12 (t, J=19.2 Hz, 3H), 1.13 (d, J=6.4 Hz, 6H). LC-MS: m/z 439.2 (M+H)⁺.

Compound 678—2-{4-[4-(2-Hydroxy-2-methyl-propylamino)-6-(6-trifluoromethyl-pyridin-2-yl)-[1,3,5]triazin-2-ylamino]-pyridin-2-yl}-2-methyl-propionitrile

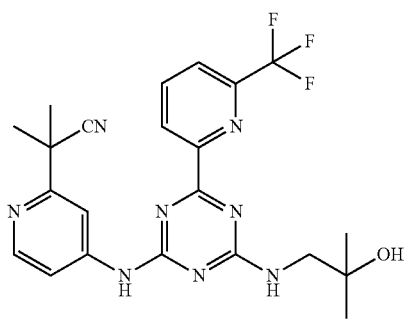 [SMILES: CC(C)(O)CNc1nc(Nc2ccnc(C(C)(C)C#N)c2)nc(-c2cccc(C(F)(F)F)n2)n1]

333

¹H NMR (METHANOL-d₄) δ 8.80-8.78 (m, 1H), 8.45 (s, 1H), 8.40 (t, J=5.6 Hz, 1H), 8.22 (t, J=7.8 Hz, 1H), 8.79 (d, J=8.0 Hz, 1H), 7.60 (dd, J=3.6 Hz, 2.0 Hz, 1H), 3.63 (d, J=11.6 Hz, 2H), 1.80 (s, 6H), 1.31 (d, J=6.0 Hz, 6H). LC-MS: m/z 473.2 (M+H)⁺.

Example 11: Preparation of compounds of Formula I where Ring A is 6-aminopyridyl Scheme 11

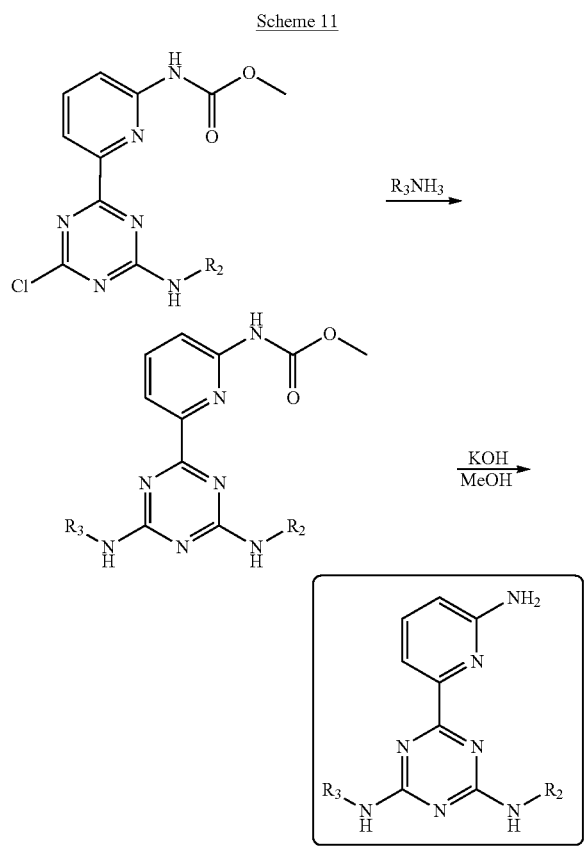

Example 11, Step 1

The preparations of the following intermediates are analogous to the procedure as Scheme 3, Step 4, using the appropriate starting materials and intermediates:

Compound 679—Methyl (6-(4-(isopropylamino)-6-((2-(trifluoromethyl)pyridin-4-yl)amino)-1,3,5-triazin-2-yl)pyridin-2-yl)carbamate

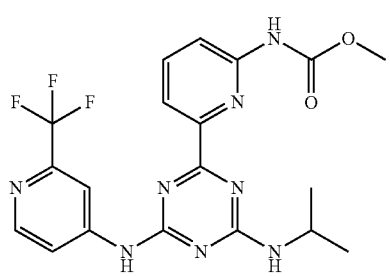

LCMS: m/z 449.3 (M+H)⁺.

334

Compound 680—Methyl 6-(4-(2-hydroxy-2-methylpropylamino)-6-(2-(trifluoromethyl)pyridin-4-ylamino)-1,3,5-triazin-2-yl)pyridin-2-yl-carbamate

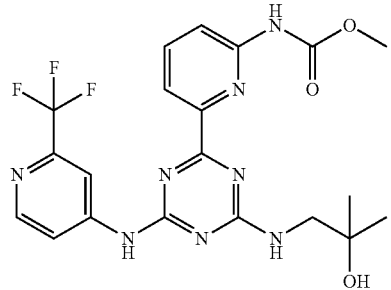 [SMILES: COC(=O)Nc1cccc(-c2nc(NCC(C)(C)O)nc(Nc3ccnc(C(F)(F)F)c3)n2)n1]

LCMS: m/z 479.3 (M+H)⁺.

Compound 681—Methyl 6-(4-(neopentylamino)-6-(2-(trifluoromethyl)pyridin-4-ylamino)-1,3,5-triazin-2-yl)pyridin-2-ylcarbamate

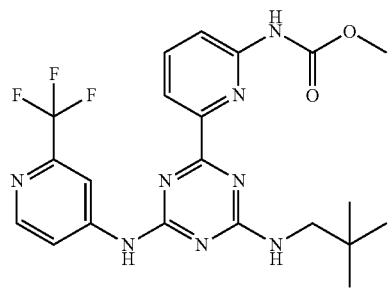 [SMILES: COC(=O)Nc1cccc(-c2nc(NCC(C)(C)C)nc(Nc3ccnc(C(F)(F)F)c3)n2)n1]

LCMS: m/z 477.3 (M+H)⁺.

Compound 682—Methyl 6-(4-(3,5-difluorophenylamino)-6-(1-methylcyclopropylamino)-1,3,5-triazin-2-yl)pyridin-2-ylcarbamate

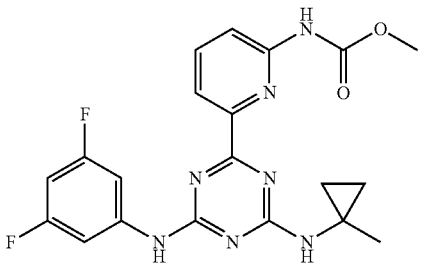

LCMS: m/z 428.2 (M+H)⁺.

Methyl 6-(4-(1-methylcyclopropylamino)-6-(2-(trifluoromethyl)pyridin-4-ylamino)-1,3,5-triazin-2-yl)pyridin-2-ylcarbamate

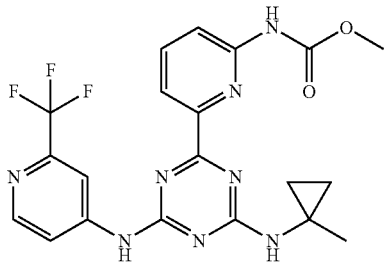 [SMILES: COC(=O)Nc1cccc(-c2nc(Nc3ccnc(C(F)(F)F)c3)nc(NC3(C)CC3)n2)n1]

LCMS: m/z 461.3 (M+H)⁺.

Compound 683—Methyl 6-(4-(2-(trifluoromethyl)pyridin-4-ylamino)-6-(1,1,1-trifluoro-propan-2-ylamino)-1,3,5-triazin-2-yl)pyridin-2-ylcarbamate

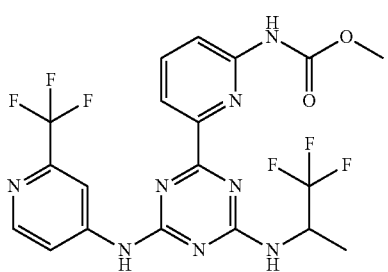 [SMILES: COC(=O)Nc1cccc(-c2nc(Nc3ccnc(C(F)(F)F)c3)nc(NC(C)C(F)(F)F)n2)n1]

LCMS: m/z 503.2 (M+H)⁺.

Compound 684—Methyl 6-(4-(3,5-difluorophenylamino)-6-(2-hydroxy-2-methylpropyl-amino)-1,3,5-triazin-2-yl)pyridin-2-ylcarbamate

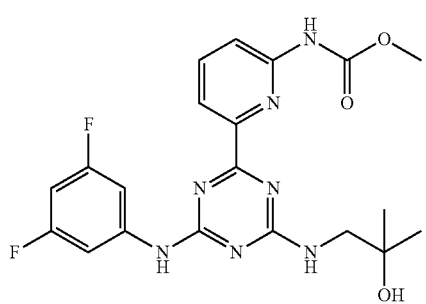 [SMILES: COC(=O)Nc1cccc(-c2nc(NCC(C)(C)O)nc(Nc3cc(F)cc(F)c3)n2)n1]

LCMS: m/z 446.1 (M+H)⁺.

Preparation of methyl 6-(4-(tert-butylamino)-6-(2-(trifluoromethyl)pyridin-4-ylamino)-1,3,5-triazin-2-yl)pyridin-2-ylcarbamate Using the standard procedure described above to give Compound 685—methyl 6-(4-(tert-butylamino)-6-(2-(trifluoromethyl)pyridin-4-ylamino)-1,3,5-triazin-2-yl) pyridin-2-ylcarbamate

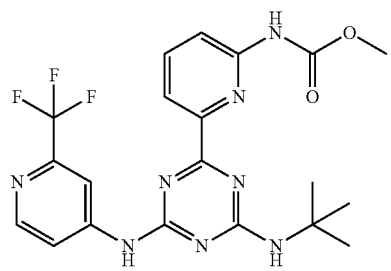 [SMILES: COC(=O)Nc1cccc(-c2nc(Nc3ccnc(C(F)(F)F)c3)nc(NC(C)(C)C)n2)n1]

LCMS: m/z 463.3 (M+H)⁺.

Compound 686—Methyl 6-(4-(2-(1,1-difluoroethyl)pyridin-4-ylamino)-6-(isopropyl-amino)-1,3,5-triazin-2-yl)pyridin-2-ylcarbamate

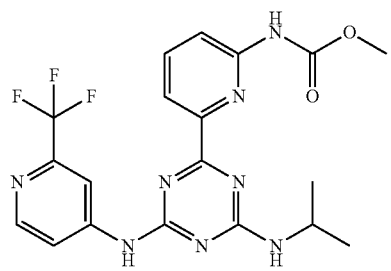

LCMS: m/z 445.1 (M+H)⁺.

Example 11, Step 2: Preparation of 6-(6-aminopyridin-2-yl)-N2-isopropyl-N4-(2-(trifluoromethyl)pyridin-4-yl)-1,3,5-triazine-2,4-diamine To a solution of 6-(6-Chloro-pyridin-2-yl)-N-oxetan-3-yl-N'-(2-trifluoromethyl-pyridin-4-yl)-[1,3,5]triazine-2,4-diamine (170 mg, 0.38 mmol) in methanol (6 mL) was added 5 pellets of KOH. The mixture was heated to 80° C. for 12 hours. TLC (ethyl acetate) showed that the reaction was complete. The mixture was adjusted pH to 7 and filtered, the filtrate was concentrated and purified by a standard method to give 6-(6-aminopyridin-2-yl)-N2-isopropyl-N4-(2-(trifluoromethyl)pyridin-4-yl)-1,3,5-triazine-2,4-diamine.

The following compounds were prepared according to the procedure set forth in Example 11, Step 2, using appropriate starting materials and reagents:

Compound 687—6-(6-aminopyridin-2-yl)-N2-isopropyl-N4-(2-(trifluoromethyl)pyridin-4-yl)-1,3,5-triazine-2,4-diamine

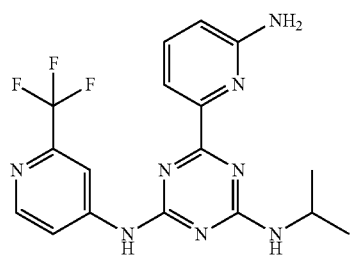 [SMILES: CC(C)Nc1nc(Nc2ccnc(C(F)(F)F)c2)nc(-c2cccc(N)n2)n1]

¹H NMR (METHANOL-d₄): δ 8.5-8.65 (m, 1.5H), 7.8-8.3 (m, 3.5H), 7.2 (m, 1H), 4.2-4.6 (m, 1H), 1.25-1.4 (m, 6H). LC-MS: m/z 391.3 (M+H)⁺.

Compound 689—6-(6-aminopyridin-2-yl)-N2-neopentyl-N4-(2-(trifluoromethyl)pyridin-4-yl)-1,3,5-triazine-2,4-diamine

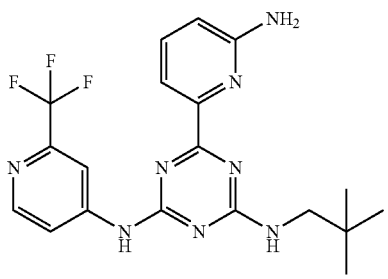 [SMILES: CC(C)(C)CNc1nc(Nc2ccnc(C(F)(F)F)c2)nc(-c2cccc(N)n2)n1]

¹H NMR (METHANOL-d₄): δ 8.75 (m, 1H), 8.1-8.6 (m, 2H), 7.6-7.8 (m, 2H), 6.85 (m, 1H), 3.4-3.5 (m, 2H), 1.0 (s, 9H). LC-MS: m/z 419.3 (M+H)⁺.

Compound 690—6-(6-aminopyridin-2-yl)-N2-isobutyl-N4-(2-(trifluoromethyl)pyridin-4-yl)-1,3,5-triazine-2,4-diamine

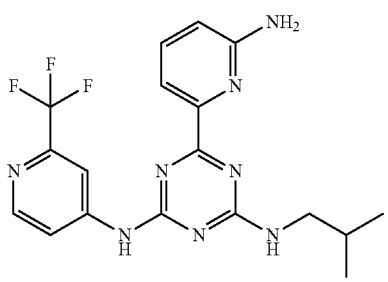 [SMILES: CC(C)CNc1nc(Nc2ccnc(C(F)(F)F)c2)nc(-c2cccc(N)n2)n1]

Compound 691—1-(4-(6-aminopyridin-2-yl)-6-(3,5-difluorophenylamino)-1,3,5-triazin-2-ylamino)-2-methylpropan-2-ol

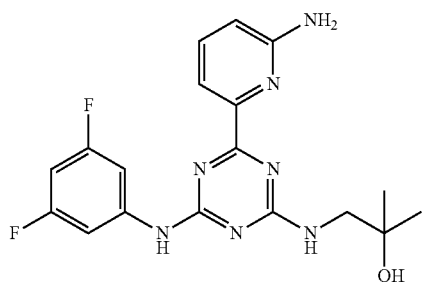 [SMILES: CC(C)(O)CNc1nc(Nc2cc(F)cc(F)c2)nc(-c2cccc(N)n2)n1]

1H NMR (METHANOL-d₄): δ 8.6-7.6 (m, 3H), 7.55-6.5 (m, 3H), 3.5-3.7 (m, 2H), 1.1-1.4 (m, 6H). LC-MS: m/z 338.2 (M+H)⁺.

Compound 692—6-(6-aminopyridin-2-yl)-N2-(1-methylcyclopropyl)-N4-(2-(trifluoromethyl)pyridin-4-yl)-1,3,5-triazine-2,4-diamine

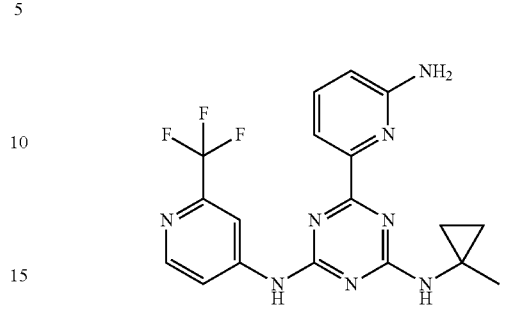

1H NMR (METHANOL-d₄): δ 8.88 (m, 1H), 8.5 (m, 1H), 7.85 (m, 1H), 7.7 (m, 1H), 7.6 (m, 1H), 6.75 (m, 1H), 1.52 (s, 3H), 0.75-0.95 (m, 4H). LC-MS: m/z 403.2 (M+H)⁺.

Compound 693—6-(6-aminopyridin-2-yl)-N2-(3,5-difluorophenyl)-N4-(1-methylcyclopropyl)-1,3,5-triazine-2,4-diamine

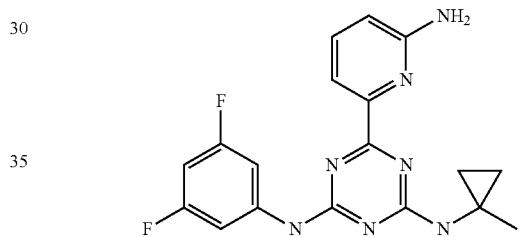

1H NMR (METHANOL-d₄): δ 7.5-7.58 (m, 4H), 6.5-6.8 (m, 2H), 1.5 (s, 3H), 0.75-0.95 (m, 4H). LC-MS: m/z 370.2 (M+H)⁺.

Compound 694—6-(6-aminopyridin-2-yl)-N2-(2-(trifluoromethyl)pyridin-4-yl)-N4-(1,1,1-trifluoropropan-2-yl)-1,3,5-triazine-2,4-diamine

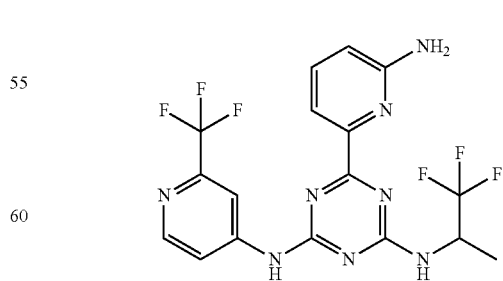

¹H NMR (METHANOL-d₄): δ 78.63-7.75 (m, 4H), 7.6 (m, 1H), 6.68 (m, 1H), 5.5-5.0 (m, 1H), 1.48 (m, 3H). LC-MS: m/z 445.2 (M+H)⁺.

Compound 695—6-(6-aminopyridin-2-yl)-N2-tert-butyl-N4-(2-(trifluoromethyl)pyridin-4-yl)-1,3,5-triazine-2,4-diamine

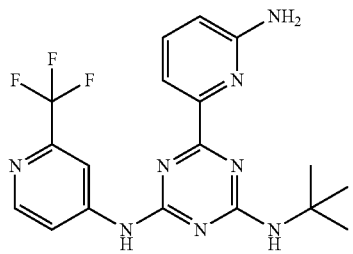 [SMILES: CC(C)(C)Nc1nc(Nc2ccnc(C(F)(F)F)c2)nc(-c2cccc(N)n2)n1]

$^1$H NMR (METHANOL-$d_4$): δ 8.55-8.65 (m, 2H), 7.9-8.25 (m, 2H), 7.8-7.9 (m, 1H), 7.2 (m, 1H), 1.55 (m, 9H). LC-MS: m/z 405.2 (M+H)$^+$.

Compound 696—6-(6-aminopyridin-2-yl)-N2-(2-(1,1-difluoroethyl)pyridin-4-yl)-N4-isopropyl-1,3,5-triazine-2,4-diamine

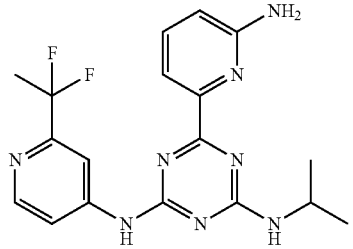 [SMILES: CC(C)Nc1nc(Nc2ccnc(C(C)(F)F)c2)nc(-c2cccc(N)n2)n1]

$^1$H NMR (METHANOL-$d_4$): δ 8.55-8.2 (m, 2H), 8.0-7.55 (m, 3H), 6.75 (m, 1H), 4.55-4.2 (m, 1H), 2.0 (t, 3H), 1.3 (d, J=6.4 Hz, 3H). LC-MS: m/z 387.3 (M+H)$^+$.

Compound 697—N-(6-(4-(isopropylamino)-6-(2-(trifluoromethyl)pyridin-4-ylamino)-1,3,5-triazin-2-yl)pyridin-2-yl)acetamide

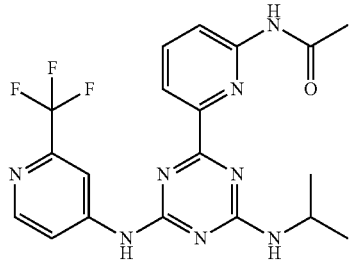 [SMILES: CC(=O)Nc1cccc(-c2nc(Nc3ccnc(C(F)(F)F)c3)nc(NC(C)C)n2)n1]

$^1$H NMR (METHANOL-$d_4$): δ 8.7-8.5 (m, 2H), 8.3-7.8 (m, 4H), 4.5-4.2 (m, 1H), 2.23 (s, 3H), 1.25-1.35 (m, 6H). LC-MS: m/z 433.2 (M+H)$^+$.

Compound 698—6-(6-aminopyridin-2-yl)-N2-(tert-butyl)-N4-(3,5-difluorophenyl)-1,3,5-triazine-2,4-diamine

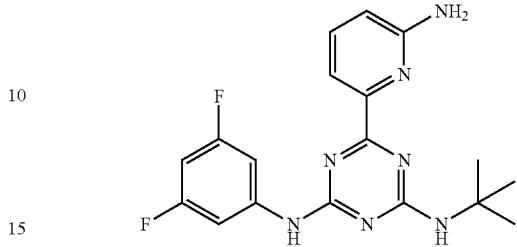

1H NMR (METHANOL-$d_4$): δ 7.68-7.48 (m, 4H), 6.73-6.55 (m, 2H), 1.58 (s, 9H). LC-MS: m/z 372.2 (M+H)$^+$.

Compound 699—6-(6-aminopyridin-2-yl)-N2-(cyclopropylmethyl)-N4-(3,5-difluorophenyl)-1,3,5-triazine-2,4-diamine

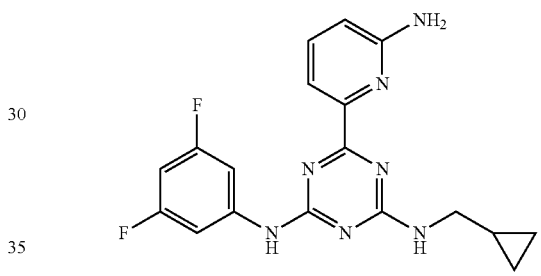

$^1$H NMR (METHANOL-$d_4$): δ 7.71-7.50 (m, 4H), 6.74-6.72 (m, 1H), 6.56-6.54 (m, 1H), 3.43-3.36 (m, 2H), 1.18-1.72 (m, 1H), 0.56-0.54 (m, 2H), 0.32-0.31 (m, 2H). LC-MS: m/z 370.1 (M+H)$^+$.

Example 12. Enzymatic and Cell Assays

Enzymatic Assay.

Compounds are assayed for IDH2 R172K inhibitory activity through a cofactor depletion assay. Compounds are preincubated with enzyme, then the reaction is started by the addition of NADPH and α-KG, and allowed to proceed for 60 minutes under conditions previously demonstrated to be linear with respect for time for consumption of both cofactor and substrate. The reaction is terminated by the addition of a second enzyme, diaphorase, and a corresponding substrate, resazurin. Diaphorase reduces resazurin to the highly fluorescent resorufin with the concomitant oxidation of NADPH to NADP, both halting the IDH2 reaction by depleting the available cofactor pool and facilitating quantitation of the amount of cofactor remaining after a specific time period through quantitative production of an easily detected fluorophore.

Specifically, into each of 12 wells of a 384-well plate, 1 μl of 100× compound dilution series is placed, followed by the addition of 40 μl of buffer (50 mM potassium phosphate ($K_2HPO_4$), pH 7.5; 150 mM NaCl; 10 mM $MgCl_2$, 10% glycerol, 0.05% bovine serum albumin, 2 mM beta-mercaptoethanol) containing 1.25 μg/ml IDH2 R172K. The test compound is then incubated for one hour at room temperature with the enzyme; before starting the IDH2 reaction with the addition of 10 μl of substrate mix containing 50 μM NADPH and 6.3 mM α-KG in the buffer described above. After a further one hour of incubation at room temperature, the reaction is halted and the remaining NADPH measured through conversion of resazurin to resorufin by the addition of 25 μl Stop Mix (36 μg/ml diaphorase enzyme and 60 μM resazurin; in buffer). After one minute of incubation the plate is read on a plate reader at Ex544/Em590.

For determination of the inhibitory potency of compounds against IDH2 R140Q in an assay format similar to the above, a similar procedure is performed, except that the final testing concentration is 0.25 μg/ml IDH2 R140Q protein, 4 μM NADPH and 1.6 mM α-KG.

For determination of the inhibitory potency of compounds against IDH2 R140Q in a high throughput screening format, a similar procedure is performed, except that 0.25 μg/ml IDH2 R140Q protein was utilized in the preincubation step, and the reaction is started with the addition of 4 μM NADPH and 8 μM α-KG.

U87MG pLVX-IDH2 R140Q-neo Cell Based Assay.

U87MG pLVX-IDH2 R140Q-neo cells are grown in T125 flasks in DMEM containing 10% FBS, 1× penicillin/streptomycin and 500 μg/mL G418. They are harvested by trypsin and seeded into 96 well white bottom plates at a density of 5000 cell/well in 100 μl/well in DMEM with 10% FBS. No cells are plated in columns 1 and 12. Cells are incubated overnight at 37° C. in 5% $CO_2$. The next day compounds are made up at 2× concentration and 100 ul are added to each cell well. The final concentration of DMSO is 0.2% and the DMSO control wells are plated in row G. The plates are then placed in the incubator for 48 hours. At 48 hours, 100 ul of media is removed from each well and analyzed by LC-MS for 2-HG concentrations. The cell plate is placed back in the incubator for another 24 hours. At 72 hours post compound addition, 10 mL/plate of Promega Cell Titer Glo reagent is thawed and mixed. The cell plate is removed from the incubator and allowed to equilibrate to room temperature. Then 100 ul of reagent is added to each well of media. The cell plate is then placed on an orbital shaker for 10 minutes and then allowed to sit at room temperature for 20 minutes. The plate is then read for luminescence with an integration time of 500 ms to determine compound effects on growth inhibition.

The data for various compounds of one aspect of the invention in the R140Q enzymatic assay, R140Q cell-based assay and R172K enzymatic assay as described above or similar thereto are presented below in Table 2. For each assay, values indicated as "A" represent an IC50 of less than 100 nM; values indicated as "B" represent an IC50 of between 100 nM and 1 μM; values indicated as "C" represent an IC50 of greater than 1 μM to 10 μM; values indicated as "D" represent an IC50 of greater than 10 μM; values indicated as "no fit" are inactives and blank values represent that the compound was either inactive or not tested in that particular assay.

TABLE 2

Enzymatic and Cellular Activity of Compounds.

| Cmpd No | Enz R140Q | Cell R140Q | Enz R172K |
|---|---|---|---|
| 100 | A | A | A |
| 103 | B | C | C |
| 108 | B | | |
| 109 | B | C | C |
| 110 | A | A | B |
| 111 | A | A | A |
| 112 | A | B | B |
| 113 | A | A | B |
| 114 | B | C | C |
| 115 | A | B | B |
| 116 | B | | C |
| 117 | B | | C |
| 118 | A | B | B |
| 119 | B | C | D |
| 120 | A | A | B |
| 121 | A | A | A |
| 122 | B | C | C |
| 123 | A | B | B |
| 126 | A | A | B |
| 128 | B | C | C |
| 129 | A | B | C |
| 130 | A | A | B |
| 132 | A | A | B |
| 133 | B | | D |
| 135 | B | C | D |
| 137 | B | | C |
| 139 | A | B | C |
| 140 | A | B | C |
| 141 | A | B | B |
| 143 | A | B | B |
| 145 | B | C | D |
| 146 | A | A | B |
| 147 | B | B | C |
| 148 | B | B | C |
| 149 | A | A | A |
| 150 | B | B | C |
| 151 | B | B | B |
| 154 | A | B | C |
| 155 | B | No Fit | D |
| 156 | B | B | C |
| 158 | A | B | B |
| 159 | B | B | C |
| 160 | A | B | B |
| 162 | B | C | C |
| 165 | B | | C |
| 167 | A | A | B |
| 168 | A | A | B |
| 169 | A | B | B |
| 170 | B | C | B |
| 172 | A | B | B |
| 173 | A | A | A |
| 174 | A | A | B |
| 175 | A | A | B |
| 176 | A | B | B |
| 177 | A | A | B |
| 178 | A | A | A |
| 179 | A | A | A |
| 181 | A | A | B |
| 182 | B | | |
| 183 | A | A | B |
| 184 | A | B | C |
| 185 | A | B | B |
| 186 | A | A | B |
| 187 | A | A | B |
| 188 | A | A | B |
| 189 | A | B | C |
| 190 | A | A | B |
| 191 | A | A | B |
| 193 | A | A | B |
| 194 | A | A | A |
| 195 | A | A | B |
| 196 | A | A | B |
| 197 | A | A | B |
| 198 | A | A | B |
| 199 | A | A | A |
| 200 | A | A | B |
| 201 | A | B | C |
| 202 | A | A | A |
| 203 | A | B | C |

TABLE 2-continued

Enzymatic and Cellular Activity of Compounds.

| Cmpd No | Enz R140Q | Cell R140Q | Enz R172K |
|---|---|---|---|
| 204 | A | B | C |
| 205 | A | A | B |
| 206 | A | B | B |
| 207 | B | | |
| 208 | A | B | B |
| 209 | A | B | B |
| 210 | A | A | B |
| 211 | A | B | B |
| 212 | A | A | B |
| 213 | A | A | B |
| 214 | A | B | B |
| 215 | A | B | C |
| 216 | A | B | B |
| 217 | A | | C |
| 218 | A | B | C |
| 219 | A | A | B |
| 220 | A | A | B |
| 221 | B | B | C |
| 222 | B | | |
| 223 | A | A | A |
| 224 | A | B | B |
| 225 | A | B | C |
| 226 | A | B | B |
| 227 | A | A | B |
| 228 | A | B | B |
| 229 | A | A | A |
| 230 | B | B | B |
| 231 | B | | |
| 232 | A | B | B |
| 233 | A | A | B |
| 234 | No Fit | | |
| 235 | B | B | C |
| 236 | B | B | C |
| 237 | B | B | C |
| 238 | B | B | C |
| 239 | A | A | B |
| 240 | A | B | C |
| 241 | A | B | C |
| 242 | B | B | C |
| 243 | B | | C |
| 244 | B | C | B |
| 245 | A | B | B |
| 246 | B | A | B |
| 247 | A | A | A |
| 248 | A | B | C |
| 249 | A | B | B |
| 250 | A | B | B |
| 251 | B | | |
| 252 | B | | C |
| 253 | A | A | B |
| 254 | A | B | B |
| 255 | A | A | B |
| 256 | C | | |
| 257 | A | B | B |
| 258 | C | | |
| 259 | B | B | D |
| 260 | A | A | A |
| 261 | A | A | B |
| 262 | B | B | C |
| 263 | A | B | C |
| 264 | C | | |
| 265 | B | C | |
| 266 | A | B | C |
| 267 | A | B | C |
| 268 | A | B | B |
| 269 | A | A | B |
| 270 | A | B | B |
| 271 | No Fit | | |
| 272 | B | B | |
| 273 | D | | |
| 274 | D | | |
| 275 | B | B | |
| 276 | B | | |
| 277 | A | B | |
| 278 | No Fit | | |
| 279 | D | | |
| 280 | D | | |
| 281 | A | B | |
| 282 | No Fit | | |
| 283 | No Fit | | |
| 284 | B | B | |
| 285 | C | | |
| 286 | D | | |
| 287 | B | | |
| 288 | A | A | |
| 289 | A | B | |
| 290 | B | A | |
| 291 | No Fit | No Fit | |
| 292 | No Fit | No Fit | |
| 293 | A | A | |
| 294 | No Fit | No Fit | |
| 295 | A | A | |
| 296 | B | A | |
| 297 | A | A | |
| 298 | A | A | |
| 299 | A | B | |
| 300 | B | B | |
| 301 | B | A | |
| 302 | A | B | |
| 303 | C | No Fit | |
| 304 | C | No Fit | |
| 305 | D | No Fit | |
| 306 | B | A | |
| 308 | A | B | |
| 309 | A | A | |
| 310 | B | A | |
| 311 | B | B | |
| 312 | B | C | |
| 313 | A | A | |
| 314 | C | No Fit | |
| 315 | A | A | |
| 316 | B | B | |
| 317 | A | A | |
| 318 | A | A | |
| 319 | B | A | |
| 320 | A | A | |
| 321 | A | A | |
| 322 | B | A | |
| 323 | B | A | |
| 324 | B | C | |
| 325 | A | A | |
| 326 | B | A | |
| 327 | B | B | |
| 328 | A | A | |
| 329 | A | A | |
| 330 | B | A | |
| 331 | B | A | |
| 332 | D | No Fit | |
| 334 | B | A | A |
| 335 | B | A | A |
| 336 | B | A | B |
| 337 | B | B | C |
| 340 | A | A | A |
| 341 | A | A | B |
| 342 | B | C | C |
| 343 | B | B | |
| 344 | B | A | A |
| 345 | B | B | B |
| 346 | A | B | |
| 347 | B | | |
| 348 | D | | |
| 350 | B | B | C |
| 351 | A | B | |
| 352 | A | A | |
| 353 | B | A | |
| 354 | B | A | |
| 355 | B | A | |
| 356 | B | A | |
| 358 | B | A | B |
| 359 | B | B | |

TABLE 2-continued

Enzymatic and Cellular Activity of Compounds.

| Cmpd No | Enz R140Q | Cell R140Q | Enz R172K |
|---|---|---|---|
| 360 | B | B | |
| 361 | B | B | |
| 362 | B | B | |
| 363 | B | A | |
| 364 | C | B | |
| 365 | C | | |
| 366 | B | A | |
| 367 | B | A | |
| 368 | C | A | |
| 369 | A | A | |
| 370 | A | A | |
| 371 | A | A | |
| 372 | A | A | A |
| 374 | A | A | A |
| 376 | B | A | |
| 377 | B | A | |
| 378 | B | A | |
| 379 | B | A | |
| 380 | B | B | |
| 381 | B | A | |
| 382 | B | A | |
| 383 | B | A | |
| 384 | B | A | |
| 385 | C | B | |
| 386 | B | A | A |
| 387 | A | A | |
| 388 | C | B | |
| 389 | C | A | |
| 390 | C | B | |
| 391 | B | A | |
| 392 | B | A | |
| 393 | B | A | |
| 394 | A | A | |
| 395 | B | A | |
| 396 | B | A | |
| 397 | B | B | |
| 398 | A | A | |
| 399 | B | A | |
| 400 | B | A | |
| 401 | B | A | |
| 402 | B | A | |
| 403 | B | A | |
| 404 | B | A | |
| 405 | C | B | |
| 406 | B | A | |
| 407 | B | B | |
| 408 | B | A | |
| 409 | B | A | B |
| 410 | D | B | |
| 411 | C | A | |
| 412 | C | | |
| 413 | D | | |
| 414 | B | B | |
| 415 | D | | |
| 416 | A | A | B |
| 450 | B | A | |
| 451 | B | A | |
| 452 | B | C | D |
| 454 | B | B | C |
| 455 | B | A | A |
| 456 | B | A | B |
| 458 | B | A | B |
| 459 | A | A | A |
| 460 | A | A | A |
| 461 | A | A | A |
| 462 | B | B | B |
| 463 | B | A | A |
| 464 | B | A | A |
| 465 | B | A | A |
| 466 | B | A | B |
| 467 | B | B | B |
| 468 | B | A | A |
| 469 | A | A | A |
| 470 | B | A | B |
| 471 | B | A | B |
| 472 | A | A | B |
| 473 | A | A | A |
| 474 | B | A | A |
| 475 | A | A | A |
| 476 | A | A | B |
| 477 | B | A | A |
| 478 | B | A | A |
| 479 | B | A | B |
| 480 | B | A | B |
| 481 | B | A | A |
| 482 | B | A | A |
| 483 | B | B | C |
| 484 | B | A | B |
| 485 | B | A | B |
| 486 | | B | B |
| 491 | B | A | A |
| 492 | B | A | A |
| 493 | | A | A |
| 495 | B | A | A |
| 496 | B | A | A |
| 497 | B | A | B |
| 498 | B | B | C |
| 499 | B | A | A |
| 500 | B | A | A |
| 501 | B | B | C |
| 502 | B | B | C |
| 503 | C | A | A |
| 504 | B | A | A |
| 505 | B | A | B |
| 508 | B | A | B |
| 509 | B | A | B |
| 510 | B | A | A |
| 511 | B | A | B |
| 512 | B | A | B |
| 513 | C | A | B |
| 514 | B | A | A |
| 516 | B | A | A |
| 517 | B | A | A |
| 518 | B | A | A |
| 519 | B | A | B |
| 521 | B | A | A |
| 522 | B | A | B |
| 523 | B | A | A |
| 524 | B | A | A |
| 526 | B | A | A |
| 527 | B | A | A |
| 528 | B | A | B |
| 529 | B | A | A |
| 530 | B | A | B |
| 531 | B | A | A |
| 532 | B | A | A |
| 533 | B | A | A |
| 534 | B | A | A |
| 535 | B | A | B |
| 536 | C | A | B |
| 537 | B | A | A |
| 538 | C | A | B |
| 540 | B | A | B |
| 541 | B | A | B |
| 542 | B | A | A |
| 543 | B | A | B |
| 544 | B | A | B |
| 545 | B | A | B |
| 546 | B | A | B |
| 547 | B | A | A |
| 548 | B | A | B |
| 549 | B | A | A |
| 550 | B | A | A |
| 551 | B | A | A |
| 552 | B | A | B |
| 554 | B | A | B |
| 555 | B | A | C |
| 556 | B | A | A |
| 559 | B | A | A |
| 560 | B | A | A |

TABLE 2-continued

Enzymatic and Cellular Activity of Compounds.

| Cmpd No | Enz R140Q | Cell R140Q | Enz R172K |
|---|---|---|---|
| 561 | B | A | A |
| 562 | B | A | A |
| 563 | B | A | A |
| 564 | B | A | A |
| 565 | B | A | A |
| 567 | B | A | A |
| 568 | B | A | B |
| 569 | B | B | B |
| 570 | B | A | A |
| 571 | B | A | B |
| 572 | B | A | B |
| 574 | B | A | A |
| 576 | B | A | B |
| 577 | C | A | B |
| 581 | B | A | A |
| 582 | B | A | A |
| 583 | B | A | A |
| 584 | B | A | A |
| 585 | B | A | A |
| 587 | B | A | A |
| 588 | B | A | B |
| 592 | B | A | B |
| 593 | B | A | A |
| 594 | B | A | B |
| 595 | B | A | A |
| 596 | B | A | A |
| 597 | B | A | A |
| 598 | B | A | A |
| 599 | B | A | A |
| 600 | B | A | A |
| 601 | B | A | A |
| 602 | B | A | A |
| 603 | B | A | A |
| 604 | B | A | A |
| 605 | B | A | B |
| 606 | B | A | A |
| 607 | B | A | B |
| 608 | B | A | A |
| 609 | B | A | A |
| 610 | B | A | A |
| 611 | B | A | B |
| 612 | B | A | A |
| 613 | B | A | A |
| 614 | B | A | A |
| 615 | B | A | B |
| 616 | B | A | A |
| 617 | B | A | A |
| 618 | B | A | A |
| 619 | B | A | A |
| 621 | B | B | C |
| 622 | B | B | B |
| 623 | B | B | C |
| 624 | B | A | B |
| 625 | A | A | B |
| 626 | B | B | C |
| 627 | A | A | A |
| 628 | A | A | B |
| 629 | A | A | A |
| 630 | A | A | A |
| 631 | A | A | A |
| 632 | B | A | B |
| 633 | B | A | A |
| 634 | B | A | A |
| 635 | B | B | B |
| 636 | A | A | B |
| 637 | B | A | B |
| 638 | B | A | B |
| 639 | B | A | A |
| 640 | A | A | A |
| 641 | B | A | A |
| 642 | B | A | A |
| 644 | B |   | C |
| 645 | B | A | B |
| 646 | B | A | A |
| 647 | B | A | B |
| 648 | B | A | B |
| 649 | A | B | B |
| 650 | B | B | C |
| 651 | B | A | B |
| 652 | B | B | B |
| 653 | B | A | B |
| 654 | B | A | D |
| 655 | B | B | B |
| 657 | B | A | B |
| 658 | B | A | A |
| 660 | B | C |   |
| 662 |   | B | C |
| 663 |   | A | A |
| 665 |   | A | A |
| 667 | B | B | B |
| 669 | B | A | A |
| 670 | B | A | B |
| 671 | B | A | A |
| 672 | B | A | B |
| 673 | B | A | A |
| 674 | B | A | B |
| 675 | B | A | A |
| 676 | B | A | A |
| 677 | B | A | A |
| 678 | C | A | B |
| 679 | B | B | D |
| 687 | B | A | A |
| 689 | B | A | A |
| 690 | B | A | A |
| 691 | B | A | B |
| 692 | B | A | A |
| 693 | B | A | A |
| 694 | B | A | A |
| 695 | B | A | A |
| 696 | B | A | B |
| 697 | B | B | C |
| 698 | B | A | A |
| 699 | B | A | A |

In some embodiments, one aspect of the invention provides a compound selected from any one of Compounds Nos 100, 110, 111, 112, 113, 115, 118, 120, 121, 123, 126, 129, 130, 132, 139, 140, 141, 143, 146, 149, 154, 158, 160, 167, 168, 169, 172, 173, 174, 175, 176, 177, 178, 179, 181, 183, 184, 185, 186, 187, 188, 189, 190, 191, 193, 194, 195, 196, 197, 198, 199, 200, 201, 202, 203, 204, 205, 206, 208, 209, 210, 211, 212, 213, 214, 215, 216, 217, 218, 219, 220, 223, 224, 225, 226, 227, 228, 229, 232, 233, 239, 240, 241, 245, 246, 247, 248, 249, 250, 253, 254, 255, 257, 260, 261, 263, 266, 267, 268, 269, 270, 277, 281, 288, 289, 290, 293, 295, 296, 297, 298, 299, 301, 302, 306, 308, 309, 310, 313, 315, 317, 318, 319, 320, 321, 322, 323, 325, 326, 328, 329, 330, 331, 334, 335, 336, 340, 341, 344, 346, 351, 352, 353, 354, 355, 356, 358, 363, 366, 367, 369, 370, 371, 372, 374, 376, 377, 378, 379, 381, 382, 383, 384, 386, 387, 391, 392, 393, 394, 395, 396, 398, 399, 400, 401, 402, 403, 404, 406, 408, 409, 416, 450, 455, 456, 458, 459, 460, 461, 463, 464, 465, 466, 468, 469, 470, 471, 472, 473, 474, 475, 476, 477, 478, 479, 480, 481, 482, 484, 485, 491, 492, 493, 495, 496, 497, 499, 500, 504, 505, 508, 509, 510, 511, 512, 514, 516, 517, 518, 519, 521, 522, 523, 524, 526, 527, 528, 529, 530, 531, 532, 533, 534, 535, 537, 540, 541, 542, 543, 544, 545, 546, 547, 548, 549, 550, 551, 552, 554, 555, 556, 559, 560, 561, 562, 563, 564, 565, 567, 568, 570, 571, 572, 574, 576, 581, 582, 583, 584, 585, 587, 588, 592, 593, 594, 595, 596, 597, 598, 599, 600, 601, 602, 603, 604, 605, 606, 607, 608, 609, 610, 611, 612, 613, 614, 615, 616, 617, 618, 619, 624, 625, 627, 628, 629, 630, 631, 632, 633, 634, 636, 637, 638, 639, 640, 641, 642, 645, 646, 647, 648, 649, 651, 653, 654, 657, 658, 663, 665, 669, 670, 671, 672, 673, 674, 675, 676, 677, 687, 689, 690, 691, 692, 693, 694, 695, 696, 698 and 699. In a more specific aspect of this embodiment, the invention provides a compound selected from any one of Compound Nos. 100, 110, 111, 113, 120, 121, 126, 130, 132, 146, 149, 167, 168, 173, 174, 175, 177, 178, 179, 181, 183, 186, 187, 188, 190, 191, 193, 194, 195, 196, 197, 198, 199, 200, 202, 205, 210, 212, 213, 219, 220, 223, 227, 229, 233, 239, 246, 247, 253, 255, 260, 261, 269, 288, 290, 293, 295, 297, 298, 301, 306, 309, 310, 313, 315, 317, 318, 319, 320, 321, 323, 325, 326, 328, 329, 330, 331, 336, 340, 341, 352, 353, 354, 355, 356, 358, 363, 366, 367, 369, 370, 371, 372, 374, 376, 377, 378, 379, 381, 382, 383, 384, 387, 391, 392, 393, 394, 395, 396, 398, 399, 400, 401, 402, 403, 404, 406, 408, 409, 416, 450, 451, 456, 458, 459, 460, 461, 466, 469, 470, 471, 472, 473, 475, 476, 479, 480, 484, 485, 493, 497, 505, 508, 509, 511, 512, 519, 522, 528, 530, 535, 540, 541, 543, 544, 545, 546, 548, 552, 554, 555, 568, 571, 572, 576, 588, 592, 594, 605, 607, 611, 615, 624, 625, 627, 628, 629, 630, 631, 632, 636, 637, 638, 640, 645, 647, 648, 651, 653, 654, 657, 663, 665, 670, 672, 674, 691 and 696.

In some embodiments, one aspect of the invention provides a compound selected from any one of Compounds Nos 100, 110, 111, 112, 113, 115, 118, 120, 121, 123, 126, 129, 130, 132, 139, 140, 141, 143, 146, 149, 154, 158, 160, 167, 168, 169, 172, 173, 174, 175, 176, 177, 178, 179, 181, 183, 184, 185, 186, 187, 188, 189, 190, 191, 193, 194, 195, 196, 197, 198, 199, 200, 201, 202, 203, 204, 205, 206, 208, 209, 210, 211, 212, 213, 214, 215, 216, 217, 218, 219, 220, 223, 224, 225, 226, 227, 228, 229, 232, 233, 239, 240, 241, 245, 246, 247, 248, 249, 250, 253, 254, 255, 257, 260, 261, 263, 266, 267, 268, 269, 270, 277, 281, 288, 289, 290, 293, 295, 296, 297, 298, 299, 301, 302, 306, 308, 309, 310, 313, 315, 317, 318, 319, 320, 321, 322, 323, 325, 326, 328, 329, 330, 331, 334, 335, 336, 340, 341, 344, 346, 351, 352, 353, 354, 355, 356, 358, 363, 366, 367, 369, 370, 371, 372, 374, 376, 377, 378, 379, 381, 382, 383, 384, 386, 387, 391, 392, 393, 394, 395, 396, 398, 399, 400, 401, 402, 403, 404, 406, 408, 409, and 416. In a more specific aspect of this embodiment, the invention provides a compound selected from any one of Compound Nos. 100, 110, 111, 113, 120, 121, 126, 130, 132, 146, 149, 167, 168, 173, 174, 175, 177, 178, 179, 181, 183, 186, 187, 188, 190, 191, 193, 194, 195, 196, 197, 198, 199, 200, 202, 205, 210, 212, 213, 219, 220, 223, 227, 229, 233, 239, 247, 253, 255, 260, 261, 269, 288, 293, 295, 297, 298, 309, 313, 315, 317, 318, 320, 321, 325, 328, 329, 340, 341, 352, 369, 370, 371, 372, 374, 387, 394, 398, and 416.

Having thus described several aspects of several embodiments, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

The invention claimed is:

1. A compound which is

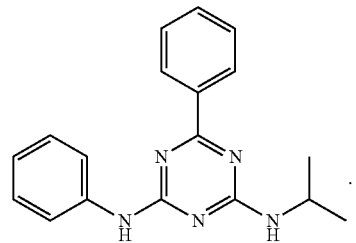 [SMILES: CC(C)Nc1nc(Nc2ccccc2)nc(-c2ccccc2)n1]

or a pharmaceutically acceptable salt or hydrate thereof.

2. A pharmaceutical composition comprising a compound of claim 1, and a pharmaceutically acceptable carrier.

3. A method of treating a cancer characterized by the presence of an IDH2 mutation, wherein the IDH2 mutation results in a new ability of the enzyme to catalyze the NADPH dependent reduction of a ketoglutarate to R(−) 2 hydroxyglutarate in a patient, comprising the step of administering to the patient in need thereof a compound of claim 1.

4. The method of claim 3, wherein the IDH2 mutation is an IDH2 R140Q or R172K mutation.

5. The method of claim 3, wherein the IDH2 mutation is an IDH2 R140Q mutation.

6. The method of claim 3, wherein the cancer is selected from the group consisting of glioblastoma, myelodysplastic syndrome, myeloproliferative neoplasm, acute myelogenous leukemia, sarcoma, melanoma, non small cell lung cancer, chondrosarcoma, cholangiocarcinomas and angioimmunoblastic non-Hodgkin's lymphoma.

7. The method of claim 3, wherein the cancer is acute myelogenous leukemia.

8. The method of claim 3, further comprising administering to the patient in need thereof a second therapeutic agent useful in the treatment of cancer.

* * * * *